United States Patent
Brito et al.

(10) Patent No.: US 10,426,737 B2
(45) Date of Patent: Oct. 1, 2019

(54) LIPIDS AND LIPID COMPOSITIONS FOR THE DELIVERY OF ACTIVE AGENTS

(71) Applicant: Novartis AG, Basel (CH)

(72) Inventors: Luis Brito, Cambridge, MA (US); Delai Chen, Cambridge, MA (US); Gabriel Grant Gamber, Cambridge, MA (US); Andrew Geall, Cambridge, MA (US); Kevin Love, Somerville, MA (US); Thomas Zabawa, Cambridge, MA (US); Frederic Zecri, Cambridge, MA (US)

(73) Assignee: Novartis AG, Basel (CH)

( * ) Notice: Subject to any disclaimer, the term of this patent is extended or adjusted under 35 U.S.C. 154(b) by 260 days.

(21) Appl. No.: 15/104,723

(22) PCT Filed: Dec. 17, 2014

(86) PCT No.: PCT/US2014/070891
§ 371 (c)(1),
(2) Date: Jun. 15, 2016

(87) PCT Pub. No.: WO2015/095346
PCT Pub. Date: Jun. 25, 2015

(65) Prior Publication Data
US 2016/0317458 A1  Nov. 3, 2016

Related U.S. Application Data

(60) Provisional application No. 61/918,941, filed on Dec. 20, 2013, provisional application No. 61/918,182, filed on Dec. 19, 2013.

(51) Int. Cl.
| | |
|---|---|
| *C07C 219/06* | (2006.01) |
| *C07C 219/16* | (2006.01) |
| *C07C 229/12* | (2006.01) |
| *C07C 235/08* | (2006.01) |
| *C07C 323/52* | (2006.01) |
| *A61K 9/51* | (2006.01) |
| *C07D 319/06* | (2006.01) |
| *C07D 233/60* | (2006.01) |
| *C07D 207/12* | (2006.01) |
| *C07D 207/16* | (2006.01) |
| *C07D 211/22* | (2006.01) |
| *C07D 295/088* | (2006.01) |
| *C07D 211/62* | (2006.01) |

(Continued)

(52) U.S. Cl.
CPC .......... *A61K 9/5123* (2013.01); *A61K 9/1272* (2013.01); *A61K 31/713* (2013.01); *A61K 31/7105* (2013.01); *A61K 38/1816* (2013.01); *A61K 38/2264* (2013.01); *A61K 39/12* (2013.01); *A61K 47/18* (2013.01); *C07C 219/06* (2013.01); *C07C 219/16* (2013.01); *C07C 229/12* (2013.01); *C07C 235/08* (2013.01); *C07C 323/52* (2013.01); *C07D 207/12* (2013.01); *C07D 207/16* (2013.01); *C07D 211/06* (2013.01); *C07D 211/22* (2013.01); *C07D 211/46* (2013.01); *C07D 211/62* (2013.01); *C07D 233/60* (2013.01); *C07D 233/64* (2013.01); *C07D 295/088* (2013.01); *C07D 295/13* (2013.01); *C07D 319/06* (2013.01); *C12N 7/00* (2013.01); *C12N 15/1137* (2013.01); *C12N 15/88* (2013.01); *A61K 2039/53* (2013.01); *C12N 2310/14* (2013.01); *C12N 2320/32* (2013.01); *C12N 2760/00034* (2013.01); *C12N 2760/00071* (2013.01)

(58) Field of Classification Search
None
See application file for complete search history.

(56) References Cited

U.S. PATENT DOCUMENTS

| | | |
|---|---|---|
| 4,987,071 A | 1/1991 | Cech et al. |
| 5,589,332 A | 12/1996 | Shih et al. |

(Continued)

FOREIGN PATENT DOCUMENTS

| | | |
|---|---|---|
| WO | WO 1998027104 | 6/1998 |
| WO | WO 1999029842 | 6/1999 |

(Continued)

OTHER PUBLICATIONS

Rehman. Journal of Controlled Release, 2013, 166, 46-56 (Year: 2013).*

(Continued)

*Primary Examiner* — Noble E Jarrell
(74) *Attorney, Agent, or Firm* — Brinks Gilson & Lione

(57) ABSTRACT

This invention provides for a compound of formula (I) or a pharmaceutically acceptable salt thereof, wherein $R^1$-$R^3$, n, p, $L_1$ and $L_2$ are defined herein. The compounds of formula (I) and pharmaceutically acceptable salts thereof are cationic lipids useful in the delivery of biologically active agents to cells and tissues.

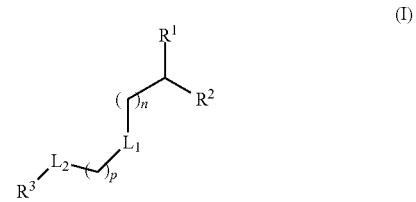

29 Claims, 1 Drawing Sheet
Specification includes a Sequence Listing.

(51) Int. Cl.

| | | |
|---|---|---|
| A61K 47/18 | (2017.01) | |
| A61K 9/127 | (2006.01) | |
| A61K 31/7105 | (2006.01) | |
| A61K 31/713 | (2006.01) | |
| C12N 15/88 | (2006.01) | |
| A61K 38/18 | (2006.01) | |
| A61K 38/22 | (2006.01) | |
| A61K 39/12 | (2006.01) | |
| C07D 211/06 | (2006.01) | |
| C07D 211/46 | (2006.01) | |
| C07D 233/64 | (2006.01) | |
| C07D 295/13 | (2006.01) | |
| C12N 7/00 | (2006.01) | |
| C12N 15/113 | (2010.01) | |
| A61K 39/00 | (2006.01) | |

(56) References Cited

U.S. PATENT DOCUMENTS

| | | |
|---|---|---|
| 5,741,679 A | 4/1998 | George et al. |
| 5,834,186 A | 11/1998 | George et al. |
| 5,837,282 A | 11/1998 | Fenske et al. |
| 5,849,902 A | 12/1998 | Arrow et al. |
| 5,871,914 A | 2/1999 | Nathan |
| 7,348,314 B2 | 3/2008 | John et al. |
| 7,811,602 B2 | 10/2010 | Cullis et al. |
| 2009/0048197 A1 | 2/2009 | Chen et al. |

FOREIGN PATENT DOCUMENTS

| | | | |
|---|---|---|---|
| WO | WO 1999032619 | 7/1999 | |
| WO | WO 2000024931 | 5/2000 | |
| WO | WO 2000026226 | 5/2000 | |
| WO | WO 2000044895 | 8/2000 | |
| WO | WO 2001029058 | 4/2001 | |
| WO | WO 2002002606 | 1/2002 | |
| WO | WO 2002034771 | 5/2002 | |
| WO | WO 2003018054 | 3/2003 | |
| WO | WO 2005002619 | 1/2005 | |
| WO | WO 2005032582 | 4/2005 | |
| WO | WO 2005111066 | 11/2005 | |
| WO | WO 2006091517 | 2/2006 | |
| WO | WO 2006089264 | 8/2006 | |
| WO | WO 2006110413 | 10/2006 | |
| WO | WO 2006138004 | 12/2006 | |
| WO | WO 2007049155 | 3/2007 | |
| WO | WO 2008020330 | 2/2008 | |
| WO | WO 2009016515 | 2/2009 | |
| WO | WO 2009031043 | 3/2009 | |
| WO | WO 2009104092 | 8/2009 | |
| WO | WO 2009109860 | 9/2009 | |
| WO | WO 2009129395 | 10/2009 | |
| WO | WO 2010119343 | 10/2010 | |
| WO | WO 2011005799 | 1/2011 | |
| WO | WO 2011076807 | 6/2011 | |
| WO | WO 2012006372 | 1/2012 | |
| WO | WO 2013086354 | 6/2013 | |
| WO | WO-2015095351 A1 * | 6/2015 | ........... A61K 9/0019 |

OTHER PUBLICATIONS

Akhtar and Juliano, "Cellular Uptake and Intracellular Fate of Antisense Oligonucleotides," Trends in Cell Biology, vol. 2, (1992), pp. 139-144.
Allen and Cullis, "Liposomal Drug Delivery Systems: From Concept to Clinical Applications," Advanced Drug Delivery Reviews, vol. 65, (2013), pp. 36-48.
Bangham et al., "Diffusion of Univalent Ions Across the Lamellae of Swollen Phospholipids," Journal of Molecular Biology, vol. 13, No. 1, (1965), pp. 238-252.
Brigham et al., "Rapid Communication: in vivo Transfection of Murine Lungs with a Functioning Prokaryotic Gene using a Liposome Vehicle," Am. J. Med. Sci., vol. 298, No. 4, (1989), pp. 278-281.
Cech, "Ribozymes and Their Medical Implications," JAMA, vol. 260, No. 20, (1988), pp. 3030-3034.
Duval-Valentin et al., "Specific Inhibition of Transcription by Triple Helix-Forming Oligonucleotides," Proc. Natl. Acad. Sci. USA, vol. 89, (1992), pp. 504-508.
Egholm et al., "PNA Hybridizes to Complementary Oligonucleotides Obeying the Watson-Crick Hydrogen-Bonding Rules," Nature, vol. 365, (1993), pp. 566-568.
Elbashir et al., "Duplexes of 21-Nucleotide RNAs Mediate RNA Interference in Cultured Mammalian Cells," Nature, vol. 411, (2001), pp. 494-498.
Falsini et al., "Advances in Lipid-Based Platforms for RNAi Therapeutics," J. Med. Chem., (2013), pp. A-I.
Felgner et al., "Lipofection: A Highly Efficient, Lipid-Mediated DNA-Transfection Procedure," Proc. Natl. Acad. Sci. USA, vol. 84, (1987), pp. 7413-7417.
Felgner, "Cationic Lipid/Polynucleotide Condensates for in vitro and in vivo Polynucleotide Delivery—the Cytofectins," Journal of Liposomal Research, vol. 3, No. 1, (1993), pp. 3-16.
Felgner, "Particulate Systems and Polymers for in vitro and in vivo Delivery of Polynucleotides," Advanced Drug Delivery Reviews, vol. 5, No. 3, (1990), pp. 163-187.
Fox, "Targeting DNA with Triplexes," Current Medicinal Chemistry, vol. 7, (2000), pp. 17-37.
Gallas et al., "Chemistry and Formulations for siRNA Therapeutics," Chem. Soc. Rev., vol. 42, (2013), pp. 7983-7997.
Geall et al., "Nonviral Delivery of Self-Amplifying RNA Vaccines," PNAS, vol. 109, No. 37, (2012), pp. 14604-14609.
Giuliani et al., "A Universal Vaccine for Serogroup B Meningococcus," PNAS, vol. 103, No. 29, (2006), pp. 10834-10839.
Hammann et al., "Length Variation of Helix III in a Hammerhead Ribozyme and its Influence on Cleavage Activity," Antisense & Nucleic Acid Drug Development, vol. 9, (1999), pp. 25-31.
International Preliminary Report on Patentability, issued in PCT/US2014/070891, dated Jun. 21, 2016.
International Search Report, issued in PCT/US2014/070891, dated Feb. 25, 2015.
Janowski et al., "Inhibiting Gene Expression at Transcription Start Sites in Chromosomal DNA with Antigene RNAs," Nature Chemical Biology, vol. 1, No. 4, (2005), pp. 216-222.
Jayaraman et al., "Maximizing the Potency of siRNA Lipid Nanoparticles for Hepatic Gene Silencing in Vivo," Agnew. Chem. Int. Ed., vol. 51, (2012), pp. 8529-8533.
Jeffs et al., "A Scalable, Extrusion-Free Method for Efficient Liposomal Encapsulation of Plasmid DNA," Pharmaceutical Research, vol. 22, No. 3, (2005), pp. 362-372.
Leung et al., "Lipid Nanoparticles Containing siRNA Synthesized by Microfluidic Mixing Exhibit an Electron-Dense Nanostructured Core," J. Phys. Chem., vol. 116, (2012), pp. 18440-18450.
Maier et al., "Biodegradable Lipids Enabling Rapidly Eliminated Lipid Nanoparticles for Systemic Delivery of RNAi Therapeutics," The American Society of Gene & Cell Therapy, vol. 21, No. 8, (2013), pp. 1570-1578.
Maurer et al., "Spontaneous Entrapment of Polynucleotides upon Electrostatic Interaction with Ethanol-Destabilized Cationic Liposomes," Biophysical Journal, vol. 80, (2001), pp. 2310-2326.
Morrissey et al., "Potent and Persistent in vivo Anti-HBV Activity of Chemically Modified siRNAs," Nature Biology, vol. 23, No. 8, (2005), pp. 1002-1007.
Obika et al., "Symmetrical Cationic Triglycerides," Bioorganic and Medicinal Chemistry, vol. 9, No. 2, (2001), pp. 245-254, Search Report.
Player and Torrence, "The 2-5A System: Modulation of Viral and Cellular Processes Through Acceleration of RNA Degradation," Pharmacol. Ther., vol. 78, No. 2, (1998), pp. 55-113.
Praseuth et al., "Triple Helix Formation and the Antigene Strategy for Sequence-Specific Control of Gene Expression," Biochimica et Biophysica Acta, vol. 1489, (1999), pp. 181-206.

(56) References Cited

OTHER PUBLICATIONS

Rejman et al, "Characterization and Transfection Properties of Lipoplexes Stabilized with Novel Exchangeable Polyethylene Glycol-Lipid Conjugates," Biochimica et Biophysica Acta, vol. 1660, (2004), pp. 41-52.
Romberg et al., "Sheddable Coatings for Long-Circulating Nanoparticles," Pharmaceutical Research, vol. 25, No. 1, (2008), pp. 55-71.
Semple et al., "Rational Design of Cationic Lipids for siRNA Delivery," Nature Biotechnology, vol. 28, No. 2, (2010), pp. 172-178.
Silverman et al., "Selective RNA Cleavage by Isolated RNase L Activated with 2-5A Antisense Chimeric Oligonucleotides," Methods in Enzymology, vol. 313, pp. 522-533.
Stein and Cheng, "Antisense Oligonucleotides as Therapeutic Agents—Is the Bullet Really Magical?" Science, vol. 261, (1993), pp. 1004-1012.
Torrence et al., Targeting RNA for Degradation with a (2'-5')oligoadenylate-antisense Chimera, Proc. Natl. Acad. Sci. USA, vol. 90, (1993), pp. 1300-1304.
Werner and Uhlenbeck, "The Effect of Base Mismatches in the Substrate Recognition Helices of Hammerhead Ribozymes on Binding and Catalysis," Nucleic Acids Research, vol. 23, No. 12, (1995), pp. 2092-2096.
Xu and Szoka, "Mechanism of DNA Release from Cationic Liposome/DNA Complexes used in Cell Transfection," Biochemistry, vol. 35, (1996), pp. 5616-5623.
Zamore et al., "Ribognome: The Big World of Small RNAs," Science, vol. 308, (2005), pp. 1519-1524.
Zamore et al., "RNAi: Double-Stranded RNA Directs the ATP-Dependent Cleavage of mRNA at 21 to 23 Nucleotide Intervals," Cell, vol. 101, (2000), pp. 25-33.
Zhang et al., "Interaction of Cholesterol-Conjugated Ionizable Amino Lipids with Biomembranes: Lipid Polymorphism, Structure—Activity Relationship, and Implications of siRNA Delivery," Langmuir, vol. 27, (2011), pp. 9473-9483.
Zimmermann et al., "RNAi-Mediated Gene Silencing in Non-Human Primates," Nature, vol. 441, (2006), pp. 111-114.

* cited by examiner

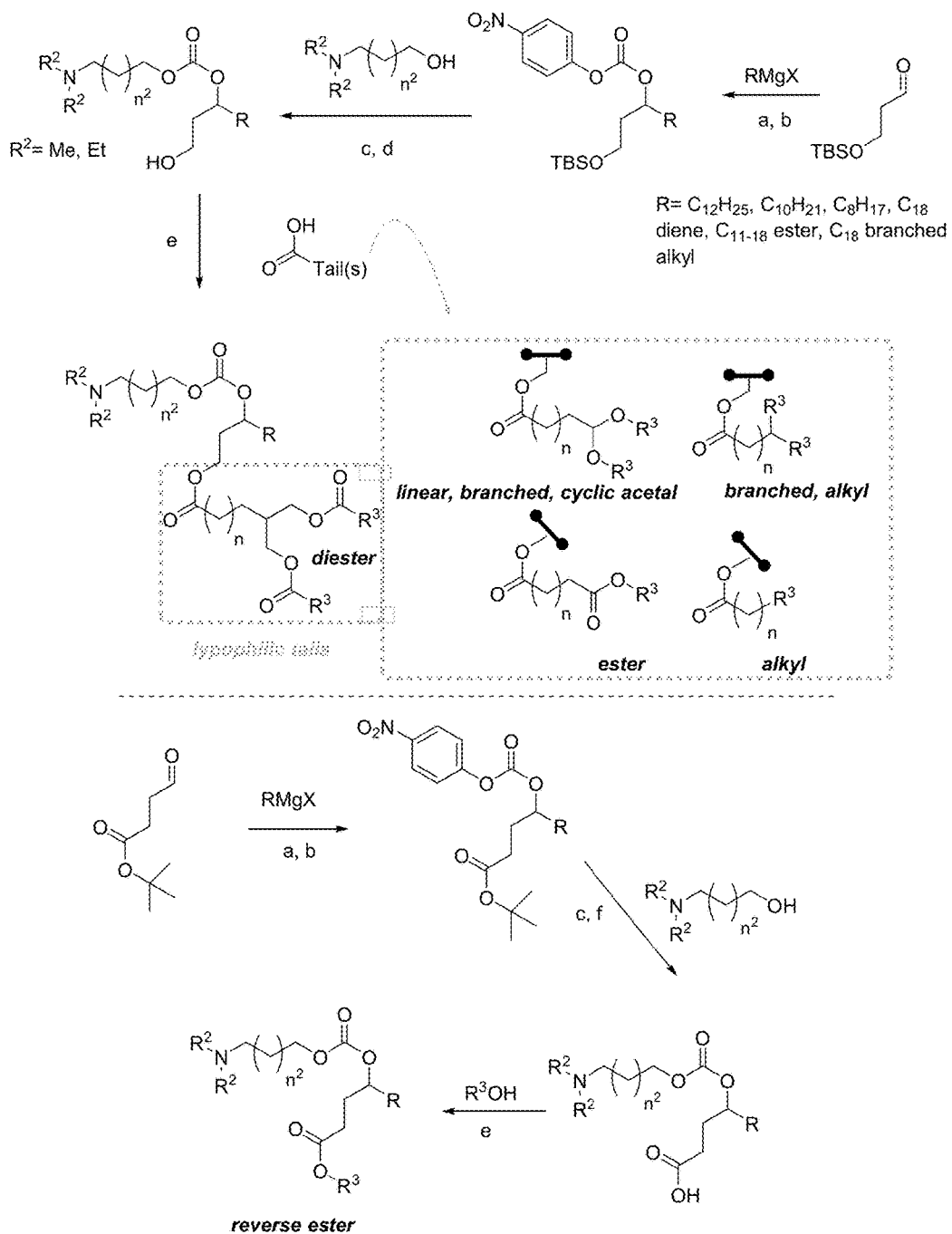
a) Grignard addition to aldehyde. b) *p*-Nitro phenylcarbonate formation. c) Carbonate formation with appropriate amino alcohol. d) Silyl ether deprotection. e) EDC, or comparable esterification coupling. f) Ester hydrolysis.

SEQUENCE LISTING

```
<160> NUMBER OF SEQ ID NOS: 13

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: 2'-O-methyl-nucleotide
<220> FEATURE:
<221> NAME/KEY: modified_base
<222> LOCATION: (13)..(13)
<223> OTHER INFORMATION: 2'-O-methyl-nucleotide
<220> FEATURE:
<221> NAME/KEY: modified_base
<222> LOCATION: (18)..(18)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotide

<400> SEQUENCE: 1
uuuaauugaa accaagacau u                                             21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl-nucleotide
<220> FEATURE:
<221> NAME/KEY: modified_base
<222> LOCATION: (3)..(6)
<223> OTHER INFORMATION: 2'-O-methyl-nucleotide
<220> FEATURE:
```

```
<221> NAME/KEY: modified_base
<222> LOCATION: (9)..(12)
<223> OTHER INFORMATION: 2'-O-methyl-nucleotide
<220> FEATURE:
<221> NAME/KEY: modified_base
<222> LOCATION: (15)..(16)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotide

<400> SEQUENCE: 2
ugucuugguu ucaauuaaau u                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: 2'-O-methyl-nucleotide
<220> FEATURE:
<221> NAME/KEY: modified_base
<222> LOCATION: (17)..(17)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotide

<400> SEQUENCE: 3
uauuuaagga gggugaucuu u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(7)
<223> OTHER INFORMATION: 2'-O-methyl-nucleotide
<220> FEATURE:
<221> NAME/KEY: modified_base
<222> LOCATION: (11)..(14)
<223> OTHER INFORMATION: 2'-O-methyl-nucleotide
<220> FEATURE:
<221> NAME/KEY: modified_base
<222> LOCATION: (19)..(21)
<223> OTHER INFORMATION: 2'-O-methyl-nucleotide

<400> SEQUENCE: 4
agaucacccu ccuuaaauau u                                              21

<210> SEQ ID NO 5
<211> LENGTH: 5427
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gacggatcgg gagatctccc gatcccctat ggtgcactct cagtacaatc tgctctgatg     60
```

```
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaacgg gccctctaga ctcgagcggc cgccactgtg ctggatatct gcagaattcc      960
accacactgg actagtggat ccgagctcgg taccaagctt aagtttaaac cgctgatcag     1020
cctcgactgt gccttctagt tgccagccat ctgttgtttg cccctccccc gtgccttcct     1080
tgaccctgga aggtgccact cccactgtcc tttcctaata aaatgaggaa attgcatcgc     1140
attgtctgag taggtgtcat tctattctgg gggtgggggt ggggcaggac agcaagggggg    1200 aggattggga agacaatagc aggcatgctg gggatgcggt gggctctatg cttctgagg     1260 cggaaagaac cagctgggc tctagggggt atccccacgc gccctgtagc ggcgcattaa      1320
gcgcggcggg tgtggtggtt acgcgcagcg tgaccgctac acttgccagc gccctagcgc     1380
ccgctccttt cgctttcttc ccttccttc tcgccacgtt cgccggcttt ccccgtcaag     1440
ctctaaatcg ggggctccct ttagggttcc gatttagtgc tttacggcac ctcgacccca     1500
aaaaacttga ttagggtgat ggttcacgta gtgggccatc gccctgatag acggtttttc     1560
gccctttgac gttggagtcc acgttcttta atagtggact cttgttccaa actggaacaa     1620
cactcaaccc tatctcggtc tattcttttg atttataagg gattttgccg atttcggcct     1680
attggttaaa aaatgagctg atttaacaaa aatttaacgc gaattaattc tgtggaatgt     1740
gtgtcagtta gggtgtggaa agtccccagg ctccccagca ggcagaagta tgcaaagcat     1800
gcatctcaat tagtcagcaa ccaggtgtgg aaagtcccca ggctcccag caggcagaag      1860 tatgcaaagc atgcatctca attagtcagc aaccatagtc cgcccctaa ctccgcccat      1920 cccgcccta actccgccca gttccgccca ttctccgccc catggctgac taatttttttt    1980 tatttatgca gaggccgagg ccgcctctgc ctctgagcta ttccagaagt agtgaggagg     2040
cttttttgga ggcctaggct tttgcaaaaa gctcccggga gcttgtatat ccattttcgg     2100
atctgatcaa gagacaggat gaggatcgtt tcgcatgatt gaacaagatg gattgcacgc     2160
aggttctccg gccgcttggg tggagaggct attcggctat gactgggcac aacagacaat     2220
cggctgctct gatgccgccg tgttccggct gtcagcgcag gggcgcccgg ttcttttgt      2280 caagaccgac ctgtccggtg ccctgaatga actgcaggac gaggcagcgc ggctatcgtg     2340
gctggccacg acgggcgttc cttgcgcagc tgtgctcgac gttgtcactg aagcgggaag     2400
ggactggctg ctattgggcg aagtgccggg gcaggatctc ctgtcatctc accttgctcc     2460
```

-continued

```
tgccgagaaa gtatccatca tggctgatgc aatgcggcgg ctgcatacgc ttgatccggc      2520
tacctgccca ttcgaccacc aagcgaaaca tcgcatcgag cgagcacgta ctcggatgga      2580
agccggtctt gtcgatcagg atgatctgga cgaagagcat caggggctcg cgccagccga      2640
actgttcgcc aggctcaagg cgcgcatgcc cgacggcgag gatctcgtcg tgacccatgg      2700
cgatgcctgc ttgccgaata tcatggtgga aaatggccgc ttttctggat tcatcgactg      2760
tggccggctg ggtgtggcgg accgctatca ggacatagcg ttggctaccc gtgatattgc      2820
tgaagagctt ggcggcgaat gggctgaccg cttcctcgtg ctttacggta tcgccgctcc      2880
cgattcgcag cgcatcgcct tctatcgcct tcttgacgag ttcttctgag cgggactctg      2940
gggttcgaaa tgaccgacca agcgacgccc aacctgccat cacgagattt cgattccacc      3000
gccgccttct atgaaaggtt gggcttcgga atcgttttcc gggacgccgg ctggatgatc      3060
ctccagcgcg gggatctcat gctggagttc ttcgcccacc ccaacttgtt tattgcagct      3120
tataatggtt acaaataaag caatagcatc acaaatttca caaataaagc attttttca      3180 ctgcattcta gttgtggttt gtccaaactc atcaatgtat cttatcatgt ctgtataccg      3240
tcgacctcta gctagagctt ggcgtaatca tggtcatagc tgtttcctgt gtgaaattgt      3300
tatccgctca caattccaca acatacga gccggaagca taaagtgtaa agcctggggt      3360
gcctaatgag tgagctaact cacattaatt gcgttgcgct cactgcccgc tttccagtcg      3420
ggaaacctgt cgtgccagct gcattaatga atcggccaac gcgcggggag aggcggtttg      3480
cgtattgggc gctcttccgc ttcctcgctc actgactcgc tgcgctcggt cgttcggctg      3540
cggcgagcgg tatcagctca ctcaaaggcg gtaatacggt tatccacaga atcaggggat      3600
aacgcaggaa agaacatgtg agcaaaaggc cagcaaaagg ccaggaaccg taaaaaggcc      3660
gcgttgctgg cgtttttcca taggctccgc cccctgacg agcatcacaa aatcgacgc      3720 tcaagtcaga ggtggcgaaa cccgacagga ctataaagat accaggcgtt tccccctgga      3780
agctccctcg tgcgctctcc tgttccgacc ctgccgctta ccggatacct gtccgccttt      3840
ctcccttcgg gaagcgtggc gctttctcat agctcacgct gtaggtatct cagttcggtg      3900
taggtcgttc gctccaagct gggctgtgtg cacgaacccc ccgttcagcc cgaccgctgc      3960
gccttatccg gtaactatcg tcttgagtcc aacccggtaa gacacgactt atcgccactg      4020
gcagcagcca ctggtaacag gattagcaga gcgaggtatg taggcggtgc tacagagttc      4080
ttgaagtggt ggcctaacta cggctacact agaagaacag tatttggtat ctgcgctctg      4140
ctgaagccag ttaccttcgg aaaaagagtt ggtagctctt gatccggcaa acaaaccacc      4200
gctggtagcg gtttttttgt ttgcaagcag cagattacgc gcagaaaaaa aggatctcaa      4260
gaagatcctt tgatctttc tacggggtct gacgctcagt ggaacgaaaa ctcacgttaa      4320
gggattttgg tcatgagatt atcaaaaagg atcttcacct agatcctttt aaattaaaaa      4380
tgaagtttta atcaatcta aagtatatat gagtaaactt ggtctgacag ttaccaatgc      4440
ttaatcagtg aggcacctat ctcagcgatc tgtctatttc gttcatccat agttgcctga      4500
ctccccgtcg tgtagataac tacgatacgg gagggcttac catctggccc cagtgctgca      4560
atgataccgc gagacccacg ctcaccggct ccagatttat cagcaataaa ccagccagcc      4620
ggaagggccg agcgcagaag tggtcctgca actttatccg cctccatcca gtctattaat      4680
tgttgccggg aagctagagt aagtagttcg ccagttaata gtttgcgcaa cgttgttgcc      4740
attgctacag gcatcgtggt gtcacgctcg tcgtttggta tggcttcatt cagctccggt      4800
```

```
tcccaacgat caaggcgagt tacatgatcc cccatgttgt gcaaaaaagc ggttagctcc    4860
ttcggtcctc cgatcgttgt cagaagtaag ttggccgcag tgttatcact catggttatg    4920
gcagcactgc ataattctct tactgtcatg ccatccgtaa gatgcttttc tgtgactggt    4980
gagtactcaa ccaagtcatt ctgagaatag tgtatgcggc gaccgagttg ctcttgcccg    5040
gcgtcaatac gggataatac cgcgccacat agcagaactt taaaagtgct catcattgga    5100
aaacgttctt cggggcgaaa actctcaagg atcttaccgc tgttgagatc cagttcgatg    5160
taacccactc gtgcacccaa ctgatcttca gcatctttta ctttcaccag cgtttctggg    5220
tgagcaaaaa caggaaggca aaatgccgca aaaaagggaa taaggcgac acggaaatgt     5280 tgaatactca tactcttcct ttttcaatat tattgaagca tttatcaggg ttattgtctc    5340
atgagcggat acatatttga atgtatttag aaaaataaac aaatagggt tccgcgcaca     5400 tttccccgaa aagtgccacc tgacgtc                                       5427
```

<210> SEQ ID NO 6
<211> LENGTH: 4523
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1203)..(1203)
<223> OTHER INFORMATION: a, c, t, g, unknown or other
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: modified_base
<222> LOCATION: (1224)..(1225)
<223> OTHER INFORMATION: a, c, t, g, unknown or other
<220> FEATURE:
<221> NAME/KEY: misc_feature
<222> LOCATION: (1224)..(1225)
<223> OTHER INFORMATION: n is a, c, g, or t

<400> SEQUENCE: 6

```
gatccggagg ccggagaatt gtaatacgac tcactatagg gagacgcgtg ttaaataaca      60
aatctcaaca caacatatac aaaacaaacg aatctcaagc aatcaagcat tctacttcta     120
ttgcagcaat ttaaatcatt tcttttaaag caaaagcaat tttctgaaaa ttttcaccat     180
ttacgaacga tagccgccac catgcactgg ggaaccctgt gcggattcct gtggctgtgg     240
ccctacctgt tctatgtgca agccgtgccc atccagaagg tgcaggacga caccaagacc     300
ctgatcaaga ccatcgtgac ccggatcaac gacatcagcc acacccagag cgtgtccagc     360
aagcagaaag tgaccggcct ggacttcatc cccggcctgc accctatcct gaccctgtcc     420
aagatggacc agaccctggc cgtgtaccag cagatcctga ccagcatgcc cagccggaac     480
gtgatccaga tcagcaacga cctggaaaac ctgcgggacc tgctgcacgt gctggccttc     540
agcaagagct gccatctgcc ttgggccagc ggcctggaaa ccctggattc tctgggcgga     600
gtgctggaag ccagcggcta ctctacagag gtggtggccc tgagcagact gcagggcagc     660
ctgcaggata tgctgtggca gctggatctg agccccggct gctaatagcg gaccggcgat     720
agatgaagct cgctttcttg ctgtccaatt tctattaaag gttccttgt tccctaagtc      780 caactactaa actgggggat attatgaagg gccttgagca tctggattct gcctaataaa     840
aaacatttat tttcattgca gctcgctttc ttgctgtcca atttctatta aaggttcctt     900
```

```
tgttccctaa gtccaactac taaactgggg gatattatga agggccttga gcatctggat    960
tctgcctaat aaaaaacatt tattttcatt gcggccgcaa aaaaaaaaa aaaaaaaaa     1020
aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaga agagcaagct ttcgatagcg    1140
ctgttcgtag aaaaaaaga agtaaataat tactacttgc catatagact aaatagctgc    1200
gcntaataca tctacacttt ctannattga caagtgatac gttgcaaaag gagcaacacc   1260
ccacagactc gatgactgcg cagtcataca gtgaaattgc cctaatgtct tacctctgaa   1320
agggctaaac gaaagtagag cactattccg cgtagctatt tagtgcgatc ttttagaaat   1380
atcagcccag agagctgggc tgataaatat tttatccgac aagacgaatt ttgctcaaat   1440
gagttaaaac gatgctacca ctatctgctg cttttacgag atcagcccac cattgcatca   1500
tcggacgacg ttgctcaaga taatcactgc ggttataagc gcgacgcacc tcattttgt    1560
ctacatgagc aagcgctgct tcaatgacat caggtggaaa tccttcctca ttgagtgccg   1620
tactggcgat agaacgcaag ccgtgtgaaa caagtacacc tcctaagcca gcacgcttga   1680
gtgctgcatt cactgtttgg ctattcattg gttggttggg cttgatacgg ctaggaaaga   1740
taaattctcg gccaccactg agaggcttca tcatttccag aatagcaaga gccccatcag   1800
atagtggaac cgtatggtcc cggttcatct tcattcgagc tgcaggaatt ttccattcgc   1860
tagcattgaa atcgatctca tcccatcgag cctcagcagc ttcggcaggg cgggtgatgg   1920
ttagaagttg ccacatgaac aggcatcttg tggacatgct gatacttgcc gtacgcatgg   1980
tgtgcattag ctgcggaagt tgatccgcc ggatgcttgg catgttttc ttttgcggtt     2040
tctcgaaagc ttgagtattc tatagtgtca cctaaatagc ttggcgtaat catggtcata   2100
gctgtttcct gtgtgaaatt gttatccgct cacaattcca cacaacatac gagccggaag   2160
cataaagtgt aaagcctggg gtgcctaatg agtgagctaa ctcacattaa ttgcgttgcg   2220
ctcactgccc gctttccagt cgggaaacct gtcgtgccag ctgcattaat gaatcggcca   2280
acgcgcgggg agaggcggtt tgcgtattgg gcgctattcc gcttcctcgc tcactgactc   2340
gctgcgctcg tcgttcggc tgcggcgagc ggtatcagct cactcaaagg cggtaatacg    2400
gttatccaca gaatcagggg ataacgcagg aaagaacatg tgagcaaaag gccagcaaaa   2460
ggccaggaac cgtaaaaagg ccgcgttgct ggcgtttttc gataggctcc gcccccctga   2520
cgagcatcac aaaaatcgac gctcaagtca gaggtggcga aacccgacag gactataaag   2580
ataccaggcg tttccccctg gaagctccct cgtgcgctct cctgttccga ccctgccgct   2640
taccggatac ctgtccgcct ttctcccttc gggaagcgtg gcgctttctc atagctcacg   2700
ctgtaggtat ctcagttcgg tgtaggtcgt tcgctccaag ctgggctgtg tgcacgaacc   2760
ccccgttcag cccgaccgct gcgccttatc cggtaactat cgtcttgagt ccaacccggt   2820
aagacacgac ttatcgccac tggcagcagc cactggtaac aggattagca gagcgaggta   2880
tgtaggcggt gctacagagt tcttgaagtg gtggcctaac tacggctaca ctagaaggac   2940
agtatttggt atctgcgctc tgctgaagcc agttaccttc ggaaaaagag ttggtagctc   3000
ttgatccggc aaacaaacca ccgctggtag cggtggtttt tttgtttgca agcagcagat   3060
tacgcgcaga aaaaaggat ctcaagaaga tcctttgatc ttttctacgg ggtctgacgc    3120
tcagtggaac gaaaactcac gttaagggat tttggtcatg agattatcaa aaaggatctt   3180
cacctagatc cttttaaatt aaaaatgaag ttttaaatca atctaaagta tatatgagta   3240
aacttggtct gacagttacc aatgcttaat cagtgaggca cctatctcag cgatctgtct   3300
```

```
atttcgttca tccatagttg cctgactccc cgtcgtgtag ataactacga tacgggaggg    3360
cttaccatct ggccccagtg ctgcaatgat accgcgagac ccacgctcac cggctccaga    3420
tttatcagca ataaaccagc cagccggaag ggccgagcgc agaagtggtc ctgcaacttt    3480
atccgcctcc atccagtcta ttaattgttg ccgggaagct agagtaagta gttcgccagt    3540
taatagtttg cgcaacgttg ttggcattgc tacaggcatc gtggtgtcac gctcgtcgtt    3600
tggtatggct tcattcagct ccggttccca acgatcaagg cgagttacat gatccccat     3660 gttgtgcaaa aaagcggtta gctccttcgg tcctccgatc gttgtcagaa gtaagttggc    3720
cgcagtgtta tcactcatgg ttatggcagc actgcataat tctcttactg tcatgccatc    3780
cgtaagatgc ttttctgtga ctggtgagta ctcaaccaag tcattctgag aatagtgtat    3840
gcggcgaccg agttgctctt gcccggcgtc aatacgggat aataccgcgc cacatagcag    3900
aactttaaaa gtgctcatca ttggaaaacg ttcttcgggg cgaaaactct caaggatctt    3960
accgctgttg agatccagtt cgatgtaacc cactcgtgca cccaactgat cttcagcatc    4020
ttttactttc accagcgttt ctgggtgagc aaaaacagga aggcaaaatg ccgcaaaaaa    4080
gggaataagg cgacacgga aatgttgaat actcatactc ttccttttc aatattattg      4140 aagcatttat cagggttatt gtctcatgag cggatacata tttgaatgta tttagaaaaa    4200
taaacaaata ggggttccgc gcacatttcc ccgaaaagtg ccacctgacg tctaagaaac    4260
cattattatc atgacattaa cctataaaaa taggcgtatc acgaggccct ttcgtctcgc    4320
gcgtttcggt gatgacggtg aaaacctctg acacatgcag ctcccggaga cggtcacagc    4380
ttgtctgtaa gcggatgccg ggagcagaca agcccgtcag ggcgcgtcag cgggtgttgg    4440
cgggtgtcgg ggctggctta actatgcggc atcagagcag attgtactga gagtgcacca    4500
taaattcgag ctcggtaccc ggg                                            4523
```

<210> SEQ ID NO 7
<211> LENGTH: 1080
<212> TYPE: RNA
<213> ORGANISM: Artificial Sequence
<220> FEATURE:
<223> OTHER INFORMATION: Description of Artificial Sequence: Synthetic
polynucleotide

<400> SEQUENCE: 7

```
gggagacgcg uguuaaauaa caaaucucaa cacaacauau acaaaacaaa cgaaucucaa      60
gcaaucaagc auucuacuuc uauugcagca auuuaaauca uuucuuuuaa agcaaaagca     120
auuuucugaa aauuuucacc auuuacgaac gauagccgcc accaugcacu ggggaacccu     180
gugcggauuc cuguggcugu ggcccuaccu guucuaugug caagccgugc ccauccagaa     240
ggugcaggac gacaccaaga cccugaucaa gaccaucgug acccggauca acgacaucag     300
ccacacccag agcguguccca gcaagcagaa agugaccggc cuggacuuca uccccggccu     360
gcacccuauc cugacccgu ccaagaugga ccagacccug ccgguuaccc agcagauccu      420
gaccagcaug cccagccgga acgugaucca daucagcaac gaccuggaaa accugcggga     480
ccugcugcac gugcuggccu ucagcaagag cugccaucug ccuugggcca gcggccugga     540
aacccuggau ucucugggcg agugcugga agccagcggc uacucuacag gauggugg       600 ccugagcaga cugcagggca gccugcagga uaugcugugg cagcggaauc ugagccccgg     660
cugcuaauag cggaccggcg auagaugaag cucgcuuucu ugcugccaa uuucuauuaa      720 agguuccuuu guucccuaag uccaacuacu aaacuggggg auauuaugaa gggccuugag     780
```

```
caucuggauu cugccuaaua aaaaacauuu auuuucauug cagcucgcuu ucuugcuguc    840
caauuucuau uaaagguucc uuuguucccu aaguccaacu acuaaacugg gggauauuau    900
gaagggccuu gagcaucugg auucugccua auaaaaaaca uuuauuuuca uugcggccgc    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080
```

<210> SEQ ID NO 8
<211> LENGTH: 1128
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8

```
gggagacgcg uguuaaauaa caaaucucaa cacaacauau acaaaacaaa cgaaucucaa     60
gcaaucaagc auucuacuuc uauugcagca auuuaaauca uuucuuuuaa agcaaaagca    120
auuuucugaa aauuuucacc auuuacgaac gauagccgcc accaugggcg ugcccgaaag    180
accuacacuc cugcugcugc ugucacugcu gcugaucccu cugggccugc cugugcugug    240
ugcccccccu agacugaucu gcgacagcag agugcuggaa cgguacaucc uggaagccaa    300
agaggccgag aacgugacga ugggaugugc cgagggcccc agacugagcg agaacaucac    360
cgugcccgac accaaaguga acuucuacgc cuggaagcgg auggaagugg aagaacaggc    420
caucgaagug uggcagggcc ugagccugcu gagcgaggcu auucgcaggc acaggcucu    480 gcuggccaac agcagccagc uccugagaca cugcagcug cacaucgaca aggccaucag    540
cggccugaga agccugaccu cccgcgag ggugcuggga gcccagaaag aacugaugag    600 cccccgac accacccccc cugcuccucu gagaacucug accguggaca ccuucugcaa    660
gcuguuccgg guguacgcca acuuccgcg gggcaagcug aagcguaca ccggcgaagu    720 gugcagacgg ggcgacagau gaagcucgcu ucuugcugu ccaauuucua uuaaagguuc    780
cuuuguuccc uaaguccaac uacuaaacug ggggauauua ugaagggccu ugagcaucug    840
gauucugccu aauaaaaaac auuuauuuuc auugcagcuc gcuucuugc uguccaauuu    900 cuauuaaagg uuccuuuguu cccuaaguccc aacuacuaaa cuggggauauu auugaaggg    960 ccuugagcau cuggauucug ccuaauaaaa aacauuuauu uucauugcaa aaaaaaaaa   1020 aaaaaaaaaa aaaaaaaaaa aaaaaaaaaa aaaaaaaaaa aaaaaaaaaa aaaaaaaaaa   1080
aaaaaaaaaa aaaaaaaaaa aaaaaaaaaa aaaaaaaaaa aaaaaaaa              1128
```

<210> SEQ ID NO 9
<211> LENGTH: 1962
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 9

```
gggagacgcg uguuaaauaa caaaucucaa cacaacauau acaaaacaaa cgaaucucaa     60
gcaaucaagc auucuacuuc uauugcagca auuuaaauca uuucuuuuaa agcaaaagca    120
```

```
auuuucugaa aauuuucacc auuuacgaac gauagccgcc accaugcagc gcgugaacau    180
gauuauggcc gagagcccug gccugaucac caucugccug cugggcuacc ugcugagcgc    240
cgagugcacc guguuucugg accacgagaa cgccaacaag auccugaacc ggcccaagcg    300
guacaacagc ggcaagcugg aagaguucgu gcagggcaac cuggaacgcg agugcaugga    360
agagaagugc agcuucgaag aggccagaga ggucuucgag aacaccgagc ggaccaccga    420
guucuggaag caguacgugg acggcgacca gugcgagagc aaccccuguc ugaauggcgg    480
cagcugcaag gacgacauca acagcuacga gugcuggugc cccuucggcu ucgagggcaa    540
gaacugcgag cuggacguga ccugcaacau caagaacggc agaugcgagc aguucugcaa    600
gaacagcgcc gacaacaagg ucgugugcuc cugcaccgag ggcuacagac uggccgagaa    660
ccagaaguco ugcgagcccg ccgugccuuu cccaugugga agagugccg ugcccagac    720
cagcaagcug accagagccg agacaguguu ccccgacgug gacuacguga acagcaccga    780
ggccgagaca auccuggaca acaucaccca gagcacccag uccuucaacg acuucaccag    840
agucgugggc ggcgaggaug ccaagccugg acaguucccg uggcagguugg ugcugaacgg    900
aaagguggac gccuuuugcg gcggcagcau cgugaacgag aaguggaucg ugacagccgc    960
ccacugcgug gaaaccggcg ugaagauuac aguggugcc ggcgagcaca acaucgagga   1020
aaccgagcac acagagcaga aacggaacgu gaucagaauc auccccacc acaacuacaa   1080
cgccgccauc aacaaguaca accacgauau cgcccugcug gaacuggacg agccccuggu   1140
gcugaauagc uacgugaccc ccaucuguau cgccgacaaa gaguacacca acaucuuucu   1200
gaaguucgga gcggcuacg uguccggcug gggcagagug uuucacaagg gcagauccgc   1260
ucuggugcug caguaccuga gagugccucu ggugaccgg gccaccuguc ugagaagcac   1320
caaguucacc aucuacaaca acauguucug cgccggcuuu cacgggcg gcagagauag   1380
cugucagggc gauucuggcg gcccucacgu gacagaggug gaaggcacca gcuuucugac   1440
cggcaucauc agcugggcg aggaaugcgc caugaagggg aaguacggca ucuacaccaa   1500
ggugccaga uacgugaacu ggaucaaaga aaagaccaag cugacauaau gacggaccgg   1560
cgauagauga agcucgcuuu cuugcugucc aauuucuauu aaaaggauccu uugucccua   1620
aguccaacua cuaaacuggg ggauauuaug aagggccuug agcaucugga uucugccuaa   1680
uaaaaaacau uuauuuucau ugcagcucgc uuucuugcug uccaauuucu auuaaagguu   1740
ccuuuguucc cuaaguccaa cuacuaaacu ggggauauu augaagggcc uugagcaucu   1800
ggauucugcu aauaaaaaa cauuuauuuu caugcggcc gcaaaaaaaa aaaaaaaaa   1860
aaaaaaaaa aaaaaaaaa aaaaaaaaaa aaaaaaaaaa aaaaaaaaaa aaaaaaaaaa   1920
aaaaaaaaaa aaaaaaaaaa aaaaaaaaaa aaaaaaaaaa aa                    1962
```

<210> SEQ ID NO 10
<211> LENGTH: 2226
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 10

```
gggagacgcg uguuaaauaa caaaucucaa cacaacauau acaaaacaaa cgaaucucaa    60
gcaaucaagc auucuacuuc uauugcagca auuuaaauca uuucuuuuaa agcaaaagca   120
```

```
auuuucugaa aauuuucacc auuuacgaac gauagccgcc accauggaag acgccaaaaa    180
cauaaagaaa ggcccggcgc cauucuaucc gcuggaagau ggaaccgcug gagagcaacu    240
gcauaaggcu augaagagau acgcccuggu uccuggaaca auugcuuuua cagaugcaca    300
uaucgaggug gacaucacuu acgcugagua cuucgaaaug uccguucggu uggcagaagc    360
uaugaaacga uaugggcuga auacaaauca cagaaucguc guaugcagug aaaacucucu    420
ucaauucuuu augccggugu ugggcgcguu auuuaucgga guugcaguug cgcccgcgaa    480
cgacauuuau aaugaacgug aauugcucaa caguauggc auuucgcagc cuaccguggu     540
guucguuucc aaaaagggu ugcaaaaaau uuugaacgu caaaaaaagc ucccaaucau     600
ccaaaaaauu auuaucaugg auucuaaaac ggauuaccag ggauuucagu cgauguacac    660
guucgucaca ucucaucuac cucccgguuu uaaugaauac gauuuugugc cagaguccuu    720
cgauagggac aagacaauug cacugaucau gaacccucu ggaucuacug gucugccuaa     780
aggugucgcu cugccucaua gaacugccug cgugagauuc ucgcaugcca gagauccuau    840
uuuuggcaau caaaucauuc cggauacugc gauuuuaagu guuguccau uccaucacgg     900 uuuuggaaug uuuacuacac ucggauauuu gauaugugga uucgagucg cuuaaugua     960 uagauuugaa gaggagcugu uucugaggag ccuucaggau uacaagauuc aaagugcgcu   1020
gcuggugcca acccuauucu ccuucuucgc caaaagcacu cugauugaca aauacgauuu   1080
aucuaauuua cacgaaauug cuucuggugg cgcuccccuc ucuaaggaag ucggggaagc   1140
gguugccaag agguuccauc ugccagguau caggcaagga uaugggcuca cugagacuac   1200
aucagcuauu cugauuacac ccgaggggga ugauaaaccg ggcgcggucg guaaaguugu   1260
uccauuuuuu gaagcgaagg uuguggaucu ggauaccggg aaaacgcugg gcguuaauca   1320
aagaggcgaa cuguguguga gagguccuau gauuaugucc gguuauguaa acaauccgga   1380
agcgaccaac gccuugauug acaaggaugg auggcuacau ucuggagaca uagcuuacug   1440
ggacgaagac gaacacuucu ucaucguuga ccgccugaag ucucugauua aguacaaagg   1500
cuaucaggug gcucccgcug aauuggaauc caucuugcuc caacaccca acaucuucga   1560 cgcaggguc gcaggucuuc ccgacgauga cgccggugaa cuucccgccg ccguuguugu    1620
uuuggagcac ggaaagacga ugacggaaaa agagaucgug gauuacgucc cagucaagu   1680 aacaaccgcg aaaaaguugc gcggaggagu uguguuugu gacgaaguac cgaaaggucu    1740
uaccggaaaa cucgacgcaa gaaaaaucag agagauccuc auaaaggcca agaagggcgg   1800
aaagaucgcc gugugacgga ccggcgauag augaagcucg cuucuugcu guccaauuuc    1860 uauuaaaggu ccuuuguuc ccuaagucca acuacaaac uggggauau uaugaagggc      1920 cuugagcauc uggauucgc cuaauaaaaa acauuuauuu ucauugcagc ucgcuuucuu    1980
gcuguccaau uucuauuaaa gguuccuuug ucccuaagu ccaacuacua aacuggggga    2040
uauuaugaag ggccuugagc aucuggauuc ugccuaauaa aaacauuua uuucauugc     2100 ggccgcaaaa aaaaaaaaaa aaaaaaaaaa aaaaaaaaaa aaaaaaaaaa aaaaaaaaaa   2160
aaaaaaaaaa aaaaaaaaaa aaaaaaaaaa aaaaaaaaaa aaaaaaaaaa aaaaaaaaaa   2220
aaaaaa                                                              2226
```

<210> SEQ ID NO 11
<211> LENGTH: 1010
<212> TYPE: RNA
<213> ORGANISM: Artificial Sequence
<220> FEATURE:

<223> OTHER INFORMATION: Description of Artificial Sequence: Synthetic
polynucleotide

<400> SEQUENCE: 11

```
gggagacgcg uguuucugac auccggcgga auucugacau ccggcggaau ucugacaucc      60
ggcggaauuc ugacauccgg cggaauucug acauccggcg gaagacucac aaccccagaa     120
acagacagcc accaugggag ucaaaguucu guuugcccug aucugcaucg cuguggccga     180
ggccaagccc accgagaaca acgaagacuu caacaucgug gccguggcca gcaacuucgc     240
gaccacggau cucgaugcug accgcgggaa guugcccggc aagaagcugc cgcuggaggu     300
gcucaaagag auggaagcca augcccggaa agcuggcugc accaggggcu gucugaucug     360
ccuguccac aucaagugca cgcccaagau gaagaaguuc aucccaggac gcugccacac     420
cuacgaaggc gacaaagagu ccgcacaggg cggcauaggc gaggcgaucg ucgacauucc     480
ugagauuccu ggguucaagg acuuggagcc aauggagcag uucaucgcac aggucgaucu     540
gugugggac ugcacaacug gcugccucaa agggcuugcc aacgugcagu guucugaccu     600
gcucaagaag uggcugccgc aacgcugugc gaccuuugcc agcaagaucc agggccaggu     660
ggacaagauc aagggggccg guggugacua acggaccgaa aacucaaugu auuucugagg     720
aagcgugug cauaaugcca cgcagugucu acauaaucaa uuuauuauuu ucuuuuauuu     780
uauucacaua aaaacucaau guauuucuga ggaagcugug ugcauaaugc cacgcagugu     840
cuacauaauc aauuuauuau uuucuuuuau uuuauucaca uagcggccgc aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa              1010
```

<210> SEQ ID NO 12
<211> LENGTH: 250
<212> TYPE: RNA
<213> ORGANISM: Artificial Sequence
<220> FEATURE:
<223> OTHER INFORMATION: poly (A) tail

<400> SEQUENCE: 12

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa                                                            250
```

<210> SEQ ID NO 13
<211> LENGTH: 120
<212> TYPE: RNA
<213> ORGANISM: Artificial Sequence
<220> FEATURE:
<223> OTHER INFORMATION: poly (A)

<400> SEQUENCE: 13

```
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
```

LIPIDS AND LIPID COMPOSITIONS FOR THE DELIVERY OF ACTIVE AGENTS

RELATED APPLICATIONS

This application is the U.S. National Phase under 35 U.S.C. § 371 of International Patent Application No. PCT/US2014/070891, filed Dec. 17, 2014, which claims priority to and the benefit of U.S. Provisional Application Ser. No. 61/918,941, filed Dec. 20, 2013, and U.S. Provisional Application Ser. No. 61/918,182, filed Dec. 19, 2013. The entire disclosures of these applications are hereby incorporated by reference.

SEQUENCE LISTING

The instant application contains a Sequence Listing which has been submitted electronically in ASCII format and is hereby incorporated by reference in its entirety. Said ASCII copy, created on Jun. 14, 2016, is named PAT055894-US-PCT_ST25.txt and is 27 KB in size.

FIELD OF THE INVENTION

This invention relates to cationic lipid compounds and to compositions comprising such compounds. This invention also relates to processes for making such compounds and compositions, and to methods and uses of such compounds and compositions, e.g., to deliver biologically active agents, such as RNA agents, to cells and tissues.

BACKGROUND OF THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilize specific carrier molecules and carrier compositions which are allowed selective entry into the cell. Lipid carriers, biodegradable polymers and various conjugate systems can be used to improve delivery of biologically active agents to cells.

One class of biologically active agents that is particularly difficult to deliver to cells is a bio therapeutic (including nucleosides, nucleotides, polynucleotides, nucleic acids and derivatives, such as mRNA, RNAi, and self-replicating RNA agents). In general, nucleic acids are stable for only a limited duration in cells or plasma. The development of RNA interference, RNAi therapy, mRNA therapy, RNA drugs, antisense therapy, gene therapy, and nucleic acid vaccines (e.g., RNA vaccines), among others, has increased the need for an effective means of introducing active nucleic acid agents into cells. For these reasons, compositions that can stabilize and deliver nucleic acid-based agents into cells are of particular interest.

The most well-studied approaches for improving the transport of foreign nucleic acids into cells involve the use of viral vectors or formulations with cationic lipids. Viral vectors can be used to transfer genes efficiently into some cell types, but they generally cannot be used to introduce chemically synthesized molecules into cells.

An alternative approach is to use delivery compositions incorporating cationic lipids which interact with a biologically active agent at one part and interact with a membrane system at another part. Such compositions are reported to provide liposomes, miscelles, lipoplexes, or lipid nanoparticles, depending on the composition and method of preparation (for reviews, see Feigner, 1990, Advanced Drug Delivery Reviews, 5, 162-187; Feigner, 1993, J. Liposome Res., 3, 3-16; Gallas, 2013, Chem. Soc. Rev., 42, 7983-7997; Falsini, 2013, J. Med. Chem. dx.doi.org/10.1021/jm400791q; and references therein).

Since the first description of liposomes in 1965 by Bangham (J. Mol. Biol. 13, 238-252), there has been a sustained interest and effort in developing lipid-based carrier systems for the delivery of biologically active agents (Allen, 2013, Advanced Drug Delivery Reviews, 65, 36-48). The process of introducing functional nucleic acids into cultured cells by using positively charged liposomes was first described by Philip Feigner et al. *Proc. Natl. Acad. Sci.*, USA, 84, 7413-7417 (1987). The process was later demonstrated in vivo by K. L. Brigham et al., *Am. J. Med. Sci.*, 298, 278-281 (1989). More recently, lipid nanoparticle formulations have been developed with demonstrated efficacy in vitro and in vivo. (Falsini, 2013, J. Med. Chem. dx.doi.org/10.1021/jm400791q; Morrissey, 2005, Nat. Biotech., 23, 1002-1007; Zimmerman, 2006, Nature, 441, 111-114; Jayaraman, 2012, Angew. Chem. Int. Ed., 51, 8529-8533.) Lipid formulations are attractive carriers since they can protect biological molecules from degradation while improving their cellular uptake. Out of the various classes of lipid formulations, formulations which contain cationic lipids are commonly used for delivering polyanions (e.g. nucleic acids). Such formulations can be formed using cationic lipids alone and optionally including other lipids and amphiphiles such as phosphatidylethanolamine. It is well known in the art that both the composition of the lipid formulation as well as its method of preparation affect the structure and size of the resultant aggregate (Leung, 2012, J. Phys Chem. C, 116, 18440-18450).

The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, Trends Cell Bio., 2, 139; Xu et al., 1996, Biochemistry 35, 5616). Further, it is believed that the molecular shape, conformation, and properties of the cationic lipids provide enhanced delivery efficiency from endosomal compartments to the cytosol (Semple, 2010, Nat. Biotech, 28, 172-176; Zhang, 2011, 27, 9473-9483)

Although the use of cationic lipids for cellular delivery of biologically active agents has been shown to have several advantages, there still remains a need for further cationic lipids that facilitate the systemic and local delivery of biologically active agents such as mRNA and RNAi agents to cells. There is also a need for cationic lipids that, relative to those cationic lipids that are known in the art, improve the systemic and local delivery of biologically active agents to cells. There is a further need for lipid formulations that have optimized physical characteristics for improved systemic and local delivery of biologically active agents to specific organs and to tumors, especially tumors outside the liver.

In addition, there is a need for further cationic lipids that provide decreased toxicity (or improved therapeutic index), relative to those cationic lipids that are known in the art. Traditional cationic lipids have been employed for RNA and DNA delivery to the liver or tumors but suffer from nonoptimal delivery efficiency along with tissue and organ toxicity at higher doses. One method of reducing exposure and increasing biocompatability of cationic lipids is to incorporate chemically or biochemically degradable functionalities, (such as ester, amide, acetal, imine, etc.), which can lead to enhanced in vivo clearance (Maier, 2013, 21, 1570-1578).

SUMMARY OF THE INVENTION

The present invention provides a cationic lipid scaffold that demonstrates enhanced efficacy along with lower toxicity (improved therapeutic index) as a result of lower sustained lipid levels in the relevant tissues, and for local delivery applications (eye, ear, skin, lung); delivery to muscle (i.m.), fat, or sub cutaneous cells (s.c. dosing).

In one aspect, this invention provides for a compound of formula (I):

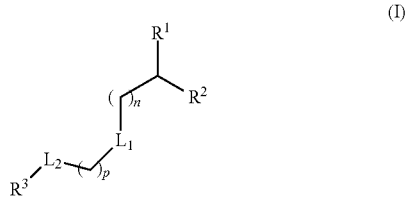

or a pharmaceutically acceptable salt thereof, wherein $R^1$-$R^3$, n, p, $L_1$ and $L_2$ are defined herein. The compounds of formula (I) and pharmaceutically acceptable salts thereof are cationic lipids useful in the delivery of biologically active agents to cells and tissues.

In a second aspect, this invention provides for a lipid composition comprising a compound according to formula (I) (i.e. a lipid composition of the invention), or a pharmaceutically acceptable salt thereof. In one embodiment, the lipid composition further comprises at least one other lipid component. In another embodiment, the lipid composition further comprises a biologically active agent, optionally in combination with on one more other lipid components. In another embodiment the lipid composition is in the form of a liposome. In another embodiment the lipid composition is in the form of a lipid nanoparticle (LNP). In another embodiment the lipid composition is suitable for delivery to the liver. In another embodiment the lipid composition is suitable for delivery to a tumor. In another embodiment the lipid composition is suitable for immunization purposes. In another embodiment the lipid composition is suitable for local delivery applications (eye, ear, skin, lung); delivery to muscle (i.m.), fat, or sub cutaneous cells (s.c. dosing).

In a third aspect, this invention provides for a pharmaceutical composition (i.e. formulation) comprising a lipid composition of the invention and a pharmaceutically acceptable carrier or excipient. In one embodiment, the pharmaceutical composition comprises at least one other lipid component in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is an RNA or DNA. In another embodiment the lipid composition is suitable for immunization purposes, and the biologically active agent is a RNA or DNA which encodes an immunogen.

In a fourth aspect, this invention provides a method for the treatment of a disease or condition comprising the step of administering a therapeutically effective amount of a lipid composition of the invention to a patient in need of treatment thereof. In one embodiment, the disease or condition is treatable by administering an RNA or DNA agent. In another embodiment the lipid composition is suitable for immunization purposes, and the biologically active agent is an RNA or DNA which encodes an immunogen.

In a fifth aspect, this invention provides for the use of a lipid composition of the invention in treating a disease or condition in a patient. In one embodiment, the disease or condition is treatable by administering an RNA or DNA agent.

In a sixth aspect, this invention provides a method for inducing an immune response in a subject against an immunogen of interest comprising administering an immunologically effective amount of a lipid composition of the invention to the subject, in combination with a RNA or DNA that encodes the immunogen.

In a seventh aspect, this invention provides for the use of a lipid composition of the invention in inducing an immune response in a subject against an immunogen of interest (e.g., in the preparation or manufacture of a medicament). The lipid is used in combination with a RNA which encodes an immunogen.

BRIEF DESCRIPTION OF THE DRAWINGS

The embodiments will be further described in connection with the attached figure. It is intended that the drawing included as part of the specification be illustrative of the embodiments and should in no way be considered as a limitation on the scope of the invention.

FIG. 1 shows a synthetic scheme, Scheme 1, which illustrates a preparation of final compounds of formula (I).

DETAILED DESCRIPTION OF THE INVENTION

In a first embodiment, the invention is a compound, or salt thereof, of formula (I) (a "lipid provided by the invention"):

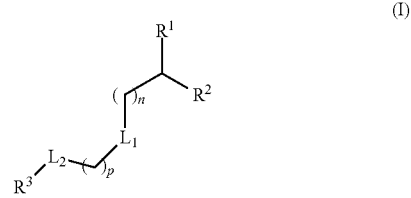

Wherein n is 0, 1, 2, 3 or 4; p is 0, 1, 2, 3, 4, 5, 6, 7 or 8; $L_1$ is —O— or a bond; $L_2$ is —OC(O)— or —C(O)O—; $R^1$ is selected from:

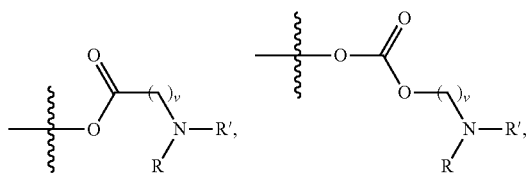

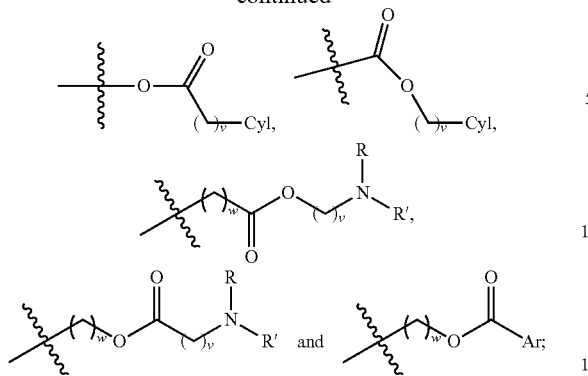

v is 0, 1, 2, 3 or 4; w is 0, 1, 2, or 3; Cyl is 5-7 membered nitrogen containing heterocycle optionally substituted with one or two alkyl groups; Ar is an aryl group, optionally substituted with $C_{1-8}$ alkly amino group; R and R' are each, independently, hydrogen or $C_{1-8}$ is alkyl; and $R^2$ is selected from $C_{6-20}$ alkyl optionally substituted with a hydroxyl, $C_{15-19}$ alkenyl, $C_{1-12}$alkyl-OC(O)—$C_{5-20}$alkyl, $C_{1-12}$alkyl-C(O)O—$C_{5-20}$alkyl and

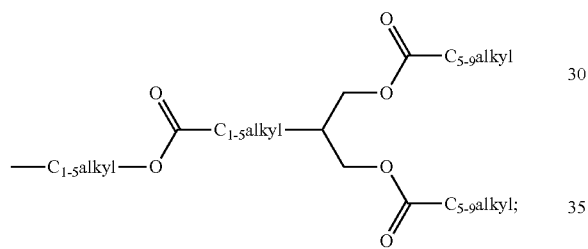

$R^3$ is selected from: $C_{4-22}$ alkyl, $C_{12-22}$ alkenyl,

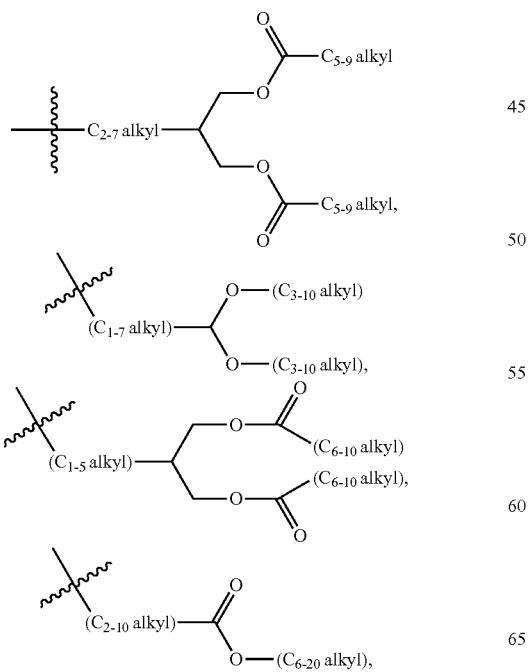

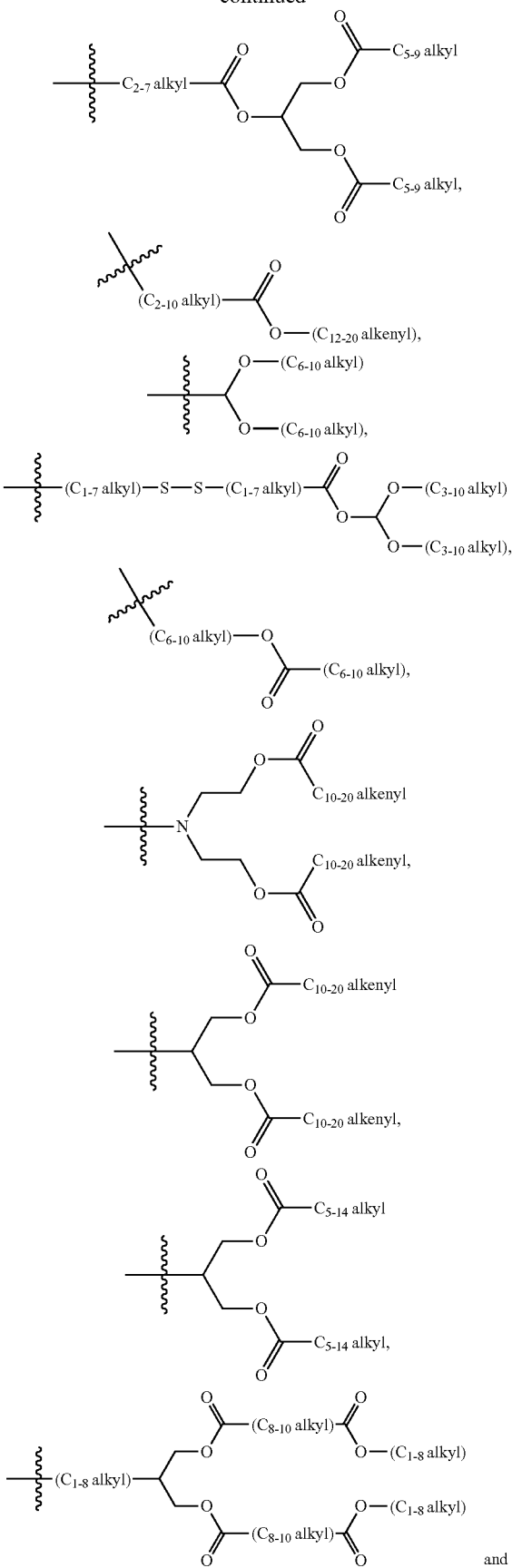

and

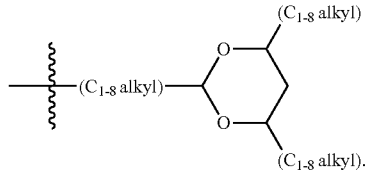

In a second embodiment, the invention is a compound, or salt thereof, according to the first embodiment, wherein the compound is of formula (I):

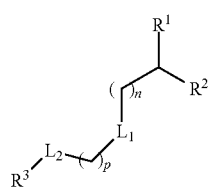

n is 0, 1, 2, 3 or 4; p is 0, 1, 2, 3, 4, 5, 6, 7 or 8; $L_1$ is —O— or a bond; $L_2$ is —OC(O)— or —C(O)O—; $R^1$ is selected from:

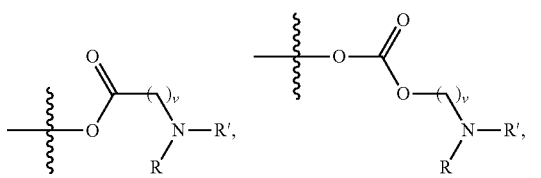

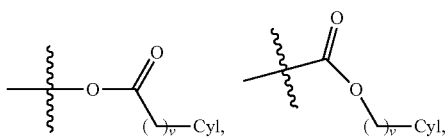

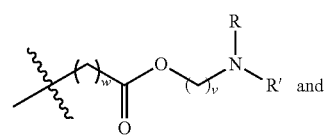

v is 0, 1, 2, 3 or 4; w is 0, 1, 2, or 3; Cyl is 5-7 membered nitrogen containing heterocycle optionally substituted with one or two alkyl groups; R and R' are each, independently, hydrogen or $C_{1-8}$ alkyl; and $R^2$ is selected from $C_{6-20}$ alkyl optionally substituted with a hydroxyl, $C_{15-19}$ alkenyl, $C_{1-12}$alkyl-OC(O)—$C_{5-20}$alkyl, $C_{1-12}$alkyl-C(O)O—$C_{5-20}$ alkyl and

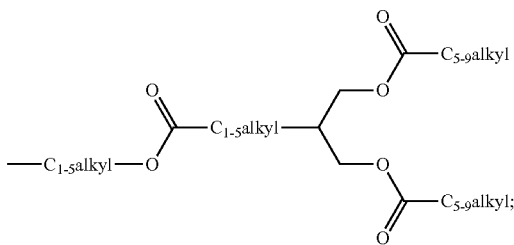

$R^3$ is selected from: $C_{4-22}$ alkyl, $C_{12-22}$ alkenyl,

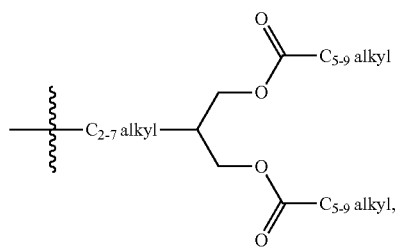

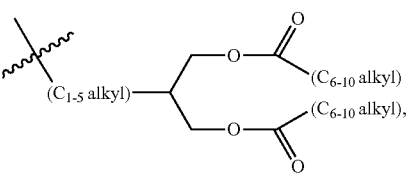

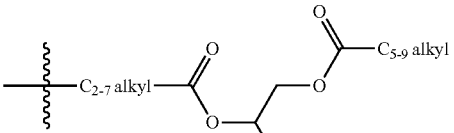

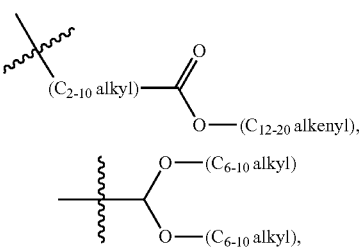

-continued

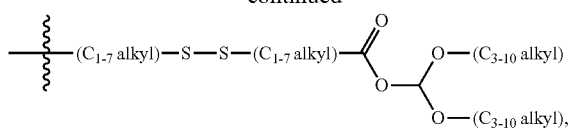

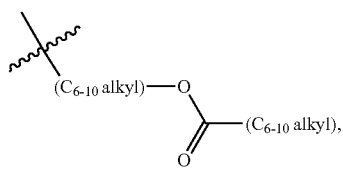

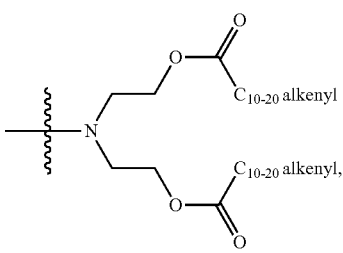

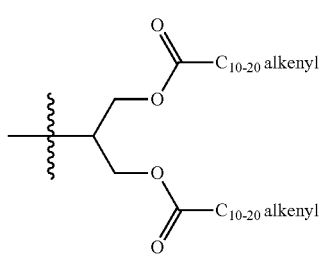

and

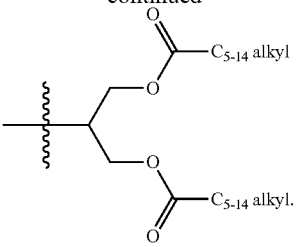

In a third embodiment, the inventiob is the compound, or salt thereof, according to the first or osecond embodiments, wherein the compound is of formula (II):

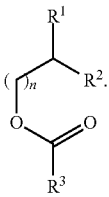

(II)

In a fourth embodiment, the invention is the compound, or salt thereof, according to any one of the first through third embodiments, wherein the compound is of formula (III):

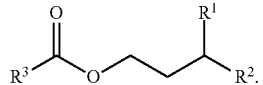

(III)

In a fifth embodiment, the invention is the compound, or salt thereof, according to any one of the first through fourth embodiments, wherein $R^2$ is selected from:

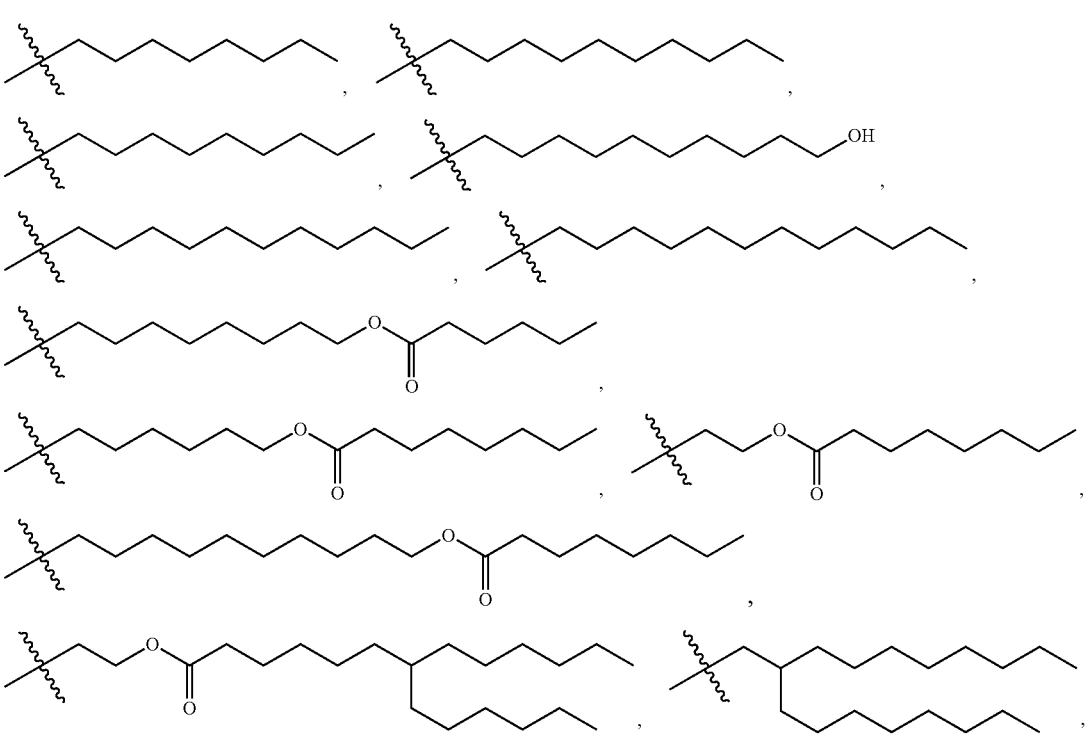

-continued
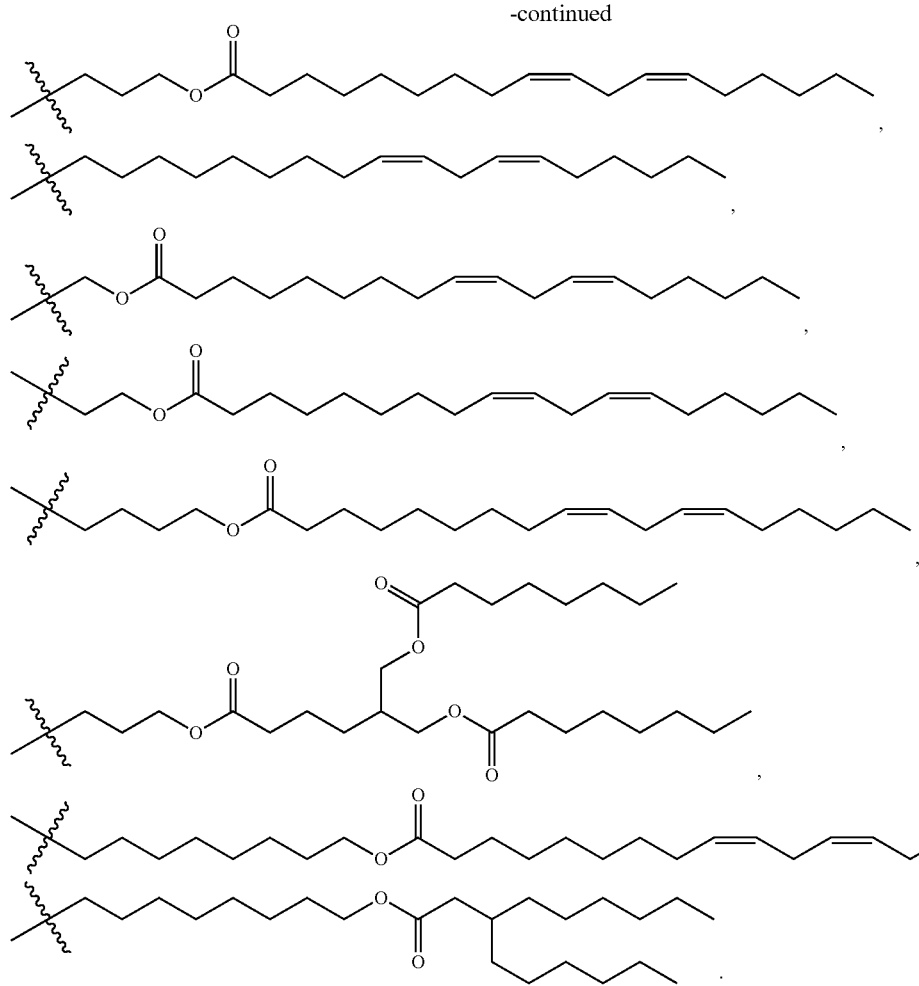
In a sixth embodiment, the invention is the compound, or salt thereof, according to any one of the first through fifth embodiments, wherein $R^2$ is selected from:
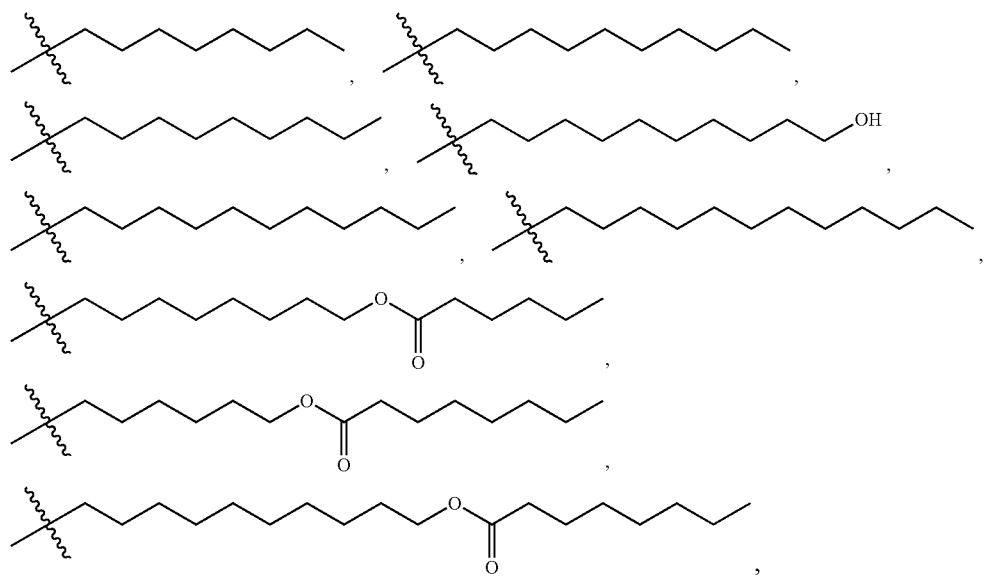

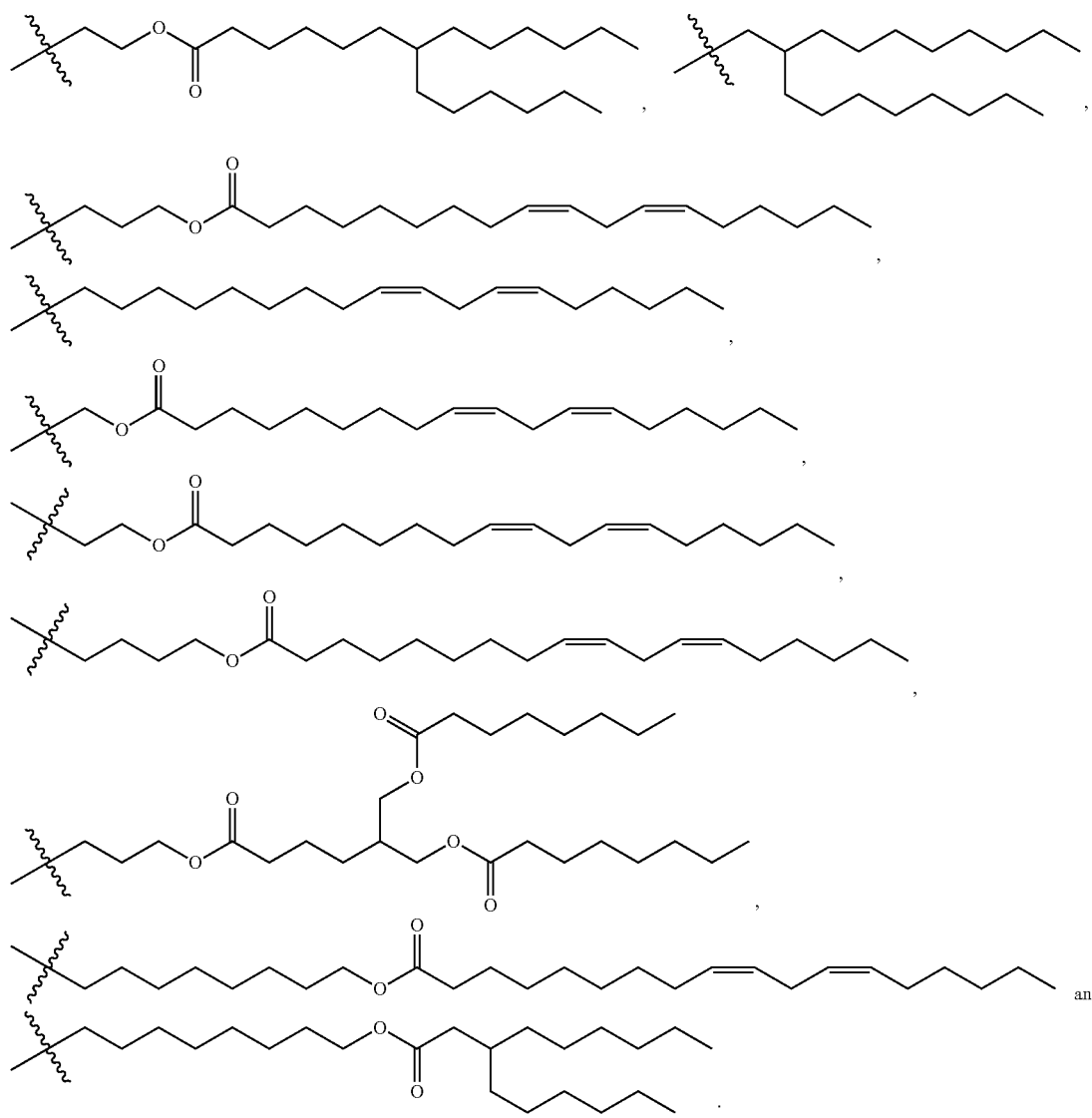

In a seventh embodiment, the invention is the compound, or salt thereof, according to any one of the first through sixth embodiments, wherein $R^2$ is

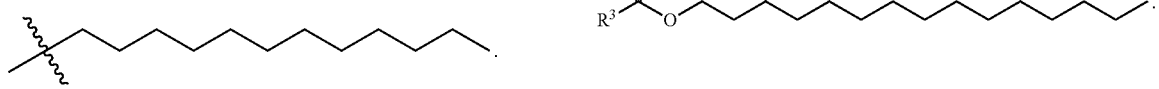

In an eighth embodiment, the invention is the compound, or salt thereof, of any one of the first through seventh embodiments, wherein the compound is of formula (IV):

$$\text{(IV)}$$

[Structure of formula (IV) showing $R^3$-C(=O)-O-CH$_2$-CH$_2$-CH($R^1$)-(CH$_2$)$_{10}$-CH$_3$]

In a ninth embodiment, the invention is the compound, or salt thereof, according to any one of the first through eighth embodiments, wherein $R^3$ is selected from:

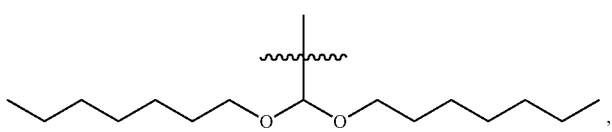

-continued
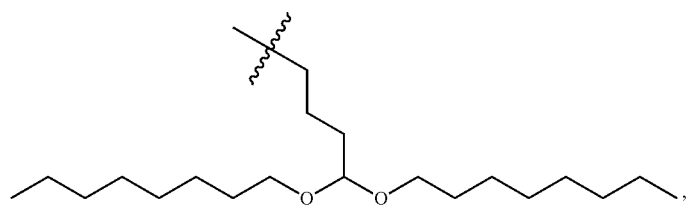,
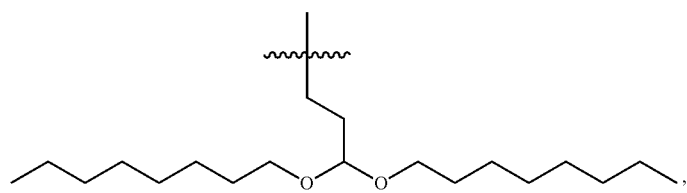,
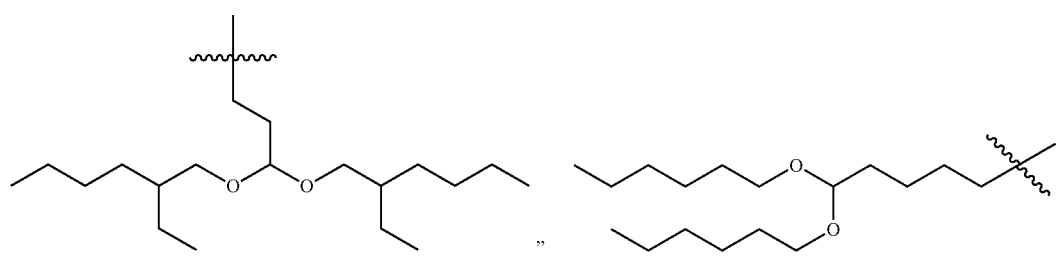,
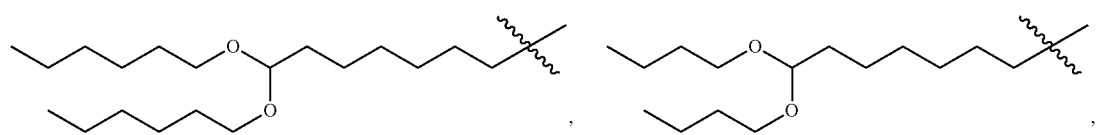,
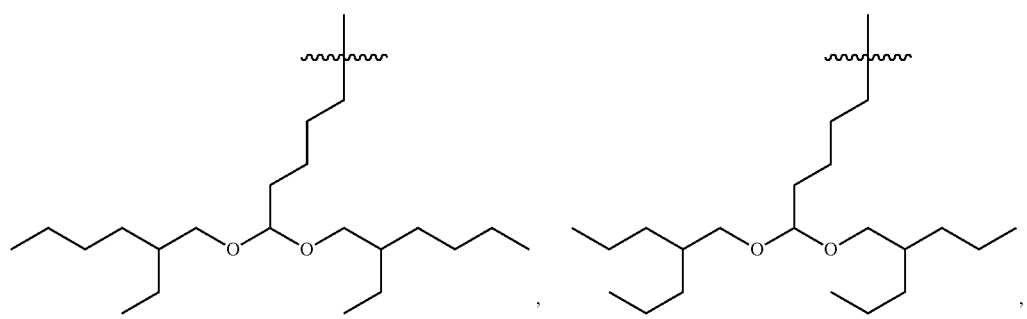,
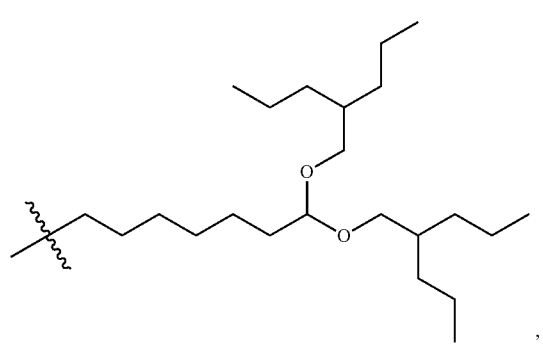,

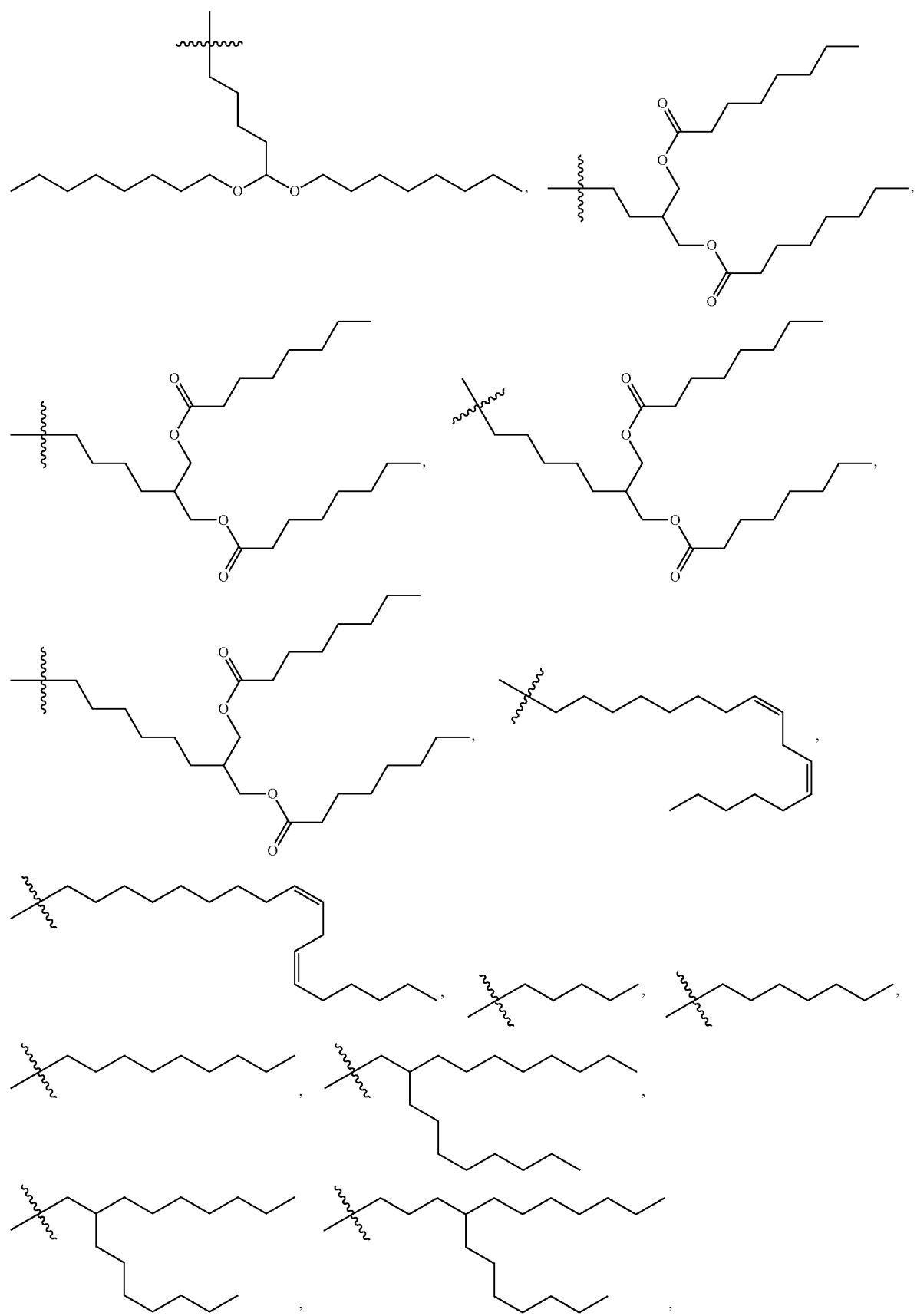

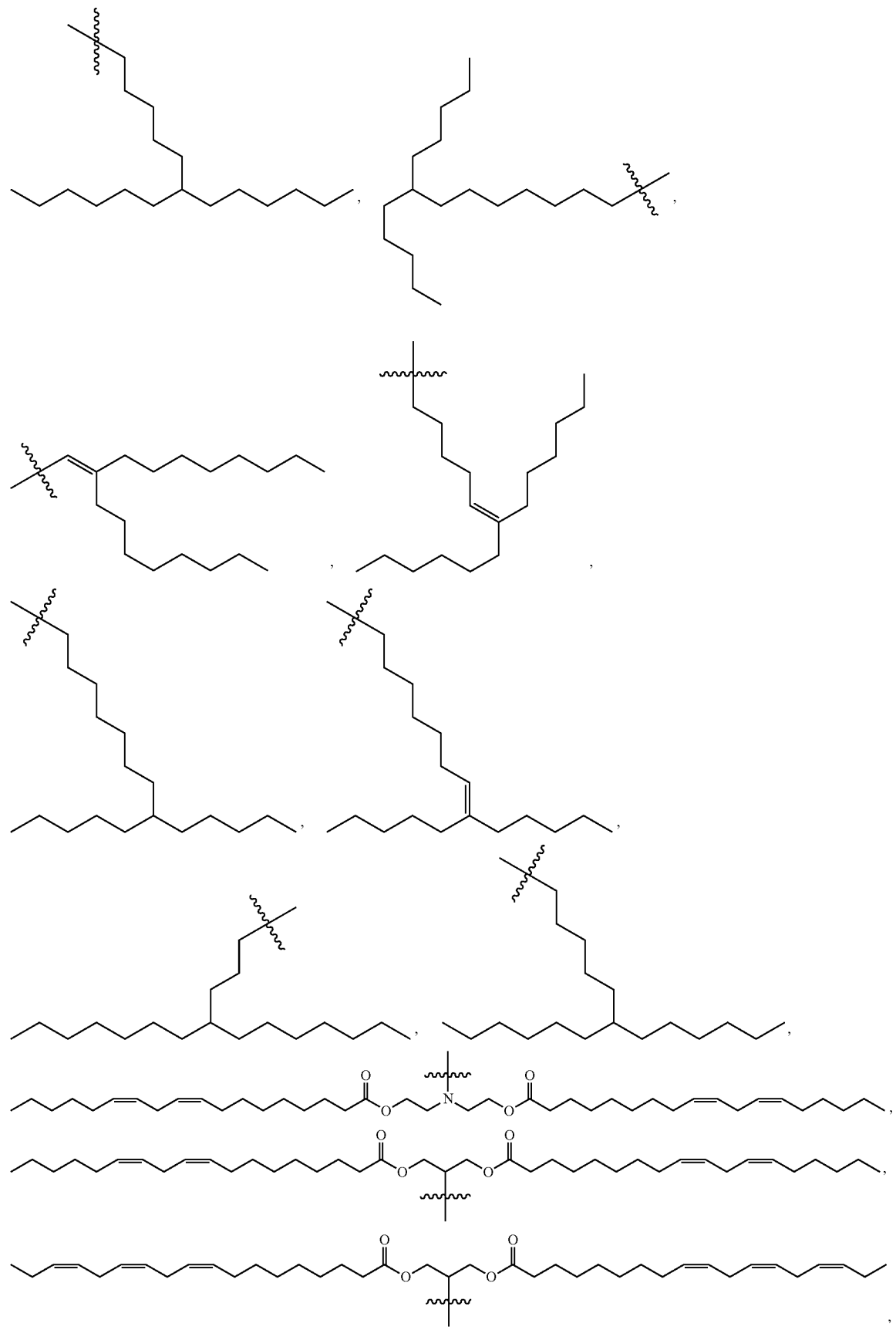

-continued
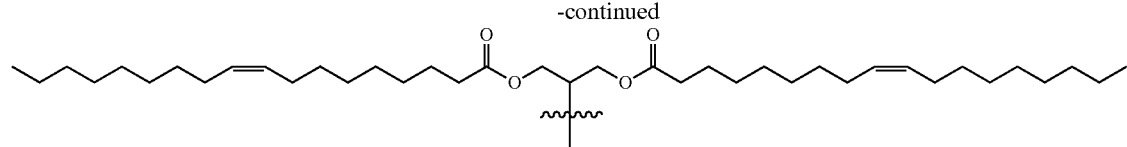
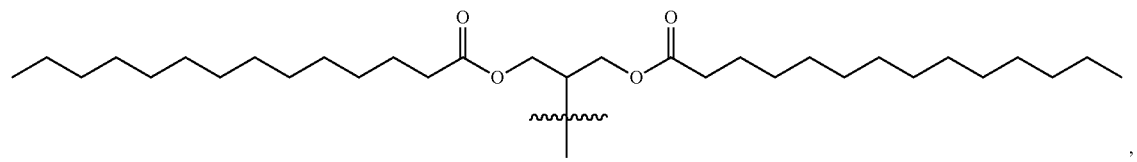
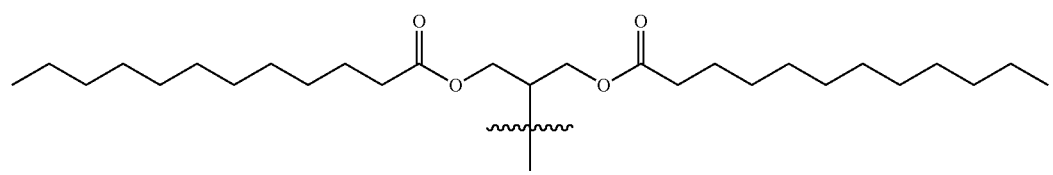
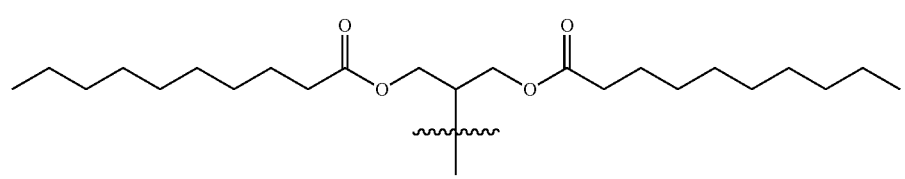
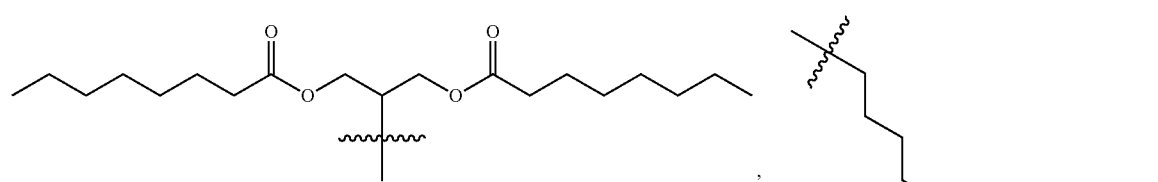
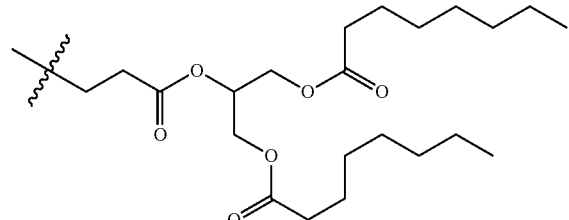
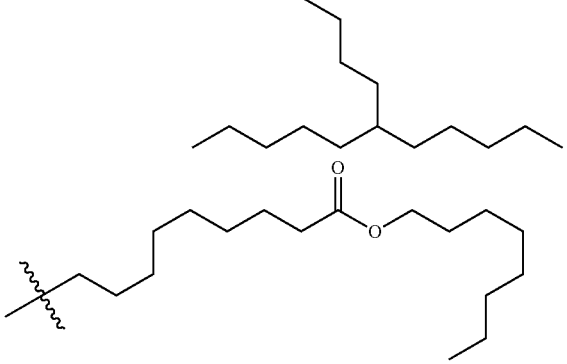
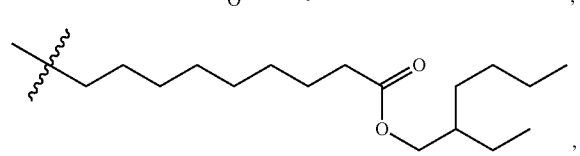
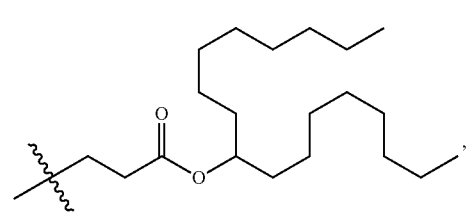
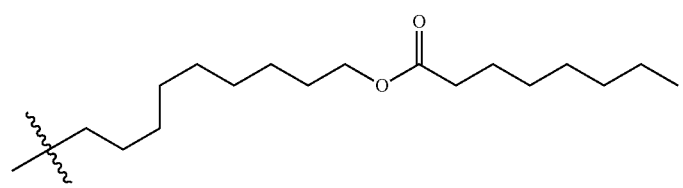

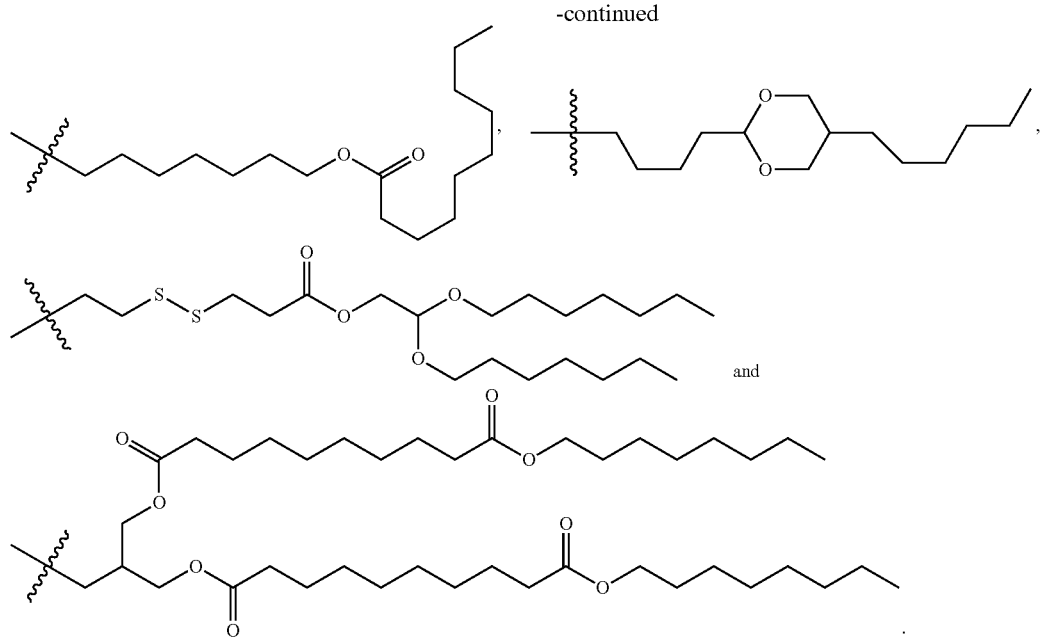
In a tenth embodiment, the invention is the compound, or salt thereof, according to any one of the first through ninth embodiments, wherein $R^3$ is selected from:
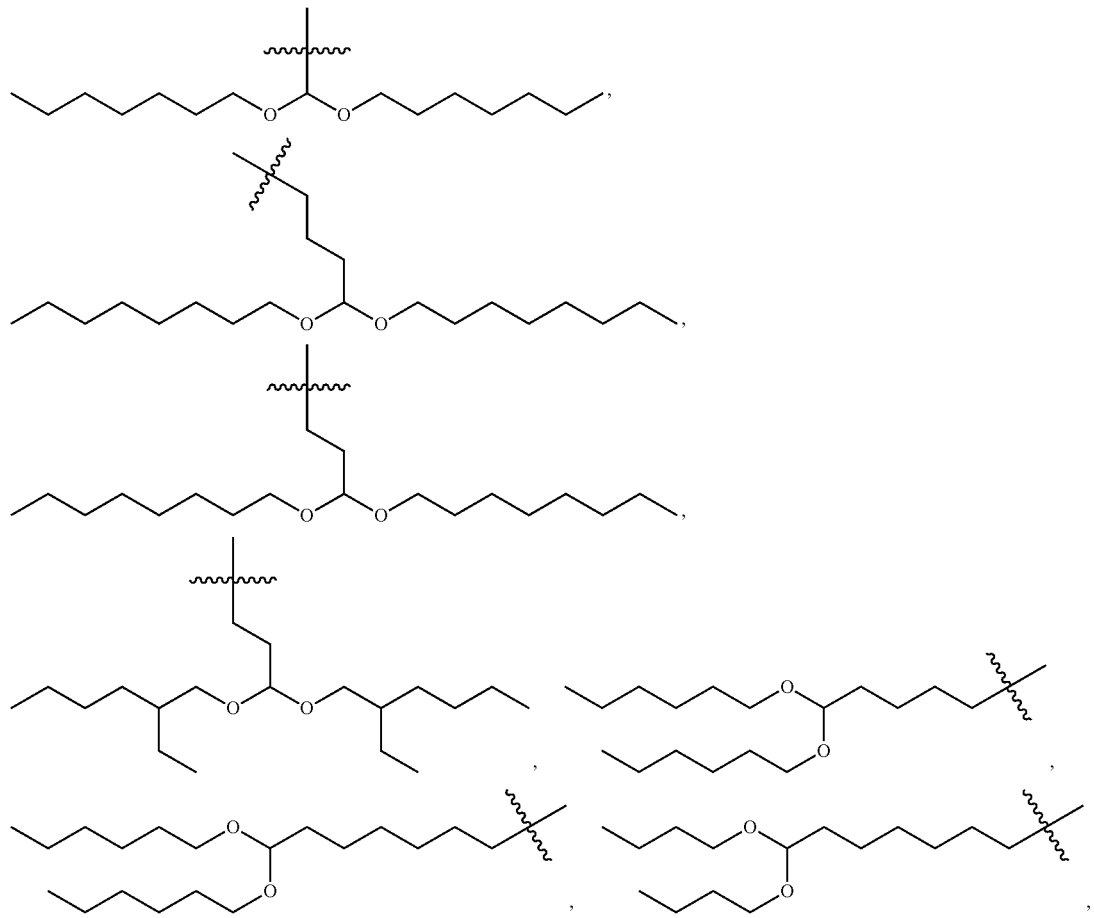

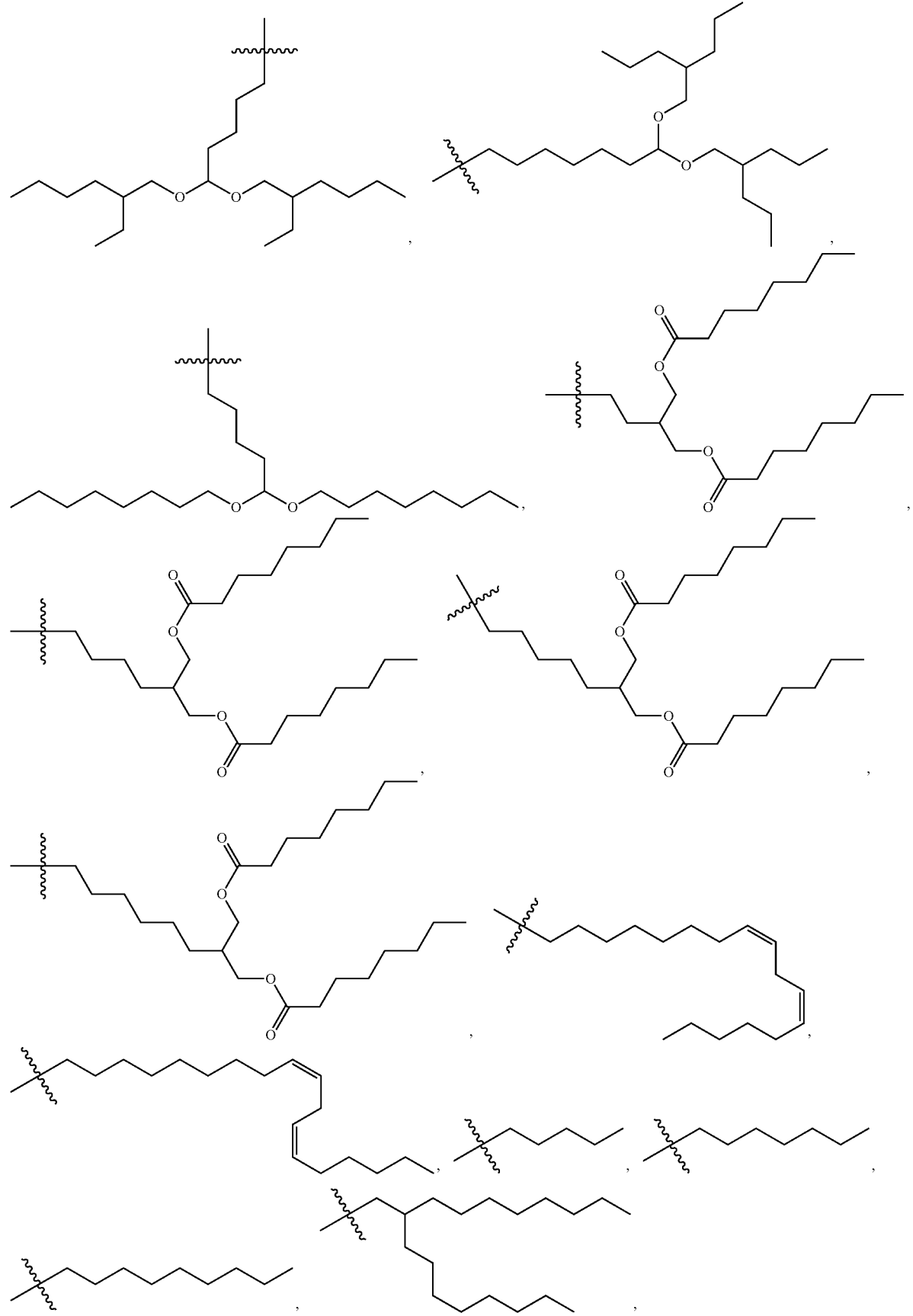

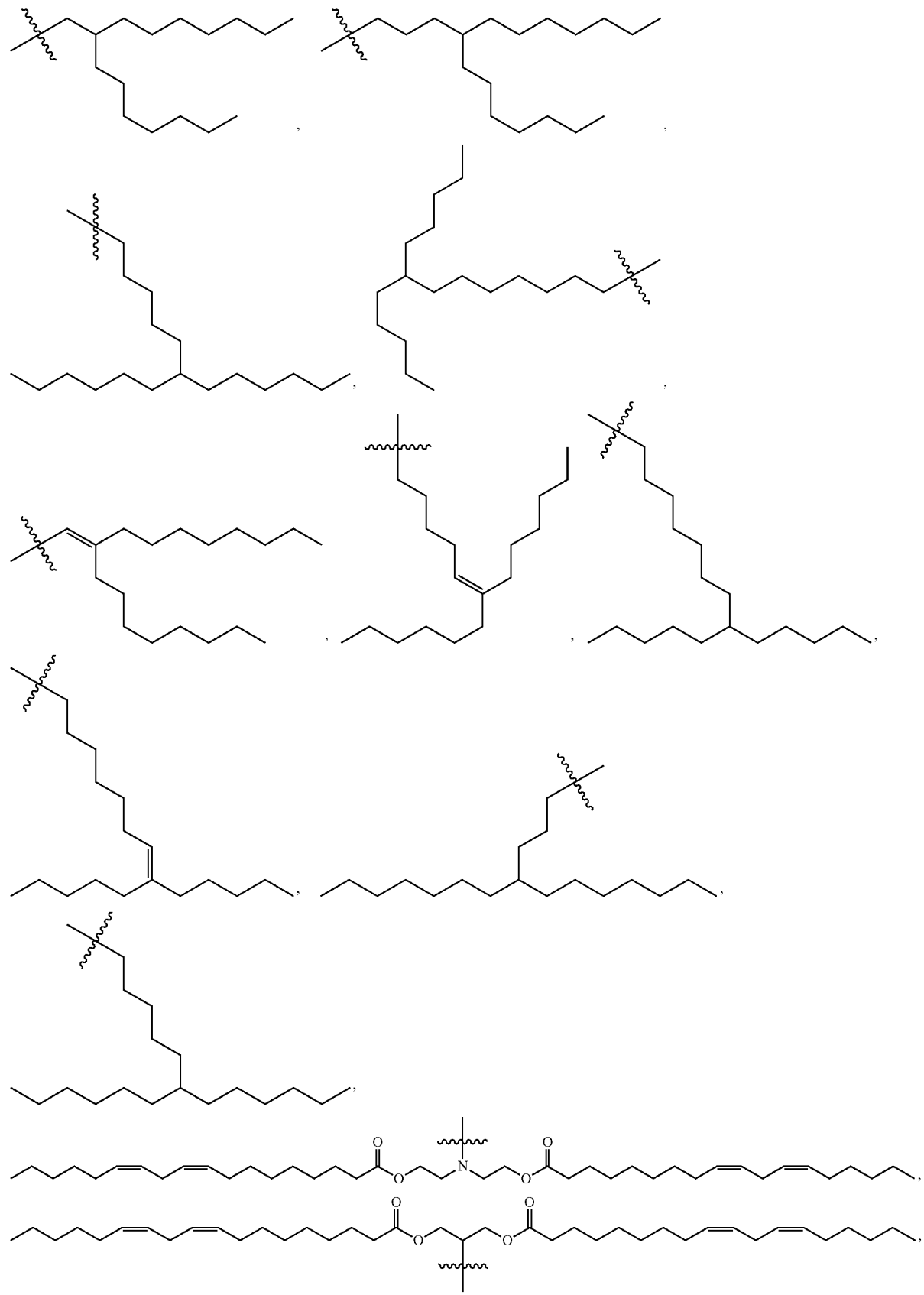

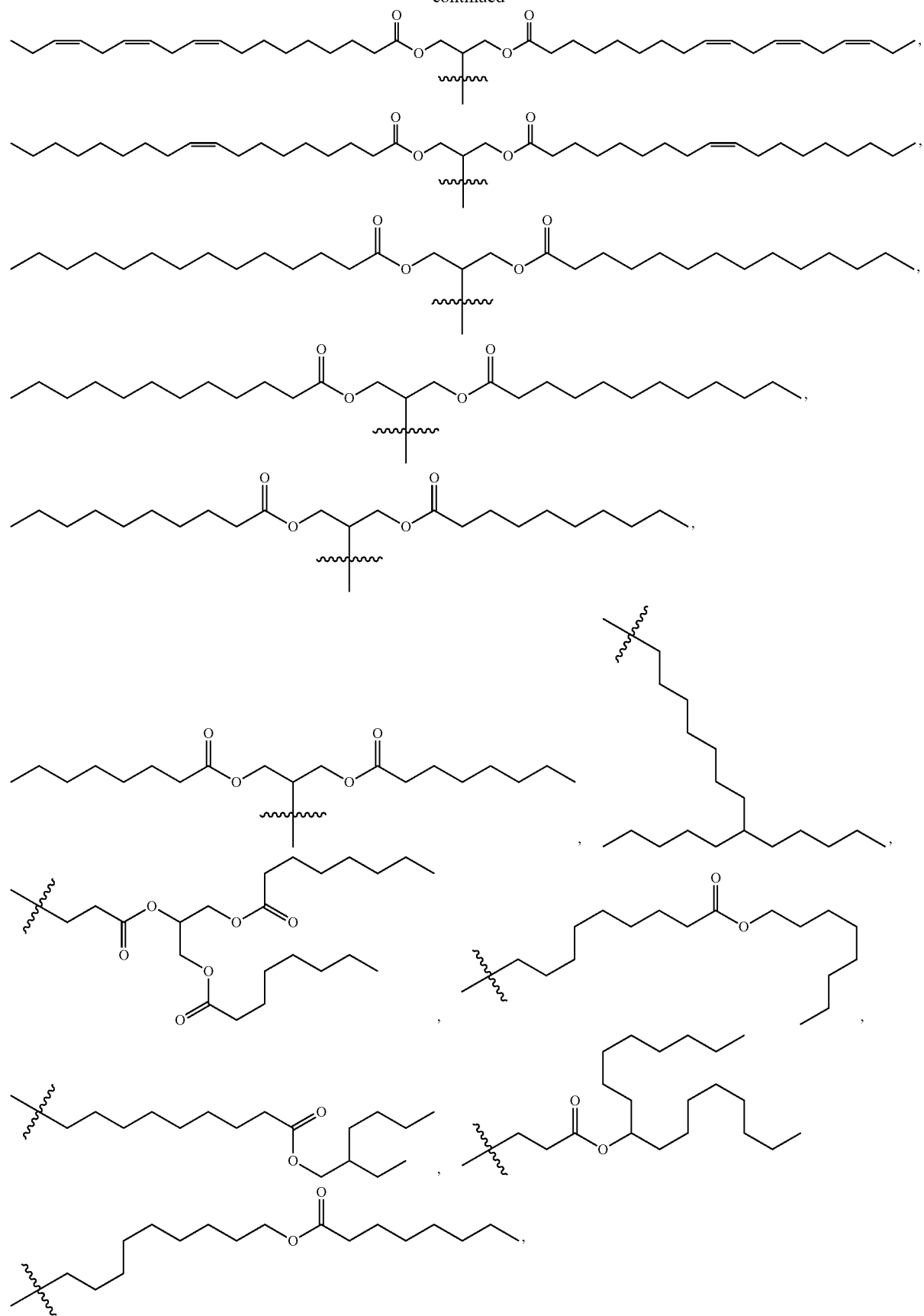

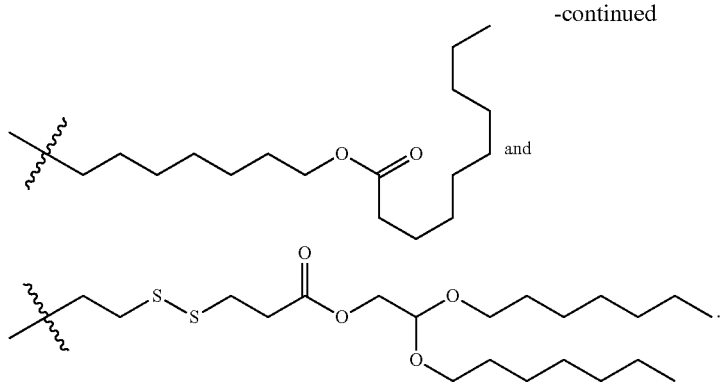

In an eleventh embodiment, the invention is the compound, or salt thereof, according to any one of the first through tenth embodiments, wherein $R^3$ is

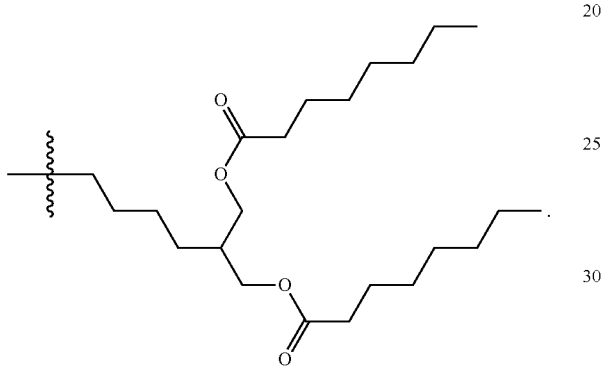

In a twelfth embodiment, the invention is the compound, or salt thereof, according to any one of the first through eleventh embodiments, wherein the compound is of formula (V):

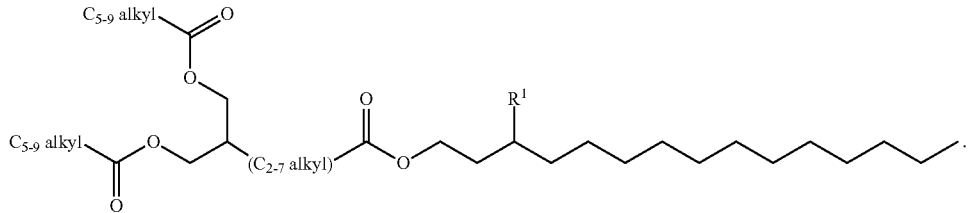

In a thirteenth embodiment, the invention is the compound, or salt thereof, according to any one of the first through twelfth embodiments, wherein the compound is of formula (VI):

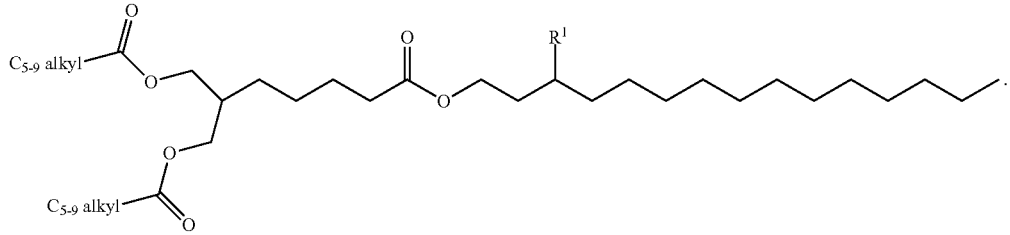

In a fourteenth embodiment, the invention is the compound, or salt thereof, according to any one of the first through thirteenth embodiments, wherein the compound is of formula (VII):

(VII)
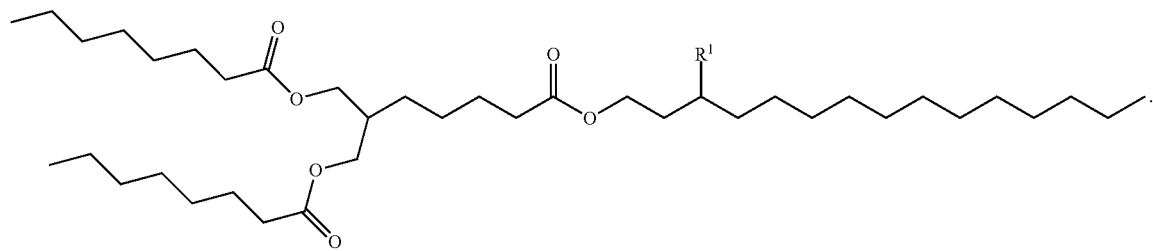
In a fifteenth embodiment, the invention is the compound, or salt thereof, of any one of the first through fourteenth embodiments, wherein $R^1$ is selected from:
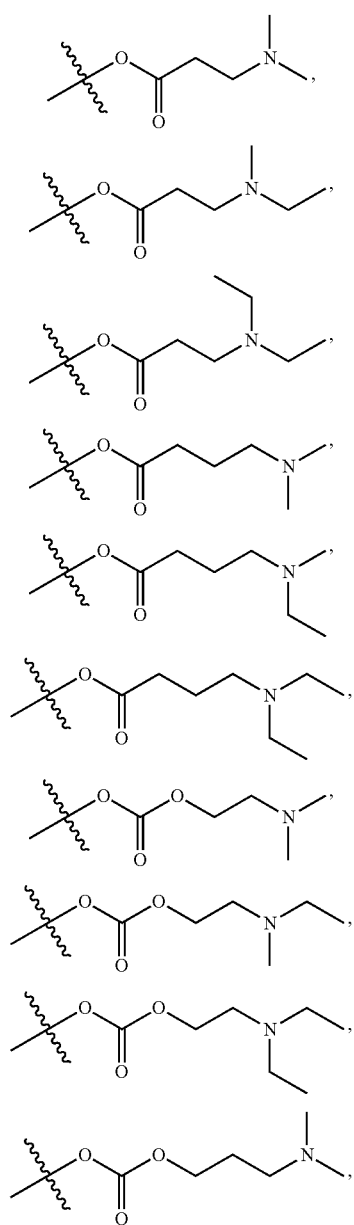
-continued
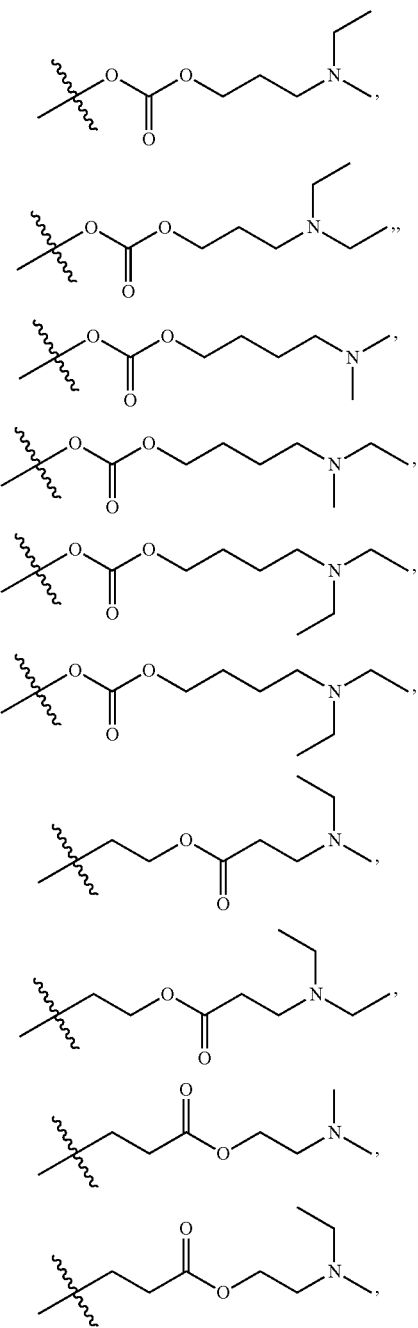

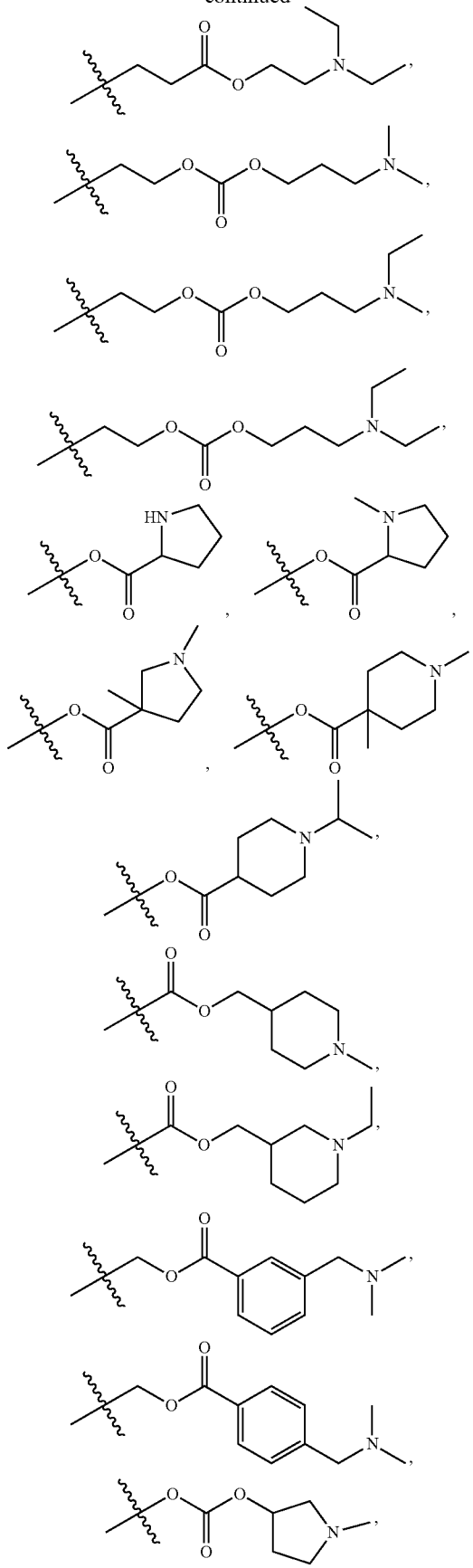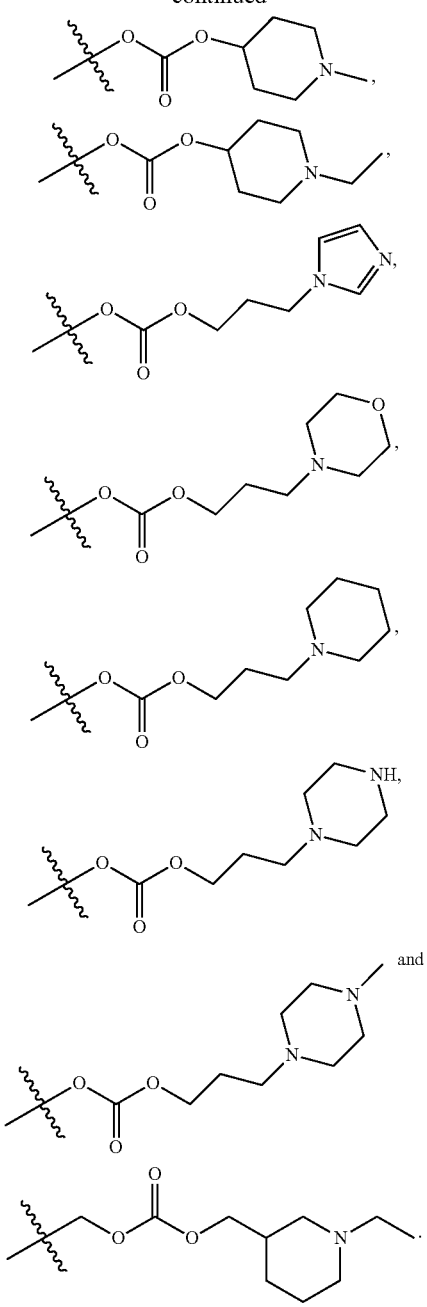
In a sixteenth embodiment, the invention is the compound, or salt thereof, of any one of of the first through fifteenth embodiments, wherein $R^1$ is selected from:
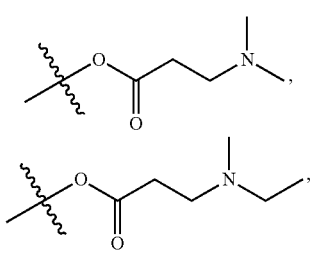

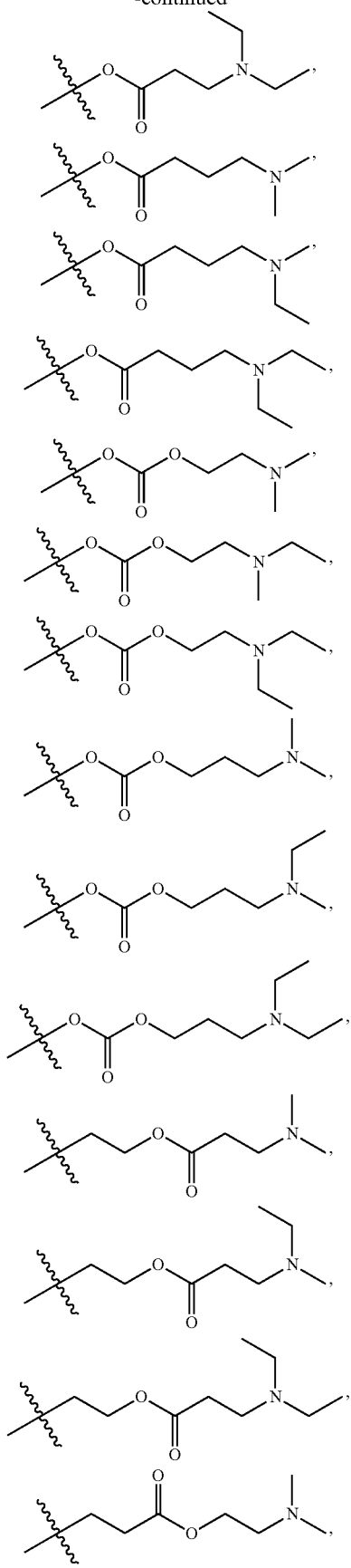

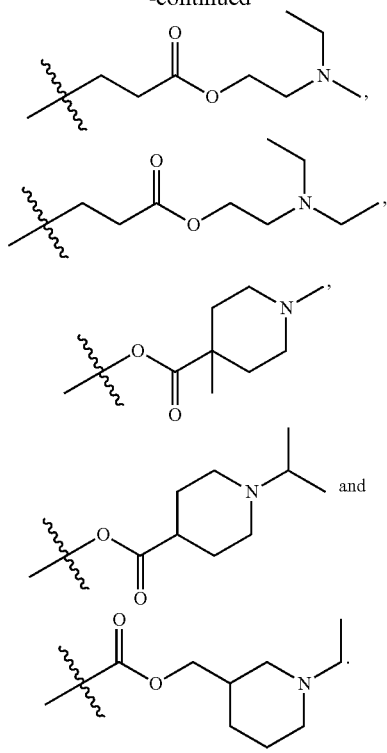

In a seventeenth embodiment, the invention is the compound, or salt thereof, of any one of the first through sixteenth embodiments, wherein R¹ is

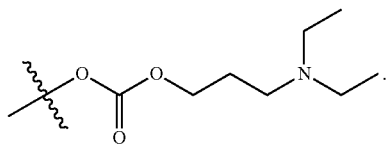 [SMILES: *OC(=O)OCCCN(CC)CC]

In an eighteenth embodiment, the invention is the compound, or salt thereof, according to any one of the first through seventeenth embodiments, wherein the compound is selected from:
2-(10-dodecyl-3-ethyl-8,14-dioxo-7,9,13-trioxa-3-azaoctadecan-18-yl)propane-1,3-diyl dioctanoate;
2-(9-dodecyl-2-methyl-7,13-dioxo-6,8,12-trioxa-2-azaheptadecan-17-yl)propane-1,3-diyl dioctanoate;
2-(9-dodecyl-2-methyl-7,13-dioxo-6,8,12-trioxa-2-azapentadecan-15-yl)propane-1,3-diyl dioctanoate;
2-(10-dodecyl-3-ethyl-8,14-dioxo-7,9,13-trioxa-3-azahexadecan-16-yl)propane-1,3-diyl dioctanoate;
2-(8-dodecyl-2-methyl-6,12-dioxo-5,7,1-trioxa-2-azaheptadecan-17-yl)propane-1,3-diyl dioctanoate;
2-(10-dodecyl-3-ethyl-8,14-dioxo-7,9,13-trioxa-3-azanonadecan-19-yl)propane-1,3-diyl dioctanoate;
2-(9-dodecyl-2-methyl-7,13-dioxo-6,8,12-trioxa-2-azaoctadecan-18-yl)propane-1,3-diyl dioctanoate;
2-(8-dodecyl-2-methyl-6,12-dioxo-5,7,1-trioxa-2-azaoctadecan-18-yl)propane-1,3-diyl dioctanoate;
2-(10-dodecyl-3-ethyl-8,14-dioxo-7,9,13-trioxa-3-aza-icosan-20-yl)propane-1,3-diyl dioctanoate;
2-(9-dodecyl-2-methyl-7,13-dioxo-6,8,12-trioxa-2-azanonadecan-19-yl)propane-1,3-diyl dioctanoate;

3-(((3-(diethylamino)propoxy)carbonyl)oxy)pentadecyl 4,4-bis(octyloxy)butanoate;
3-(((3-(diethylamino)propoxy)carbonyl)oxy)pentadecyl 4,4-bis((2-ethylhexyl)oxy)butanoate;
3-(((3-(diethylamino) propoxy)carbonyl)oxy)pentadecyl 4,4-bis((2-propylpentyl)oxy)butanoate;
3-(((3-(ethyl(methyl)amino)propoxy)carbonyl)oxy)pentadecyl 4,4-bis((2-propylpentyl)oxy)butanoate;
3-(((3-(dimethylamino)propoxy)carbonyl)oxy)pentadecyl 4,4-bis((2-propylpentyl)oxy)butanoate;
3-(((3-(diethylamino)propoxy)carbonyl)oxy)pentadecyl 6,6-bis(octyloxy)hexanoate;
3-(((3-(diethylamino)propoxy)carbonyl)oxy)pentadecyl 6,6-bis(hexyloxy)hexanoate;
3-(((3-(diethylamino) propoxy)carbonyl)oxy)pentadecyl 6,6-bis((2-ethylhexyl)oxy)hexanoate;
3-(((3-(diethylamino)propoxy)carbonyl)oxy)pentadecyl 8,8-bis(hexyloxy)octanoate;
3-(((3-(diethylamino) propoxy)carbonyl)oxy)pentadecyl 8,8-dibutoxyoctanoate;
3-(((3-(diethylamino)propoxy)carbonyl)oxy)pentadecyl 8,8-bis((2-propylpentyl)oxy)octanoate;
3-(((3-(ethyl(methyl)amino)propoxy)carbonyl)oxy)pentadecyl 8,8-bis((2-propylpentyl)oxy)octanoate;
3-(((3-(dimethylamino)propoxy)carbonyl)oxy)pentadecyl 8,8-bis((2-propylpentyl)oxy)octanoate;
3-(((3-(dimethylamino) propoxy)carbonyl)oxy)pentadecyl 3-octylundecanoate;
3-(((3-(dimethylamino)propoxy)carbonyl)oxy)pentadecyl 3-octylundec-2-enoate;
3-(((3-(dimethylamino)propoxy)carbonyl)oxy)pentadecyl 7-hexyltridec-6-enoate;
3-(((3-(dimethylamino)propoxy)carbonyl)oxy)pentadecyl 9-pentyltetradecanoate;
3-(((3-(dimethylamino) propoxy)carbonyl)oxy)pentadecyl 9-pentyltetradec-8-enoate;
3-(((3-(dimethylamino)propoxy)carbonyl)oxy)pentadecyl 5-heptyldodecanoate;
3-(((3-(dimethylamino) propoxy)carbonyl)oxy)tridecyl 5-heptyldodecanoate;
3-(((3-(dimethylamino)propoxy)carbonyl)oxy)undecyl 5-heptyldodecanoate;
1,3-bis(octanoyloxy)propan-2-yl (3-(((2-(dimethylamino)ethoxy)carbonyl)oxy)pentadecyl) succinate;
1,3-bis(octanoyloxy)propan-2-yl (3-(((3-(dimethylamino)propoxy)carbonyl)oxy)pentadecyl) succinate;
1-(3-(((3-(dimethylamino)propoxy)carbonyl)oxy)pentadecyl) 10-octyl decanedioate;
1-(3-(((3-(diethylamino)propoxy)carbonyl)oxy)pentadecyl) 10-octyl decanedioate;
1-(3-(((3-(ethyl(methyl)amino)propoxy)carbonyl)oxy)pentadecyl) 10-octyl decanedioate;
1-(3-(((3-(diethylamino)propoxy)carbonyl)oxy)pentadecyl) 10-(2-ethylhexyl) decanedioate;
1-(3-(((3-(ethyl(methyl)amino)propoxy)carbonyl)oxy)pentadecyl) 10-(2-ethylhexyl) decanedioate;
3-(((3-(dimethylamino)propoxy)carbonyl)oxy)pentadecyl 10-(octanoyloxy)decanoate;
8-dodecyl-2-methyl-6,12-dioxo-5,7,11-trioxa-2-azanonadecan-19-yl decanoate;
3-(((3-(diethylamino)propoxy)carbonyl)oxy)pentadecyl 10-(octanoyloxy)decanoate;
3-(((3-(ethyl(methyl)amino)propoxy)carbonyl)oxy)pentadecyl 10-(octanoyloxy)decanoate;
(9Z,12Z)-3-(((3-(diethylamino)propoxy)carbonyl)oxy)pentadecyl octadeca-9,12-dienoate;
(9Z,12Z)-3-(((3-(diethylamino)propoxy)carbonyl)oxy)pentadecyl octadeca-9,12-dienoate;
(9Z,12Z)-3-(((3-(ethyl(methyl)amino)propoxy)carbonyl)oxy)pentadecyl octadeca-9,12-dienoate;
(9Z,12Z)-3-(((2-(dimethylamino)ethoxy)carbonyl)oxy)pentadecyl octadeca-9,12-dienoate;
1-((9Z,12Z)-octadeca-9,12-dienoyloxy)pentadecan-3-yl 1,4-dimethylpiperidine-4-carboxylate;
2-(((3-(diethylamino)propoxy)carbonyl)oxy)tetradecyl 4,4-bis((2-ethylhexyl)oxy)butanoate;
(9Z,12Z)-(12Z,15Z)-3-((3-(dimethylamino)propanoyl)oxy)henicosa-12,15-dien-1-yl octadeca-9,12-dienoate;
(12Z,15Z)-3-((4-(dimethylamino)butanoyl)oxy)henicosa-12,15-dien-1-yl 3-octylundecanoate;
(12Z,15Z)-3-((4-(dimethylamino)butanoyl)oxy)henicosa-12,15-dien-1-yl 5-heptyldodecanoate;
(12Z,15Z)-3-((4-(dimethylamino)butanoyl)oxy)henicosa-12,15-dien-1-yl 7-hexyltridecanoate;
(12Z,15Z)-3-((4-(dimethylamino)butanoyl)oxy)henicosa-12,15-dien-1-yl 9-pentyltetradecanoate;
(12Z,15Z)-1-((((9Z,12Z)-octadeca-9,12-dien-1-yloxy)carbonyl)oxy)henicosa-12,15-dien-3-yl 3-(dimethylamino)propanoate;
(13Z,16Z)-4-(((2-(dimethylamino)ethoxy)carbonyl)oxy)docosa-13,16-dien-1-yl 2,2-bis(heptyloxy)acetate;
(13Z,16Z)-4-(((3-(diethylamino)propoxy)carbonyl)oxy)docosa-13,16-dien-1-yl 2,2-bis(heptyloxy)acetate;
2,2-bis(heptyloxy)ethyl 3-((3-ethyl-10-((9Z,12Z)-octadeca-9,12-dien-1-yl)-8,15-dioxo-7,9,14-trioxa-3-azaheptadecan-17-yl)disulfanyl)propanoate;
(13Z,16Z)-4-(((3-(dimethylamino)propoxy)carbonyl)oxy)docosa-13,16-dien-1-yl heptadecan-9-yl succinate;
(9Z,12Z)-2-(((11Z,14Z)-2-((3-(dimethylamino)propanoyl)oxy)icosa-11,14-dien-1-yl)oxy)ethyl octadeca-9,12-dienoate;
(9Z,12Z)-3-(((3-(dimethylamino)propoxy)carbonyl)oxy)-13-(octanoyloxy)tridecyl octadeca-9,12-dienoate;
3-(((3-(dimethylamino)propoxy)carbonyl)oxy)-13-(octanoyloxy)tridecyl 3-octylundecanoate;
3-(((3-(dimethylamino)propoxy)carbonyl)oxy)-13-hydroxytridecyl 5-heptyldodecanoate;
3-(((3-(dimethylamino)propoxy)carbonyl)oxy)-13-(octanoyloxy)tridecyl 5-heptyldodecanoate;
3-(((3-(dimethylamino)propoxy)carbonyl)oxy)-13-(octanoyloxy)tridecyl 7-hexyltridecanoate;
3-(((3-(dimethylamino)propoxy)carbonyl)oxy)-13-hydroxytridecyl 9-pentyltetradecanoate;
3-(((3-(dimethylamino)propoxy)carbonyl)oxy)-13-(octanoyloxy)tridecyl 9-pentyltetradecanoate;
1-(3-(((3-(dimethylamino)propoxy)carbonyl)oxy)-13-(octanoyloxy)tridecyl) 10-octyl decanedioate;
3-(((3-(dimethylamino)propoxy)carbonyl)oxy)-13-(octanoyloxy)tridecyl 10-(octanoyloxy)decanoate;
(9Z,12Z)-3-(((3-(dimethylamino)propoxy)carbonyl)oxy)-5-octyltridecyl octadeca-9,12-dienoate;
3-(((3-(dimethylamino)propoxy)carbonyl)oxy)-5-octyltridecyl decanoate;
5-(((3-(dimethylamino)propoxy)carbonyl)oxy)-7-octylpentadecyl octanoate;
(9Z,12Z)-5-(((3-(dimethylamino)propoxy)carbonyl)oxy)-7-octylpentadecyl octadeca-9,12-dienoate;
9-(((3-(dimethylamino)propoxy)carbonyl)oxy)-1-octylnonadecyl octanoate;
9-(((3-(dimethylamino)propoxy)carbonyl)oxy)-11-octylnonadecyl decanoate;
(9Z,12Z)-9-(((3-(dimethylamino)propoxy)carbonyl)oxy)nonadecyl octadeca-9,12-dienoate;

9-(((3-(dimethylamino)propoxy)carbonyl)oxy)nonadecyl hexanoate;
9-(((3-(dimethylamino)propoxy)carbonyl)oxy)nonadecyl 3-octylundecanoate;
9-((4-(dimethylamino)butanoyl)oxy)nonadecyl hexanoate;
9-((4-(dimethylamino)butanoyl)oxy)nonadecyl 3-octylundecanoate;
(9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate);
(9Z,9'Z,12Z,12'Z)-2-((4-(((3-(diethylamino)propoxy)carbonyl)oxy)hexadecanoyl)oxy)propane-1,3-diyl bis(octadeca-9,12-dienoate);
(9Z,9'Z,12Z,12'Z,15Z,15'Z)-2-((4-(((3-(dimethylamino)propoxy)carbonyl)oxy) hexadecanoyl)oxy)propane-1,3-diyl bis(octadeca-9,12,15-trienoate);
(Z)-2-((4-(((3-(dimethylamino)propoxy)carbonyl)oxy) hexadecanoyl)oxy)propane-1,3-diyl dioleate;
2-((4-(((3-(diethylamino)propoxy)carbonyl)oxy)hexadecanoyl)oxy)propane-1,3-diyl ditetradecanoate;
2-((4-(((3-(dimethylamino)propoxy)carbonyl)oxy)hexadecanoyl)oxy)propane-1,3-diyl ditetradecanoate;
2-((4-(((3-(ethyl(methyl)amino)propoxy)carbonyl)oxy) hexadecanoyl)oxy)propane-1,3-diyl ditetradecanoate;
2-((4-(((3-(dimethylamino)propoxy)carbonyl)oxy)hexadecanoyl)oxy)propane-1,3-diyl didodecanoate;
2-((4-(((3-(diethylamino) propoxy)carbonyl)oxy)hexadecanoyl)oxy)propane-1,3-diyl didodecanoate;
2-((4-(((3-(ethyl(methyl)amino)propoxy)carbonyl)oxy) hexadecanoyl)oxy)propane-1,3-diyl didodecanoate;
2-((4-(((3-(diethylamino) propoxy)carbonyl)oxy)hexadecanoyl)oxy)propane-1,3-diyl bis(decanoate);
2-((4-(((3-(ethyl(methyl)amino)propoxy)carbonyl)oxy) hexadecanoyl)oxy)propane-1,3-diyl bis(decanoate);
2-((4-(((3-(diethylamino)propoxy)carbonyl)oxy)hexadecanoyl)oxy)propane-1,3-diyl dioctanoate;
2-((4-(((3-(ethyl(methyl)amino)propoxy)carbonyl)oxy) hexadecanoyl)oxy)propane-1,3-diyl dioctanoate;
2-(((13Z,16Z)-4-(((3-(dimethylamino)propoxy)carbonyl)oxy)docosa-13,16-dienoyl)oxy)propane-1,3-diyl dioctanoate;
2-(((13Z,16Z)-4-(((3-(diethylamino)propoxy)carbonyl)oxy)docosa-13,16-dienoyl)oxy)propane-1,3-diyl dioctanoate;
(9Z,9'Z,12Z,12'Z)-2-((2-(((3-(diethylamino)propoxy)carbonyl)oxy)tetradecanoyl)oxy)propane-1,3-diyl bis(octadeca-9,12-dienoate);
(9Z,9'Z,12Z,12'Z)-2-((2-(((3-(dimethylamino)propoxy)carbonyl)oxy)dodecanoyl)oxy)propane-1,3-diyl bis(octadeca-9,12-dienoate);
(9Z,9'Z,12Z,12'Z)-2-((2-(((3-(dimethylamino)propoxy)carbonyl)oxy)tetradecanoyl)oxy)propane-1,3-diyl bis(octadeca-9,12-dienoate);
(9Z,9'Z,12Z,12'Z)-2-((2-(((3-(diethylamino)propoxy)carbonyl)oxy)dodecanoyl)oxy)propane-1,3-diyl bis(octadeca-9,12-dienoate);
2-((2-(((3-(diethylamino)propoxy)carbonyl)oxy)tetradecanoyl)oxy)propane-1,3-diyl dioctanoate;
4,4-bis(octyloxy)butyl 4-(((3-(dimethylamino)propoxy)carbonyl)oxy)hexadecanoate;
4,4-bis(octyloxy)butyl 2-(((3-(diethylamino)propoxy)carbonyl)oxy)dodecanoate;
(9Z,12Z)-10-dodecyl-3-ethyl-14-(2-((9Z,12Z)-octadeca-9,12-dienoyloxy)ethyl)-8,13-dioxo-7,9-dioxa-3,14-diazahexadecan-16-yl octadeca-9,12-dienoate;
2-((4-(((3-(diethylamino)propoxy)carbonyl)oxy)-11-(octanoyloxy)undecanoyl)oxy)propane-1,3-diyl dioctanoate;
(9Z,9'Z,12Z,12'Z)-2-(9-dodecyl-2-methyl-7,12-dioxo-6,8,13-trioxa-2-azatetradecan-14-yl)propane-1,3-diyl bis(octadeca-9,12-dienoate);
3-(((3-(dimethylamino)propoxy)carbonyl)oxy)pentadecyl 4,4-bis(octyloxy)butanoate;
3-(((3-(piperidin-1-yl)propoxy)carbonyl)oxy)pentadecyl 6,6-bis(octyloxy)hexanoate;
3-(((3-(piperazin-1-yl)propoxy)carbonyl)oxy)pentadecyl 6,6-bis(octyloxy)hexanoate;
3-(((4-(diethylamino)butoxy)carbonyl)oxy)pentadecyl 6,6-bis(octyloxy)hexanoate;
3-(((3-(4-methylpiperazin-1-yl)propoxy)carbonyl)oxy)pentadecyl 6,6-bis(octyloxy)hexanoate;
3-((((1-methylpiperidin-4-yl)methoxy)carbonyl)oxy)pentadecyl 6,6-bis(octyloxy)hexanoate;
3-(((3-morpholinopropoxy)carbonyl)oxy)pentadecyl 6,6-bis(octyloxy)hexanoate;
3-(((2-(diethylamino)ethoxy)carbonyl)oxy)pentadecyl 6,6-bis(octyloxy)hexanoate;
3-(((3-(dimethylamino)propoxy)carbonyl)oxy)pentadecyl 6,6-bis(octyloxy)hexanoate;
3-(((3-(diethylamino) propoxy)carbonyl)oxy)pentadecyl 6,6-bis((2-propylpentyl)oxy)hexanoate;
3-(((3-(dimethylamino)propoxy)carbonyl)oxy)pentadecyl 6,6-bis((2-propylpentyl)oxy)hexanoate
LXR420: 3-(((3-(dimethylamino)propoxy)carbonyl)oxy) pentadecyl 6,6-bis((3-ethylpentyl)oxy)hexanoate;
(2R)-1-((6,6-bis(octyloxy)hexanoyl)oxy)pentadecan-3-yl 1-methylpyrrolidine-2-carboxylate;
(2S)-1-((6,6-bis(octyloxy)hexanoyl)oxy)pentadecan-3-yl 1-methylpyrrolidine-2-carboxylate;
(2R)-1-((6,6-bis(octyloxy)hexanoyl)oxy)pentadecan-3-yl pyrrolidine-2-carboxylate;
1-((6,6-bis(octyloxy)hexanoyl)oxy)pentadecan-3-yl 1,3-dimethylpyrrolidine-3-carboxylate;
3-((3-(1-methylpiperidin-4-yl)propanoyl)oxy)pentadecyl 6,6-bis(octyloxy)hexanoate;
1-((6,6-bis(octyloxy)hexanoyl)oxy)pentadecan-3-yl 1,4-dimethylpiperidine-4-carboxylate;
3-((5-(diethylamino)pentanoyl)oxy)pentadecyl 6,6-bis(octyloxy)hexanoate;
3-(((3-(diethylamino) propoxy)carbonyl)oxy)pentadecyl 5-(4,6-diheptyl-1,3-dioxan-2-yl)pentanoate;
3-(((3-(diethylamino)propoxy)carbonyl)oxy)undecyl 6,6-bis(octyloxy)hexanoate;
3-(((3-(diethylamino)propoxy)carbonyl)oxy)tridecyl 6,6-bis(octyloxy)hexanoate;
(12Z,15Z)-3-(((3-(diethylamino)propoxy)carbonyl)oxy) henicosa-12,15-dien-1-yl 6,6-bis(octyloxy)hexanoate;
6-((6,6-bis(octyloxy)hexanoyl)oxy)-4-(((3-(diethylamino) propoxy)carbonyl)oxy)hexyl octanoate;
4,4-bis(octyloxy)butyl 5-(((3-(diethylamino)propoxy)carbonyl)oxy)heptadecanoate;
4,4-bis(octyloxy)butyl (3-(diethylamino)propyl) pentadecane-1,3-diyl dicarbonate;
2-(5-((4-((1,4-dimethyl piperidine-4-carbonyl)oxy)hexadecyl)oxy)-5-oxopentyl)propane-1,3-diyl dioctanoate;
2-(5-((4-((1,3-dimethylpyrrolidine-3-carbonyl)oxy)hexadecyl)oxy)-5-oxopentyl)propane-1,3-diyl dioctanoate;
2-(5-oxo-5-((4-(((S)-pyrrolidine-2-carbonyl)oxy)hexadecyl)oxy)pentyl)propane-1,3-diyl dioctanoate;
2-(5-((4-(((((S)-1-methylpyrrolidin-3-yl)oxy)carbonyl)oxy) hexadecyl)oxy)-5-oxopentyl)propane-1,3-diyl dioctanoate;
2-(5-((4-(((((R)-1-methylpyrrolidin-3-yl)oxy)carbonyl)oxy) hexadecyl)oxy)-5-oxopentyl)propane-1,3-diyl dioctanoate;

2-(5-((4-(((((1-ethylpiperidin-3-yl)methoxy)carbonyl)oxy) hexadecyl)oxy)-5-oxopentyl)propane-1,3-diyl dioctanoate;

2-(5-((4-(((((1-methylpiperidin-4-yl)oxy)carbonyl)oxy) hexadecyl)oxy)-5-oxopentyl)propane-1,3-diyl dioctanoate;

2-(10-dodecyl-3-ethyl-8,15-dioxo-7,9,14-trioxa-3-azanonadecan-19-yl)propane-1,3-diyl dioctanoate;

2-(11-dodecyl-3-ethyl-9,15-dioxo-8,10,14-trioxa-3-azanonadecan-19-yl)propane-1,3-diyl dioctanoate;

2-(5-((3-(((3-(1H-imidazol-1-yl)propoxy)carbonyl)oxy) pentadecyl)oxy)-5-oxopentyl)propane-1,3-diyl dioctanoate;

2-(5-oxo-5-((3-(((3-(piperidin-1-yl)propoxy)carbonyl)oxy) pentadecyl)oxy)pentyl)propane-1,3-diyl dioctanoate; and 2-(12-dodecyl-3-ethyl-8,14-dioxo-7,9,13-trioxa-3-azaoctadecan-18-yl)propane-1,3-diyl dioctanoate.

In a nineteenth embodiment, the invention is the compound, or salt thereof, according to any one of the first through eighteenth embodiments, wherein the compound is selected from:

2-(10-dodecyl-3-ethyl-8,14-dioxo-7,9,13-trioxa-3-azaoctadecan-18-yl)propane-1,3-diyl dioctanoate;

2-(9-dodecyl-2-methyl-7,13-dioxo-6,8,12-trioxa-2-azaheptadecan-17-yl)propane-1,3-diyl dioctanoate;

2-(9-dodecyl-2-methyl-7,13-dioxo-6,8,12-trioxa-2-azapentadecan-15-yl)propane-1,3-diyl dioctanoate;

2-(10-dodecyl-3-ethyl-8,14-dioxo-7,9,13-trioxa-3-azahexadecan-16-yl)propane-1,3-diyl dioctanoate;

2-(8-dodecyl-2-methyl-6,12-dioxo-5,7,11-trioxa-2-azaheptadecan-17-yl)propane-1,3-diyl dioctanoate;

2-(10-dodecyl-3-ethyl-8,14-dioxo-7,9,13-trioxa-3-azanonadecan-19-yl)propane-1,3-diyl dioctanoate;

2-(9-dodecyl-2-methyl-7,13-dioxo-6,8,12-trioxa-2-azaoctadecan-18-yl)propane-1,3-diyl dioctanoate;

2-(8-dodecyl-2-methyl-6,12-dioxo-5,7,11-trioxa-2-azaoctadecan-18-yl)propane-1,3-diyl dioctanoate;

2-(1-dodecyl-3-ethyl-8,14-dioxo-7,9,13-trioxa-3-azaicosan-20-yl)propane-1,3-diyl dioctanoate;

2-(9-dodecyl-2-methyl-7,13-dioxo-6,8,12-trioxa-2-azanonadecan-19-yl)propane-1,3-diyl dioctanoate;

3-(((3-(diethylamino)propoxy)carbonyl)oxy)pentadecyl 4,4-bis(octyloxy)butanoate;

3-(((3-(diethylamino)propoxy)carbonyl)oxy)pentadecyl 4,4-bis((2-ethylhexyl)oxy)butanoate;

3-(((3-(diethylamino)propoxy)carbonyl)oxy)pentadecyl 4,4-bis((2-propylpentyl)oxy)butanoate;

3-(((3-(ethyl(methyl)amino)propoxy)carbonyl)oxy)pentadecyl 4,4-bis((2-propylpentyl)oxy)butanoate;

3-(((3-(dimethylamino)propoxy)carbonyl)oxy)pentadecyl 4,4-bis((2-propylpentyl)oxy)butanoate;

3-(((3-(diethylamino)propoxy)carbonyl)oxy)pentadecyl 6,6-bis(octyloxy)hexanoate;

3-(((3-(diethylamino)propoxy)carbonyl)oxy)pentadecyl 6,6-bis(hexyloxy)hexanoate;

3-(((3-(diethylamino)propoxy)carbonyl)oxy)pentadecyl 6,6-bis((2-ethylhexyl)oxy)hexanoate;

3-(((3-(diethylamino)propoxy)carbonyl)oxy)pentadecyl 8,8-bis(hexyloxy)octanoate;

3-(((3-(diethylamino)propoxy)carbonyl)oxy)pentadecyl 8,8-dibutoxyoctanoate;

3-(((3-(diethylamino)propoxy)carbonyl)oxy)pentadecyl 8,8-bis((2-propylpentyl)oxy)octanoate;

3-(((3-(ethyl(methyl)amino)propoxy)carbonyl)oxy)pentadecyl 8,8-bis((2-propylpentyl)oxy)octanoate;

3-(((3-(dimethylamino)propoxy)carbonyl)oxy)pentadecyl 8,8-bis((2-propylpentyl)oxy)octanoate;

3-(((3-(dimethylamino)propoxy)carbonyl)oxy)pentadecyl 3-octylundecanoate;

3-(((3-(dimethylamino)propoxy)carbonyl)oxy)pentadecyl 3-octylundec-2-enoate;

3-(((3-(dimethylamino)propoxy)carbonyl)oxy)pentadecyl 7-hexyltridec-6-enoate;

3-(((3-(dimethylamino)propoxy)carbonyl)oxy)pentadecyl 9-pentyltetradecanoate;

3-(((3-(dimethylamino) propoxy)carbonyl)oxy)pentadecyl 9-pentyltetradec-8-enoate;

3-(((3-(dimethylamino)propoxy)carbonyl)oxy)pentadecyl 5-heptyldodecanoate;

3-(((3-(dimethylamino)propoxy)carbonyl)oxy)tridecyl 5-heptyldodecanoate;

3-(((3-(dimethylamino)propoxy)carbonyl)oxy)undecyl 5-heptyldodecanoate;

1,3-bis(octanoyloxy)propan-2-yl (3-(((2-(dimethylamino) ethoxy)carbonyl)oxy)pentadecyl) succinate;

1,3-bis(octanoyloxy)propan-2-yl (3-(((3-(dimethylamino) propoxy)carbonyl)oxy)pentadecyl) succinate;

1-(3-(((3-(dimethylamino)propoxy)carbonyl)oxy)pentadecyl) 10-octyl decanedioate;

1-(3-(((3-(diethylamino)propoxy)carbonyl)oxy)pentadecyl) 10-octyl decanedioate;

1-(3-(((3-(ethyl(methyl)amino)propoxy)carbonyl)oxy)pentadecyl) 10-octyl decanedioate;

1-(3-(((3-(diethylamino)propoxy)carbonyl)oxy)pentadecyl) 10-(2-ethylhexyl) decanedioate;

1-(3-(((3-(ethyl(methyl)amino)propoxy)carbonyl)oxy)pentadecyl) 10-(2-ethylhexyl) decanedioate;

3-(((3-(dimethylamino)propoxy)carbonyl)oxy)pentadecyl 10-(octanoyloxy)decanoate;

8-dodecyl-2-methyl-6,12-dioxo-5,7,11-trioxa-2-azanonadecan-19-yl decanoate;

3-(((3-(diethylamino)propoxy)carbonyl)oxy)pentadecyl 10-(octanoyloxy)decanoate;

3-(((3-(ethyl(methyl)amino)propoxy)carbonyl)oxy)pentadecyl 10-(octanoyloxy)decanoate;

(9Z,12Z)-3-(((3-(dimethylamino)propoxy)carbonyl)oxy) pentadecyl octadeca-9,12-dienoate;

(9Z,12Z)-3-(((3-(diethylamino)propoxy)carbonyl)oxy)pentadecyl octadeca-9,12-dienoate;

(9Z,12Z)-3-(((3-(ethyl(methyl)amino)propoxy)carbonyl) oxy)pentadecyl octadeca-9,12-dienoate;

(9Z,12Z)-3-(((2-(dimethylamino)ethoxy)carbonyl)oxy)pentadecyl octadeca-9,12-dienoate;

1-((9Z,12Z)-octadeca-9,12-dienoyloxy)pentadecan-3-yl 1,4-dimethylpiperidine-4-carboxylate;

2-(((3-(diethylamino)propoxy)carbonyl)oxy)tetradecyl 4,4-bis((2-ethylhexyl)oxy)butanoate;

(9Z,12Z)-(12Z,15Z)-3-((3-(dimethylamino)propanoyl)oxy) henicosa-12,15-dien-1-yl octadeca-9,12-dienoate;

(12Z,15Z)-3-((4-(dimethylamino)butanoyl)oxy)henicosa-12,15-dien-1-yl 3-octylundecanoate;

(12Z,15Z)-3-((4-(dimethylamino)butanoyl)oxy)henicosa-12,15-dien-1-yl 5-heptyldodecanoate;

(12Z,15Z)-3-((4-(dimethylamino)butanoyl)oxy)henicosa-12,15-dien-1-yl 7-hexyltridecanoate;

(12Z,15Z)-3-((4-(dimethylamino)butanoyl)oxy)henicosa-12,15-dien-1-yl 9-pentyltetradecanoate;

(12Z,15Z)-1-(((((9Z,12Z)-octadeca-9,12-dien-1-yloxy)carbonyl)oxy)henicosa-12,15-dien-3-yl 3-(dimethylamino) propanoate;

(13Z,16Z)-4-(((2-(dimethylamino)ethoxy)carbonyl)oxy)docosa-13,16-dien-1-yl 2,2-bis(heptyloxy)acetate;

(13Z,16Z)-4-(((3-(diethylamino)propoxy)carbonyl)oxy)docosa-13,16-dien-1-yl 2,2-bis(heptyloxy)acetate;

2,2-bis(heptyloxy)ethyl 3-((3-ethyl-10-((9Z,12Z)-octadeca-9,12-dien-1-yl)-8,15-dioxo-7,9,14-trioxa-3-azaheptadecan-17-yl)disulfanyl)propanoate;
(13Z,16Z)-4-(((3-(dimethylamino)propoxy)carbonyl)oxy) docosa-13,16-dien-1-yl heptadecan-9-yl succinate;
(9Z,12Z)-2-(((11Z,14Z)-2-((3-(dimethylamino)propanoyl) oxy)icosa-11,14-dien-1-yl)oxy)ethyl octadeca-9,12-dienoate;
(9Z,12Z)-3-(((3-(dimethylamino)propoxy)carbonyl)oxy)-13-(octanoyloxy)tridecyl octadeca-9,12-dienoate;
3-(((3-(dimethylamino)propoxy)carbonyl)oxy)-13-(octanoyloxy)tridecyl 3-octylundecanoate;
3-(((3-(dimethylamino)propoxy)carbonyl)oxy)-13-hydroxytridecyl 5-heptyldodecanoate;
3-(((3-(dimethylamino)propoxy)carbonyl)oxy)-13-(octanoyloxy)tridecyl 5-heptyldodecanoate;
3-(((3-(dimethylamino)propoxy)carbonyl)oxy)-13-(octanoyloxy)tridecyl 7-hexyltridecanoate;
3-(((3-(dimethylamino)propoxy)carbonyl)oxy)-13-hydroxytridecyl 9-pentyltetradecanoate;
3-(((3-(dimethylamino)propoxy)carbonyl)oxy)-13-(octanoyloxy)tridecyl 9-pentyltetradecanoate;
1-(3-(((3-(dimethylamino)propoxy)carbonyl)oxy)-13-(octanoyloxy)tridecyl) 10-octyl decanedioate;
3-(((3-(dimethylamino)propoxy)carbonyl)oxy)-13-(octanoyloxy)tridecyl 10-(octanoyloxy)decanoate;
(9Z,12Z)-3-(((3-(dimethylamino)propoxy)carbonyl)oxy)-5-octyltridecyl octadeca-9,12-dienoate;
3-(((3-(dimethylamino)propoxy)carbonyl)oxy)-5-octyltridecyl decanoate;
5-(((3-(dimethylamino)propoxy)carbonyl)oxy)-7-octylpentadecyl octanoate;
(9Z,12Z)-5-(((3-(dimethylamino)propoxy)carbonyl)oxy)-7-octylpentadecyl octadeca-9,12-dienoate;
9-(((3-(dimethylamino)propoxy)carbonyl)oxy)-11-octylnonadecyl octanoate;
9-(((3-(dimethylamino)propoxy)carbonyl)oxy)-11-octylnonadecyl decanoate;
(9Z,12Z)-9-(((3-(dimethylamino)propoxy)carbonyl)oxy) nonadecyl octadeca-9,12-dienoate;
9-(((3-(dimethylamino)propoxy)carbonyl)oxy)nonadecyl hexanoate;
9-(((3-(dimethylamino)propoxy)carbonyl)oxy)nonadecyl 3-octylundecanoate;
9-((4-(dimethylamino)butanoyl)oxy)nonadecyl hexanoate;
9-((4-(dimethylamino)butanoyl)oxy)nonadecyl 3-octylundecanoate;
(9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate);
(9Z,9'Z,12Z,12'Z)-2-((4-(((3-(diethylamino)propoxy)carbonyl)oxy)hexadecanoyl)oxy)propane-1,3-diyl bis(octadeca-9,12-dienoate);
(9Z,9'Z,12Z,12Z,15Z,15'Z)-2-((4-(((3-(dimethylamino) propoxy)carbonyl)oxy) hexadecanoyl)oxy)propane-1,3-diyl bis(octadeca-9,12,15-trienoate);
(Z)-2-((4-(((3-(dimethylamino)propoxy)carbonyl)oxy) hexadecanoyl)oxy)propane-1,3-diyl dioleate;
2-((4-(((3-(diethylamino)propoxy)carbonyl)oxy)hexadecanoyl)oxy)propane-1,3-diyl ditetradecanoate;
2-((4-(((3-(dimethylamino)propoxy)carbonyl)oxy)hexadecanoyl)oxy)propane-1,3-diyl ditetradecanoate;
2-((4-(((3-(ethyl(methyl)amino)propoxy)carbonyl)oxy) hexadecanoyl)oxy)propane-1,3-diyl ditetradecanoate;
2-((4-(((3-(dimethylamino)propoxy)carbonyl)oxy)hexadecanoyl)oxy)propane-1,3-diyl didodecanoate;
2-((4-(((3-(diethylamino)propoxy)carbonyl)oxy)hexadecanoyl)oxy)propane-1,3-diyl didodecanoate;
2-((4-(((3-(ethyl(methyl)amino)propoxy)carbonyl)oxy) hexadecanoyl)oxy)propane-1,3-diyl didodecanoate;
2-((4-(((3-(diethylamino)propoxy)carbonyl)oxy)hexadecanoyl)oxy)propane-1,3-diyl bis(decanoate);
2-((4-(((3-(ethyl(methyl)amino)propoxy)carbonyl)oxy) hexadecanoyl)oxy)propane-1,3-diyl bis(decanoate);
2-((4-(((3-(diethylamino)propoxy)carbonyl)oxy)hexadecanoyl)oxy)propane-1,3-diyl dioctanoate;
2-((4-(((3-(ethyl(methyl)amino)propoxy)carbonyl)oxy) hexadecanoyl)oxy)propane-1,3-diyl dioctanoate;
2-(((13Z,16Z)-4-(((3-(dimethylamino)propoxy)carbonyl) oxy)docosa-13,16-dienoyl)oxy)propane-1,3-diyl dioctanoate;
2-(((13Z,16Z)-4-(((3-(diethylamino)propoxy)carbonyl)oxy) docosa-13,16-dienoyl)oxy)propane-1,3-diyl dioctanoate;
(9Z,9'Z,12Z,12'Z)-2-((2-(((3-(diethylamino)propoxy)carbonyl)oxy)tetradecanoyl)oxy)propane-1,3-diyl bis(octadeca-9,12-dienoate);
(9Z,9'Z,12Z,12'Z)-2-((2-(((3-(dimethylamino)propoxy)carbonyl)oxy)dodecanoyl)oxy)propane-1,3-diyl bis(octadeca-9,12-dienoate);
(9Z,9'Z,12Z,12'Z)-2-((2-(((3-(dimethylamino)propoxy)carbonyl)oxy)tetradecanoyl)oxy)propane-1,3-diyl bis(octadeca-9,12-dienoate);
(9Z,9'Z,12Z,12'Z)-2-((2-(((3-(diethylamino)propoxy)carbonyl)oxy)dodecanoyl)oxy)propane-1,3-diyl bis(octadeca-9,12-dienoate);
2-((2-(((3-(diethylamino)propoxy)carbonyl)oxy)tetradecanoyl)oxy)propane-1,3-diyl dioctanoate;
4,4-bis(octyloxy)butyl 4-(((3-(dimethylamino)propoxy)carbonyl)oxy)hexadecanoate;
4,4-bis(octyloxy)butyl 2-(((3-(diethylamino)propoxy)carbonyl)oxy)dodecanoate;
(9Z,12Z)-10-dodecyl-3-ethyl-14-(2-((9Z,12Z)-octadeca-9,12-dienoyloxy)ethyl)-8,13-dioxo-7,9-dioxa-3,14-diazahexadecan-16-yl octadeca-9,12-dienoate;
2-((4-(((3-(diethylamino)propoxy)carbonyl)oxy)-11-(octanoyloxy)undecanoyl)oxy)propane-1,3-diyl dioctanoate; and
(9Z,9'Z,12Z,12'Z)-2-(9-dodecyl-2-methyl-7,12-dioxo-6,8,13-trioxa-2-azatetradecan-14-yl)propane-1,3-diyl bis(octadeca-9,12-dienoate).

In a twentieth embodiment, the invention is a lipid composition comprising a compound according to anyone of the first through nineteenth embodiments, or a pharmaceutically acceptable salt thereof.

In a twentyfirst embodiment, the invention is the lipid composition according to the twentieth embodiment further comprising a biologically active agent.

In a twentysecond embodiment, the invention is the lipid composition according to the twentyfirst embodiment, wherein the biologically active agent is a nucleic acid.

In a twentythird embodiment, the invention is the lipid composition according to any one of the twentyfirst or twentysecond embodiments, wherein the biologically active agent is a DNA, siRNA or mRNA.

In a twentyfourth embodiment, the invention is the lipid composition according to any one of the twentyfirst through twentythird embodiments, wherein the biologically active agent is a mRNA.

In a twentyfifth embodiment, the invention is the lipid composition according to any one of the twentyfirst through twentythird embodiments, wherein the biologically active agent is a siRNA.

In a twentysixth embodiment, the invention is the lipid composition according to any one of the twentieth through twentyfifth embodiments, further comprising a helper lipid.

In a twentyseventh embodiment, the invention is the lipid composition according to any one of the twentieth through twentysixth embodiments further comprising a neutral lipid.

In a twentyeighth embodiment, the invention is the lipid composition according to any one of the twentieth through twentyseventh embodiments further comprising a stealth lipid.

In a twentyninth embodiment, the invention is the lipid composition according to any one of the twentieth through twentyeighth embodiments, wherein the helper lipid is cholesterol, the neutral lipid is DSPC, and the stealth lipid is PEG-DMG, S010, S011 or S024.

In a thirtieth embodiment, the invention is the lipid composition according to any one of the twentieth through twentyninth embodiments, wherein the lipid composition is in the form of a lipid nanoparticle.

In a thirtyfirst embodiment, the invention is the lipid composition according to any one of the twentieth through thirtieth embodiments, having 30-60% of a compound of formula (I), 5-10% cholesterol/30-60% DSPC, and 0.1-5% PEG-DMG, S010, S011 or S024

In a thirtysecond embodiment, the invention is the lipid composition according to any one of the twentieth through thirtyfirst embodiments, wherein the pH of said lipid composition is 4-6 at the time of encapsulation and/or formulation.

In a thirtythird embodiment, the invention is the lipid composition according to any one of the twentieth through thirtysecond embodiments, wherein the pH of said lipid composition is 5-6 at the time of encapsulation and/or formulation.

In a thirtyfourth embodiment, the invention is the lipid composition according to any one of the twentieth through thirtythird embodiments, wherein the pH of said lipid composition is 5.6-6.0 at the time of encapsulation and/or formulation.

In a thirtyfifthe embodiment, the invention is a pharmaceutical composition comprising a lipid composition according to any one of the twentieth through thirtyfourth embodiments and a pharmaceutically acceptable carrier or excipient.

In a thirtysixth embodiment, the invention is a method for the treatment of a disease or condition comprising the step of administering a therapeutically effective amount of lipid composition according to any one of the twentieth through thirtyfifth embodiments to a patient in need of treatment thereof.

In a thirtyseventh embodiment, the invention is a method for the treatment of a disease or condition comprising the step of administering a therapeutically effective amount of pharmaceutical composition according to the thirtysixth embodiment.

In a thirtyeighth embodiment, the invention is the composition of any one of the twentieth through thirtyfifth embodiment, wherein the composition comprises a RNA molecule that encodes an immunogen.

In a thirtyninth embodiment, the invention is the composition of the thirtyeighth embodiment, wherein the lipid is in the form of a lipid nanoparticle (LNP) and the RNA is associated with the LNP.

In a fortieth embodiment, the invention is the composition of thirtyninth embodiment wherein the LNP is a liposome.

In a fortyfirst embodiment, the invention is the composition of of the fortieth embodiment, wherein the liposome has a diameter in the range of about: 60-180 nm, e.g., about: 80-160 nm.

In a fortysecond embodiment, the invention is the composition of the fortieth or fortyfirst embodiment, wherein the liposome is is about: 80-160 nm and wherein at least half of the molar percentage of the RNA molecules are encapsulated in the liposomes.

In a fortythird embodiment, the invention is the composition of any one of the fortieth through fortysecond embodiments, wherein said liposome further comprises a lipid comprising a zwitterionic head group.

In a fortyfourth embodiment, the invention is the composition of any one of the fortieth through fortythird embodiments, wherein said liposome further comprises DlinDMA (1,2-dilinoleyloxy-N,N-dimethyl-3-aminopropane), DSPC (1,2-Diastearoyl-sn-glycero-3-phosphocholine), a cholesterol, a PEGylated lipid, or a combination thereof.

In a fortyfifth embodiment, the invention is a pharmaceutical composition comprising the composition of any one of the fortieth through fortyfourth embodiments and a pharmaceutical excipient.

In a fortysixth embodiment, the invention is a pharmaceutical composition comprising liposomes and immunogen-encoding RNA molecules, wherein the liposomes comprise the compound of any one of the first through nineteenth embodiments, and wherein at least half of the molar percentage of the RNA molecules are encapsulated in the liposomes.

In a fortyseventh embodiment, the invention is the pharmaceutical composition of the fortysixth embodiment, wherein (i) at least 80% by number of the liposomes have diameters in the range of about: 60-180 nm, (ii) the average diameter of the liposomes is in the range of about: 60-180 nm, or (iii) the diameters of the liposomes have a polydispersity index of <0.2.

In a fortyeighth embodiment, the invention is the composition of any one of the fortieth through fortyseventh embodiments, wherein the RNA is a self-replicating RNA.

In a fortyninth embodiment, the invention is the composition of of the fortyeighth embodiment, wherein the self-replicating RNA encodes a RNA-dependent RNA polymerase.

In a fiftieth embodiment, the invention is the composition of the fortyeighth or fortyninth embodiments, wherein the self-replicating RNA comprises a first open reading frame that encodes an alphavirus replicase and a second open reading frame that encodes the immunogen.

In a fiftyfirst embodiment, the invention is the composition of any one of the fortyeighth through fiftieth embodiments, wherein the self-replicating RNA is greater than about 2000 nucleotides, such as greater than about: 9000, 12000, 15000, 18000, 21000, 24000, or more nucleotides long.

In a fiftysecond embodiment, the invention is the composition of any one of the thirtyeighth through fiftyfirst embodiments, wherein the immunogen can elicit an immune response in vivo against a bacterium, a virus, a fungus or a parasite.

In a fiftythird embodiment, the invention is a method for inducing an immune response to an immunogen in a vertebrate, comprising administering an effective amount of the composition of any one of the thirtyeighth through fiftysecond embodiments to the vertebrate.

In a fiftyfourth embodiment, the invention is the composition of any one of the thirtyeighth through fiftysecond embodiments for inducing an immune response in a vertebrate to an immunogen.

As used herein, the term "alkyl" refers to a fully saturated branched or unbranched hydrocarbon chain having the specified number of carbon atoms. For example, $C_{1-8}$ alkyl refers to an alkyl group having from 1 to 8 carbon atoms. For example, $C_{4-22}$ alkyl refers to an alkyl group having from 4 to 22 carbon atoms. For example, $C_{6-10}$ alkyl refers to an alkyl group having from 6 to 10 carbon atoms. For example, $C_{12-22}$ alkyl refers to an alkyl group having from 12 to 22 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecanyl, n-dodecanyl, n-tridecanyl, 9-methylheptadecanyl, 1-heptyldecyl, 2-octyldecyl, 6-hexyldodecyl, 4-heptylundecyl, and the like.

As used herein, the term "alkylene" refers to divalent alkyl group as defined herein above. Representative examples of alkylene include, but are not limited to, methylene, ethylene, n-propylene, iso-propylene, n-butylene, sec-butylene, iso-butylene, tert-butylene, n-pentylene, iso-pentylene, neopentylene, n-hexylene, 3-methylhexylene, 2,2-dimethylpentylene, 2,3-dimethylpentylene, n-heptylene, n-octylene, n-nonylene, n-decylene, and the like.

As used herein, the term "alkenyl" refers to an unsaturated branched or unbranched hydrocarbon chain having the specified number of carbon atoms and one or more carbon-carbon double bonds within the chain. For example, $C_{12-22}$ alkenyl refers to an alkenyl group having 12 to 22 carbon atoms with one or more carbon-carbon double bonds within the chain. In certain embodiments alkenyl groups have one carbon-carbon double bond within the chain. In other embodiments, alkenyl groups have more than one carbon-carbon double bond within the chain. Alkyenyl groups may be optionally substituted with one or more substituents as defined in formula (I). Representative examples of alkenyl include, but are not limited to, ethylenyl, propenyl, butenyl, pentenyl, hexenyl and the like. Other examples of alkenyl include, but are not limited to: Z-octadec-9-enyl, Z-undec-7-enyl, Z-heptadeca-8-enyl, (9Z,12Z)-octadeca-9,12-dienyl, (8Z,11Z)-heptadeca-8,11-dienyl, (8Z,11Z,14Z)-heptadeca-8,11,14-trienyl, linolenyl, 2-octyldeca-1-enyl, linoleyl and olelyl.

As used herein, the term "alkenylene" refers a divalent alkenyl group as defined herein above. Representative examples of alkenylene include, but are not limited to, ethenylene, propenylene, butenylene, pentenylene, hexenylene and the like.

As used herein, the term "alkoxy" refers to refers to any alkyl moiety attached through an oxygen bridge (i.e. a —O—$C_{1-3}$ alkyl group wherein $C_{1-3}$ alkyl is as defined herein). Examples of such groups include, but are not limited to, methoxy, ethoxy, and propoxy.

As used herein, the term "cycloalkyl" refers to a saturated monocyclic, bicyclic or tricyclic hydrocarbon ring having the specified number of carbon atoms. For example, $C_{3-7}$ cycloalkyl refers to a cycloalkyl ring having from 3 to 7 carbon atoms. Cycloalkyl groups may be optionally substituted with one or more substituents as defined in formula (I). Representative examples of cycloalkyl include, but are not limited to, cyclopropyl, cyclobutyl, cyclopentyl, cyclohexyl, bicyclo[2.1.1]hexyl, bicyclo[2.2.1]heptyl, adamantyl and the like.

As used herein, the term "halo" refers to fluoro, chloro, bromo, and iodo.

As used herein, the term "heterocyclic" refers to a 4 to 12 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic groups are monocyclic, spiro, or fused or bridged bicyclic ring systems. Examples of monocyclic heterocyclic groups include tetrahydrofuranyl, dihydrofuranyl, 1,4-dioxanyl, morpholinyl, 1,4-dithianyl, azetidinyl, piperazinyl, piperidinyl, 1,3-dioxolanyl, imidazolidinyl, imidazolinyl, pyrrolinyl, pyrrolidinyl, tetrahydropyranyl, dihydropyranyl, 1,2,3,6-tetrahydropyridinyl, oxathiolanyl, dithiolanyl, 1,3-dioxanyl, 1,3-dithianyl, oxathianyl, thiomorpholinyl, 1,4,7-trioxa-10-azacyclododecanyl, azapanyl and the like. Examples of spiro heterocyclic rings include, but are not limited to, 1,5-dioxa-9-azaspiro[5.5]undecanyl, 1,4-dioxa-8-azaspiro[4.5]decanyl, 2-oxa-7-azaspiro[3.5]nonanyl, and the like. Fused heterocyclic ring systems have from 8 to 11 ring atoms and include groups wherein a heterocyclic ring is fused to a phenyl ring. Examples of fused heterocyclic rings include, but are not limited to decahydroqunilinyl, (4aS, 8aR)-decahydroisoquinolinyl, (4aS,8aS)-decahydroisoquinolinyl, octahydrocyclopenta[c]pyrrolyl, isoinolinyl, (3aR,7aS)-hexahydro-[1,3]dioxolo[4.5-c]pyridinyl, octahydro-1H-pyrrolo[3,4-b]pyridinyl, tetrahydroisoquinolinyl and the like.

As used herein, the term "heterocyclyl$C_{1-8}$alkyl" refers to a heterocyclic ring as defined above which is attached to the rest of the molecule by a single bond or by a $C_{1-8}$alkyl radical as defined above.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryl$C_{1-8}$alkyl" refers to a heteroaryl ring as defined above which is attached to the rest of the molecule by a single bond or by a $C_{1-8}$alkyl radical as defined above. As used herein, the term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory)

which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)— or (S)—.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition salt of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

General Methods for Synthesizing Cationic Lipids

The present invention also includes processes for the preparation of compounds of formula (I). In the reactions described, it could be necessary to protect reactive functional groups, for example hydroxyl, amino, iminio, thio or carboxy groups, where these are desired in the final product, to avoid their unwanted participation in the reactions.

The compounds and processes of the present invention will be better understood in connection with the following synthetic schemes, which are merely intended to illustrate methods by which the compounds may be generally prepared and are not intended to limit the scope of the invention as defined in the claims.

Final compounds of formula (I) can be prepared as described in FIG. 1.

Lipid Compositions

The present invention provides for a lipid composition comprising at least one compound of formula (I), i.e. a lipid composition of the invention. In one embodiment, at least one other lipid component is present. Such compositions can also contain a biologically active agent, optionally in combination with one or more other lipid components.

One embodiment of the present invention provides for a lipid composition comprising a compound of formula (I) and another lipid component. Such other lipid components include, but are not limited to, cationic lipids, neutral lipids, anionic lipids, helper lipids, and stealth lipids.

Cationic lipids suitable for use in a lipid composition of the invention include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Chol, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP). In one embodiment the cationic lipid is DOTAP or DLTAP.

"Neutral lipids" suitable for use in a lipid composition of the invention include, for example, a variety of neutral, uncharged or zwitterionic lipids. Examples of neutral phospholipids suitable for use in the present invention include, but are not limited to: 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), I-myristoyl-2-palmitoyl phosphatidylcholine (MPPC), I-palmitoyl-2-myristoyl phosphatidylcholine (PMPC), I-palmitoyl-2-stearoyl phosphatidylcholine (PSPC), I,2-diarachidoyl-sn-glycero-3-phosphocholine (DBPC), I-stearoyl-2-palmitoyl phosphatidylcholine (SPPC), I,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid is selected from the group consisting of distearoylphosphatidylcholine (DSPC) and dimyristoyl phosphatidyl ethanolamine (DMPE).

Anionic lipids suitable for use in the present invention include, but are not limited to, phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine cholesterol hemisuccinate (CHEMS), and lysyl-phosphatidylglycerol.

Suitable neutral and anionic lipids also include those described in US 2009/0048197.

"Helper lipids" are lipids that enhance transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Helper lipids suitable for use in the present invention include, but are not limited to, cholesterol, 5-heptadecylresorcinol, and cholesterol hemisuccinate.

Stealth lipids are lipids that increase the length of time for which the nanoparticles can exist in vivo (e.g. in the blood). Stealth lipids suitable for use in a lipid composition of the invention include, but are not limited to, stealth lipids having a hydrophilic head group linked to a lipid moiety. Examples of such stealth lipids include compounds of formula (XI), as described in WO2011/076807,

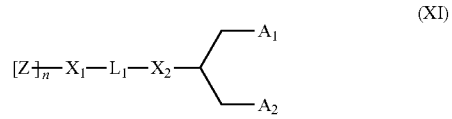

or a salt or pharmaceutically acceptable derivative thereof, wherein:

$Z_n$ is a hydrophilic polymer moiety selected from PEG poly(ethyleneoxide) or polymers based on poly(oxazoline), poly(vinyl alcohol), poly(glycerol), poly(N-vinylpyrrolidone), poly[N-(2-hydroxypropyl)methacrylamide], polysaccharides and poly(amino acid) s or a combination of the foregoing, wherein the polymer may be linear or branched, and wherein each Z is independently and optionally may be optionally substituted;

wherein Z is polymerized by n subunits;

n is a number-averaged degree of polymerization between 10 and 200 units of Z, wherein n is optimized for different polymer types;

$L_1$ is an optionally substituted $C_{1-10}$ alkylene or $C_{1-10}$ heteroalkylene linker including zero, one, two or more of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;

wherein R' is independently selected from —H, —NH—, —NH$_2$, —O—, —S—, a phosphate or an optionally substituted $C_{1-10}$ alkylene;

$X_1$ and $X_2$ are independently selected from a carbon or a heteroatom selected from —NH—, —O—, —S— or a phosphate;

$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

Specific stealth lipids include, but are not limited to, those listed in Table 1.

TABLE 1
Stealth Lipids
| Stealth Lipid | Lipid |
|---|---|
| S001 | 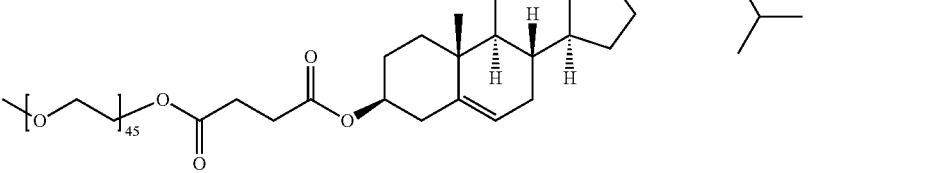 |
| S002 |  |
| S003 | 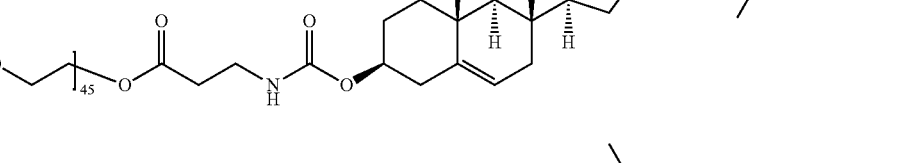 |
| S004 | 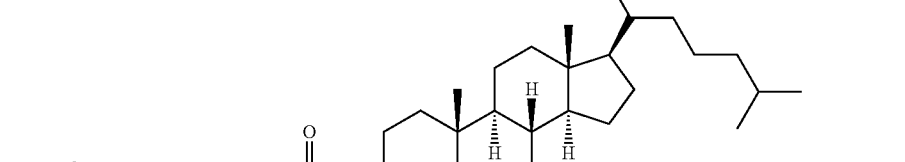 |
| S005 | 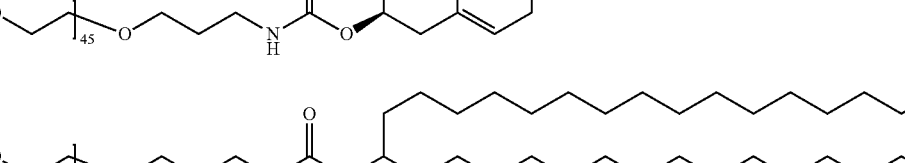 |
| S006 | 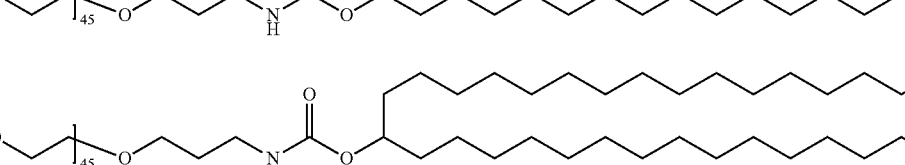 |
| S007 | 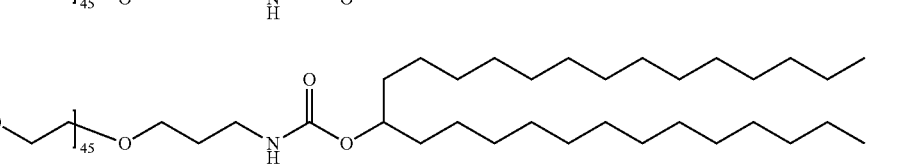 |
| S008 | 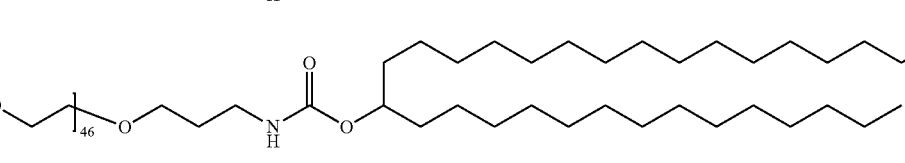 |

TABLE 1-continued

Stealth Lipids

| Stealth Lipid | Lipid |
|---|---|
| S009 | |
| S010 | |
| S011 | |
| S012 | |
| S013 | |
| S014 | |
| S015 | |
| S016 | |
| S017 | |
| S018 | |

TABLE 1-continued

Stealth Lipids

| Stealth Lipid | Lipid |
|---|---|
| S019 | |
| S020 | |
| S021 | |
| S022 | |
| S023 | |
| S024 | |
| S025 | |
| S026 | |
| S027 | |
| S028 | |

TABLE 1-continued

Stealth Lipids

| Stealth Lipid | Lipid |
|---|---|
| S029 | |
| S030 | |
| S031 | |
| S032 | |
| S033 | |

Other stealth lipids suitable for use in a lipid composition of the present invention and information about the biochemistry of such lipids can be found in Romberg et al., Pharmaceutical Research, Vol. 25, No. 1, 2008, p. 55-71 and Hoekstra et al., Biochimica et Biophysica Acta 1660 (2004) 41-52.

In one embodiment, the suitable stealth lipid comprises a group selected from PEG (sometimes referred to as poly(ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. Additional suitable PEG lipids are disclosed, e.g., in WO 2006/007712.

Specific suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol, PEG-dimyristylglycerol (PEG-DMG) (catalog # GM-020 from NOF, Tokyo, Japan), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000] (catalog #880150P from Avanti Polar Lipids, Alabaster, Ala., USA).

In one embodiment the stealth lipid is S010, S024, S027, S031, or S033.

In another embodiment the stealth lipid is S024.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment PEG is unsubstituted. In one embodiment the PEG is substituted, e.g., by one or more alkyl, alkoxy, acyl, hydroxy or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment about 150 to about 30,000, in a sub-embodiment about 150 to about 20,000, in a sub-embodiment about 150 to about 15,000, in a sub-embodiment about 150 to about 10,000, in a sub-embodiment about 150 to about 6000, in a sub-embodiment about 150 to about 5000, in a sub-embodiment about 150 to about 4000, in a sub-embodiment about 150 to about 3000, in a sub-embodiment about 300 to about 3000, in a sub-embodiment about 1000 to about 3000, and in a sub-embodiment about 1500 to about 2500.

In certain embodiments the PEG (e.g., conjugated to a lipid, such as a stealth lipid) is a "PEG-2K", also termed "PEG 2000", which has an average molecular weight of about 2000 daltons. PEG-2K is represented herein by the following formula (XIIa), wherein n is 45, meaning that the number-averaged degree of polymerization comprises about 45 subunits. However, other PEG embodiments known in the art may be used, including, e.g., those where the number-averaged degree of polymerization comprises about 23 subunits (n=23) and/or 68 subunits (n=68).

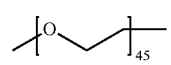

(XIIa)

The lipid compositions of the invention can also include one or more biologically active agents including, but not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid" (messenger RNA, mRNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occurring or synthetic, and may be chemically modified. In one embodiment the biologically active agent is an RNAi agent, short interfering nucleic acid (siNA), short interfering RNA (siRNA), double-stranded RNA (dsRNA), micro-RNA (miRNA), or a short hairpin RNA (shRNA) molecule. In one embodiment the biologically active agent is a RNAi agent useful for mediating RNA interference (RNAi). In another embodiment the biologically active agent is a mRNA.

Various methods for loading biologically active agents into lipid compositions, such as liposomes and lipid nanoparticles are available in the art, including both passive and active loading methods. The exact method used may be chosen based on multiple factors that include, but are not limited to, e.g., the biologically active agent to be loaded, the storage method to be used once loaded, the size of the resulting particle, and the dosage regimen contemplated. Methods include, e.g., mechanical mixing of the drug and lipids at the time the liposomes are formed or reconstituted, dissolving all components in an organic solvent and concentrating them into a dry film, forming a pH or ion gradient to draw the active agent into the interior of the liposome, creating a transmembrane potential, and ionophore mediated loading. See, e.g., PCT Publication No. WO 95/08986, U.S. Pat. Nos. 5,837,282, 5,837,282, and 7,811,602.

By "lipid nanoparticle" is meant a particle that comprises a plurality of (i.e. more than one) lipid molecules physically associated with each other by intermolecular forces. The lipid nanoparticles may be, e.g., microspheres (including unilamellar and multilamellar vesicles, e.g. "liposomes"—lamellar phase libid bilayers that, in some embodiments are substantially spherical, and, in more particular embodiments can comprise an aqueous core, e.g., comprising a substantial portion of RNA molecules), a dispersed phase in an emulsion, micelles or an internal phase in a suspension.

The lipid nanoparticles have a size of about 1 to about 2,500 nm, about 10 to about 1,500 nm, about 20 to about 1,000 nm, in a sub-embodiment about 50 to about 600 nm, in a sub-embodiment about 50 to about 400 nm, in a sub-embodiment about 50 to about 250 nm, and in a sub-embodiment about 50 to about 150 nm. Unless indicated otherwise, all sizes referred to herein are the average sizes (diameters) of the fully formed nanoparticle, as measured by dynamic light scattering on a Malvern Zetasizer. The nanoparticle sample is diluted in phosphate buffered saline (PBS) so that the count rate is approximately 200-400 kcts. The data is presented as a weighted average of the intensity measure.

One embodiment of the present invention provides for a lipid composition comprising a compound of formula (I) and another lipid component. Another embodiment provides for a lipid composition comprising a compound of formula (I) and a helper lipid, for example cholesterol. Another embodiment provides for a lipid composition comprising a compound of formula (I), a helper lipid, for example cholesterol, and a neutral lipid, for example DSPC. Another embodiment of the present invention provides for a lipid composition comprising a compound of formula (I), a helper lipid, for example cholesterol, a neutral lipid, for example DSPC, and a stealth lipid, for example S010, S024, S027, S031, or S033. Another embodiment of the present invention provides for a lipid composition comprising a compound of formula (I), a helper lipid, for example cholesterol, a neutral lipid, for example DSPC, a stealth lipid, for example S010, S024, S027, S031, or S033, and a biologically active agent, for example a RNA or DNA. Another embodiment of the present invention provides for a lipid nanoparticle comprising a compound of formula (I) a helper lipid, for example cholesterol, a neutral lipid, for example DSPC, and a stealth lipid, for example S010, S024, S027, S031, or S033, and a biologically active agent, for example a mRNA, siRNA or DNA.

Embodiments of the present invention also provide lipid compositions described according to the respective molar ratios of the component lipids in the formulation, wherein a slash ("/") indicates the respective components, as provided herein.

Another embodiment of the present invention is a lipid composition comprising a compound of formula (I) and a helper lipid, for example cholesterol, in a lipid molar ratio of 55-40 compound of formula (I)/55-40 helper lipid. Another embodiment provides for a lipid composition comprising a compound of formula (I), a helper lipid, for example cholesterol, and a neutral lipid, for example DPSC in a lipid molar ratio of 55-40 compound of formula (I)/55-40 helper lipid/15-5 neutral lipid. Another embodiment provides for a lipid composition comprising a compound of formula (I), a helper lipid, for example cholesterol, a neutral lipid, for example DSPC, and a stealth lipid, for example S010, S024, S027, S031, or S033 in a lipid molar ratio of 55-40 compound of formula (I)/55-40 helper lipid/15-5 neutral lipid/ 10-1 stealth lipid.

Another embodiment of the present invention is a lipid composition comprising a compound of formula (I) and a helper lipid, for example cholesterol, in a lipid molar ratio of 50-40 compound of formula (I)/50-40 helper lipid. Another embodiment provides for a lipid composition comprising a compound of formula (I), a helper lipid, for example cholesterol, and a neutral lipid, for example DPSC in a lipid molar ratio of 50-40 compound of formula (I)/50-40 helper lipid/15-5 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of 50-40 compound of formula (I)/50-40 helper lipid/15-5 neutral lipid/ 5-1 stealth lipid.

Another embodiment of the present invention is a lipid composition comprising a compound of formula (I) and a helper lipid, for example cholesterol, in a lipid molar ratio of 47-43 compound of formula (I)/47-43 helper lipid. Another embodiment provides for a lipid composition comprising a compound of formula (I), a helper lipid, for example cholesterol, and a neutral lipid, for example DPSC in a lipid molar ratio of 47-43 compound of formula (I)/47-43 helper lipid/12-7 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of 47-43 compound of formula (I)/47-43 helper lipid/12-7 neutral lipid/ 4-1 stealth lipid.

Another embodiment of the present invention is a lipid composition comprising a compound of formula (I) and a helper lipid, for example cholesterol, in a lipid molar ratio of about 45 compound of formula (I)/about 44 helper lipid. Another embodiment provides for a lipid composition comprising a compound of formula (I), a helper lipid, for example cholesterol, and a neutral lipid, for example DPSC in a lipid molar ratio of about 45 compound of formula (I)/about 44 helper lipid/about 9 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of about 45 compound of formula (I)/about 44 helper lipid/about 9 neutral lipid/about 2 stealth lipid, for example S010, S024, S027, S031, or S033.

Preferred compounds of formula (I) for use in the above lipid compositions are given in Examples 1-36. Particularly preferred compounds are given in Examples 1 and 80. Preferred biologically active agents are RNA's and DNA's.

Lipid compositions of the present invention can be further optimized by one skilled in the art by combining cationic lipids with the desired pKa range, stealth lipids, helper lipids, and neutral lipids into formulations, including, e.g., liposome formulations, lipid nanoparticles (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, formulation methods and/or dosing regimen (e.g., number of doses administered over time, actual dose in mg/kg, timing of the doses, combinations with other therapeutics, etc.). The various optimization techniques known to those of skill in the art pertaining to the above listed embodiments are considered as part of this invention.

General Methods for Making Lipid Nanoparticles

The following methods can be used to make lipid nanoparticles of the invention. To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition of the invention typically comprises providing an aqueous solution, such as citrate buffer, comprising a biologically active agent in a first reservoir, providing a second reservoir comprising an organic solution, such as an organic alcohol, for example ethanol, of the lipid(s) and then mixing the aqueous solution with the organic lipid solution. The first reservoir is optionally in fluid communication with the second reservoir. The mixing step is optionally followed by an incubation step, a filtration or dialysis step, and a dilution and/or concentration step. The incubation step comprises allowing the solution from the mixing step to stand in a vessel for about 0 to about 100 hours (preferably about 0 to about 24 hours) at about room temperature and optionally protected from light. In certain embodiments, the temperature may be about 4° C. during incubation. In one embodiment, a dilution step follows the incubation step. The dilution step may involve dilution with aqueous buffer (e.g. citrate buffer or pure water) e.g., using a pumping apparatus (e.g. a peristaltic pump). The filtration step is ultrafiltration or dialysis. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent). Dialysis comprises solvent (buffer) exchange through a suitable membrane (e.g. 10,000 mwc snakeskin membrane). Alternatively, in some embodiments, dialysis may be accomplished using buffer exchange columns (e.g., PD-10 columns from GE healthcare).

In one embodiment, the mixing step provides a clear single phase.

In one embodiment, after the mixing step, the organic solvent is removed to provide a suspension of particles, wherein the biologically active agent is encapsulated by the lipid(s).

The selection of an organic solvent will typically involve consideration of solvent polarity and the ease with which the solvent can be removed at the later stages of particle formation. The organic solvent, which is also used as a solubilizing agent, is preferably in an amount sufficient to provide a clear single phase mixture of biologically active agents and lipids. The organic solvent may be selected from one or more (e.g. two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, isobutanol, pentanol and hexanol.

The mixing step can take place by any number of methods, e.g., by mechanical means such as a vortex mixer.

The methods used to remove the organic solvent will typically involve diafiltration or dialysis or evaporation at reduced pressures or blowing a stream of inert gas (e.g. nitrogen or argon) across the mixture.

In other embodiments, the method further comprises adding nonlipid polycations which are useful to effect the transformation of cells using the present compositions. Examples of suitable nonlipid polycations include, but are limited to, hexadimethrine bromide (sold under the brandname POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine.

In certain embodiments, the formation of the lipid nanoparticles can be carried out either in a mono-phase system (e.g. a Bligh and Dyer monophase or similar mixture of aqueous and organic solvents) or in a two-phase system with suitable mixing. The lipid nanoparticle may be formed in a mono- or a bi-phase system. In a mono-phase system, the cationic lipid(s) and biologically active agent are each dissolved in a volume of the mono-phase mixture. Combining the two solutions provides a single mixture in which the complexes form. In a bi-phase system, the cationic lipids bind to the biologically active agent (which is present in the aqueous phase), and "pull" it into the organic phase.

In one embodiment, the lipid nanoparticles are prepared by a method which comprises: (a) contacting the biologically active agent with a solution comprising noncationic lipids and a detergent to form a compound-lipid mixture; (b) contacting cationic lipids with the compound-lipid mixture to neutralize a portion of the negative charge of the biologically active agent and form a charge-neutralized mixture of biologically active agent and lipids; and (c) removing the detergent from the charge-neutralized mixture.

In one group of embodiments, the solution of neutral lipids and detergent is an aqueous solution. Contacting the biologically active agent with the solution of neutral lipids and detergent is typically accomplished by mixing together a first solution of the biologically active agent and a second solution of the lipids and detergent. Preferably, the biologically active agent solution is also a detergent solution. The amount of neutral lipid which is used in the present method is typically determined based on the amount of cationic lipid used, and is typically of from about 0.2 to 5 times the amount of cationic lipid, preferably from about 0.5 to about 2 times the amount of cationic lipid used.

The biologically active agent-lipid mixture thus formed is contacted with cationic lipids to neutralize a portion of the negative charge which is associated with the molecule of interest (or other polyanionic materials) present. The amount of cationic lipids used is typically 3-8 fold more than the calculated molar ratio of negative charge (phosphates).

The methods used to remove the detergent typically involve dialysis. When organic solvents are present, removal is typically accomplished by diafiltration or evaporation at reduced pressures or by blowing a stream of inert gas (e.g. nitrogen or argon) across the mixture.

There is herein disclosed an apparatus for making a composition of the present invention. The apparatus typically includes a first reservoir for holding an aqueous solution comprising a biologically active agent and a second reservoir for holding an organic lipid solution. The apparatus also typically includes a pump mechanism configured to pump the aqueous and the organic lipid solutions into a mixing region or mixing chamber at substantially equal flow rates. In one embodiment, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof. In other embodiments, a microfluidic device, such as a NANO-ASSEMBLR™, can be used for making a composition provided by the invention.

Methods for Delivering Biologically Active Agents and the Treatment of Disease

The cationic lipids of formula (I) and lipid compostions thereof are useful in pharmaceutical compositions or formulations used for delivery of biologically active agents. Formulations containing cationic lipids of formula (I) or lipid compositions thereof may be in various forms, including, but not limited to, particle forming delivery agents including microparticles, nanoparticles and transfection agents that are useful for delivering various molecules to cells. Specific formulations are effective at transfecting or delivering biologically active agents, such as antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozymes, decoys and analogs thereof, plasmids and other types of expression vectors, and small nucleic acid molecules, mRNA, RNAi agents, short interfering nucleic acid (siNA), short interfering RNA (siRNA), double-stranded RNA (dsRNA), micro-RNA (miRNA), short hairpin RNA (shRNA), and "self-replicating RNA" (encoding a replicase enzyme activity and capable of directing its own replication or amplification in vivo) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. The above list of biologically active agents is exemplary only, and is not intended to be limiting. Such compounds may be purified or partially purified, and may be naturally occurring or synthetic, and may be chemically modified.

Such formulations containing biologically active agents are useful, e.g., in providing compositions to prevent, inhibit, or treat diseases, conditions, or traits in a cell, subject or organism. Diseases, conditions or traits include, but are not limited to, proliferative diseases, including cancer, inflammatory disease, transplant and/or tissue rejection, autoimmune diseases or conditions, age-related disease, neurological or neurodegenerative disease, respiratory disease, cardiovacular disease, ocular disease, metabolic disease, dermatological disease, auditory disease, a liver disease, a kidney or renal disease, etc.

The amount of active agent administered per dose is an amount above the minimal therapeutic dose but below a toxic dose. The actual amount per dose may be determined by a physician depending on a number of factors, such as the medical history of the patient, the use of other therapies, the biologically active agent to be provided, and the nature of the disease. The amount of biologically active agent administered may be adjusted throughout treatment, depending on the patient's response to treatment and the presence or severity of any treatment-associated side effects. Exemplary dosages and treatment for compounds that have been approved by an appropriate regulatory agency are known and available to those skilled in the art. See, e.g., Physician's Desk Reference, 64th ed., Physician's Desk Reference Inc. (2010), Remington's Pharmaceutical Sciences, Mack Publishing Company, Philadelphia, Pa. (1985), and Remington The Science and Practice of Pharmacy, 21st ed., Lippincott Williams & Williams Publishers (2005).

In one embodiment, a single dose is administered of a biologically active agent to a patient in need thereof. In one embodiment, multiple doses are administered, wherein the multiple doses may be administered concurrently, sequentially or alternating. In one embodiment, the same formulation is administered over multiple doses. In one embodiment, the formulations differ over multiple doses. In various embodiments, the doses may be administered once a day, or for one, two, three, four or more consecutive days. In one embodiment, the doses are administered once a week. In one embodiment, the doses are administered once every other week. In one embodiment, patients receive at least two courses of a treatment regimen, and potentially more, depending on the response of the patient to the treatment. In single agent regimens, total courses of treatment are determined by the patient and physician based on observed responses and toxicity. The above dosage regimens are to be considered as non-limiting examples. Other dosage regimens are contemplated as being within the scope of the invention, and depend on the therapeutic effect desired.

The invention also provides a method for the treatment of a disease or condition comprising the step of administering a therapeutically effective amount of a lipid composition of the invention to a patient in need of treatment thereof. In one embodiment, the disease or condition is treatable by administering a RNA agent.

The invention also provides for use of a lipid composition of the invention in treating a disease or condition in a patient. In one embodiment, the disease or condition is treatable by administering a siRNA or mRNA agent.

The total amount of lipid provided by the invention in the composition being administered is, in one embodiment, from about 5 to about 30 mg lipid per mg biologically active agent (e.g. RNA), in another embodiment from about 5 to about 25 mg lipid per mg biologically active agent (e.g. RNA), in another embodiment from about 7 to about 25 mg lipid per mg biologically active agent (e.g. RNA) and in one embodiment from about 7 to about 15 mg lipid per mg biologically active agent (e.g. RNA).

As used herein, "treatment" includes ameliorative, curative and prophylactic treatment. As used herein, a "patient" means an animal, preferably a mammal, preferably a human, in need of treatment.

The term "therapeutically effective amount" refers to the amount of the compound of the invention and the biologically active agent (e.g. the therapeutic compound) needed to treat or ameliorate a targeted disease or condition.

The term "immunologically effective amount" refers to the amount of the compound of the invention and of RNA which encodes an immunogen needed to elicit an immune response which recognizes the immunogen (e.g. in the context of a pathogen). The term "immunogen" refers to any substance or organism that provokes an immune response when introduced into the body. The phrase "RNA which encodes an immunogen" refers to a polynucleotide, such as a messenger RNA or a replicon (e.g., self-replicating RNA), that when administered to a cell or organism is capable of being translated into a polypeptide according to the codon sequence of such RNA.

By "proliferative disease" as used herein is meant any disease, condition, trait, genotype or phenotype characterized by unregulated cell growth or replication as is known in the art. In one embodiment, the proliferative disease is cancer. In one embodiment, the proliferative disease is a tumor. In one embodiment, the proliferative disease includes, but are not limited to, e.g., liquid tumors such as, e.g., leukemias, e.g., acute myelogenous leukemia (AML), chronic myelogenous leukemia (CML), acute lymphocytic leukemia (ALL), multiple myeloma, and chronic lymphocytic leukemia; and solid tumors, e.g., AIDS related cancers such as Kaposi's sarcoma; breast cancers; bone cancers; brain cancers; cancers of the head and neck, non-Hodgkins lymphoma, adenoma, squamous cell carcinoma, laryngeal carcinoma, gallbladder and bile duct cancers, cancers of the retina, cancers of the esophagus, gastrointestinal cancers, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, endometrial sarcoma, multidrug resistant cancers. In one embodiment, the proliferative disease includes neovascularization associated with tumor angiogenesis, macular degeneration (e.g. wet/dry age related macular degeneration), corneal neovascularization, diabetic retinopathy, neovascular glaucoma, myopic degeneration. In one embodiment, the proliferative disease includes restenosis and polycystic kidney disease.

By "autoimmune disease" as used herein is meant any disease, condition, trait, genotype or phenotype characterized by autoimmunity as is known in the art. Autoimmune diseases include, but are not limited to, e.g., multiple sclerosis, diabetes mellitus, lupus, scleroderms, fibromyalgia, transplantation rejection (e.g. prevention of allograft rejection), pernicious anemia, rheumatoid arthritis, systemic lupus erythematosus, dermatomyositis, myasthenia gravis, lupus erythematosus, multiple sclerosis, and Grave's disease.

By "infectious disease" is meant any disease, disorder or condition associated with an infectious agent, such as a virus, bacteria, fungus, prion or parasite. The invention can be used to immunize against pathogens which cause infectious disease. Examples of such pathogens are given below.

By "neurologic disease" is meant any disease, disorder, or condition affecting the central or peripheral nervous system. Neurologic diseases include, but are not limited to, diseases or disorders of either the peripheral or the central nervous system including, e.g., Alzheimer's Disease, Aneurysm, Brain Injury, Carpal Tunnel Syndrome, Cerebral Aneurysm, Chronic Pain, Creutzfeldt-Jakob Disease, Epilepsy, Huntington's Disease, Meningitis, Seizure Disorders, and other neurologic diseases, disorders and syndromes.

By "respiratory disease" is meant any disease or condition affecting the respiratory tract. Respiratory diseases include, but are not limited to, e.g., asthma, chronic obstructive pulmonary disease (COPD), allergic rhinitis, sinusitis, allergies, impeded respiration, respiratory distress syndrome, cystic fibrosis, pulmonary hypertension or vasoconstriction and emphysema.

By "cardiovascular disease" is meant and disease or condition affecting the heart and vasculature. Cardiovascular diseases include, but are not limited to, e.g., coronary heart disease (CHD), cerebrovascular disease (CVD), aortic stenosis, peripheral vascular disease, myocardial infarction (heart attack), arrhythmia, ischemia, and congestive heart failure.

By "ocular disease" as used herein is meant any disease, condition, trait, genotype or phenotype of the eye and related structures. Ocular diseases include, but are not limited to, e.g., cystoid macular edema, diabetic retinopathy, lattice degeneration, retinal vein occlusion, retinal artery occlusion, macular degeneration (e.g. age related macular degeneration such as wet AMD or dry AMD), toxoplasmosis, retinitis pigmentosa, conjunctival laceration, corneal laceration, glaucoma, and the like.

By "metabolic disease" is meant any disease or condition affecting metabolic pathways. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes obesity, insulin resistance, and diabetes (e.g. type I and/or type II diabetes).

By "dermatological disease" is meant any disease or condition of the skin, dermis, or any substructure therein such as a hair, a follicle, etc. Dermatological diseases, disorders, conditions, and traits can include psoriasis, ectopic dermatitis, skin cancers such as melanoma and basal cell carcinoma, hair loss, hair removal and alterations in pigmentation.

By "auditory disease" is meant any disease or condition of the auditory system, including the ear, such as the inner ear, middle ear, outer ear, auditory nerve, and any substructures therein. Auditory diseases, disorders, conditions, and traits can include hearing loss, deafness, tinnitus, vertigo, balance and motion disorders.

By "regenerative disease" is meant any disease or condition where insufficient cell or tissue generation or regeneration in vivo or in vitro prevents the establishment or restoration of proper organ function before or after injury, prevents or slows wound healing or resolution of ulcerative lesions, accelerates ageing, or prevents effective cell-based therapy. The term "messenger ribonucleic acid" (messenger RNA, mRNA) refers to a ribonucleic acid (RNA) molecule that mediates the transfer of genetic information to ribosomes in the cytoplasm, where it serves as a template for protein synthesis. It is synthesized from a DNA template during the process of transcription. See, *The American Heritage® Dictionary of the English Language, Fourth Edition* (Updated in 2009). Houghton Mifflin Company.

In eukaryotes, mRNA is transcribed in vivo at the chromosomes by the cellular enzyme RNA polymerase. During or after transcription in vivo, a 5' cap (also termed an RNA cap, an RNA 7-methylguanosine cap, or an RNA m7G cap) is added in vivo to the 5' end of the mRNA. The 5' cap is terminal 7-methylguanosine residue that is linked through a 5'-5'-triphosphate bond to the first transcribed nucleotide. In addition, most eukaryotic mRNA molecules have a polyadenylyl moiety ("poly(A) tail") at the 3' end of the mRNA molecule. In vivo, the eukaryotic cell adds the poly(A) tail after transcription, often at a length of about 250 adenosine residues (SEQ ID NO: 12). Thus, a typical mature eukaryotic mRNA has a structure that begins at the 5' end with an mRNA cap nucleotide followed by a 5' untranslated region (5'UTR) of nucleotides, then an open reading frame that begins with a start codon which is an AUG triplet of nucleotide bases, that is the coding sequence for a protein, and that ends with a stop codon that may be a UAA, UAG, or UGA triplet of nucleotide bases, then a 3' untranslated region (3'UTR) of nucleotides and ending with a polyadenosine tail. While the features of the typical mature eukaryotic mRNA are made naturally in a eukaryotic cell in vivo, the same or structurally and functionally equivalent features can be made in vitro using the methods of molecular biology. Accordingly, any RNA having the structure similar to a typical mature eukaryotic mRNA can function as a mRNA and is within the scope of the term "messenger ribonucleic acid".

The mRNA molecule is generally of a size that it can be encapsulated in a lipid nanoparticle of the invention. While the size of a mRNA molecule varies in nature depending upon the identity of the mRNA species that encodes for a particular protein, an average size for a mRNA molecule is average mRNA size is 500-10,000 bases.

DNA can exist in at least two forms, which have different sizes. The first form of DNA is a very large-sized polymer called a chromosome. A chromosome contains the genetic information for many or most of the proteins in a cell and also contains information whereby the cell can control the replication of the DNA molecule. A bacterial cell may contain one or more chromosome. A eukaryotic cell usually contains more than one cell chromosome, each chromosome The second form of DNA is a shorter sized form. Many DNA molecules of the second form are of a size that it can be encapsulated in a lipid nanoparticle of the invention. Some of these shorter forms of DNA can be of a size to usefully encode for proteins. Examples of these second, shorter, useful forms of DNA include plasmids and other vectors. For a fuller description, see, Alberts B et al. (2007) *Molecular Biology of the Cell, Fifth Edition*, Garland Science.

A plasmid is a small DNA molecule that is physically separate from, and can replicate independently of, chromosomal DNA within a cell. Plasmids commonly exist in vivo as small circular, double-stranded DNA molecules. In nature, plasmids carry genes that can be transcribed and translated to proteins that may benefit survival of an organism (e.g. antibiotic resistance). In nature, plasmids can frequently be transmitted from one organism to another by horizontal gene transfer. Artificial or recombinant plasmids are widely used in molecular biology, serving to permit the replication of recombinant DNA sequences and the expression of useful proteins within host organisms. Plasmid sizes can vary from about 1 to over 25 kilobase pairs. A recombinant plasmid can be recombinantly made to be of a size that it can be encapsulated in a lipid nanoparticle of the invention.

In molecular biology, a vector is a DNA molecule used as a vehicle to artificially carry genetic material from one cell or from a biochemical reaction in vitro into another cell, where the DNA can be replicated and/or expressed. A vector containing foreign DNA is termed recombinant. Among the types of useful vectors are plasmids and viral vectors. Insertion of a vector into the target cell is usually called transformation for bacterial cells, transfection for eukaryotic cells, although insertion of a viral vector is often called transduction.

Viral vectors are generally recombinant viruses carrying modified viral DNA or RNA that has been rendered noninfectious, but that still contain viral promoters and also the transgene, thus allowing for translation of the transgene through a viral promoter. Viral vectors, in some embodiments, are designed for permanent incorporation of the insert into the host genome (integrate), and thus leave distinct genetic markers in the host genome after incorporating the transgene. A viral vector can be recombinantly made to be of a size that it can be encapsulated in a lipid nanoparticle of the invention.

The term "short interfering nucleic acid" (siNA) as used herein refers to any nucleic acid molecule capable of inhibiting or down regulating gene expression or viral replication by mediating RNA interference (RNAi) or gene silencing in a sequence-specific manner. It includes short interfering RNA (siRNA), microRNA (miRNA), short interfering oligonucleotides and chemically-modified short interfering nucleic acid molecules. siRNAs are responsible for RNA interference, the process of sequence-specific post-transcriptional gene silencing in animals and plants. siRNAs are generated by ribonuclease III cleavage from longer double-stranded RNA (dsRNA) which are homologous to, or specific to, the silenced gene target.

The term "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, *Science,* 309, 1519-1524; Zamore et al., 2000, *Cell,* 101, 25-33; Elbashir et al., 2001, *Nature,* 411, 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al., 2005, Nature Chemical Biology, 1, 216-222.

The term "RNAi inhibitor" is any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g, up-regulate or down-regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term "RNAi inhibitor" is used interchangeably with the term "siNA" in various embodiments herein.

The term "enzymatic nucleic acid" as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 *JAMA* 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 *Proc. Natl. Acad. Sci. USA* 90, 1300; Silverman et al., 2000, *Methods Enzymol.*, 313, 522-533; Player and Torrence, 1998, *Pharmacol. Ther.*, 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504; Fox, 2000, *Curr. Med. Chem.*, 7, 17-37; Praseuth et. al., 2000, *Biochim. Biophys. Acta*, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule, or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186; 5,741,679; 5,589,332; 5,871,914; and PCT publication Nos. WO 00/24931, WO 00/26226, WO 98/27104, and WO 99/29842.

The term "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

Formulation of Lipid Compositions

For pharmaceutical use, the lipid compositions of the invention may be administered by enteral or parenteral routes, including intravenous, intramuscular, subcutaneous, transdermal, airway (aerosol), oral, intranasal, rectal, vaginal, buccal, nasopharangeal, gastrointestinal or sublingual administration. The administration may be systemic (e.g., IV) or local (e.g., IM, SC, TD, intranasal, or topical). Topical administration may involve, e.g., catheterization, implantation, osmotic pumping, direct injection, dermal/transdermal application, stenting, ear/eye drops or portal vein administration. The compounds of formula (I) should be assessed for their biopharmaceutical properties, such as solubility and solution stability (across pH), permeability, etc., in order to select the most appropriate dosage form and route of administration for treatment of the proposed indication.

The compositions of the invention will generally, but not necessarily, be administered as a formulation in association with one or more pharmaceutically acceptable excipients. The term "excipient" includes any ingredient other than the compound(s) of the invention, the other lipid component(s) and the biologically active agent. An excipient may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

The excipient may be an aqueous solution carrier which may optionally contain a buffer (e.g. a PBS buffer) and/or a sugar.

A thorough discussion of pharmaceutically acceptable excipients is available in Gennaro, *Remington: The Science and Practice of Pharmacy* 2000, 20th edition (ISBN: 0683306472).

The compositions of the invention may be administered orally. Oral administration may involve swallowing, so that the compound enters the gastrointestinal tract, and/or buccal, lingual, or sublingual administration by which the compound enters the blood stream directly from the mouth.

The compositions of the invention can be administered parenterally. The compounds and compositions of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, e.g., by lyophilisation, may readily be accomplished using standard pharmaceutical techniques well known to the skilled person.

The solubility of the compounds and compositions used in the preparation of parenteral solutions may be increased by the use of appropriate formulation techniques, such as the incorporation of co-solvents and/or solubility-enhancing agents such as surfactants, micelle structures and cyclodextrins.

The compositions of the invention can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebuliser contains a solution or suspension of the compound(s) of the invention comprising, e.g., ethanol, aqueous ethanol, or a suitable alternative agent for dispersing, solubilising, or extending release of the compositions of the invention, a propellant(s) as solvent and an optional surfactant, such as sorbitan trioleate, oleic acid, or an oligolactic acid.

Prior to use in a dry powder or suspension formulation, the composition is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, e.g., from gelatin or hydroxypropylmethylcellulose), blisters and cartridges for use in an inhaler or insufflator may be formulated to contain a powder mix of the compound or composition of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, e.g., PGLA. Modified release formulations include delayed-, sustained-, pulsed-, controlled-, targeted and programmed release.

Suitable formulations for transdermal application include a therapeutically effective amount of a compound or composition of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Lipid compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Lipid compositions of the invention can be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Suitable formulations for use in the present invention can be found, e.g., in Remington's Pharmaceutical Sciences, Mack Publishing Company, Philadelphia, Pa., 17.sup.th Ed. (1985). Often, compositions will comprise a solution of the lipid nanoparticles suspended in an acceptable carrier, such as an aqueous carrier.

In one embodiment, this invention provides for a pharmaceutical composition (i.e. formulation) comprising a lipid composition of the invention and a pharmaceutically acceptable carrier or excipient. In another embodiment at least one other lipid component is present in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is a RNA or DNA.

For immunization purposes a composition will generally be prepared as an injectable, and will be administered by injection (e.g. by intramuscular injection).

The invention also provides a delivery device (e.g. syringe, nebuliser, sprayer, inhaler, dermal patch, etc.) containing a composition of the invention. This device can be used to administer a pharmaceutical composition to a subject e.g. to a human for immunization.

Cells and Organs Targeted by the Invention

The compounds, compositions, methods and uses of the invention can be used to deliver a biologically active agent to one or more of the following in a patient: the liver or liver cells (e.g. hepatocytes);

a kidney or kidney cells;

a tumor or tumor cells;

the CNS or CNS cells (Central Nervous System, e.g. brain and/or spinal cord);

the PNS or PNS cells (Peripheral Nervous System);

a lung or lung cells;

the vasculature or vascular cells;

the skin or skin cells (e.g. dermis cells and/or follicular cells);

an eye or ocular cells (e.g. macula, fovea, cornea, retina), and an ear or cells of the ear (e.g. cells of the inner ear, middle ear and/or outer ear).

The compounds, compositions, methods and uses of the invention can also be used to deliver a biologically active agent (e.g. RNA which encodes an immunogen) to cells of the immune system.

In one embodiment, the compounds, compositions, methods and uses of the invention are for delivering a biologically active agent to liver cells (e.g. hepatocytes). In one embodiment, the compounds, compositions, methods and uses of the invention are for delivering a biologically active agent to a tumor or to tumor cells (e.g. a primary tumor or metastatic cancer cells). In another embodiment, the compounds, compositions, methods and uses are for delivering a biologically active agent to the skin adipose, muscle and lymph nodes (i.e. sc dosing).

For delivery of a biologically active agent to the liver or liver cells, in one embodiment a composition of the invention is contacted with the liver or liver cells of the patient as is generally known in the art, such as via parental administration (e.g. intravenous, intramuscular, subcutaneous administration) or local administration (e.g. direct injection, portal vein injection, catheterization, stenting), to facilitate delivery.

For delivery of a biologically active agent to the kidney or kidney cells, in one embodiment a composition of the invention is contacted with the kidney or kidney cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to a tumor or tumor cells, in one embodiment a composition of the invention is contacted with the tumor or tumor cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to the CNS or CNS cells (e.g. brain cells and/or spinal cord cells), in one embodiment a composition of the invention is contacted with the CNS or CNS cells (e.g. brain cells and/or spinal cord cells) of the patient as is generally known in the art, such as via parental administration (e.g. intravenous, intramuscular, subcutaneous administration) or local administration (e.g. direct injection, catheterization, stenting, osmotic pump administration (e.g. intrathecal or ventricular)), to facilitate delivery.

For delivery of a biologically active agent to the PNS or PNS cells, in one embodiment a composition of the invention is contacted with the PNS or PNS cells of the patient as is generally known in the art, such as via parental administration (e.g. intravenous, intramuscular, subcutaneous administration) or local administration (e.g. direct injection), to facilitate delivery.

For delivery of a biologically active agent to a lung or lung cells, in one embodiment a composition of the invention is contacted with the lung or lung cells of the patient as is generally known in the art, such as via parental administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a composition of the invention is contacted with the vasculature or vascular cells of the patient as is generally known in the art, such as via parental administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a composition of the invention is contacted with the skin or skin cells (e.g. dermis cells and/or follicular cells) of the patient as is generally known in the art, such as via parental administration (e.g. intravenous, intramuscular, subcutaneous administration) or local administration (e.g. direct dermal application, iontophoresis), to facilitate delivery.

For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient as is generally known in the art, such as via parental administration (e.g. intravenous, intramuscular, subcutaneous administration) or local administration (e.g. direct injection, intraocular injection, periocular injection, subretinal, iontophoresis, use of eyedrops, implants), to facilitate delivery.

For delivery of a biologically active agent to an ear or cells of the ear (e.g. cells of the inner ear, middle ear and/or outer ear), in one embodiment composition of the invention is contacted with the ear or cells of the ear (e.g. cells of the inner ear, middle ear and/or outer ear) of the patient as is generally known in the art, such as via parental administration (e.g. intravenous, intramuscular, subcutaneous administration) or local administration (e.g. direct injection), to facilitate delivery.

For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA. Such immune cells can include macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. (e.g. see WO2012/006372).

Immunization According to the Invention

For immunization purposes, in some embodiments, the invention encompasses delivering a RNA that encodes an immunogen. The immunogen elicits an immune response which recognizes the immunogen, and so can be used to provide immunity against a pathogen, or against an allergen, or against a tumor antigen. Immunising against disease and/or infection caused by a pathogen is preferred.

The RNA is delivered with a lipid composition of the invention (e.g. formulated as a liposome or LNP). In some embodiments, the invention utilises liposomes within which immunogen-encoding RNA is encapsulated. Encapsulation within liposomes can protect RNA from RNase digestion. The encapsulation efficiency does not have to be 100%. Presence of external RNA molecules (e.g. on the exterior surface of liposome) or "naked" RNA molecules (RNA molecules not associated with a liposome) is acceptable. Preferably, for a composition comprising liposomes and RNA molecules, at least half of the RNA molecules (e.g., at least 50%, at least 55%, at least 60%, at least 65%, at least 70%, at least 75%, at least 80%, at least 85%, at least 90%, or at least 95% of the RNA molecules) are encapsulated in liposomes.

RNA molecules may also be complexed with LNPs. For example, it is not necessary that the lipid forms liposomes (with aqueous core) only. Some lipid nanoparticles may comprise a lipid core (e.g., the composition may comprise a mixture of liposomes and nanoparticles with a lipid core). In such cases, the RNA molecules may be encapsulated by LNPs that have an aqueous core, and complexed with the LNPs that have a lipid core by non-covalent interactions (e.g., ionic interactions between negatively charged RNA and cationic lipid). Encapsulation and complexation with LNPs (whether with a lipid or aqueous core) can protect RNA from RNase digestion. The encapsulation/complexation efficiency does not have to be 100%. Presence of "naked" RNA molecules (RNA molecules not associated with a liposome) is acceptable. Preferably, for a composition comprising a population of LNPs and a population of RNA molecules, at least half of the population of RNA molecules (e.g., at least 50%, at least 55%, at least 60%, at least 65%, at least 70%, at least 75%, at least 80%, at least 85%, at least 90%, or at least 95% of the RNA molecules) are either encapsulated in LNPs, or complexed with LNPs.

Liposomes and LNPs

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter <50 nm, and LUVs have a diameter >50 nm. For delivery of immunogen-coding RNA, preferred range of diameters is in the range of 60-180 nm, and more preferably in the range of 80-160 nm.

The lipid composition can also be LNPs. The composition can comprise a mixture of nanoparticles having an aqueous core and nanoparticles having a lipid core. For delivery of immunogen-coding RNA, preferred range of diameters is in the range of 60-180 nm, and in more particular embodiments, in the range of 80-160 nm.

A liposome or LNP can be part of a composition comprising a population of liposomes or LNPs, and the liposomes or LNPs within the population can have a range of diameters. For a composition comprising a population of liposomes or LNPs with different diameters, it is preferred that (i) at least 80% by number of the liposomes or LNPs have diameters in the range of 60-180 nm, e.g., in the range of 80-160 nm, (ii) the average diameter (by intensity e.g. Z-average) of the population is ideally in the range of 60-180 nm, e.g., in the range of 80-160 nm; and/or (iii) the diameters within the plurality have a polydispersity index <0.2.

To obtain liposomes or LNPs with the desired diameter(s), mixing can be performed using a process in which two feed streams of aqueous RNA solution are combined in a single mixing zone with one stream of an ethanolic lipid solution, all at the same flow rate e.g. in a microfluidic channel.

Useful mixtures of lipids, for forming lipid compositions (e.g., liposomes or LNPs) for immunization uses, comprise: a lipid of formula (I); cholesterol; and a PEGylated lipid, such as PEG-DMG i.e. PEG-conjugated 1,2-dimyristoyl-sn-glycero-3-phosphoethanolamine-N-[methoxy(polyethylene glycol). This mixture may also include a neutral zwitterionic lipid, such as DSPC (1,2-Diastearoyl-sn-glycero-3-phosphocholine) or DPyPE. These (and other) mixtures are used in the examples.

In certain embodiments, the lipid compositions provided by the invention (such as liposomes or LNPs) have adjuvant activity, i.e., in the absence of an immunogen, such as protein antigen or a nucleic acid (DNA or RNA), such as a nucleic acid encoding such an antigen. Therefore the lipids and lipid composition provided by the invention can be formulated with any manner of antigen, e.g., polypeptide, nucleic acid, small molecule, et cetera. Thus, in some embodiments, compositions provided by the invention can be used in methods of generating an immune response to an immunogen, e.g., by administering a composition comprising a lipid or lipid composition provided by the invention together with an immunogen.

RNA Molecules

After in vivo administration of an immunization composition, the delivered RNA is released and is translated inside a cell to provide the immunogen in situ. In certain embodiments, the the RNA is plus ("+") stranded, so it can be translated by cells without needing any intervening replication steps such as reverse transcription. It may also bind to TLR7 receptors expressed by immune cells, thereby initiating an adjuvant effect. Additionally or alternatively, the RNA may bind other receptors such as RIG I, MDA5, or RIG I and MDA5.

In certain embodiments, the RNA is a self-replicating RNA. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus, in certain embodiments, a (+) strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is a huge amplification in the number of the introduced replicon RNAs and so the encoded immunogen becomes a major polypeptide product of the host cells.

One suitable system for achieving self-replication is to use an alphavirus-based RNA replicon. These (+) stranded replicons are translated after delivery to a cell to give of a replicase (or replicase-transcriptase). The replicase is translated as a polyprotein which auto cleaves to provide a replication complex which creates genomic (−) strand copies of the (+) strand delivered RNA. These (−) strand transcripts can themselves be transcribed to give further copies of the + stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc. Mutant or wild-type viruses sequences can be used e.g. the attenuated TC83 mutant of VEEV has been used in replicons.

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non structural replicase polyprotein, in particular embodiments, a self-replicating RNA molecule of the invention does not encode alphavirus structural proteins. Thus a particular self replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. One open reading frame encodes a replicase, e.g., the first, (5') open reading frame; the other open reading frame encodes an immunogen, e.g., the second, (3') open reading frame. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically 5000-25000 nucleotides long e.g. 8000-15000 nucleotides, or 9000-12000 nucleotides. Thus the RNA is longer than seen in siRNA or conventional mRNA delivery. In some embodiments, the self-replicating RNA is greater than about 2000 nucleotides, such as greater than about: 9000, 12000, 15000, 18000, 21000, 24000, or more nucleotides long A RNA molecule may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly A tail. It may also include a poly A polymerase recognition sequence (e.g. AAUAAA) near its 3' end.

A RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT transcribed RNA can function efficiently as a substrate for its self-encoded replicase.

As discussed in WO2011/005799, the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first 1, 2 or 3 5' ribonucleotides may be methylated at the 2' position of the ribose.

A RNA used with the invention for immunization purposes ideally includes only phosphodiester linkages between nucleosides, but in some embodiments it can contain phosphoramidate, phosphorothioate, and/or methylphosphonate linkages.

The invention includes embodiments where multiple species of RNAs are formulated with a lipid composition provided by the invention, such as 2, 3, 4, 5, 6, 7, 8, 9, 10, or more species of RNA, including different classes of RNA (such as mRNA, siRNA, self-replicating RNAs, and combinations thereof).

Immunogens

RNA molecules used with the invention for immunization purposes, in some embodiments, encode a polypeptide immunogen. In these embodiments, after administration, the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognises the corresponding pathogen (or allergen or tumor) polypeptide, but in some embodiments the polypeptide may act as a mimotope to elicit an immune response which recognises a saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

In certain embodiments, polypeptide immunogens (e.g., 1, 2, 3, 4, 5, 6, 7, 8, 9, 10, or more immunogens) may be used, either alone or together with a RNA molecule, such as a self-replicating RNA, encoding one or more immunogens (either the same or different as the polypeptide immunogens).

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in Giuliani et al. (2006) *Proc Natl Acad Sci USA* 103(29):10834-9.

*Streptococcus pneumoniae*: useful polypeptide immunogens are disclosed in WO2009/016515. These include, but are not limited to, the RrgB pilus subunit, the beta-N-acetylhexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in WO02/34771 and WO2005/032582.

*Moraxella catarrhalis.*

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in WO2010/119343, such as a hemolysin, esxA, esxB, ferrichrome-binding protein (sta006) and/or the sta011 lipoprotein.

*Clostridium tetani*: the typical immunogen is tetanus toxoid.

*Corynebacterium diphtheriae*: the typical immunogen is diphtheria toxoid.

*Haemophilus influenzae*: Useful immunogens include, but are not limited to, the polypeptides disclosed in WO2006/110413 and WO2005/111066.

*Pseudomonas aeruginosa*

*Streptococcus agalactiae*: useful immunogens include, but are not limited to, the polypeptides disclosed in WO02/34771.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in WO2005/002619). LcrE (WO2006/138004) and HtrA (WO2009/109860) are two preferred immunogens.

*Chlamydia pneumoniae*: Useful immunogens include, but are not limited to, the polypeptides disclosed in WO02/02606.

*Helicobacter pylori*: Useful immunogens include, but are not limited to, CagA, VacA, NAP, and/or urease (WO003/018054).

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in WO2006/091517 and WO2008/020330. Useful MNEC immunogens are disclosed in WO2006/089264. A useful immunogen for several *E. coli* types is AcfD (WO2009/104092).

*Bacillus anthracis*

*Yersinia pestis*: Useful immunogens include, but are not limited to, those disclosed in WO2007/049155 and WO2009/031043.

*Staphylococcus epidermis*
*Clostridium perfringens* or *Clostridium botulinums*
*Legionella pneumophila*
*Coxiella burnetii*
*Brucella*, such as *B. abortus, B. canis, B. melitensis, B. neotomae, B. ovis, B. suis, B. pinnipediae.*

*Francisella*, such as *F. novicida, F. philomiragia, F. tularensis.*
*Neisseria gonorrhoeae*
*Treponema pallidum*
*Haemophilus ducreyi*
*Enterococcus faecalis* or *Enterococcus faecium*
*Staphylococcus saprophyticus*
*Yersinia enterocolitica*
*Mycobacterium tuberculosis*
*Rickettsia*
*Listeria monocytogenes*
*Vibrio cholerae*
*Salmonella typhi*
*Borrelia burgdorferi*
*Porphyromonas gingivalis*
*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: immunogens include, but are not limited to, those derived from Orthopoxvirus such as Variola vera, including but not limited to, Variola major and Variola minor.

Picomavirus: immunogens include, but are not limited to, those derived from Picomaviruses, such as Enteroviruses, Rhinoviruses, Hepamavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Hepamavirus: immunogens include, but are not limited to, those derived from a Hepamavirus, such as hepatitis A virus (HAV).

Filovirus: immunogens include, but are not limited to, those derived from a filovirus, such as an Ebola virus (including a Zaire, Ivory Coast, Reston or Sudan ebolavirus) or a Marburg virus.

Togavirus: immunogens include, but are not limited to, those derived from a Togavirus, such as a Rubivirus, an Alphavirus, or an Arterivirus. This includes rubella virus.

Flavivirus: immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: immunogens include, but are not limited to, those derived from a Pestivirus, such as Bovine viral diarrhea (BVDV), Classical swine fever (CSFV) or Border disease (BDV).

Hepadnavirus: immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: immunogens include, but are not limited to, those derived from a Rhabdovirus, such as a Lyssavirus (e.g. a Rabies virus) and Vesiculovirus (VSV).

Caliciviridae: immunogens include, but are not limited to, those derived from Calciviridae, such as Norwalk virus (Norovirus), and Norwalk-like Viruses, such as Hawaii Virus and Snow Mountain Virus.

Coronavirus: immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: immunogens include, but are not limited to, those derived from an Oncovirus, a Lentivirus (e.g. HIV-1 or HIV-2) or a Spumavirus.

Reovirus: immunogens include, but are not limited to, those derived from an Orthoreovirus, a Rotavirus, an Orbivirus, or a Coltivirus.

Parvovirus: immunogens include, but are not limited to, those derived from Parvovirus B19.

Herpesvirus: immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: immunogens include those derived from serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum var. album, var. discoides, var. ochraceum, Trichophyton violaceum,* and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria.

In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dactylis, Holcus, Phalaris, Secale,* and Sorghum, the orders of Asterales and Urticales including herbs of the genera *Ambrosia, Artemisia,* and *Parietaria*. Other important inhalation allergens are those from house dust mites of the genus *Dermatophagoides* and Euroglyphus, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (*Apidae*), wasps (*Vespidea*), and ants (*Formicoidae*).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

A pharmaceutical composition of the invention, particularly one useful for immunization, may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Such agonist(s) can, in some embodiments, be encapsulated with the RNA inside liposomes, or encapsulated or complexed with LNPs, but in other embodiments they are unencapsulated or uncomplexed.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2 phenoxyethanol. Mercury-free compositions can be made and preservative-free vaccines can be prepared.

Compositions comprise an immunologically effective amount of lipid compositions described herein (e.g., liposomes and LNPs), as well as any other components, as needed. Immunologically effective amount refers to the amount administered to an individual, either in a single dose or as part of a series, is effective for treatment (e.g., prophylactic immune response against a pathogen). This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. The compositions of the invention will generally be expressed in terms of the amount of RNA per dose. A preferred dose has ≤100 μg RNA (e.g. from 10-100 μg, such as about 10 μg, 25 μg, 50 μg, 75 μg or 100 μg), but expression can be seen at much lower levels e.g. ≤1 μg/dose, ≤100 ng/dose, ≤10 ng/dose, ≤1 ng/dose, etc.

The invention also provides a delivery device (e.g. syringe, nebuliser, sprayer, inhaler, dermal patch, etc.) containing a pharmaceutical composition of the invention. This device can be used to administer the composition to a vertebrate subject.

Liposomes or LNPs of the invention do not comprise ribosomes.

Methods of Treatment and Medical Uses

The liposome-formulated or LNP-formulated RNA and pharmaceutical compositions described herein are for in vivo use for inducing an immune response against an immunogen of interest.

The invention provides a method for inducing an immune response in a vertebrate comprising administering an effective amount of the liposome-formulated or LNP-formulated RNA, or pharmaceutical composition, as described herein. The immune response is preferably protective and preferably involves antibodies and/or cell-mediated immunity. The compositions may be used for both priming and boosting purposes. Alternatively, a prime-boost immunization schedule can be a mix of RNA and the corresponding polypeptide antigen (e.g., RNA prime, protein boost).

The invention also provides a liposome, LNP, or pharmaceutical composition for use in inducing an immune response in a vertebrate.

The invention also provides the use of a liposome, LNP, or pharmaceutical composition in the manufacture of a medicament for inducing an immune response in a vertebrate.

By inducing an immune response in the vertebrate by these uses and methods, the vertebrate can be protected against various diseases and/or infections e.g. against bacterial and/or viral diseases as discussed above. The liposomes, LNPs, and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). As used herein "large mammal" refers to mammals having a typical or average adult weight of at least 5 kg, preferably at least 7 kg. Such large mammals can include, for example, humans, non-human primates, dogs, pigs, cattle, deerd, goats, and is meant to exclude small mammals, such as mice, rats, guinea pigs, and other rodents.

Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population. Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; intraglossal injection is not typically used for immunization purposes. Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to induce systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

EXAMPLES

Cationic Lipids of Formula (I)

The following examples are intended to illustrate the invention and are not to be construed as being limitations thereon. Temperatures are given in degrees centigrade. If not mentioned otherwise, all evaporative concentrations are performed under reduced pressure, preferably between about 15 mm Hg and 100 mm Hg (=20-133 mbar). The structure of final products, intermediates and starting materials is confirmed by standard analytical methods, e.g., microanalysis or spectroscopic characteristics, e.g., MS, IR, or NMR. Abbreviations used are those conventional in the art, some of which are defined below.

Flash column purification is preferably carried out on silica gel using an appropriate eluent of isocratic or gradient composition.

HPLC analysis is performed on a Waters Atlantis dC18 column (4.6×150 mm, 3 mm), with gradient elution (0% to 95% acetonitrile in water modified with 0.1% v/v trifluoroacetic acid over 20 min and a flow rate of 1.4 mL/min), unless otherwise described.

1H NMR spectra were recorded on a Bruker Avance II 400 MHz spectrometer. All chemical shifts are reported in parts per million (δ) relative to tetramethylsilane. The following abbreviations are used to denote signal patterns: s=singlet, d=doublet, t=triplet, q=quartet, m=multiplet, br=broad. ES-MS data were recorded using a Waters LTC Premier mass spectrometer with a dual electrospray ionization source on an Agilent 1100 liquid chromatograph. Sulfadimethoxine [Sigma, m/z=311.0814 (M+1)] was used as a reference acquired through the LockSpray™ channel every third scan. The mass accuracy of the system has been found to be <5 ppm.

ABBREVIATIONS

AcOH acetic acid
Aq aqueous
Ar aryl
Atm atmosphere
BOC tert-Butyl-carbonate
br.s., bs broad singlet
° C. Celsius
$CD_2Cl_2$ deuterated dichloromethane
$CDCl_3$ deuterated chloroform
$CH_2Cl_2$, DCM dichloromethane
$CH_3CN$, MeCN acetonitrile
d doublet
dd doublet of doublets
ddd doublet of doublets of doublets
DIPEA N-ethyldiisopropylamine
DME 1,4-dimethoxyethane
DMF N,N-dimethylformamide
DMAP dimethyl aminopyridine
DMSO dimethylsulfoxide
dt doublet of triplets
EDC 1-ethyl-3-(3-dimethylaminopropyl)carbodiimide
EtOAc ethyl acetate
EtOH ethanol
FCC flash column chromatography
G gauge
h hour HBTU (2-(1H-benzotriazole-1-yl)-1,1,3,3-tetramethyluronium hexafluorophosphate
HCl hydrochloric acid
HMPA hexamethylphosphoramide
HPLC high pressure liquid chromatography
HT high throughput
IBX 2-Iodoxybenzoic acid
i-PrOH isopropyl alcohol
$H_2O$ water
K kelvin
KOH potassium hydroxide
LC liquid chromatography
M molar
m multiplet, mass
MeOH methanol
$MgSO_4$ magnesium sulfate
MHz megahertz
mL milliliter
mm millimeter
mmol millimole
min. minute
mRNA messenger ribonucleic acid
MS mass spectroscopy
mw microwave
NaH sodium hydride
NaHMDS sodium hexamethyldisilazane
NaOEt sodium ethoxide
NaOH sodium hydroxide
$Na_2SO_4$ sodium sulfate
$NEt_3$ triethylamine
ng nanogram
$NH_3$ ammonia
NMR nuclear magnetic resonance
quint. quintuplet
Pd/C palladium on carbon
ppt precipitate
rbf round bottom flask
Rf retardation factor
rt room temperature
Rt Retention time
s singlet
sat. saturated
siRNA small interfering ribonucleic acid
SM starting material
t triplet
TFA trifluoroacetic acid
THF tetrahydrofuran
TLC thin layer chromatography
UPLC ultra performance liquid chromatography
wt weight
μg microgram
μL microliter
IBX 2-iodobenzoic acid
PMA phosphomolybdic acid
PPTS pyridinium p-toluenesulfonate
TBDPS tert-butyl diphenyl silyl
TBDPSCl tert-butyl diphenyl silyl chloride
TBS tert-butyl silyl All compounds are named using AutoNom.

LC Specificity:

LC Method 1: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 0.1/99.9 was applied over 1.4 min., then held for 0.6 min. (1.0 mL/min. as solvent flow) at an oven temperature of 50° C.

LC Method 2: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 0.1/99.9 was applied over 3.4 min., then held for 1.6 min. (1.0 mL/min. as solvent flow) at an oven temperature of 50° C.

LC Method 3: The retention times (Rt) were obtained on an Agilent 1100 system with an Inertsil C8 Column, 3.0 μm, 3.0×30 mm. A gradient of $H_2O$ (+0.1% formic acid)/$CH_3CN$ (+0.1% formic acid) 60/40 to 5/95 was applied over 1.0 min., then held for 1.0 min. (2.0 mL/min. as solvent flow) at an oven temperature of 50° C.

LC Method 4: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 0/100 was applied over 2.0 min., then held for 3.0 min. (1.0 mL/min. as solvent flow) at an oven temperature of 50° C.

LC Method 5: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 0/100 was applied over 1.0 min., then held for 1.0 min. (1.0 mL/min. as solvent flow) at an oven temperature of 50° C.

LC Method 6: The retention times (Rt) were obtained on an Agilent 1100 system on an Inertsil C8 Column, 3.0 μm, 3.0×30 mm. A gradient of $H_2O$ (+0.1% formic acid)/$CH_3CN$ (+0.1% formic acid) 60/40 to 5/95 was applied over 1.0 min., then held for 1.0 min. (2.0 mL/min. as solvent flow) at an oven temperature of 50° C.

LC Method 7: The retention times (Rt) were obtained on an Agilent 1100 system with an XBridge C8 Column, 3.0 μm, 3.0×30 mm. A gradient of $H_2O$ (+0.1% formic acid)/$CH_3CN$ (+0.1% formic acid) 60/40 to 5/95 was applied over 1.0 min., then held for 1.0 min. (2.0 mL/min. as solvent flow) at an oven temperature of 50° C.

LC Method 8: The retention times (Rt) were obtained on an Agilent 1100 system with an XBridge C8 Column, 3.0 μm, 3.0×30 mm. A gradient of $H_2O$ (+5 mM Ammonium Formate, 2% ACN)/$CH_3CN$ 60/40 to 5/95 was applied over 1.0 min., then held for 1.0 min. (2.0 mL/min. as solvent flow) at an oven temperature of 50° C.

LC Method 9: The retention times (Rt) were obtained on an Agilent 1100 system with an Atlantis C18 Column, 3.5 μm, 3.0×30 mm. A gradient of $H_2O$ (+0.05% trifluoroacetic acid)/$CH_3CN$ 60/40 to 2/98 was applied over 1.7 min., then held for 0.3 min. (2.0 mL/min. as solvent flow), then changed to 60/40 over 0.1 min at an oven temperature of 40° C.

LC Method 10: The retention times (Rt) were obtained on an Agilent 1100 system with an XBridge C18 Column, 3.5 μm, 2.1×50 mm. A gradient of $H_2O$ (+0.1% formic acid)/$CH_3CN$ 95/5 to 5/95 was applied over 1.7 min., then held for 0.2 min. (2.0 mL/min. as solvent flow), then changed to 95/5 over 0.1 min at an oven temperature of 40° C.

LC Method 11: The retention times (Rt) were obtained on an Agilent 1100 system with an XBridge C18 Column, 3.5 μm, 2.1×50 mm. A gradient of $H_2O$ (+0.1% formic acid)/$CH_3CN$ 95/5 to 5/95 was applied over 1.7 min., then held for 0.2 min. (2.0 mL/min. as solvent flow), then changed to 95/5 over 0.1 min at an oven temperature of 40° C.

LC method 12: The retention times (Rt) were obtained on a Waters Acquity SDS system with an Acquity BEH C18 1.7 μm 2.1×50 mm column. A gradient of $H_2O$ (+0.1% formic acid)/$CH_3CN$ (+0.1% formic acid) 45/55 to 1/99 was applied over 1.4 min., then a gradient of 1/99 to 0/100 was applied over 3.7 min. (1.0 mL/min. as solvent flow) at an oven temperature of 50° C.

LC method 13: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 2/98 was applied over 3.4 min., then held for 1.7 min. (1.0 mL/min. as solvent flow) at an oven temperature of 50° C.

LC method 14: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 1/99 was applied over 0.7 min., then held for 1.3 min. (1.0 mL/min. as solvent flow) at an oven temperature of 50° C.

Synthesis of Example 1: 2-(10-dodecyl-3-ethyl-8,14-dioxo-7,9,13-trioxa-3-azaoctadecan-18-yl)propane-1,3-diyl dioctanoate Intermediate 1a: 5-(benzyloxy)pentyl methanesulfonate

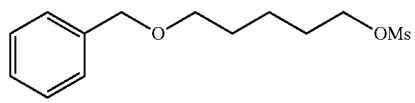 [SMILES: CS(=O)(=O)OCCCCCOCc1ccccc1]

Et$_3$N (10.79 mL, 78 mmol) was added in one portion via syringe to a solution of 5-Benzyloxy-1-pentanol (10.08 g, 51.9 mmol) in DCM (75 mL) in a round bottom flask charged with a magnetic stir bar at 0° C. under $N_2$. Next, MsCl (4.85 mL, 62.3 mmol) was added dropwise via syringe in 4 separate portions at a rate such that the internal temperature did not exceed 15° C. The reaction was allowed to continue to stir for 1 hour, after which it was diluted with $H_2O$ (200 mL) and DCM (150 mL). The organic layer was separated, and the aqueous layer was washed with DCM (225 mL). The combined organic layers were washed with brine (200 mL), dried with $Na_2SO_4$, filtered, and concentrated under reduced pressure to provide the title compound as a crude orange oil (14.46 g, 99%). MS (M+1)=272.9, Rt=1.33 min (LC method 10).

Intermediate 1b: diethyl 2-(5-(benzyloxy)pentyl)malonate

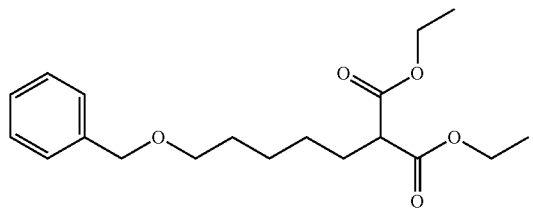 [SMILES: CCOC(=O)C(CCCCCOCc1ccccc1)C(=O)OCC]

To a cold, 0° C., solution of diethyl malonate (7.5 g, 46.8 mmol) in dry DMF (100 mL) under $N_2$ atmosphere was added 60% NaH (2.23 g, 56.2 mmol) portionwise over 10 min. The evolution of gas was observed. The mixture was stirred at 0° C. for 30 min then Intermediate 1a (14.46 g, 51.5 mmol) in dry DMF (41 mL) was added dropwise over 10 min followed by tetrabutylammonium iodide (1.73 g, 4.68 mmol). The mixture was then heated at 100° C. for 1.5 h. The mixture was cooled at rt and left overnight. The mixture was then quenched with sat. NH$_4$Cl (50 mL) and diluted with $H_2O$ (100 mL). The mixture was extracted with EtOAc (2×200 mL). The combined organic layers were washed with $H_2O$ (100 mL), brine (100 mL), dried over MgSO$_4$, filtered, and concentrated on vacuo. The residue was purified by silica gel column chromatography eluting with 0-30% EtOAc/heptane to afford the title compound as an oil (11.7 g, 74%). MS (M+1)=336.6, Rt=1.64 min (LC method 10).

Intermediate 1c: 2-(5-(benzyloxy)pentyl)propane-1,3-diol

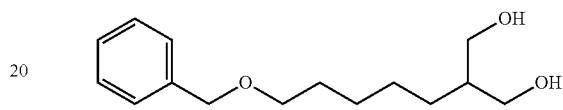

To a cold solution, 0° C., of Intermediate 1b (5.5 g, 16.35 mmol) in dry THF (20 mL) under $N_2$ was added 2.0 M LiAlH$_4$ in THF (24.52 mL, 49.0 mmol) dropwise over 15 min. The mixture was allowed to warm to rt and stirred overnight. The mixture was cooled to 0° C., treated again with 2.0 M LiAlH$_4$ in THF (16.35 mL, 32.7 mmol), allowed to warm to rt, and stirred over the weekend. The reaction was cooled to 0° C. and quenched with EtOAc (9.30 mL) dropwise over 10 min. The mixture was then treated with $H_2O$ (3.10 mL) dropwise, a 15% NaOH solution (3.10 mL) solution dropwise, and then additional $H_2O$ (9.30) dropwise. The mixture was stirred for 30 min at rt. The mixture was filtered through a pad of Celite. The Celite was washed with EtOAc. The filtrate was concentrated under reduced pressure to afford the title compound as a semi-wax solid (1.52 g, 37%). MS (M+1)=253.0, Rt=1.37 min (LC method 10).

Intermediate 1d: 2-(5-(benzyloxy)pentyl)propane-1,3-diyl dioctanoate

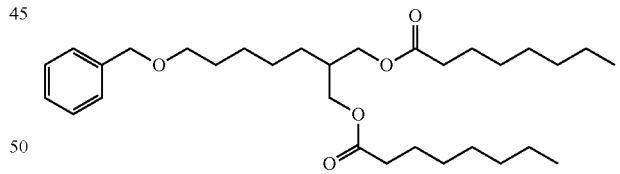

Pyridine (1.21 mL, 14.96 mmol) was added dropwise via syringe over ~30 seconds to a solution of Intermediate 1c (1.51 g, 5.98 mmol) in DCM (20 mL) in a round bottom flask charged with a magnetic stir bar at 0° C. under $N_2$. Next, octanoyl chloride (2.145 mL, 12.57 mmol) was added dropwise via syringe over several minutes, and the reaction was allowed to warm to rt and stirred overnight. The mixture was diluted with sat. NH$_4$Cl (100 mL) and CH$_2$Cl$_2$ (100 mL). The organic was separated. The aqueous was extracted with CH$_2$Cl$_2$ (100 mL). The combined organics were dried over MgSO$_4$, filtered, and concentrated under reduced pressure. The crude material was purified by silica gel column chromatography eluting with 0-10% EtOAc/heptane to afford the title compound as a colorless oil (2.88 g, 95%). MS (M+1)=505.6, Rt=1.77 min (LC method 1).

Intermediate 1e:
2-(5-hydroxypentyl)propane-1,3-diyl dioctanoate

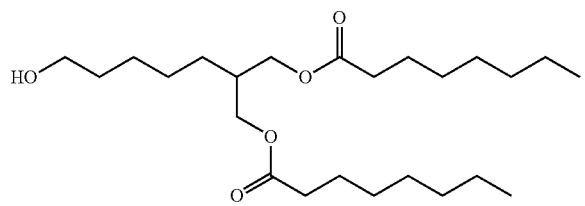 [SMILES: CCCCCCCC(=O)OCC(CCCCCO)COC(=O)CCCCCCC]

To a solution of Intermediate 1d (2.5 g, 4.95 mmol) in MeOH (25 ml) at rt was added 10% Pd/C, wet degussa type (264 mg). The mixture was stirred under a $H_2$ balloon overnight. The crude reaction mixture was filtered through a pad of celite and filtrate was concentrated under reduced pressure to afford the title compound as a colorless oil (2.0 g, 97%). $^1$H NMR (400 MHz, $CD_2Cl_2$) δ 4.11-3.96 (m, 4H), 3.59 (t, J=6.5 Hz, 2H), 2.28 (t, J=7.5 Hz, 4H), 2.04-1.91 (m, 1H), 1.66-1.48 (m, 7H), 1.41-1.34 (m, 6H), 1.34-1.20 (m, 16H), 0.88 (t, J=6.8 Hz, 6H).

Intermediate 1f:
7-(octanoyloxy)-6-((octanoyloxy)methyl)heptanoic acid

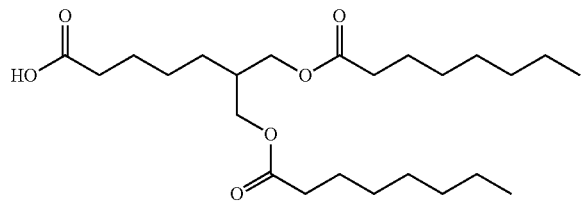 [SMILES: CCCCCCCC(=O)OCC(CCCCC(=O)O)COC(=O)CCCCCCC]

TEMPO (0.151 g, 0.965 mmol) was added in one portion to Intermediate 1e (2.0 g, 4.82 mmol) in MeCN:$H_2O$ (46.84 mL, 1:1 ratio) in a vial charged with a magnetic stir bar at rt. Next, iodobenzene diacetate (3.42 g, 10.61 mmol) was added in one portion, and the reaction was allowed to continue to stir at rt overnight, after which the reaction was quenched with 15% aqueous sodium thiosulfate (50 mL). The reaction was diluted with $H_2O$ and extracted with EtOAc (3×100 mL). The combined organic layers were dried with $Na_2SO_4$, filtered, and concentrated under reduced pressure to provide a pale yellow oil. The oil was dissolved in toluene (15 mL) and concentrated under reduced pressure (×6) to provide a pale yellow oil, which was dissolved in DCM and concentrated under reduced pressure (×3) to provide the title compound (plus minor aromatic impurities which could correspond to either residual toluene or iodobenzene) as a pale yellow oil (2.0 g, 97%). MS (M−1)= 427.2, Rt=1.73 min (LC method 9).

Intermediate 1g:
3-((tert-butyldimethylsilyl)oxy)propanal

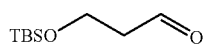

In a 1 L round-bottom flask equipped with a stir bar, Tertbutyldimethylsilyloxypropanol (20 g, 105 mmol) was dissolved in DCM (500 mL). $Et_3N$ (43.9 mL, 315 mmol) was added. In a second 500 mL flask equipped with a stirbar, $SO_3$·Py (25.08 g, 158 mmol) was dissolved in DMSO (100 mL, 1409 mmol). The resulting solution was added dropwise to the alcohol solution at 0° C. (in an ice-water bath). The reaction was stirred while warming to rt over the weekend. Water and DCM were added to the mixture in a separatory funnel. The organics were then washed with water, extracted in DCM, dried over $MgSO_4$, filtered and concentrated (cold) under reduced pressure to give crude product mixture. Purification by silica gel column chromatography (330 g column, 100% DCM) provided the title compound (17.7 g, 89%). $^1$H NMR (400 MHz, $CDCl_3$) δ=9.81 (t, J=2.1 Hz, 1H), 3.99 (t, J=6.0 Hz, 2H), 2.61 (td, J=6.0, 2.3 Hz, 2H), 0.88 (s, 9H), 0.07 (s, 6H).

Intermediate 1h:
1-((tert-butyldimethylsilyl)oxy)pentadecan-3-ol

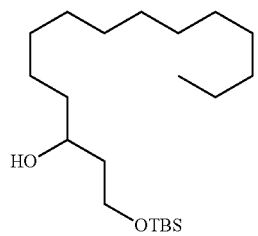

In a 500 mL round-bottom flask, Intermediate 1g (17.7 g, 94 mmol) was dissolved in THF (100 mL), and cooled to 0° C. in an ice-water bath. Dodecylmagnesiumbromide, 1M in diethyl ether (132 mL, 132 mmol) was then added to the aldehyde dropwise over 10 min via pipette, the ice-bath was removed, and reaction was stirred at rt for 30 min. The reaction flask was cooled again to 0° C. in an ice-bath. Sat. $NH_4Cl$ soln was added slowly to adjust to pH ~7 (600 mL), and the mixture was poured into a 1 L separatory funnel. The organics were then washed with sat. ammonium chloride solution, extracted in EtOAc, dried over $MgSO_4$, filtered and concentrated under reduced pressure to give the crude product mixture. Purification by silica gel column chromatography (330 g column, 100% Heptanes for 2 column volumes, 0% to 2% EtOAc/Heptane for 1 column volume, 2% EtOAc/Heptane for 3 column volumes, 2% to 5% EtOAc/Heptane for 1 column volume, then 5% EtOAc/Heptane for 10 column volumes) provided the title compound (24.9 g, 74%). $^1$H NMR (400 MHz, $CDCl_3$) δ 3.97-3.87 (m, 1H), 3.87-3.77 (m, 2H), 1.69-1.60 (m, 2H), 1.57-1.36 (m, 3H), 1.36-1.19 (br, 19H), 0.93-0.84 (m, 12H), 0.09 (s, 6H).

Intermediate 1i: 1-((tert-butyldimethylsilyl)oxy)pentadecan-3-yl (4-nitrophenyl) carbonate

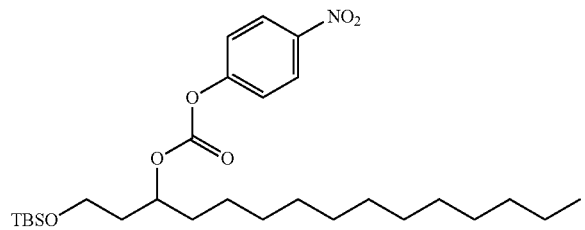 [SMILES: CCCCCCCCCCCCC(CCO[Si](C)(C)C(C)(C)C)OC(=O)Oc1ccc([N+](=O)[O-])cc1]

4-nitrophenyl carbonochloridate (2.084 g, 9.92 mmol) was added in one portion to a solution of Intermediate 1h (2.9660 g, 8.27 mmol) in DCM (28 mL) in a round bottom flask charged with a magnetic stir bar at rt. The reaction was fitted with a septum and placed under $N_2$, after which pyridine (1.003 mL, 12.40 mmol) was added dropwise via syringe over several minutes. The reaction was allowed to stir at rt overnight. After 24 hours of reaction time, the reaction was diluted with $H_2O$ (100 mL) and DCM (125 mL). The organic layer was separated, and the aqueous layer was washed with DCM (125 mL). The combined organic layers were washed with brine (100 mL), dried with $Na_2SO_4$, filtered, and concentrated under reduced pressure to provide an off white residue. The crude residue was purified by silica gel column chromatography (80 g column, liquid loading, 0-2.5% EtOAc:heptane) to provide 3.144 g (73%) of the title compound (plus minor unidentified impurity peaks) as a colorless oil. $^1$H NMR (400 MHz, $CD_2Cl_2$) δ 8.29-8.24 (m, 2H), 7.41-7.35 (m, 2H), 5.03-4.95 (m, 1H), 3.73 (dd, J=6.6, 5.7 Hz, 2H), 1.95-1.80 (m, 2H), 1.80-1.63 (m, 2H), 1.45-1.19 (m, 20H), 0.92-0.83 (m, 12H), 0.06 (s, 6H).

Intermediate 1j: 1-((tert-butyldimethylsilyl)oxy)pentadecan-3-yl (3-(diethylamino)propyl) carbonate

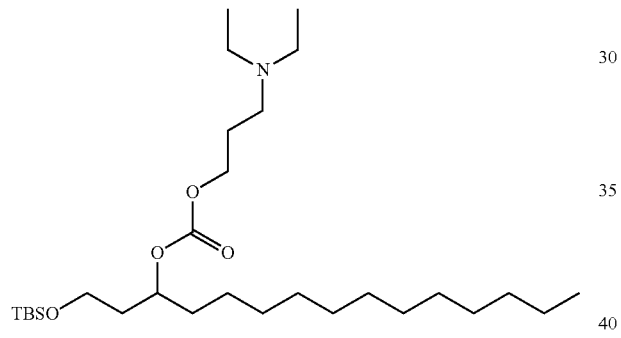

3-(diethylamino)propan-1-ol (3.48 mL, 22.26 mmol) was added dropwise via syringe over a few minutes to Intermediate 1i (2.9153 g, 5.57 mmol) in DCM (40 mL) in a round bottom flask charged with a magnetic stir bar under $N_2$. Next, pyridine (2.251 mL, 27.8 mmol) was added dropwise via syringe over ~30 seconds, followed by the addition of DMAP (0.136 g, 1.113 mmol) in one portion. The reaction was allowed to continue to stir at rt overnight. After 22 hours of reaction time, the reaction was diluted with $H_2O$ (200 mL) and DCM (200 mL). The organic layer was separated and the aqueous layer was washed with DCM (200 mL). The combined organic layers were washed with brine (100 mL), dried with $Na_2SO_4$, filtered, and concentrated under reduced pressure to provide a crude yellow-orange oil, which was purified by silica gel column chromatography (120 g column, liquid loading (in DCM), 0-8% MeOH:DCM) to provide a yellow oil. The yellow oil was passed through a bond elut NH2 column (10 g), eluting with DCM. The filtrate was concentrated under reduced pressure to provide a pale yellow oil. The bond elut procedure was repeated again to provide the title compound as a colorless oil (2.0887 g, 73%). MS (M+1)=516.4, Rt=1.42 min (LC method 9).

Intermediate 1k: 3-(diethylamino)propyl (1-hydroxypentadecan-3-yl) carbonate

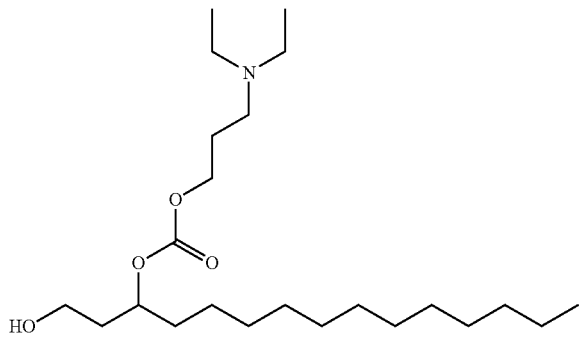 [SMILES: CCCCCCCCCCCCC(CCO)OC(=O)OCCCN(CC)CC]

To a solution of Intermediate 1j (2.2 g, 4.26 mmol) in MeOH (50 mL) at rt was added CAN (5.14 g, 9.38 mmol) in one portion. The mixture was stirred at rt and followed by TLC (70% EtOAc/heptane, $KMnO_4$ stain). After the consumption of starting material was observed, the mixture was diluted with $CH_2Cl_2$ (100 mL), and washed with sat. $NaHCO_3$ (2×100 mL). The aqueous layer was extracted with $CH_2Cl_2$ (100 mL). The combined organics were dried over $Na_2SO_4$, filtered, and concentrated under reduced pressure to afford the title compound (along with some minor impurities) as an oil. MS (M+1)=402.2, Rt=0.76 min (LC Method 9).

Preparation of Final Compounds

Scheme X

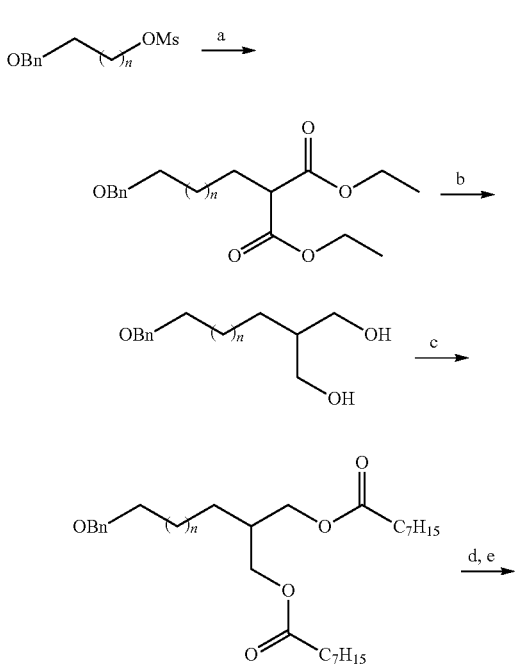

101
-continued

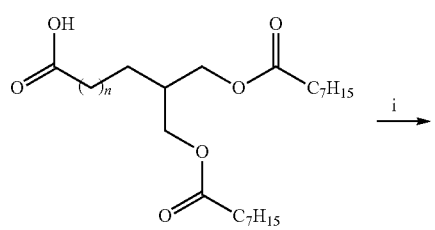

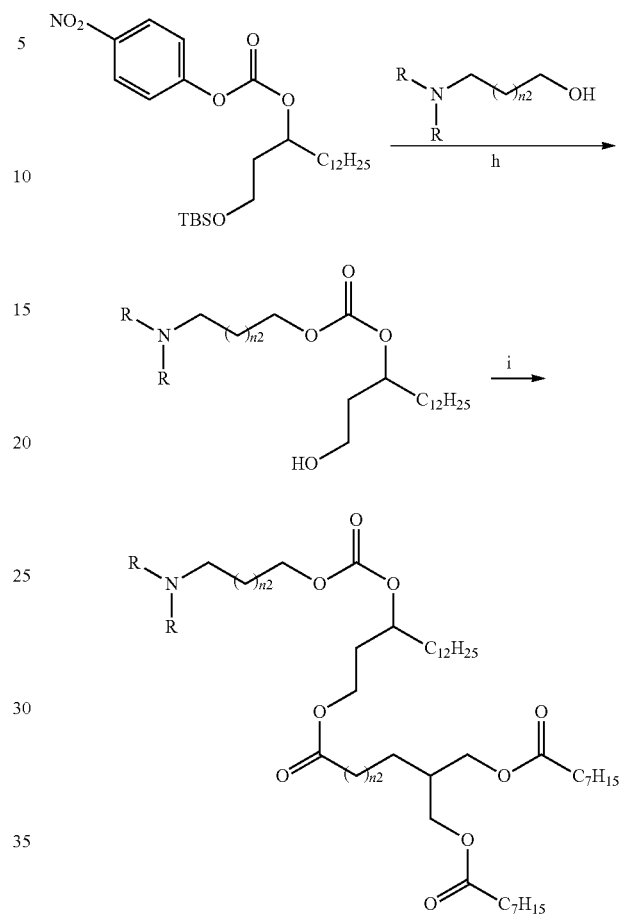

102
-continued a) Treatment with diethyl malonate and NaH. b) LAH reduction. c) Esterification with octanoyl chloride, pyridine. d) Hydrogenation over Pd/C. e) TEMPO, BAIB oxidation. f) Treatment with dodecylmagnesiumbromide. g) Carbonate formation with 4-nitrophenyl chloroformate. h) Displacement with appropriate alcohols. i) EDC coupling.

Example 1: Synthesis of 2-(10-Dodecyl-3-Ethyl-8,14-Dioxo-7,9,13-Trioxa-3-Azaoctadecan-18-yl)propane-1,3-diyl dioctanoate

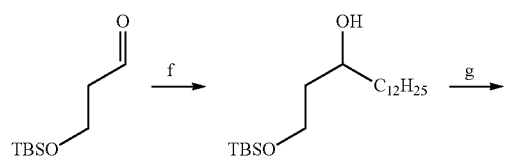

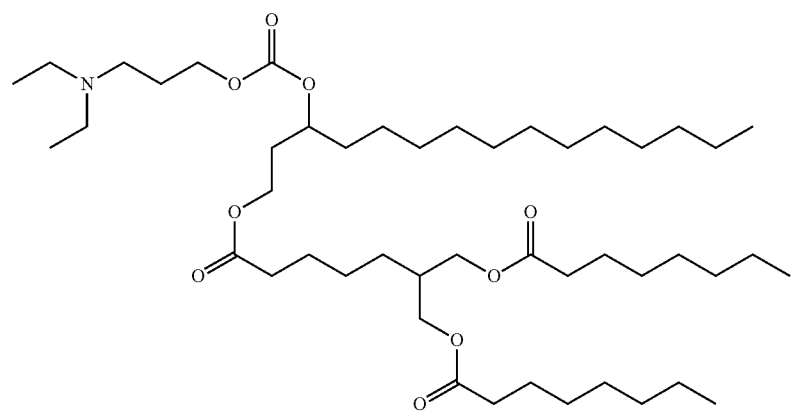 [SMILES: CCCCCCCCCCCCC(CCOC(=O)CCCCC(COC(=O)CCCCCCC)COC(=O)CCCCCCC)OC(=O)OCCCN(CC)CC]

In a round bottom flask, Intermediate 1f (1.99 g, 4.66 mmol), DMAP (0.207 g, 1.693 mmol), DIPEA (1.48 mL, 8.47 mmol), and Intermediate 1k (1.7 g, 13.07 mmol) were taken into dichloromethane (20 mL). EDC.HCl (1.62 g, 8.47 mmol) was added in one portion, and the reaction was stirred at ambient temperature. After 24 h, the reaction was concentrated under reduced pressure. The residue was purified by silica gel column chromatography (0% to 5% MeOH in $CH_2Cl_2$). Fractions were collected and solvents were removed under reduced pressure to provide a yellow oil (3.8 g). The oil was repurified by silica gel column chromatography (0-75% EtOAc/heptane) to afford the title compound as an off-white oil (2.6 g, 71.8%). $^1$H NMR (400 MHz, $CDCl_3$) δ=4.80 (t, J=6.1 Hz, 1H), 4.25-3.96 (m, 8H), 2.62 (br. s., 4H), 2.30 (t, J=7.5 Hz, 6H), 2.05-1.85 (m, 5H), 1.71-1.53 (m, 8H), 1.43-1.21 (m, 42H), 1.21-0.98 (m, 6H), 0.96-0.79 (m, 9H). $^{13}$C NMR (101 MHz, $CDCl_3$) δ=174.15 (s, 2C), 173.71, 155.20, 75.90, 66.41, 64.14 (s, 2C), 60.85, 49.32, 47.10 (s, 2C), 37.46, 34.56 (s, 3C), 34.52, 34.29, 33.28, 32.22, 31.97 (s, 2C), 29.95 (s, 2C), 29.88, 29.80, 29.76, 29.66, 29.41 (s, 2C), 29.23 (s, 2C), 28.20, 26.64, 25.36, 25.25 (s, 4C), 23.00, 22.90 (s, 2C), 14.44, 14.38 (s, 2C), 11.37 (s, 2C).

The following examples can be prepared using similar coupling methods to those employed for the synthesis of Example 1.

Example 2: 2-(9-dodecyl-2-methyl-7,13-dioxo-6,8,12-trioxa-2-azaheptadecan-17-yl)propane-1,3-diyl dioctanoate

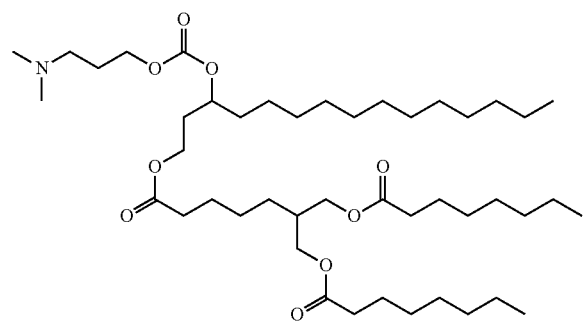 [SMILES: CCCCCCCCCCCCC(CCOC(=O)CCCCC(COC(=O)CCCCCCC)COC(=O)CCCCCCC)OC(=O)OCCCN(C)C]

$^1$H NMR (400 MHz, $CDCl_3$) δ=4.80 (t, J=5.4 Hz, 1H), 4.28-3.98 (m, 8H), 2.65-2.35 (m, 8H), 2.30 (t, J=7.5 Hz, 6H), 2.09-1.84 (m, 5H), 1.74-1.50 (m, 8H), 1.48-1.33 (m, 8H), 1.33-1.18 (m, 32H), 0.88 (t, J=6.8 Hz, 9H). $^{13}$C NMR (101 MHz, $CDCl_3$) δ=173.47 (2C), 173.06, 154.53, 75.34, 63.55 (3C), 60.18, 55.48, 44.41 (2C), 36.90, 33.95 (2C), 33.91, 33.68, 32.70, 31.59, 31.34 (2C), 29.33 (2C), 29.31, 29.24, 29.17, 29.12, 29.02, 28.79 (2C), 28.59 (2C), 27.61, 26.02 (2C), 24.73, 24.64 (3C), 22.36, 22.26 (2C), 13.78, 13.73 (2C).

Example 3: 2-(9-dodecyl-2-methyl-7,13-dioxo-6,8,12-trioxa-2-azapentadecan-15-yl)propane-1,3-diyl dioctanoate

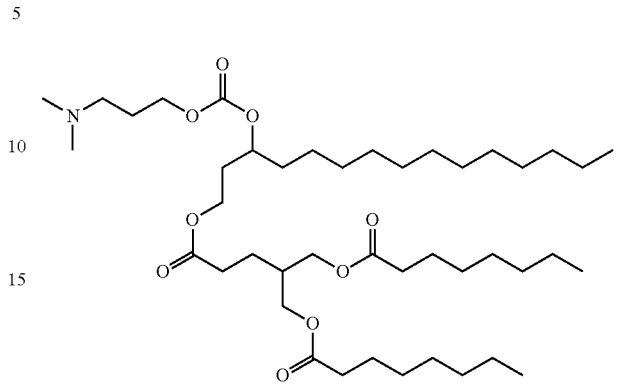

$^1$H NMR (400 MHz, $CDCl_3$) δ=4.88-4.71 (m, 1H), 4.28-3.98 (m, 8H), 2.54 (br. s., 2H), 2.48-2.35 (m, 6H), 2.31 (t, J=7.7 Hz, 6H), 2.13-1.98 (m, 2H), 1.98-1.85 (m, 3H), 1.71 (q, J=7.5 Hz, 2H), 1.65-1.49 (m, 6H), 1.40-1.16 (m, 36H), 0.97-0.80 (m, 9H). $^{13}$C NMR (101 MHz, $CDCl_3$) δ=173.69 (2C), 172.89, 154.84, 75.60, 63.55 (3C), 60.72, 55.77, 45.05-44.29 (2C), 36.80, 34.24, 34.20 (2C), 33.00, 31.90, 31.64 (2C), 31.42, 29.65, 29.63 (2C), 29.56, 29.49, 29.44, 29.33, 29.09 (2C), 28.90 (2C), 25.06, 24.91 (3C), 23.44, 22.66, 22.58 (2C), 14.10, 14.04 (2C).

Example 4: 2-(10-dodecyl-3-ethyl-8,14-dioxo-7,9,13-trioxa-3-azahexadecan-16-yl)propane-1,3-diyl dioctanoate

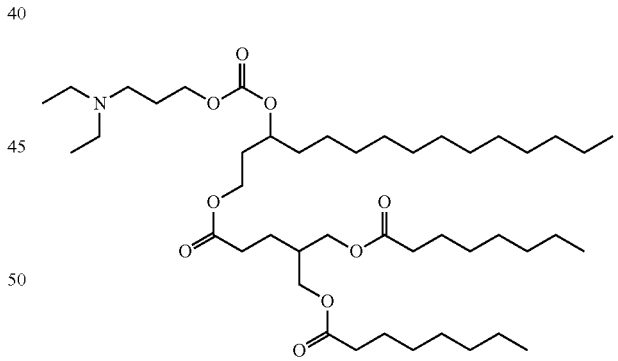

$^1$H NMR (400 MHz, $CDCl_3$) δ=4.80 (t, J=6.0 Hz, 1H), 4.28-3.98 (m, 8H), 2.63 (br. s., 6H), 2.40 (t, J=7.7 Hz, 2H), 2.31 (t, J=7.5 Hz, 4H), 2.11-2.00 (m, 1H), 2.00-1.84 (m, 4H), 1.71 (q, J=7.5 Hz, 2H), 1.66-1.49 (m, 6H), 1.40-1.21 (m, 36H), 1.09 (br. s., 6H), 0.88 (t, J=6.8 Hz, 9H). $^{13}$C NMR (101 MHz, $CDCl_3$) δ=173.73 (2C), 172.89, 154.92, 75.44, 66.31 (2C), 63.50 (2C), 60.79, 48.99, 46.82 (2C), 36.71, 34.22, 34.18 (2C), 32.95, 31.89, 31.63 (2C), 31.37, 29.62 (3C), 29.55, 29.48, 29.45, 29.34, 29.08 (2C), 28.90 (2C), 25.04, 24.89 (2C), 23.37, 22.67, 22.58 (2C), 14.11, 14.05 (2C), 11.33 (2C).

Example 5: 2-(8-dodecyl-2-methyl-6,12-dioxo-5,7,11-trioxa-2-azaheptadecan-17-yl)propane-1,3-diyl dioctanoate

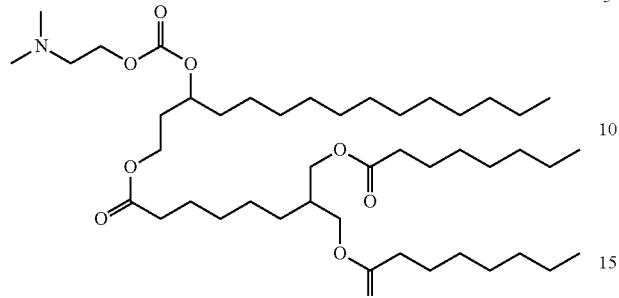

¹H NMR (400 MHz, CDCl₃) δ=4.91-4.71 (m, 1H), 4.29-4.18 (m, 2H), 4.18-3.96 (m, 6H), 2.60 (t, J=5.8 Hz, 2H), 2.39-2.23 (m, 10H), 2.05-1.85 (m, 3H), 1.71-1.51 (m, 8H), 1.42-1.19 (m, 44H), 0.96-0.82 (m, 9H). ¹³C NMR (101 MHz, CDCl₃) δ=173.81 (2C), 173.50, 155.02, 75.68, 65.46, 63.96 (2C), 60.60, 57.63, 45.69 (2C), 37.29, 34.27 (2C), 34.20, 34.10, 33.01, 31.91, 31.66 (2C), 29.65, 29.63 (2C), 29.55, 29.49, 29.44, 29.34, 29.26, 29.11 (2C), 28.91 (2C), 28.08, 26.50, 25.02, 24.96 (2C), 24.72, 22.68, 22.58 (2C), 14.10, 14.05 (2C).

Example 6: 2-(10-dodecyl-3-ethyl-8,14-dioxo-7,9,13-trioxa-3-azanonadecan-19-yl)propane-1,3-diyl dioctanoate

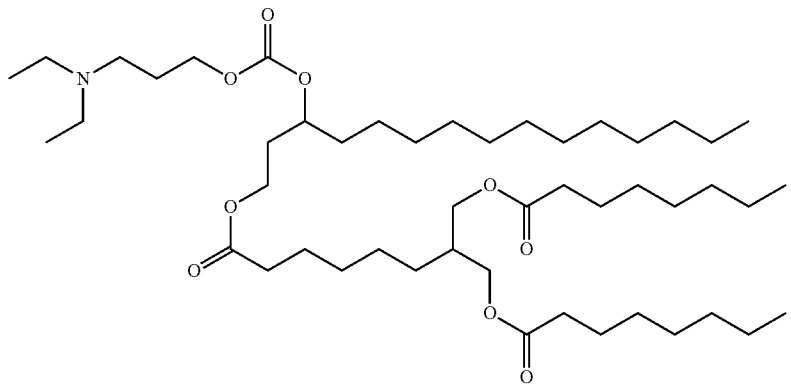 [SMILES: CCCCCCCCCCCCC(CCOC(=O)CCCCCC(COC(=O)CCCCCCC)COC(=O)CCCCCCC)OC(=O)OCCCN(CC)CC]

¹H NMR (400 MHz, CDCl₃) δ=4.89-4.72 (m, 1H), 4.26-3.96 (m, 8H), 2.62-2.40 (m, 6H), 2.40-2.21 (m, 6H), 2.04-1.87 (m, 3H), 1.87-1.74 (m, 2H), 1.74-1.52 (m, 8H), 1.41-1.17 (m, 42H), 1.01 (t, J=7.2 Hz, 6H), 0.96-0.80 (m, 9H). ¹³C NMR (101 MHz, CDCl₃) δ=173.86 (2C), 173.54, 154.99, 75.49, 66.57, 63.92 (2C), 60.61, 49.03, 46.89 (2C), 37.22, 34.26 (2C), 34.20, 34.08, 32.98, 31.91, 31.66 (2C), 29.65, 29.63 (2C), 29.56, 29.49, 29.45, 29.35, 29.25, 29.10 (2C), 28.92 (2C), 28.02, 26.49, 26.47, 25.04, 24.94 (2C), 24.70, 22.68, 22.59 (2C), 14.13, 14.07 (2C), 11.78 (2C).

Example 7: 2-(9-dodecyl-2-methyl-7,13-dioxo-6,8,12-trioxa-2-azaoctadecan-18-yl)propane-1,3-diyl dioctanoate

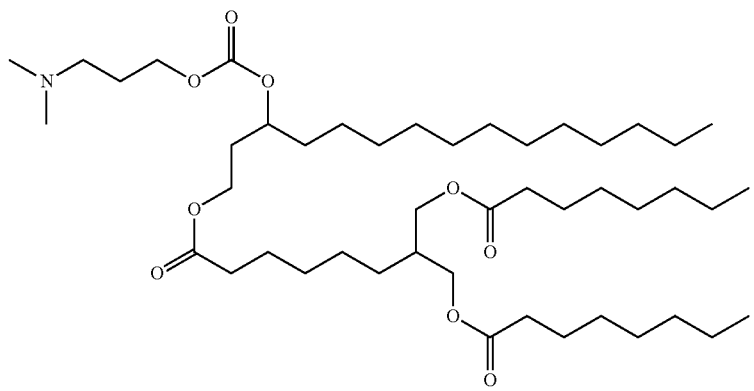 [SMILES: CCCCCCCCCCCCC(CCOC(=O)CCCCCC(COC(=O)CCCCCCC)COC(=O)CCCCCCC)OC(=O)OCCCN(C)C]

¹H NMR (400 MHz, CDCl₃) δ 4.80 (t, J=6.15 Hz, 1H), 3.97-4.27 (m, 8H), 2.46 (t, J=7.28 Hz, 2H), 2.18-2.39 (m, 12H), 1.83-2.05 (m, 5H), 1.53-1.72 (m, 8H), 1.19-1.44 (m, 42H), 0.88 (t, J=6.65 Hz, 9H). ¹³C NMR (101 MHz, CDCl₃) δ=173.86 (2C), 173.55, 154.89, 75.60, 66.10, 63.90 (2C), 60.54, 55.70, 44.89 (2C), 37.21, 34.25 (2C), 34.19, 34.08, 32.95, 31.90, 31.65 (2C), 29.62 (2C), 29.56, 29.48, 29.44, 29.34, 29.24, 29.09 (2C), 28.91 (2C), 28.01 (2C), 26.49, 26.39, 25.03, 24.94 (2C), 24.70, 22.68, 22.59, 14.12, 14.07 (2C).

Example 8: 2-(8-dodecyl-2-methyl-6,12-dioxo-5,7,11-trioxa-2-azaoctadecan-18-yl)propane-1,3-diyl dioctanoate ¹H NMR (400 MHz, CDCl₃) δ=4.92-4.73 (m, 1H), 4.26-3.97 (m, 8H), 2.52 (d, J=6.6 Hz, 6H), 2.38-2.23 (m, 6H), 2.02-1.88 (m, 3H), 1.88-1.74 (m, 2H), 1.69-1.53 (m, 8H), 1.41-1.19 (m, 44H), 1.02 (t, J=7.1 Hz, 6H), 0.94-0.80 (m, 9H). ¹³C NMR (101 MHz, CDCl₃) δ=173.81 (2C), 173.59, 155.01, 75.55, 66.55, 63.99 (2C), 60.59, 49.10, 46.94 (2C), 37.31, 34.29, 34.22, 34.16, 33.03, 31.91, 31.66 (2C), 29.65, 29.63 (2C), 29.56, 29.49, 29.44 (2C), 29.34, 29.11 (2C), 29.03, 28.91 (2C), 28.19, 26.64, 26.53, 25.04, 24.97 (2C), 24.83, 22.68, 22.58 (2C), 14.10, 14.05 (2C), 11.80 (2C).

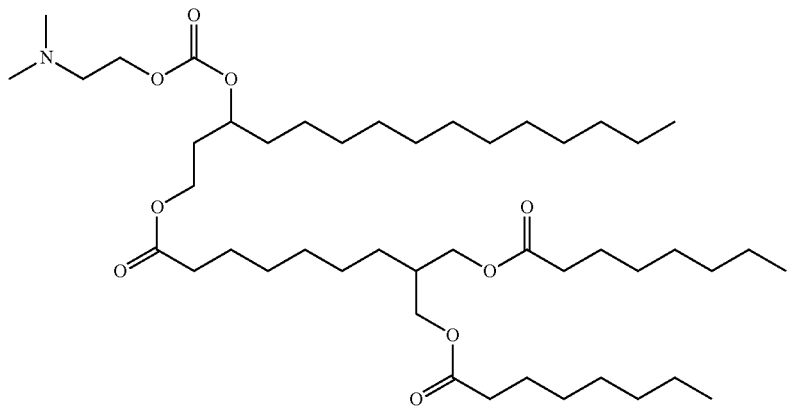 [SMILES: CCCCCCCCCCCCC(CCOC(=O)CCCCCCC(COC(=O)CCCCCCC)COC(=O)CCCCCCC)OC(=O)OCCN(C)C]

¹H NMR (400 MHz, CDCl₃) δ=4.95-4.70 (m, 1H), 4.28-4.17 (m, 2H), 4.17-3.96 (m, 6H), 2.60 (t, J=5.8 Hz, 2H), 2.36-2.24 (m, 12H), 2.03-1.86 (m, 3H), 1.72-1.49 (m, 8H), 1.44-1.18 (m, 44H), 0.97-0.80 (m, 9H). ¹³C NMR (101 MHz, CDCl₃) δ=173.50 (2C), 173.28, 154.71, 75.38, 65.17, 63.67 (2C), 60.26, 57.32, 45.40 (2C), 36.99, 33.97 (2C), 33.87, 33.84, 32.69, 31.59, 31.34 (2C), 29.33, 29.31 (2C), 29.23, 29.17, 29.12 (2C), 29.02, 28.79 (2C), 28.71, 28.59 (2C), 27.87, 26.32, 24.70, 24.65 (2C), 24.51, 22.36, 22.26 (2C), 13.78, 13.73 (2C).

Example 9: 2-(10-dodecyl-3-ethyl-8,14-dioxo-7,9,13-trioxa-3-azaicosan-20-yl)propane-1,3-diyl dioctanoate

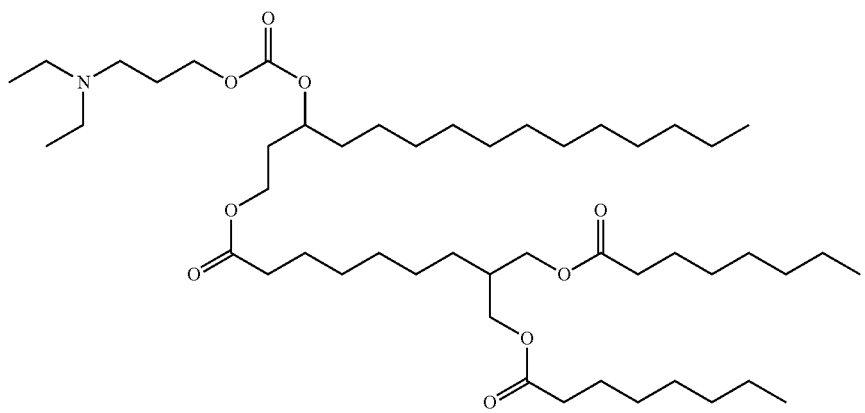 [SMILES: CCCCCCCCCCCCC(CCOC(=O)CCCCCCC(COC(=O)CCCCCCC)COC(=O)CCCCCCC)OC(=O)OCCCN(CC)CC]

Example 10: 2-(9-dodecyl-2-methyl-7,13-dioxo-6,8,12-trioxa-2-azanonadecan-19-yl)propane-1,3-diyl dioctanoate

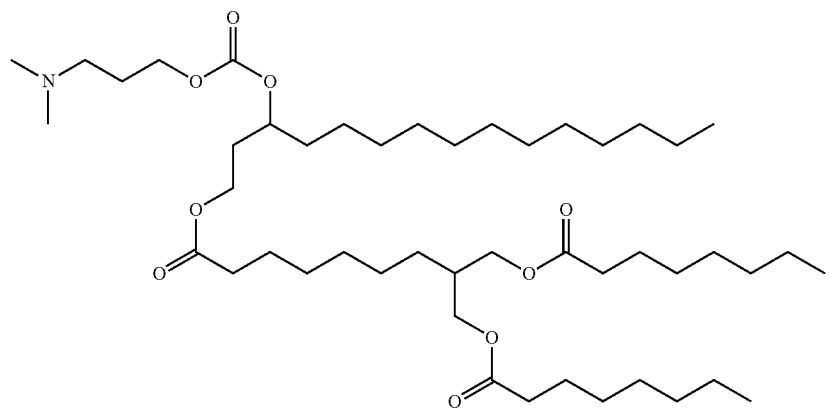 [SMILES: CCCCCCCCCCCCC(CCOC(=O)CCCCCCC(COC(=O)CCCCCCC)COC(=O)CCCCCCC)OC(=O)OCCCN(C)C]

$^1$H NMR (400 MHz, CDCl$_3$) δ=4.95-4.72 (m, 1H), 4.28-3.98 (m, 8H), 2.48-2.26 (m, 8H), 2.23 (s, 6H), 2.02-1.89 (m, 3H), 1.89-1.78 (m, 2H), 1.69-1.58 (m, 8H), 1.41-1.19 (m, 44H), 0.96-0.79 (m, 9H). $^{13}$C NMR (101 MHz, CDCl$_3$) δ=173.82 (2C), 173.60, 154.97, 75.60, 66.34, 63.99 (2C), 60.59, 56.00, 45.46 (2C), 37.31, 34.29 (2C), 34.21, 34.16, 33.02, 31.91, 31.66 (2C), 29.65, 29.63 (2C), 29.55, 29.49, 29.44 (2C), 29.34, 29.11 (2C), 29.03, 28.91 (2C), 28.19, 26.99, 26.64, 25.05, 24.97 (2C), 24.83, 22.68, 22.58 (2C), 14.10, 14.05 (2C).

Synthesis of Example 11

Intermediate 11a: 4,4-bis(octyloxy)butanenitrile

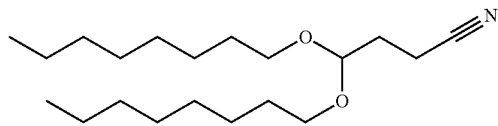 [SMILES: CCCCCCCCOC(CCC#N)OCCCCCCCC]

To a mixture of 4,4-diethoxybutanenitrile (15 g, 95 mmol) and octanol (37.3 g, 286 mmol) was added pyridinium p-toluenesulfonate (1.2 g, 4.77 mmol) and the mixture was heated in a 105° C. bath. After 72 h, the reaction mixture was cooled to ambient temperature and purified on silica gel using ethyl acetate/heptane as eluent to provide 9.34 g of the expected product. $^1$H NMR (400 MHz, CDCl$_3$): δ=4.56 (t, J=5.40 Hz, 1H), 3.61 (dt, J=9.16, 6.59 Hz, 2H), 3.44 (dt, J=9.22, 6.68 Hz, 2H), 2.43 (t, J=7.28 Hz, 2H), 1.95 (td, J=7.34, 5.40 Hz, 2H), 1.50-1.66 (m, 4H), 1.17-1.44 (m, 20H), 0.80-0.95 (m, 6H).

Intermediate 11b: 4,4-bis(octyloxy)butanoic acid

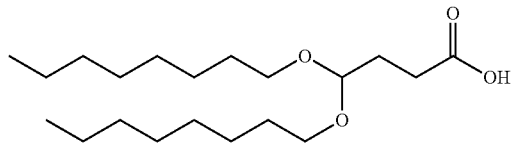 [SMILES: CCCCCCCCOC(CCC(=O)O)OCCCCCCCC]

In a high pressure reaction vessel, Intermediate 11a (9.34 g, 28.7 mmol) is dissolved in 30 mL EtOH. KOH (4.83 g) was dissolved in 30 mL water and the KOH solution was added to the EtOH solution. The tube was sealed and heated in a 110° C. bath overnight. The mixture was cooled and diluted with EtOAc. 1 N HCl was added to adjust pH to 5, and the aqueous phase was extracted with EtOAc twice. The combined organic extracts were dried over MgSO4, filtered, and concentrated under reduced pressure to provide 10.9 g of the expected product. $^1$H NMR (400 MHz, CDCl$_3$): δ=4.46 (t, J=5.52 Hz, 1H), 3.46-3.59 (m, 2H), 3.08-3.46 (m, 3H), 2.18 (t, J=7.28 Hz, 2H), 1.72-1.89 (m, 2H), 1.46-1.63 (m, 4H), 1.28 (d, J=3.76 Hz, 20H), 0.79-0.96 (m, 6H).

Preparation of Final Compounds

Scheme X

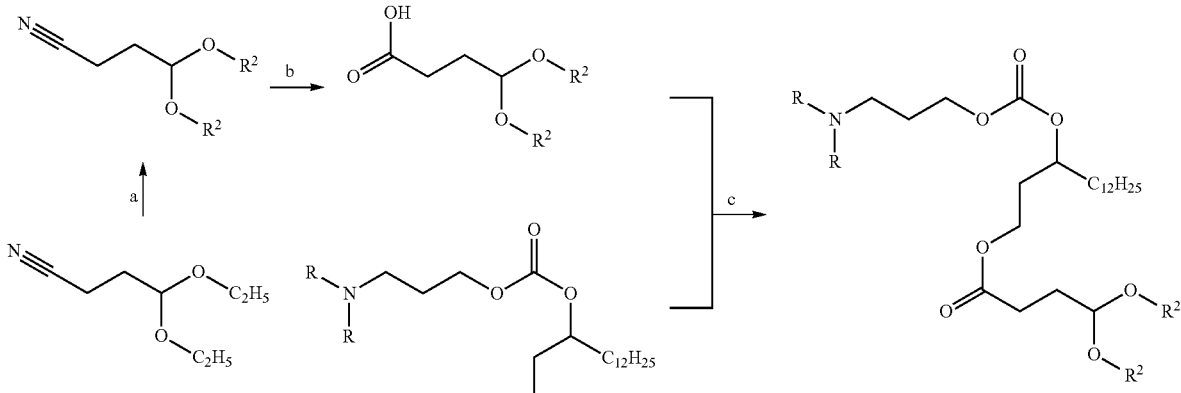

a) Acetal exchange with R$^2$OH, and PPTS. b) Base hydrolysis. c) EDC, or similar coupling.

The following examples (Examples 11-15) can be prepared using similar methods to those employed for the synthesis of Example 1.

Example 11: 3-(((3-(diethylamino)propoxy)carbonyl)oxy)pentadecyl 4,4-bis(octyloxy)butanoate

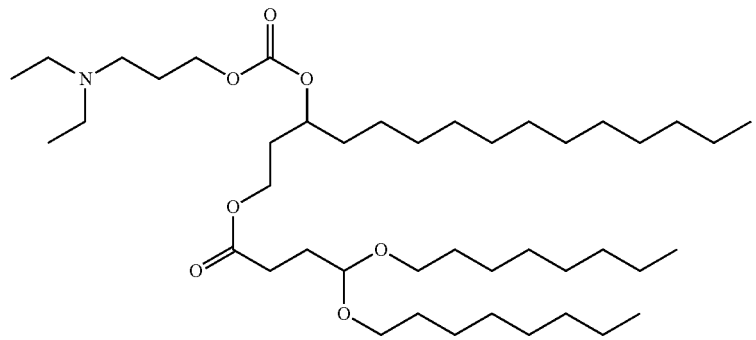 [SMILES: CCCCCCCCCCCCC(CCOC(=O)CCC(OCCCCCCCC)OCCCCCCCC)OC(=O)OCCCN(CC)CC]

$^1$H NMR (400 MHz, CDCl$_3$) δ=4.89-4.72 (m, 1H), 4.50 (t, J=5.6 Hz, 1H), 4.28-4.09 (m, 4H), 3.68-3.48 (m, 2H), 3.41 (td, J=6.8, 9.2 Hz, 2H), 2.61-2.45 (m, 6H), 2.39 (t, J=7.5 Hz, 2H), 1.99-1.88 (m, 4H), 1.81 (quin, J=7.0 Hz, 2H), 1.72-1.47 (m, 8H), 1.42-1.20 (m, 38H), 1.02 (t, J=7.2 Hz, 6H), 0.94-0.82 (m, 9H). $^{13}$C NMR (101 MHz, CDCl$_3$) δ=173.27, 154.98, 102.03, 75.50, 66.57, 66.07 (2C), 60.73, 49.03, 46.89 (2C), 34.21, 32.96, 31.91, 31.83 (2C), 29.84 (2C), 29.64 (3C), 29.56, 29.50, 29.44 (2C), 29.36 (3C), 29.28 (2C), 28.67, 26.45, 26.22 (2C), 25.05, 22.66 (3C), 14.11 (3C), 11.78 (2C).

Example 12: 3-(((3-(diethylamino)propoxy)carbonyl)oxy)pentadecyl 4,4-bis((2-ethylhexyl)oxy)butanoate

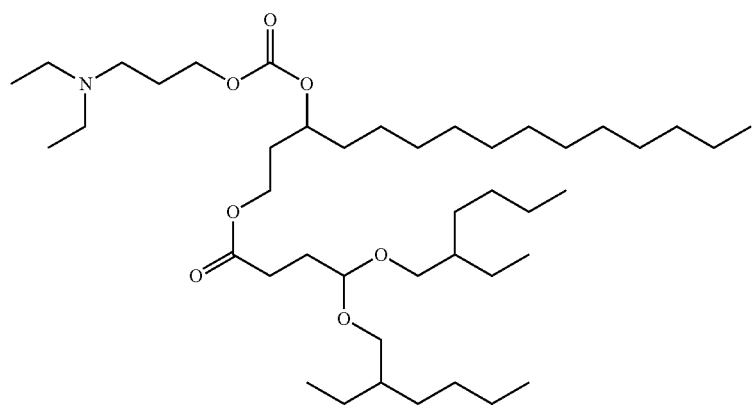 [SMILES: CCCCCCCCCCCCC(CCOC(=O)CCC(OCC(CC)CCCC)OCC(CC)CCCC)OC(=O)OCCCN(CC)CC]

$^1$H NMR (400 MHz, CDCl$_3$) δ=4.80 (t, J=6.3 Hz, 1H), 4.46 (t, J=5.5 Hz, 1H), 4.27-3.99 (m, 4H), 3.55-3.41 (m, 2H), 3.28 (dt, J=5.8, 8.9 Hz, 2H), 2.56 (br. s., 4H), 2.39 (t, J=7.5 Hz, 2H), 2.00-1.77 (m, 6H), 1.75-1.53 (m, 4H), 1.53-1.44 (m, 2H), 1.44-1.23 (m, 36H), 1.05 (d, J=6.8 Hz, 6H), 0.98-0.76 (m, 15H). MS (M+1)=728.3, Rt=2.09 min (LC Method 4).-

Example 13: 3-(((3-(diethylamino)propoxy)carbonyl)oxy)pentadecyl 4,4-bis((2-propylpentyl)oxy)butanoate

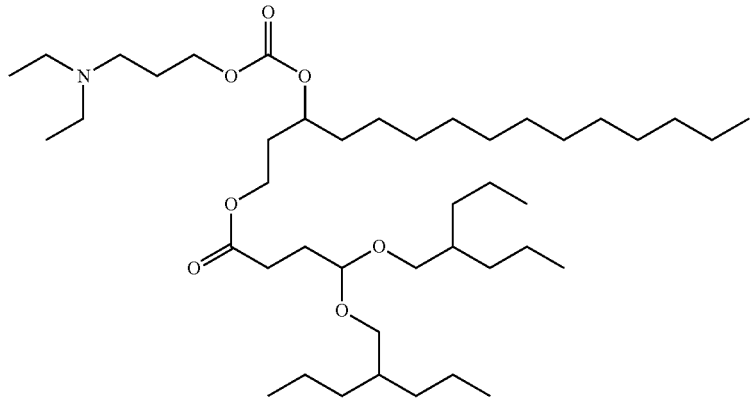 [SMILES: CCCCCCCCCCCCC(CCOC(=O)CCC(OCC(CCC)CCC)OCC(CCC)CCC)OC(=O)OCCCN(CC)CC]

$^1$H NMR (400 MHz, CDCl$_3$) δ=4.80 (t, J=6.1 Hz, 1H), 4.45 (t, J=5.6 Hz, 1H), 4.25-4.06 (m, 4H), 3.47 (dd, J=5.8, 9.0 Hz, 2H), 3.27 (dd, J=5.8, 9.3 Hz, 2H), 2.75-2.45 (m, 6H), 2.38 (t, J=7.7 Hz, 2H), 2.01-1.80 (m, 6H), 1.72-1.47 (m, 4H), 1.43-1.18 (m, 36H), 1.18-0.98 (m, 6H), 0.97-0.81 (m, 15H). $^{13}$C NMR (101 MHz, CDCl$_3$) δ=173.34, 154.89, 102.40, 75.58, 69.00 (2C), 66.25, 60.63, 49.02, 46.81 (2C), 37.91 (2C), 34.19, 33.66 (4C), 32.95, 31.90, 29.63 (3C), 29.55, 29.49, 29.44, 29.38, 29.34, 28.63, 26.07, 25.04, 22.68, 19.96 (2C), 19.92 (2C), 14.47 (4C), 14.12, 11.39 (2C).

Example 14: 3-(((3-(ethyl(methyl)amino)propoxy)carbonyl)oxy)pentadecyl 4,4-bis((2-propylpentyl)oxy)butanoate

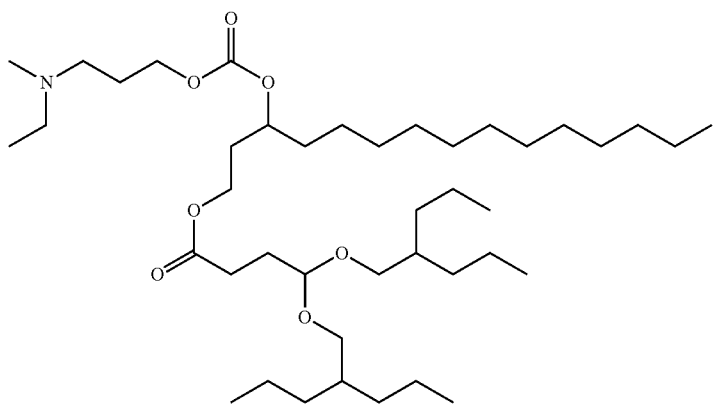 [SMILES: CCCCCCCCCCCCC(CCOC(=O)CCC(OCC(CCC)CCC)OCC(CCC)CCC)OC(=O)OCCCN(C)CC]

$^1$H NMR (400 MHz, CDCl$_3$) δ=4.80 (t, J=6.1 Hz, 1H), 4.45 (t, J=5.5 Hz, 1H), 4.27-4.06 (m, 4H), 3.47 (dd, J=5.8, 9.0 Hz, 2H), 3.27 (dd, J=5.8, 9.0 Hz, 2H), 2.38 (t, J=7.5 Hz, 9H), 2.03-1.84 (m, 6H), 1.73-1.47 (m, 4H), 1.38-1.09 (m, 39H), 0.96-0.78 (m, 15H). $^{13}$C NMR (101 MHz, CDCl$_3$) δ=173.37, 154.82, 102.39, 75.65, 69.01 (2C), 65.87 (br), 60.57, 53.27, 51.30, 40.69 (br), 37.90 (2C), 34.19 (2C), 33.66 (4C), 32.94, 31.90, 29.63 (2C), 29.55, 29.49, 29.44, 29.38, 29.34, 28.63, 25.87 (br), 25.05, 22.68, 19.96 (2C), 19.92 (2C), 14.47 (4C), 14.12, 11.02.

Example 15: 3-(((3-(dimethylamino)propoxy)carbonyl)oxy)pentadecyl 4,4-bis((2-propylpentyl)oxy)butanoate

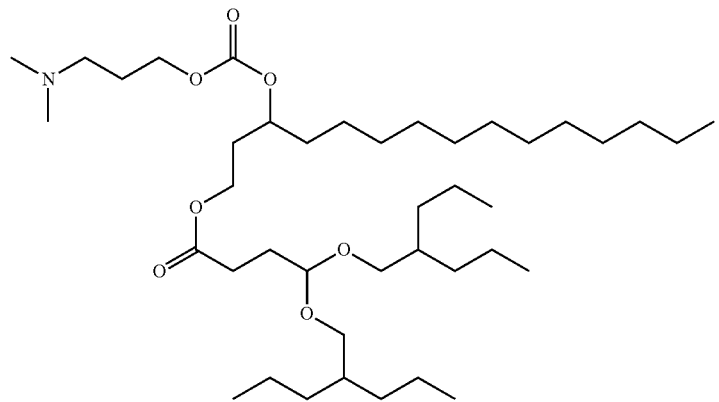 [SMILES: CCCCCCCCCCCCC(CCOC(=O)CCC(OCC(CCC)CCC)OCC(CCC)CCC)OC(=O)OCCCN(C)C]

$^1$H NMR (400 MHz, CDCl$_3$) δ=4.91-4.69 (m, 1H), 4.45 (t, J=5.5 Hz, 1H), 4.28-4.03 (m, 4H), 3.47 (dd, J=5.8, 9.0 Hz, 2H), 3.27 (dd, J=5.8, 9.3 Hz, 2H), 2.52 (br. s., 2H), 2.44-2.26 (m, 8H), 2.02-1.85 (m, 6H), 1.72-1.48 (m, 4H), 1.40-1.16 (m, 36H), 0.99-0.83 (m, 15H). $^{13}$C NMR (101 MHz, CDCl$_3$) δ=173.36, 154.83, 102.39, 75.64, 69.03, 69.00, 65.90, 60.60, 55.84, 44.90 (2C), 37.90 (2C), 34.19, 33.66 (4C), 32.94, 31.90, 29.65 (2C), 29.62, 29.55, 29.49, 29.43, 29.38, 29.34, 28.63, 26.34, 25.04, 22.68, 19.96 (2C), 19.92 (2C), 14.47 (4C), 14.12.

Synthesis of Example 16

Intermediate 16a: methyl 6,6-dimethoxyhexanoate

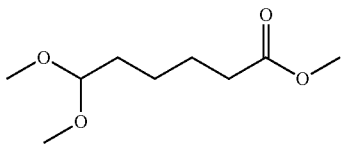

Methyl 6-oxohexanoate (11 g, 76 mmol) was taken into methanol (60 mL) and conc. sulfuric acid (244 uL, 4.58 mmol) was added. The reaction was heated to reflux overnight. The reaction was cooled to ambient temperature and diluted with water. The mixture was extracted with ethyl acetate. The combined organic extracts were dried over sodium sulfate, filtered, and concentrated under reduced pressure. The concentrate was purified on silica gel with ethyl acetate/heptane as eluent to afford 12.1 g of the desired compound. $^1$H NMR (400 MHz, CDCl$_3$) δ=4.37 (t, J=5.77 Hz, 1H), 3.68 (s, 3H), 3.33 (s, 6H), 2.34 (t, J=7.53 Hz, 2H), 1.57-1.73 (m, 4H), 1.34-1.46 (m, 2H) ppm.

Intermediate 16b: octyl 6,6-bis(octyloxy)hexanoate

Intermediate 16a (3.06 g, 16.09 mmol) was dissolved in 1-octanol (10.17 ml, 64.3 mmol) and potassium bisulfate (0.110 g, 0.804 mmol) was added The mixture was heated to 70° C., and stirred for 4 h. The mixture was diluted with 40 mL of water, and extracted with EtOAc (2×50 mL). The organic layers were combined, washed with brine (100 mL), dried over sodium sulfate, then concentrated in vacuo. The crude mixture was purified by chromatography on silica gel (0-10% EtOAc/heptane gradient) to provided 5.07 g of the title compound (65% yield). $^1$H NMR (400 MHz, CDCl$_3$) δ=4.46 (t, J=5.69 Hz, 1H), 4.02-4.12 (m, 2H), 3.56 (dt, J=9.29, 6.66 Hz, 2H), 3.40 (dt, J=9.32, 6.71 Hz, 2H), 2.31 (t, J=7.58 Hz, 2H), 1.51-1.72 (m, 12H), 1.20-1.45 (m, 30H), 0.81-0.97 (m, 9H).

Intermediate 16c: 6,6-bis(octyloxy)hexanoic acid

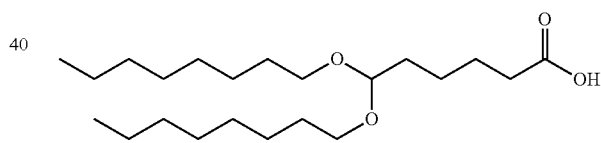

To intermediate 16b (5.07 g, 10.46 mmol) was added water (34.9 ml), MeOH (34.9 ml), and NaOH (2.091 g, 52.3 mmol). The mixture was heated to reflux, and stirred for 2 h. The mixture was neutralized with 1N HCl, then extracted with EtOAc (2×50 mL). The organic layers were combined, washed with brine (100 mL), then dried over sodium sulfate, filtered, and concentrated. The crude material was used in the next step without further purification. $^1$H NMR (400 MHz, DMSO-d$_6$) δ=4.38 (t, J=5.62 Hz, 1H), 3.42-3.51 (m, 2H), 3.28-3.38 (m, 2H), 1.96 (t, J=7.34 Hz, 2H), 1.39-1.55 (m, 8H), 1.19 (m., 23H), 0.80-0.93 (m, 6H).

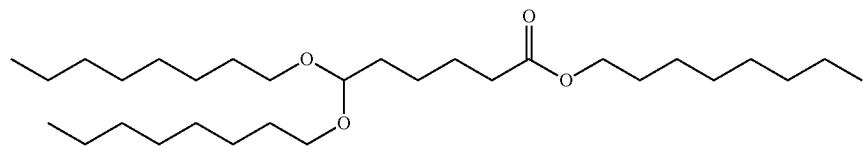 [SMILES: CCCCCCCCOC(=O)CCCCC(OCCCCCCCC)OCCCCCCCC]

Preparation of Final Compounds

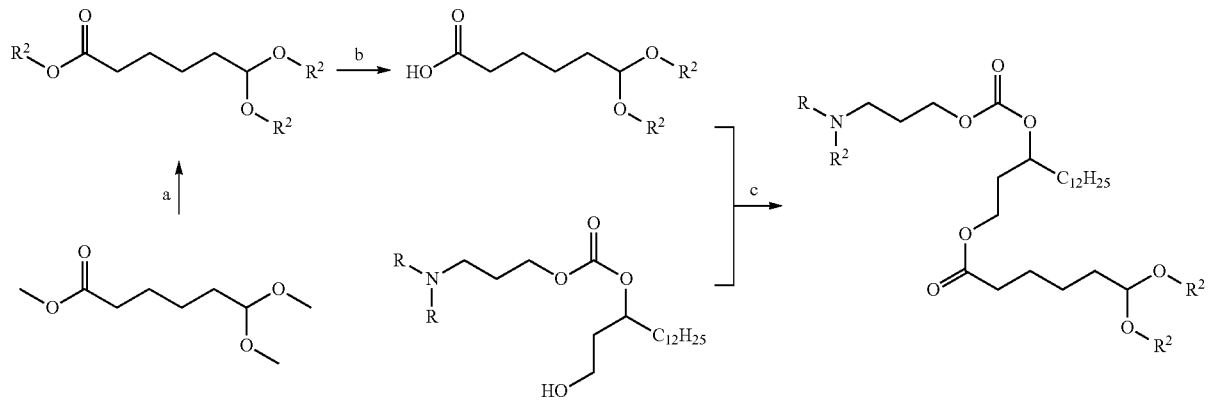

a) Acetal exchange with $R^2OH$, and PPTS. b) Base hydrolysis. c) EDC, or similar coupling.

The following examples (Examples 16-23) can be prepared using similar methods to those employed for the synthesis of Example 1.

Example 16: 3-(((3-(diethylamino)propoxy)carbonyl)oxy)pentadecyl 6,6-bis(octyloxy)hexanoate

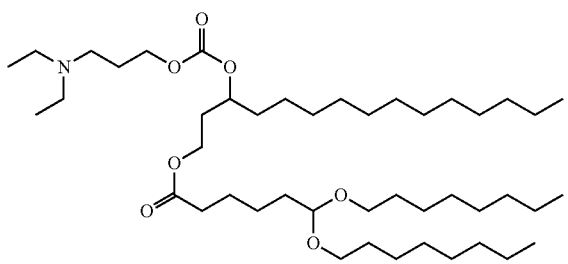 [SMILES: CCCCCCCCCCCCC(CCOC(=O)CCCCC(OCCCCCCCC)OCCCCCCCC)OC(=O)OCCCN(CC)CC]

$^1$H NMR (400 MHz, CDCl$_3$) δ=4.69-4.95 (m, 1H), 4.46 (t, J=5.65 Hz, 1H), 4.06-4.27 (m, 4H), 3.56 (td, J=6.78, 9.29 Hz, 2H), 3.40 (td, J=6.78, 9.29 Hz, 2H), 2.43-2.58 (m, 6H), 2.31 (t, J=7.65 Hz, 2H), 1.92 (q, J=6.27 Hz, 2H), 1.81 (td, J=6.87, 14.12 Hz, 2H), 1.49-1.73 (m, 12H), 1.19 (br. s., 40H), 1.01 (t, J=7.15 Hz, 6H), 0.89 (t, J=6.78 Hz, 9H). $^{13}$C NMR (101 MHz, CDCl$_3$) δ=173.54, 154.99, 102.81, 75.51, 66.57, 65.55 (2C), 60.59, 49.03, 46.89 (2C), 34.20, 34.15, 33.13, 32.97, 31.91, 31.83 (2C), 29.89 (2C), 29.64, 29.56 (2C), 29.49 (2C), 29.44 (3C), 29.35 (3C), 29.28 (2C), 26.46, 26.26 (2C), 25.04, 24.74, 24.36, 22.66 (2C), 14.11 (2C), 11.78 (2C).

Example 17: 3-(((3-(diethylamino)propoxy)carbonyl)oxy)pentadecyl 6,6-bis(hexyloxy)hexanoate

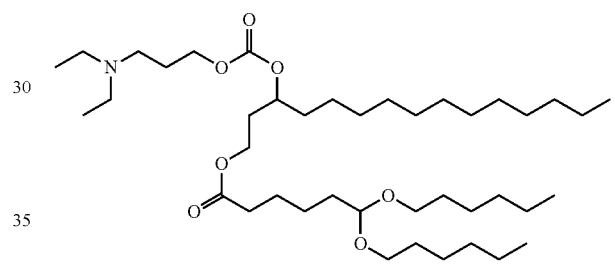

$^1$H NMR (400 MHz, CDCl$_3$) δ=4.80 (t, J=6.15 Hz, 1H), 4.46 (t, J=5.77 Hz, 1H), 4.04-4.27 (m, 4H), 3.56 (dt, J=9.29, 6.78 Hz, 2H), 3.40 (dt, J=9.29, 6.78 Hz, 2H), 2.55 (br. s., 4H), 2.31 (t, J=7.53 Hz, 2H), 1.92 (q, J=6.53 Hz, 2H), 1.77-1.89 (m, 2H), 1.48-1.74 (m, 10H), 1.18-1.48 (m, 36H), 1.04 (t, J=7.03 Hz, 6H), 0.89 (dq, J=6.68, 3.38 Hz, 9H). MS (M+1)=700.7, Rt=1.71 min (LC Method 4).

Example 18: 3-(((3-(diethylamino)propoxy)carbonyl)oxy)pentadecyl 6,6-bis((2-ethylhexyl)oxy) hexanoate

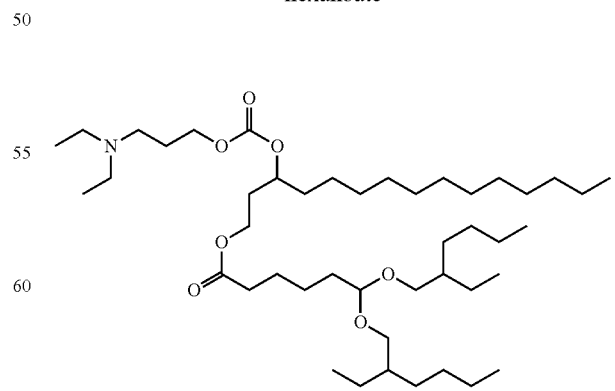

$^1$H NMR (400 MHz, CDCl$_3$) δ=4.89-4.71 (m, 1H), 4.42 (t, J=5.6 Hz, 1H), 4.28-4.06 (m, 4H), 3.46 (dt, J=6.0, 8.3 Hz,

2H), 3.37-3.17 (m, 2H), 2.55 (br. s., 4H), 2.31 (t, J=7.5 Hz, 2H), 2.01-1.76 (m, 4H), 1.73-1.54 (m, 6H), 1.54-1.43 (m, 2H), 1.43-1.23 (m, 40H), 1.04 (t, J=6.7 Hz, 6H), 0.97-0.77 (m, 15H). MS (M+1)=756.5, Rt=2.23 min (LC Method 4).

Example 19: 3-(((3-(diethylamino)propoxy)carbonyl)oxy)pentadecyl 8,8-bis(octyloxy)octanoate

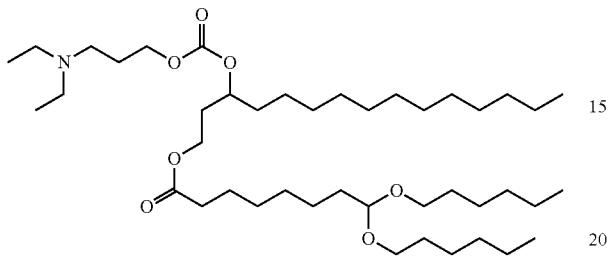

$^1$H NMR (400 MHz, CDCl$_3$) δ=4.81 (t, J=6.15 Hz, 1H), 4.45 (t, J=5.77 Hz, 1H), 4.05-4.26 (m, 4H), 3.56 (dt, J=9.22, 6.68 Hz, 2H), 3.40 (dt, J=9.22, 6.68 Hz, 2H), 2.57 (br. s., 6H), 2.29 (t, J=7.65 Hz, 2H), 1.79-1.98 (m, 4H), 1.49-1.75 (m, 10H), 1.15-1.44 (m, 38H), 0.98-1.09 (m, 6H), 0.75-0.98 (m, 9H). $^{13}$C NMR (101 MHz, CDCl$_3$) δ=173.71, 154.94, 103.01, 75.58, 66.38, 65.44 (2C), 60.51, 49.01, 46.82 (2C), 34.19 (2C), 33.39, 32.95, 31.90, 31.67 (2C), 29.85 (2C), 29.65 (2C), 29.62, 29.55, 29.48, 29.43, 29.34, 29.13, 29.09, 26.14, 25.93 (2C), 25.04, 24.82, 24.64, 22.68, 22.62 (2C), 14.12, 14.06 (2C), 11.44 (2C).

Example 20: 3-(((3-(diethylamino)propoxy)carbonyl)oxy)pentadecyl 8,8-dibutoxyoctanoate

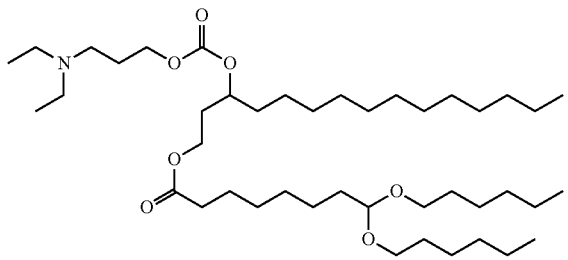 [SMILES: CCCCCCCCCCCCC(CCOC(=O)CCCCCCC(OCCCCCC)OCCCCCC)OC(=O)OCCCN(CC)CC]

$^1$H NMR (400 MHz, CDCl$_3$) δ=4.46 (t, J=5.65 Hz, 1H) 4.81 (t, J=6.15 Hz, 1H), 4.05-4.25 (m, 4H), 3.57 (dt, J=9.35, 6.62 Hz, 2H), 3.41 (dt, J=9.29, 6.65 Hz, 2H), 2.57 (br. s., 4H), 2.29 (t, J=7.53 Hz, 2H), 1.72-1.97 (m, 4H), 1.48-1.72 (m, 12H), 1.19-1.48 (m, 30H), 1.06 (br. s., 6H), 0.78-0.99 (m, 9H). $^{13}$C NMR (101 MHz, CDCl$_3$) δ=173.72, 154.94, 103.02, 75.59, 66.38, 65.12 (2C), 60.51, 49.03, 46.84 (2C), 34.19 (2C), 33.38, 32.96, 31.97 (2C), 31.90, 29.65, 29.63 (2C), 29.56, 29.49, 29.44, 29.35, 29.14, 29.09, 26.23, 25.04, 24.82, 24.63, 22.68, 19.44 (2C), 14.13, 13.92 (2C), 11.48 (2C).

Example 21: 3-(((3-(diethylamino)propoxy)carbonyl)oxy)pentadecyl 8,8-bis((2-propylpentyl)oxy)octanoate

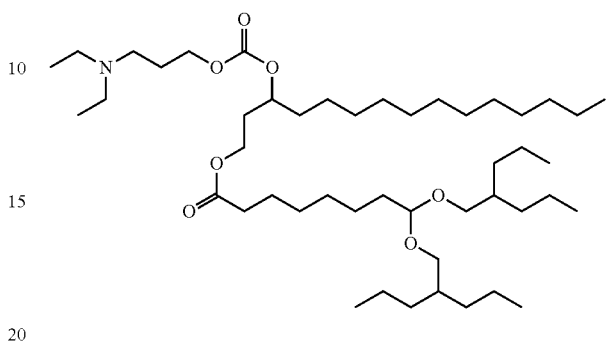

$^1$H NMR (400 MHz, CDCl$_3$) δ=4.81 (t, J=6.3 Hz, 1H), 4.40 (t, J=5.6 Hz, 1H), 4.26-4.06 (m, 4H), 3.45 (dd, J=5.6, 9.2 Hz, 2H), 3.26 (dd, J=5.9, 9.2 Hz, 2H), 2.59 (br. s., 6H), 2.29 (t, J=7.5 Hz, 2H), 1.92 (q, J=6.3 Hz, 4H), 1.72-1.49 (m, 10H), 1.38-1.16 (m, 40H), 1.07 (br. s., 6H), 0.98-0.80 (m, 15H). $^{13}$C NMR (101 MHz, CDCl$_3$) δ=173.39, 154.59, 103.14, 75.28, 68.10 (2C), 65.92, 60.16, 48.70, 46.50 (2C), 37.62 (2C), 33.87 (2C), 33.42 (2C), 33.37 (2C), 32.99, 32.64, 31.58, 29.31 (3C), 29.24, 29.16, 29.11, 29.03, 28.83, 28.81, 25.68, 24.72, 24.51, 24.38, 22.36, 19.63 (4C), 14.16 (4C), 13.81, 11.01 (2C).

Example 22: 3-(((3-(ethyl(methyl)amino)propoxy)carbonyl)oxy)pentadecyl 8,8-bis((2-propylpentyl)oxy)octanoate

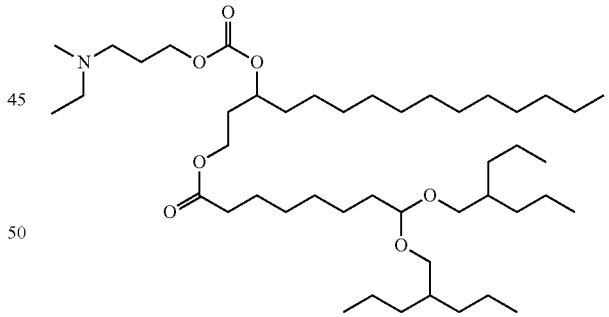

$^1$H NMR (400 MHz, CDCl$_3$) δ=4.80 (t, J=6.1 Hz, 1H), 4.40 (t, J=5.8 Hz, 1H), 4.26-4.04 (m, 4H), 3.45 (dd, J=5.8, 9.3 Hz, 2H), 3.32-3.17 (m, 2H), 2.51 (br. s., 4H), 2.36-2.20 (m, 5H), 1.92 (q, J=6.3 Hz, 4H), 1.73-1.46 (m, 10H), 1.46-1.17 (m, 40H), 1.17-1.01 (m, 3H), 0.98-0.78 (m, 15H). $^{13}$C NMR (101 MHz, CDCl$_3$) δ=173.70, 154.90, 103.45 (2C), 75.61, 68.41 (2C), 66.22, 60.47, 53.37, 51.37, 41.23, 37.94 (2C), 34.19 (2C), 33.73 (2C), 33.69 (2C), 33.31, 32.95, 31.90, 29.62 (2C), 29.55, 29.48, 29.43, 29.34, 29.15, 29.12, 26.25, 25.03, 24.83, 24.69, 22.68, 19.95 (4C), 14.48 (4C), 14.12, 11.86.

Example 23: 3-(((3-(dimethylamino)propoxy)carbonyl)oxy)pentadecyl 8,8-bis((2-propylpentyl)oxy)octanoate

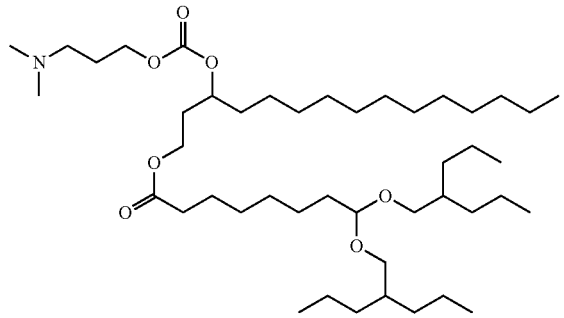 [SMILES: CCCCCCCCCCCCC(CCOC(=O)CCCCCCC(OCC(CCC)CCC)OCC(CCC)CCC)OC(=O)OCCCN(C)C]

¹H NMR (400 MHz, CDCl₃) δ=4.80 (t, J=6.1 Hz, 1H), 4.40 (t, J=5.8 Hz, 1H), 4.26-4.04 (m, 4H), 3.45 (dd, J=5.8, 9.3 Hz, 2H), 3.26 (dd, J=5.9, 9.2 Hz, 2H), 2.53-2.36 (m, 2H), 2.36-2.20 (m, 8H), 1.91 (td, J=6.2, 12.2 Hz, 4H), 1.71-1.48 (m, 10H), 1.44-1.16 (m, 40H), 0.98-0.79 (m, 15H). ¹³C NMR (101 MHz, CDCl₃) δ=173.71, 154.89, 103.45, 75.63, 68.41 (2C), 66.08, 60.47, 55.90, 45.15 (2C), 37.94 (2C), 34.19 (2C), 33.73 (2C), 33.69 (2C), 33.31, 32.94, 31.90, 29.62 (2C), 29.54 (2C), 29.48, 29.42, 29.34, 29.14, 29.12, 26.61, 25.03, 24.83, 24.69, 22.68, 19.95 (4C), 14.48 (4C), 14.12.

Synthesis of Example 24

Intermediate 24a: ethyl 3-octylundec-2-enoate

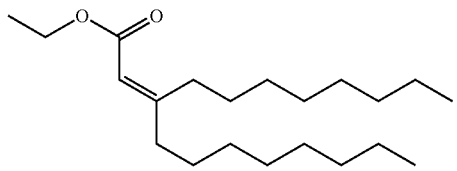 [SMILES: CCCCCCCCC(=CC(=O)OCC)CCCCCCCC]

A solution of 9-heptadecanone (15 g, 59 mmol) and triethylphosphonoacetate (13.2 g, 59 mmol) was stirred in THF (100 mL). To this mixture was added NaOEt (26.4 mL, 21% in EtOH, 70.7 mmol) and the resulting solution was heated to reflux for 48 h. The reaction was acidified with 1M HCl and then diluted with EtOAc. The organic layer was collected and washed with saturated aqueous sodium bicarbonate. The resulting organic material was dried over sodium sulfate and the volatiles removed under reduced pressure to yield a crude material that was purified by silica gel chromatography using heptanes/EtOAc as eluent, providing 11.7 g of the desired product. ¹H NMR (400 MHz, CDCl₃): δ=5.62 (s, 1H), 4.01-4.26 (m, 2H), 2.49-2.68 (m, 2H), 2.13 (m, 2H), 1.44 (dd, J=7.33, 4.80 Hz, 4H), 1.17-1.35 (m, 23H), 0.83-0.98 (m, 6H).

Intermediate 24b: ethyl 3-octylundecanoate

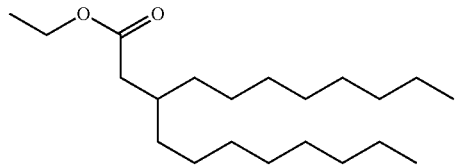 [SMILES: CCCCCCCCC(CCCCCCCC)CC(=O)OCC]

Intermediate 24a (11.75 g, 36.2 mmol) was stirred in DCM (16.5 mL) and MeOH (165 mL). 10% Pd/C (3.85 g,) was added and the reaction flask was fitted with a balloon filled with hydrogen. The reaction was stirred at room temperature for 24 h. The reaction was degassed with nitrogen and filtered through celite with a wash of DCM and MeOH. The filtrate was collected and the volatiles removed under reduced pressure to provide 10.6 g of the desired product, which was utilized without further purification. ¹H NMR (400 MHz, CDCl₃) δ=(q, J=7.16 Hz, 2H), 2.39 (t, J=7.45 Hz, 2H), 2.22 (d, J=6.82 Hz, 2H), 1.84 (br. s., 1H), 1.56 (t, J=7.20 Hz, 2H), 1.19-1.36 (m, 27H), 0.81-0.95 (m, 6H).

Intermediate 24c: 3-octylundecanoic acid

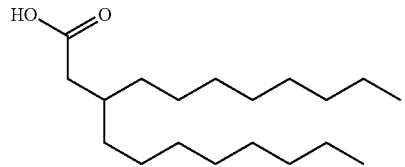 [SMILES: CCCCCCCCC(CCCCCCCC)CC(=O)O]

Intermediate 24b (10.6 g, 32.5 mmol) was stirred with NaOH (9.74 mL, 10 M, 97.4 mmol) in MeOH (100 mL) and DCM (10 mL). The reaction was heated to reflux overnight. Aqueous HCl was added to neutralize the solution, the volatiles were removed under reduced pressure and the resulting material was taken back up in DCM. The organics were washed with aqueous saturated sodium bicarbonate and the resulting aqueous layer was back-extracted with DCM. The combined organics were dried over magnesium sulfate, filtered, and concentrated under reduced pressure. The crude material was purified by silica gel chromatography using heptanes/EtOAc as eluent. The resulting material was taken up in DCM and loaded onto an NH₂ functionalized column. The column was washed with DCM and then DCM/MeOH. The product was eluted with acidic methanol and the eluent concentrated under reduced pressure. The residue was taken up in DCM and washed with saturated aqueous sodium bicarbonate, dried over magnesium sulfate, filtered, and concentrated under reduced pressure to provide 6.5 g of the desired product. ¹H NMR (400 MHz, CDCl₃) δ=2.28 (d, J=7.07 Hz, 2H) 1.86 (br. s., 1H) 1.15-1.44 (m, 28H) 0.82-0.97 (m, 6H).

Example 24: 3-(((3-(dimethylamino)propoxy)carbonyl)oxy)pentadecyl 3-octylundecanoate

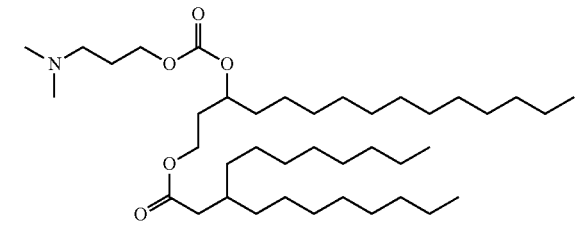 [SMILES: CCCCCCCCCCCCC(CCOC(=O)CC(CCCCCCCC)CCCCCCCC)OC(=O)OCCCN(C)C]

Example 24 can be prepared using similar methods to those employed for the synthesis of Example 1

$^1$H NMR (400 MHz, CDCl$_3$) δ=4.71-4.88 (m, 1H) 4.01-4.31 (m, 4H) 2.71 (br. s., 2H) 2.50 (br. s., 6H) 2.17-2.28 (m, 2H) 2.06 (br. s., 2H) 1.88-1.99 (m, 2H) 1.83 (br. s., 1H) 1.50-1.75 (m, 2H) 1.17-1.40 (m, 48H) 0.80-0.96 (m, 9H). $^{13}$C NMR (101 MHz, CDCl$_3$) δ=173.27, 154.46, 75.52, 65.14, 59.94, 55.37, 43.93 (2C), 38.90, 34.71, 33.89, 33.53 (2C), 32.72, 31.58 (3C), 29.60, 29.34 (2C), 29.31 (2C), 29.28 (2C), 29.18, 29.14, 29.02 (2C), 29.00 (2C), 26.21 (3C), 24.75, 22.35 (3C), 13.78 (3C).

Synthesis of Example 25

Intermediate 25a: 3-octylundec-2-enoic acid

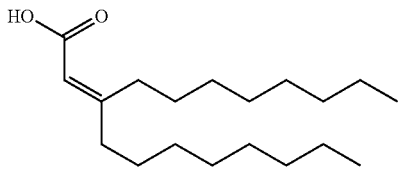 [SMILES: CCCCCCCCC(=CC(=O)O)CCCCCCCC]

Intermediate 25a can be synthesized from Intermediate 24a utilizing similar methods to those used for the synthesis of Intermediate 24c.

TLC (silica gel, 10% ethyl acetate in hexanes): R$_f$=0.18

Example 25: 3-(((3-(dimethylamino)propoxy)carbonyl)oxy)pentadecyl 3-octylundec-2-enoate

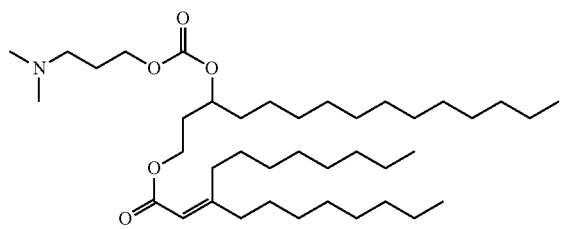 [SMILES: CCCCCCCCCCCCC(CCOC(=O)C=C(CCCCCCCC)CCCCCCCC)OC(=O)OCCCN(C)C]

Example 25 can be prepared using similar methods to those employed for the synthesis of Example 1

$^1$H NMR (400 MHz, CDCl$_3$) δ=5.20-5.41 (m, 1H) 4.81 (dt, J=13.45, 6.54 Hz, 1H) 4.04-4.27 (m, 4H) 2.58 (m, 2H) 2.30-2.48 (m, 2H) 2.24 (s, 6H) 1.99-2.16 (m, 4H) 1.82-1.98 (m, 4H) 1.50-1.74 (m, 2H) 1.43 (dd, J=14.15, 6.57 Hz, 2H) 1.17-1.40 (m, 40H) 0.80-1.00 (m, 9H). MS (M+1)=652.5, Rt=1.44 min (LC Method 4).

Synthesis of Example 26

Intermediate 26a: methyl 3-hexylnon-2-enoate

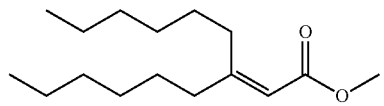 [SMILES: CCCCCCC(=CC(=O)OC)CCCCCC]

To a suspension of sodium hydride (60% in parafin oil, 14.16 g, 335 mmol) in THF (500 mL), cooled in an ice-water bath, was slowly added trimethyl phosphonoacetate (50.74 g, 278.8 mmol) to control gas evolution. After the addition was finished, the reaction was stirred for 2 h then tridecan-7-one (6.5 g, 32.8 mmol) was slowly added, and the reaction was warmed to ambient temperature. After 1 h additional, the reaction was heated to reflux. After 4d, the reaction was cooled, and 1N HCl (aq) was added to quench the reaction. The reaction was extracted with ethyl acetate (3×200 mL). The combined organic extracts were dried over sodium sulfate, filtered, and concentrated under reduced pressure. The concentrate was purified on silica gel, using ethyl acetate/hexanes as eluent to provide 8.0 g of the desired product. TLC (silica gel, 10% ethyl acetate in hexanes): R$_f$=0.72.

Intermediate 26b: 3-hexylnon-2-en-1-ol

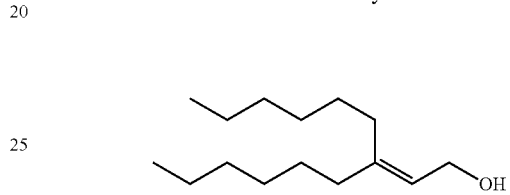

To a solution of Intermediate 26a (8.1 g, 31.9 mmol) in THF (100 mL), cooled in an ice-water bath, was added diisobutylaluminum hydride (25% in toluene, 54.4 mL, 95.6 mmol). After 30 minutes the reaction was brought to ambient temperature. After an additional 6 h, the reaction was cooled in an ice-water bath and quenched with ice-cold water (50 mL) and 1N HCl (aq, 15 mL). The reaction was extracted with ethyl acetate (2×50 mL). The combined organic extractes were washed with water (2×60 mL) and brine (60 mL). The organic extract was dried over sodium sulfate, filtered, and concentrated under reduced pressure. The concentrate was purified on silica-gel, using ethyl acetate/hexanes as eluent to provide 6.8 g of the desired product. TLC (silica gel, 20% ethyl acetate in hexanes): R$_f$=0.29.

Intermediate 26c: 3-hexylnon-2-enal

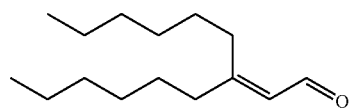 [SMILES: CCCCCCC(=CC=O)CCCCCC]

To a stirred suspension of IBX (21.0 g, 75.12 mmol) in DMSO (30 mL), warmed to 30° C., was added Intermediate 26b in THF (100 mL). The reaction was maintained at 25-30° C. for 2 h. The reaction was diluted with diethyl ether and filtered through celite with diethyl ether washes. The filtrate was washed with water (2×200 mL) and brine (200 mL). The organic extract was dried over sodium sulfate, filtered, and concentrated under reduced pressure to provide 6.0 g of the desired product, which was used without further purification. TLC (silica gel, 10% ethyl acetate in hexanes): R$_f$=0.50.

Intermediate 26d: 7-hexyltridec-4,6-dienoic acid

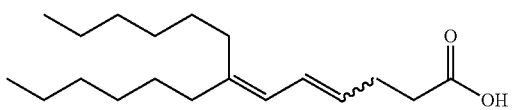 [SMILES: CCCCCCC(=CC=CCCC(=O)O)CCCCCC]

To a suspension of (3-carboxypropyl)triphenylphosphonium bromide (19.09 g, 44.6 mmol) in THF (80 mL) and HMPA (5 mL), cooled in an ice-water bath, was added NaHMDS (1.0M in THF, 111 mL, 111 mmol). Intermediate 26c (5.0 g, 22.3 mmol) in THF (20 mL), was slowly added, and the reaction was warmed to 30° C. After 16 h, the reaction was diluted with 200 mL water and acidified with 2N HCl (aq). The reaction was extracted with ethyl acetate (3×100 mL). The combined organic extracts were dried over sodium sulfate, filtered, and concentrated under reduced pressure. The concentrate was purified on silica gel with ethyl acetate/hexanes as eluent to provide 4.0 g of the desired product. TLC (silica gel, 30% ethyl acetate in n-hexane): $R_f$=0.21.

Intermediate 26e: 7-hexyltridec-6-enoic acid

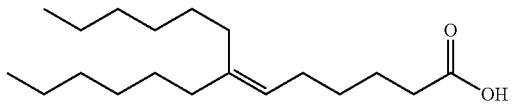 [SMILES: CCCCCCC(=CCCCCC(=O)O)CCCCCC]

To a solution of Intermediate 26d (1.0 g) in methanol (60 mL) was added 10% Pd/C (300 mg). The reaction was stirred at ambient temperature under a balloon of hydrogen gas for 14 h. The reaction mixture was filtered over celite and the residue rinsed with methanol. The filtrate was concentrated under reduced pressure. The concentrate was purified on silica gel with ethyl acetate/hexanes as eluent to provide the desired product. TLC (silica gel, 10% ethyl acetate in n-hexane): $R_f$=0.16

Example 26: 3-(((3-(dimethylamino)propoxy)carbonyl)oxy)pentadecyl 7-hexyltridec-6-enoate

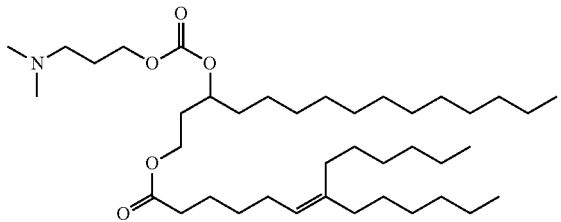 [SMILES: CCCCCCCCCCCCC(CCOC(=O)CCCCC=C(CCCCCC)CCCCCC)OC(=O)OCCCN(C)C]

Example 26 can be prepared using similar methods to those employed for the synthesis of Example 1

$^1$H NMR (400 MHz, CDCl$_3$) δ=5.02-5.20 (m, 1H) 4.80 (t, J=5.18 Hz, 1H) 4.00-4.30 (m, 4H) 2.74 (br. s., 2H) 2.53 (br. s., 6H) 2.30 (t, J=7.58 Hz, 2H) 1.84-2.14 (m, 8H) 1.50-1.78 (m, 4H) 1.21-1.42 (m, 40H) 0.80-0.98 (m, 9H). $^{13}$C NMR (101 MHz, CDCl$_3$) δ=173.41, 154.46, 139.95, 123.49, 75.49, 65.05, 59.99, 55.37, 43.86 (2C), 36.62, 35.12, 33.90, 32.70, 31.59 (2C), 31.50, 29.76, 29.33 (2C), 29.31 (3C), 29.24, 29.17, 29.12, 29.02, 28.83, 28.15, 27.93, 26.99, 26.91, 24.74, 24.33, 22.36 (3C), 13.78 (3C).

Synthesis of Example 27

Intermediate 27a: (E)-9-pentyltetradeca-6,8-dienoic acid

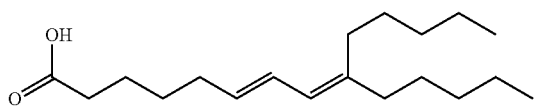 [SMILES: CCCCCC(=C/C=C/CCCCC(=O)O)CCCCC]

Intermediate 27a can be synthesized utilizing similar methods to those in used to produce intermediate 26d.

TLC (silica gel, 10% ethyl acetate in n-hexane): $R_f$=0.31

Intermediate 27b: 9-pentyltetradecanoic acid

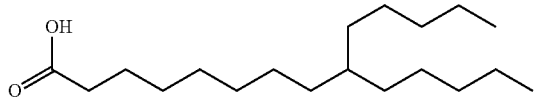 [SMILES: CCCCCC(CCCCC)CCCCCCCC(=O)O]

To a solution of Intermediate 27a (2.0 g, 6.80 mmol) in methanol (70 mL) was added 10% Pd/C (300 mg). The reaction was stirred at ambient temperature under a balloon of hydrogen gas for 4 h. The reaction mixture was filtered over celite, and the residue washed with methanol. The filtrate was concentrated under reduced pressure. The concentrate was purified on silica gel with ethyl acetate/n-hexane as eluent to provide the desired product. TLC (silica gel, 10% ethyl acetate in n-hexane): $R_f$=0.26

Example 27: 3-(((3-(dimethylamino)propoxy)carbonyl)oxy)pentadecyl 9-pentyltetradecanoate

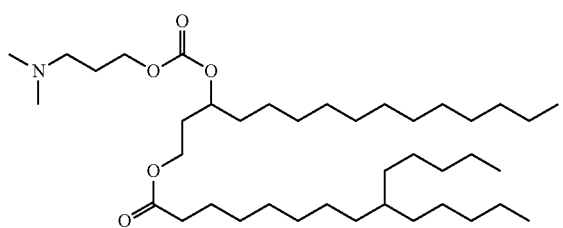 [SMILES: CCCCCCCCCCCCC(CCOC(=O)CCCCCCCC(CCCCC)CCCCC)OC(=O)OCCCN(C)C]

Example 27 can be prepared using similar methods to those employed for the synthesis of Example 1

$^1$H NMR (400 MHz, CDCl$_3$) δ=4.81 (t, J=5.05 Hz, 1H) 4.01-4.30 (m, 4H) 2.68-2.89 (m, 1H) 2.55 (br. s., 6H) 2.30 (t, J=7.58 Hz, 2H) 2.11 (br. s., 2H) 1.84-2.02 (m, 2H) 1.61 (dt, J=14.65, 7.33 Hz, 4H) 1.12-1.38 (m, 48H) 0.77-0.99 (m, 9H). $^{13}$C NMR (101 MHz, CDCl$_3$) δ=173.81, 154.79, 75.79, 65.46, 60.30, 55.71, 44.29 (2C), 37.42, 34.29, 34.21, 33.69, 33.63 (s, 2C), 33.02, 32.38 (s, 2C), 31.91, 29.98, 29.65, 29.63 (s, 2C), 29.56, 29.49, 29.43, 29.34 (s, 2C), 29.21, 26.68, 26.36 (s, 3C), 25.06, 24.95, 22.71 (s, 2C), 22.68, 14.13 (s, 2C), 14.10.

Example 28: 3-(((3-(dimethylamino)propoxy)carbonyl)oxy)pentadecyl 9-pentyltetradec-8-enoate

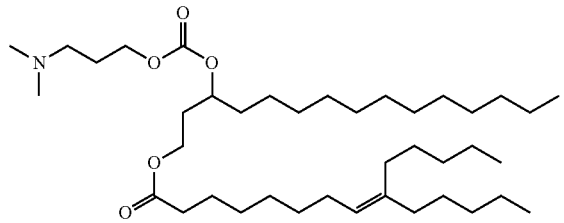 [SMILES: CCCCCCCCCCCCC(CCOC(=O)CCCCCCC=C(CCCCC)CCCCC)OC(=O)OCCCN(C)C]

Example 28 can be prepared using similar methods to those employed for the synthesis of Example 26

$^1$H NMR (400 MHz, CDCl$_3$) δ=ppm 5.02-5.17 (m, 1H) 4.74-4.90 (m, 1H) 4.05-4.27 (m, 4H) 2.38 (br. s., 2H) 2.16-2.34 (m, 8H) 1.80-2.08 (m, 10H) 1.49-1.72 (m, 6H) 1.15-1.37 (m, 36H) 0.81-0.97 (m, 9H). MS (M+1)=652.3, Rt=1.41 min (LC Method 4).

Synthesis of Example 29

Intermediate 29a: 3-heptyldec-2-enal

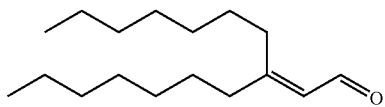 [SMILES: CCCCCCCC(=CC=O)CCCCCCC]

Intermediate 29a can be prepared using similar methods to those employed for the preparation of Intermediate 26c. TLC (silica gel, 10% ethyl acetate in hexanes): R$_f$=0.63.

Intermediate 29b: methyl 5-heptyldodeca-2,4-dienoate

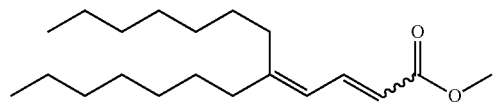 [SMILES: CCCCCCCC(=CC=CC(=O)OC)CCCCCCC]

To a suspension of sodium hydride (55% in paraffin oil, 3.5 g, 74.3 mmol) in THF (70 mL), cooled in an ice-water bath, was slowly added trimethylphosphonoacetate (9.6 mL, 59.5 mmol). After 10 min, Intermediate 29a (7.5 g, 29.7 mmol) in THF (10 mL) was added, and the reaction was allowed to warm to ambient temperature. After an additional 2 h, the reaction was quenched by slow addition of ice-cold water (20 mL). The reaction was extracted with ethyl acetate (2×100 mL). The organic extracts were washed with water and brine. The organics were dried over sodium sulfate, filtered, and concentrated under reduced pressure to provide 8.0 g of the desired product, which was used without further purification. TLC (silica gel, 10% ethyl acetate in hexanes): R$_f$=0.75.

Intermediate 29c: methyl 5-heptyldodecanoate

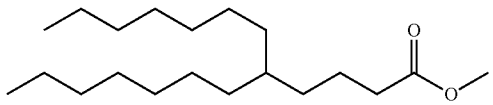 [SMILES: CCCCCCCC(CCCCCCC)CCCC(=O)OC]

To a solution of Intermediate 29b (8.0 g, 25.95 mmol) in methanol (350 mL) was added 10% Pd/C (1.0 g). The reaction was carried out under a atmosphere of hydrogen delivered by a balloon. After 14 h, the reaction was filtered through celite with methanol washes. The filtrate was concentrated under reduced pressure to provide 7.7 g of the desired product, which was used without further purification. TLC (silica gel, 5% methanol in dichloromethane): R$_f$=0.63.

Intermediate 29d: 5-heptyldodecanoic acid

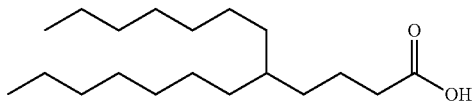 [SMILES: CCCCCCCC(CCCCCCC)CCCC(=O)O]

To a mixture of 5N aq sodium hydroxide (125 mL) and methanol (350 mL) was added Intermediate 29c (7.7 g, 24.7 mmol), and the reaction was heated to reflux. After 16 h, the reaction was cooled in an ice-water bath and quenched by addition of concentrated aqueous HCl until acidic. The mixture was extracted with ethyl acetate (2×250 mL). The organic extracts were dried over sodium sulfate, filtered, and concentrated under reduced pressure. The concentrate was purified on silica gel with ethyl acetate/hexanes as eluent to provide 7.0 g of the desired product. Rf=0.82, 50% EtOAc/heptane The following examples (Examples 29-31) can be prepared using similar methods to those employed for the synthesis of Example 1.

Example 29: 3-(((3-(dimethylamino)propoxy)carbonyl)oxy)pentadecyl 5-heptyldodecanoate

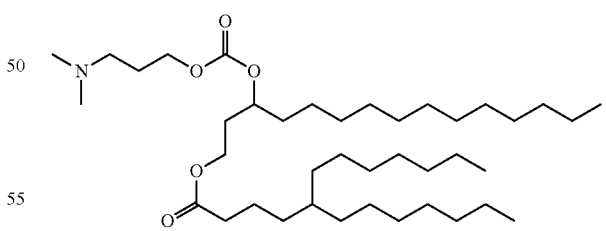

$^1$H NMR (400 MHz, CDCl$_3$) δ=4.69-4.88 (m, 1H) 4.03-4.30 (m, 4H) 2.64 (br. s., 2H) 2.45 (br. s., 6H) 2.28 (t, J=7.58 Hz, 2H) 1.97-2.12 (m, 2H) 1.85-1.97 (m, 2H) 1.51-1.73 (m, 3H) 1.14-1.38 (m, 48H) 0.82-0.96 (m, 9H). $^{13}$C NMR (101 MHz, CDCl$_3$) δ=173.79, 154.82, 75.79, 65.59, 60.37, 55.75, 44.50 (2C), 37.23, 34.67, 34.20, 33.50 (2C), 33.21, 33.02, 31.92 (2C), 31.90, 30.07 (2C), 29.65, 29.63 (2C), 29.56, 29.48, 29.43, 29.36 (2C), 29.33, 26.65 (2C), 25.95, 25.05, 22.67 (3C), 22.18, 14.10 (3C).

Example 30: 3-(((3-(dimethylamino)propoxy)carbonyl)oxy)tridecyl 5-heptyldodecanoate

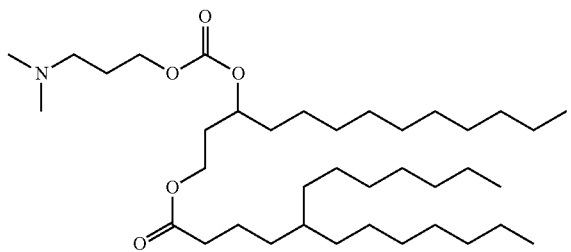 [SMILES: CCCCCCCCCCC(CCOC(=O)CCCC(CCCCCCC)CCCCCCC)OC(=O)OCCCN(C)C]

$^1$H NMR (400 MHz, CDCl$_3$) δ=0.89 (t, J=6.65 Hz, 9H) 1.15-1.42 (m, 42H) 1.49-1.77 (m, 5H) 1.77-1.99 (m, 4H) 2.18-2.37 (m, 8H) 2.43 (br. s., 2H) 4.02-4.29 (m, 4H) 4.81 (t, J=6.27 Hz, 1H). $^{13}$C NMR (101 MHz, CDCl$_3$) δ=173.81, 154.90, 75.66, 66.14, 60.51, 55.93, 45.23 (2C), 37.19, 34.65, 34.19, 33.44 (2C), 33.14, 32.96, 31.93 (2C), 31.89, 30.07 (2C), 29.58, 29.56, 29.49, 29.44, 29.38 (2C), 29.32, 26.70, 26.63 (2C), 25.04, 22.69 (3C), 22.13, 14.13 (3C).

Example 31: 3-(((3-(dimethylamino)propoxy)carbonyl)oxy)undecyl 5-heptyldodecanoate

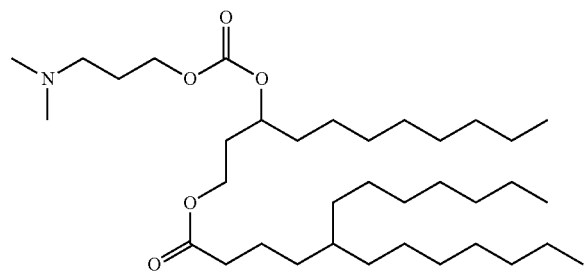 [SMILES: CCCCCCCCC(CCOC(=O)CCCC(CCCCCCC)CCCCCCC)OC(=O)OCCCN(C)C]

$^1$H NMR (400 MHz, CDCl$_3$) δ=0.76-0.97 (m, 9H) 1.16-1.46 (m, 40H) 1.46-1.75 (m, 5H) 1.92 (dt, J=12.61, 6.37 Hz, 4H) 2.17-2.39 (m, 6H) 2.39-2.56 (m, 2H) 4.03-4.33 (m, 4H) 4.81 (t, J=6.15 Hz, 1H). $^{13}$C NMR (101 MHz, CDCl$_3$) δ=173.82, 154.88, 75.67, 66.07, 60.49, 55.82, 45.02 (2C), 37.19, 34.64, 34.17, 33.43 (2C), 33.14, 32.95, 31.92 (2C), 31.82, 30.07 (2C), 29.42 (2C), 29.38 (2C), 29.21, 26.62 (2C), 26.50, 25.03, 22.68 (2C), 22.64, 22.12, 14.13 (2C), 14.10.

Synthesis of Example 32

Intermediate 32a: 4-((1,3-bis(octanoyloxy)propan-2-yl)oxy)-4-oxobutanoic acid

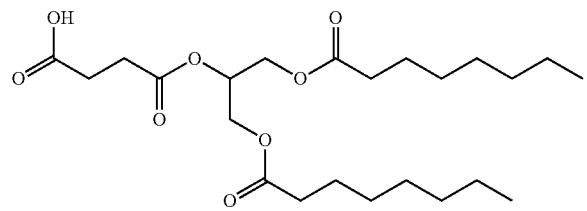 [SMILES: CCCCCCCC(=O)OCC(COC(=O)CCCCCCC)OC(=O)CCC(=O)O]

In a 30 mL microwave vial equipped with a stirbar, 1,3-Dicaprylin (2 g, 5.81 mmol) and succinic anhydride (0.581 g, 5.81 mmol) are dissolved in Toluene (Volume: 10 ml). DMAP (0.284 g, 2.322 mmol) is added, and mixture microwaved at 140 C for 40 min. The crude mixture was evaporated under reduced pressure to obtain a crude oil.

Purification by silica gel column chromatography (80 g column, 0-10% EtOAc/Heptane) provided the title compound as a colorless oil (0.900 g, 70%). $^1$H NMR (400 MHz, CDCl$_3$) δ=5.35-5.22 (m, 1H), 4.39-4.25 (m, 2H), 4.24-4.09 (m, 2H), 2.76-2.60 (m, 4H), 2.39-2.26 (m, 4H), 1.70-1.53 (m, 4H), 1.39-1.19 (m, 16H), 0.97-0.82 (m, 6H). $^{13}$C NMR (101 MHz, CDCl$_3$) δ=177.01, 173.38 (s, 2C), 171.22, 69.57, 61.12 (s, 2C), 33.97 (s, 2C), 31.63 (s, 2C), 29.02 (s, 2C), 28.89 (s, 2C), 28.74, 28.60, 24.80 (s, 2C), 22.58 (s, 2C), 14.29 (s, 2C).

The following examples (Examples 32 and 33) can be prepared using similar methods to those employed for the synthesis of Example 1.

Example 32: 1,3-bis(octanoyloxy)propan-2-yl (3-(((2-(dimethylamino)ethoxy)carbonyl)oxy)pentadecyl) succinate

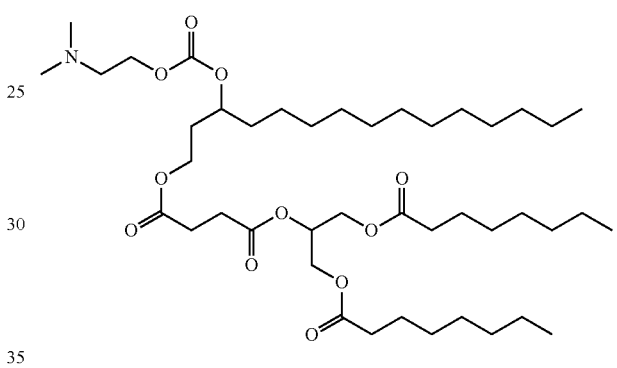

$^1$H NMR (400 MHz, CDCl$_3$) δ=5.31-5.22 (m, 1H), 4.81 (s, 1H), 4.41-4.23 (m, 4H), 4.23-4.09 (m, 4H), 2.79-2.58 (m, 6H), 2.46-2.25 (m, 10H), 2.01-1.86 (m, 2H), 1.74-1.51 (m, 7H), 1.42-1.18 (m, 35H), 0.97-0.82 (m, 9H). MS (M+1)=787.0, Rt=1.60 min (LC Method 5).

Example 33: 1,3-bis(octanoyloxy)propan-2-yl (3-(((3-(dimethylamino)propoxy)carbonyl)oxy)pentadecyl) succinate

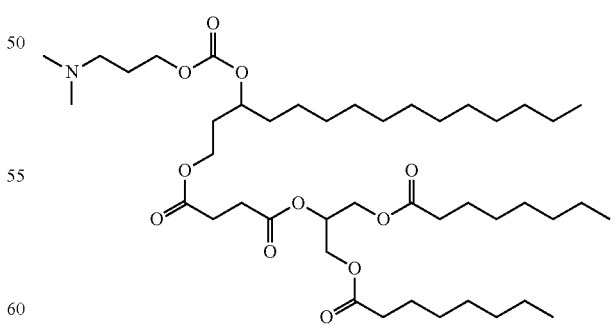

$^1$H NMR (400 MHz, CDCl$_3$) δ=5.33-5.22 (m, 1H), 4.80 (br. s., 1H), 4.36-4.25 (m, 2H), 4.24-4.08 (m, 6H), 2.70-2.51 (m, 6H), 2.45-2.27 (m, 10H), 2.01 (s, 2H), 2.00-1.86 (m, 4H), 1.70-1.51 (m, 6H), 1.39-1.18 (m, 34H), 0.95-0.82 (m, 9H). MS (M+1)=801.7, Rt=1.27 min (LC Method 4).

Synthesis of Example 34

Intermediate 34a: 10-(octyloxy)-10-oxodecanoic acid

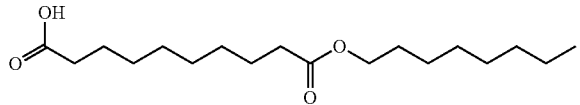 [SMILES: CCCCCCCCOC(=O)CCCCCCCCC(=O)O]

To a solution of sebacic acid (5.0 g, 24.7 mmol) in dichloromethane (40 mL) was added EDC.HCl (7.2 g, 37.1 mmol) and DMAP (3.0 g, 24.7 mmol). The reaction was stirred at ambient temperature for 1 h, then 1-octanol (2.9 g, 22.2 mmol) was added. The reaction was stirred for an additional 72 h. The reaction was diluted with water and the aqueous was extracted with dichloromethane (2×30 mL). The combined dichloromethane extracts were washed with brine, dried over sodium sulfate, and filtered. The filtrate was concentrated under reduced pressure, and the resulting crude material was purified on silica gel with ethyl acetate and hexane as eluent to provide the desired product. TLC (silica gel, 40% ethyl acetate in hexanes): $R_f$=0.42

The following examples (Examples 34-38) can be prepared using similar methods to those employed for the synthesis of Example 1.

Example 34: 1-(3-(((3-(dimethylamino)propoxy)carbonyl)oxy)pentadecyl) 10-octyl decanedioate

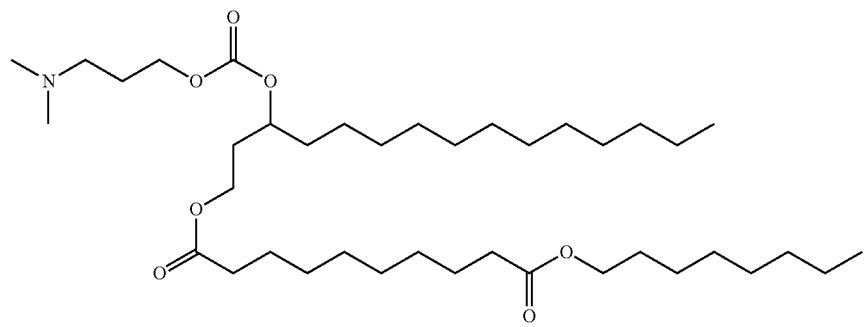 [SMILES: CCCCCCCCCCCCC(CCOC(=O)CCCCCCCCC(=O)OCCCCCCCC)OC(=O)OCCCN(C)C]

$^1$H NMR (400 MHz, CDCl$_3$) δ=4.69-4.94 (m, 1H) 4.19 (t, J=6.53 Hz, 2H) 4.13 (t, J=6.53 Hz, 2H) 4.06 (t, J=6.78 Hz, 2H) 2.42 (t, J=6.40 Hz, 2H) 2.21-2.37 (m, 10H) 1.76-1.98 (m, 4H) 1.50-1.69 (m, 8H) 1.18-1.41 (m, 38H) 0.78-0.98 (m, 6H). MS (M+1)=670.5, Rt=1.11 min (LC Method 4).

Example 35: 1-(3-(((3-(diethylamino)propoxy)carbonyl)oxy)pentadecyl) 10-octyl decanedioate

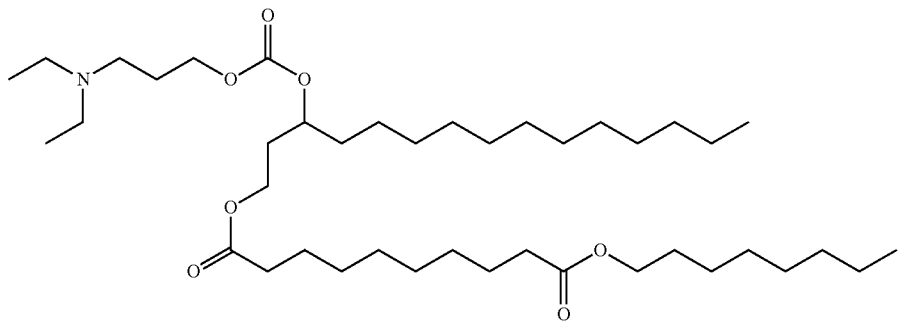 [SMILES: CCCCCCCCCCCCC(CCOC(=O)CCCCCCCCC(=O)OCCCCCCCC)OC(=O)OCCCN(CC)CC]

$^1$H NMR (400 MHz, CDCl$_3$) δ=4.81 (s, 1H), 4.24-4.09 (m, 4H), 4.06 (t, J=6.8 Hz, 2H), 2.56 (br. s., 6H), 2.29 (t, J=7.5 Hz, 4H), 1.99-1.78 (m, 4H), 1.61 (d, J=6.3 Hz, 8H), 1.41-1.18 (m, 38H), 1.05 (t, J=6.8 Hz, 6H), 0.88 (t, J=6.8 Hz, 6H). $^{13}$C NMR (101 MHz, CDCl$_3$) δ 174.0, 173.7, 154.9, 75.6, 66.4, 64.4, 60.5, 49.0, 46.8 (2C), 34.3, 34.2 (2C), 33.0, 31.9, 31.8, 29.7, 29.6 (2C), 29.5, 29.4, 29.3, 29.2 (3C), 29.1 (4C), 28.6, 26.1, 25.9, 25.0 (2C), 24.8, 22.7, 22.6, 14.1 (2C), 11.4 (2C).

Example 36: 1-(3-(((3-(ethyl(methyl)amino)propoxy)carbonyl)oxy)pentadecyl) 10-octyl decanedioate

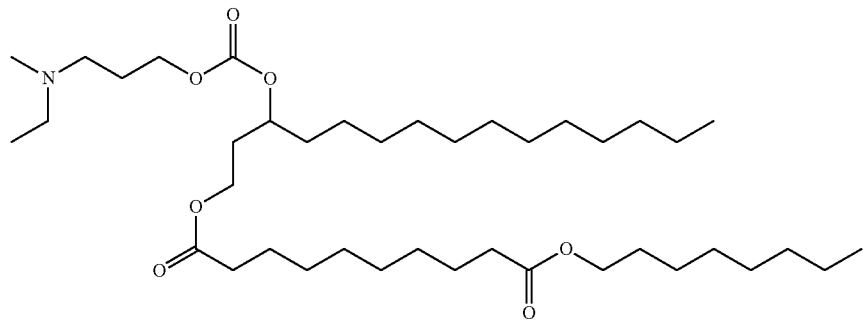 [SMILES: CCCCCCCCCCCCC(CCOC(=O)CCCCCCCCC(=O)OCCCCCCCC)OC(=O)OCCCN(C)CC]

$^1$H NMR (400 MHz, CDCl$_3$) δ=4.81 (s, 1H), 4.10-4.25 (m, 4H), 4.06 (t, J=6.78 Hz, 2H), 2.50 (br. s., 4H), 2.19-2.38 (m, 7H), 1.83-1.99 (m, 4H), 1.61 (d, J=6.27 Hz, 8H), 1.18-1.42 (m, 38H), 1.09 (t, J=7.03 Hz, 3H), 0.89 (t, J=6.78 Hz, 6H). $^{13}$C NMR (101 MHz, CDCl$_3$) δ=174.0, 173.7, 154.9, 75.6, 66.3, 64.4, 60.5, 53.3, 51.3, 41.2, 34.3, 34.2 (2C), 32.9, 31.9, 31.8, 29.7 (3C), 29.6, 29.5, 29.4, 29.3, 29.2 (2C), 29.1 (4C), 28.6, 26.3, 25.9, 25.1, 25.0, 24.8, 22.7, 22.6, 14.1 (2C), 11.9.

Example 37: 1-(3-(((3-(diethylamino)propoxy)carbonyl)oxy)pentadecyl) 10-(2-ethylhexyl) decanedioate

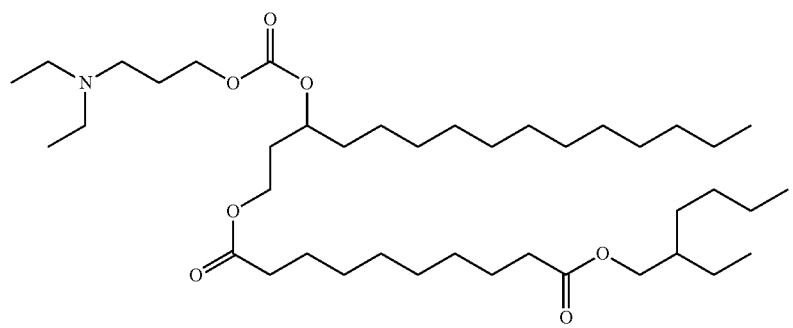 [SMILES: CCCCCCCCCCCCC(CCOC(=O)CCCCCCCCC(=O)OCC(CC)CCCC)OC(=O)OCCCN(CC)CC]

$^1$H NMR (400 MHz, CDCl$_3$) δ=4.90-4.68 (m, 1H), 4.28-4.08 (m, 4H), 3.98 (dd, J=1.9, 5.9 Hz, 2H), 2.53 (d, J=6.5 Hz, 6H), 2.29 (dt, J=3.5, 7.5 Hz, 4H), 1.92 (q, J=6.5 Hz, 2H), 1.83 (td, J=6.5, 13.6 Hz, 2H), 1.74-1.48 (m, 7H), 1.43-1.17 (m, 36H), 1.03 (t, J=7.0 Hz, 6H), 0.96-0.82 (m, 9H). $^{13}$C NMR (101 MHz, CDCl$_3$) δ=174.08, 173.73, 154.97, 75.55, 66.61, 66.49, 60.54, 49.03, 46.87 (2C), 38.68, 34.39, 34.20 (2C), 32.96, 31.90, 30.37, 29.65, 29.62 (2C), 29.55, 29.48, 29.43, 29.34, 29.10 (3C), 28.89, 26.35 (2C), 25.04, 24.99, 24.85, 23.74, 22.96, 22.68, 14.12, 14.05, 11.66 (2C), 10.98.

Example 38: 1-(3-(((3-(ethyl(methyl)amino) propoxy)carbonyl)oxy)pentadecyl) 10-(2-ethyl-hexyl) decanedioate

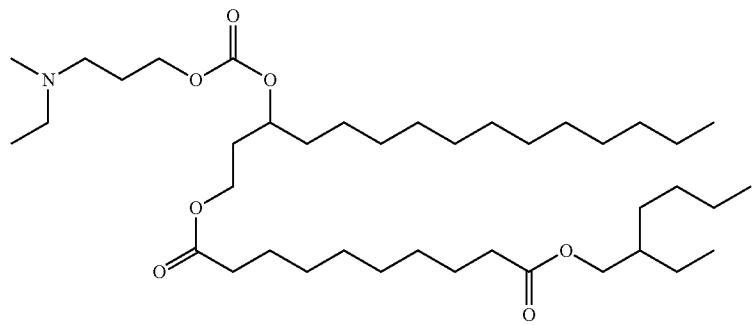 [SMILES: CCCCCCCCCCCCC(CCOC(=O)CCCCCCCCC(=O)OCC(CC)CCCC)OC(=O)OCCCN(C)CC]

$^1$H NMR (400 MHz, CDCl$_3$) δ=4.81 (t, J=6.1 Hz, 1H), 4.26-4.08 (m, 4H), 3.98 (dd, J=1.9, 5.9 Hz, 2H), 2.45 (d, J=6.8 Hz, 4H), 2.30 (dt, J=3.4, 7.5 Hz, 4H), 2.24 (s, 3H), 1.97-1.81 (m, 4H), 1.72-1.50 (m, 7H), 1.43-1.20 (m, 36H), 1.07 (t, J=7.2 Hz, 3H), 0.96-0.82 (m, 9H). $^{13}$C NMR (101 MHz, CDCl$_3$) δ=174.08, 173.73, 154.97, 75.55, 66.61, 66.49, 60.54, 49.0, 46.87 (2C), 38.68, 34.39, 34.20 (2C), 32.96, 31.90, 30.37, 29.65, 29.62 (2C), 29.55, 29.48, 29.43, 29.34, 29.10 (3C), 28.89, 26.35 (2C), 25.04, 24.99, 24.85, 23.74, 22.96, 22.68, 14.12, 14.05, 11.66 (2C), 10.98.

Synthesis of Example 39

Intermediate 39a: 10-(octanoyloxy)decanoic acid

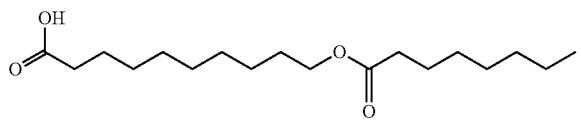 [SMILES: CCCCCCCC(=O)OCCCCCCCCCC(=O)O]

To a solution of octanoic acid (766 mg, 5.32 mmol) in dichloromethane (25 mL) was added EDC.HCl (1.02 g, 5.32 mmol) and DIPEA (0.95 mL, 5.32 mmol). The reaction was stirred for 1 h at ambient temperature, then 10-hydroxydecanoic acid (500 mg, 2.66 mmol) and DMAP (162 mg, 1.33 mmol) were added. The reaction was stirred for an additional 24 h. The reaction was diluted with water, and the aqueous layer was extracted with dichloromethane (2×30 mL). the combined dichloromethane extracts were washed with brine, dried over sodium sulfate and filtered. The filtrate was concentrated under reduced pressure and the crude material was purified on silica gel with methanol/dichloromethane as eluent to provide the desired product. TLC (silica gel, 10% methanol in dichloromethane): R$_f$=0.69

The following examples (Examples 39-42) can be prepared using similar methods to those employed for the synthesis of Example 1.

Example 39: 3-(((3-(dimethylamino)propoxy)carbonyl)oxy)pentadecyl 10-(octanoyloxy)decanoate

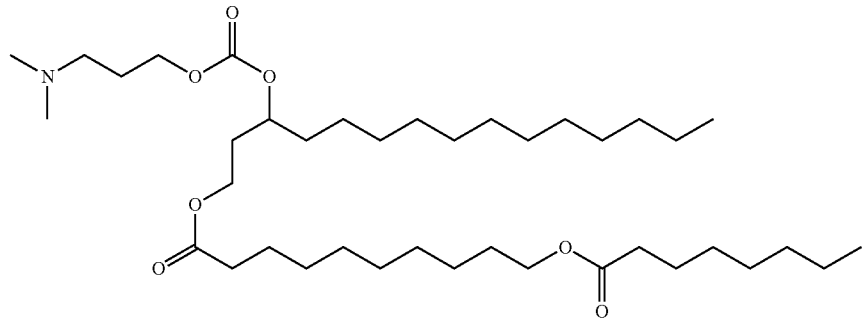 [SMILES: CCCCCCCCCCCCC(CCOC(=O)CCCCCCCCCOC(=O)CCCCCCC)OC(=O)OCCCN(C)C]

$^1$H NMR (400 MHz, CDCl$_3$) δ=4.72-4.91 (m, 1H) 4.13-4.35 (m, 4H) 3.97-4.13 (m, 4H) 2.85 (br. s., 2H) 2.62 (br. s., 6H) 2.30 (t, J=7.45 Hz, 4H) 2.14 (br. s., 2H) 1.81-2.04 (m, 2H) 1.50-1.73 (m, 8H) 1.15-1.42 (m, 36H) 0.79-0.98 (m, 6H). MS (M+1)=670.8, Rt=1.19 min (LC Method 4).

Example 40: 8-dodecyl-2-methyl-6,12-dioxo-5,7,11-trioxa-2-azanonadecan-19-yl decanoate

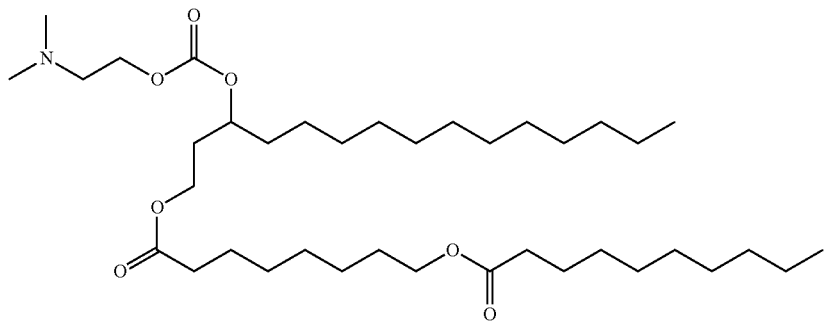 [SMILES: CCCCCCCCCCCCC(CCOC(=O)CCCCCCCOC(=O)CCCCCCCCC)OC(=O)OCCN(C)C]

$^1$H NMR (400 MHz, CDCl$_3$) δ=4.88-4.74 (m, 1H), 4.25 (t, J=5.4 Hz, 2H), 4.21-4.09 (m, 2H), 4.05 (t, J=6.7 Hz, 2H), 2.66 (br. s., 2H), 2.41-2.24 (m, 9H), 1.92 (q, J=6.4 Hz, 2H), 1.73-1.51 (m, 9H), 1.48-1.18 (m, 38H), 0.96-0.81 (m, 6H). MS (M+1)=657.9, Rt=1.76 min (LC Method 4).

Example 41: 3-(((3-(diethylamino)propoxy)carbonyl)oxy)pentadecyl 10-(octanoyloxy)decanoate

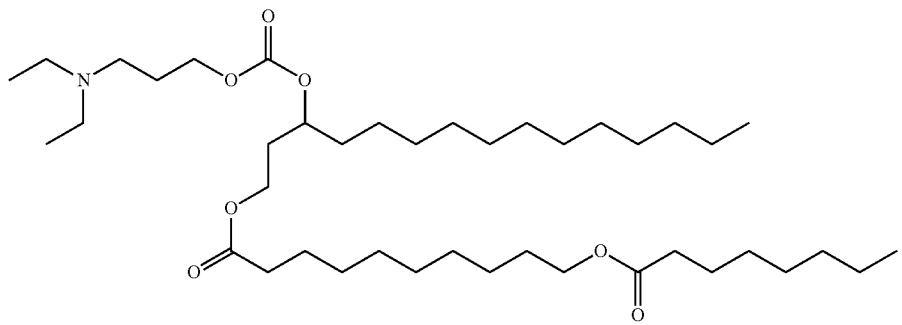 [SMILES: CCCCCCCCCCCCC(CCOC(=O)CCCCCCCCCOC(=O)CCCCCCC)OC(=O)OCCCN(CC)CC]

$^1$H NMR (400 MHz, CDCl$_3$) δ=0.80-0.94 (m, 6H) 1.03 (t, J=6.53 Hz, 6H) 1.18-1.41 (m, 38H) 1.52-1.72 (m, 8H) 1.84 (br. s., 2H) 1.92 (q, J=6.36 Hz, 2H) 2.29 (t, J=7.53 Hz, 4H) 2.54 (br. s., 6H) 4.05 (t, J=6.78 Hz, 2H) 4.10-4.28 (m, 4H) 4.81 (t, J=6.27 Hz, 1H). $^{13}$C NMR (101 MHz, CDCl$_3$) □=174.04, 173.75, 154.96, 75.56, 66.46, 64.35, 60.53, 49.03, 46.86 (2C), 34.38, 34.22, 34.19, 32.96, 31.90, 31.65, 29.65, 29.63 (2C), 29.56, 29.48, 29.43, 29.34, 29.33, 29.19 (2C), 29.11, 29.10, 28.92, 28.62, 26.51-26.06 (m, 1C), 25.90, 25.04, 25.00, 24.86, 22.68, 22.59, 14.12, 14.07, 11.59 (2C).

Example 42: 3-(((3-(ethyl(methyl)amino)propoxy)carbonyl)oxy)pentadecyl 10-(octanoyloxy)decanoate

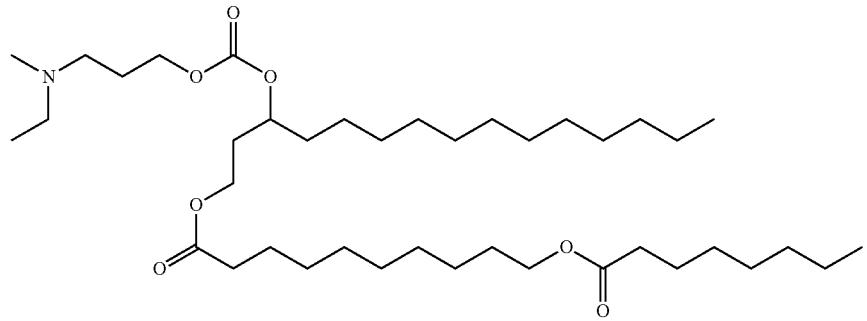 [SMILES: CCCCCCCCCCCCC(CCOC(=O)CCCCCCCCCOC(=O)CCCCCCC)OC(=O)OCCCN(C)CC]

$^1$H NMR (400 MHz, CDCl$_3$) δ=4.93-4.67 (m, 1H), 4.25-4.09 (m, 4H), 4.05 (t, J=6.7 Hz, 2H), 2.42 (q, J=7.4 Hz, 4H), 2.29 (t, J=7.5 Hz, 4H), 2.21 (s, 3H), 2.00-1.79 (m, 4H), 1.67-1.50 (m, 8H), 1.41-1.15 (m, 38H), 1.05 (t, J=7.2 Hz, 3H), 0.88 (t, J=6.7 Hz, 6H). $^{13}$C NMR (101 MHz, CDCl$_3$) δ=174.03, 173.74, 154.96, 75.57, 66.47, 64.35, 60.54, 53.46, 51.42, 41.56, 34.38, 34.21, 34.18, 32.95, 31.90, 31.65, 29.62 (3C), 29.55, 29.48, 29.43, 29.33 (2C), 29.19 (2C), 29.10 (2C), 28.92, 28.61, 26.63, 25.90, 25.03, 25.00, 24.86, 22.68, 22.59, 14.12, 14.07, 12.28.

The following examples (Examples 43-46) can be prepared using similar methods to those employed for the synthesis of Example 1.

Example 43: (9Z,12Z)-3-(((3-(dimethylamino)propoxy)carbonyl)oxy)pentadecyl octadeca-9,12-dienoate

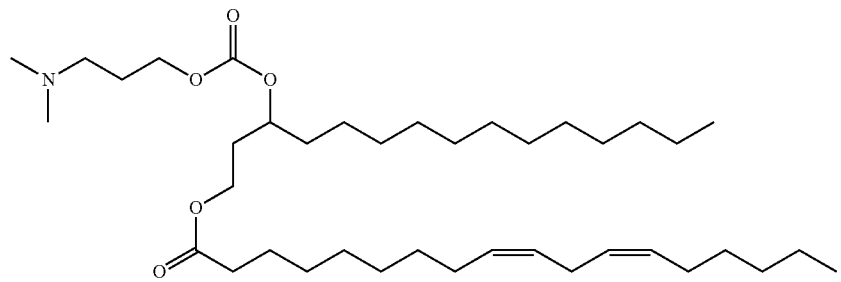

$^1$H NMR (400 MHz, CDCl$_3$) δ=5.23-5.48 (m, 4H) 4.81 (t, J=5.31 Hz, 1H) 4.01-4.29 (m, 4H) 2.71-2.85 (m, 2H) 2.63 (br. s., 2H) 2.44 (br. s., 6H) 2.30 (t, J=7.58 Hz, 2H) 2.06 (q, J=7.07 Hz, 6H) 1.84-1.97 (m, 2H) 1.49-1.71 (m, 4H) 1.34-1.42 (m, 4H) 1.18-1.34 (m, 30H) 0.79-0.98 (m, 6H). MS (M+1)=636.5, Rt=1.12 min (LC Method 6).

Example 44: (9Z,12Z)-3-(((3-(diethylamino)propoxy)carbonyl)oxy)pentadecyl octadeca-9,12-dienoate

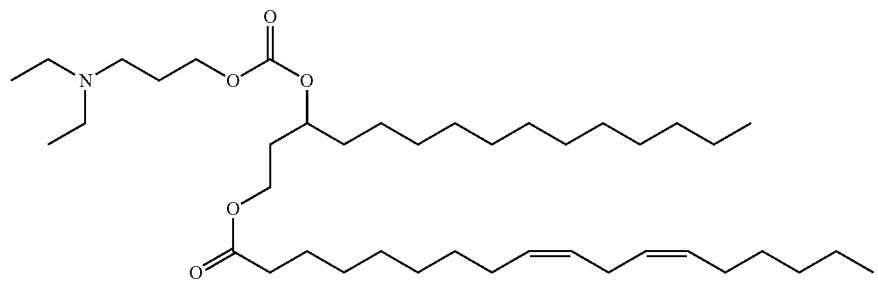 [SMILES: CCCCC/C=C\C/C=C\CCCCCCCC(=O)OCCC(CCCCCCCCCCCC)OC(=O)OCCCN(CC)CC]

$^1$H NMR (400 MHz, CDCl$_3$) δ=0.79-0.98 (m, 6H) 1.04 (t, J=7.15 Hz, 6H) 1.16-1.45 (m, 34H) 1.51-1.72 (m, 5H) 1.76-1.99 (m, 5H) 2.05 (q, J=6.78 Hz, 4H) 2.30 (t, J=7.65 Hz, 2H) 2.47-2.64 (m, 4H) 2.78 (t, J=6.53 Hz, 2H) 4.05-4.28 (m, 4H) 4.81 (t, J=6.15 Hz, 1H) 5.24-5.53 (m, 4H). MS (M+1)=665.6, Rt=1.40 min (LC Method 7).

Example 45: (9Z,12Z)-3-(((3-(ethyl(methyl)amino) propoxy)carbonyl)oxy)pentadecyl octadeca-9,12-dienoate

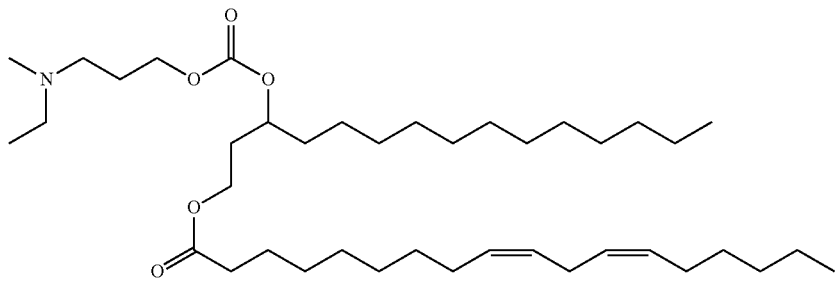 [SMILES: CCCCC/C=C\C/C=C\CCCCCCCC(=O)OCCC(CCCCCCCCCCCC)OC(=O)OCCCN(C)CC]

¹H NMR (400 MHz, CDCl₃) δ=5.29-5.46 (m, 4H), 4.83 (quin, J=6.20 Hz, 1H), 4.20 (t, J=6.53 Hz, 2H), 4.15 (t, J=6.50 Hz, 2H), 2.79 (t, J=6.53 Hz, 2H), 2.52 (br. s., 4H), 2.23-2.37 (m, 5H), 2.07 (q, J=6.78 Hz, 4H), 1.94 (q, J=6.50 Hz, 4H), 1.53-1.78 (m, 4H), 1.23-1.43 (m, 34H), 1.06-1.18 (m, 3H), 0.86-0.96 (m, 6H). MS (M+1)=650.6, Rt=1.92 min (LC Method 7).

Example 46: (9Z,12Z)-3-(((2-(dimethylamino) ethoxy)carbonyl)oxy)pentadecyl octadeca-9,12-dienoate

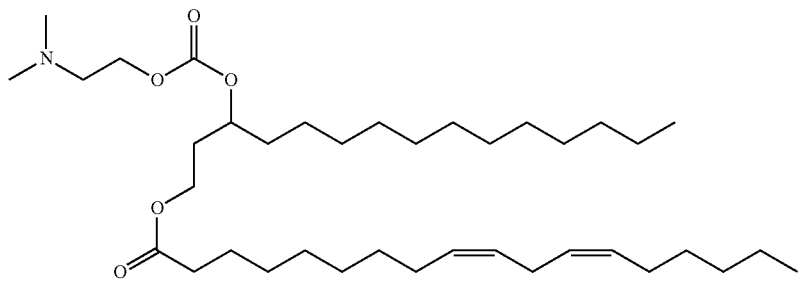 [SMILES: CCCCC/C=C\C/C=C\CCCCCCCC(=O)OCCC(CCCCCCCCCCCC)OC(=O)OCCN(C)C]

¹H NMR (400 MHz, CDCl₃) δ=5.45-5.28 (m, 4H), 4.81 (t, J=6.1 Hz, 1H), 4.24 (t, J=5.6 Hz, 2H), 4.19-4.07 (m, 2H), 2.78 (t, J=6.7 Hz, 2H), 2.64 (br. s., 2H), 2.38-2.25 (m, 8H), 2.05 (q, J=6.9 Hz, 4H), 1.92 (q, J=6.4 Hz, 2H), 1.73-1.51 (m, 5H), 1.43-1.20 (m, 33H), 0.89 (dt, J=4.0, 6.8 Hz, 6H). MS (M+1)=623.3, Rt=1.70 min (LC Method 7).

Synthesis of Example 47: 1-((9Z,12Z)-octadeca-9, 12-dienoyloxy)pentadecan-3-yl 1,4-dimethylpiperidine-4-carboxylate Intermediate 47a: 1-((tert-butyldimethylsilyl)oxy) pentadecan-3-yl 1,4-dimethylpiperidine-4-carboxylate

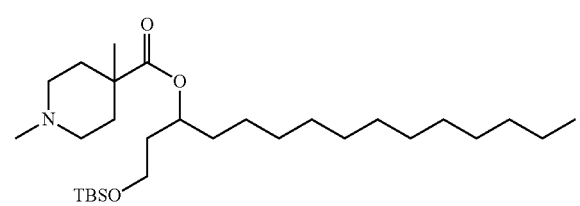 [SMILES: CCCCCCCCCCCCC(CCO[Si](C)(C)C(C)(C)C)OC(=O)C1(C)CCN(C)CC1]

In a round-bottom flask equipped with a stir bar, 1,4-dimethylpiperidine-4-carboxylic acid hydrochloride (0.612 g, 3.07 mmol) is dissolved in DCM (Volume: 20 ml). DIPEA (1.461 ml, 8.36 mmol) is added, followed by DMAP (0.136 g, 1.115 mmol), Intermediate 1g (1 g, 2.79 mmol), and finally, EDC.HCl (0.695 g, 3.62 mmol). Mixture was stirred at rt overnight. The volatiles were evaporated under reduced pressure. The crude mixture was purified by silica gel column chromatography (80 g column, 0-30% EtOAc/Heptane, then 0-5% MeOH/DCM) to provide the title compound as a colorless oil (0.373 g, 27%). ¹H NMR (400 MHz, CDCl₃) δ=5.00 (d, J=6.3 Hz, 1H), 3.73-3.53 (m, 2H), 2.98-2.54 (m, 2H), 2.28 (s, 3H), 2.15 (m, 3H), 1.78 (q, J=6.8 Hz, 2H), 1.56 (d, J=6.8 Hz, 4H), 1.25 (s, 21H), 1.19 (s, 3H), 0.99-0.82 (m, 12H), 0.16-0.00 (m, 6H).

Intermediate 47b: 1-hydroxypentadecan-3-yl 1,4-dimethylpiperidine-4-carboxylate

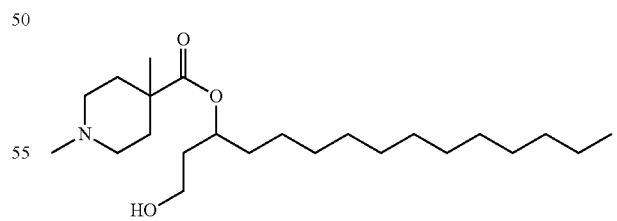

In a 250 ml round-bottom flask equipped with a stir bar, Intermediate 47a (373 mg, 0.749 mmol) is dissolved in MeOH (Volume: 10 ml) at rt. CAN (1068 mg, 1.948 mmol) is added, and mixture is stirred at rt for 2 hrs. Sat. sodium bicarbonate solution and DCM are added to the mixture in a separatory funnel. The organics are then washed with bicarb, extracted in DCM, dried over MgSO4, filtered and concentrated under pressure to give crude product mixture. Purification by silica gel column chromatography (80 g Example 47: 1-((9Z,12Z)-octadeca-9,12-dienoyloxy)pentadecan-3-yl 1,4-dimethylpiperidine-4-carboxylate

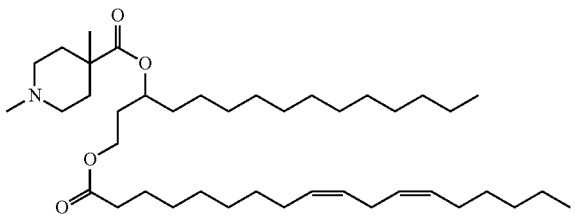 [SMILES: CCCCC/C=C\C/C=C\CCCCCCCC(=O)OCCC(CCCCCCCCCCCC)OC(=O)C1(C)CCN(C)CC1]

In a 50 ml round-bottom flask equipped with a stirbar, Linoleic acid (252 mg, 0.898 mmol) and Intermediate 47b (287 mg, 0.748 mmol) are dissolved in DCM (Volume: 10 ml). DIPEA (0.523 ml, 2.99 mmol) is added, followed by DMAP (36.6 mg, 0.299 mmol) and finally, EDC.HCl (229 mg, 1.197 mmol). Mixture is stirred at rt overnite. The solvent was evaporated under pressure. Purification by silica gel chromatography (40 g column, 0-60% EtOAc/heptanes) afforded the title compound as a colorless oil (270 mg, 53%). $^1$H NMR (400 MHz, CDCl$_3$) δ=5.46-5.27 (m, 4H), 5.01 (br. s., 1H), 4.17-4.00 (m, 2H), 2.77 (t, J=6.5 Hz, 2H), 2.73-2.56 (m, 2H), 2.37-2.24 (m, 6H), 2.15 (d, J=12.8 Hz, 4H), 2.05 (q, J=6.8 Hz, 5H), 1.98-1.81 (m, 3H), 1.69-1.48 (m, 7H), 1.44-1.22 (m, 30H), 1.20 (s, 3H), 0.89 (dt, J=4.3, 6.8 Hz, 6H). $^{13}$C NMR (100 MHz, CDCl$_3$) δ=176.3, 173.8, 130.2, 130.0, 128.1, 127.9, 70.8, 60.5 (2C), 53.0 (2C), 46.1, 41.0, 34.6, 34.2, 34.1, 33.1, 31.9, 31.5, 29.7, 29.6 (3C), 29.5 (2C), 29.4, 29.3 (3C), 29.2, 29.1, 27.2 (2C), 25.6, 25.1, 24.9, 22.7, 22.6 (2C), 14.1 (2C).

Synthesis of Example 48

Intermediate 48a: 1-((tert-butyldimethylsilyl)oxy)tetradecan-2-ol

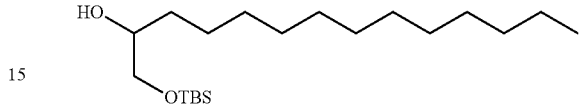

A suspension of tetradecane-1,2-diol (10 g, 43.4 mmol), imidazole (2.95 g, 43.4 mmol) and TBSCl (7.20 g, 477 mmol) in THF was stirred for 15 h at rt, then poured into water (300 mL) and extracted with EtOAc. The organic extract was washed with brine and dried over MgSO4, filtered, and concentrated under reduced pressure. The residue was purified on silica gel with EtOAc/heptane as eluent to afford 11.96 g of the desired product. $^1$H NMR (400 MHz, CDCl$_3$) δ=3.59-3.70 (m, 2H), 3.31-3.44 (m, 1H), 2.44 (br. s., 1H), 1.35-1.51 (m, 2H), 1.26 (s, 20H), 0.81-0.98 (m, 12H), 0.08 (s, 6H).

Intermediate 48b: 1-((tert-butyldimethylsilyl)oxy)tetradecan-2-yl (3-(diethylamino)propyl) carbonate

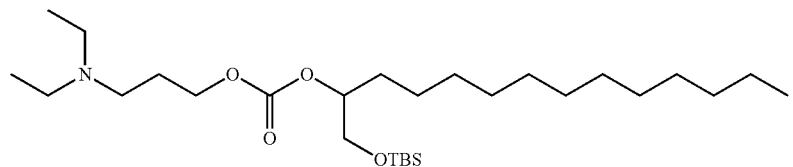 [SMILES: CCCCCCCCCCCCC(CO[Si](C)(C)C(C)(C)C)OC(=O)OCCCN(CC)CC]

Intermediate 48b can be prepared using similar methods to those employed for the synthesis of Intermediate 1j. $^1$H NMR (400 MHz, CDCl$_3$) δ=4.66-4.83 (m, 1H), 4.18 (t, J=6.53 Hz, 2H), 3.66 (d, J=5.27 Hz, 2H), 2.57 (br. s., 6H), 1.86 (d, J=5.77 Hz, 2H), 1.48-1.78 (m, 2H), 1.26 (s, 20H), 1.05 (t, J=6.65 Hz, 6H), 0.81-0.97 (m, 12H), 0.05 (d, J=1.76 Hz, 6H).

Intermediate 48c: 3-(diethylamino)propyl (1-hydroxytetradecan-2-yl) carbonate

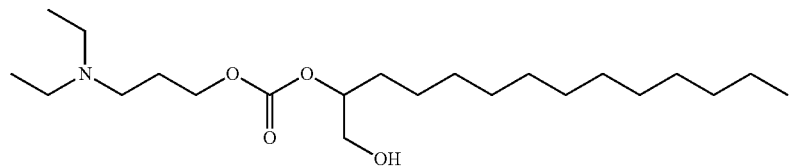 [SMILES: CCCCCCCCCCCCC(CO)OC(=O)OCCCN(CC)CC]

In a plastic tube, Intermediate 48b (3.27 g, 6.52 mmol) was dissolved in 10 mL THF and cooled in an ice bath. HF.Py (3.43 mL, 195 mmol) was added dropwise. The mixture was then warmed to ambient temperature and stirred for one hour. Sat. NaHCO$_3$ was added and the aqueous phase was extracted with EtOAc three times. The organic phases were combined and dried over MgSO4, filtered, and concentrated under reduced pressure to provide 2.5 g of the desired product, which was used without further purification. Rf=0.25, 15% MeOH in DCM

Example 48: 2-(((3-(diethylamino)propoxy)carbonyl)oxy)tetradecyl 4,4-bis((2-ethylhexyl)oxy)butanoate

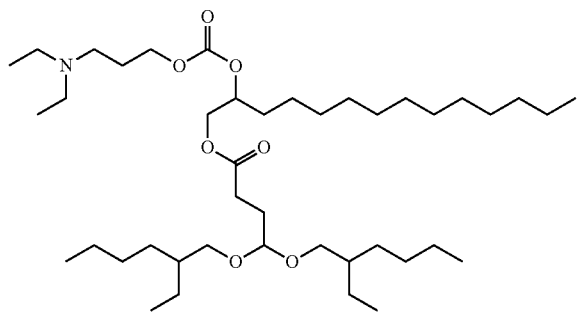 [SMILES: CCCCCCCCCCCCC(COC(=O)CCC(OCC(CC)CCCC)OCC(CC)CCCC)OC(=O)OCCCN(CC)CC]

Example 48 can be prepared using similar methods to those employed for the synthesis of Example 12. $^1$H NMR (400 MHz, CDCl$_3$) δ=4.83-4.96 (m, 1H), 4.45 (t, J=5.40 Hz, 1H), 4.30 (dd, J=11.92, 2.64 Hz, 1H), 4.14-4.26 (m, 2H), 4.05 (dd, J=12.05, 6.53 Hz, 1H), 3.42-3.54 (m, 2H), 3.28 (td, J=9.03, 6.02 Hz, 2H), 2.59 (br. s., 6H), 2.41 (t, J=7.65 Hz, 2H), 1.79-2.01 (m, 3H), 1.52-1.74 (m, 3H), 1.19-1.52 (m, 38H), 1.07 (br. s., 6H), 0.77-0.96 (m, 15H). MS (M+1)=715.0, Rt=1.96 min (LC Method 11).

Synthesis of Example 49

Intermediate 49a: (12Z,15Z)-1-((tert-butyldimethylsilyl)oxy)henicosa-12,15-dien-3-ol

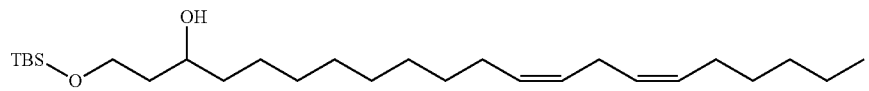

Magnesium turnings (0.516 mg, 21.2 mmol) were weighed into a pre-dried 100 mL flask. The flask was charged with nitrogen, sealed with a septum pierced with a 16G needle outlet and put in an oven at 120'C for 2 hours. The flask was removed from the oven, the needle was removed, and the flask was allowed to cool to ambient temperature. To the flask, 40 mL of anhydrous THF and a catalytic amount of iodine was added, followed by the addition of linoelyl bromide (5.25 g, 16.0 mmol). The flask was connected with a condenser and the reaction was refluxed under N$_2$ until most of magnesium was consumed (about 1 hr), then cooled to room temperature.

To a solution of 3-(tert-butyldimethylsilyloxy) propanal (Intermediate 1g, 2.5 g, 13.3 mmol) in 50 ml THF, cooled in an ice-water bath, the above prepared Grinard reagent was added dropwise. The reaction stirred for 30 min. The reaction was quenched with Sat. NaHCO$_3$, and extracted with ethyl acetate. The combined organic extracts were dried, concentrated under reduced pressure, and purified on silica gel with 10% ethylacetate/heptane as eluent to afford 2.7 g of the desired product. 1H NMR (400 MHz, CDCl$_3$) δ=5.17-5.37 (m, 4H), 3.78-3.87 (m, 1H), 3.67-3.78 (m, 2H), 2.68 (t, J=4.0 Hz, 2H), 1.89-2.05 (m, 4H), 1.53-1.64 (m, 2H), 1.12-1.44 (m, 18H), 0.77-0.85 (m, 14H), 0.00 (s, 6H).

Intermediate 49b: (12Z,15Z)-henicosa-12,15-diene-1,3-diol

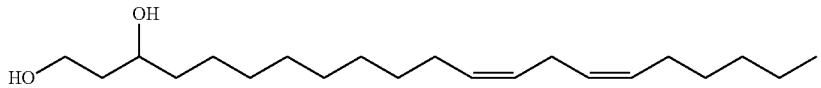 [SMILES: CCCCC/C=C\C/C=C\CCCCCCCCC(O)CCO]

To a solution of Intermediate 49a (1.1 g, 2.5 mmol) in 15 ml THF at room temperature, TBAF (3.01 ml 1.0M THF solution, 3.01 mmol) was added. The reaction was stirred for 1 hr. The reaction was extracted between brine and ethyl acetate. The combined organics were dried over sodium sulfate, concentrated under reduced pressure, and purified on silica gel with 50% ethylacetate/heptane as eluent to afford the desired product (0.78 g, 96%). $^1$H NMR (CDCl$_3$) δ=5.24-5.56 (m, 4H), 3.82-4.00 (m, 3H), 2.70-2.87 (m, 2H), 2.19 (br. s., 2H), 2.07 (q, J=6.7 Hz, 4H), 1.64-1.82 (m, 2H), 1.20-1.54 (m, 20H), 0.89-0.97 (m, 3H) Intermediate 49c:

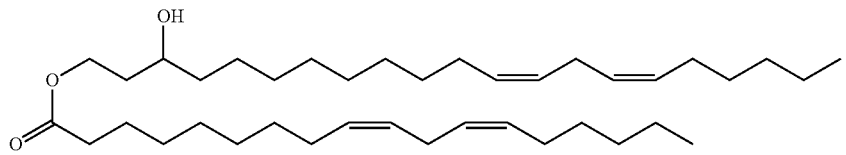 [SMILES: CCCCC/C=C\C/C=C\CCCCCCCCC(O)CCOC(=O)CCCCCCC/C=C\C/C=C\CCCCC]

To a solution of Intermediate 49b (390 mg, 1.20 mmol) in DCM (10 mL), linoleic acid (404 mg, 1.44 mmol) was added, followed by DIPEA (0.210 mL, 1.20 mmol), DMAP (58.7 mg, 0.48 mmol), and EDC.HCl (323 mg, 1.68 mmol). The reaction stirred at room temperature for 90 min. The reaction was extracted between brine and ethyl acetate. The combined organics were dried over sodium sulfate and filtered. The filtrate was concentrated under reduced pressure and the residue was purified on silica gel with 15% ethyl acetate/heptane as eluent to provide the title compound. $^1$H NMR (400 MHz, CDCl$_3$) δ=5.30-5.45 (m, 8H), 4.39 (ddd, J=11.23, 8.60, 5.02 Hz, 1H), 4.15 (dt, J=11.17, 5.71 Hz, 1H), 3.61-3.73 (m, 1H), 2.79 (t, J=6.27 Hz, 4H), 2.33 (t, J=7.65 Hz, 2H), 2.07 (q, J=6.94 Hz, 8H), 1.83 (dddd, J=14.40, 8.69, 5.77, 3.26 Hz, 1H), 1.54-1.75 (m, 3H), 1.42-1.54 (m, 3H), 1.23-1.42 (m, 32H), 0.85-0.96 (m, 6H)

Example 49: (9Z,12Z)-(12Z,15Z)-3-((3-(dimethylamino)propanoyl)oxy)henicosa-12,15-dien-1-yl octadeca-9,12-dienoate

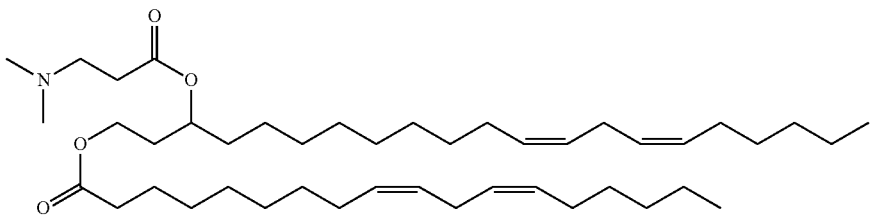 [SMILES: CCCCC/C=C\C/C=C\CCCCCCCCC(CCOC(=O)CCCCCCC/C=C\C/C=C\CCCCC)OC(=O)CCN(C)C]

Example 49 can be prepared using similar methods to those employed for the synthesis of Example 1. $^1$H NMR (400 MHz, CDCl$_3$) δ=5.16-5.40 (m, 8H), 4.92 (s, 1H), 3.91-4.16 (m, 2H), 2.70 (t, J=6.3 Hz, 4H), 2.49-2.59 (m, 2H), 2.36-2.45 (m, 2H), 2.21 (t, J=7.5 Hz, 2H), 2.18 (s, 6H), 1.98 (q, J=7.1 Hz, 8H), 1.74-1.86 (m, 2H), 1.43-1.59 (m, 4H), 1.14-1.35 (m, 32H), 0.69-0.90 (m, 6H). MS (M+1)= 686.5, Rt=1.13 min (LC Method 6).

The following examples (Examples 50-53) can be prepared using similar methods to those employed for the synthesis of Example 49.

Example 50: (12Z,15Z)-3-((4-(dimethylamino)butanoyl)oxy)henicosa-12,15-dien-1-yl 3-octylundecanoate, Formate Salt

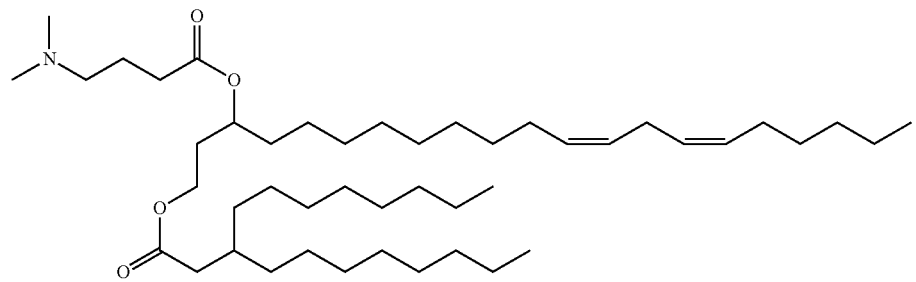 [SMILES: CCCCC/C=C\C/C=C\CCCCCCCCC(CCOC(=O)CC(CCCCCCCC)CCCCCCCC)OC(=O)CCCN(C)C]

$^1$H NMR (400 MHz, CDCl$_3$) δ=8.53 (s, 1H), 5.27-5.47 (m, 4H), 4.93-5.05 (m, 1H), 4.09 (t, J=6.65 Hz, 2H), 2.79 (t, J=6.80 Hz, 2H), 2.67 (dd, J=9.03, 6.53 Hz, 2H), 2.50 (s, 6H), 2.39 (t, J=7.15 Hz, 2H), 2.23 (d, J=6.78 Hz, 2H), 2.07 (q, J=6.80 Hz, 4H), 1.78-1.99 (m, 5H), 1.48-1.69 (m, 3H), 1.20-1.44 (m, 46H), 0.83-0.96 (m, 9H). MS (M+1)=718.4, Rt=1.34 min (LC Method 6).

Example 51: (12Z,15Z)-3-((4-(dimethylamino)bu-tanoyl)oxy)henicosa-12,15-dien-1-yl 5-heptyldodecanoate

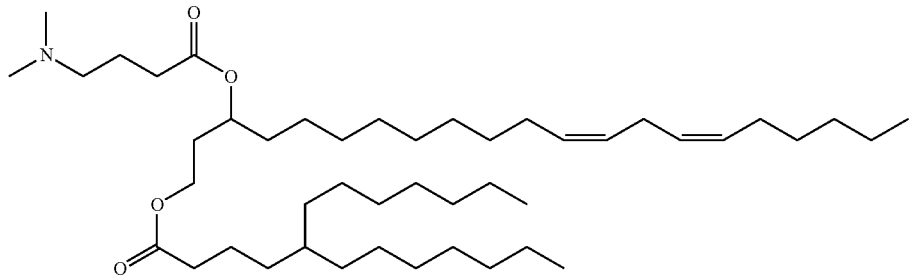 [SMILES: CCCCC/C=C\C/C=C\CCCCCCCCC(CCOC(=O)CCCC(CCCCCCC)CCCCCCC)OC(=O)CCCN(C)C]

$^1$H NMR (400 MHz, CDCl$_3$) δ =5.23-5.49 (m, 4H), 4.84-5.08 (m, 1H), 3.95-4.19 (m, 2H), 2.74-2.83 (m, 2H), 2.56 (br. s., 6H), 2.42 (t, J=6.82 Hz, 2H), 2.27 (t, J=7.58 Hz, 2H), 2.06 (q, J=6.91 Hz, 6H), 1.77-1.97 (m, 2H), 1.48-1.67 (m, 5H), 1.14-1.42 (m, 46H), 0.81-0.96 (m, 9H). MS (M+1)=718.5, Rt=1.25 min (LC Method 5).

Example 52: (12Z,15Z)-3-((4-(dimethylamino)bu-tanoyl)oxy)henicosa-12,15-dien-1-yl 7-hexyltridecanoate

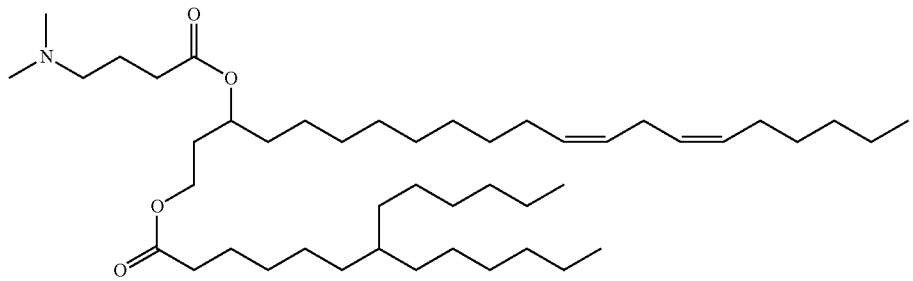 [SMILES: CCCCC/C=C\C/C=C\CCCCCCCCC(CCOC(=O)CCCCCC(CCCCCC)CCCCCC)OC(=O)CCCN(C)C]

$^1$H NMR (400 MHz, CDCl$_3$) δ=5.25-5.48 (m, 4H), 4.91-5.06 (m, 1H), 4.00-4.21 (m, 2H), 2.78 (t, J=6.53 Hz, 2H), 2.24-2.48 (m, 12H), 1.99-2.13 (m, 4H), 1.71-1.99 (m, 7H), 1.48-1.71 (m, 4H), 1.24-1.48 (m, 30H), 1.22 (br. s., 12H), 0.76-0.99 (m, 9H). $^{13}$C NMR (101 MHz, CDCl$_3$) δ=173.90, 173.10, 130.19, 130.10, 127.96 (2C), 71.12, 60.55, 58.82, 45.26 (2C) 37.35, 34.32, 34.23, 33.60 (2C) 33.49, 33.02, 32.09, 31.94 (2C) 31.51, 29.82 (3C), 29.66 (2C), 29.48 (2C), 29.34, 29.29, 27.22, 27.18, 26.62 (2C), 26.37, 25.60, 25.19, 24.99, 22.71 (2C), 22.57, 22.54, 14.14 (2C), 14.09.

Example 53: (12Z,15Z)-3-((4-(dimethylamino)bu-tanoyl)oxy)henicosa-12,15-dien-1-yl 9-pentyltetradecanoate

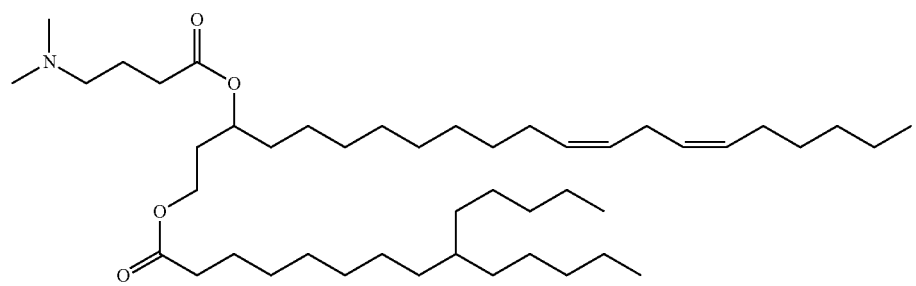 [SMILES: CCCCC/C=C\C/C=C\CCCCCCCCC(CCOC(=O)CCCCCCCC(CCCCC)CCCCC)OC(=O)CCCN(C)C]

¹H NMR (400 MHz, CDCl₃) δ=5.22-5.49 (m, 4H), 4.84-5.09 (m, 1H), 3.96-4.21 (m, 2H), 2.67-2.83 (m, 3H), 2.57 (br. s., 6H), 2.42 (t, J=6.82 Hz, 2H), 2.29 (t, J=7.58 Hz, 2H), 2.06 (q, J=6.91 Hz, 6H), 1.77-1.98 (m, 2H), 1.48-1.67 (m, 4H), 1.14-1.43 (m, 46H), 0.82-0.97 (m, 9H). MS (M+1)=718.5, Rt=1.17 min (LC Method 6).

Synthesis of Example 54

Intermediate 54a: (9Z,12Z)-octadeca-9,12-dien-1-yl carbonochloridate

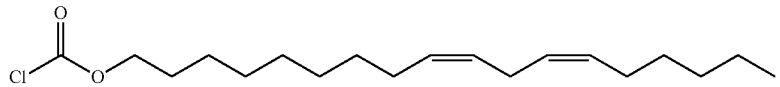 [SMILES: CCCCC/C=C\C/C=C\CCCCCCCCOC(=O)Cl]

To a solution of linoleyl alcohol (2.09 g, 7.5 mmol) in 40 mL ethylacetate, cooled in an ice-water bath, was added triphosgene (1.11 g, 3.8 mmol), followed by DIPEA (2.1 ml, 12.0 mmol). The reaction was warmed to room temperature and stirred for further 10 min. The reaction was then filtered, concentrated under reduced pressure and purified on silica gel with 20% DCM/heptane to afford desired product (2.0 g, 81%). ¹H NMR (CDCl₃) δ=5.25-5.54 (m, 4H), 4.34 (t, J=6.8 Hz, 2H), 2.80 (t, J=6.4 Hz, 2H), 2.07 (q, J=6.9 Hz, 4H), 1.63-1.82 (m, 2H), 1.19-1.46 (m, 16H), 0.81-0.99 (m, 3H)

Intermediate 54b: (12Z,15Z)-3-hydroxyhenicosa-12,15-dien-1-yl (9Z,12Z)-octadeca-9,12-dien-1-yl carbonate

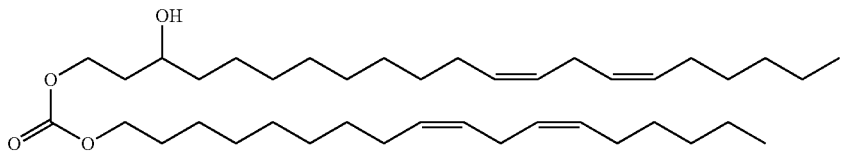 [SMILES: CCCCC/C=C\C/C=C\CCCCCCCCOC(=O)OCCC(O)CCCCCCCC/C=C\C/C=C\CCCCC]

To a solution of Intermediate 49b (50.0 mg, 0.15 mmol) in 2.0 ml DCM, cooled in an ice-water bath, was added Intermediate 54a (60.8 mg, 0.185 mmol), followed by pyridine (48.7 mg, 0.616 mmol). The reaction was stirred at for 4.5 hrs. The reaction was quenched with sat. aq. NaHCO₃ and extracted with ethyl acetate. The combined organics were dried over sodium sulfate and filtered. The filtrate was concentrated under reduced pressure and the residue was purified on silica gel with 15% ethylacetate/heptane to afford the title compound. ¹H NMR (CDCl₃) δ=5.27-5.57 (m, 8H), 4.34-4.49 (m, 1H), 4.20-4.32 (m, 1H), 4.15 (t, J=6.7 Hz, 2H), 3.75 (d, J=6.1 Hz, 1H), 2.80 (t, J=6.4 Hz, 4H), 2.07 (q, J=6.8 Hz, 8H), 1.82-1.96 (m, 1H), 1.57-1.78 (m, 6H), 1.22-1.52 (m, 34H), 0.84-0.98 (m, 6H)

Example 54: (12Z,15Z)-1-((((9Z,12Z)-octadeca-9,12-dien-1-yloxy)carbonyl)oxy)henicosa-12,15-dien-3-yl 3-(dimethylamino)propanoate

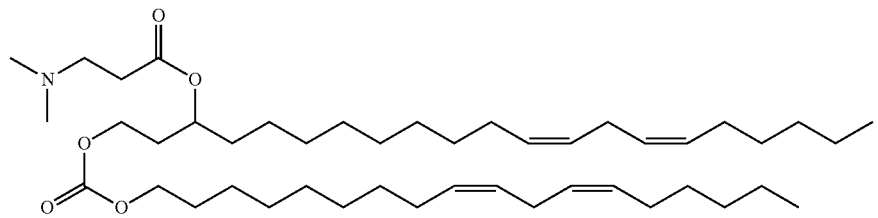 [SMILES: CCCCC/C=C\C/C=C\CCCCCCCCOC(=O)OCCC(CCCCCCCC/C=C\C/C=C\CCCCC)OC(=O)CCN(C)C]

Example 54 can be prepared using similar methods to those employed for the synthesis of Example 49. 1H NMR (CDCl₃) δ=5.26-5.51 (m, 8H), 5.02 (br. s., 1H), 4.15 (dt, J=19.7, 6.7 Hz, 4H), 2.79 (t, J=6.4 Hz, 4H), 2.57-2.67 (m, 2H), 2.41-2.57 (m, 2H), 2.26 (s, 6H), 2.06 (q, J=6.9 Hz, 8H), 1.86-2.00 (m, 2H), 1.64-1.73 (m, 2H), 1.23-1.42 (m, 36H), 0.85-0.97 (m, 6H). MS (M+1)=716.8. Rt=1.12 min. (LC Method 11).

Synthesis of Example 55

Intermediate 55a: heptyl 2,2-bis(heptyloxy)acetate

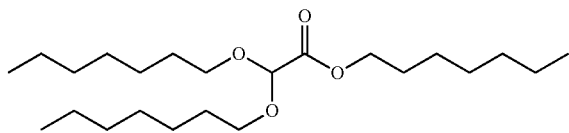 [SMILES: CCCCCCCOC(=O)C(OCCCCCCC)OCCCCCCC]

To a solution of methyl 2,2-dimethoxyacetate (5.0 g, 37.3 mmol) in heptanol (26.3 mL, 186 mmol) was added camphorsulfonic acid (0.43 g, 1.86 mmol), and the reaction was heated to 100° C., overnight. The reaction was cooled to ambient temperature and concentrated under reduced pressure. The concentrate was purified on silica gel with dichloromethane/heptane as eluent to provide 4.0 g of the desired compound. $^1$H NMR (400 MHz, CDCl$_3$): δ=4.86 (s, 1H), 4.21 (t, J=6.78 Hz, 2H), 3.52-3.69 (m, 4H), 1.55-1.77 (m, 6H), 1.20-1.45 (m, 24H), 0.82-0.98 (m, 9H) ppm.

Intermediate 55b: 2,2-bis(heptyloxy)acetic acid

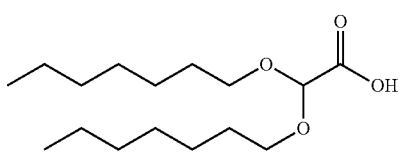 [SMILES: CCCCCCCOC(OCCCCCCC)C(=O)O]

To a solution of Intermediate 26a (4.06 g, 10.5 mmol) in methanol (50 mL) was added sodium hydroxide (2N aq, 7.88 mL, 15.8 mmol), and the mixture was stirred at ambient temperature overnight. The reaction was diluted with ethyl acetate and brine. The aqueous layer was titrated to neutral pH with 1N aq HCl, and was extracted with ethyl acetate. The combined organics were dried over sodium sulfate, filtered, and concentrated under reduced pressure. The concentrate was purified on silica gel (equilibrated with 0.4N ammonia and 2% methanol in dichloromethane) with methanol/dichloromethane as eluent to provide 2.3 g of the desired compound. $^1$H NMR (400 MHz, CDCl$_3$): δ=4.88 (s, 1H), 3.53-3.71 (m, 4H), 1.63 (quin, J=6.84 Hz, 4H), 1.18-1.43 (m, 16H), 0.84-0.97 (m, 6H) ppm.

Intermediate 55c

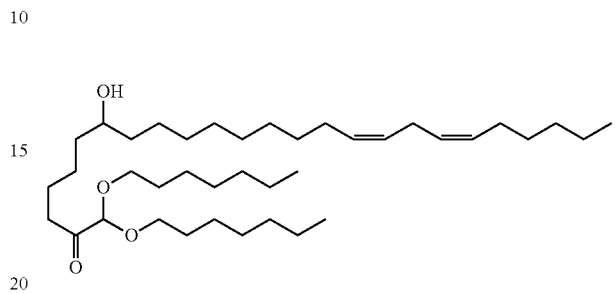

Example 55c can be prepared using similar methods to those employed for the synthesis of Intermediate 49c. $^1$H NMR (400 MHz, CDCl$_3$) δ=5.30-5.46 (m, 4H), 4.90 (s, 1H), 4.17-4.30 (m, 2H), 3.53-3.70 (m, 5H), 2.80 (t, J=6.44 Hz, 2H), 2.07 (q, J=6.82 Hz, 4H), 1.71-1.96 (m, 2H), 1.59-1.70 (m, 4H), 1.42-1.54 (m, 4H), 1.19-1.42 (m, 34H), 0.80-0.99 (m, 9H)

Example 55: (13Z,16Z)-4-(((2-(dimethylamino)ethoxy)carbonyl)oxy)docosa-13,16-dien-1-yl 2,2-bis(heptyloxy)acetate

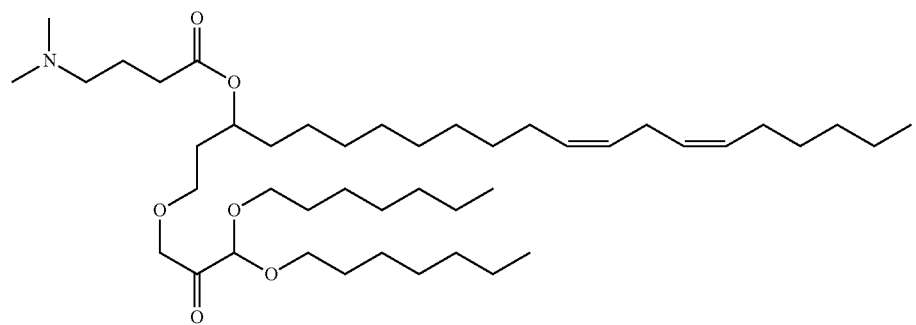 [SMILES: CCCCC/C=C\C/C=C\CCCCCCCCC(CCOCC(=O)C(OCCCCCCC)OCCCCCCC)OC(=O)CCCN(C)C]

To a solution of Intermediate 55c (174 mg, 0.286 mmol) in DCM (4.0 mL) cooled in an ice-water bath, was added pyridine (0.035 mL, 0.429 mmol) followed by triphosgene (42.4 mg, 0.143 mmol). After 30 min, 2-(dimethylamino)ethanol (0.086 mL, 0.857 mmol) was added and the resultant mixture was stirred at room temperature for 1 hr. The reaction was extracted between sat. NaHCO$_3$ and DCM. The combined organics were dried over sodium sulfate and the filtrate was concentrated under reduced pressure and the residue purified on silica gel with 60% ethyl acetate/heptane eluent to provide the title compound. $^1$H NMR (CDCl$_3$) δ=5.19-5.37 (m, 4H), 4.81 (s, 1H), 4.64 (s, 1H), 4.07-4.18 (m, 4H), 3.43-3.59 (m, 4H), 2.66-2.74 (m, 2H), 2.52 (t, J=5.9 Hz, 2H), 2.21 (s, 6H), 1.92-2.02 (m, 4H), 1.38-1.76 (m, 12H), 1.12-1.36 (m, 32H), 0.72-0.88 (m, 9H). MS (M+1)=724.4, Rt=1.21 min (LC Method 6)

Example 56: (13Z,16Z)-4-(((3-(diethylamino)propoxy)carbonyl)oxy)docosa-13,16-dien-1-yl 2,2-bis(heptyloxy)acetate

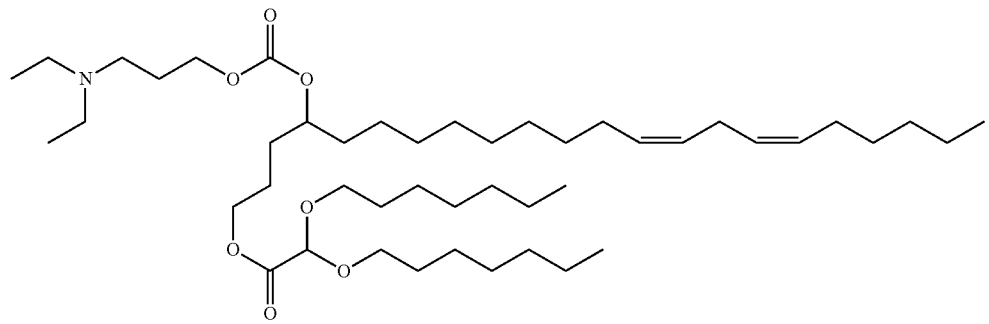 [SMILES: CCCCC/C=C\C/C=C\CCCCCCCCC(CCCOC(=O)C(OCCCCCCC)OCCCCCCC)OC(=O)OCCCN(CC)CC]

$^1$H NMR (CDCl$_3$) δ=5.25-5.51 (m, 4H), 4.89 (s, 1H), 4.61-4.79 (m, 1H), 4.09-4.29 (m, 4H), 3.44-3.71 (m, 4H), 2.79 (t, J=6.4 Hz, 2H), 2.45-2.61 (m, 6H), 2.00-2.15 (m, 4H), 1.71-1.89 (m, 4H), 1.47-1.71 (m, 8H), 1.24-1.43 (m, 34H), 1.02 (t, J=7.2 Hz, 6H), 0.86-0.95 (m, 9H). MS (M+1)=766.5, Rt=1.22 min (LC Method 6).

Synthesis of Example 57

Intermediate 57a: ((2,2-bis(heptyloxy)ethoxy)methyl)benzene

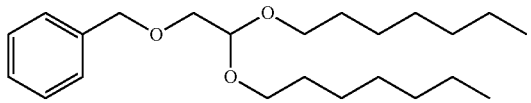 [SMILES: CCCCCCCOC(COCc1ccccc1)OCCCCCCC]

Benzyloxylacetaldehyde (2 g, 13.3 mmol), heptanol (4.64 g, 40.0 mmol) and PPTS (33.0 mg, 0.13 mmol) were combined in a round bottom flask. The mixture was heated at 110° C. for 72 h. The reaction was directly loaded onto silica gel and purified with 3% ethyl acetate/heptane to afford the desired product (3.0 g, 62%). $^1$H NMR (CDCl$_3$) δ=7.30-7.40 (m, 5H), 4.68 (t, J=5.3 Hz, 1H), 4.61 (s, 2H), 3.61-3.66 (m, 2H), 3.48-3.55 (m, 4H), 1.60-1.72 (m, 4H), 1.27-1.38 (m, 16H), 0.87-0.93 (m, 6H).

Intermediate 57b: 2,2-bis(heptyloxy)ethanol

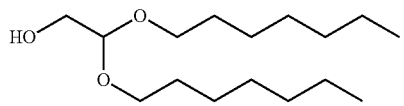 [SMILES: CCCCCCCOC(CO)OCCCCCCC]

To a solution of Intermediate 57a (2.7 g, 7.41 mmol) in 40 ml EtOAc/MeOH (1:1) at room temperature, 10% Pd/C (0.788 g 0.74 mmol) was added. The reaction atmosphere was exchanged with H$_2$ and treated with an H$_2$ ballon at room temperature for 3 h. The reaction was filtered, concentrated under reduced pressure, and purified on silica gel with 12% ethylacetate/heptane to afford the desired product (1.0 g, 49%). $^1$H NMR (CDCl$_3$) δ=4.55 (t, J=5.4 Hz, 1H), 3.70 (dt, J=9.3, 6.8 Hz, 2H), 3.59 (d, J=4.8 Hz, 2H), 3.51 (dt, J=9.3, 6.8 Hz, 2H), 1.61 (dt, J=14.3, 6.9 Hz, 4H), 1.21-1.43 (m, 16H), 0.83-0.96 (m, 6H).

Intermediate 57c: 3-((3-(2,2-bis(heptyloxy)ethoxy)-3-oxopropyl)disulfanyl)propanoic acid

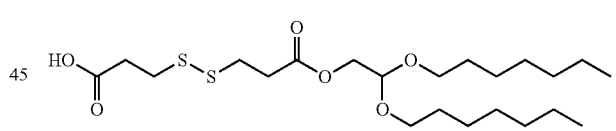

To a suspension of disulfidedipropanoic acid (115 mg, 0.547 mmol) in 3.0 ml DCM, Intermediate 57b (100 mg, 0.364 mmol), DMAP (17.81 mg, 0.656 mmol) and DIPEA (32 ul, 0.182 mmol) were added. EDC (126 mg, 0.656 mmol) was added last. The mixture became clear and was stirred at room temperature for 1 hr. The reaction was extracted between brine and ethyl acetate. The combined organics were dried over sodium sulfate, concentrated under reduced pressure and purified on silica gel with 30% ethyl acetate/heptane to afford the desired product (75 mg, 44%). $^1$H NMR (CDCl$_3$) δ=4.72 (t, J=5.4 Hz, 1H), 4.15 (d, J=5.3 Hz, 2H), 3.65 (dt, J=9.3, 6.8 Hz, 2H), 3.51 (dt, J=9.3, 6.8 Hz, 2H), 2.90-3.03 (m, 4H), 2.75-2.86 (m, 4H), 1.60 (quin, J=7.0 Hz, 4H), 1.19-1.43 (m, 16H), 0.81-0.97 (m, 6H).

Example 57: 2,2-bis(heptyloxy)ethyl 3-((3-ethyl-10-((9Z,12Z)-octadeca-9,12-dien-1-yl)-8,15-dioxo-7,9,14-trioxa-3-azaheptadecan-17-yl)disulfanyl)propanoate

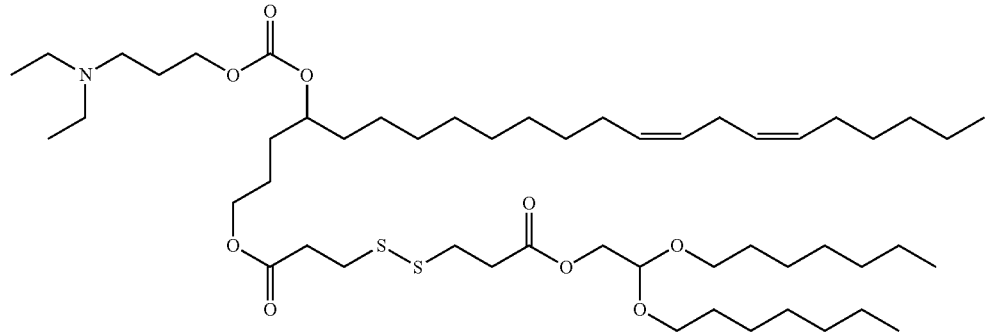 [SMILES: CCCCC/C=C\C/C=C\CCCCCCCCC(CCCOC(=O)CCSSCCC(=O)OCC(OCCCCCCC)OCCCCCCC)OC(=O)OCCCN(CC)CC]

Example 57 can be prepared using similar methods to those employed for the synthesis of Example 55. ¹H NMR (CDCl₃) δ=5.23-5.44 (m, 4H), 4.65-4.74 (m, 1H), 4.63 (t, J=5.4 Hz, 1H), 4.14 (td, J=6.5, 1.8 Hz, 2H), 4.00-4.11 (m, 4H), 3.59 (dt, J=9.2, 6.7 Hz, 2H), 3.44 (dt, J=9.1, 6.7 Hz, 2H), 2.83-2.95 (m, 4H), 2.65-2.79 (m, 6H), 2.41-2.52 (m, 6H), 2.01 (q, J=6.9 Hz, 4H), 1.73-1.84 (m, 2H), 1.45-1.73 (m, 10H), 1.16-1.38 (m, 34H), 0.97 (t, J=7.2 Hz, 6H), 0.78-0.89 (m, 9H). MS (M+1)=944.5, Rt=1.25 min (LC Method 6).

Synthesis of Example 58

Example 58a

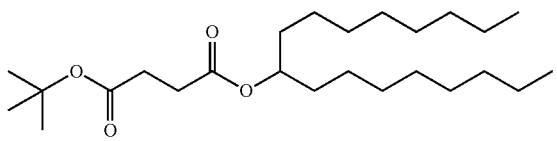 [SMILES: CCCCCCCCC(CCCCCCCC)OC(=O)CCC(=O)OC(C)(C)C]

In a 500 ml round-bottom flask equipped with a stir bar, 9-heptadecanol (1.12 g, 4.37 mmol) was dissolved in DCM (30 ml). 4-(tert-butoxy)-4-oxobutanoic acid (0.913 g, 5.24 mmol) and DMAP (0.107 g, 0.873 mmol) were added, followed by DIPEA (3.05 ml, 17.47 mmol). The mixture is stirred at rt for a minute before addition of EDC.HCl (1.172 g, 6.11 mmol). The mixture is then stirred at rt overnight. The mixture was concentrated under reduced pressure, and the concentrate was purified on silica gel with ethyl acetate/heptane as eluent to provide the title compound. ¹H NMR (400 MHz, CDCl₃) δ=4.89 (quin, J=6.27 Hz, 1H), 2.48-2.65 (m, 4H), 1.48-1.57 (m, 4H), 1.42-1.48 (m, 9H), 1.18-1.38 (m, 24H), 0.84-0.96 (m, 6H)

Example 58b

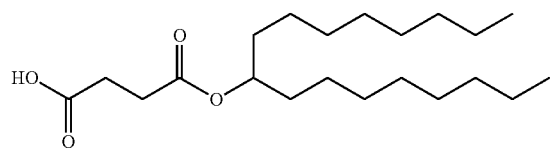 [SMILES: CCCCCCCCC(CCCCCCCC)OC(=O)CCC(=O)O]

Intermediate 58a was treated with TFA (3.36 ml, 43.7 mmol), and stirred at rt for ~30 min. The reaction was concentrated to dryness under reduced pressure to provide the title compound, which was used without further purification. ¹H NMR (400 MHz, CDCl₃) δ=7.94 (br. s., 1H), 4.91 (quin, J=6.27 Hz, 1H), 2.54-2.83 (m, 4H), 1.50-1.62 (m, 4H), 1.18-1.39 (m, 24H), 0.82-1.00 (m, 6H)

Example 58: (13Z,16Z)-4-(((3-(dimethylamino)propoxy)carbonyl)oxy)docosa-13,16-dien-1-yl heptadecan-9-yl succinate

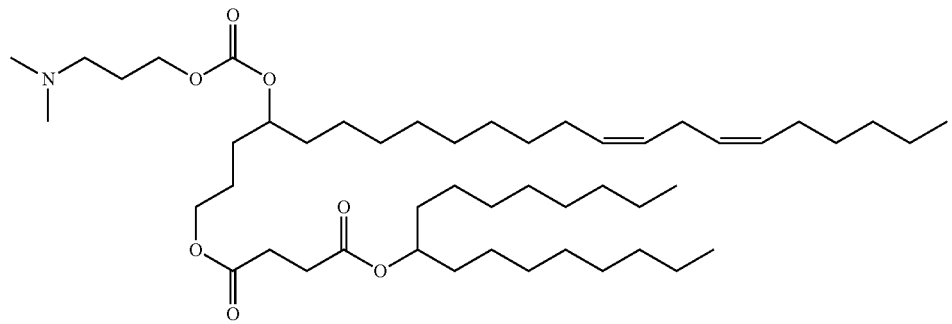 [SMILES: CCCCC/C=C\C/C=C\CCCCCCCCC(CCCOC(=O)CCC(=O)OC(CCCCCCCC)CCCCCCCC)OC(=O)OCCCN(C)C]

¹H NMR (400 MHz, CDCl₃) δ=5.46-5.26 (m, 4H), 4.87 (t, J=6.1 Hz, 1H), 4.72 (br. s., 1H), 4.19 (t, J=6.5 Hz, 2H), 4.14-4.04 (m, 2H), 2.78 (t, J=6.5 Hz, 2H), 2.62 (s, 4H), 2.43 (d, J=6.5 Hz, 2H), 2.29 (s, 6H), 2.05 (q, J=7.0 Hz, 4H), 1.97-1.83 (m, 2H), 1.79-1.44 (m, 10H), 1.42-1.17 (m, 42H), 0.95-0.82 (m, 9H) ppm. LC-MS m/z=807.2 (MH+). Rt=2.01 min (LC Method 11).

Synthesis of Example 59

Intermediate 59a: 2-(2-((tert-butyldimethylsilyl)oxy)ethoxy)acetaldehyde

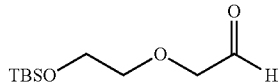 [SMILES: CC(C)(C)[Si](C)(C)OCCOCC=O]

To a solution of DMSO (1.04 ml, 14.7 mmol) in 35 mL DCM, cooled in a dy-ice/acetone bath, was added oxalyl chloride (0.96 ml, 11.03 mmol), dropwise. After 30 min., a solution of 2-(2-((tert-butyldimethylsilyl)oxy)ethoxy)ethanol (1.62 g, 7.35 mmol) in 5 ml DCM was added dropwise. The reaction stirred for 45 min. and TEA (5.12 ml, 36.8 mmol) was added. After 15 min. the reaction was warmed to room temperature. Sat. aq. $NH_4Cl$ was added and the reaction was extracted with ethyl acetate. The combined organics were dried over sodium sulfate, concentrated under reduced pressure and purified on silica gel with 30% EtOAc/hexane to afford the desired product (1.0 g, 62%). $^1$H NMR (400 MHz, $CDCl_3$) δ=9.67 (s, 1H), 4.10 (d, J=1.0 Hz, 2H), 3.73-3.77 (m, 2H), 3.56-3.60 (m, 2H), 0.81-0.83 (m, 9H), −0.02 (s, 6H).

Intermediate 59b: (11Z,14Z)-1-(2-((tert-butyldimethylsilyl)oxy)ethoxy)icosa-11,14-dien-2-ol

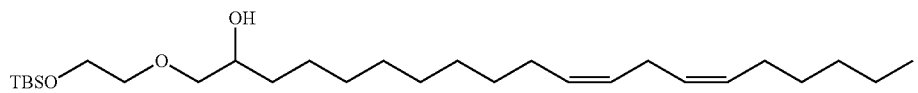 [SMILES: CCCCC/C=C\C/C=C\CCCCCCCCC(O)COCCO[Si](C)(C)C(C)(C)C]

To a solution of Intermediate 59a (0.78 g, 3.57 mmol) in 6.0 ml THF, cooled in an ice-water bath, was added linoleylmagnesium bromide (12.50 ml, 0.4M THF solution, 5.0 mmol), dropwise. The reaction was stirred for 30 min. The reaction was quenched with Sat. aq. $NaHCO_3$ and extracted with ethyl acetate. The combined organics were dried over sodium sulfate, concentrated under reduced pressure, and purified on silica gel with 10% ethyl acetate/heptane to afford the desired product (0.85 g, 51%). $^1$H NMR (400 MHz, $CDCl_3$) δ=5.17-5.40 (m, 4H), 3.63-3.77 (m, 3H), 3.42-3.57 (m, 3H), 3.22 (dd, J=12.0, 8.0 Hz, 1H), 2.69 (m, 2H), 1.97 (m, 4H), 1.11-1.43 (m, 21H), 0.74-0.86 (m, 12H), −0.05-0.04 (s, 6H).

Intermediate 59c: (11Z,14Z)-1-(2-((tert-butyldimethylsilyl)oxy)ethoxy)icosa-11,14-dien-2-yl 3-(dimethylamino)propanoate

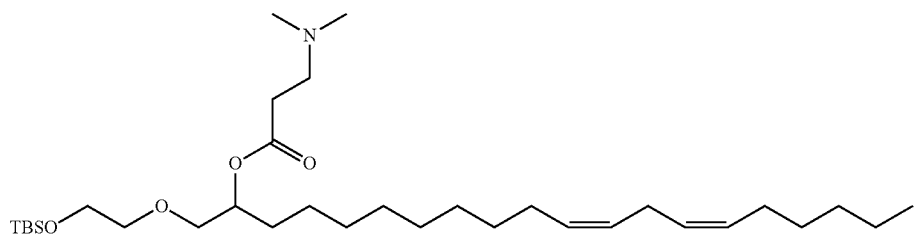 [SMILES: CCCCC/C=C\C/C=C\CCCCCCCCC(COCCO[Si](C)(C)C(C)(C)C)OC(=O)CCN(C)C]

To a solution of Intermediate 59b (450 mg, 0.96 mmol) and dimethylaminopropanoic acid (188 mg, 1.15 mmol) in 10 ml DCM, were added DMAP (46.9 mg, 0.38 mmol) and DIPEA (0.50 ml, 2.88 mmol). EDC (258 mg, 1.15 mmol) was added last. The resulting mixture was stirred at room temperature overnight. The reaction was extracted between brine and ethyl acetate. The combined organics were dried over sodium sulfate, concentrated under reduced pressure, and purified on silica gel with 6% MeOH/DCM to afford the desired product (370 mg, 68%). $^1$H NMR (400 MHz, $CDCl_3$) δ=5.20-5.43 (m, 4H), 4.91-5.04 (m, 1H), 3.61-3.73 (m, 2H), 3.38-3.56 (m, 4H), 2.71 (t, J=4.0 Hz, 2H), 2.53-2.64 (m, 2H), 2.38-2.50 (m, 2H), 2.20 (s, 6H), 1.92-2.05 (m, 4H), 1.12-1.35 (m, 20H), 0.76-0.88 (m, 12H), 0.00 (s, 6H).

Intermediate 59d: (11Z,14Z)-1-(2-hydroxyethoxy)icosa-11,14-dien-2-yl 3-(dimethylamino)propanoate

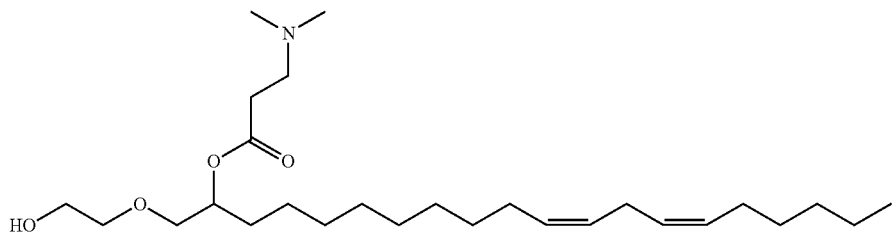 [SMILES: CCCCC/C=C\C/C=C\CCCCCCCCC(COCCO)OC(=O)CCN(C)C]

To a solution of Intermediate XXc (370 mg, 0.651 mmol) in 10 ml THF, TBAF (0.717 ml 1.0M in THF solution, 0.717 mmol) was added dropwise. The resulting mixture was stirred at room temperature for 2 h. The reaction was extracted between brine and ethyl acetate. The combined organics were dried over sodium sulfate, filtered, and concentrated under reduced pressure to provide the desired product, which was used without further purification. $^1$H NMR (400 MHz, CDCl$_3$) δ=5.26 (s, 4H), 4.93-5.11 (m, 1H), 3.55-3.63 (m, 2H), 3.46-3.54 (m, 1H), 3.39-3.46 (m, 3H), 2.39-2.82 (m, 6H), 2.27 (s, 6H), 1.89-2.00 (m, 4H), 1.10-1.29 (m, 20H), 0.77-0.81 (m, 3H).

Example 59: (9Z,12Z)-2-(((11Z,14Z)-2-((3-(dimethylamino)propanoyl)oxy)icosa-11,14-dien-1-yl)oxy)ethyl octadeca-9,12-dienoate

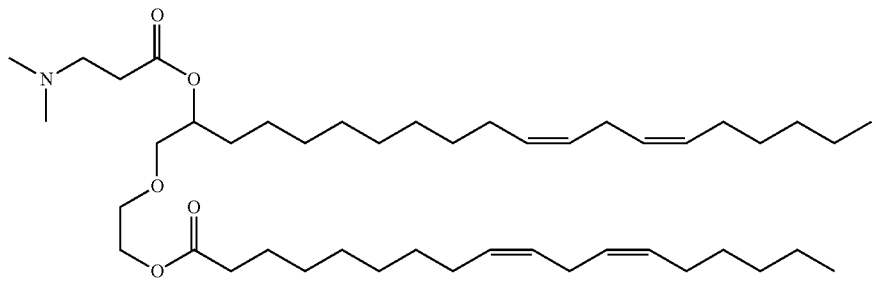 [SMILES: CCCCC/C=C\C/C=C\CCCCCCCCC(COCCOC(=O)CCCCCCC/C=C\C/C=C\CCCCC)OC(=O)CCN(C)C]

Example 59 can be prepared using similar methods to those employed for the synthesis of Example 1. $^1$H NMR (CDCl$_3$) δ=5.18-5.62 (m, 8H), 5.04 (s, 1H), 4.21 (t, J=4.9 Hz, 2H), 3.68-3.79 (m, 1H), 3.60-3.68 (m, 1H), 3.54 (t, J=4.5 Hz, 2H), 2.79 (t, J=6.3 Hz, 4H), 2.60-2.69 (m, 2H), 2.46-2.55 (m, 2H), 2.33 (t, J=7.6 Hz, 2H), 2.26 (s, 6H), 2.06 (q, J=7.2 Hz, 8H), 1.54-1.71 (m, 4H), 1.22-1.44 (m, 32H), 0.85-0.99 (m, 6H). MS (M+1)=717.1, Rt=1.32 min (LC Method 6).

Synthesis of Example 60

Intermediate 60a: 2-((10-bromodecyl)oxy)tetrahydro-2H-pyran

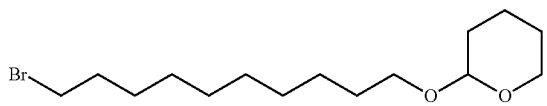 [SMILES: BrCCCCCCCCCCOC1CCCCO1]

To a solution of 10-bromo-1-decanol (85% purity, 6.0 g, 25.3 mmol) in dichloromethane was added dihydropyran (2.75 mL, 30.4 mmol) and p-toluenesulfonic acid monohydrate (2.5 g, 12.6 mmol). The resulting mixture was stirred at 30° C. for 2 h. The reaction was diluted with water and extracted with dichloromethane (2×50 mL). The combined dichloromethane extracts were washed with brine (50 mL), dried over sodium sulfate, and filtered. The filtrate was concentrated under reduced pressure and the crude material was purified on silica gel with ethyl acetate/hexanes as eluent to provide the desired product. TLC (silica gel, 20% ethyl acetate:hexane): R$_f$=0.73.

Intermediate 60b: 2-((10-iododecyl)oxy)tetrahydro-2H-pyran

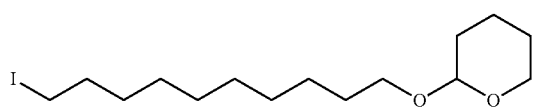 [SMILES: ICCCCCCCCCCOC1CCCCO1]

To a solution of Intermediate 60a (6.0 g, 18.74 mmol) in acetone (80 mL) was added sodium iodide (8.4 g, 56.2 mmol). The reaction was heated to reflux for 24 h. the reaction mixture was cooled to ambient temperature and concentrated under reduced pressure. The concentrate was diluted with water (100 mL) and extracted with dichloromethane (2×50 mL). The combined dichloromethane extracts were washed with brine (100 mL), dried over sodium sulfate, and filtered. The filtrate was concentrated under reduced pressure to provide the desired product, which was used without further purification. TLC (silica gel, 20% ethyl acetate:hexane): R$_f$=0.73.

Intermediate 60c: 1-((tert-butyldimethylsilyl)oxy)-13-((tetrahydro-2H-pyran-2-yl)oxy)tridecan-3-ol

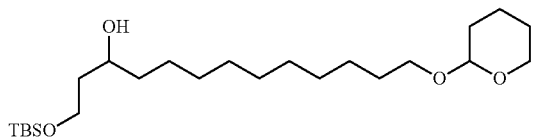 [SMILES: CC(C)(C)[Si](C)(C)OCCC(O)CCCCCCCCCCOC1CCCCO1]

To a solution of Intermediate 60b (6.00 g, 16.30 mmol) in pentane (75 mL) and diethyl ether (25 mL), under an argon atmosphere and cooled in a dry-ice/acetone bath, was added tert-butyl lithium (1.5M in pentane, 22 mL, 32.6 mmol). A solution of 3-((tert-butyldimethylsilyl)oxy) propanal in diethyl ether (20 mL) was added. The reaction was quenched with aqueous saturated ammonium chloride (50 mL), and the reaction was allowed to warm to ambient temperature. The aqueous layer was extracted with diethyl ether (2×100 mL). The combined organic extracts were dried over sodium sulfate and filtered. The filtrate was concentrated under reduced pressure, and the crude material was purified on silica gel with ethyl acetate/hexanes as eluent to provide the desired product. TLC (silica gel, 10% ethyl acetate:hexane): $R_f$=0.19.

Intermediate 60d: 1-((tert-butyldimethylsilyl)oxy)-13-((tetrahydro-2H-pyran-2-yl)oxy)tridecan-3-yl (4-nitrophenyl) carbonate

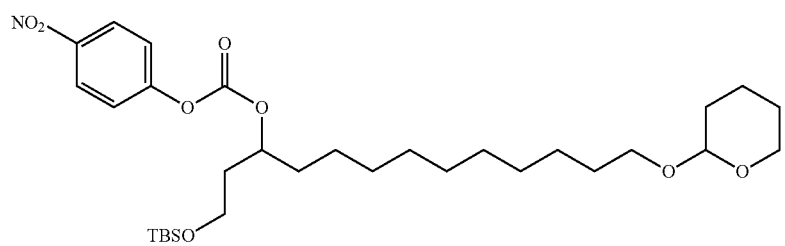 [SMILES: CC(C)(C)[Si](C)(C)OCCC(CCCCCCCCCCOC1CCCCO1)OC(=O)Oc1ccc([N+](=O)[O-])cc1]

To a solution of Intermediate 60c (2.5 g, 5.81 mmol) in dichloromethane (20 mL) was added 4-nitrophenyl chloroformate (1.75 g, 8.71 mmol) and pyridine (1.5 mL, 17.43 mmol). The reaction was stirred at 30° C. for 2 h. The reaction mixture was diluted with water (50 mL) and the aqueous layer was extracted with dichloromethane (2×50 mL). the combined dichloromethane extracts were washed with brine (50 mL), dried over sodium sulfate, and filtered. The filtrate was concentrated under reduced pressure, and the crude material was purified on silica gel with ethyl acetate/hexanes as eluent to provide the desired product. TLC (silica gel, 20% ethyl acetate:hexane): $R_f$=0.73.

Intermediate 60e: 1-((tert-butyldimethylsilyl)oxy)-13-((tetrahydro-2H-pyran-2-yl)oxy)tridecan-3-yl (3-(dimethylamino)propyl) carbonate

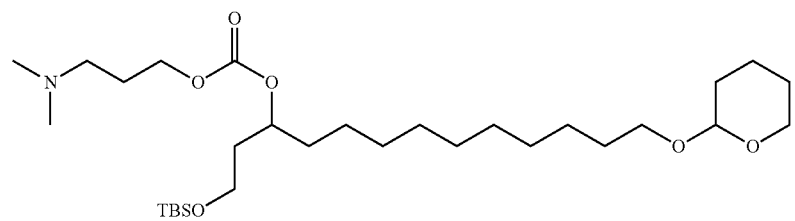

To a solution of Intermediate 60d (2.6 g, 4.37 mmol) in dichloromethane was added 2-(dimethylamino)-1-propanol (1.0 mL, 8.73 mmol), pyridine (1.1 mL, 13.3 mmol), and DMAP (0.53 g, 4.37 mmol). The resulting mixture was stirred at 30° C. for 8 h, then additional 2-(dimethylamino)-1-propanol (1.0 mL, 8.73 mmol), pyridine (1.1 mL, 13.3 mmol), and DMAP (0.53 g, 4.37 mmol) were added. The reaction was stirred for an additional 16 h, then additional 2-(dimethylamino)-1-propanol (1.0 mL, 8.73 mmol), pyridine (1.1 mL, 13.3 mmol), and DMAP (0.53 g, 4.37 mmol) were added. The reaction was stirred for an additional 24 h. The reaction mixture was diluted with water (100 mL), and the aqueous layer was extracted with dichloromethane (2×100 mL). The combined dichloromethane extracts were washed with brine (100 mL), dried over sodium sulfate, and filtered. The filtrate was concentrated under reduced pressure, and the crude material was purified on silica gel with methanol/dichloromethane as eluent to provide the desired product. TLC (silica gel, 10% methanol:dichloromethane): $R_f$=0.45.

Intermediate 60f: 3-(dimethylamino)propyl (1-hydroxy-13-((tetrahydro-2H-pyran-2-yl)oxy)tridecan-3-yl) carbonate

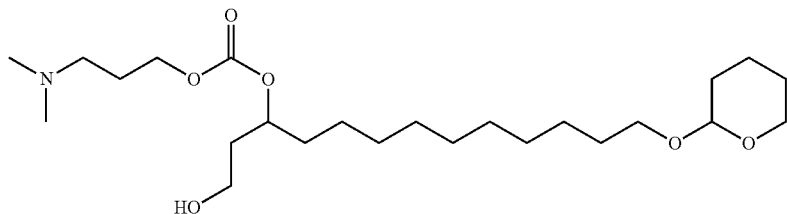 [SMILES: CN(C)CCCOC(=O)OC(CCO)CCCCCCCCCCOC1CCCCO1]

To a mixture of ceric ammonium nitrate (800 mg, 1.46 mmol) in water (20 mL) was added 50% pyridine in water to titrate the solution to pH=6. A solution of Intermediate 60e (1.7 g, 3.04 mmol) in THF (30 mL) was added, and the mixture was stirred at 30° C. for 24 h. The reaction was diluted with water (30 mL) and extracted with ethyl acetate (2×50 mL). The combined organic extracts were washed with brine (50 mL), dried over sodium sulfate, and filtered. The filtrate was concentrated under reduced pressure to provide the desired product, which was used without further purification. TLC (silica gel, 10% methanol:dichloromethane): $R_f$=0.24.

Intermediate 60g: (9Z,12Z)-3-(((3-(dimethylamino)propoxy)carbonyl)oxy)-13-((tetrahydro-2H-pyran-2-yl)oxy)tridecyl octadeca-9,12-dienoate

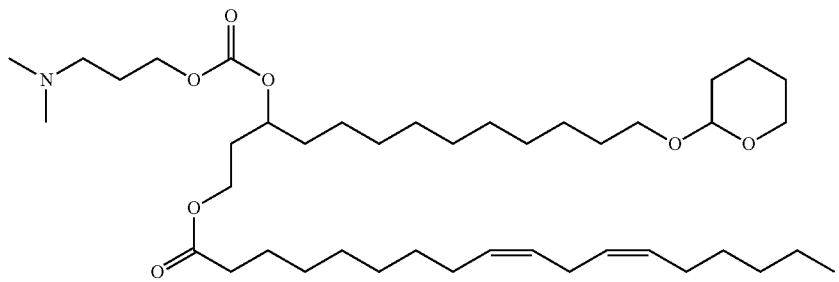 [SMILES: CCCCC/C=C\C/C=C\CCCCCCCC(=O)OCCC(CCCCCCCCCCOC1CCCCO1)OC(=O)OCCCN(C)C]

To a solution of Intermediate 60f (1.2 g, 2.69 mmol) in dichloromethane (50 mL), was added linoleic acid (1.13 g, 4.04 mmol), EDC.HCl (1.03 g, 5.39 mmol), DIPEA (1.4 mL, 8.09 mmol), and DMAP (165 mg, 1.35 mmol). The resulting mixture was stirred at 30° C. for 16 h. The reaction mixture was diluted with water (50 mL), and the aqueous layer was extracted with dichloromethane (2×100 mL). The combined dichloromethane extracts were washed with brine (100 mL), dried over sodium sulfate, and filtered. The filtrate was concentrated under reduced pressure, and the crude material was purified on silica gel with methanol/dichloromethane as eluent to provide the desired product. TLC (silica gel, 10% methanol:dichloromethane): $R_f$=0.67

Intermediate 60h: (9Z,12Z)-3-(((3-(dimethylamino)propoxy)carbonyl)oxy)-13-hydroxytridecyl octadeca-9,12-dienoate

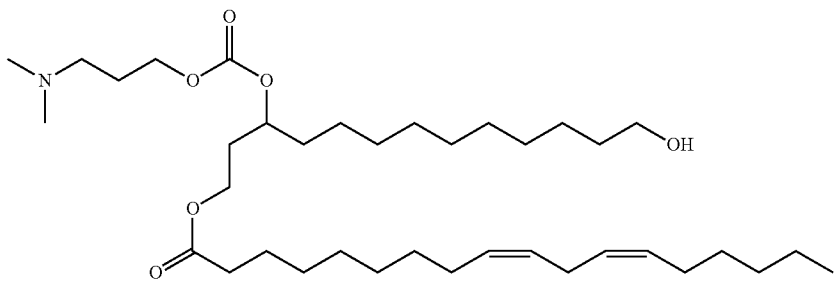 [SMILES: CCCCC/C=C\C/C=C\CCCCCCCC(=O)OCCC(CCCCCCCCCCO)OC(=O)OCCCN(C)C]

To a solution of Intermediate 60g (500 mg, 0.706 mmol) in THF (10 mL), cooled in an ice-water bath, was added 6N HCl (aq, 10 mL). the resulting mixture was stirred for 2 h, then warmed to ambient temperature. The reaction was neutralized with saturated sodium bicarbonate solution, and the reaction was extracted with ethyl acetate (2×40 mL). The combined organic extracts were washed with brine, dried over sodium sulfate, and filtered. The filtrate was concentrated under reduced pressure, and the crude material was purified on silica gel with methanol/dichloromethane as eluent to provide the desired product. TLC (silica gel, 10% methanol:dichloromethane): $R_f$=0.39

Example 60: (9Z,12Z)-3-(((3-(dimethylamino)propoxy)carbonyl)oxy)-13-(octanoyloxy)tridecyl octadeca-9,12-dienoate $^1$H NMR (400 MHz, CDCl$_3$) δ=4.81 (quin, J=6.25 Hz, 1H) 4.16-4.26 (m, 2H) 4.09-4.16 (m, 2H) 4.06 (t, J=6.69 Hz, 2H) 2.41 (br. s., 2H) 2.19-2.36 (m, 8H) 1.77-2.01 (m, 5H) 1.50-1.74 (m, 10H) 1.14-1.41 (m, 48H) 0.77-1.00 (m, 9H).
$^{13}$C NMR (101 MHz, CDCl$_3$) δ=173.68, 173.23, 154.61, 75.35, 65.89, 64.05, 60.12, 55.64, 44.97 (2C), 38.89, 34.69, 34.09, 33.90, 33.55 (2C), 32.74, 31.58 (4C), 31.34, 29.60 (2C), 29.28 (2C), 29.17 (2C), 29.00 (2C), 28.93, 28.79, 28.60, 28.35, 26.22 (3C), 25.63, 24.75, 24.70, 22.35 (2C), 22.26, 13.78 (2C), 13.73.

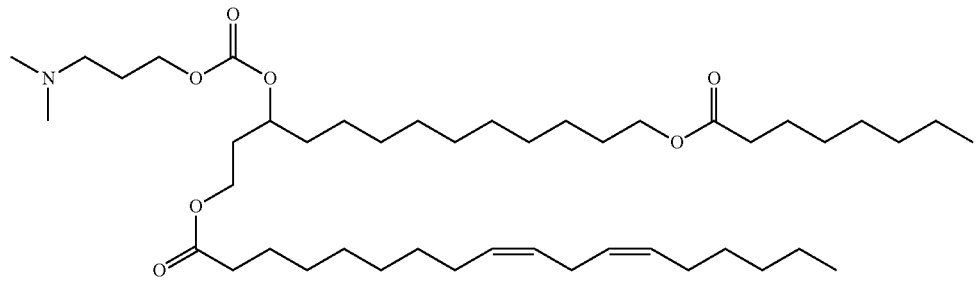 [SMILES: CCCCC/C=C\C/C=C\CCCCCCCC(=O)OCCC(CCCCCCCCCCOC(=O)CCCCCCC)OC(=O)OCCCN(C)C]

To a solution of octanoic acid (320 mg, 0.513 mmol) in dichloromethane (20 mL) was added EDC.HCl (295 mg, 1.54 mmol) and DIPEA (0.45 mL, 2.57 mmol). The reaction was stirred at 30° C. for 1 h, then Intermediate 60 h (320 mg, 0.513 mmol) and DMAP (63 mg, 0.513 mmol) were added and the reaction stirred for an additional 23 h. the reaction was diluted with water (20 mL) and the aqueous layer was extracted with dichloromethane (2×30 mL). the combined dichloromethane extracts were washed with brine (20 mL), dried over sodium sulfate and filtered. The filtrate was concentrated under reduced pressure, and the crude material was purified on silica gel with methanol/dichloromethane as eluent to provide the desired product. $^1$H NMR (400 MHz, CDCl$_3$) δ=5.27-5.47 (m, 4H) 4.81 (t, J=6.19 Hz, 1H) 4.10-4.25 (m, 4H) 4.06 (t, J=6.82 Hz, 2H) 2.78 (t, J=6.57 Hz, 2H) 2.16-2.45 (m, 10H) 2.06 (q, J=6.82 Hz, 4H) 1.77-1.99 (m, 4H) 1.48-1.71 (m, 8H) 1.24-1.44 (m, 38H) 0.81-0.96 (m, 6H). MS (M+1)=750.7, Rt=1.25 min (LC Method 5).

Example 61: 3-(((3-(dimethylamino)propoxy)carbonyl)oxy)-13-(octanoyloxy)tridecyl 3-octylundecanoate Example 62: 3-(((3-(dimethylamino)propoxy)carbonyl)oxy)-13-hydroxytridecyl 5-heptyldodecanoate

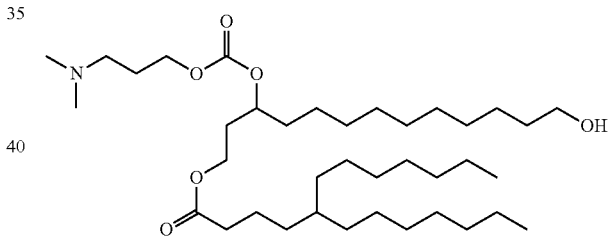

$^1$H NMR (400 MHz, CDCl$_3$) δ=4.74 (quin, J=6.50 Hz, 1H), 4.12 (t, J=6.40 Hz, 2H), 4.01-4.09 (m, 2H), 3.57 (t, J=6.53 Hz, 2H), 2.46 (br. s, 2H), 2.29 (br. s., 6H), 2.20 (t, J=7.65 Hz, 2H), 1.80-1.95 (m, 4H), 1.44-1.63 (m, 6H), 1.38 (br. s, 1H), 1.07-1.33 (m, 41H), 0.75-0.87 (m, 6H). $^{13}$C NMR (101 MHz, CDCl$_3$): L=173.87, 154.89, 75.72, 65.93, 63.03, 60.48, 55.87, 44.93 (2C), 37.23, 34.69, 34.19, 33.48

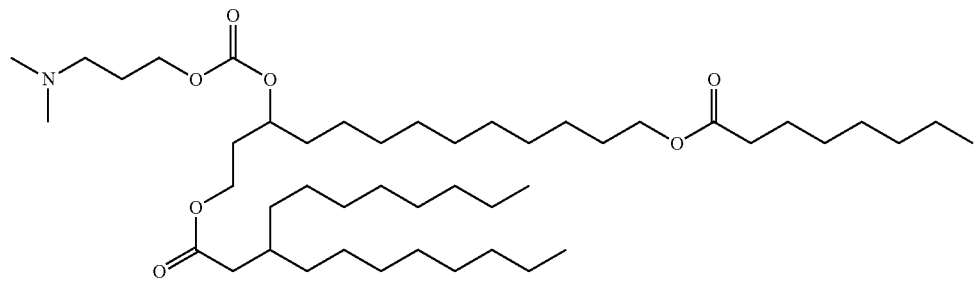 [SMILES: CCCCCCCCC(CCCCCCCC)CC(=O)OCCC(CCCCCCCCCCOC(=O)CCCCCCC)OC(=O)OCCCN(C)C]

(2C), 33.18, 33.02, 32.80, 31.96 (2C), 30.11, 29.72, 29.52, 29.45-29.35 (6C), 26.66 (2C), 26.34, 25.72, 25.01, 22.72 (2C), 22.17, 14.17 (2C).

Example 63: 3-(((3-(dimethylamino)propoxy)carbonyl)oxy)-13-(octanoyloxy)tridecyl 5-heptyldodecanoate

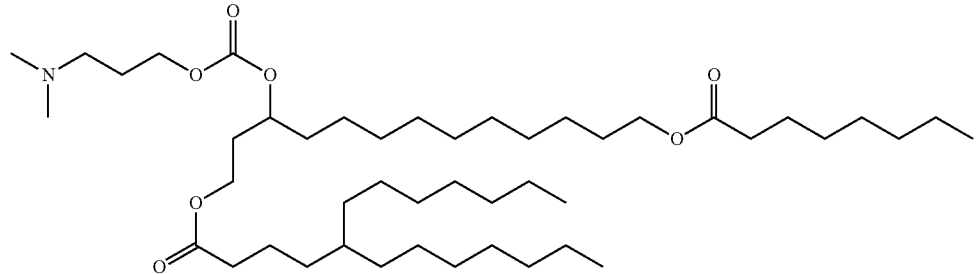 [SMILES: CCCCCCCC(=O)OCCCCCCCCCCC(CCOC(=O)CCCC(CCCCCCC)CCCCCCC)OC(=O)OCCCN(C)C]

$^1$H NMR (400 MHz, CDCl$_3$) δ=4.73 (quin, J=6.20 Hz, 1H), 4.12 (t, J=6.40 Hz, 2H), 4.02-4.09 (m, 2H), 3.98 (t, J=6.78 Hz, 2H), 2.34-2.59 (m, 2H), 2.26 (br. s., 6H), 2.21 (q, J=7.19 Hz, 4H), 1.78-1.92 (m, 4H), 1.44-1.65 (m, 8H), 1.10-1.30 (m, 49H), 0.81 (quin, J=6.50 Hz, 9H). MS (M+1)= 768.7, Rt=1.23 min (LC Method 6).

Example 64: 3-(((3-(dimethylamino)propoxy)carbonyl)oxy)-13-(octanoyloxy)tridecyl 7-hexyltridecanoate

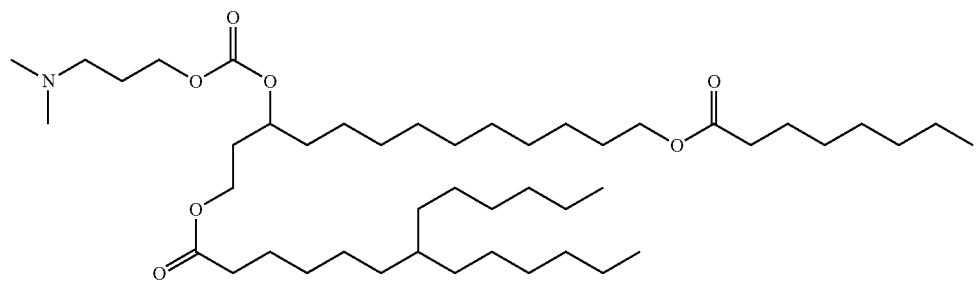 [SMILES: CCCCCCCC(=O)OCCCCCCCCCCC(CCOC(=O)CCCCCC(CCCCCC)CCCCCC)OC(=O)OCCCN(C)C]

$^1$H NMR (400 MHz, CDCl$_3$) δ=4.89-4.76 (m, 1H), 4.24-4.10 (m, 4H), 4.06 (t, J=6.8 Hz, 2H), 2.44-2.33 (m, 2H), 2.30 (t, J=7.6 Hz, 4H), 2.23 (s, 6H), 1.98-1.77 (m, 4H), 1.73-1.48 (m, 9H), 1.42-1.15 (m, 48H), 0.97-0.79 (m, 9H). $^{13}$C NMR (101 MHz, CDCl$_3$) δ=173.99, 173.76, 154.97, 75.62, 66.34, 64.37, 60.55, 56.00, 45.46 (2C), 37.40, 34.40, 34.30, 34.22, 33.66 (2C), 33.55, 33.02, 31.95 (2C), 31.66, 29.81 (2C), 29.68, 29.49 (4C), 29.25, 29.11, 28.92, 28.67, 27.00, 26.65 (2C), 26.40, 25.94, 25.07, 25.02, 24.98, 22.70 (2C), 22.58, 14.11 (2C), 14.05.

Example 65: 3-(((3-(dimethylamino)propoxy)carbonyl)oxy)-13-hydroxytridecyl 9-pentyltetradecanoate

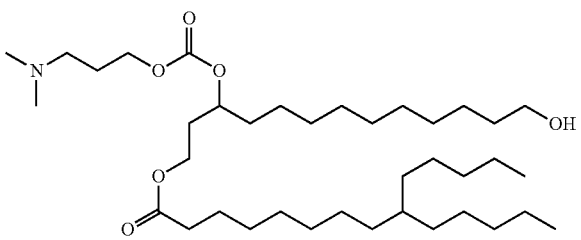 [SMILES: CCCCCC(CCCCC)CCCCCCCC(=O)OCCC(CCCCCCCCCCO)OC(=O)OCCCN(C)C]

H NMR (400 MHz, CDCl$_3$) δ=4.74 (quin, J=6.21 Hz, 1H), 4.11 (td, J=6.50, 1.76 Hz, 2H), 4.06 (t, J=6.50 Hz, 2H), 3.57 (t, J=6.65 Hz, 2H), 2.37 (t, J=6.78 Hz, 2H), 2.22 (s, 6H), 1.77-1.89 (m, 4H), 1.43-1.62 (m, 6H), 1.07-1.33 (m, 43H), 0.81 (t, J=7.03 Hz, 6H). MS (M+1)=642.5, Rt=0.95 min (LC Method 6).

Example 66: 3-(((3-(dimethylamino)propoxy)carbonyl)oxy)-13-(octanoyloxy)tridecyl 9-pentyltetradecanoate

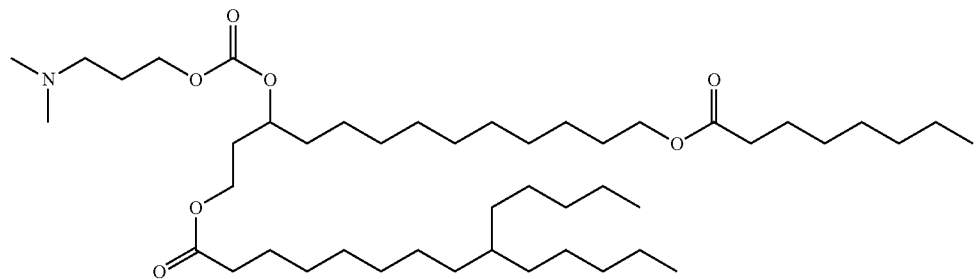 [SMILES: CCCCCCCC(=O)OCCCCCCCCCCC(CCOC(=O)CCCCCCCC(CCCCC)CCCCC)OC(=O)OCCCN(C)C]

$^1$H NMR (400 MHz, CDCl$_3$) δ=4.81 (quin, J=6.25 Hz, 1H) 4.19 (t, J=6.57 Hz, 2H) 4.14 (t, J=6.57 Hz, 2H) 4.06 (t, J=6.69 Hz, 2H) 2.35-2.55 (m, 2H) 2.19-2.35 (m, 9H) 1.80-1.99 (m, 4H) 1.49-1.73 (m, 12H) 1.13-1.42 (m, 46H) 0.79-0.98 (m, 9H). MS (M+1)=769.0, Rt=3.11 min (LC Method 4).

Example 67: 1-(3-(((3-(dimethylamino)propoxy)carbonyl)oxy)-13-(octanoyloxy)tridecyl)10-octyl decanedioate

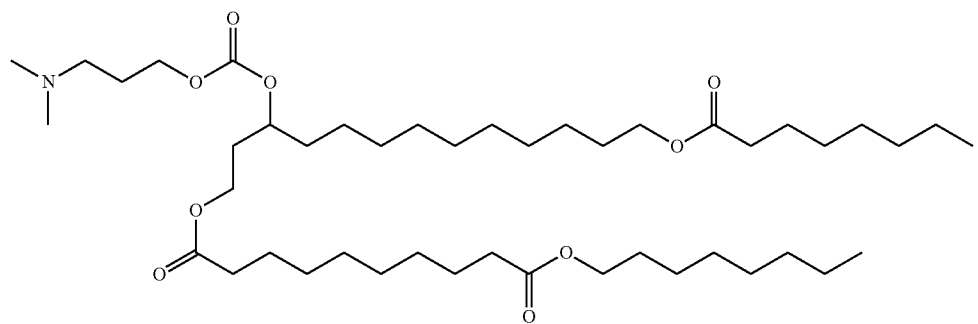 [SMILES: CCCCCCCCOC(=O)CCCCCCCCC(=O)OCCC(CCCCCCCCCCOC(=O)CCCCCCC)OC(=O)OCCCN(C)C]

$^1$H NMR (400 MHz, CDCl$_3$) δ=4.71-4.89 (m, 1H), 4.18 (t, J=6.53 Hz, 2H), 4.08-4.16 (m, 2H), 4.05 (t, J=6.78 Hz, 4H), 2.44 (t, J=7.15 Hz, 2H), 2.21-2.35 (m, 12H), 1.81-2.01 (m, 4H), 1.56-1.73 (m, 11H), 1.54 (br. s., 1H), 1.18-1.41 (m, 40H), 0.78-0.95 (m, 6H). MS (M+1)=784.5, Rt=0.99 min (LC Method 6).

Example 68: 3-(((3-(dimethylamino)propoxy)carbonyl)oxy)-13-(octanoyloxy)tridecyl 10-(octanoyloxy)decanoate

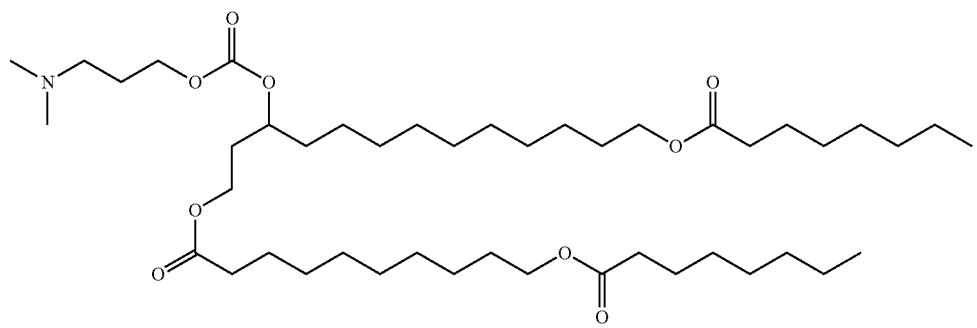 [SMILES: CCCCCCCC(=O)OCCCCCCCCCCC(CCOC(=O)CCCCCCCCCOC(=O)CCCCCCC)OC(=O)OCCCN(C)C]

¹H NMR (400 MHz, CDCl₃) δ=4.67-4.92 (m, 1H), 4.29 (ddd, J=11.31, 6.63, 4.80 Hz, 1H), 4.13-4.24 (m, 2H), 3.98-4.13 (m, 5H), 3.20 (t, J=6.57 Hz, 2H), 2.89 (s, 6H), 2.29 (t, J=7.45 Hz, 6H), 2.09-2.23 (m, 2H), 1.80-2.05 (m, 2H), 1.50-1.74 (m, 12H), 1.28 (d, J=8.59 Hz, 40H), 0.77-0.98 (m, 6H). MS (M+1)=784.6, Rt=1.11 min (LC Method 6).

Synthesis of Example 69

Intermediate 69a

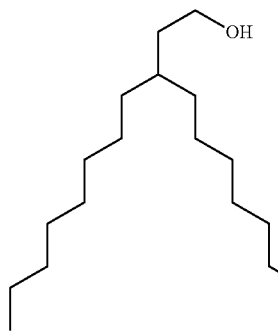

To a solution of Intermediate 24c (2.75 g, 9.21 mmol) in THF (30.7 mL) was added lithium aluminum hydride (1M in diethyl ether, 10.1 mL, 10.1 mmol) dropwise. The reaction was stirred at ambient temperature for 1.5 hr. Several drops of EtOAc were added to quench the reaction, followed by sat. aq. NH₄Cl. The reaction was filtered with ethyl acetate washes, and the filtrate was concentrated under reduced pressure to provide 2.4 g of the title compound, which was used without further purification. ¹H NMR (400 MHz, CDCl₃) δ=3.67 (t, J=6.95 Hz, 2H), 1.48-1.59 (m, 2H), 1.42 (br. s., 1H), 1.18-1.37 (m, 29H), 0.83-0.96 (m, 6H)

Intermediate 69b: 3-octylundecanal

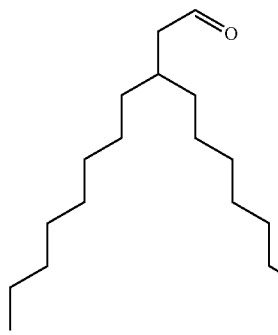

TEA (5.31 ml, 38.3 mmol) was added dropwise via syringe to a solution of Intermediate 69a (3.63 g, 12.76 mmol) in DCM (100 ml) and cooled in an ice-water bath. In a separate flask, SO₃.Py (3.05 g, 19.14 mmol) and DMSO (8.16 ml, 115 mmol) were added together and this mixture was added to the first rbf slowly via syringe. The reaction was stirred for 30 min, then the ice bath was removed. The reaction was stirred at ambient temperature for an additional 24 hr. The reaction mixture was quenched with water. The DCM layer was collected, and the water was re-extracted with EtOAc×1. The organic layers were combined, dried over MgSO₄, filtered, and concentrated under reduced pressure. The crude oil was filtered over a silica gel plug with heptanes (250 ml). The solvents were removed under reduced pressure to provide compound the title compound as a colorless oil (3.3 g, 91%), which was used without further purification. ¹H NMR (400 MHz, CDCl₃) δ=9.77 (t, J=2.40 Hz, 1H), 2.33 (dd, J=6.57, 2.27 Hz, 2H), 1.95 (br. s., 1H), 1.17-1.43 (m, 28H), 0.81-0.97 (m, 6H)

Intermediate 69c: 5-octyltridec-1-en-3-ol

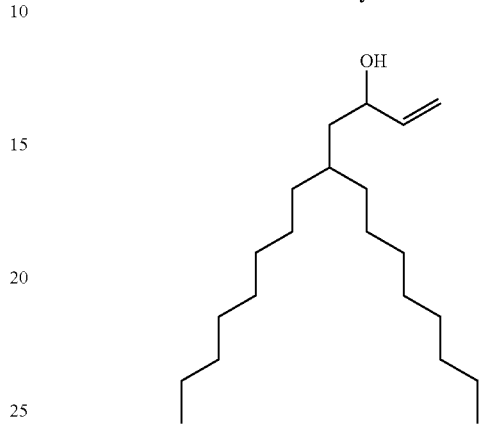

Vinyl magnesium bromide (12.85 mL, 12.85 mmol) was added dropwise via syringe to a round bottom flask charged with anhydrous THF (75 ml), coiled in an ice-water bath and under N₂. Intermediate 69b (3.3 g, 11.68 mmol) was slowly added as a solution in 25 mL of THF via syringe. The reaction was stirred for 1.5 h. maintained in the ice-water bath, the reaction was quenched with sat. aq. NH₄Cl, and filtered over celite with EtOAc washes. The filtrate was poured into a sep funnel, and diluted further with EtOAc. The layers were separated and the aqueous layer was extracted with EtOAc once more. The combined organics were dried over Na₂SO₄, filtered, and the filtrate was concentrated under reduced pressure. The crude oil was purified on silica gel with 0-50% EtOAc/heptanes to provide the title compound as a colorless oil (2.8 g, 77%). ¹H NMR (400 MHz, CDCl₃) δ=5.87 (ddd, J=17.05, 10.48, 6.32 Hz, 1H), 5.23 (dt, J=17.18, 1.39 Hz, 1H), 5.10 (dt, J=10.36, 1.26 Hz, 1H), 4.13-4.24 (m, 1H), 1.36-1.59 (m, 3H), 1.18-1.36 (m, 28H), 0.79-0.98 (m, 6H).

Intermediate 69d: 5-octyl-1-(4,4,5,5-tetramethyl-1,3,2-dioxaborolan-2-yl)tridecan-3-ol

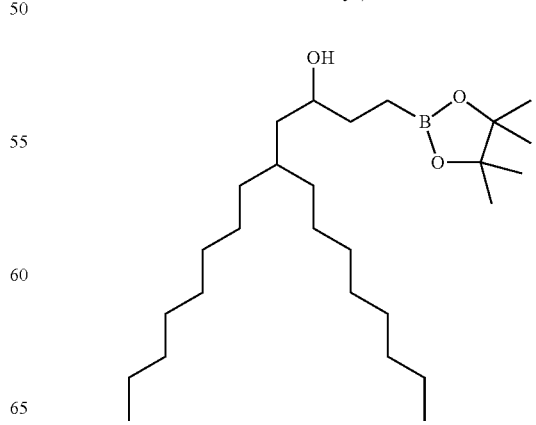

[Ir(cod)Cl]$_2$ (0.073 g, 0.161 mmol) and DPPE (0.096 g, 0.242 mmol), were dissolved in DCM in a round bottom flask charged with nitrogen. Pinacolborane (1.402 mL, 9.66 mmol) was added, followed by a solution of Intermediate 69c (2.5 g, 8.05 mmol) in 5 ml DCM. After 4 hr of stirring at ambient temperature, another 1.5 ml of pinacolboronate was added. The reaction was stirred overnight. Several water droplets were added carefully to quench the reaction. The reaction was diluted with DCM and washed with aqueous sodium bicarbonate solution. The aqueous layer was back extracted with DCM×1. The combined organics were dried over sodium sulfate, filtered, and concentrated under reduced pressure. The crude material was purified on silica gel with 0-30% EtOAc/heptanes to provide the title compound as a colorless oil (1 g, 28%). $^1$H NMR (400 MHz, CDCl$_3$) δ=4.15-4.34 (m, 1H), 1.38-1.63 (m, 4H), 1.16-1.38 (m, 38H), 0.93-1.09 (m, 2H), 0.83-0.93 (m, 8H).

Intermediate 69e: 5-octyltridecane-1,3-diol

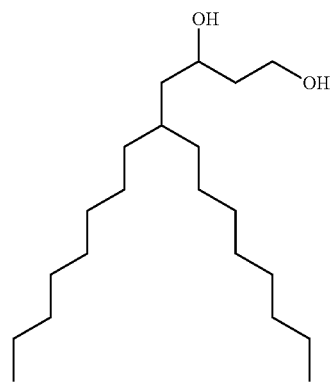 [SMILES: CCCCCCCCC(CCCCCCCC)CC(O)CCO]

Intermediate 69d (180 mg, 0.410 mmol) was dissolved in MeOH (2 ml) and THF (2 ml). 3N NaOH (0.410 ml, 1.231 mmol) was added, followed by 43 uL (0.493 mmol) of a 35% solution of H$_2$O$_2$. The reaction was stirred at ambient temperature for 2 h. The solvents were removed under reduced pressure, and the crude mixture was purified on silica gel with 0-100% EtOAc/heptanes to provide the title compound as a colorless oil (180 mg). $^1$H NMR (400 MHz, CDCl$_3$) δ=3.78-4.02 (m, 3H), 1.60-1.73 (m, 2H), 1.42-1.58 (m, 3H), 1.14-1.39 (m, 28H), 0.88 (t, J=6.82 Hz, 6H).

Intermediate 69f:
(9Z,12Z)-3-hydroxy-5-octyltridecyl octadeca-9,12-dienoate

Linoleic acid (164 mg, 0.584 mmol), EDC.HCl (112 mg, 0.584 mmol), and DMAP (47.6 mg, 0.390 mmol) were dissolved in 3 ml DCE. DIPEA (0.255 ml, 1.461 mmol) was added and the reaction was stirred at ambient temperature for 30 min. A solution of Intermediate 69e (160 mg, 0.487 mmol) in 3 ml DCE was added. The reaction was stirred at ambient temperature overnight. The crude reaction mixture was purified on silica gel (pre-equilibrated with 1% NH4OH in MeOH) eluting with 0-15% EtOAc/heptanes to provide the title compound (180 mg, 63%). $^1$H NMR (400 MHz, CDCl$_3$) δ=5.16-5.46 (m, 4H), 4.36 (ddd, J=11.18, 8.53, 5.31 Hz, 1H), 4.15 (dt, J=11.18, 5.65 Hz, 1H), 3.74 (dd, J=7.58, 4.04 Hz, 1H), 2.77 (t, J=6.57 Hz, 2H), 2.25-2.38 (m, 2H), 1.99-2.13 (m, 4H), 1.93-1.99 (m, 1H), 1.73-1.87 (m, 1H), 1.56-1.73 (m, 3H), 1.40-1.55 (m, 2H), 1.21-1.40 (m, 42H), 0.89 (dq, J=6.82, 3.45 Hz, 9H).

Example 69: (9Z,12Z)-3-(((3-(dimethylamino) propoxy)carbonyl)oxy)-5-octyltridecyl octadeca-9, 12-dienoate Intermediate 69f (180 mg, 0.305 mmol), DMAP (37.2 mg, 0.305 mmol), and pyridine (49.2 μL, 0.609 mmol) were dissolved into DCE (5000 μL). 4-nitrophenyl chloroformate (80 mg, 0.396 mmol) was added. The reaction was stirred at ambient temperature overnight. Then, 500 uL of 3-(dimethylamino)propan-1-ol was added and the reaction was stirred for 30 min. The crude yellow mixture was purified on silica gel with 0-100% EtOAc/heptanes, then with 0-10% MeOH/DCM. The material was then purified on PL-HCO3 MP-SPE columns eluting with 0-50% MeOH/DCM. The solvents were removed to provide the title compound (100 mg, 46%). $^1$H NMR (400 MHz, CDCl$_3$) δ=5.24-5.47 (m, 4H), 4.78-4.97 (m, 1H), 4.16 (dt, J=16.86, 6.60 Hz, 4H), 2.78 (t, J=6.57 Hz, 2H), 2.39 (br. s., 2H), 2.23-2.35 (m, 8H), 2.06 (q, J=6.82 Hz, 4H), 1.79-1.99 (m, 4H), 1.53-1.73 (m, 3H), 1.17-1.46 (m, 44H), 0.82-0.98 (m, 9H). $^{13}$C NMR (101 MHz, CDCl$_3$) δ=173.37, 154.59, 129.90, 129.72, 127.72, 127.59, 73.88, 65.89, 60.22, 55.65, 44.99 (2C), 38.41, 33.95, 33.59, 33.31, 33.25, 33.04, 31.59 (2C), 31.20, 29.73, 29.71, 29.30 (4C), 29.03 (4C), 28.88, 28.83, 26.88 (2C), 26.02, 25.94, 25.31, 24.59, 22.36 (2C), 22.24, 13.78 (2C), 13.74.

Synthesis of Example 70

Intermediate 70a: 3-hydroxy-5-octyltridecyl decanoate

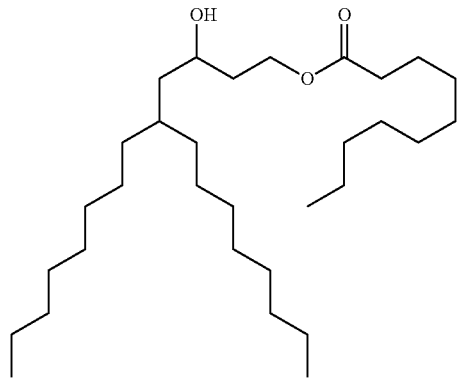 [SMILES: CCCCCCCCCC(=O)OCCC(O)CC(CCCCCCCC)CCCCCCCC]

Intermediate 69e (300 mg, 0.913 mmol) and decanoic acid (189 mg, 1.096 mmol) were dissolved in DCE (10 ml). EDC.HCl (210 mg, 1.096 mmol) and DMAP (66.9 mg, 0.548 mmol) were added. Lastly, DIPEA (638 μL, 3.65 mmol) was added. The reaction was stirred at ambient temperature overnight. The crude reaction mixture was purified on silica gel with 0-50% EtOAc/heptanes to provide the title compound as a colorless oil (250 mg, 57%). $^1$H NMR (400 MHz, CDCl$_3$) δ=4.38 (ddd, J=5.1, 8.5, 11.2 Hz, 1H), 4.15 (td, J=5.7, 11.2 Hz, 1H), 3.83-3.65 (m, 1H), 2.37-2.25 (m, 2H), 1.81 (dddd, J=3.3, 5.7, 8.7, 14.4 Hz, 2H), 1.73-1.57 (m, 3H), 1.54-1.40 (m, 2H), 1.40-1.14 (m, 40H), 0.89 (t, J=6.7 Hz, 9H).

Example 70: 3-(((3-(dimethylamino)propoxy)carbonyl)oxy)-5-octyltridecyl decanoate

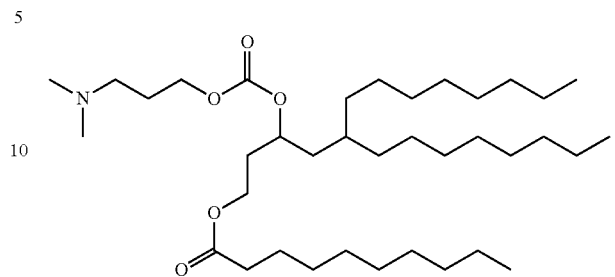

$^1$H NMR (400 MHz, CDCl$_3$) δ=4.80-4.99 (m, 1H) 4.06-4.27 (m, 4H) 2.43 (t, J=7.20 Hz, 2H) 2.21-2.34 (m, 8H) 1.81-2.00 (m, 4H) 1.55-1.71 (m, 3H) 1.35-1.51 (m, 2H) 1.12-1.35 (m, 40H) 0.78-0.95 (m, 9H). MS (M+1)=612.8, Rt=0.94 min (LC Method 6). Synthesis of Example 71

Intermediate 71a: 7-octyl-1-((tetrahydro-2H-pyran-2-yl)oxy)pentadecan-5-ol

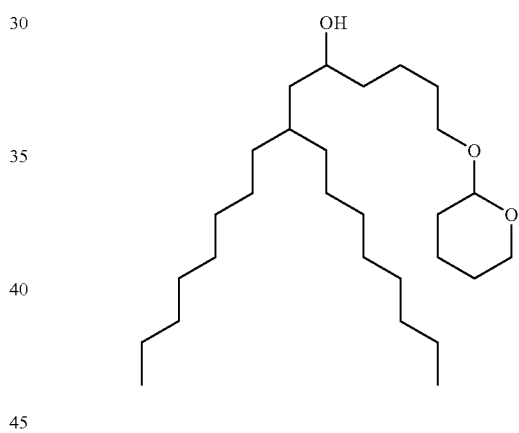

In an oven dried round bottom flask charged with N$_2$, were added magnesium turnings (0.196 g, 8.07 mmol) and THF (10 mL). 2-(4-Bromobutoxy)tetrahydro-2H-pyran (1.595 g, 6.73 mmol) and iodine (0.017 g, 0.067 mmol) were added. The mixture was heated to reflux, then cooled and stirred for 1 h at room temp. The reaction was cooled in an ice-water bath, and Intermediate 69b (1.9 g, 6.73 mmol) was added. The reaction was stirred for 30 min, then the ice bath was removed and the reaction stirred for an additional 1 h. The reaction was quenched with sat. aq. NH$_4$Cl and then filtered over celite with EtOAc washes. The organic layer was collected, and the aqueous layer was extracted once more with EtOAc. The combined organics were dried over Na$_2$SO$_4$, filtered, and the filtrate was concentrated under reduced pressure. The crude material was purified on silica gel with 0-100% EtOAc/heptane to provide the title compound as a colorless oil (1.7 g, 57%). $^1$H NMR (400 MHz, CDCl$_3$) δ=4.52-4.64 (m, 1H), 3.82-3.95 (m, 1H), 3.63-3.82 (m, 2H), 3.46-3.57 (m, 1H), 3.34-3.46 (m, 1H), 1.79-1.96 (m, 1H), 1.68-1.79 (m, 1H), 1.37-1.67 (m, 11H), 1.14-1.37 (m, 30H), 0.82-0.98 (m, 6H).

Intermediate 71b: 3-(dimethylamino)propyl (7-octyl-1-((tetrahydro-2H-pyran-2-yl)oxy)pentadecan-5-yl) carbonate

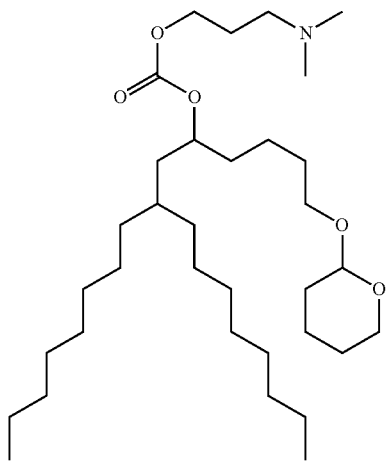 [SMILES: CCCCCCCCC(CCCCCCCC)CC(CCCCOC1CCCCO1)OC(=O)OCCCN(C)C]

p-Nitrophenyl chloroformate (1.244 g, 6.17 mmol) and pyridine (0.936 mL, 11.57 mmol) were dissolved in DCM (30 mL). Intermediate 71a (1.7 g, 3.86 mmol) in 10 mL of DCM was added via syringe. DMAP (0.236 g, 1.929 mmol) was then added and the mixture was stirred at ambient temperature for 6 h, then 3-(dimethylamino)propan-1-ol (0.796 g, 7.71 mmol) was added and the reaction is stirred overnight. The reaction mixture was purified on silica gel with 0-100% EtOAc/heptanes, then 0-10% MeOH/DCM to provide the title compound (320 mg, 15%). $^1$H NMR (400 MHz, CDCl$_3$) δ=4.78 (br. s., 1H), 4.64-4.52 (m, 1H), 4.32-4.02 (m, 4H), 3.94-3.80 (m, 1H), 3.78-3.67 (m, 1H), 3.61-3.46 (m, 2H), 3.46-3.30 (m, 1H), 2.65-2.44 (m, 2H), 2.35 (s, 6H), 1.99-1.88 (m, 2H), 1.72 (d, J=3.0 Hz, 1H), 1.70-1.47 (m, 7H), 1.47-1.33 (m, 4H), 1.33-1.08 (m, 28H), 1.07-0.77 (m, 6H).

Intermediate 71c: 3-(dimethylamino)propyl (1-hydroxy-7-octylpentadecan-5-yl) carbonate

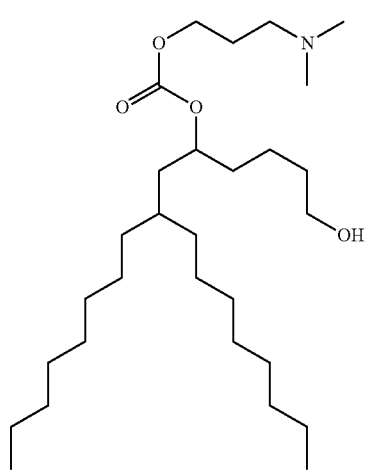 [SMILES: CCCCCCCCC(CCCCCCCC)CC(CCCCO)OC(=O)OCCCN(C)C]

1 N HCl (2.91 ml, 2.91 mmol) was added to a solution of Intermediate 71b (553 mg, 0.970 mmol) in MeOH (10 ml) and DCM (1 mL). The reaction was stirred at ambient temperature for 18 h. The reaction was concentrated under reduced pressure, then the residue was rediluted with DCM and washed with aq sodium bicarbonate solution. The aqueous layer was back-extracted with DCM. The combined organic extracts were dried over MgSO$_4$, then filtered, and the filtrate was concentrated under reduced pressure to provide the title compound (490 mg), which was used without further purification. $^1$H NMR (400 MHz, CDCl$_3$) δ=4.74-4.87 (m, 1H), 4.10-4.27 (m, 2H), 3.59-3.71 (m, 2H), 2.30-2.45 (m, 2H), 2.23 (s, 6H), 1.85 (quin, J=6.95 Hz, 2H), 1.51-1.71 (m, 5H), 1.35-1.51 (m, 4H), 1.16-1.35 (m, 28H), 0.80-0.97 (m, 6H).

Example 71: 5-(((3-(dimethylamino)propoxy)carbonyl)oxy)-7-octylpentadecyl octanoate

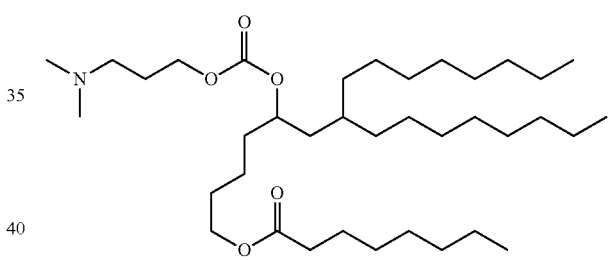

Intermediate 71c (250 mg, 0.515 mmol) and decanoic acid (82 mg, 0.566 mmol) were dissolved in DCE (5146 μL). EDC.HCl (118 mg, 0.618 mmol) and DMAP (62.9 mg, 0.515 mmol) were added. Then, DIPEA (270 μL, 1.544 mmol) was added. The reaction was stirred at ambient temperature for 3 h. The reaction was transferred to a sealed vial and was heated under microwave irradiation to 80° C. for 20 min. The crude mixture was purified on silica gel with 0-100% EtOAc/heptanes, then 0-15% MeOH/DCM to provide the title compound (168 mg, 53%). $^1$H NMR (400 MHz, CDCl$_3$) δ=4.69-4.88 (m, 1H), 4.13-4.26 (m, 2H), 4.06 (t, J=6.57 Hz, 2H), 2.36 (t, J=7.33 Hz, 2H), 2.29 (t, J=7.58 Hz, 2H), 2.23 (s, 6H), 1.85 (quin, J=7.01 Hz, 2H), 1.51-1.74 (m, 7H), 1.35-1.50 (m, 4H), 1.15-1.35 (m, 36H), 0.80-0.97 (m, 9H). MS (M+1)=612.5, Rt=1.01 min (LC Method 6).

Example 72: (9Z,12Z)-5-(((3-(dimethylamino)propoxy)carbonyl)oxy)-7-octylpentadecyl octadeca-9,12-dienoate

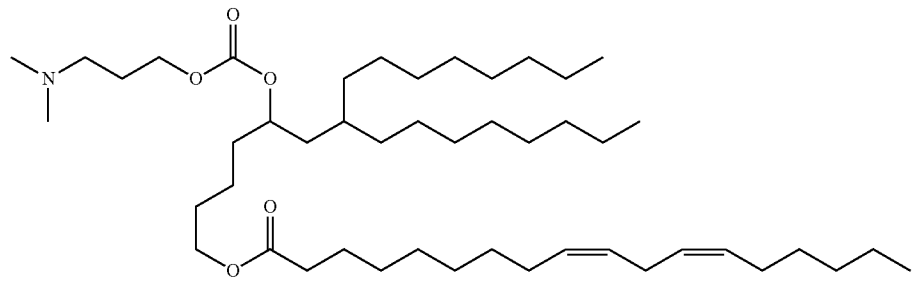 [SMILES: CCCCC/C=C\C/C=C\CCCCCCCC(=O)OCCCCC(CC(CCCCCCCC)CCCCCCCC)OC(=O)OCCCN(C)C]

¹H NMR (400 MHz, CDCl₃) δ=5.27-5.46 (m, 4H), 4.73-4.86 (m, 1H), 4.12-4.26 (m, 2H), 4.06 (t, J=6.69 Hz, 2H), 2.78 (t, J=6.69 Hz, 2H), 2.32-2.42 (m, 2H), 2.29 (t, J=7.58 Hz, 2H), 2.23 (s, 6H), 2.06 (q, J=6.82 Hz, 4H), 1.78-1.91 (m, 2H), 1.51-1.73 (m, 7H), 1.17-1.46 (m, 46H), 0.81-0.95 (m, 9H). MS (M+1)=748.6, Rt=1.33 min (LC Method 6).

Example 73: 9-(((3-(dimethylamino)propoxy)carbonyl)oxy)-11-octylnonadecyl octanoate

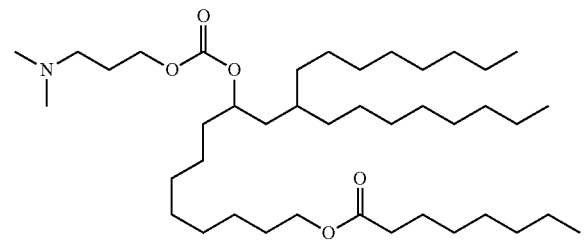 [SMILES: CCCCCCCCC(CCCCCCCC)CC(CCCCCCCCOC(=O)CCCCCCC)OC(=O)OCCCN(C)C]

¹H NMR (400 MHz, CDCl₃) δ=4.72-4.85 (m, 1H), 4.18 (t, J=6.44 Hz, 2H), 4.06 (t, J=6.69 Hz, 2H), 2.42-2.57 (m, 2H), 2.25-2.37 (m, 8H), 1.85-1.99 (m, 2H), 1.49-1.71 (m, 7H), 1.38 (br. s., 3H), 1.16-1.34 (m, 45H), 0.84-0.95 (m, 9H). MS (M+1)=668.5, Rt=1.83 min (LC Method 4).

Example 74: 9-(((3-(dimethylamino)propoxy)carbonyl)oxy)-11-octylnonadecyl decanoate

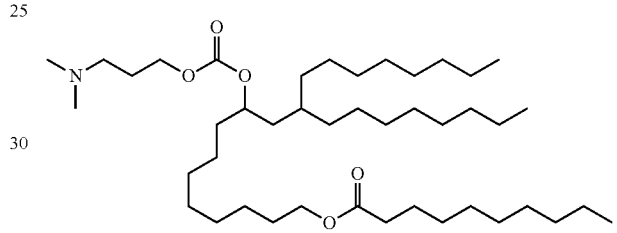

¹H NMR (400 MHz, CDCl₃) δ=4.72-4.86 (m, 1H), 4.18 (t, J=6.69 Hz, 2H), 4.06 (t, J=6.82 Hz, 2H), 2.37 (t, J=7.45 Hz, 2H), 2.29 (t, J=7.58 Hz, 2H), 2.23 (s, 6H), 1.75-1.93 (m, 2H), 1.51-1.70 (m, 7H), 1.34-1.46 (m, 4H), 1.16-1.34 (m, 48H), 0.81-0.94 (m, 9H). MS (M+1)=696.3, Rt=2.49 min (LC Method 4).

Example 75: (9Z,12Z)-9-(((3-(dimethylamino)propoxy)carbonyl)oxy)nonadecyl octadeca-9,12-dienoate

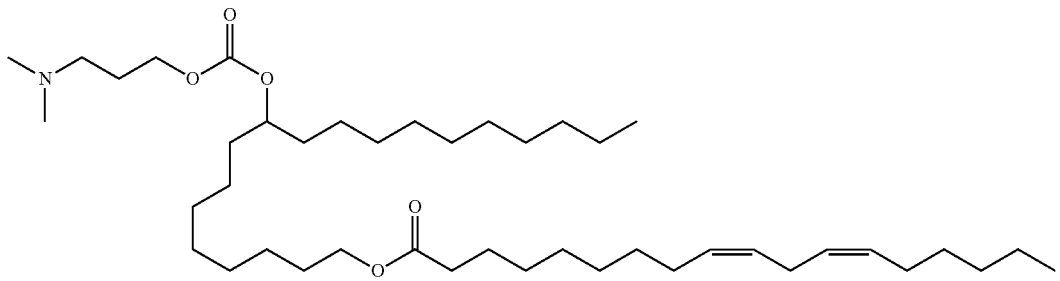 [SMILES: CCCCC/C=C\C/C=C\CCCCCCCC(=O)OCCCCCCCCC(CCCCCCCCCC)OC(=O)OCCCN(C)C]

¹H NMR (400 MHz, CDCl₃) δ=5.31-5.46 (m, 4H), 4.62-4.76 (m, 1H), 4.19 (t, J=6.57 Hz, 2H), 4.06 (t, J=6.82 Hz, 2H), 2.78 (t, J=6.57 Hz, 2H), 2.39 (t, J=7.33 Hz, 2H), 2.29 (t, J=7.45 Hz, 2H), 2.25 (s, 6H), 1.99-2.12 (m, 4H), 1.79-1.95 (m, 2H), 1.47-1.71 (m, 8H), 1.19-1.45 (m, 40H), 0.79-0.97 (m, 6H). MS (M+1)=692.5, Rt=1.22 min (LC Method 6).

Example 76: 9-(((3-(dimethylamino)propoxy)carbonyl)oxy)nonadecyl hexanoate

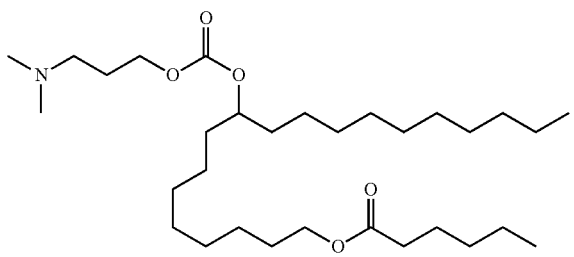 [SMILES: CCCCCCCCCCC(CCCCCCCCOC(=O)CCCCC)OC(=O)OCCCN(C)C]

$^1$H NMR (400 MHz, CDCl$_3$) δ=4.57-4.78 (m, 1H), 4.19 (t, J=6.57 Hz, 2H), 4.06 (t, J=6.82 Hz, 2H), 2.41 (br. s., 2H), 2.27 (d, J=4.29 Hz, 6H), 1.81-1.99 (m, 2H), 1.48-1.69 (m, 8H), 1.20-1.42 (m, 32H), 0.90 (d, J=6.82 Hz, 6H). MS (M+1)=528.3, Rt=1.04 min (LC Method 6).

Example 77: 9-(((3-(dimethylamino)propoxy)carbonyl)oxy)nonadecyl 3-octylundecanoate

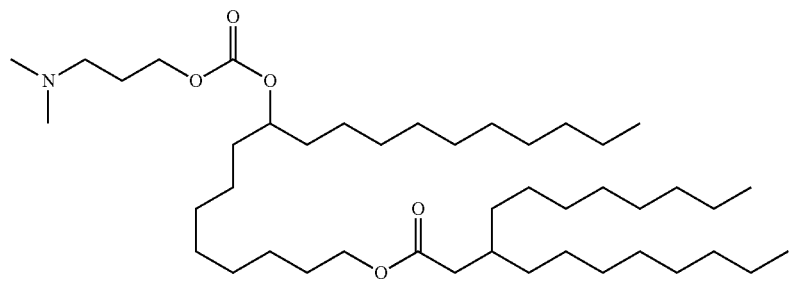 [SMILES: CCCCCCCCCCC(CCCCCCCCOC(=O)CC(CCCCCCCC)CCCCCCCC)OC(=O)OCCCN(C)C]

$^1$H NMR (400 MHz, CDCl$_3$) δ=4.60-4.76 (m, 1H), 4.18 (t, J=6.57 Hz, 2H), 4.05 (t, J=6.69 Hz, 2H), 2.39 (s, 2H), 2.20-2.31 (m, 8H), 1.75-1.94 (m, 3H), 1.43-1.67 (m, 6H), 1.21-1.39 (m, 54H), 0.84-1.05 (m, 9H). MS (M+1)=710.5, Rt=1.33 min (LC Method 6).

Example 78: 9-((4-(dimethylamino)butanoyl)oxy)nonadecyl hexanoate

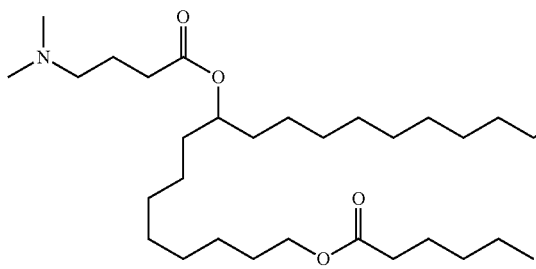

$^1$H NMR (400 MHz, CDCl$_3$) δ=4.87 (t, J=6.19 Hz, 1H), 4.05 (t, J=6.69 Hz, 2H), 2.30 (td, J=7.89, 5.68 Hz, 4H), 2.25-2.37 (m, 2H), 2.22 (s, 6H), 1.79 (dq, J=7.58, 7.41 Hz, 2H), 1.55-1.70 (m, 4H), 1.50 (d, J=6.06 Hz, 4H), 1.17-1.39 (m, 30H), 0.89 (q, J=6.99 Hz, 6H). $^{13}$C NMR $^{13}$C NMR (101 MHz, CDCl$_3$) δ=173.97, 173.37, 74.19, 64.34 (2C), 58.95, 45.44 (2C), 34.35, 34.13 (2C), 32.47, 31.89, 31.31, 29.57, 29.53 (2C), 29.44, 29.41, 29.31, 29.17, 28.63, 25.89, 25.31, 25.30, 24.69, 23.17, 22.66, 22.31, 14.09, 13.90.

Example 79: 9-((4-(dimethylamino)butanoyl)oxy)nonadecyl 3-octylundecanoate

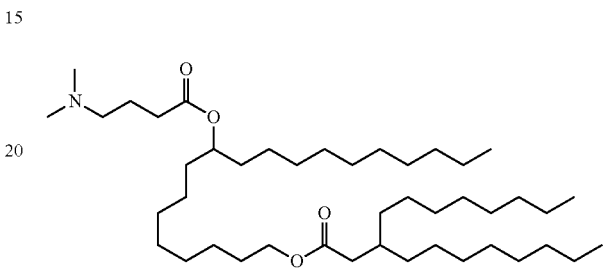

$^1$H NMR (400 MHz, CDCl$_3$) δ=4.86 (t, J=6.19 Hz, 1H), 4.04 (t, J=6.69 Hz, 2H), 2.30 (dt, J=16.48, 7.42 Hz, 4H), 2.21 (s, 6H), 2.22 (d, J=6.82 Hz, 2H), 1.71-1.88 (m, 3H), 1.59 (d, J=7.33 Hz, 2H), 1.50 (d, J=5.81 Hz, 4H), 1.25 (s, 48H), 1.30 (br. s., 6H), 0.88 (d, J=13.64 Hz, 9H). $^{13}$C NMR (101 MHz, CDCl$_3$) δ=173.75, 173.35, 74.18, 64.23, 58.93, 45.41 (2C), 39.34, 35.08, 34.12, 33.88, 32.45, 31.88 (3C), 29.89 (3C), 29.56 (4C), 29.52 (2C), 29.47, 29.43, 29.29 (3C), 29.20, 28.65, 26.51 (2C), 25.95, 25.31 (2C), 23.14, 22.65 (4C), 14.08 (3C)

Synthesis of Example 80

Intermediate 80a

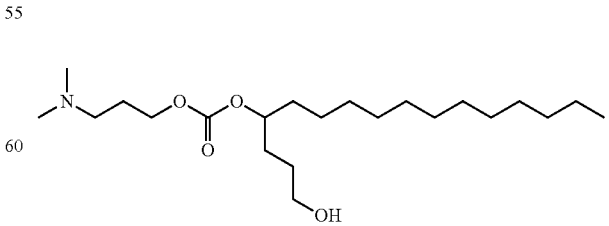

Intermediate 80a can be synthesized using methods similar to those used for the synthesis of Intermediate 1k. MS (M+1)=387.9, Rt=0.41 min (LC Method 4).

Intermediate 80b: Synthesis of 3-(dimethylamino)propyl (1-oxohexadecan-4-yl) carbonate

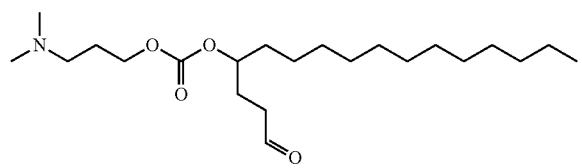 [SMILES: CCCCCCCCCCCCC(CCC=O)OC(=O)OCCCN(C)C]

Intermediate 80a was dissolved in DCM (50 ml) and cooled in an ice bath. TEA (7.80 ml, 56.3 mmol) was then added. In another flask, $SO_3.Py$ (5.97 g, 37.5 mmol) was dissolved in DMSO (17.59 g, 225 mmol), and the resultant solution was added dropwise to the cold DCM solution. The resultant mixture was stirred at room temperature overnight. The reaction was then diluted with 800 mL ethyl acetate and the organic phase was washed with water three times.

The combined aqueous phase was back-extracted with 200 mL EtOAc twice. The combined organic extracts were dried over sodium sulfate and filtered. The filtrate was concentrated under reduced pressure and purified on silica gel with 0-10% MeOH/DCM to afford 4.8 g of the title compound. MS (M+1)=386.6, Rt=1.28 min (LC Method 11).

Intermediate 80c: Synthesis of 4-(((3-(dimethylamino)propoxy)carbonyl)oxy)hexadecanoic acid

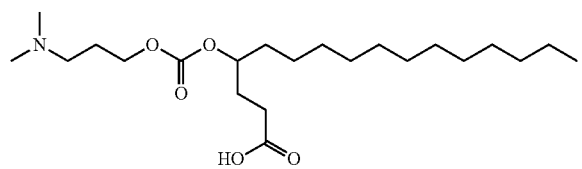 [SMILES: CCCCCCCCCCCCC(CCC(=O)O)OC(=O)OCCCN(C)C]

In a 500 mL round-bottomed flask Intermediate 80b (5 g, 12.97 mmol) and 2-methylbut-2-ene (4.55 gram, 64.8 mmol) were dissolved in t-BuOH (Volume: 25 ml, Ratio: 1.000) and 4N formic acid buffer, pH 3.5 (25 ml). A 2 M aq solution of $NaClO_2$ (9.73 ml, 19.45 mmol) was added. The reaction was stirred at ambient temperature for one hour. The mixture was diluted with 800 mL DCM and 50 mL water. 1 N HCl was added to adjust the pH of the aqueous layer to 5 The aqueous layer was extracted with 5% MeOH in DCM. The combined organics were dried over $Na_2SO_4$ and filtered. The filtrate was concentrated under reduced pressure and purified on silica gel The material was redissolved in 5% MeOH in DCM and washed with sat. aq. $NaHCO_3$. The organic phase was dried over $Na_2SO_4$, filtered and the filtrate concentrated concentrated under reduced pressure to afford 4.5 g of the title compound. MS (M+1)=402.6, Rt=1.23 min (LC Method 11).

Example 80: (9Z,9'Z,12Z,12'Z)-2-((4-(((3-(dimethylamino)propoxy)carbonyl)oxy)hexadecanoyl)oxy) propane-1,3-diyl bis(octadeca-9,12-dienoate)

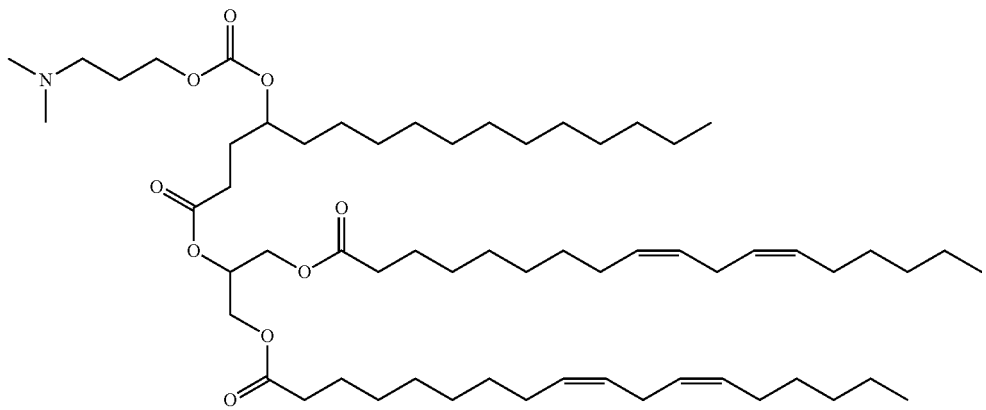 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

In a round bottom flask, Intermediate 80c (4.5 g, 11.21 mmol), DMAP (548 mg, 4.48 mmol), and 1,3-Dilinolein (10.37 g, 16.81 mmol) were taken into dichloromethane (100 ml). EDC.HCl (4.3 g, 22.41 mmol) was added in one portion followed by DIPEA (3.91 ml, 22.41 mmol), dropwise, and the reaction was stirred at ambient temperature. After 24 h, the reaction was concentrated under reduced pressure. The residue was purified on silica gel with 0-60% ethyl acetate/heptane to provide the title compound (6.17 g). $^1$H NMR (400 MHz, $CDCl_3$) δ=5.19-5.48 (m, 9H), 4.65-4.81 (m, 1H), 4.30 (dd, J=11.80, 4.27 Hz, 2H), 4.08-4.25 (m, 4H), 2.77 (t, J=6.40 Hz, 4H), 2.36-2.52 (m, 4H), 2.20-2.36 (m, 10H), 2.05 (q, J=6.78 Hz, 8H), 1.81-2.00 (m, 5H), 1.48-1.71 (m, 7H), 1.16-1.44 (m, 46H), 0.81-0.96 (m, 9H). MS (M+1)=1001.4, Rt=1.30 min (LC Method 4).

Example 81: (9Z,9'Z,12Z,12'Z)-2-((4-(((3-(diethylamino)propoxy)carbonyl)oxy)hexadecanoyl)oxy)propane-1,3-diyl bis(octadeca-9,12-dienoate)

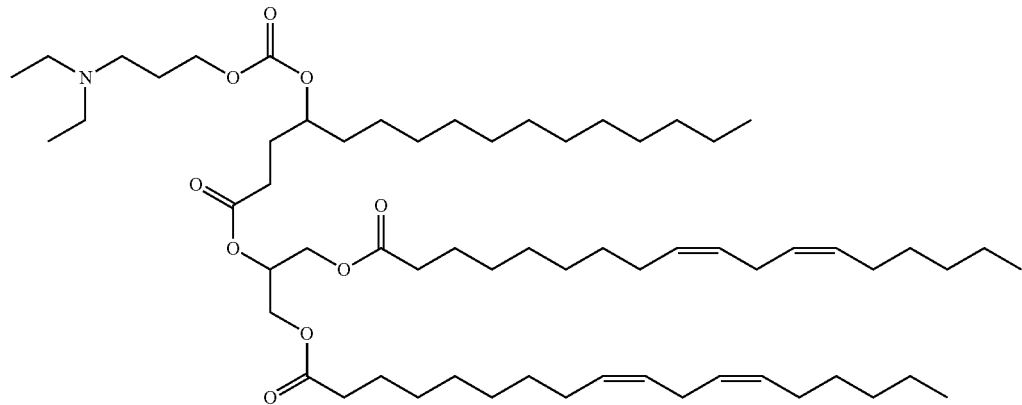 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(CC)CC]

$^1$H NMR (400 MHz, CDCl$_3$) δ=5.20-5.48 (m, 9H), 4.72 (br. s., 1H), 4.30 (dd, J=11.80, 4.27 Hz, 2H), 4.06-4.25 (m, 4H), 2.78 (t, J=6.65 Hz, 4H), 2.47-2.60 (m, 6H), 2.37-2.47 (m, 2H), 2.25-2.37 (m, 4H), 2.05 (q, J=6.78 Hz, 7H), 1.73-2.01 (m, 4H), 1.48-1.73 (m, 6H), 1.17-1.45 (m, 48H), 1.02 (t, J=7.15 Hz, 6H), 0.81-0.95 (m, 9H). MS (M+1)=1029.0, Rt=1.51 min (LC Method 6).

Example 82: (9Z,9'Z,12Z,12'Z,15Z,15'Z)-2-((4-(((3-(dimethylamino)propoxy)carbonyl)oxy)hexadecanoyl)oxy)propane-1,3-diyl bis(octadeca-9,12,15-trienoate)

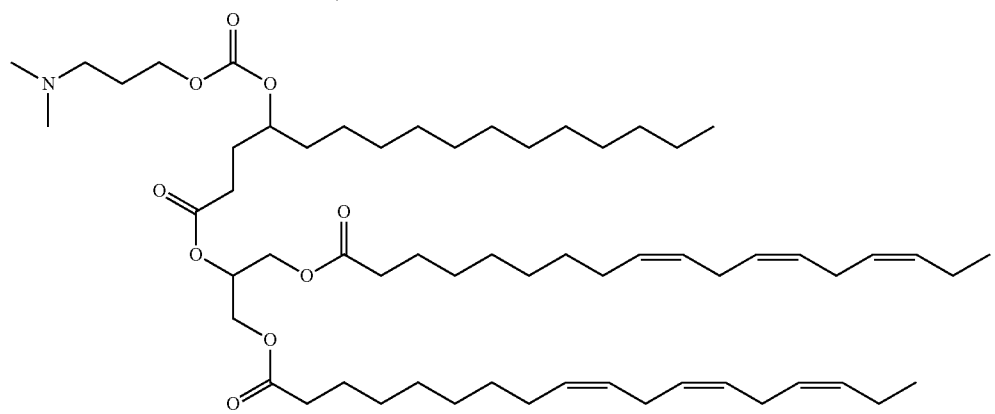 [SMILES: CC/C=C\C/C=C\C/C=C\CCCCCCCC(=O)OCC(COC(=O)CCCCCCC/C=C\C/C=C\C/C=C\CC)OC(=O)CCC(CCCCCCCCCCCC)OC(=O)OCCCN(C)C]

$^1$H NMR (400 MHz, CDCl$_3$) δ=5.48-5.19 (m, 13H), 4.79-4.63 (m, 1H), 4.30 (dd, J=4.1, 11.9 Hz, 2H), 4.24-4.05 (m, 4H), 2.91-2.68 (m, 8H), 2.52-2.26 (m, 8H), 2.23 (s, 6H), 2.15-2.01 (m, 8H), 2.01-1.77 (m, 4H), 1.70-1.45 (m, 6H), 1.42-1.28 (m, 20H), 1.26 (m, 16H), 0.98 (t, J=7.5 Hz, 6H), 0.92-0.83 (m, 3H). $^{13}$C NMR (101 MHz, CDCl$_3$) δ=173.26 (2C), 172.05, 155.02, 131.94 (2C), 130.22 (2C), 128.26 (2C), 128.21 (2C), 127.70 (2C), 127.07 (2C), 77.53, 69.20, 66.32, 61.99, 61.96, 55.96, 45.46 (2C), 34.07, 33.96 (2C), 31.90, 30.01, 29.66, 29.63 (2C), 29.57 (2C), 29.50, 29.46, 29.35, 29.17 (2C), 29.11 (2C), 29.07 (2C), 28.96, 27.19 (3C), 26.95, 25.59 (2C), 25.50 (2C), 25.14, 24.79 (2C), 22.68, 20.53 (2C), 14.28 (2C), 14.13.

Example 83: (Z)-2-((4-(((3-(dimethylamino)propoxy)carbonyl)oxy)hexadecanoyl)oxy)propane-1,3-diyl dioleate

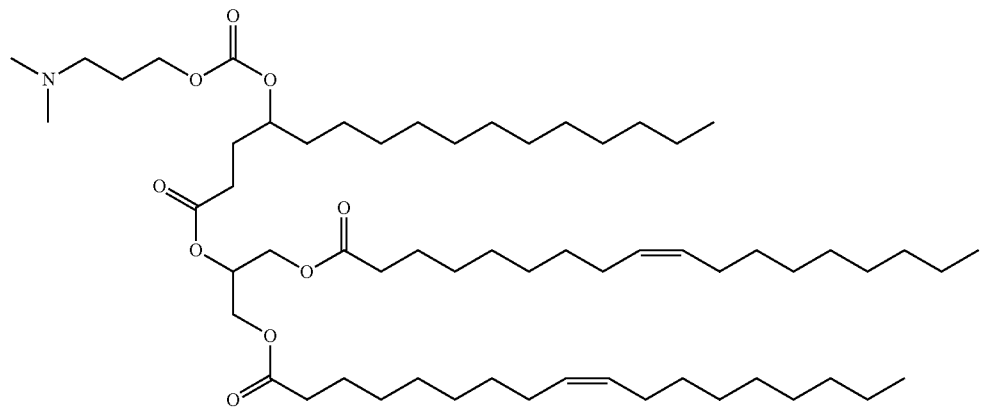 [SMILES: CCCCCCCC/C=C\CCCCCCCC(=O)OCC(COC(=O)CCCCCCC/C=C\CCCCCCCC)OC(=O)CCC(CCCCCCCCCCCC)OC(=O)OCCCN(C)C]

$^1$H NMR (400 MHz, CDCl$_3$) δ=5.44-5.30 (m, 4H), 5.30-5.20 (m, 1H), 4.82-4.63 (m, 1H), 4.30 (dd, J=4.4, 11.9 Hz, 2H), 4.25-4.07 (m, 4H), 2.50-2.27 (m, 8H), 2.23 (s, 6H), 2.07-1.93 (m, 9H), 1.93-1.76 (m, 3H), 1.70-1.48 (m, 6H), 1.42-1.17 (m, 60H), 0.94-0.81 (m, 9H). $^{13}$C NMR (101 MHz, CDCl$_3$) δ=173.28 (2C), 172.05, 155.02, 129.99 (2C), 129.70 (2C), 77.53, 69.20, 66.33, 61.99, 61.95, 55.97, 45.47 (2C), 34.08, 33.97 (2C), 31.90 (3C), 30.01, 29.75 (2C), 29.70 (2C), 29.66 (3C), 29.64 (2C), 29.57, 29.52 (3C), 29.46, 29.35, 29.32 (5C), 29.18, 29.11, 29.09, 28.97, 27.20 (2C), 27.16 (2C), 26.96, 25.15, 24.80 (2C), 22.68 (3C), 14.13 (3C).

Example 84: 2-((4-(((3-(diethylamino)propoxy)carbonyl)oxy)hexadecanoyl)oxy)propane-1,3-diyl ditetradecanoate

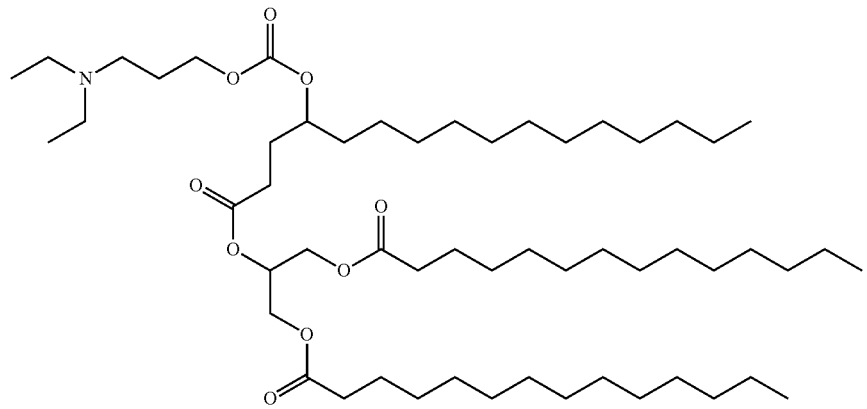 [SMILES: CCCCCCCCCCCCCC(=O)OCC(COC(=O)CCCCCCCCCCCCC)OC(=O)CCC(CCCCCCCCCCCC)OC(=O)OCCCN(CC)CC]

$^1$H NMR (400 MHz, CDCl$_3$) δ=5.22-5.30 (m, 1H), 4.67-4.78 (m, 1H), 4.30 (dd, J=12.05, 4.27 Hz, 2H), 4.10-4.24 (m, 4H), 2.54 (m, 6H), 2.37-2.48 (m, 2H), 2.26-2.37 (m, 4H), 1.78-2.04 (m, 4H), 1.48-1.69 (m, 6H), 1.26 (m, 60H), 1.03 (t, J=7.15 Hz, 6H), 0.83-0.93 (m, 9H). $^{13}$C NMR (101 MHz, CDCl$_3$): δ ppm 173.3 (s, 2C), 172.1, 155.0, 77.5, 69.2, 66.5, 62.0 (d, 2C), 49.0, 46.9 (s, 2C), 34.1, 34.0 (s, 2C), 31.9 (s, 3C), 30.0, 29.7-29.3 (overlap, 23), 29.1 (s, 2C), 29.0, 26.3 (br s, 1C), 25.1, 24.8 (s, 2C), 22.7 (s, 2C), 14.1 (s, 2C), 11.6 (br s, 2C)

Example 85: 2-((4-(((3-(dimethylamino)propoxy)carbonyl)oxy)hexadecanoyl)oxy)propane-1,3-diyl ditetradecanoate
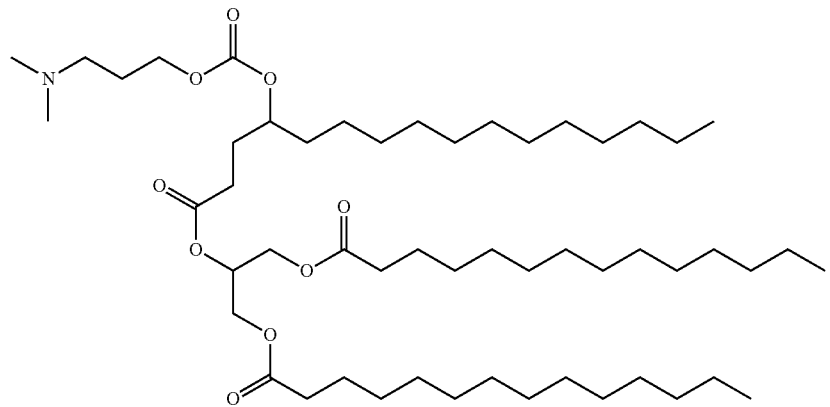 [SMILES: CCCCCCCCCCCCCC(=O)OCC(COC(=O)CCCCCCCCCCCCC)OC(=O)CCC(CCCCCCCCCCCC)OC(=O)OCCCN(C)C]
$^1$H NMR (400 MHz, CDCl$_3$) δ=5.20-5.33 (m, 1H), 4.66-4.79 (m, 1H), 4.25-4.37 (m, 2H), 4.08-4.24 (m, 4H), 2.35-2.48 (m, 4H), 2.28-2.35 (m, 4H), 2.25 (s, 6H), 1.81-2.02 (m, 4H), 1.49-1.70 (m, 6H), 1.20-1.40 (m, 60H), 0.84-0.93 (m, 9H). MS (M+1)=896.9, Rt=1.51 min (LC Method 6).
Example 86: 2-((4-(((3-(ethyl(methyl)amino)propoxy)carbonyl)oxy)hexadecanoyl)oxy)propane-1,3-diyl ditetradecanoate
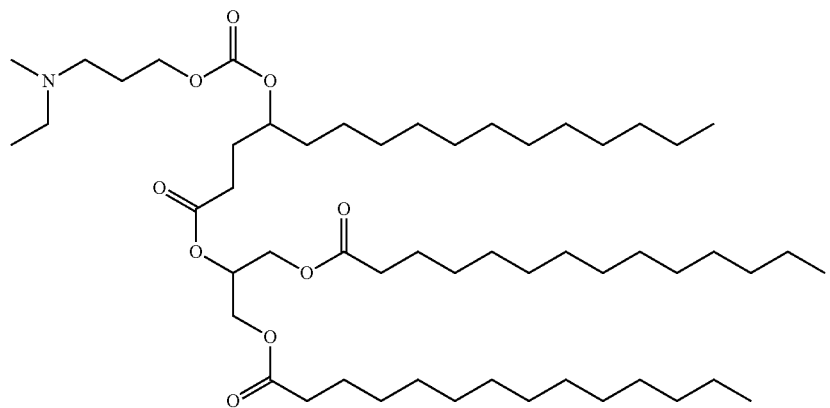 [SMILES: CCCCCCCCCCCCCC(=O)OCC(COC(=O)CCCCCCCCCCCCC)OC(=O)CCC(CCCCCCCCCCCC)OC(=O)OCCCN(C)CC]
$^1$H NMR (400 MHz, CDCl$_3$) δ=5.17-5.35 (m, 1H), 4.65-4.79 (m, 1H), 4.30 (dd, J=11.92, 4.39 Hz, 2H), 4.08-4.24 (m, 4H), 2.18-2.78 (m, 13H), 1.80-2.06 (m, 4H), 1.47-1.71 (m, 6H), 1.17-1.40 (m, 60H), 1.05-1.17 (m, 3H), 0.80-0.96 (m, 9H). MS (M+1)=911.0, Rt=4.54 min (LC Method 4).

Example 87: 2-((4-(((3-(dimethylamino)propoxy) carbonyl)oxy)hexadecanoyl)oxy)propane-1,3-diyl didodecanoate

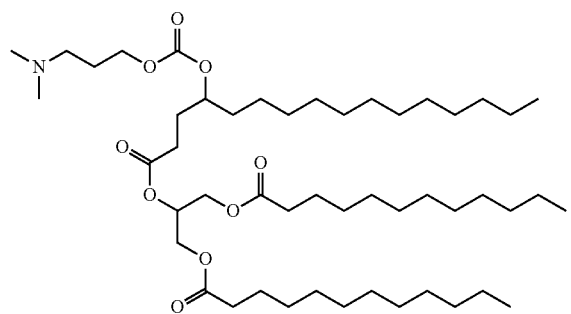 [SMILES: CCCCCCCCCCCCC(CCC(=O)OC(COC(=O)CCCCCCCCCCC)COC(=O)CCCCCCCCCCC)OC(=O)OCCCN(C)C]

$^1$H NMR (400 MHz, CDCl$_3$) δ=5.26 (m, 1H), 4.65-4.80 (m, 1H), 4.30 (dd, J=11.92, 4.39 Hz, 2H), 4.04-4.24 (m, 4H), 2.35-2.49 (m, 4H), 2.28-2.35 (m, 4H), 2.25 (s, 6H), 1.93-2.03 (m, 1H), 1.80-1.93 (m, 3H), 1.48-1.70 (m, 6H), 1.17-1.45 (m, 52H), 0.83-0.94 (m, 9H). MS (M+1)=840.8, Rt=1.32 min (LC Method 3).

Example 88: 2-((4-(((3-(diethylamino)propoxy)carbonyl)oxy)hexadecanoyl)oxy)propane-1,3-diyl didodecanoate

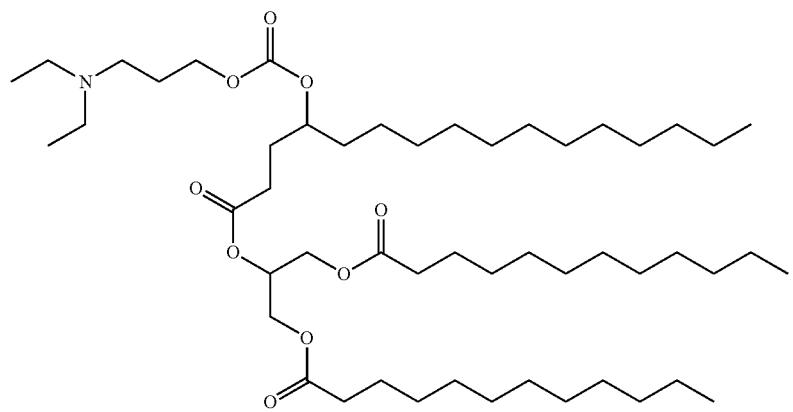 [SMILES: CCCCCCCCCCCCC(CCC(=O)OC(COC(=O)CCCCCCCCCCC)COC(=O)CCCCCCCCCCC)OC(=O)OCCCN(CC)CC]

$^1$H NMR (400 MHz, CDCl$_3$) δ=5.26 (quin, J=5.08 Hz, 1H) 4.66-4.79 (m, 1H) 4.30 (dd, J=11.92, 4.39 Hz, 2H) 4.09-4.24 (m, 4H) 2.54 (m, 6H) 2.36-2.49 (m, 2H) 2.24-2.36 (m, 4H) 1.78-2.02 (m, 4H) 1.49-1.69 (m, 6H) 1.18-1.40 (m, 52H) 1.03 (t, J=7.03 Hz, 6H) 0.88 (t, J=6.78 Hz, 9H). MS (M+1)=868.9, Rt=1.96 min (LC Method 7).

Example 89: 2-((4-(((3-(ethyl(methyl)amino) propoxy)carbonyl)oxy)hexadecanoyl)oxy)propane-1, 3-diyl didodecanoate

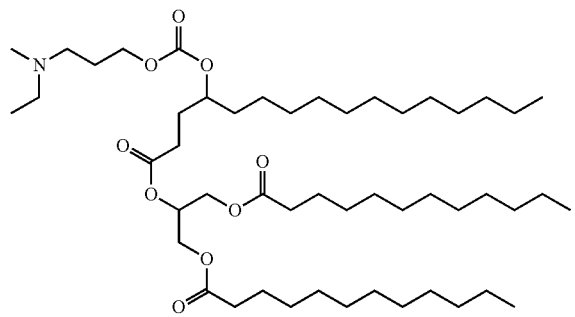 [SMILES: CCCCCCCCCCCCC(CCC(=O)OC(COC(=O)CCCCCCCCCCC)COC(=O)CCCCCCCCCCC)OC(=O)OCCCN(C)CC]

$^1$H NMR (400 MHz, CDCl$_3$) δ=5.20-5.31 (m, 1H), 4.67-4.78 (m, 1H), 4.30 (dd, J=12.05, 4.27 Hz, 2H), 4.06-4.24 (m, 4H), 2.46-2.71 (m, 4H), 2.37-2.46 (m, 2H), 2.20-2.37 (m, 7H), 1.79-2.05 (m, 4H), 1.47-1.71 (m, 6H), 1.18-1.45 (m, 52H), 1.12 (br. s., 3H), 0.79-0.94 (m, 9H). MS (M+1)=855.0, Rt=3.13 min (LC Method 4).

Example 90: 2-((4-(((3-(diethylamino)propoxy)carbonyl)oxy)hexadecanoyl)oxy)propane-1,3-diyl bis (decanoate)

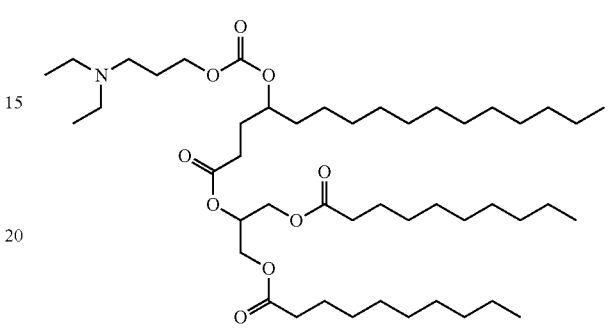

$^1$H NMR (400 MHz, CDCl$_3$) δ=5.21-5.31 (m, 1H), 4.67-4.78 (m, 1H), 4.30 (dd, J=12.05, 4.27 Hz, 2H), 4.10-4.25 (m, 4H), 2.48-2.64 (m, 6H), 2.36-2.48 (m, 2H), 2.27-2.36 (m, 4H), 1.78-2.02 (m, 4H), 1.48-1.69 (m, 6H), 1.19-1.41 (m, 44H), 1.03 (t, J=7.15 Hz, 6H), 0.88 (t, J=6.78 Hz, 9H). MS (M+1)=813.0, Rt=1.45 min (LC Method 7).

Example 91: 2-((4-(((3-(ethyl(methyl)amino) propoxy)carbonyl)oxy)hexadecanoyl)oxy)propane-1, 3-diyl bis(decanoate)

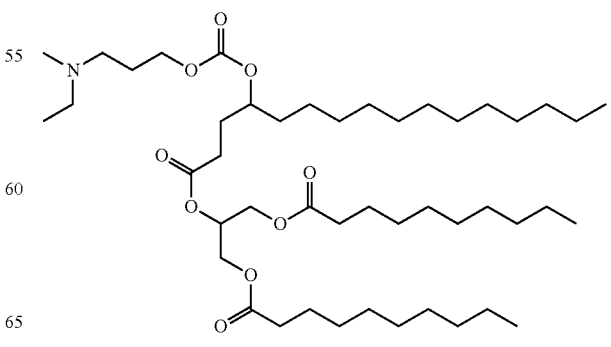

¹H NMR (400 MHz, CDCl₃) δ=5.26 (quin, J=5.02 Hz, 1H), 4.67-4.78 (m, 1H), 4.30 (dd, J=11.80, 4.27 Hz, 2H), 4.08-4.24 (m, 4H), 2.44-2.63 (m, 4H), 2.36-2.44 (m, 2H), 2.20-2.36 (m, 7H), 1.79-2.04 (m, 4H), 1.48-1.72 (m, 6H), 1.19-1.38 (m, 44H), 1.10 (t, J=6.53 Hz, 3H), 0.80-0.94 (m, 9H). MS (M+1)=798.9, Rt=1.57 min (LC Method 7).

Example 92: 2-((4-(((3-(diethylamino)propoxy)carbonyl)oxy)hexadecanoyl)oxy)propane-1,3-diyl dioctanoate

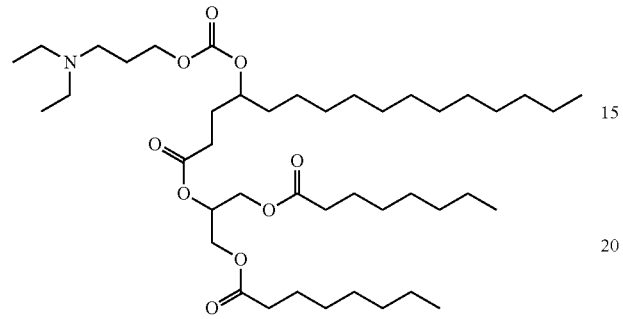

¹H NMR (400 MHz, CDCl₃) δ=5.26 (quin, J=5.0 Hz, 1H), 4.78-4.66 (m, 1H), 4.30 (dd, J=4.3, 11.8 Hz, 2H), 4.24-4.10 (m, 4H), 2.64-2.47 (m, 6H), 2.47-2.37 (m, 2H), 2.37-2.26 (m, 4H), 2.02-1.78 (m, 4H), 1.70-1.48 (m, 6H), 1.39-1.19 (m, 36H), 1.03 (t, J=7.2 Hz, 6H), 0.88 (t, J=6.8 Hz, 9H). MS (M+1)=755.9, Rt=1.89 min (LC Method 7).

Example 93: 2-((4-(((3-(ethyl(methyl)amino)propoxy)carbonyl)oxy)hexadecanoyl)oxy)propane-1,3-diyl dioctanoate

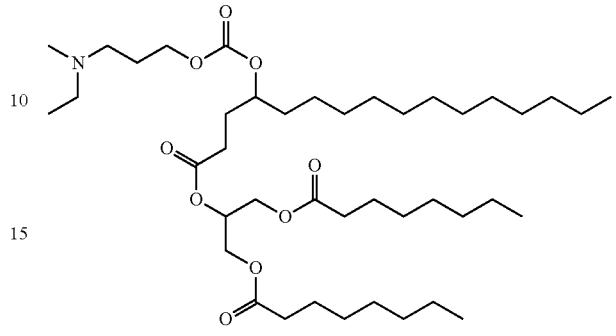

¹H NMR (400 MHz, CDCl₃) δ=5.19-5.32 (m, 1H), 4.66-4.79 (m, 1H), 4.30 (dd, J=11.92, 4.39 Hz, 2H), 4.05-4.24 (m, 4H), 2.44-2.70 (m, 4H), 2.37-2.44 (m, 2H), 2.20-2.37 (m, 7H), 1.80-2.05 (m, 4H), 1.48-1.71 (m, 6H), 1.18-1.42 (m, 36H), 1.10 (d, J=6.53 Hz, 3H), 0.76-0.95 (m, 9H). MS (M+1)=742.7, Rt=1.34 min (LC Method 7).

Synthesis of Example 94

Intermediate 94a

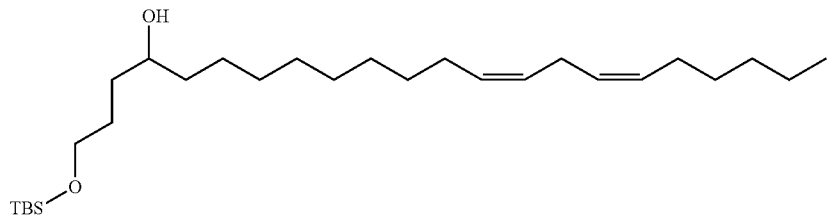

Intermediate 94a can be synthesized using methods similar to those exemplified for the synthesis of Intermediate 49a. ¹H NMR (400 MHz, CDCl₃) δ=5.26-5.47 (m, 4H), 3.64-3.73 (m, 2H), 3.54-3.64 (m, 1H), 2.78 (t, J=6.40 Hz, 2H), 2.06 (q, J=6.94 Hz, 4H), 1.56-1.74 (m, 3H), 1.40-1.52 (m, 4H), 1.16-1.40 (m, 18H), 0.91 (s, 9H), 0.86-0.90 (m, 3H), 0.08 (s, 6H).

Example 94: 2-(((13Z,16Z)-4-(((3-(dimethylamino)propoxy)carbonyl)oxy)docosa-13,16-dienoyl)oxy)propane-1,3-diyl dioctanoate

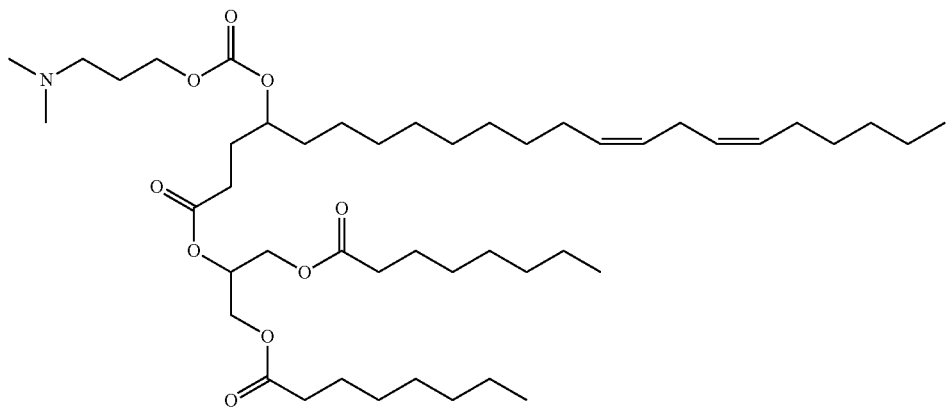 [SMILES: CCCCC/C=C\C/C=C\CCCCCCCCC(CCC(=O)OC(COC(=O)CCCCCCC)COC(=O)CCCCCCC)OC(=O)OCCCN(C)C]

Example 94 can be synthesized using methods similar to those exemplified for the synthesis of Example 80. $^1$H NMR (400 MHz, CDCl$_3$) δ=5.45-5.21 (m, 5H), 4.73 (d, J=4.3 Hz, 1H), 4.30 (dd, J=4.3, 11.8 Hz, 2H), 4.23-4.07 (m, 4H), 2.77 (t, J=6.3 Hz, 2H), 2.49-2.36 (m, 4H), 2.36-2.21 (m, 9H), 2.12-1.80 (m, 7H), 1.70-1.48 (m, 6H), 1.40-1.20 (m, 36H), 0.94-0.81 (m, 9H) ppm. LC-MS m/z=808.5 (M+1). Rt=1.59 min (LC Method 7).

Example 95: 2-(((13Z,16Z)-4-(((3-(diethylamino) propoxy)carbonyl)oxy)docosa-13,16-dienoyl)oxy) propane-1,3-diyl dioctanoate

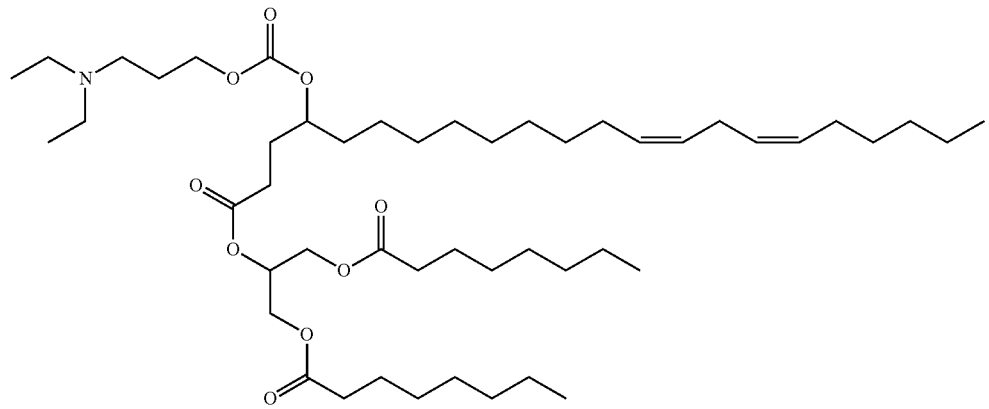 [SMILES: CCCCC/C=C\C/C=C\CCCCCCCCC(CCC(=O)OC(COC(=O)CCCCCCC)COC(=O)CCCCCCC)OC(=O)OCCCN(CC)CC]

$^1$H NMR (CDCl$_3$) δ=5.30-5.46 (m, 4H), 5.21-5.30 (m, 1H), 4.73 (ddd, J=7.2, 4.2, 2.8 Hz, 1H), 4.30 (dd, J=12.0, 4.4 Hz, 2H), 4.10-4.26 (m, 4H), 2.78 (t, J=6.4 Hz, 2H), 2.55 (d, J=5.1 Hz, 6H), 2.36-2.47 (m, 2H), 2.27-2.36 (m, 4H), 2.02-2.12 (m, 4H), 1.76-2.02 (m, 4H), 1.48-1.72 (m, 6H), 1.21-1.42 (m, 34H), 1.04 (t, J=6.9 Hz, 6H), 0.89 (dq, J=6.9, 3.4 Hz, 9H). MS (M+1)=836.6, Rt=1.01 min (LC Method 6).

Synthesis of Example 96

Intermediate 96a: 2-(((3-(diethylamino)propoxy) carbonyl)oxy)tetradecanoic acid

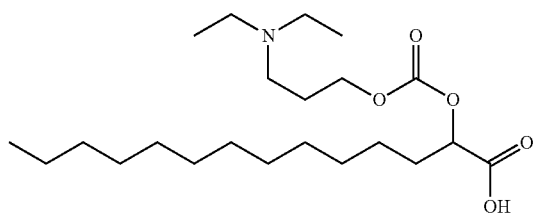 [SMILES: CCCCCCCCCCCCC(OC(=O)OCCCN(CC)CC)C(=O)O]

To a solution of Intermediate 48c (2 g, 5.16 mmol), dissolved in acetone (20 mL), cooled in an ice-water bath, was added Jones reagent (5.16 mL, 10.32 mmol, 2 M solution in H2O), dropwise. The cooling bath was removed, and stirring was continued overnight. iPrOH (1 mL) was added, the mixture was filtered, and the filtrate was removed under reduced pressure. The residue was diluted with water and heptane. The heptane layer was separated and discarded, and the aqeuous phase was washed with EtOAc, which was also discarded. The pH of the aqueous layer was adjusted to 6 and the mixture was extracted with 5% MeOH/DCM (5×40 mL). The combined dichloromethane extracts were dried over sodium sulfate and filtered. The filtrate was concentrated under reduced pressure to afford 1 g of the title compound, which was used without further purification. $^1$H NMR (400 MHz, CDCl$_3$) δ=4.67-4.78 (m, 1H), 4.23-4.41 (m, 1H), 4.16 (dt, J=10.98, 5.43 Hz, 1H), 2.97-3.27 (m, 4H), 2.89 (br. s., 1H), 1.98-2.15 (m, 2H), 1.75-1.98 (m, 2H), 1.55-1.75 (m, 1H), 1.39-1.55 (m, 3H), 1.09-1.39 (m, 24H), 0.89 (t, J=6.53 Hz, 3H)

Example 96: (9Z,9'Z,12Z,12'Z)-2-((2-(((3-(diethyl-amino)propoxy)carbonyl)oxy)tetradecanoyl)oxy) propane-1,3-diyl bis(octadeca-9,12-dienoate)

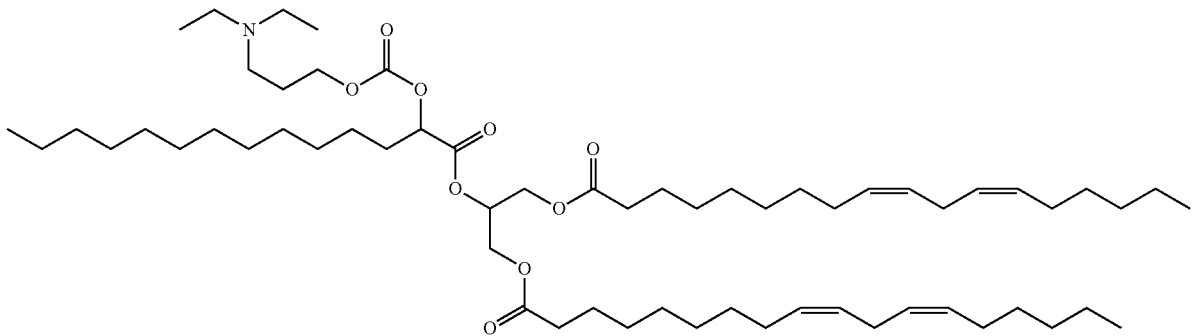 [SMILES: CCCCC/C=C\C/C=C\CCCCCCCC(=O)OCC(COC(=O)CCCCCCC/C=C\C/C=C\CCCCC)OC(=O)C(CCCCCCCCCCCC)OC(=O)OCCCN(CC)CC]

1H NMR (400 MHz, CDCl$_3$) δ=5.28-5.45 (m, 9H), 4.89 (t, J=6.27 Hz, 1H), 4.25-4.35 (m, 2H), 4.10-4.25 (m, 4H), 2.77 (t, J=6.53 Hz, 4H), 2.56 (br. s., 6H), 2.26-2.37 (m, 4H), 2.05 (q, J=6.78 Hz, 8H), 1.78-1.95 (m, 3H), 1.61 (m, 5H), 1.19-1.50 (m, 48H), 1.06 (br. s., 6H), 0.84-0.94 (m, 9H). MS (M+1)=1000.9, Rt=1.43 min (LC Method 4).

Example 97: (9Z,9'Z,12Z,12'Z)-2-((2-(((3-(dimethylamino)propoxy)carbonyl)oxy)dodecanoyl)oxy)propane-1,3-diyl bis(octadeca-9,12-dienoate)

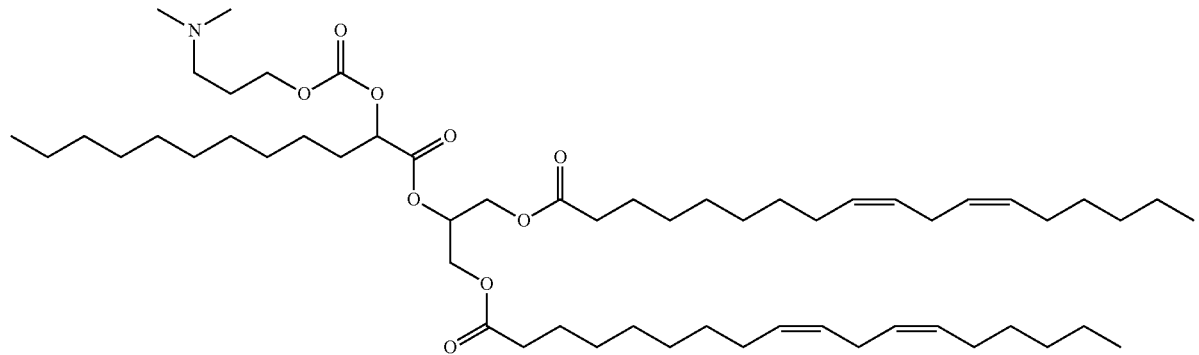

$^1$H NMR (400 MHz, CDCl$_3$) δ=5.27-5.45 (m, 9H), 4.89 (t, J=6.27 Hz, 1H), 4.25-4.35 (m, 2H), 4.10-4.25 (m, 4H), 2.77 (t, J=6.53 Hz, 4H), 2.37-2.48 (m, 2H), 2.22-2.37 (m, 10H), 2.05 (q, J=6.69 Hz, 8H), 1.79-1.95 (m, 5H), 1.61 (br. s., 5H), 1.21-1.49 (m, 42H), 0.84-0.95 (m, 9H). $^{13}$C NMR (101 MHz, CDCl$_3$) δ ppm 173.28, 173.17, 169.42, 154.63, 130.25 (s, 2C), 130.03 (d, 2C), 128.07 (s, 2C), 127.90 (s, 2C), 75.13, 70.14, 66.88, 61.90, 61.83, 55.85, 45.33 (s, 2C), 33.96, 33.93, 31.93, 31.54, 31.13, 29.65-29.13 (overlap, 16C), 27.22 (s, 4C), 26.70, 25.64 (s, 2C), 24.98, 24.80, 24.77, 22.71, 22.60 (s, 2C), 14.16, 14.12 (s, 2C).

Example 98: (9Z,9'Z,12Z,12'Z)-2-((2-(((3-(dimethylamino)propoxy)carbonyl)oxy)tetradecanoyl)oxy)propane-1,3-diyl bis(octadeca-9,12-dienoate)

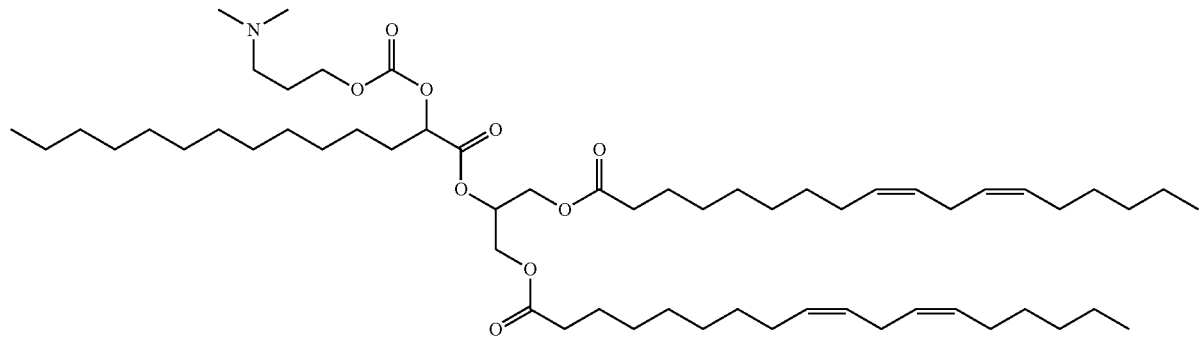 [SMILES: CCCCC/C=C\C/C=C\CCCCCCCC(=O)OCC(COC(=O)CCCCCCC/C=C\C/C=C\CCCCC)OC(=O)C(CCCCCCCCCCCC)OC(=O)OCCCN(C)C]

$^1$H NMR (400 MHz, CDCl$_3$) δ=5.27-5.46 (m, 9H), 4.89 (t, J=6.27 Hz, 1H), 4.29 (ddd, J=12.30, 8.66, 4.14 Hz, 2H), 4.09-4.25 (m, 4H), 2.77 (t, J=6.53 Hz, 4H), 2.44 (br. s., 2H), 2.23-2.37 (m, 10H), 2.05 (q, J=6.78 Hz, 8H), 1.78-1.98 (m, 4H), 1.61 (br. s., 4H), 1.23-1.50 (m, 48H), 0.83-0.96 (m, 9H). MS (M+1)=972.8, Rt=4.25 min (LC Method 4).

Example 99: (9Z,9'Z,12Z,12'Z)-2-((2-(((3-(diethylamino)propoxy)carbonyl)oxy)dodecanoyl)oxy)propane-1,3-diyl bis(octadeca-9,12-dienoate)

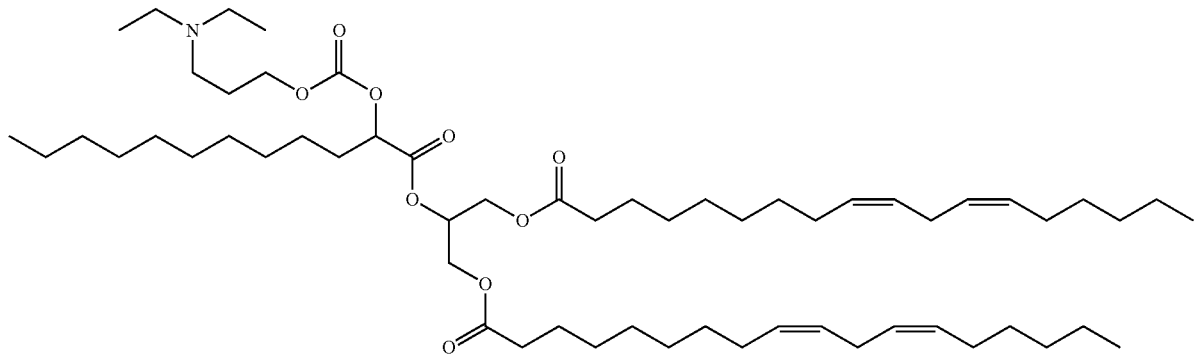 [SMILES: CCCCC/C=C\C/C=C\CCCCCCCC(=O)OCC(COC(=O)CCCCCCC/C=C\C/C=C\CCCCC)OC(=O)C(CCCCCCCCCC)OC(=O)OCCCN(CC)CC]

$^1$H NMR (400 MHz, CDCl$_3$) δ=5.27-5.46 (m, 9H), 4.89 (t, J=6.27 Hz, 1H), 4.25-4.35 (m, 2H), 4.10-4.25 (m, 4H), 2.77 (t, J=6.27 Hz, 4H), 2.57 (br. s., 6H), 2.26-2.38 (m, 4H), 2.05 (q, J=6.69 Hz, 8H), 1.78-1.96 (m, 4H), 1.61 (d, J=3.01 Hz, 4H), 1.20-1.50 (m, 44H), 1.06 (br. s., 6H), 0.82-0.95 (m, 9H). MS (M+1)=972.8, Rt=4.25 min (LC Method 4).

Example 100: 2-((2-(((3-(diethylamino)propoxy)carbonyl)oxy)tetradecanoyl)oxy)propane-1,3-diyl dioctanoate

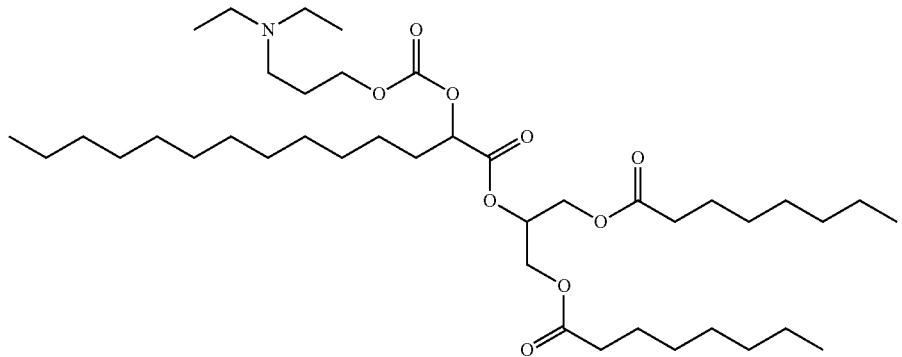 [SMILES: CCCCCCCCCCCCC(OC(=O)OCCCN(CC)CC)C(=O)OC(COC(=O)CCCCCCC)COC(=O)CCCCCCC]

$^1$H NMR (400 MHz, CDCl$_3$) δ=5.31-5.41 (m, 1H), 4.89 (t, J=6.15 Hz, 1H), 4.25-4.36 (m, 2H), 4.09-4.25 (m, 4H), 2.59 (br. s., 6H), 2.24-2.37 (m, 4H), 1.78-2.03 (m, 4H), 1.61 (d, J=3.26 Hz, 4H), 1.43 (br. s., 2H), 1.18-1.37 (m, 34H), 1.07 (br. s., 6H), 0.88 (t, J=6.65 Hz, 9H). MS (M+1)=728.5, Rt=1.37 min (LC Method 7).

Synthesis of Example 101

Intermediate 101a

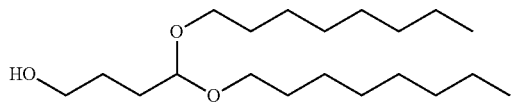 [SMILES: CCCCCCCCOC(CCCO)OCCCCCCCC]

A 1.0 M solution of DIBAL (15.4 mL, 15.4 mmol) in toluene was added to a DCM (60 mL) solution of Intermediate 11a (5 g, 15.4 mmol), cooled in a dry-ice/acetone bath. After 1.5 h, the mixture was allowed to warm to rt, and was then treated with sat. aq. ammonium chloride solution (20 mL) and water (10 mL). The reaction was extracted with DCM. The combined dichloromethane extracts were washed with brine twice, dried over MgSO$_4$ and filtered. The filtrate was concentrated under reduced pressure and the residue was dissolved in MeOH (20 mL). NaBH$_4$ (581 mg, 15.4 mmol) was added and the mixture was stirred at rt. After 1 hour, water was added to the mixture and MeOH was removed under reduced pressure. The resulting mixture was extracted with EtOAc. The organic extracts were washed with sat. aq. NaHCO$_3$, dried over Na$_2$SO$_4$ and filtered. The filtrate was concentrated under reduced pressure and the residue was purified on silica gel with 0-20% EtOAc/heptane to afford 2.46 g of the title compound. $^1$H NMR (400 MHz, DMSO-d$_6$) δ=4.35-4.45 (m, 2H), 3.47 (dt, J=9.41, 6.46 Hz, 2H), 3.28-3.40 (m, 4H), 1.35-1.57 (m, 8H), 1.24 (br. s., 20H), 0.79-0.91 (m, 6H).

Example 101: 4,4-bis(octyloxy)butyl 4-(((3-(dimethylamino)propoxy)carbonyl)oxy)hexadecanoate

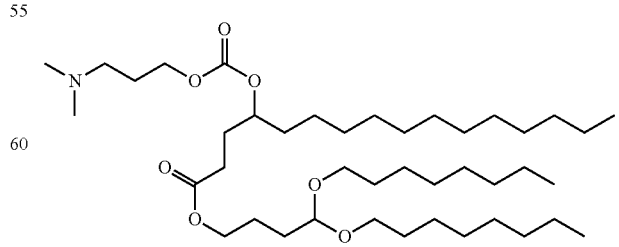

$^1$H NMR (400 MHz, CDCl$_3$) δ=4.67-4.77 (m, 1H), 4.44-4.52 (m, 1H), 4.13-4.25 (m, 2H), 4.09 (t, J=5.90 Hz, 2H), 3.56 (dt, J=9.16, 6.71 Hz, 2H), 3.41 (dt, J=9.22, 6.68 Hz,

2H), 2.30-2.47 (m, 4H), 2.25 (s, 6H), 1.81-2.04 (m, 6H), 1.49-1.75 (m, 10H), 1.21-1.40 (m, 38H), 0.82-0.96 (m, 9H). MS (M+1)=714.7, Rt=1.83 min (LC Method 7).

Example 102: 4,4-bis(octyloxy)butyl 2-(((3-(diethylamino)propoxy)carbonyl)oxy)dodecanoate

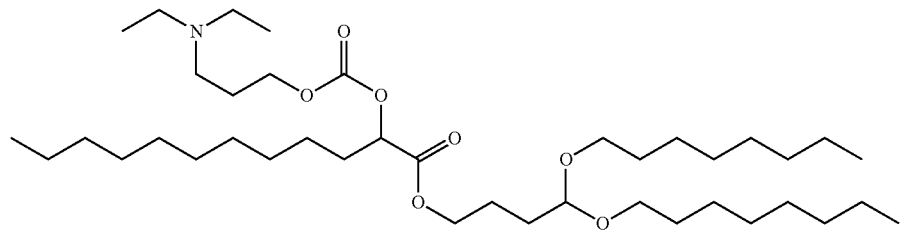 [SMILES: CCCCCCCCCCC(OC(=O)OCCCN(CC)CC)C(=O)OCCCC(OCCCCCCCC)OCCCCCCCC]

$^1$H NMR (400 MHz, CDCl$_3$) δ=4.89 (t, J=6.27 Hz, 1H), 4.47 (t, J=5.27 Hz, 1H), 4.11-4.28 (m, 4H), 3.56 (dt, J=9.03, 6.78 Hz, 2H), 3.40 (dt, J=9.22, 6.68 Hz, 2H), 2.57 (br. s., 6H), 1.79-1.98 (m, 4H), 1.62-1.77 (m, 4H), 1.56 (quin, J=6.84 Hz, 4H), 1.20-1.48 (m, 36H), 1.05 (t, J=6.27 Hz, 6H), 0.83-0.94 (m, 9H). MS (M+1)=686.6, Rt=1.57 min (LC Method 7).

Synthesis of Example 103

Intermediate 103a: 4-(((3-(diethylamino)propoxy)carbonyl)oxy)hexadecanoic acid

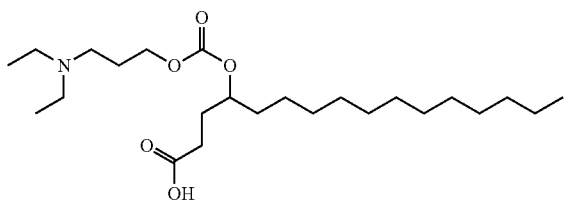 [SMILES: CCCCCCCCCCCCC(CCC(=O)O)OC(=O)OCCCN(CC)CC]

Intermediate 103a can be synthesized using methods similar to those exemplified in the synthesis of Intermediate 80c. MS (M+1)=430.2, Rt=0.73 min (LC Method 7).

Intermediate 103b: 1-(bis(2-hydroxyethyl)amino)-1-oxohexadecan-4-yl (3-(diethylamino)propyl) carbonate In a 100 ml round-bottom flask equipped with a stirbar, Intermediate 103a (465 mg, 1.082 mmol) and HATU (453 mg, 1.191 mmol) are dissolved in DCM (Volume: 20 ml). DIPEA (0.756 ml, 4.33 mmol) is added, and mixture stirred for 30 min before addition of Diethanolamine (0.311 ml, 3.25 mmol). Mixture is then stirred at rt overnite when LCMS shows product formation. The volatiles were then evaporated under pressure, and the crude material purified on silica gel with 0-20% MeOH/DCM to afford 345 mg (62%) of the title compound. LC-MS m/z=623.3 (MH+). Rt=0.43 min (LC Method 5).

Example 103: (9Z,12Z)-10-dodecyl-3-ethyl-14-(2-((9Z,12Z)-octadeca-9,12-dienoyloxy)ethyl)-8,13-dioxo-7,9-dioxa-3,14-diazahexadecan-16-yl octadeca-9,12-dienoate

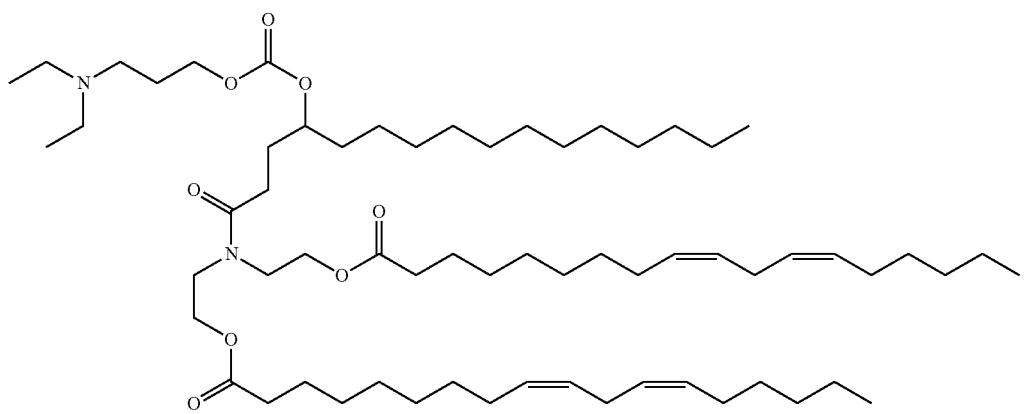 [SMILES: CCCCC/C=C\C/C=C\CCCCCCCC(=O)OCCN(CCOC(=O)CCCCCCC/C=C\C/C=C\CCCCC)C(=O)CCC(CCCCCCCCCCCC)OC(=O)OCCCN(CC)CC]

In a 500 ml round-bottom flask equipped with a stirbar, Linoleic acid (393 mg, 1.402 mmol) and Intermediate 103b (345 mg, 0.668 mmol) are dissolved in DCM (Volume: 20 ml). DIPEA (0.466 ml, 2.67 mmol) is added, followed by DMAP (32.6 mg, 0.267 mmol) and mixture stirred at rt for ~5 min before addition of EDC.HCl (282 mg, 1.469 mmol). Mixture stirred at rt overnight. The volatiles were then evaporated under reduced pressure, and the crude material purified on silica gel with (0-60% EtOAc/Heptane) to afford 389 mg (53%) of the title compound.

$^1$H NMR (400 MHz, CDCl$_3$) δ=5.46-5.27 (m, 8H), 4.82-4.66 (m, 1H), 4.30-4.08 (m, 6H), 3.68-3.52 (m, 4H), 2.78 (t, J=6.5 Hz, 4H), 2.70-2.35 (m, 8H), 2.30 (dt, J=3.3, 7.5 Hz, 4H), 2.12-1.97 (m, 9H), 1.97-1.78 (m, 3H), 1.71-1.51 (m, 8H), 1.44-1.21 (m, 46H), 1.05 (br. s., 6H), 0.95-0.82 (m, 9H). $^{13}$C NMR (100 MHz, CDCl$_3$) δ=173.6, 173.4, 172.4, 155.1, 130.2 (2C), 130.0 (2C), 128.0 (2C), 127.9 (2C), 78.3, 66.3, 62.0, 61.6, 49.0, 47.1, 46.8, 45.5 (2C), 34.3, 34.1, 34.0, 31.9, 31.5 (2C), 29.7 (2C), 29.6 (6C), 29.5 (4C), 29.3 (4C), 29.2 (2C), 29.1 (2C), 28.7, 27.2 (4C), 25.6, 25.2, 24.8 (2C), 22.7, 22.6 (2C), 14.1 (3C), 11.6 (2C) ppm.

Synthesis of Example 104

Intermediate 104a: tert-butyl 4-oxobutanoate

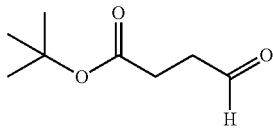

Intermediate 104a was prepared from tert-butyl 4-hydroxybutanoate in a method similar to that used for the synthesis of Intermediate 1g. $^1$H NMR (CDCl$_3$) δ=9.83 (s, 1H), 2.73-2.78 (m, 2H), 2.55-2.60 (m, 2H), 1.47 (s, 9H)

Intermediate 104b tert-butyl 4-hydroxydodec-11-enoate

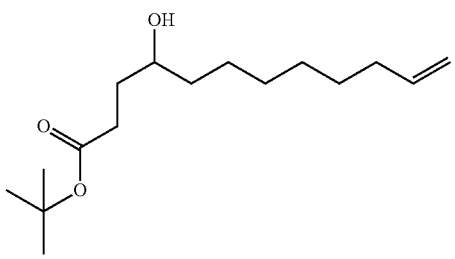 [SMILES: C=CCCCCCCC(O)CCC(=O)OC(C)(C)C]

Magnesium turnings (307 mg, 12.64 mmol) was weighed into a pre-dried flask and dried in an oven at 120° C. for 2 hours. The flask was removed from the oven, sealed, and cooled to ambient temperature. To the flask, 6 mL of anhydrous THF and one particle of iodine was added, followed by addition of 8-bromooct-1-ene (1.570 g, 8.22 mmol). A condenser was added to the flask, and the whole system was exchanged with N2 and protected under N2 ballon. The reaction was heated with a heating until the brown color from the iodine dissipated. The reaction was heated at reflux until most of magnesium was consumed (about 1.5 hr), then cooled to room temperature.

To a solution of Intermediate 104a (1.0 g, 6.32 mmol) in 25 ml THF cooled in a dry-ice acetone bath, the freshly prepared Grignard reagent was added dropwise. The reaction was stirred for 1 h, then warmed to ambient temperature. The reaction was quenched with sat. aq. NaHCO$_3$, and extracted with ethyl acetate. The combined organics were dried over sodium sulfate and filtered. The filtrate was concentrated under reduced pressure and purified on silica gel with 10% ethyl acetate/heptane to afford the desired product (890 mg, 60%). $^1$H NMR (400 MHz, CDCl$_3$) δ=5.61-5.85 (m, 1H), 4.80-4.98 (m, 2H), 3.48-3.62 (m, 1H), 2.26-2.36 (t, J=7.5 Hz, 2H), 1.50-1.78 (m, 4H), 1.35-1.44 (m, 19H).

Intermediate 104c: tert-butyl 4-hydroxy-11-oxoundecanoate

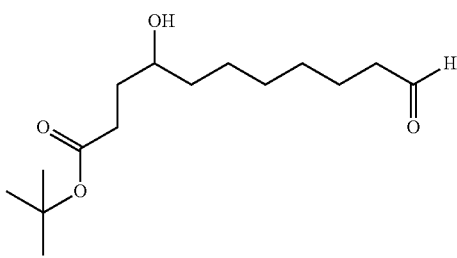 [SMILES: CC(C)(C)OC(=O)CCC(O)CCCCCCC=O]

To a solution of Intermediate 104b (300 mg, 0.78 mmol) in 8 ml dioxane/H2O (3:1), 2, 6-lutidine (0.36 ml, 3.11 mmol) was added, followed by OsO$_4$ (0.243 ml 2.5 wt. % in t-butanol, 0.02 mmol), and NaIO$_4$ (664 mg, 3.11 mmol). The slurry was stirred for 1.5 h at room temperature. The reaction was filtered through celite with ethyl acetate washes. The filtrate was then washed with brine, dried over sodium sulfate and filtered. The filtrate was concentrated under reduced pressure and purified on silica gel with 25% ethyl acetate/heptane to afford the desired product (150 mg, 71%). $^1$H NMR (400 MHz, CDCl$_3$) δ=9.76 (t, J=1.8 Hz, 1H), 3.51-3.72 (m, 1H), 2.43 (td, J=7.3, 1.9 Hz, 2H), 2.37 (t, J=7.2 Hz, 2H), 1.77 (s, 1H), 1.58-1.71 (m, 3H), 1.45 (s, 13H), 1.33 (m, 4H).

Intermediate 104d: tert-butyl 4,11-dihydroxyundecanoate

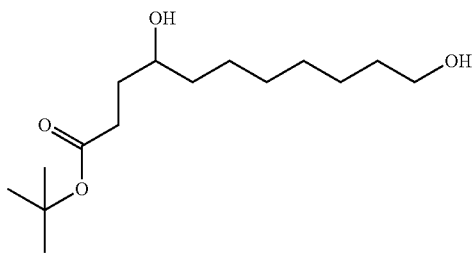 [SMILES: CC(C)(C)OC(=O)CCC(O)CCCCCCCO]

Intermediate 104c (140 mg, 0.51 mmol) was dissolved in 6 ml THF/MeOH (1:1) and cooled in an ice-water bath. NaBH$_4$ (29.2 mg, 0.77 mmol) was added and the mixture was stirred for 30 min. The reaction was warmed to ambient temperature then diluted with brine and ethyl acetate. The organic extracts were dried over sodium sulfate and filtered.

The filtrate was concentrated under reduced pressure to provide the title compound, which was used in the next step without further purification. ¹H NMR (400 MHz, CDCl₃) δ=3.57 (t, J=6.6 Hz, 3H), 2.30 (t, J=7.2 Hz, 2H), 1.45-1.77 (m, 7H), 1.33-1.42 (m, 14H), 1.22-130 (m, 4H).

Intermediate 104e: tert-butyl 4-hydroxy-11-(octanoyloxy)undecanoate

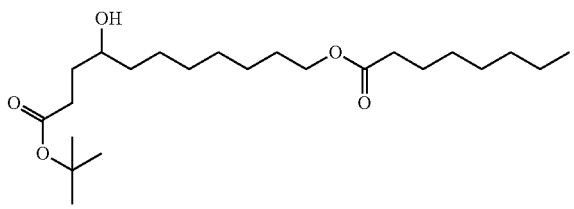 [SMILES: CCCCCCCC(=O)OCCCCCCCC(O)CCC(=O)OC(C)(C)C]

To a solution of Intermediate 104d (130 mg, 0.47 mmol) in 4.0 ml DCM, were added octanoic acid (75 mg, 0.52 mmol), DMAP (17.4 mg. 0.14 mmol), DIPEA (0.083 ml, 0.47 mmol), followed by EDC (118 mg, 0.62 mmol). The reaction was stirred at room temperature for 2 h. The reaction was diluted with brine and ethyl acetate. The organic extracts were dried over sodium sulfate and filtered. The filtrate was concentrated under reduced pressure and the residue was purified on silica gel with 10% ethylacetate/heptane to afford the desired product (110 mg, 58%). ¹H NMR (400 MHz, CDCl₃) δ=4.07 (t, J=6.7 Hz, 2H), 3.56-3.68 (m, 1H), 2.38 (t, J=7.3 Hz, 2H), 2.30 (t, J=7.6 Hz, 2H), 1.85 (m., 2H), 1.55-1.74 (m, 5H), 1.46 (m, 12H), 1.23-1.41 (m, 15H), 0.82-0.96 (m, 3H).

Intermediate 104f: tert-butyl 4-(((3-(diethylamino)propoxy)carbonyl)oxy)-11-(octanoyloxy)undecanoate

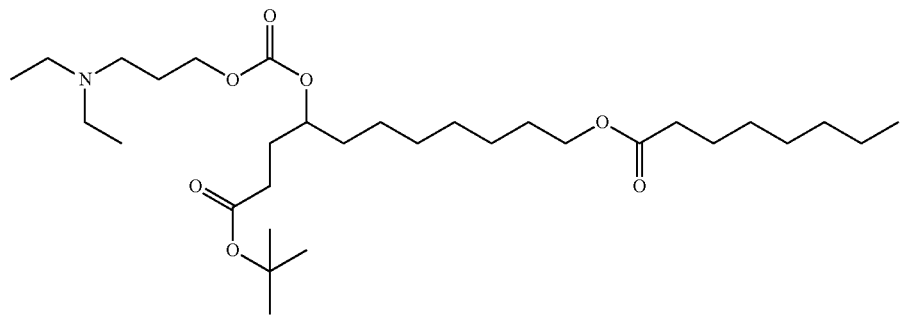 [SMILES: CCCCCCCC(=O)OCCCCCCCC(CCC(=O)OC(C)(C)C)OC(=O)OCCCN(CC)CC]

To a solution of Intermediate 104e (110 mg, 0.28 mmol) in 3.0 ml DCM, cooled in an ice-water bath, pyridine (0.033 ml, 0.41 mmol) was added, followed by triphosgene (40.7 mg, 0.14 mmol). After 30 min., 3-(diethylamino)-1-propanol (0.126 ml, 0.824 mmol) was added. The resulted mixture was stirred at room temperature for 1 h. The reaction was concentrated under reduced pressure, and the residue was purified on silica gel with 5% MeOH/DCM to afford the desired product (110 mg, 72%). ¹H NMR (400 MHz, CDCl₃) δ=4.64-4.88 (m, 1H), 4.24 (t, J=6.8 Hz, 2H), 4.06 (t, J=6.8 Hz, 2H), 3.10 (br. s., 6H), 2.18-2.43 (m, 6H), 1.76-2.00 (m, 2H), 1.50-1.72 (m, 6H), 1.46 (s, 9H), 1.22-1.45 (m, 22H), 0.86-0.94 (m, 3H).

Intermediate 104g: 4-(((3-(diethylamino)propoxy)carbonyl)oxy)-11-(octanoyloxy)undecanoic acid

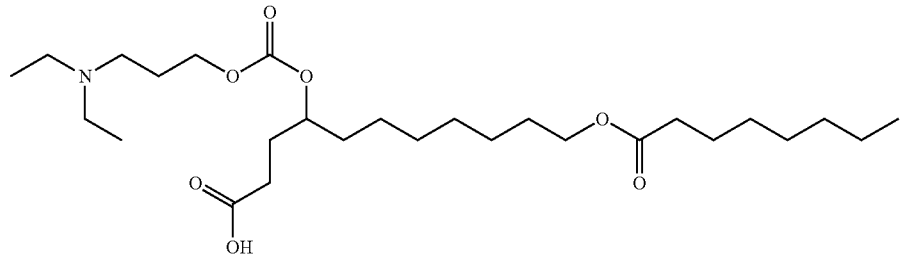 [SMILES: CCCCCCCC(=O)OCCCCCCCC(CCC(=O)O)OC(=O)OCCCN(CC)CC]

To a solution of Intermediate 104f (110 mg, 0.2 mmol) in 2.4 ml DCM, 0.6 ml TFA was added. The resulted mixture stirred at room temperature for 2 h. The reaction was dried under reduced pressure to provide the title compound, which was used in the next step without further purification. $^1$H NMR (400 MHz, CDCl$_3$) δ=10.13-10.42 (br, s, 1H), 5.75 (br. s., 6H), 4.71-4.95 (m, 1H), 4.32-4.60 (m, 1H), 4.07 (t, J=6.8 Hz, 3H), 3.08-3.52 (m, 6H), 2.47-2.64 (m, 1H), 2.37-2.47 (m, 1H), 2.32 (t, J=7.5 Hz, 2H), 2.10 (br. s., 3H), 1.85-2.02 (m, 1H), 1.19-1.44 (m, 22H), 0.80-0.99 (m, 3H).

Example 104: 2-((4-(((3-(diethylamino)propoxy)carbonyl)oxy)-11-(octanoyloxy)undecanoyl)oxy)propane-1,3-diyl dioctanoate

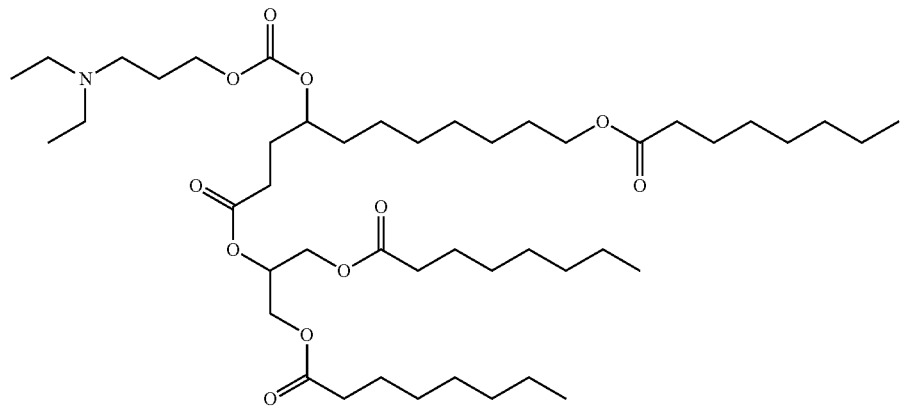 [SMILES: CCCCCCCC(=O)OCCCCCCCC(CCC(=O)OC(COC(=O)CCCCCCC)COC(=O)CCCCCCC)OC(=O)OCCCN(CC)CC]

$^1$H NMR (400 MHz, CDCl$_3$) δ=5.20-5.32 (m, 1H), 4.66-4.79 (m, 1H), 4.29 (dd, J=11.8, 4.3 Hz, 2H), 4.09-4.23 (m, 4H), 4.04 (t, J=6.7 Hz, 2H), 2.48-2.58 (m, 6H), 2.36-2.48 (m, 2H), 2.24-2.36 (m, 6H), 1.76-2.02 (m, 4H), 1.47-1.69 (m, 10H), 1.17-1.41 (m, 32H), 1.02 (t, J=7.2 Hz, 6H), 0.81-0.92 (m, 9H). MS (M+1)=828.61, Rt=0.89 min. (LC Method 6).

Synthesis of Example 105

Intermediate 105a: (9Z,9'Z,12Z,12'Z)-2-(hydroxymethyl)propane-1,3-diyl bis(octadeca-9,12-dienoate)

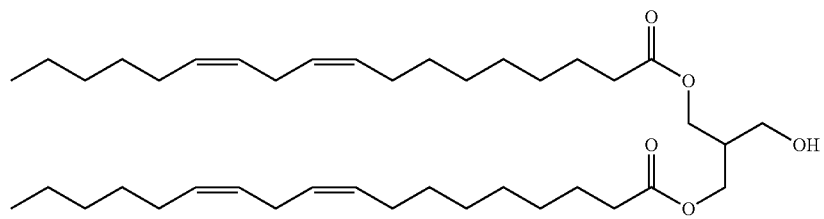 [SMILES: CCCCC/C=C\C/C=C\CCCCCCCC(=O)OCC(CO)COC(=O)CCCCCCC/C=C\C/C=C\CCCCC]

In a round bottom flask, linoleic acid (95.0 g, 339 mmol), DMAP (4.14 g, 33.90 mmol), DIPEA (74.1 ml, 424 mmol), and 2-(hydroxymethyl)propane-1,3-diol (18.0 g, 170 mmol) were taken into dichloromethane (435 ml). EDC (81.0 g, 424 mmol) was added in one portion, and the reaction was stirred at ambient temperature. After 24 h, the reaction is concentrated under reduced pressure with silica gel powder for dry loading and the residue was purified on silica gel (Biotage) using ethyl acetate/heptane (0% to 40%) as eluent, to provide 47 g (44% yield) of the desired product as a colorless oil. $^1$H NMR (400 MHz, CDCl$_3$): δ=5.19-5.50 (m, 8H), 4.19 (tt, J=11.83, 5.87 Hz, 4H), 3.51-3.69 (m, 2H), 2.78 (t, J=6.53 Hz, 4H), 2.33 (t, J=7.53 Hz, 4H), 2.20 (quint, J=5.83 Hz, 2H), 2.06 (q, J=6.78 Hz, 8H), 1.49-1.72 (m, 5H), 1.20-1.46 (m, 26H), 0.79-0.98 (m, 6H) ppm.

Example 105: (9Z,9'Z,12Z,12'Z)-2-(9-dodecyl-2-methyl-7,12-dioxo-6,8,13-trioxa-2-azatetradecan-14-yl)propane-1,3-diyl bis(octadeca-9,12-dienoate)

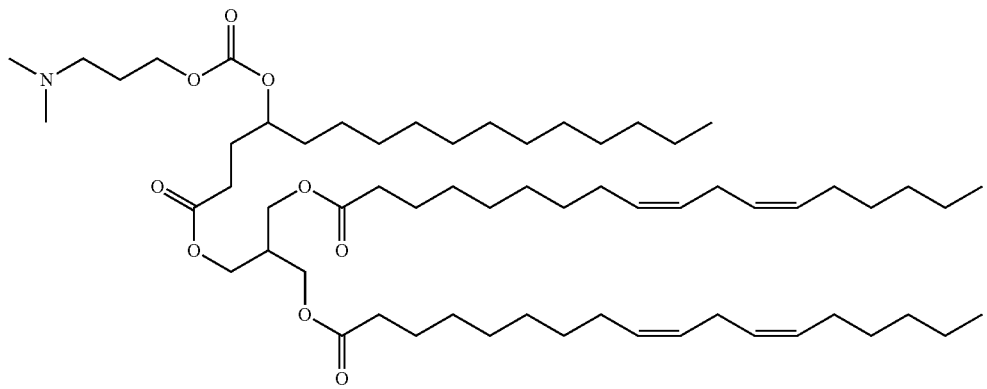 [SMILES: CCCCC/C=C\C/C=C\CCCCCCCC(=O)OCC(COC(=O)CCCCCCC/C=C\C/C=C\CCCCC)COC(=O)CCC(CCCCCCCCCCCC)OC(=O)OCCCN(C)C]

Example 105 can be prepared using similar methods to those used to synthesize Example 80. 1H NMR (400 MHz, CDCl$_3$): δ=5.55-5.18 (m, 8H), 4.71 (dq, J=6.9, 2.7 Hz, 1H), 4.33-4.01 (m, 8H), 2.77 (t, J=6.5 Hz, 4H), 2.60-2.17 (m, 15H), 2.17-1.76 (m, 12H), 1.75-1.46 (m, 7H), 1.45-1.16 (m, 47H), 0.88 (td, J=6.8, 3.9 Hz, 9H). MS (M+1): 1015.3, Rt=1.28 min (LC Method XX)

The following example can be prepared using similar sequences and methods to those employed for the synthesis of Example 11.

Example 106

3-(((3-(dimethylamino)propoxy)carbonyl)oxy)pentadecyl 4,4-bis(octyloxy)butanoate

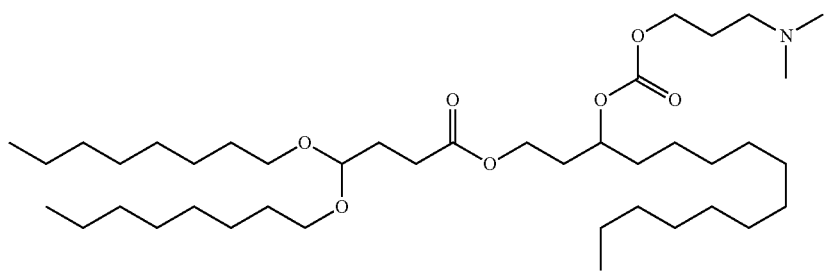 [SMILES: CCCCCCCCCCCCC(CCOC(=O)CCC(OCCCCCCCC)OCCCCCCCC)OC(=O)OCCCN(C)C]

$^1$H NMR (400 MHz, CD$_2$Cl$_2$) δ=4.72-4.82 (m, 1H), 4.45 (t, J=5.56 Hz, 1H), 4.03-4.19 (m, 4H), 3.54 (dt, J=9.23, 6.63 Hz, 2H), 3.38 (dt, J=9.20, 6.65 Hz, 2H), 2.26-2.39 (m, 4H), 2.19 (s, 6H), 1.75-1.93 (m, 6H), 1.45-1.69 (m, 8H), 1.21-1.38 (m, 38H), 0.82-0.93 (m, 9H) ppm. MS (M+1)=701.1, Rt=1.12 min (LC method 12).

The following examples can be prepared using similar sequences and methods to those employed for the synthesis of Example 16.

Example 107

3-(((3-(piperidin-1-yl)propoxy)carbonyl)oxy)penta-
decyl 6,6-bis(octyloxy)hexanoate

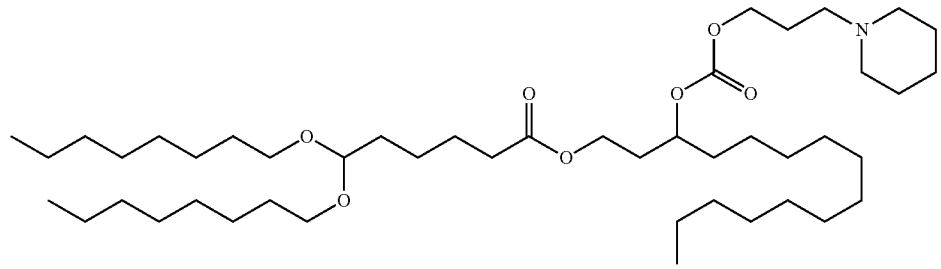 [SMILES: CCCCCCCCCCCCC(CCOC(=O)CCCCC(OCCCCCCCC)OCCCCCCCC)OC(=O)OCCCN1CCCCC1]

$^1$H NMR (400 MHz, CD$_2$Cl$_2$) δ=4.77 (quin, J=6.24 Hz, 1H), 4.41 (t, J=5.69 Hz, 1H), 4.05-4.18 (m, 4H), 3.53 (dt, J=9.29, 6.66 Hz, 2H), 3.37 (dt, J=9.29, 6.66 Hz, 2H), 2.23-2.40 (m, 8H), 1.89 (q, J=6.36 Hz, 2H), 1.80 (quin, J=6.88 Hz, 2H), 1.46-1.66 (m, 14H), 1.16-1.45 (m, 44H), 0.83-0.93 (m, 9H) ppm.

MS (M+1)=768.8, Rt=2.60 min (LC method 13).

Example 108

3-(((3-(piperazin-1-yl)propoxy)carbonyl)oxy)penta-
decyl 6,6-bis(octyloxy)hexanoate

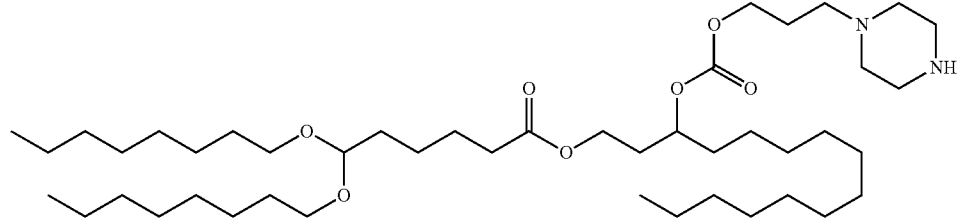 [SMILES: CCCCCCCCCCCCC(CCOC(=O)CCCCC(OCCCCCCCC)OCCCCCCCC)OC(=O)OCCCN1CCNCC1]

$^1$H NMR (400 MHz, CD$_2$Cl$_2$) δ=4.77 (quin, J=6.24 Hz, 1H), 4.41 (t, J=5.62 Hz, 1H), 4.05-4.18 (m, 4H), 3.53 (dt, J=9.29, 6.66 Hz, 2H), 3.37 (dt, J=9.35, 6.63 Hz, 2H), 2.86 (t, J=4.83 Hz, 4H), 2.34-2.64 (m, 7H), 2.29 (t, J=7.52 Hz, 2H), 1.90 (m, J=6.44, 6.44, 6.44 Hz, 2H), 1.81 (quin, J=6.91 Hz, 2H), 1.47-1.66 (m, 10H), 1.21-1.41 (m, 42H), 0.83-0.93 (m, 9H) ppm.

MS (M+1)=770.2, Rt=1.18 min (LC method 14).

Example 109

3-(((4-(diethylamino)butoxy)carbonyl)oxy)pentade-
cyl 6,6-bis(octyloxy)hexanoate

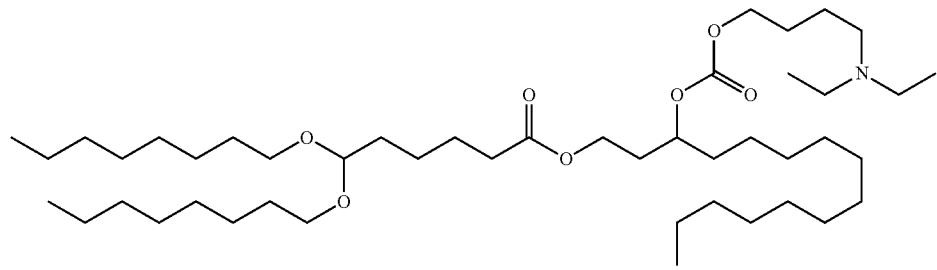 [SMILES: CCCCCCCCCCCCC(CCOC(=O)CCCCC(OCCCCCCCC)OCCCCCCCC)OC(=O)OCCCCN(CC)CC]

¹H NMR (400 MHz, CD₂Cl₂) δ=4.77 (quin, J=6.24 Hz, 1H), 4.41 (t, J=5.62 Hz, 1H), 4.02-4.20 (m, 4H), 3.53 (dt, J=9.29, 6.66 Hz, 2H), 3.37 (dt, J=9.29, 6.66 Hz, 2H), 2.35-2.56 (m, 6H), 2.28 (t, J=7.52 Hz, 2H), 1.90 (q, J=6.40 Hz, 2H), 1.42-1.73 (m, 14H) 1.21-1.40 (m, 42H) 0.98 (t, J=7.09 Hz, 6H) 0.84-0.92 (m, 9H) ppm.

MS (M+1)=771.2, Rt=2.82 min (LC method 13).

Example 110

3-(((3-(4-methylpiperazin-1-yl)propoxy)carbonyl)oxy)pentadecyl 6,6-bis(octyloxy)hexanoate

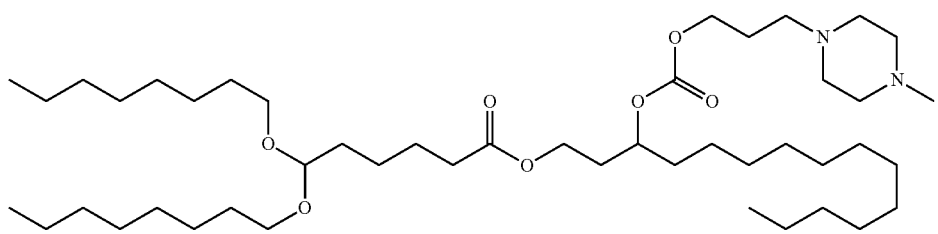 [SMILES: CCCCCCCCCCCCC(CCOC(=O)CCCCC(OCCCCCCCC)OCCCCCCCC)OC(=O)OCCCN1CCN(C)CC1]

¹H NMR (400 MHz, CD₂Cl₂) δ=4.77 (quin, J=6.24 Hz, 1H), 4.41 (t, J=5.62 Hz, 1H), 4.04-4.19 (m, 4H), 3.53 (dt, J=9.29, 6.66 Hz, 2H), 3.37 (dt, J=9.35, 6.63 Hz, 2H), 2.24-2.55 (m, 12H), 2.22 (s, 3H), 1.89 (q, J=6.36 Hz, 2H) 1.80 (quin, J=6.91 Hz, 2H), 1.48-1.66 (m, 10H), 1.19-1.42 (m, 42H), 0.81-0.95 (m, 9H) ppm.

MS (M+1)=784.2, Rt=2.64 min (LC method 13).

Example 111

3-((((1-methylpiperidin-4-yl)methoxy)carbonyl)oxy)pentadecyl 6,6-bis(octyloxy)hexanoate

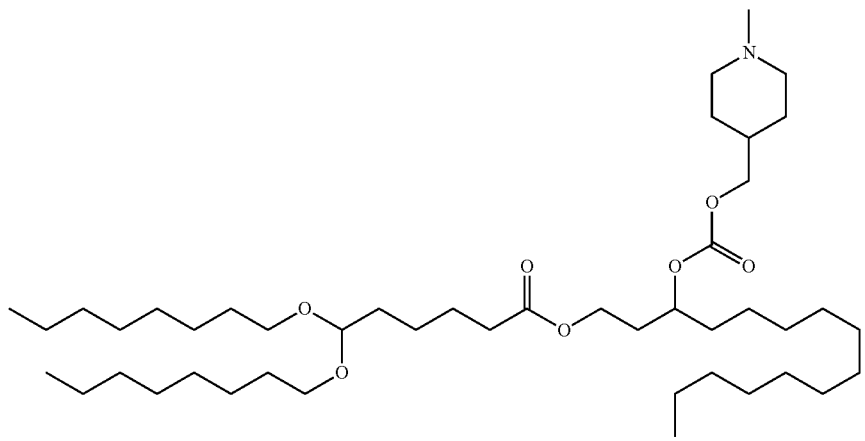 [SMILES: CCCCCCCCCCCCC(CCOC(=O)CCCCC(OCCCCCCCC)OCCCCCCCC)OC(=O)OCC1CCN(C)CC1]

¹H NMR (400 MHz, ACETONITRILE-d₃): δ=4.76 (quin, J=6.27 Hz, 1H), 4.41 (t, J=5.62 Hz, 1H), 4.07 (t, J=6.30 Hz, 2H), 4.01-3.88 (m, 2H), 3.52 (dt, J=9.38, 6.56 Hz, 2H), 3.43-3.33 (m, 2H), 2.82-2.72 (m, 2H), 2.26 (t, J=7.34 Hz, 3H), 1.90-1.80 (m, 2H) 2.16 (s, 3H), 1.68-1.46 (m, 12H), 1.38-1.20 (m, 46H), 0.88 (t, J=6.54 Hz, 9H) ppm.

MS (M+1)=755, Rt=1.20 min (LC method 12).

Example 112

3-(((3-morpholinopropoxy)carbonyl)oxy)pentadecyl 6,6-bis(octyloxy)hexanoate

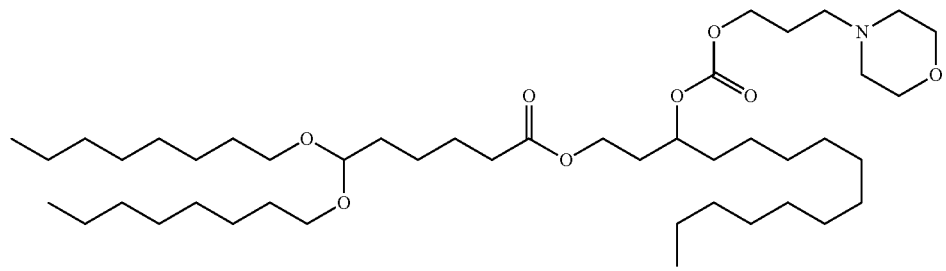 [SMILES: CCCCCCCCCCCCC(CCOC(=O)CCCCC(OCCCCCCCC)OCCCCCCCC)OC(=O)OCCCN1CCOCC1]

¹H NMR (400 MHz, CDCl₃) δ=4.85-4.76 (m, 1H), 4.45 (t, J=5.69 Hz, 1H), 4.26-4.04 (m, 4H), 3.75 (br. s., 4H), 3.56 (dt, J=9.26, 6.68 Hz, 2H), 3.40 (dt, J=9.29, 6.72 Hz, 2H), 2.54-2.39 (m, 4H), 2.35-2.26 (m, 2H), 1.96-1.88 (m, 2H), 1.70-1.51 (m, 12H), 1.37-1.22 (m, 44H), 0.93-0.85 (m, 9H) ppm.

MS (M+1)=771, Rt=1.34 min (LC method 12).

Example 113

3-(((2-(diethylamino)ethoxy)carbonyl)oxy)pentadecyl 6,6-bis(octyloxy)hexanoate

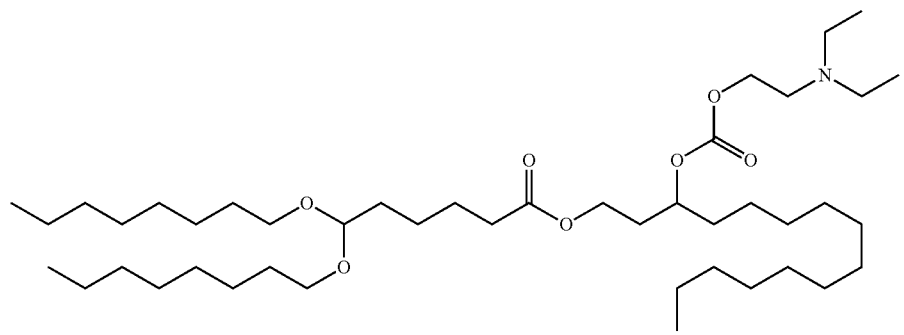 [SMILES: CCCCCCCCCCCCC(CCOC(=O)CCCCC(OCCCCCCCC)OCCCCCCCC)OC(=O)OCCN(CC)CC]

¹H NMR (400 MHz, CDCl₃) δ=4.86-4.75 (m, 1H), 4.46 (t, J=5.69 Hz, 1H), 4.37-4.23 (m, 1H), 4.21-4.06 (m, 2H), 3.56 (dt, J=9.29, 6.66 Hz, 2H), 3.40 (dt, J=9.29, 6.72 Hz, 2H), 2.31 (t, J=7.58 Hz, 2H), 1.97-1.87 (m, 2H), 1.72-1.49 (m, 12H), 1.44-1.05 (m, 53H), 0.93-0.85 (m, 9H) ppm.

MS (M+1)=743, Rt=0.86 min (LC method 12).

Synthesis of example 114

The following examples can be prepared using similar sequences and methods to those employed for the synthesis of example 16, coupling with intermediate 114a, derived from 2-propyl penanol.

Intermediate 114a:
6,6-bis((2-propylpentyl)oxy)hexanoic acid

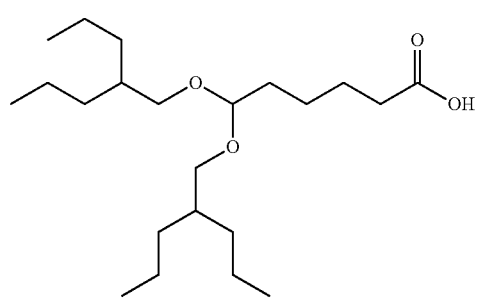 [SMILES: CCCC(CCC)COC(CCCCC(=O)O)OCC(CCC)CCC]

TLC (silica gel, 10% MeOH/DCM, PMA stain): R_f=0.14.

Example 114

3-(((3-(diethylamino)propoxy)carbonyl)oxy)penta-
decyl 6,6-bis((2-propylpentyl)oxy)hexanoate

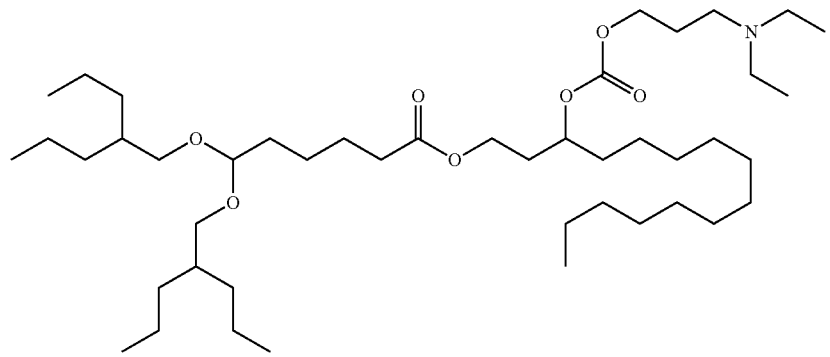 [SMILES: CCCCCCCCCCCCC(CCOC(=O)CCCCC(OCC(CCC)CCC)OCC(CCC)CCC)OC(=O)OCCCN(CC)CC]

$^1$H NMR (400 MHz, CD$_2$Cl$_2$) δ=4.77 (quin, J=6.27 Hz, 1H), 4.37 (t, J=5.62 Hz, 1H), 4.02-4.19 (m, 4H), 3.44 (dd, J=9.23, 5.69 Hz, 2H), 3.25 (dd, J=9.23, 5.69 Hz, 2H), 2.48 (q, J=7.09 Hz, 6H), 2.28 (t, J=7.58 Hz, 2H), 1.89 (q, J=6.40 Hz, 2H), 1.76 (t, J=6.85 Hz, 2H), 1.47-1.66 (m, 8H), 1.16-1.41 (m, 38H), 0.98 (t, J=7.09 Hz, 6H), 0.85-0.92 (m, 15H) ppm.

MS (M+1)=757.2, Rt=2.62 min (LC method 13).

Example 115

3-(((3-(dimethylamino)propoxy)carbonyl)oxy)penta-
decyl 6,6-bis((2-propylpentyl)oxy)hexanoate

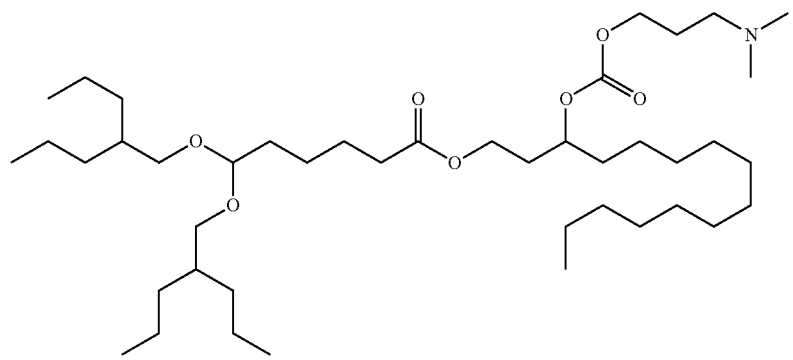 [SMILES: CCCCCCCCCCCCC(CCOC(=O)CCCCC(OCC(CCC)CCC)OCC(CCC)CCC)OC(=O)OCCCN(C)C]

$^1$H NMR (400 MHz, ACETONITRILE-d$_3$) δ=4.80-4.71 (m, 1H), 4.38 (t, J=5.62 Hz, 1H), 4.17-4.02 (m, 4H), 3.45 (dd, J=9.29, 5.62 Hz, 2H), 3.27 (dd, J=9.29, 5.62 Hz, 2H), 2.27 (td, J=7.21, 4.65 Hz, 4H), 2.14 (s, 6H), 1.90-1.82 (m, 2H), 1.76 (quin, J=6.85 Hz, 2H), 1.64-1.47 (m, 8H), 1.40-1.19 (m, 38H), 0.88 (t, J=7.03 Hz, 15H) ppm.

MS (M+1)=729, Rt=1.16 min (LC method 14).

Synthesis of Example 116

The following example can be prepared using similar sequences and methods to those employed for the synthesis of example 16, but with coupling partner intermediate 116a, derived from 3-ethyl-1-pentanol.

Intermediate 116a: 6,6-bis((3-ethylpentyl)oxy)hexanoic acid

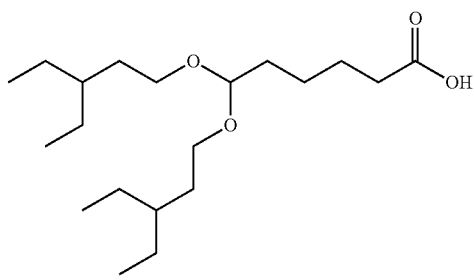 [SMILES: CCC(CC)CCOC(CCCCC(=O)O)OCCC(CC)CC]

TLC (silica gel, 10% MeOH/DCM, PMA stain): R$_f$=0.17.

Example 116

3-(((3-(dimethylamino)propoxy)carbonyl)oxy)pentadecyl 6,6-bis((3-ethylpentyl)oxy)hexanoate

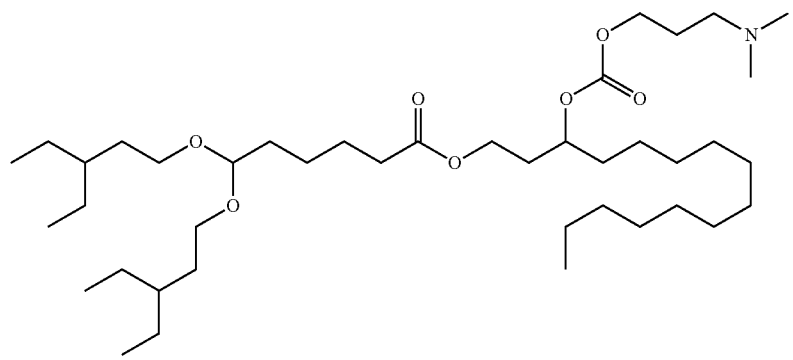 [SMILES: CCCCCCCCCCCCC(CCOC(=O)CCCCC(OCCC(CC)CC)OCCC(CC)CC)OC(=O)OCCCN(C)C]

$^1$H NMR (400 MHz, CD$_2$Cl$_2$) δ: 4.82-4.72 (m, 1H), 4.41 (t, J=5.6 Hz, 1H), 4.19-4.03 (m, 4H), 3.56 (dt, J=9.3, 7.1 Hz, 2H), 3.40 (dt, J=9.3, 7.1 Hz, 2H), 2.30 (dt, J=10.3, 7.4 Hz, 4H), 2.18 (s, 6H), 1.90 (q, J=6.4 Hz, 2H), 1.84-1.74 (m, 2H), 1.67-1.53 (m, 6H), 1.53-1.45 (m, 4H), 1.41-1.19 (m, 32H), 0.91-0.79 (m, 15H).

MS (M+1)=700.6, Rt=2.34 min (LC method 13).

The following examples can be prepared using similar sequences and methods to those employed for the synthesis of Examples 16.

Intermediate 117a: (2R)-1-((tert-butyldimethylsilyl)oxy)pentadecan-3-yl 1-methylpyrrolidine-2-carboxylate

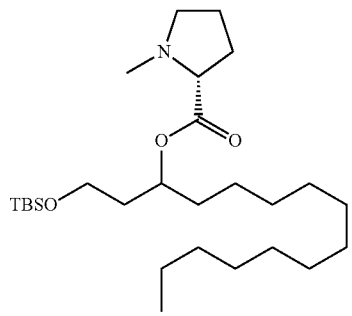 [SMILES: CCCCCCCCCCCCC(CCO[Si](C)(C)C(C)(C)C)OC(=O)[C@H]1CCCN1C]

Intermediate 1h (1.0 g, 2.79 mmol) was dissolved in DMF (30 mL). N-methyl-D-proline (0.54 g, 4.18 mmol), HATU (2.1 g, 5.58 mmol), and DIPEA (2.9 mL, 16.73 mL) were added, followed by DMAP (0.34 g, 2.79 mmol) and the mixture was stirred for 18 h at room temperature. The mixture was diluted with water (200 mL), and extracted with EtOAc (2×100 mL). The organic layers were combined, washed with brine (100 mL), dried over sodium sulfate, and concentrated to obtain a pale green oil. The crude mixture was purified by flash column chromatography over neutral alumina, eluting with 8% EtOAc/n-hexanes, to give 1.0 g of the desired product.

TLC (silica gel, 10% MeOH/DCM, PMA stain): R$_f$=0.46.

Intermediate 117b: (2R)-1-hydroxypentadecan-3-yl 1-methylpyrrolidine-2-carboxylate

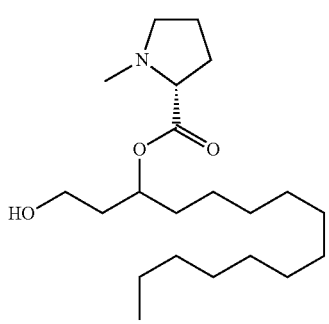 [SMILES: CCCCCCCCCCCCC(CCO)OC(=O)[C@H]1CCCN1C]

Intermediate 117a (0.60 g, 1.27 mmol) was dissolved in THF (50 mL) and the mixture was cooled to 0° C. HF.pyridne (4.5 mL of a 70% solution) was added dropwise, and the mixture was stirred for 1 h at 0° C. The mixture was then diluted with water (30 mL), and neutralized with solid NaHCO$_3$. This mixture was extracted with DCM (2×50 mL), and the organic layers were combined, washed with brine (100 mL), dried over sodium sulfate, and concentrated. The crude mixture was used in the next step without further purification.

TLC (silica gel, 10% MeOH/DCM, PMA stain): R$_f$=0.28.

The following examples can be prepared using similar methods to those employed for the synthesis of Examples 16, employing alcohols similar to intermediate 117b.

Example 117

(2R)-1-((6,6-bis(octyloxy)hexanoyl)oxy)pentadecan-3-yl 1-methylpyrrolidine-2-carboxylate

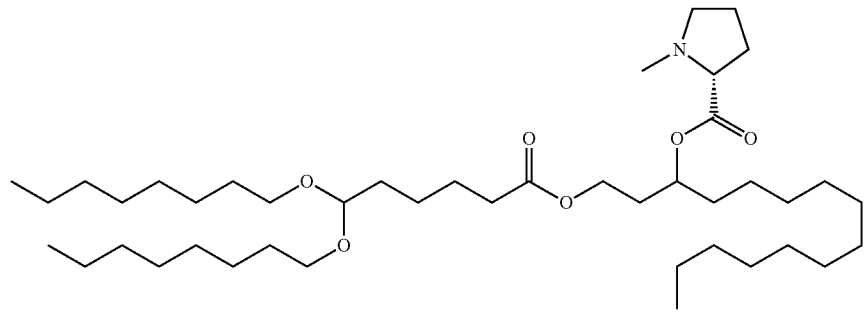 [SMILES: CCCCCCCCCCCCC(CCOC(=O)CCCCC(OCCCCCCCC)OCCCCCCCC)OC(=O)[C@H]1CCCN1C]

$^1$H NMR (400 MHz, CD$_2$Cl$_2$) δ: 5.04-4.94 (m, 1H), 4.41 (t, J=5.7 Hz, 1H), 4.13-3.99 (m, 2H), 3.53 (dt, J=9.3, 6.7 Hz, 2H), 3.37 (dt, J=9.3, 6.7 Hz, 2H), 3.11-3.00 (m, 1H), 2.96-2.85 (m, 1H), 2.35 (s, 3H), 2.32-2.23 (m, 3H), 2.17-2.01 (m, 1H), 1.96-1.68 (m, 5H), 1.66-1.47 (m, 10H), 1.40-1.20 (m, 42H), 0.93-0.83 (m, 9H).

MS (M+1)=710.7, Rt=2.70 min (LC method 13).

Example 118

(2S)-1-((6,6-bis(octyloxy)hexanoyl)oxy)pentadecan-3-yl 1-methylpyrrolidine-2-carboxylate

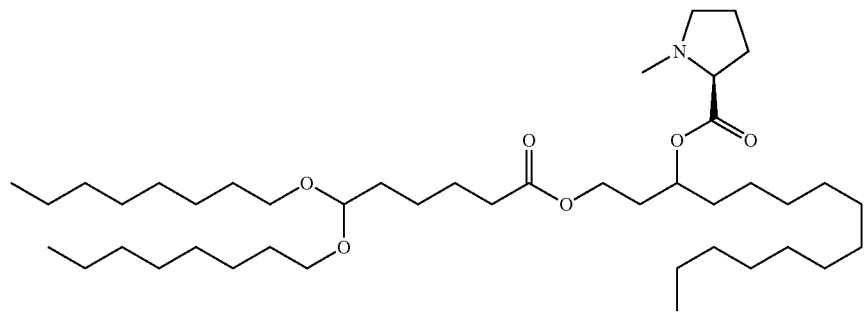 [SMILES: CCCCCCCCCCCCC(CCOC(=O)CCCCC(OCCCCCCCC)OCCCCCCCC)OC(=O)[C@@H]1CCCN1C]

$^1$H NMR (400 MHz, CD$_2$Cl$_2$) δ: 5.04-4.95 (m, 1H), 4.41 (t, J=5.6 Hz, 1H), 4.12-3.99 (m, 2H), 3.53 (dt, J=9.3, 6.7 Hz, 2H), 3.37 (dt, J=9.3, 6.7 Hz, 2H), 3.12-3.02 (m, 1H), 2.93 (br s, 1H), 2.36 (s, 3H), 2.33-2.23 (m, 3H), 2.18-2.02 (m, 1H), 1.96-1.81 (m, 4H), 1.82-1.71 (m, 1H), 1.66-1.47 (m, 11H), 1.40-1.20 (m, 41H), 0.93-0.83 (m, 9H).

MS (M+1)=711.1, Rt=2.77 min (LC method 13).

Example 119

(2R)-1-((6,6-bis(octyloxy)hexanoyl)oxy)pentadecan-3-yl pyrrolidine-2-carboxylate

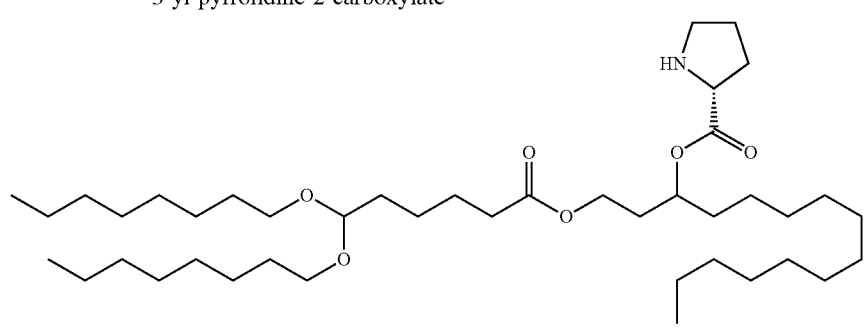

$^1$H NMR (400 MHz, CD$_2$Cl$_2$) δ: 5.03-4.91 (m, 1H), 4.41 (t, J=5.6 Hz, 1H), 4.13-4.00 (m, 2H), 3.77-3.69 (m, 1H), 3.53 (dt, J=9.3, 6.7 Hz, 2H), 3.37 (dt, J=9.3, 6.7 Hz, 2H), 3.10-3.00 (m, 1H), 2.94-2.83 (m, 1H), 2.76-2.34 (br s, 1H), 2.28 (t, J=7.5 Hz, 2H), 2.17-2.05 (m, 1H), 1.97-1.66 (m, 5H), 1.66-1.47 (m, 10H), 1.40-1.18 (m, 42H), 0.94-0.82 (m, 9H).

MS (M+2)=697.3, Rt=2.58 min (LC method 13).

Example 120

1-((6,6-bis(octyloxy)hexanoyl)oxy)pentadecan-3-yl 1,3-dimethylpyrrolidine-3-carboxylate

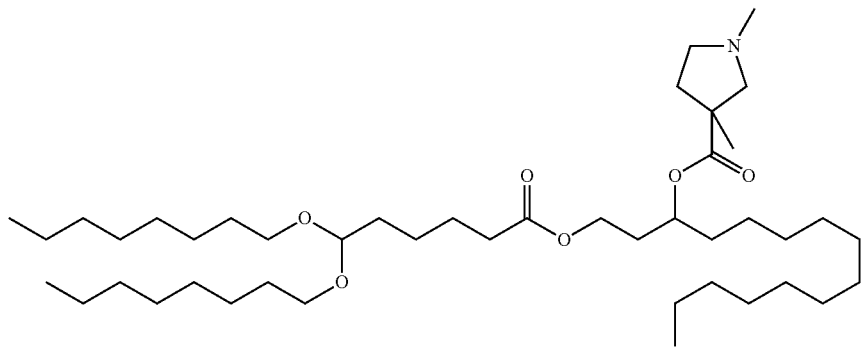 [SMILES: CCCCCCCCCCCCC(CCOC(=O)CCCCC(OCCCCCCCC)OCCCCCCCC)OC(=O)C1(C)CCN(C)C1]

$^1$H NMR (400 MHz, CDCl$_3$): δ=4.98 (m, 1H), 4.42 (t, J=8 Hz, 1H), 4.10 (q, J=8 Hz, 2H), 3.48 (q, J=8 Hz, 2H), 3.40 (q, J=4 Hz, 2H), 2.88 (d, J=8 Hz, 1H), 2.68-2.62 (m, 1H), 2.58-2.45 (m, 3H), 2.34-2.24 (m, 4H), 1.96-1.82 (m, 2H), 1.52 (m, 7H), 1.42-1.20 (m, 50H), 0.98-0.82 (m, 9H) ppm.

MS (M+1)=725.3, Rt=2.78 min (LC method 13).

Example 121

3-((3-(1-methylpiperidin-4-yl)propanoyl)oxy)pentadecyl 6,6-bis(octyloxy)hexanoate

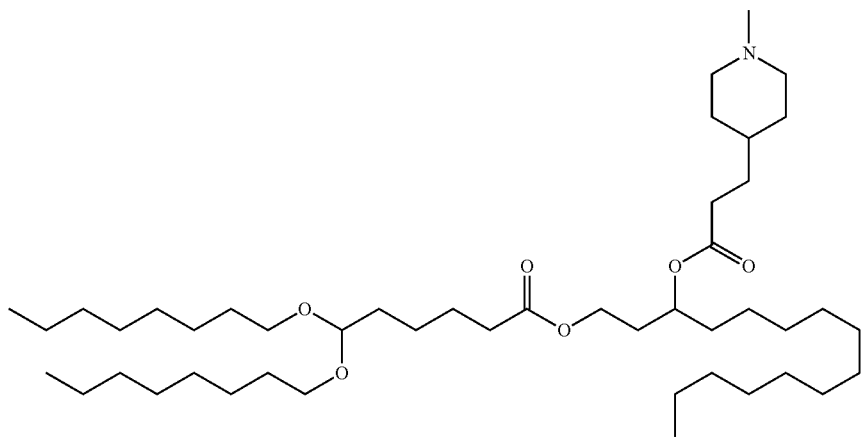 [SMILES: CCCCCCCCCCCCC(CCOC(=O)CCCCC(OCCCCCCCC)OCCCCCCCC)OC(=O)CCC1CCN(C)CC1]

$^1$H NMR (400 MHz, CDCl$_3$): =4.98 (m, 1H), 4.42 (m, 1H), 4.10 (m, 2H), 3.58-3.50 (m, 2H), 3.42-3.38 (m, 2H), 2.84 (m, 2H), 2.38-2.22 (m, 8H), 1.98-1.82 (m, 5H), 1.76-142 (m, 10H), 1.38-1.20 (m, 47H), 0.84-0.80 (m, 9H) ppm.

MS (M+1)=753.4, Rt=2.83 min (LC method 13).

Example 122

1-((6,6-bis(octyloxy)hexanoyl)oxy)pentadecan-3-yl 1,4-dimethylpiperidine-4-carboxylate

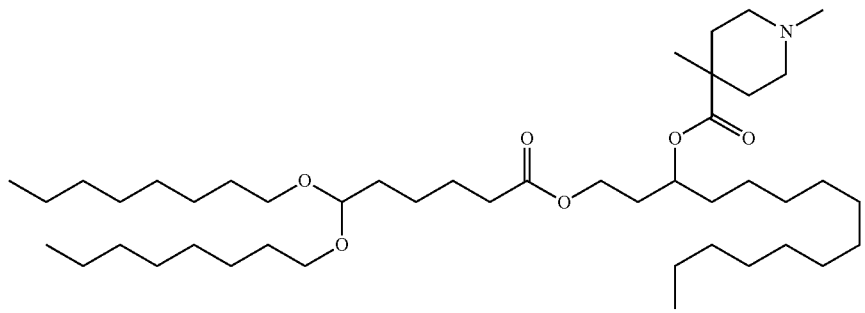 [SMILES: CCCCCCCCCCCCC(CCOC(=O)CCCCC(OCCCCCCCC)OCCCCCCCC)OC(=O)C1(C)CCN(C)CC1]

$^1$H NMR (400 MHz, CD$_2$Cl$_2$) δ=4.93-5.02 (m, 1H), 4.41 (t, J=5.62 Hz, 1H), 4.01-4.11 (m, 2H), 3.53 (dt, J=9.29, 6.66 Hz, 2H), 3.37 (dt, J=9.29, 6.66 Hz, 2H), 2.51-2.61 (m, 2H), 2.29 (t, J=7.52 Hz, 2H), 2.20 (s, 3H), 2.08 (dd, J=10.70, 3.48 Hz, 4H), 1.80-1.93 (m, 2H), 1.42-1.67 (m, 12H), 1.20-1.39 (m, 42H), 1.17 (s, 3H), 0.83-0.93 (m, 9H) ppm.

MS (M+1)=739.2, Rt=2.81 min (LC method 13).

Example 123

3-((5-(diethylamino)pentanoyl)oxy)pentadecyl 6,6-bis(octyloxy)hexanoate

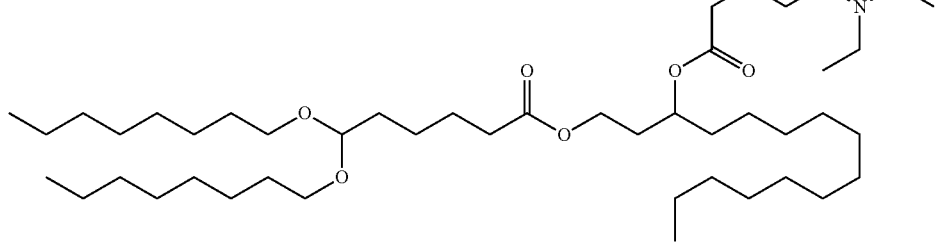

$^1$H NMR (400 MHz, CD$_2$Cl$_2$) b=4.98 (s, 1H), 4.45 (t, J=5.69 Hz, 1H), 4.03-4.14 (m, 2H), 3.57 (dt, J=9.29, 6.66 Hz, 2H), 3.41 (dt, J=9.29, 6.66 Hz, 2H), 2.40-2.59 (m, 6H), 2.32 (q, J=7.30 Hz, 4H), 1.81-1.95 (m, 2H), 1.45-1.70 (m, 14H), 1.23-1.45 (m, 42H), 1.03 (t, J=7.03 Hz, 6H), 0.87-0.97 (m, 9H) ppm.

MS (M+1)=755.2, Rt=2.68 min (LC method 13).

Synthesis of Example 124

Intermediate 124a: 1-((tert-butyldimethylsilyl)oxy)decan-3-ol

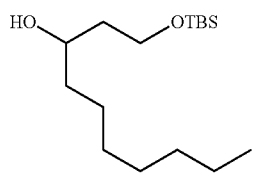 [SMILES: CCCCCCCC(O)CCO[Si](C)(C)C(C)(C)C]

Intermediate 1g (22.5 g, 119.6 mmol) was dissolved in THF (225 mL) and cooled to 0° C. Heptyl magnesium bromide (1M in diethyl ether, 143.5 mL, 143.5 mmol) was added dropwise, and the mixture was stirred for 2 h at 0° C. The reaction was quenched with the addition of aqueous ammonium chloride (100 mL) and extracted with EtOAc (2×200 mL). The organic layers were dried over sodium sulfate and concentrated to obtain the crude product. The crude mixture was purified by flash column chromatography over silica gel, eluting with 3% EtOAc/heptane to provide 12.8 g of the desired product.

TLC (silica gel, 20% EtOAc/heptane, PMA stain): R$_f$=0.55.

Intermediate 124b: 5-heptyl-2,2,9,9,10,10-hexamethyl-3,3-diphenyl-4,8-dioxa-3,9-disilaundecane

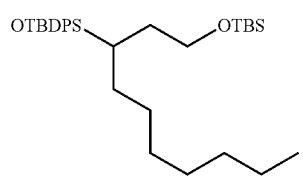

Intermediate 124a (12.8 g, 44.4 mmol) was dissolved in DCM (130 mL). Imidazole (4.53 g, 66.6 mmol) and DMAP (0.54 g, 4.44 mmol) were added, followed by TBDPSCl (11.55 mL, 44.4 mmol), and the mixture was stirred for 16 h at room temperature. The mixture was then diluted with water (200 mL) and extracted with DCM (2×100 mL). The organic layers were combined, washed with brine (100 mL), dried over sodium sulfate, and concentrated. The crude mixture was purified by flash column chromatography over silica gel, eluting with 1% EtOAc/heptane to provide 14.5 g of the desired product.

TLC (silica gel, 10% EtOAc/heptane, UV): $R_f$=0.96.

Intermediate 124c:
3-((tert-butyldiphenylsilyl)oxy)decan-1-ol

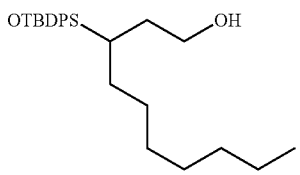

Intermediate 124b (14.5 g, 27.5 mmol) was dissolved in ethanol (145 mL) and treated with PPTS (7.61 g, 30.3 mmol). The mixture was stirred for 16 h at room temperature. The mixture was then diluted with water (300 mL) and extracted with DCM (2×100 mL). The organic layers were combined, washed with brine (100 mL), dried over sodium sulfate, and concentrated. The crude material was used in the next step without further purification TLC (silica gel, 10% EtOAc/heptane, UV): $R_f$=0.31.

Intermediate 124d:
3-((tert-butyldiphenylsilyl)oxy)decanal

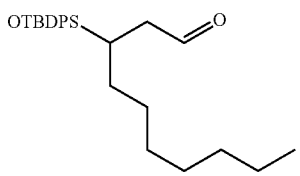

IBX (14.4 g, 51.5 mmol) was dissolved in DMSO (70 mL) and intermediate 124c (8.5 g, 20.6 mmol) was added. The mixture was stirred for 2 h at room temperature. The reaction mixture was diluted with diethyl ether (500 mL) and the resulting solid was filtered, and the filtrate was washed with brine (2×100 mL), dried over sodium sulfate, and concentrated. The crude product was used in the next step without further purification.

TLC (silica gel, 10% EtOAc/heptane, UV): $R_f$=0.66.

Intermediate 124e:
10-((tert-butyldiphenylsilyl)oxy)heptadecan-8-ol

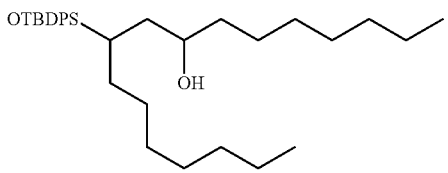

Intermediate 124d (8.0 g, 19.5 mmol) was dissolved in THF (80 mL) and cooled to 0° C. Heptyl magnesium bromide (1M in diethyl ether, 23.4 mL, 23.4 mmol) was added dropwise, and the mixture was stirred for 2 h at 0° C. The reaction was quenched with the addition of aqueous ammonium chloride (100 mL) and extracted with EtOAc (2×100 mL). The organic layers were dried over sodium sulfate and concentrated to obtain the crude product. The crude mixture was purified by flash column chromatography over silica gel, eluting with 1% EtOAc/heptane to provide 6.0 g of the desired product.

TLC (silica gel, 10% EtOAc/heptane, UV): $R_f$=0.52.

Intermediate 124f: heptadecane-8,10-diol

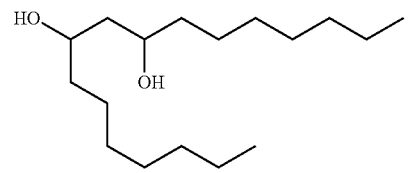 [SMILES: CCCCCCCC(O)CC(O)CCCCCCC]

Intermediate 124e (6.0 g, 11.7 mmol) was dissolved in THF (60 mL) and cooled to 0° C. HF pyridine (70%, 3.39 mL) was added dropwise, then the mixture was warmed to room temperature and stirred for 16 h. The mixture was diluted with water (100 mL) and extracted with DCM (2×50 mL). The combined organic layers were washed with brine (100 mL) dried over sodium sulfate and concentrated to obtain the crude product. The crude mixture was then triturated with pentane to provide 1.1 g of the desired product.

TLC (silica gel, 10% EtOAc/heptane, PMA stain): $R_f$=0.51.

Intermediate 124g: methyl
5-(4,6-diheptyl-1,3-dioxan-2-yl)pentanoate

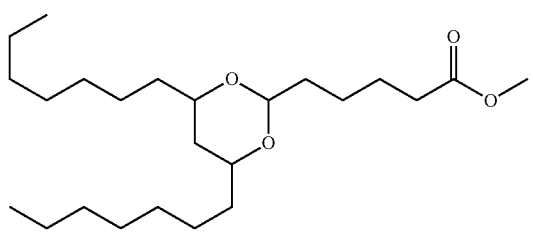 [SMILES: CCCCCCCC1CC(CCCCCCC)OC(CCCCC(=O)OC)O1]

Intermediate 16a (1.0 g, 5.2 mmol), intermediate 124f (2.1 g, 7.9 mmol) and KHSO$_4$ were combined neat, and heated to 70° C. for 4 h. The mixture was cooled to room temperature, diluted with water (40 mL), and extracted with EtOAc (2×50 mL). The combined organic layers were washed with brine (100 mL), dried over sodium sulfate, and concentrated. The crude mixture was purified by flash column chromatography over silica gel, eluting with 4% EtOAc/heptane to provide 1.1 g of the desired product.

TLC (silica gel, 10% EtOAc/heptane, PMA stain): $R_f$=0.47.

Intermediate 124h:
5-(4,6-diheptyl-1,3-dioxan-2-yl)pentanoic acid

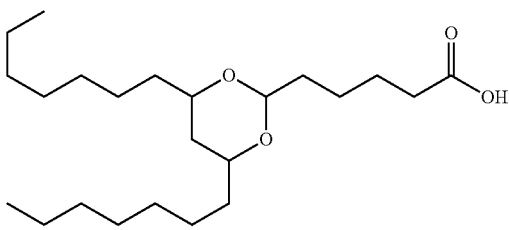 [SMILES: CCCCCCCC1CC(CCCCCCC)OC(CCCCC(=O)O)O1]

Intermediate 124g (1.0 g, 2.5 mmol) was dissolved in water/methanol (1:1, 40 mL). NaOH (0.5 g, 12.5 mmol) was added and the mixture was heated to reflux for 2 h. The mixture was then cooled to room temperature, and neutralized with 1N HCl. The mixture was then extracted with EtOAc (2×50 mL), and the organic layers were combined, washed with brine (100 mL), dried over sodium sulfate, and concentrated. The crude material was used in the next step without further purification.

TLC (silica gel, 10% EtOAc/heptane, PMA stain): $R_f$=0.14.

The following example can be prepared using similar sequences and methods to those employed for the synthesis of Example 16.

Example 124

3-(((3-(diethylamino)propoxy)carbonyl)oxy)pentadecyl 5-(4,6-diheptyl-1,3-dioxan-2-yl)pentanoate

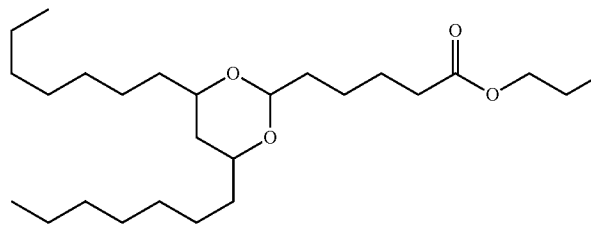

$^1$H NMR (400 MHz, CD$_2$Cl$_2$) δ: 4.81-4.74 (m, 1H), 4.73 (t, J=5.1 Hz, 1H), 4.20-4.03 (m, 4H), 4.00-3.91 (m, 1H), 3.76-3.66 (m, 1H), 2.53-2.41 (m, 6H), 2.28 (t, J=7.6 Hz, 2H), 1.99-1.84 (m, 3H), 1.81-1.67 (m, 3H), 1.64-1.54 (m, 4H), 1.54-1.42 (m, 4H), 1.42-1.20 (m, 44H), 0.98 (t, J=7.1 Hz, 6H), 0.92-0.84 (m, 9H).

MS (M+1)=769.2, Rt=2.73 min (LC method 13).

Synthesis of Example 125

Intermediate 125a:
1-((tert-butyldimethylsilyl)oxy)undecan-3-ol

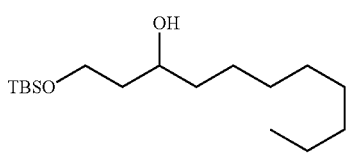 [SMILES: CCCCCCCCC(O)CCO[Si](C)(C)C(C)(C)C]

To a solution of intermediate 1g 4.0 g, 21.2 mmol) in Et$_2$O (40 mL) in a RBF charged with a magnetic stir bar under N$_2$ was added octyl magnesium bromide (2 M in Et$_2$O, 12.6 mL, 25.5 mmol) dropwise at 0° C. The resulting mixture was stirred for 2 hours at 0° C., after which the reaction was quenched with aqueous saturated NH$_4$Cl (100 mL) and extracted with EtOAc (2×200 mL). The combined organic layers were dried over Na$_2$SO$_4$ and concentrated under reduced pressure to obtain a crude liquid. The crude product was purified by silica gel chromatography eluting with EtOAc:hexane (product eluted at 3% EtOAc:hexane) to afford the desired product as a pale yellow liquid (1.8 g).

TLC: Rf=0.7 (EtOAc:Hexane, 2:8), PMA active.

Intermediate 125b: 1-((tert-butyldimethylsilyl)oxy)undecan-3-yl (3-(diethylamino)propyl) carbonate

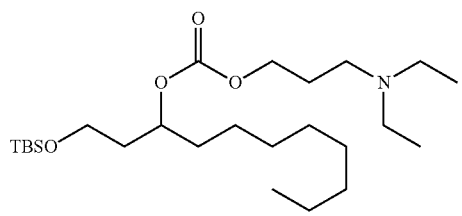 [SMILES: CCCCCCCCC(CCO[Si](C)(C)C(C)(C)C)OC(=O)OCCCN(CC)CC]

To a stirred solution of intermediate 125a (1.8 g, 5.9 mmol) in DCM (18 mL) in a RBF charged with a magnetic stir bar under N$_2$ was added pyridine (2.4 mL, 29.7 mmol) and DMAP (363 mg, 2.9 mmol), followed by 4-nitrophenyl chloroformate (2.3 g, 11.9 mmol) at rt. The reaction was stirred for 8 hours, after which 3-(diethylamino)propan-1-ol (1.5 g, 11.9 mmol) was added. The reaction was stirred at rt for 48 hours, after which it was diluted with H$_2$O and extracted with DCM (2×100 mL). The combined organic layers were dried over Na$_2$SO$_4$ and concentrated under reduced pressure to obtain a yellow liquid. The crude product was purified by silica gel chromatography eluting with EtOAc:hexane (product eluted at 2% EtOAc:hexane) to afford the desired product as a yellow liquid (1.45 g).

TLC: Rf=0.6 (EtOAc:Hexane, 2:8), PMA active.

Intermediate 125c: 3-(diethylamino)propyl (1-hydroxyundecan-3-yl) carbonate

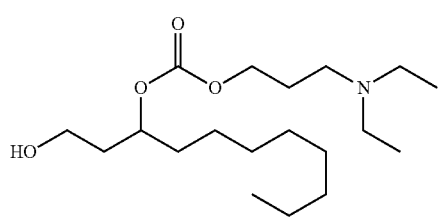 [SMILES: CCCCCCCCC(CCO)OC(=O)OCCCN(CC)CC]

To a 0° C. solution of intermediate 125b (1.0 g, 2.1 mmol) in THF (20 mL) in a round bottom flask charged with a magnetic stir bar under N₂ was added HF-pyridine (30-70%, 3.1 mL). The resulting mixture was stirred for 1 hour at 0° C., after which it was diluted with H₂O (30 mL), neutralized with solid NaHCO₃, and extracted with DCM (2×50 mL). The combined organic layers were washed with brine (100 mL), dried over Na₂SO₄, and concentrated under reduced pressure to obtain the desired product as a crude pale green liquid (730 mg). The crude material was used for the next step without purification.

TLC: Rf=0.4 (MeOH:DCM, 1:9), PMA active.

Example 125

3-(((3-(diethylamino)propoxy)carbonyl)oxy)undecyl 6,6-bis(octyloxy)hexanoate

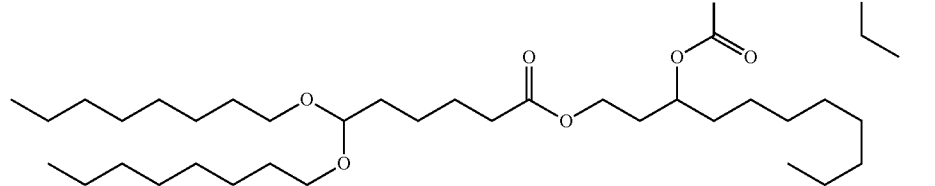

To a solution of intermediate 125c (730 mg, 2.1 mmol) in DMF (30 mL) in a RBF charged with a magnetic stir bar under N₂ were added intermediate 16c (1.10 g, 3.11 mmol), EDC.HCl (1.20 g, 6.35 mmol), DIPEA (2.2 mL, 12.7 mmol), and DMAP (258 mg, 2.11 mmol). The resulting mixture was stirred at 25-30° C. for 18 hours, after which it was diluted with H₂O (200 mL) and extracted with EtOAc (2×100 mL). The combined organic layers were washed with brine (100 mL), dried over Na₂SO₄, and concentrated under reduced pressure to obtain a crude pale green liquid. The crude product was purified by flash chromatography over neutral alumina, eluting with EtOAc:hexane (product eluted at 8% EtOAc:hexane) to afford the desired product as a colorless liquid (250 mg).

¹H NMR (400 MHz, CD₂Cl₂) δ=4.77 (quin, J=6.25 Hz, 1H), 4.41 (t, J=5.62 Hz, 1H) 4.02-4.20 (m, 4H) 3.53 (dt, J=9.22, 6.69 Hz, 2H), 3.37 (dt, J=9.22, 6.69 Hz, 2H), 2.49 (d, J=6.06 Hz, 6H), 2.28 (t, J=7.52 Hz, 2H), 1.89 (q, J=6.40 Hz, 2H), 1.71-1.82 (m, 2H), 1.46-1.67 (m, 10H), 1.20-1.42 (m, 34H), 0.99 (t, J=7.01 Hz, 6H), 0.88 (t, J=6.63 Hz, 9H) ppm.

MS (M+1)=701.1, Rt=2.33 min (LC method 13).

Synthesis of Example 126

Intermediate 126a:
1-((tert-butyldimethylsilyl)oxy)tridecan-3-ol

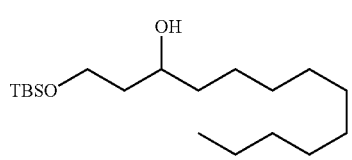 [SMILES: CCCCCCCCCCC(O)CCO[Si](C)(C)C(C)(C)C]

To a solution decyl magnesium bromide (1M in Et₂O, 26 mL) in a RBF charged with a magnetic stir bar under N₂ at 0° C. was added intermediate 1g (4.0 g, 21.2 mmol) in Et₂O (70 mL). The resulting mixture was stirred for 2 hours at 0° C., after which it was slowly quenched with saturated NH₄Cl solution (100 mL) at 0° C. and extracted with EtOAc (2×250 mL). The combined organic layers were again washed with saturated NH₄Cl solution (250 mL), dried over Na₂SO₄, and evaporated to dryness to obtain a colorless crude liquid. The crude product was purified by silica gel chromatography eluting with EtOAc:hexane (product eluted at 5% EtOAc:hexane) to afford the desired product as a colorless liquid (4.0 g).

TLC: Rf=0.6 (EtOAc:Hexane, 1:9), PMA active.

Intermediate 126b: 1-((tert-butyldimethylsilyl)oxy)tridecan-3-yl 2-(4-nitrophenyl)acetate

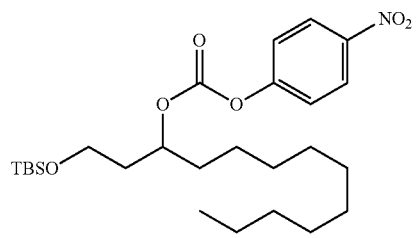 [SMILES: CCCCCCCCCCC(CCO[Si](C)(C)C(C)(C)C)OC(=O)Oc1ccc([N+](=O)[O-])cc1]

To a solution of intermediate 126a (1.5 g, 4.54 mmol) in DCM (30 mL) in a RBF charged with a magnetic stir bar under N₂ was added pyridine (1.2 mL, 13.6 mmol) followed by 4-nitrophenyl chloroformate (1.37 g, 6.81 mmol) and DMAP (1.7 g, 13.6 mmol) at 0° C. The reaction was stirred for 2 hours at 30° C., after which it was quenched with H₂O (50 mL) and extracted with EtOAc (3×100 mL). The combined organic layers were dried over Na₂SO₄ and evaporated to dryness to obtain a crude pale yellow liquid. The crude product was purified by silica gel chromatography eluting with EtOAc:hexane (product eluted at 2% EtOAc:hexane) to afford the desired product as a pale yellow liquid (1.8 g).

TLC: Rf=0.9 (EtOAc:Hexane, 0.5:9.5), PMA active.

Intermediate 126c: 1-((tert-butyldimethylsilyl)oxy)tridecan-3-yl (3-(diethylamino)propyl) carbonate

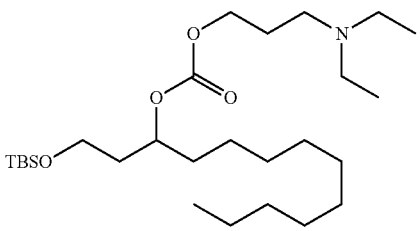 [SMILES: CCCCCCCCCCC(CCO[Si](C)(C)C(C)(C)C)OC(=O)OCCCN(CC)CC]

To a solution of intermediate 126b (1.8 g, 3.63 mmol) in DCM (15 mL) in a RBF charged with a magnetic stir bar under $N_2$ was added pyridine (0.6 mL, 7.26 mmol) followed by 3-(diethylamino)propan-1-ol (1.0 mL, 7.26 mmol) and DMAP (900 mg, 7.26 mmol). The reaction was stirred at 30° C. for 16 hours, after which it was quenched with $H_2O$ (50 mL) and extracted with DCM (3×100 mL). The combined organic layers were dried over $Na_2SO_4$ and evaporated to dryness to obtain a crude pale yellow liquid. The crude product was purified by silica gel chromatography eluting with MeOH:DCM (product eluted at 4% MeOH:DCM) to afford the desired product as a pale yellow liquid (1.4 g).

TLC: Rf=0.4 (MeOH:DCM, 1:9), PMA active.

Intermediate 126d: 3-(diethylamino)propyl (1-hydroxytridecan-3-yl) carbonate

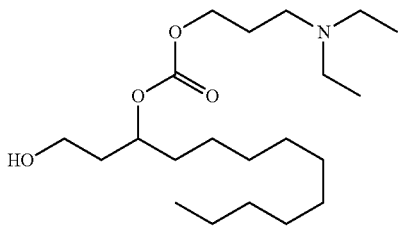 [SMILES: CCCCCCCCCCC(CCO)OC(=O)OCCCN(CC)CC]

To a solution of intermediate 126c (1.4 g, 2.87 mmol) in THF (10 mL) in a round bottom flask charged with a magnetic stir bar under $N_2$ at 0° C. was added HF-pyridine (4.9 mL, 60 equiv.). The resulting mixture was stirred for 1 hour, after which it was slowly basified with saturated $NaHCO_3$ and extracted with EtOAc (2×50 mL). The combined organic layers were dried over $Na_2SO_4$ and evaporated to dryness to obtain the desired product as a crude pale yellow oil (1.0 g). This compound was used in the next step without further purification.

TLC: Rf=0.4 (MeOH:DCM, 1:9), PMA active.

Example 126

3-(((3-(diethylamino)propoxy)carbonyl)oxy)tridecyl 6,6-bis(octyloxy)hexanoate

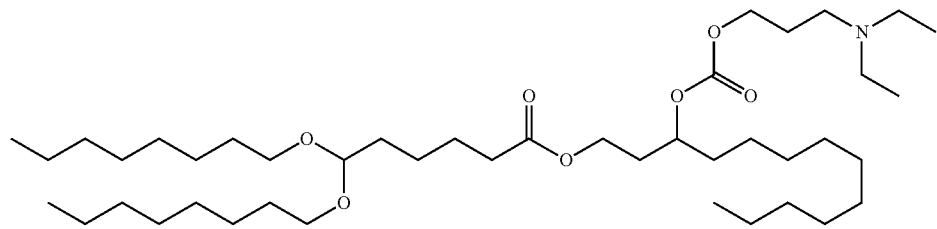 [SMILES: CCCCCCCCCCC(CCOC(=O)CCCCC(OCCCCCCCC)OCCCCCCCC)OC(=O)OCCCN(CC)CC]

To a solution of intermediate 126d (1.00 g, 2.67 mmol) and intermediate 16c (1.20 g, 3.21 mmol) in DMF (10 mL) in a RBF charged with a magnetic stir bar under $N_2$ were added HATU (2.0 g, 5.35 mmol), DIPEA (1.4 mL, 8.034 mmol), and DMAP (165 mg, 1.33 mmol). The reaction was stirred at 30° C. under $N_2$ for 16 hours, after which it was quenched with $H_2O$ (100 mL) and extracted with EtOAc (3×200 mL). The combined organic layers were washed with brine, dried over $Na_2SO_4$, and evaporated to dryness to obtain a crude pale yellow liquid. The crude product was purified by neutral alumina chromatography eluting with EtOAc:hexane (product eluted at 6% EtOAc:hexane) to afford the desired product as a pale yellow liquid (500 mg).

$^1$H NMR (400 MHz, $CD_2Cl_2$) δ=4.77 (quin, J=6.22 Hz, 1H), 4.41 (t, J=5.62 Hz, 1H), 4.02-4.21 (m, 4H), 3.53 (dt, J=9.22, 6.69 Hz, 2H), 3.37 (dt, J=9.22, 6.69 Hz, 2H), 2.49 (br. s., 6H), 2.28 (t, J=7.52 Hz, 2H), 1.90 (q, J=6.40 Hz, 2H), 1.78 (br. s., 2H), 1.46-1.67 (m, 10H), 1.20-1.41 (m, 38H), 1.00 (t, J=6.69 Hz, 6H), 0.88 (t, J=6.57 Hz, 9H) ppm.

MS (M+1)=729.2, Rt=2.60 min (LC method 13).

Synthesis of Example 127

Intermediate 127a: (6Z,9Z)-18-bromooctadeca-6,9-diene

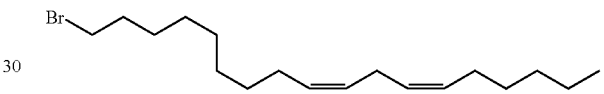

To a suspension of magnesium bromide diethyl etherate (22.5 g, 87.1 mmol) in $Et_2O$ (250 mL) in a RBF charged with a magnetic stir bar under $N_2$ was added linoleoyl mesylate (15 g, 43.5) slowly. The reaction was stirred vigorously for 40 min, after which it was quenched with ice cold $H_2O$ (200 mL). The organic layer was separated and the aqueous layer was extracted with $Et_2O$ (2×250 mL). The combined organic layers were dried over $Na_2SO_4$ and evaporated to dryness to afford the desired product as a crude pale yellow oil (14.0 g, 98%). This material was used in the next step without further purification.

TLC: Rf=0.9 (EtOAc:hexane, 2:8), PMA active.

Intermediate 127b: (6Z,9Z)-18-iodooctadeca-6,9-diene

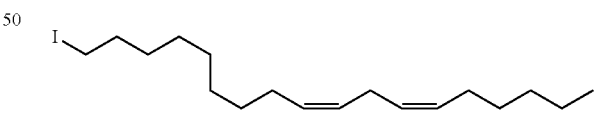

To a solution of intermediate 127a (14.0 g, 42.659 mmol) in acetone (150 mL) in a RBF charged with a magnetic stir bar under N$_2$ was added sodium iodide (12.7 g, 85.3 mmol). The reaction was heated to reflux (55° C.) for 2 hours, after which it was cooled to room temperature and the solids were filtered off. The solvent was evaporated and the remaining solids were removed by dissolution in H$_2$O (100 mL) and extraction with DCM (2×200 mL).

The combined organic layers were dried over Na$_2$SO$_4$ and evaporated to dryness to afford the desired product as a crude pale brown liquid (15.5 g, 97%). This material was used in the next step without further purification.

TLC: Rf=0.6 (100% pentane), PMA active.

Intermediate 127c: (12Z,15Z)-1-((tert-butyldimethylsilyl)oxy)henicosa-12,15-dien-3-ol

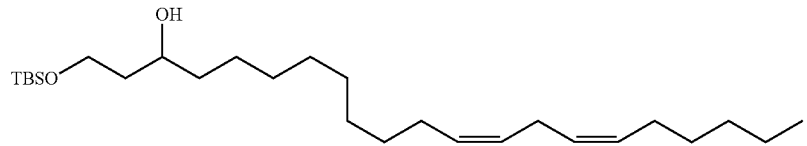

To a solution of intermediate 127b (15.0 g, 39.8 mmol) in Et$_2$O (80 mL) and pentane (20 mL) in a RBF charged with a magnetic stir bar under N$_2$ was added t-Butyl lithium (1.5 M, 53 mL, 79.7 mmol) at −78° C. Next, intermediate 1g (7.5 g, 39.8 mmol) was added as a solution in 20 mL Et$_2$O. The reaction was stirred at −78° C. for 10 minutes, after which it was quenched with saturated NH$_4$Cl solution (100 mL). The organic layer was separated and the aqueous layer was extracted with Et$_2$O (150 mL). The combined organic layers were dried over Na$_2$SO$_4$ and evaporated to dryness to obtain a crude colorless viscous liquid. The crude product was purified by silica gel chromatography eluting with EtOAc:hexane (product eluted at 4% EtOAc:hexane) to afford the desired product as a colorless viscous liquid (6.0 g).

TLC: Rf=0.5 (EtOAc:Hexane, 1:9), PMA active.

Intermediate 127d: (12Z,15Z)-1-((tert-butyldimethylsilyl)oxy)henicosa-12,15-dien-3-yl (4-nitrophenyl) carbonate

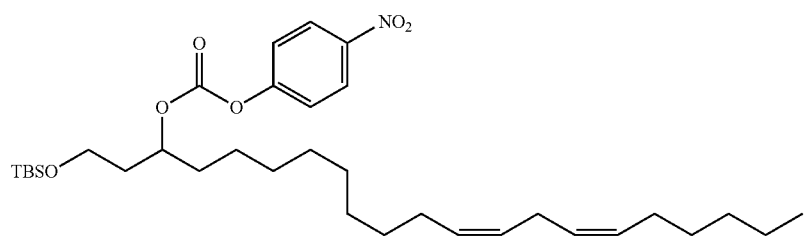 [SMILES: CCCCC/C=C\C/C=C\CCCCCCCCC(CCO[Si](C)(C)C(C)(C)C)OC(=O)Oc1ccc([N+](=O)[O-])cc1]

To a solution of intermediate 127c (1.5 g, 3.41 mmol) in DCM (30 mL) in a RBF charged with a magnetic stir bar under N$_2$ was added pyridine (0.9 mL, 10.251 mmol) followed by 4-nitrophenyl chloroformate (1.0 g, 5.12 mmol) and DMAP (1.2 g, 10.2 mmol) at 0° C. The reaction was stirred for 2 hours at 30° C., after which it was quenched with H$_2$O (50 mL) and extracted with EtOAc (3×100 mL). The combined organic layers were dried over Na$_2$SO$_4$ and evaporated to dryness to obtain a crude pale yellow liquid. The crude product was purified by silica gel chromatography eluting with EtOAc:hexane (product eluted at 2% EtOAc:hexane) to afford the desired product as a pale yellow liquid (1.6 g).

TLC: Rf=0.9 (EtOAc:Hexane, 0.5:9.5), PMA active.

Intermediate 127e: (12Z,15Z)-1-((tert-butyldimethylsilyl)oxy)henicosa-12,15-dien-3-yl (3-(diethylamino)propyl) carbonate

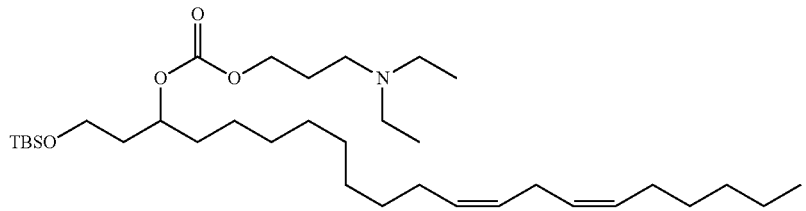 [SMILES: CCCCC/C=C\C/C=C\CCCCCCCCC(CCO[Si](C)(C)C(C)(C)C)OC(=O)OCCCN(CC)CC]

To a solution of intermediate 127d (1.6 g, 2.65 mmol) in DCM (15 mL) in a RBF charged with a magnetic stir bar under $N_2$ was added pyridine (0.5 mL, 5.30 mmol) followed by 3-(diethylamino)propan-1-ol (0.8 mL, 5.30 mmol) and DMAP (650 mg, 5.30 mmol). The reaction was stirred at 30° C. for 16 hours, after which it was quenched with $H_2O$ (50 mL) and extracted with DCM (3×100 mL). The combined organic layers were dried over $Na_2SO_4$ and evaporated to dryness to obtain a crude pale yellow liquid. The crude product was purified by silica gel chromatography eluting with MeOH:DCM (product eluted at 4% MeOH:DCM) to afford the desired product as a pale yellow liquid (1.1 g).

TLC: Rf=0.97 (MeOH:DCM, 1:9), PMA active.

Intermediate 127f: 3-(diethylamino)propyl ((12Z,15Z)-1-hydroxyhenicosa-12,15-dien-3-yl) carbonate

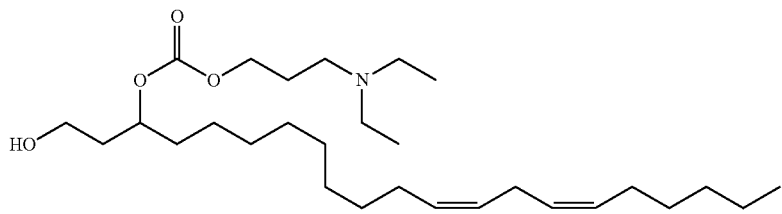 [SMILES: CCCCC/C=C\C/C=C\CCCCCCCCC(CCO)OC(=O)OCCCN(CC)CC]

To a solution of intermediate 127e (1.1 g, 2.01 mmol) in THF (10 mL) in a round bottom flask charged with a magnetic stir bar under $N_2$ at 0° C. was added HF-pyridine (3.5 mL, 60 equiv.). The resulting mixture was stirred at 0° C. for 1 hour, after which it was slowly basified with saturated $NaHCO_3$ and extracted with EtOAc (2×50 mL). The combined organic layers were dried over $Na_2SO_4$ and evaporated to dryness to afford the desired product as a crude pale yellow oil (900 mg). This compound was used in the next step without further purification.

TLC: Rf=0.4 (MeOH:DCM, 1:9), PMA active.

Example 127

(12Z,15Z)-3-(((3-(diethylamino)propoxy)carbonyl)oxy)henicosa-12,15-dien-1-yl 6,6-bis(octyloxy)hexanoate

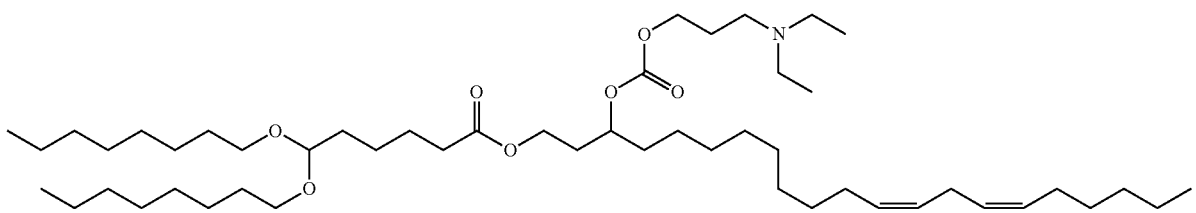 [SMILES: CCCCC/C=C\C/C=C\CCCCCCCCC(CCOC(=O)CCCCC(OCCCCCCCC)OCCCCCCCC)OC(=O)OCCCN(CC)CC]

To a solution of intermediate 127f (900 mg, 1.86 mmol) and intermediate 16c (1.4 g, 3.738 mmol) in DMF (10 mL) in a RBF charged with a magnetic stir bar under $N_2$ were added HATU (1.4 g, 3.73 mmol), DIPEA (1.0 mL, 5.607 mmol), and DMAP (115 mg, 0.93 mmol). The reaction was stirred at 30° C. under $N_2$ for 16 hours, after which it was quenched with $H_2O$ (100 mL) and extracted with EtOAc (3×200 mL). The combined organic layers were washed with brine, dried over $Na_2SO_4$, and evaporated to dryness to afford a crude pale yellow liquid. The crude product was purified by neutral alumina chromatography eluting with EtOAc:hexane (product eluted at 7% EtOAc:hexane) to afford the desired product as a pale yellow liquid (550 mg).

$^1$H NMR (400 MHz, $CD_2Cl_2$) δ=5.25-5.45 (m, 4H), 4.77 (quin, J=6.24 Hz, 1H), 4.41 (t, J=5.62 Hz, 1H), 4.04-4.19 (m, 4H), 3.53 (dt, J=9.29, 6.66 Hz, 2H), 3.37 (dt, J=9.29, 6.66 Hz, 2H), 2.78 (t, J=6.54 Hz, 2H), 2.50 (br. s., 6H), 2.29 (t, J=7.58 Hz, 2H), 2.05 (q, J=6.81 Hz, 4H), 1.90 (q, J=6.44 Hz, 2H), 1.77 (br. s., 2H), 1.45-1.67 (m, 10H), 1.21-1.41 (m, 40H), 1.01 (br. s., 6H), 0.83-0.95 (m, 9H) ppm.

MS (M+1)=837.3, Rt=1.20 min (LC method 14).

Synthesis of Example 128

Intermediate 128a: 6-(benzyloxy)-1-((tert-butyldimethylsilyl)oxy)hexan-3-ol

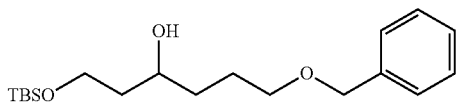 [SMILES: CC(C)(C)[Si](C)(C)OCCC(O)CCCOCc1ccccc1]

To a solution of magnesium (1.76 g, 73.6 mmol) and $I_2$ (100 mg, catalytic) in THF (50 mL) in a RBF (fitted with a reflux condenser) charged with a magnetic stir bar under $N_2$ was added benzyl 3-bromopropyl ether (14.0 g, 61.4 mmol) in THF (40 mL). The reaction was stirred for 1 hour, after which it was added to intermediate 1g (13.85 g, 73.6 mmol) in THF (60 mL) at 0° C. The reaction was allowed to warm to 25° C. for 1 hour and stir at that temperature for 17 hours, after which it was quenched with saturated $NH_4Cl$ (150 mL) and extracted with EtOAc (2×250 mL). The combined organic layers were dried over $Na_2SO_4$ and concentrated under reduced pressure to obtain a crude brown liquid. The crude product was purified by silica gel chromatography eluting with EtOAc:hexane (product eluted at 15% EtOAc:hexane) to afford the desired product as a pale yellow liquid (2.3 g).

TLC: Rf=0.2 (EtOAc:Hexane, 2:8), PMA active.

Intermediate 128b: 6-(benzyloxy)-1-((tert-butyldimethylsilyl)oxy)hexan-3-yl (4-nitrophenyl) carbonate

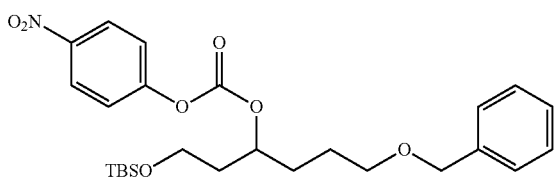 [SMILES: CC(C)(C)[Si](C)(C)OCCC(CCCOCc1ccccc1)OC(=O)Oc1ccc([N+](=O)[O-])cc1]

To a solution of intermediate 128a (2.0 g, 5.91 mmol) in DCM (40 mL) in a RBF charged with a magnetic stir bar under $N_2$ was added 4-nitrophenyl chloroformate (1.78 g, 8.86 mmol) followed by pyridine (1.45 mL, 17.7 mmol) at 0° C. The reaction was stirred for 18 hours, after which it was diluted with $H_2O$ (100 mL) and extracted with DCM (2×100 mL). The combined organic layers were washed with brine (100 mL), dried over $Na_2SO_4$, and concentrated under reduced pressure to obtain a crude gummy solid. The crude product was purified by silica gel chromatography eluting with EtOAc:hexane (product eluted at 5% EtOAc:hexane) to afford the desired product as a pale brown liquid (400 mg).

TLC: Rf=0.6 (EtOAc:Hexane, 1:9), UV & PMA active.

Intermediate 128c: 6-(benzyloxy)-1-((tert-butyldimethylsilyl)oxy)hexan-3-yl (3-(diethylamino)propyl) carbonate

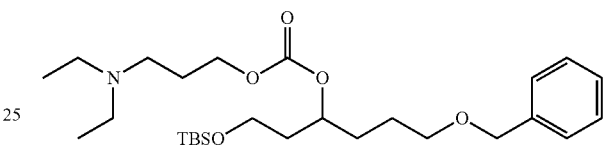

To a solution of intermediate 128b (1.9 g, 3.77 mmol) in DCM (40 mL) in a RBF charged with a magnetic stir bar under $N_2$ were added 3-(diethylamino)propan-1-ol (2.81 mL, 18.8 mmol) followed by $Et_3N$ (5.27 mL, 37.7 mmol) and DMAP (922 mg, 7.55 mmol). The reaction was stirred at rt for 3 days, after which it was diluted with $H_2O$ (200 mL) and extracted with DCM (2×200 mL). The combined organic layers were washed with brine (250 mL), dried over $Na_2SO_4$, and concentrated under reduced pressure to obtain a crude pale green liquid. The crude product was purified by silica gel chromatography eluting with MeOH:DCM (product eluted at 3% MeOH:DCM) to afford the desired product as a pale green liquid (550 mg).

TLC: Rf=0.6 (MeOH:DCM, 1:9), PMA active.

Intermediate 128d: 6-(benzyloxy)-1-hydroxyhexan-3-yl (3-(diethylamino)propyl) carbonate

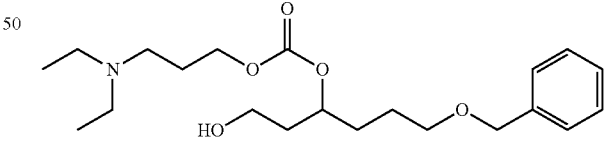

To a solution of intermediate 128c (550 mg, 1.11 mmol) in THF (20 mL) in a round bottom flask charged with a magnetic stir bar under $N_2$ at 0° C. was added HF-pyridine (30-70%, 2.0 mL). The resulting mixture was stirred at 0° C. for 1 hour, after which it was diluted with $H_2O$ (30 mL), neutralized with solid $NaHCO_3$, and extracted with DCM (2×50 mL). The combined organic layers were washed with brine (100 mL), dried over $Na_2SO_4$, and concentrated under reduced pressure to afford the desired product as a crude pale green liquid (400 mg).

TLC: Rf=0.4 (MeOH:DCM, 1:9), $I_2$ & PMA active.

Intermediate 128e: 6-(benzyloxy)-3-(((3-(diethylamino)propoxy)carbonyl)oxy)hexyl 6,6-bis(octyloxy)hexanoate

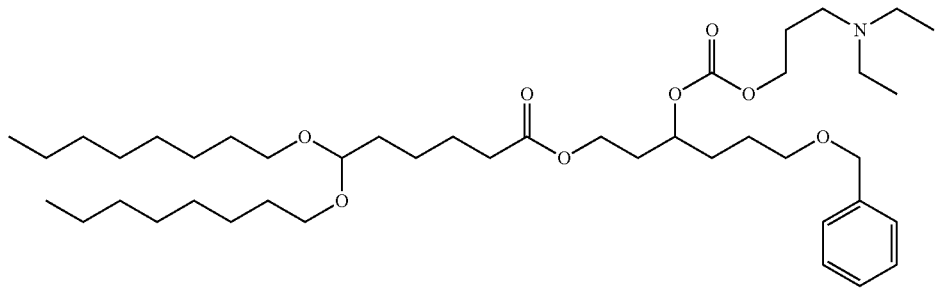 [SMILES: CCCCCCCCOC(CCCCC(=O)OCCC(CCCOCc1ccccc1)OC(=O)OCCCN(CC)CC)OCCCCCCCC]

To a solution of intermediate 128d (400 mg, 1.04 mmol) in DMF (15 mL) in a RBF charged with a magnetic stir bar under $N_2$ were added intermediate 16c (585 mg, 1.57 mmol), HATU (797 mg, 2.09 mmol), DIPEA (0.55 mL, 3.147 mmol), and DMAP (128 mg, 1.04 mmol) sequentially. The reaction was stirred at rt for 18 hours, after which it was diluted with $H_2O$ (100 mL) and extracted with EtOAc (2×50 mL). The combined organic layers were washed with brine (100 mL), dried over $Na_2SO_4$, and concentrated under reduced pressure to afford a crude pale green liquid. The crude product was purified by neutral alumina chromatography eluting with EtOAc:hexane (product eluted at 15% EtOAc:hexane) to afford the desired product as a pale green liquid (550 mg).

TLC: Rf=0.6 (MeOH:DCM, 1:9), PMA active.

Intermediate 128f: 3-(((3-(diethylamino)propoxy)carbonyl)oxy)-6-hydroxyhexyl 6,6-bis(octyloxy)hexanoate

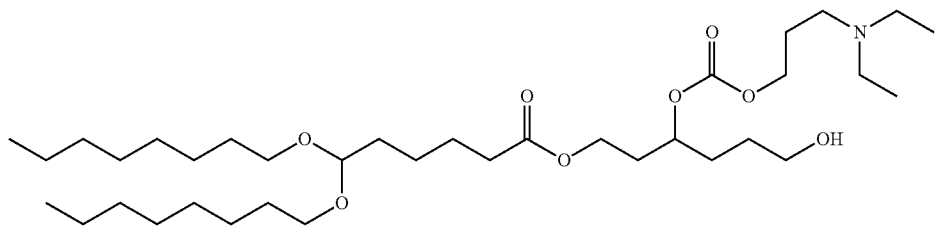 [SMILES: CCCCCCCCOC(CCCCC(=O)OCCC(CCCO)OC(=O)OCCCN(CC)CC)OCCCCCCCC]

Raney Ni (20 mg, cat.) was added to a solution of intermediate 128e (60 mg, 0.081 mmol) in EtOH (5 mL) in a RBF charged with a magnetic stir bar. The resulting mixture was stirred under atmospheric $H_2$ pressure (using a hydrogen balloon) for 24 hours at rt, after which it was filtered on a bed of celite and concentrated under reduced pressure to obtain the desired product as a colorless liquid (40 mg, 76%). This compound was used in the next step without further purification.

TLC: Rf=0.4 (MeOH:DCM, 1:9), PMA active.

Example 128

6-((6,6-bis(octyloxy)hexanoyl)oxy)-4-(((3-(diethylamino)propoxy)carbonyl)oxy)hexyl octanoate

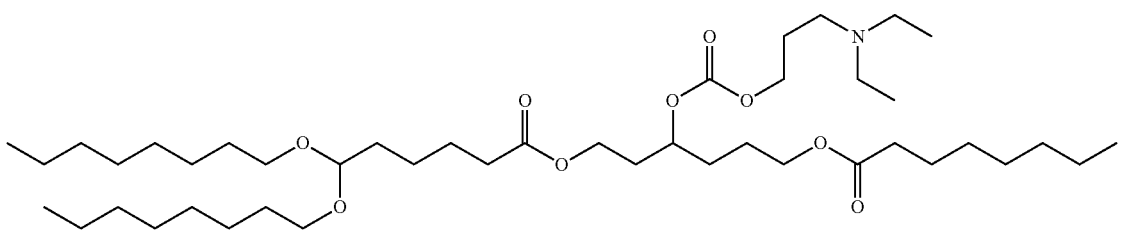 [SMILES: CCCCCCCCOC(CCCCC(=O)OCCC(CCCOC(=O)CCCCCCC)OC(=O)OCCCN(CC)CC)OCCCCCCCC]

To a solution of intermediate 128f (440 mg, 0.681 mmol) in DMF (15 mL) in a RBF charged with a magnetic stir bar under N$_2$ were added octanoic acid (0.22 mL, 1.36 mmol), HATU (777 mg, 2.04 mmol), DIPEA (0.59 mL, 3.40 mmol), and DMAP (83 mg, 0.68 mmol) sequentially. The reaction was stirred at rt for 18 hours, after which it was diluted with H$_2$O (100 mL) and extracted with EtOAc (2×50 mL). The combined organic layers were washed with brine (100 mL), dried over Na$_2$SO$_4$, and concentrated under reduced pressure to afford a crude pale green liquid. The crude product was purified by neutral alumina chromatography eluting with EtOAc:hexane (product eluted at 15% EtOAc:hexane) to afford the desired product as a colorless liquid (400 mg).

$^1$H NMR (400 MHz, CDCl$_3$):) δ=4.82 (m, 1H), 4.33 (m, 1H), 4.20-4.08 (m, 5H), 3.48 (m, 2H), 3.40 (m, 2H), 2.52 (m, 5H), 2.30 (q, J=8 Hz, 4H), 1.92 (m, 2H), 1.82 (q, J=8 Hz, 2H), 1.78-1.50 (m, 11H), 1.39-1.22 (m, 35H), 1.02 (t, J=8 Hz, 6H), 0.92-0.82 (m, 9H) ppm.

MS (M+1)=773.1, Rt=2.41 min (LC method 13).

Synthesis of Example 129

Intermediate 129a:
1-((tert-butyldimethylsilyl)oxy)heptadecan-5-ol

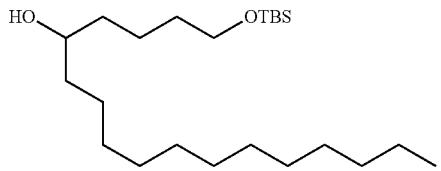 [SMILES: CCCCCCCCCCCCC(O)CCCCO[Si](C)(C)C(C)(C)C]

To a stirred solution of 5-((tert-butyldimethylsilyl)oxy) pentanal (6.00 g, 31.2 mmol) under nitrogen atmosphere at 0° C. was added 1 M dodecyl magnesium bromide (37 mL, 37 mmol) in dry diethyl ether (40 mL). The reaction was stirred for 2 h at the same temperature. Progress of the reaction was monitored by TLC. The reaction mixture was slowly quenched with 100 mL of saturated ammonium chloride solution at 0° C. and extracted with (2×250 mL) ethyl acetate. The combined organic layers were again washed with 250 mL of saturated ammonium chloride, dried over sodium sulfate and evaporated to dryness to get colorless liquid in crude form. The crude product was purified by flash chromatography eluting with 5% EtOAc in hexanes to afford 5 g of colorless oil.

TLC: Rf=0.5 (EtOAc:hexanes, 2:8); PMA active.

Intermediate 129b: 1-((tert-butyldimethylsilyl)oxy) heptadecan-5-yl (4-nitrophenyl) carbonate

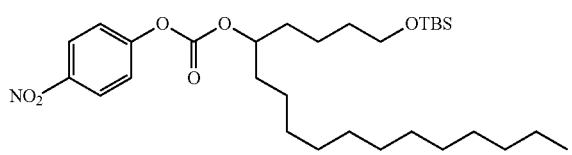 [SMILES: CCCCCCCCCCCCC(CCCCO[Si](C)(C)C(C)(C)C)OC(=O)Oc1ccc([N+](=O)[O-])cc1]

To a solution of intermediate 129a (2.50 g, 6.47 mmol) in DCM (15 mL) was added pyridine (2 mL, 25.9 mmol) and DMAP (10 mg) followed by slow addition of 4-nitrophenyl chloroformate (2.6 g, 12.9 mmol) at 0° C. and the reaction was stirred at 30° C. for 3 h. The reaction mixture was quenched with 50 mL of water and extracted with DCM (3×50 mL). The combined organic layers were dried over sodium sulfate and evaporated to dryness to afford pale yellow color liquid in crude form. The crude mixture was purified by flash chromatography eluting with 5% EtOAc in hexanes to afford 3.0 g of the desired product as a yellow oil.

TLC: Rf=0.8 (EtOAc:hexanes, 2:8); PMA active.

Intermediate 129c: 1-((tert-butyldimethylsilyl)oxy) heptadecan-5-yl (3-(diethylamino)propyl) carbonate

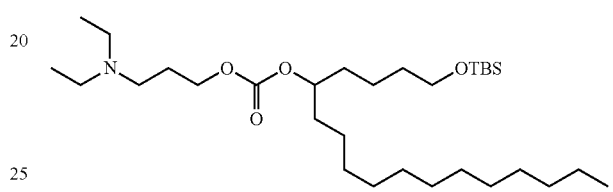

To a solution of intermediate 129b (3.0 g, 5.44 mmol) in DCM (6 mL) was added pyridine (1.7 mL, 21.76 mmol) and DMAP (332 mg, 2.72 mmol) followed by slow addition of 3-(diethylamino)propan-1-ol (1.6 mL, 10.9 mmol) and the reaction was stirred at 30° C. for 16 h. The reaction mixture was quenched with 50 mL of water and extracted with DCM (3×50 mL). The combined organic layers were dried over sodium sulfate and evaporated to dryness to afford pale yellow color liquid in crude form. The crude mixture was purified by flash-chromatography eluting with 4% MeOH in DCM to afford 2.5 g of the desired product as a yellow oil.

TLC: Rf=0.6 (MeOH:DCM, 1:9); PMA active.

Intermediate 129d: 3-(diethylamino)propyl (1-hydroxyheptadecan-5-yl) carbonate

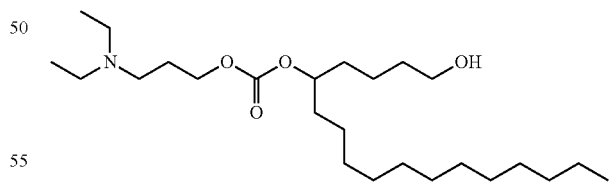

To a solution of intermediate 129c (500 mg, 0.92 mmol) in THF (5 mL) was added HF.Pyridine complex (70%, 1.6 mL, 55.2 mmol) at 0° C. and the reaction was stirred for 1 h. The reaction mixture was slowly basified with saturated sodium bicarbonate and extracted with (2×50 mL) EtOAc. The combined organic layers were dried over sodium sulfate and evaporated to dryness to afford 400 mg of the desired product as a pale yellow oil.

TLC: Rf=0.4 (MeOH:DCM, 1:9); PMA active.

Intermediate 129e: 3-(diethylamino)propyl (1-oxoheptadecan-5-yl) carbonate

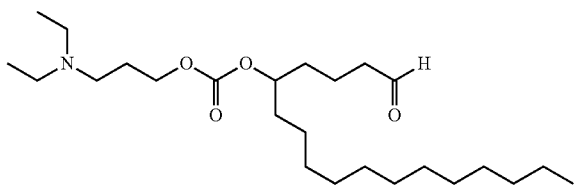 [SMILES: CCCCCCCCCCCCC(CCCC=O)OC(=O)OCCCN(CC)CC]

To a solution of intermediate 129d (400 mg, 0.931 mmol) and triethyl amine (1.2 mL, 8.37 mmol) in DCM (4.6 mL) was added sulfur trioxide pyridine complex (666 mg, 4.18 mmol) dissolved in DMSO (5.5 mL) at 0° C. The reaction was allowed to stir for 15 h at 30° C. The reaction mixture was slowly quenched with 50 mL of water and extracted with (3×50 mL) of EtOAc. The combined organic layers were dried over sodium sulfate and evaporated to dryness to afford pale yellow color liquid, 400 mg, in crude form. Material was used in the next step without further purification.

TLC: Rf=0.5 (MeOH:DCM, 1:9); PMA active.

Intermediate 129f: 5-(((3-(diethylamino)propoxy)carbonyl)oxy)heptadecanoic acid

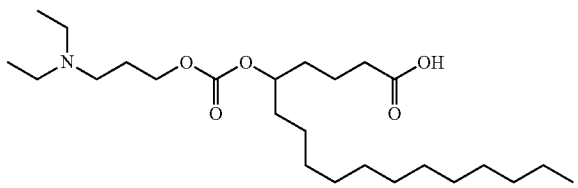 [SMILES: CCCCCCCCCCCCC(CCCC(=O)O)OC(=O)OCCCN(CC)CC]

To a stirred solution of intermediate 129e (400 mg, 0.93 mmol) in t-Butanol (5 mL) and aq. buffer (pH 4.5, NaHPO$_4$:NaH$_2$PO$_4$:H$_3$PO$_4$, 1:1:1, 5 mL) was added 2-methyl 2-butene (1.0 mL, 9.3 mmol) followed by addition of sodium chlorite (170 mg, 1.87 mmol) dissolved in 1.6 mL of water. The thick hazy solution was stirred at 30° C. for 20 h. The reaction mixture was quenched with 50 mL of water and extracted with (3×50 mL) EtOAc. The combined organic layers were dried over sodium sulfate and evaporated to dryness to afford pale yellow color liquid, 450 mg, in crude form.

TLC: Rf=0.4 (MeOH:DCM, 1:9); PMA active.

Intermediate 129g: ((4,4-dimethoxybutoxy)methyl)benzene

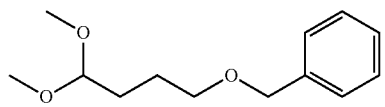 [SMILES: COC(CCCOCc1ccccc1)OC]

To the mixture of 4-(benzyloxy)butanal (16.4 g, 92.13 mmol) and trimethyl orthoformate (50 mL) in methanol (100 mL) was added sulfuric acid (200 mg) and the reaction was heated to 80° C. for 16 h under nitrogen atmosphere. Solvent was evaporated under vacuum to give a thick crude liquid which was purified by chromatography eluting with at 10% EtOAc in hexanes to afford 12 g of colorless oil.

TLC: Rf=0.6 (EtOAc:hexanes, 2:8); PMA active.

Intermediate 129h: ((4,4-bis(octyloxy)butoxy)methyl)benzene

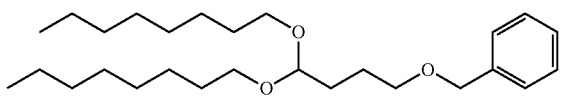 [SMILES: CCCCCCCCOC(CCCOCc1ccccc1)OCCCCCCCC]

To a mixture of intermediate 129g (12.0 g, 53.53 mmol) and 1-octanol (28.0 g, 214.15 mmol) in benzene (50 mL) was added KHSO$_4$ (1 g). The reaction was heated to 70° C. for 4 h under a nitrogen atmosphere. The reaction mixture was allowed to cool to room temperature and was purified directly by flash column chromatography, eluting with 4% EtOAc in hexanes to give 7.5 g of the desired product.

TLC: Rf=0.9 (EtOAc:hexanes, 2:8); PMA active.

Intermediate 129i: 4,4-bis(octyloxy)butan-1-ol

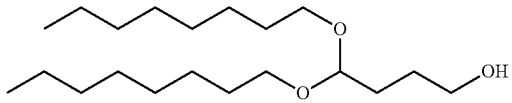 [SMILES: CCCCCCCCOC(CCCO)OCCCCCCCC]

To a solution of intermediate 129h (3.0 g, 7.13 mmol) in EtOH (50 mL) was added Raney Nickel (6.0 g) and the reaction was stirred under hydrogen balloon pressure for 7 days at 30° C. The Reaction mixture was filtered through a celite bed and solvent was evaporated to dryness to give 2 g of colorless oil.

TLC: Rf=0.5 (EtOAc:hexanes, 2:8); PMA active.

The following example can be prepared using similar sequences and methods to those employed for the synthesis of Example 11.

Example 129

4,4-bis(octyloxy)butyl 5-(((3-(diethylamino)propoxy)carbonyl)oxy)heptadecanoate

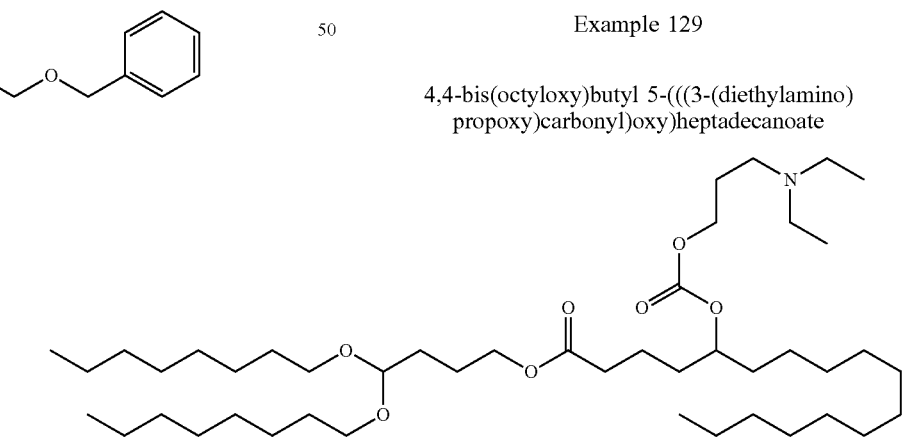

$^1$H NMR (400 MHz, CD$_2$Cl$_2$) δ=4.67 (quin, J=5.70 Hz, 1H), 4.45 (m, 1H), 4.14 (td, J=6.48, 1.71 Hz, 2H), 3.99-4.07 (m, 2H), 3.54 (m, 2H), 3.38 (m, 2H), 2.55 (m, 4H), 2.26-2.35 (m, 2H), 1.83 (d, J=6.48 Hz, 2H), 1.47-1.72 (m, 14H), 1.21-1.38 (m, 42H), 1.03 (t, J=7.03 Hz, 6H), 0.82-0.93 (m, 9H) ppm.

MS (M+1)=757.2, Rt=2.73 min (LC method 13).

Synthesis of Example 130

The following intermediates can be prepared using similar sequences and methods to those employed for the synthesis of example 129.

Intermediate 130a:
1-((tert-butyldimethylsilyl)oxy)pentadecan-3-ol

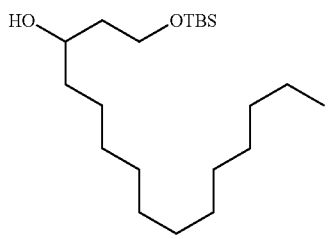 [SMILES: CCCCCCCCCCCCC(O)CCO[Si](C)(C)C(C)(C)C]

TLC: Rf=0.6 (EtOAc:hexanes, 1:9); PMA active.

Intermediate 130b: 1-((tert-butyldimethylsilyl)oxy)pentadecan-3-yl (4-nitrophenyl) carbonate

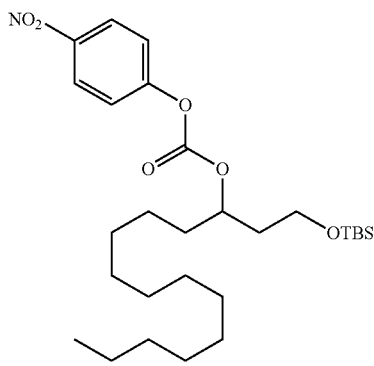 [SMILES: CCCCCCCCCCCCC(CCO[Si](C)(C)C(C)(C)C)OC(=O)Oc1ccc([N+](=O)[O-])cc1]

TLC: Rf=0.9 (EtOAc:hexanes, 0.5:9.5); PMA active.

Intermediate 130c: 1-((tert-butyldimethylsilyl)oxy)pentadecan-3-yl (3-(diethylamino)propyl) carbonate

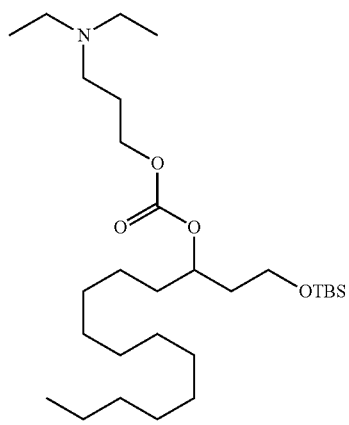 [SMILES: CCCCCCCCCCCCC(CCO[Si](C)(C)C(C)(C)C)OC(=O)OCCCN(CC)CC]

TLC: Rf=0.5 (MeOH:DCM, 1:9); PMA active.

Intermediate 130d: 3-(diethylamino)propyl (1-hydroxypentadecan-3-yl) carbonate

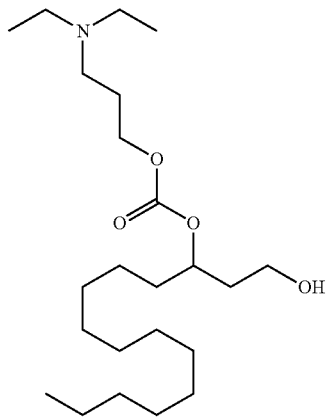 [SMILES: CCCCCCCCCCCCC(CCO)OC(=O)OCCCN(CC)CC]

TLC: Rf=0.4 (MeOH:DCM, 1:9); PMA active.

The following example can be prepared using similar sequences and methods to those employed for the synthesis of Example 11.

Example 130

4,4-bis(octyloxy)butyl (3-(diethylamino)propyl) pentadecane-1,3-diyl dicarbonate

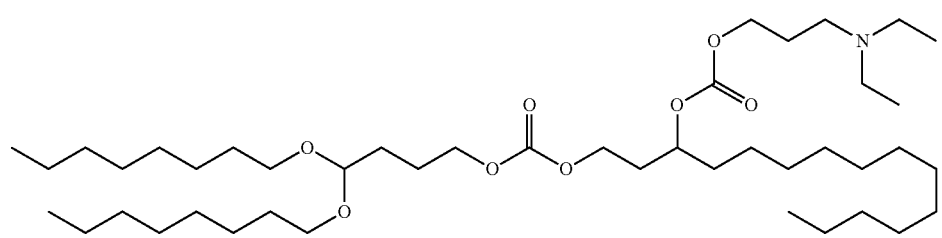 [SMILES: CCCCCCCCCCCCC(CCOC(=O)OCCCC(OCCCCCCCC)OCCCCCCCC)OC(=O)OCCCN(CC)CC]

$^1$H NMR (400 MHz, CD$_2$Cl$_2$) δ=4.74-4.81 (m, 1H), 4.44 (t, J=5.38 Hz, 1H), 4.06-4.21 (m, 6H), 3.54 (dt, J=9.29, 6.66 Hz, 2H), 3.38 (dt, J=9.29, 6.66 Hz, 2H), 2.51 (q, J=6.81 Hz, 6H), 1.89-1.97 (m, 2H), 1.75-1.82 (m, 2H), 1.68-1.74 (m, 2H), 1.49-1.66 (m, 8H), 1.22-1.37 (m, 40H), 1.00 (t, J=7.09 Hz, 6H), 0.85-0.93 (m, 9H) ppm.

MS (M+1)=759.2, Rt=2.62 min (LC method 13).

Synthesis of Example 131

Intermediate 131a:
4-((tert-butyldimethylsilyl)oxy)butanal

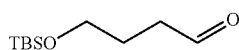 [SMILES: CC(C)(C)[Si](C)(C)OCCCC=O]

4-((tert-butyldimethylsilyl)oxy)butan-1-ol and TEA (10.2 mL, 73.4 mmol) were taken into DCM (100 mL). A solution of sulfur trioxide pyridine complex (5.84 g, 36.7 mmol) in DMSO (20.8 mL, 294 mmol) was added dropwise to the alcohol and amine solution in an ice-bath. The resultant mixture was stirred at room temperature for 4 hr. The crude mixture was partitioned between water and ethyl acetate. The organic layer was collected, dried, concentrated and purified over silica gel with 10% ethyl acetate/hexane to afford 4.5 g of the desired product as a colorless oil.

TLC: Rf=0.7, Heptane:EtOAc=1:1

Intermediate 131b:
1-((tert-butyldimethylsilyl)oxy)hexadecan-4-ol

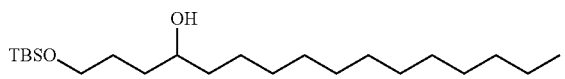 [SMILES: CCCCCCCCCCCCC(O)CCCO[Si](C)(C)C(C)(C)C]

Intermediate 131a (4.50 g, 22.2 mmol) was dissolved in 100 mL of anhydrous THF and cooled to −41° C. 1 M dodecylmagnesium bromide in THF (33.4 mL, 33.4 mmol) was added to the solution. The resulting mixture was stirred at −41 OC for one hour then warmed up to ambient temperature for one hour. Sat. NH$_4$Cl solution was added to quench the reaction. The reaction mixture was extracted with EtOAc (2×100 mL). The combined organic phases were dried over MgSO$_4$, filtered and concentrated. The residue was purified by silica gel flash column chromatography with 0-50% EtOAc/Heptane to afford 6.65 g of the desired product as a colorless oil.

$^1$H NMR (400 MHz, CD$_2$Cl$_2$) δ=3.56-3.61 (m, 2H), 3.45-3.53 (m, 1H), 1.89-1.98 (m, 1H), 1.48-1.59 (m, 3H), 1.30-1.39 (m, 3H), 1.15-1.27 (m, 20H), 0.79-0.89 (m, 12H), −0.01 (s, 6H) ppm.

Intermediate 131c: 5-dodecyl-2,2,10,10,11,11-hexamethyl-3,3-diphenyl-4,9-dioxa-3,10-disiladodecane

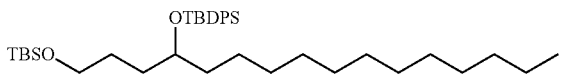

To intermediate 131b (1.5 g, 4.02 mmol) in anhydrous DCM (15 mL) was added imidazole (0.411 g, 6.04 mmol), followed by addition of tert-butyldiphenylchlorosilane (1.24 mL, 4.83 mmol). The reaction was then stirred under the presence of nitrogen for 5 h. The reaction was diluted with 30 mL of DCM and washed with 50 mL of water. The separated organic layer was dried over sodium sulfate, concentrated, and purified by flash column chromatography (0-25% EtOAc in heptane) to provide 2.4 g of the desired product as a colorless oil.

$^1$H NMR (400 MHz, CDCl$_3$) δ=7.61-7.71 (m, 4H), 7.30-7.45 (m, 6H), 3.66-3.77 (m, 1H), 3.37-3.49 (m, 2H), 1.38-1.52 (m, 5H), 1.09-1.34 (m, 21H), 1.04 (s, 9H), 0.80-0.90 (m, 12H), 0.00 (s, 6H) ppm.

Intermediate 131d:
4-((tert-butyldiphenylsilyl)oxy)hexadecan-1-ol

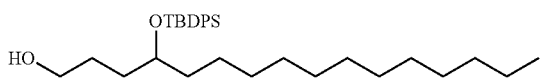

To intermediate 131c (2.4 g, 3.93 mmol) in anhydrous EtOH (15 mL) was added 10-camphorsulfonic acid (0.411 g, 1.76 mmol). The resulting mixture was stirred at room temperature for 3 h. TLC indicated completion of the reaction. The mixture was diluted with 100 mL of DCM and washed with 50 mL of sat. NaHCO$_3$. The separated aq. layer was extracted with an additional 50 mL of DCM. The combined organic layers were dried over sodium sulfate, concentrated, and purified by flash column chromatography (eluting with 0-50% EtOAc in heptane) to provide 1.4 g of the desired product as a colorless oil.

$^1$H NMR (400 MHz, CDCl$_3$) δ=7.52-7.64 (m, 4H), 7.23-7.36 (m, 6H), 3.60-3.72 (m, 1H), 3.34-3.45 (m, 2H), 1.27-1.50 (m, 7H), 0.92-1.23 (m, 20H), 0.90-1.00 (m, 9H), 0.80 (t, J=1.00 Hz, 3H) ppm.

Intermediate 131e: 2-(5-((4-((tert-butyldiphenylsilyl)oxy)hexadecyl)oxy)-5-oxopentyl)propane-1,3-diyl dioctanoate

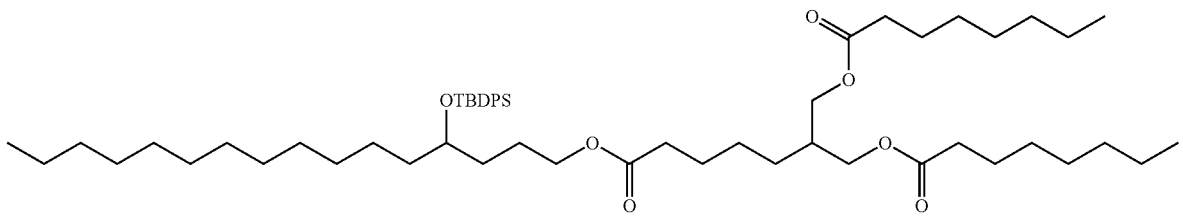

In a vial, intermediate 1f (1.20 g, 2.82 mmol), intermediate 131d (1.4 g, 2.82 mmol), DIPEA (0.984 mL, 5.64 mmol), and DMAP (0.069 g, 0.564 mmol) were taken into anhydrous dichloromethane (10 mL). EDC.HCl (1.08 g, 5.64 mmol) was added in one portion, and the reaction was stirred at ambient temperature overnight. The reaction was then diluted with water (10 mL). The organic layer was separated, and the aqueous layer was extracted with DCM (10 mL). The combined organic layers were dried over Na$_2$SO$_4$, filtered, concentrated and purified by flash column chromatography (eluting with 0-25% EtOAc:heptane) to provide 2.06 g of the desired product as a colorless oil.

$^1$H NMR (400 MHz, CDCl$_3$) δ=7.64-7.76 (m, 4H), 7.32-7.47 (m, 6H), 4.01-4.12 (m, 4H), 3.94 (t, J=6.66 Hz, 2H), 3.71-3.80 (m, 1H), 2.23-2.37 (m, 6H), 1.94-2.06 (m, 1H), 1.58-1.70 (m, 6H), 1.11-1.49 (m, 46H), 1.07 (s, 9H), 0.90 (td, J=6.88, 1.77 Hz, 9H) ppm.

Intermediate 131f: 2-(5-((4-hydroxyhexadecyl)oxy)-5-oxopentyl)propane-1,3-diyl dioctanoate

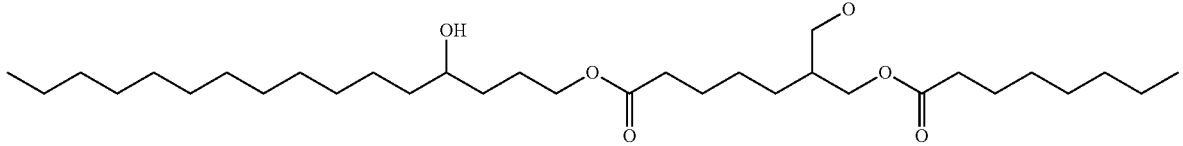

To intermediate 131e (2.06 g, 2.27 mmol) in a 100 mL RBF was added 1 M TBAF in THF (11.35 mL, 11.35 mmol). The reaction was stirred at ambient temperature under the presence of nitrogen overnight. The crude mixture was diluted with 40 mL of DCM and washed with 40 mL of sat. NaHCO$_3$. The aq. layer was extracted with an additional 40 mL of DCM. The organic layers were combined and dried over sodium sulfate, concentrated and purified by flash column chromatography (eluting with 0-100% EtOAc in heptane) to afford 800 mg of the desired product as a colorless oil.

$^1$H NMR (400 MHz, CD$_2$Cl$_2$) δ=3.99-4.14 (m, 6H), 3.62 (d, J=5.01 Hz, 1H), 2.25-2.38 (m, 6H), 1.94-2.05 (m, 1H), 1.23-1.86 (m, 53H), 0.85-0.98 (m, 9H) ppm.

Example 131

2-(5-((4-((1,4-dimethylpiperidine-4-carbonyl)oxy)hexadecyl)oxy)-5-oxopentyl)propane-1,3-diyl dioctanoate

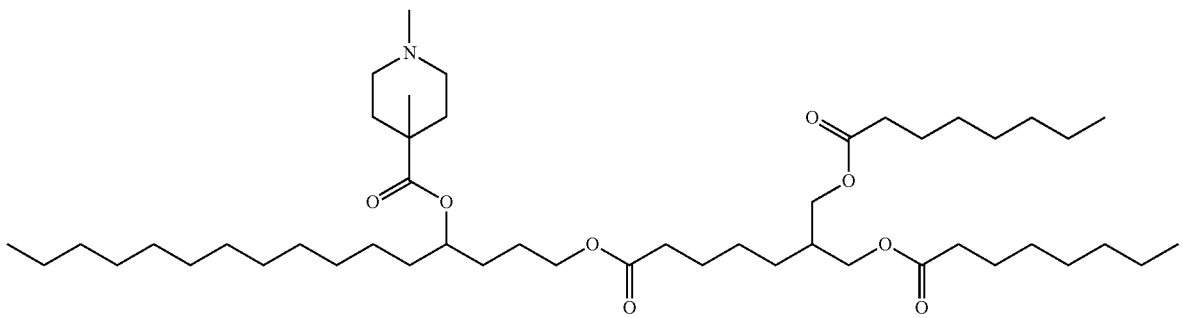

Intermediate 131f (70 mg, 0.105 mmol), 1,4-dimethylpiperidine-4-carboxylic acid HCl salt (81 mg, 0.419 mmol), DIPEA (0.110 mL, 0.628 mmol), and DMAP (10.2 mg, 0.084 mmol) were taken into anhydrous dichloromethane (2 mL). EDC.HCl (80 mg, 0.419 mmol) was added in one portion, and the reaction was stirred at ambient temperature overnight. The crude reaction was concentrated under reduced pressure and purified by flash column chromatography (eluting with 0-100% EtOAc in heptane,) to provide 62 mg of the desired product as a colorless oil.

$^1$H NMR (400 MHz, CD$_2$Cl$_2$) δ=4.83-4.93 (m, 1H), 3.96-4.07 (m, 6H), 2.48-2.58 (m, 2H), 2.28 (t, J=7.58 Hz, 6H), 2.18 (s, 3H), 2.02-2.11 (m, 4H), 1.94-2.01 (m, 1H), 1.20-1.68 (m, 54H), 1.16 (s, 3H), 0.82-0.92 (m, 9H) ppm.

MS (M+1)=809.2, Rt=2.52 min (LC method 13).

The following example can be prepared using similar sequences and methods to those employed for the synthesis of example 131.

Example 132

2-(5-((4-(((1,3-dimethylpyrrolidine-3-carbonyl)oxy)hexadecyl)oxy)-5-oxopentyl)propane-1,3-diyl dioctanoate

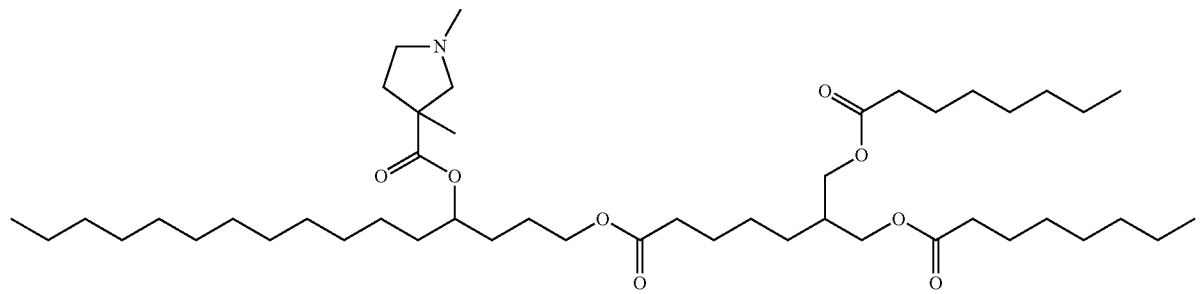 [SMILES: CCCCCCCCCCCCC(CCCOC(=O)CCCCC(COC(=O)CCCCCCC)COC(=O)CCCCCCC)OC(=O)C1(C)CCN(C)C1]

$^1$H NMR (400 MHz, CD$_2$Cl$_2$) δ=4.73-4.82 (m, 1H), 3.89-4.01 (m, 6H), 2.80 (d, J=9.17 Hz, 1H), 2.45 (d, J=7.58 Hz, 2H), 2.14-2.33 (m, 11H), 1.85-1.94 (m, 1H), 1.40-1.61 (m, 14H), 1.10-1.34 (m, 42H), 0.75-0.87 (m, 9H) ppm.
MS (M+1)=795.1, Rt=2.47 min (LC method 13).

Synthesis of Example 133

Intermediate 133a: (2S)-1-tert-butyl 2-(1-((7-(octanoyloxy)-6-((octanoyloxy)methyl)heptanoyl)oxy)hexadecan-4-yl) pyrrolidine-1,2-dicarboxylate

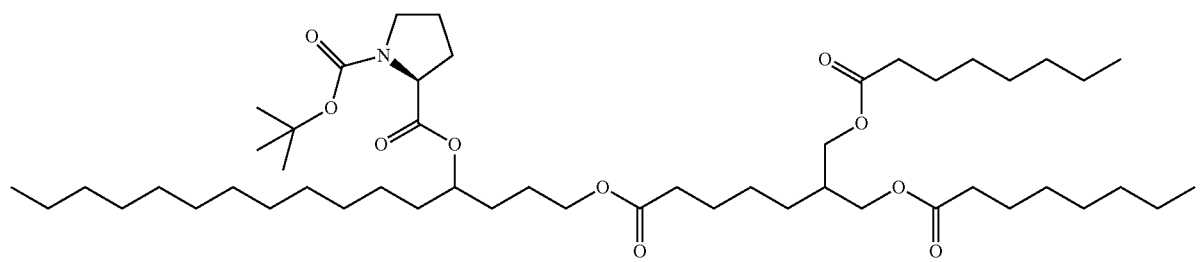 [SMILES: CCCCCCCCCCCCC(CCCOC(=O)CCCCC(COC(=O)CCCCCCC)COC(=O)CCCCCCC)OC(=O)[C@@H]1CCCN1C(=O)OC(C)(C)C]

Intermediate 133a can be prepared using similar methods to those employed for the synthesis of example 131.
$^1$H NMR (400 MHz, CD$_2$Cl$_2$) δ=4.83-4.94 (m, 1H), 4.22 (dd, J=8.74, 2.87 Hz, 1H), 3.89-4.11 (m, 6H), 3.32-3.54 (m, 2H), 2.28 (t, J=7.52 Hz, 6H), 2.12-2.23 (m, 1H), 1.81-2.02 (m, 4H), 1.51-1.69 (m, 10H), 1.19-1.48 (m, 51H), 0.88 (t, J=6.11 Hz, 9H) ppm.

Example 133

2-(5-oxo-5-((4-(((S)-pyrrolidine-2-carbonyl)oxy)hexadecyl)oxy)pentyl)propane-1,3-diyl dioctanoate

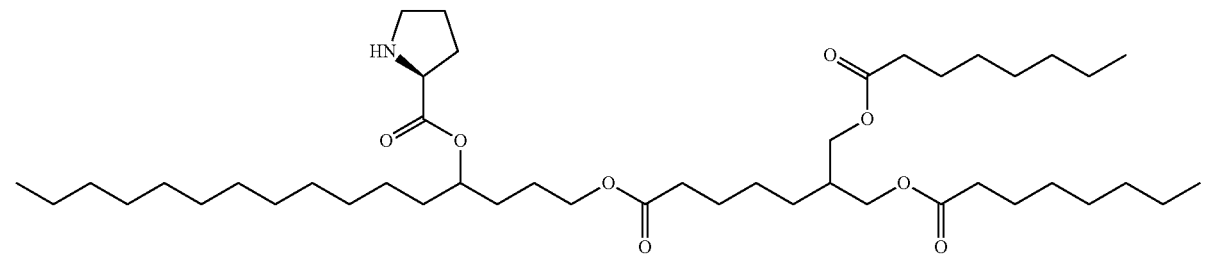 [SMILES: CCCCCCCCCCCCC(CCCOC(=O)CCCCC(COC(=O)CCCCCCC)COC(=O)CCCCCCC)OC(=O)[C@@H]1CCCN1]

4 M HCl in dioxane (1030 μl, 4.16 mmol) was added into intermediate 133a (120 mg, 0.139 mmol) in a vial. The resulting solution was stirred at ambient temperature for 1 h. The crude mixture was concentrated under reduced pressure, and redissolved in 5 mL of DCM. The organic layer was then washed with 5 mL of 2.0 N $Na_2CO_3$ solution, dried over sodium sulfate, concentrated and purified by flash column chromatography (eluting with 0-100% EtOAc in heptane) to provide 48 mg of the desired product.

$^1$H NMR (400 MHz, $CD_2Cl_2$) δ=4.85-4.96 (m, 1H), 4.02 (t, J=6.17 Hz, 6H), 3.66-3.76 (m, 1H), 3.00-3.10 (m, 1H), 2.82-2.94 (m, 1H), 2.28 (t, J=7.58 Hz, 6H), 2.05-2.17 (m, 1H), 1.91-2.04 (m, 1H), 1.67-1.86 (m, 3H), 1.50-1.66 (m, 11H), 1.20-1.43 (m, 42H), 0.81-0.92 (m, 9H) ppm.

MS (M+1)=766, Rt=2.23 min (LC method 13).

Synthesis of Example 134

Intermediate 134a: 2-(5-((4-(((4-nitrophenoxy)carbonyl)oxy)hexadecyl)oxy)-5-oxopentyl)propane-1,3-diyl dioctanoate

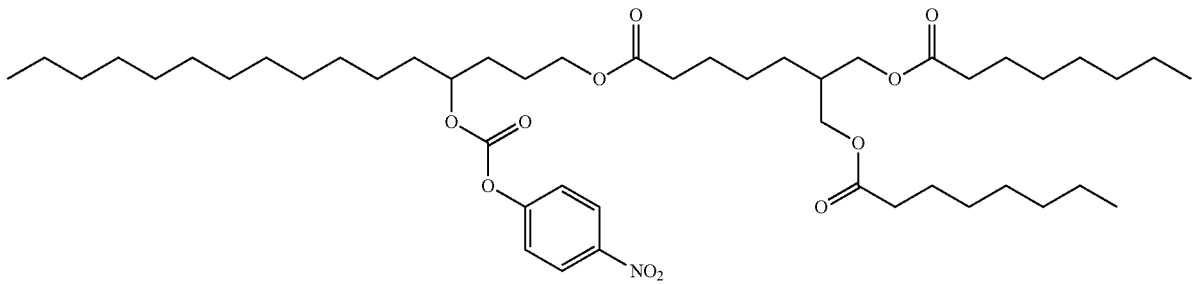 [SMILES: CCCCCCCCCCCCC(CCCOC(=O)CCCCC(COC(=O)CCCCCCC)COC(=O)CCCCCCC)OC(=O)Oc1ccc([N+](=O)[O-])cc1]

Intermediate 131f (372 mg, 0.556 mmol) was taken into DCM in a vial charged with a magnetic stir bar. 4-nitrophenyl carbonochloridate (134 mg, 0.667 mmol) was added in one portion. The reaction was capped and placed under nitrogen, after which pyridine was added dropwise via syringe. The reaction was allowed to stir at ambient temperature overnight. The reaction was then diluted with water (10 mL) and DCM (10 mL). The organic layer was separated, and the aqueous layer was washed with DCM (10 mL). The combined organic layers were washed with brine (10 mL), dried with Na2SO4, filtered, and concentrated in vacuo. The crude residue was purified by flash column chromatography (eluting with 0-25% EtOAc in heptane) to provide 420 mg of the desired product as a colorless oil.

$^1$H NMR (400 MHz, $CD_2Cl_2$) δ=8.23-8.31 (m, 2H), 7.34-7.44 (m, 2H), 4.81-4.90 (m, 1H), 3.94-4.13 (m, 6H), 2.22-2.35 (m, 6H), 1.92-2.04 (m, 1H), 1.54-1.78 (m, 12H), 1.20-1.44 (m, 40H), 0.88 (t, J=7.00 Hz, 9H) ppm.

Example 134

2-(5-((4-(((((S)-1-methylpyrrolidin-3-yl)oxy)carbonyl)oxy)hexadecyl)oxy)-5-oxopentyl)propane-1,3-diyl dioctanoate

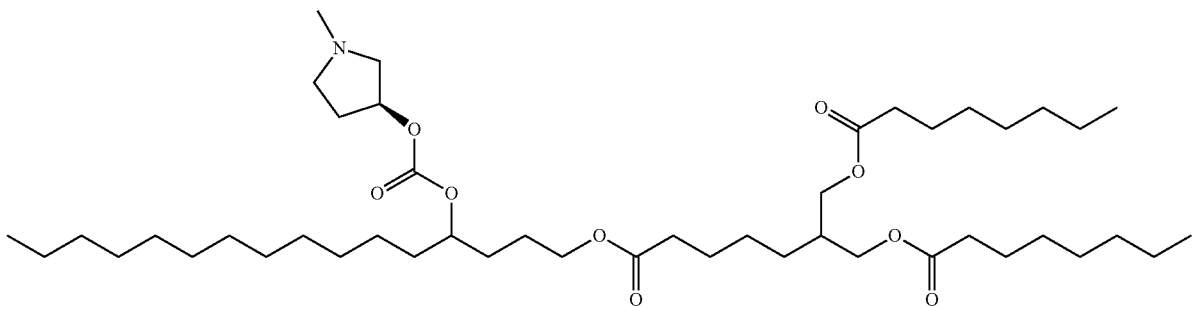 [SMILES: CCCCCCCCCCCCC(CCCOC(=O)CCCCC(COC(=O)CCCCCCC)COC(=O)CCCCCCC)OC(=O)O[C@H]1CCN(C)C1]

(S)-1-methylpyrrolidin-3-ol (34.0 mg, 0.336 mmol) in a small amount of anhydrous ACN was added dropwise to intermediate 134a (70 mg, 0.084 mmol) in anhydrous ACN (3 mL) in a vial charged with a magnetic stir bar under $N_2$.

Next, pyridine was added via syringe, followed by the addition of DMAP (dissolved in a minimal volume of MeCN) in one portion. The reaction was allowed to stir at ambient temperature for 3 days. The crude mixture was then diluted with 10 mL of water and extracted with DCM (2×10 mL). The combined organic layers were washed with 10 mL of water, dried over sodium sulfate, and purified by flash column chromatography (eluting with 0-100% EtOAc in heptane) to provide 40 mg of the desired product as a clear oil.

$^1$H NMR (400 MHz, CD$_2$Cl$_2$) δ=5.08-5.17 (m, 1H), 4.68-4.79 (m, 1H), 3.99-4.13 (m, 6H), 2.70-2.95 (m, 3H), 2.40-2.54 (m, 3H), 2.27-2.38 (m, 6H), 1.90-2.08 (m, 2H), 1.52-1.78 (m, 12H), 1.21-1.46 (m, 42H), 0.92 (t, J=7.60 Hz, 9H) ppm.

MS (M+1)=797, Rt=2.48 min (LC method 13).

The following examples can be prepared using similar sequences and methods to those employed for the synthesis of Example 134.

Example 135

2-(5-((4-(((((R)-1-methylpyrrolidin-3-yl)oxy)carbonyl)oxy)hexadecyl)oxy)-5-oxopentyl)propane-1,3-diyl dioctanoate

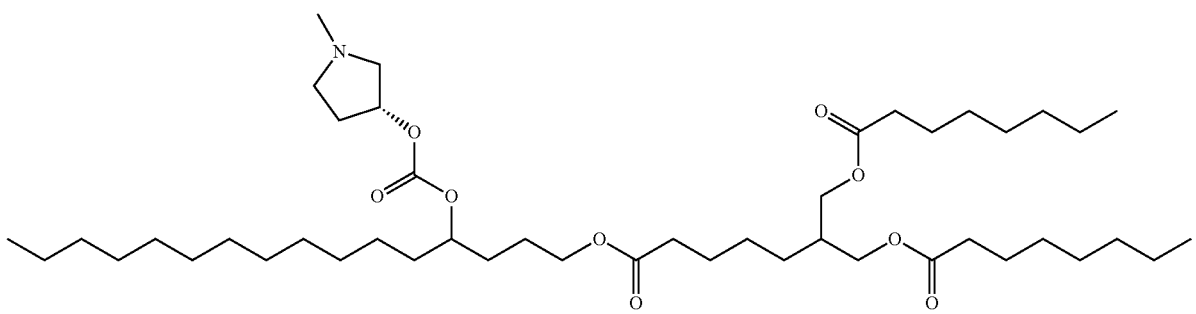 [SMILES: CCCCCCCCCCCCC(CCCOC(=O)CCCCC(COC(=O)CCCCCCC)COC(=O)CCCCCCC)OC(=O)O[C@@H]1CCN(C)C1]

$^1$H NMR (400 MHz, CD$_2$Cl$_2$) δ=5.08-5.17 (m, 1H), 4.68-4.79 (m, 1H), 3.99-4.13 (m, 6H), 2.70-2.95 (m, 3H), 2.40-2.54 (m, 3H), 2.27-2.38 (m, 6H), 1.90-2.08 (m, 2H), 1.52-1.78 (m, 12H), 1.21-1.46 (m, 42H), 0.92 (t, J=7.60 Hz, 9H) ppm.

MS (M+1)=797, Rt=2.41 min (LC method 13).

Example 136

2-(5-((4-((((1-ethylpiperidin-3-yl)methoxy)carbonyl)oxy)hexadecyl)oxy)-5-oxopentyl)propane-1,3-diyl dioctanoate

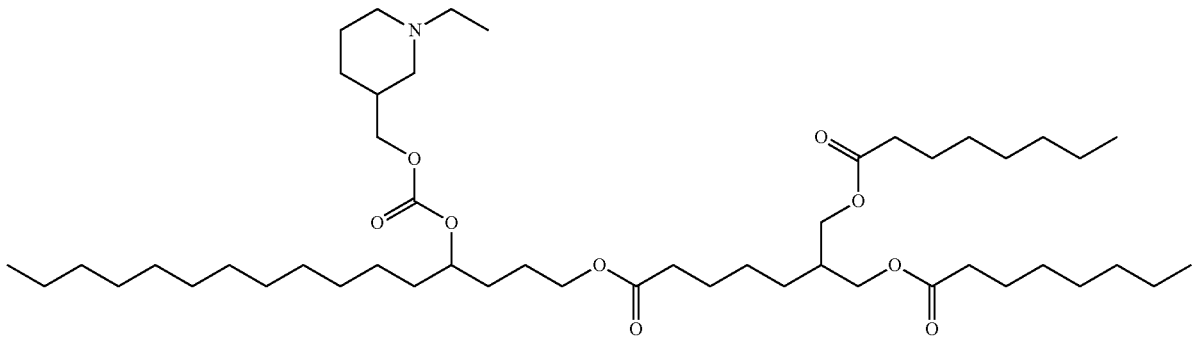 [SMILES: CCCCCCCCCCCCC(CCCOC(=O)CCCCC(COC(=O)CCCCCCC)COC(=O)CCCCCCC)OC(=O)OCC1CCCN(CC)C1]

$^1$H NMR (400 MHz, CD$_2$Cl$_2$) δ=4.59-4.92 (m, 1H), 3.85-4.12 (m, 8H), 2.69-2.88 (m, 2H), 2.22-2.39 (m, 8H), 1.83-2.04 (m, 3H), 1.46-1.78 (m, 17H), 1.18-1.42 (m, 40H), 1.02 (t, J=7.15 Hz, 3H), 0.88 (t, J=7.30 Hz, 9H) ppm.

MS (M+1)=838, Rt=2.35 min (LC method 13).

Example 137
2-(5-((4-((((1-methylpiperidin-4-yl)oxy)carbonyl)oxy)hexadecyl)oxy)-5-oxopentyl)propane-1,3-diyl dioctanoate
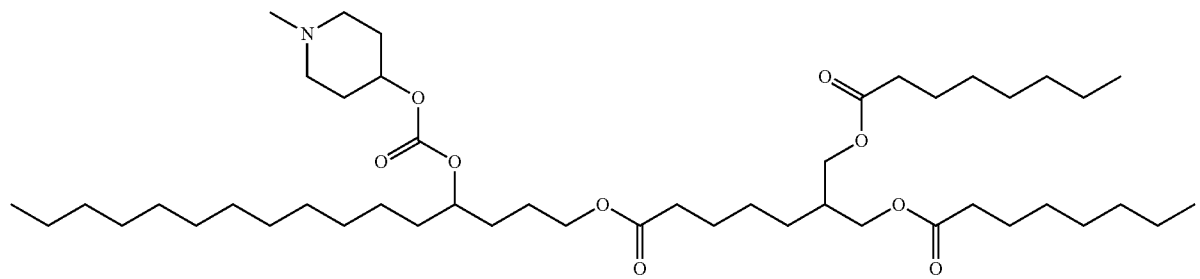 [SMILES: CCCCCCCCCCCCC(CCCOC(=O)CCCCC(COC(=O)CCCCCCC)COC(=O)CCCCCCC)OC(=O)OC1CCN(C)CC1]
¹H NMR (400 MHz, CD₂Cl₂) δ=4.51-4.92 (m, 2H), 3.93-4.17 (m, 6H), 2.56-2.89 (m, 2H), 2.15-2.50 (m, 9H), 1.92-2.07 (m, 3H), 1.73-1.89 (m, 2H), 1.43-1.71 (m, 14H), 1.17-1.42 (m, 40H), 0.88 (t, J=7.00 Hz, 9H) ppm.
MS (M+1)=811.4, Rt=2.48 min (LC method 13).
Example 138
2-(10-dodecyl-3-ethyl-8,15-dioxo-7,9,14-trioxa-3-azanonadecan-19-yl)propane-1,3-diyl dioctanoate
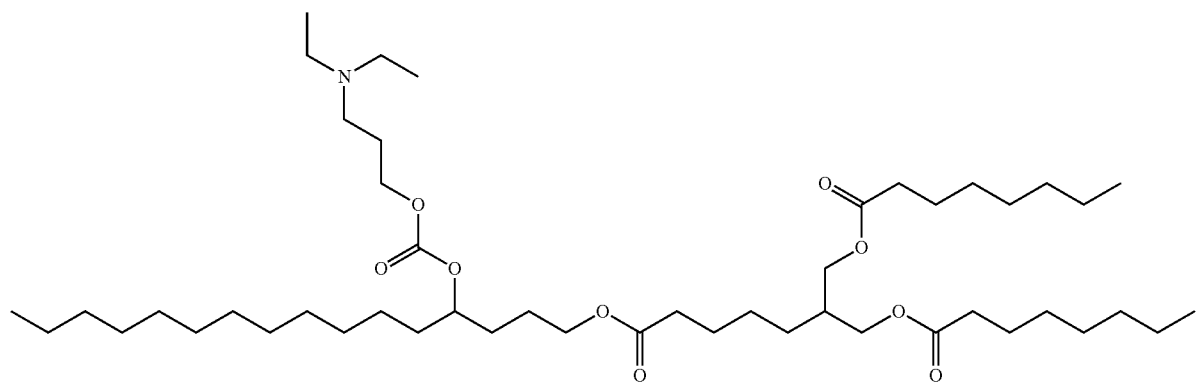 [SMILES: CCCCCCCCCCCCC(CCCOC(=O)CCCCC(COC(=O)CCCCCCC)COC(=O)CCCCCCC)OC(=O)OCCCN(CC)CC]
¹H NMR (400 MHz, CD₂Cl₂) δ=4.63-4.74 (m, 1H), 4.14 (td, J=6.51, 2.14 Hz, 2H), 3.95-4.08 (m, 6H), 2.48 (br. s., 6H), 2.28 (t, J=7.52 Hz, 6H), 1.92-2.03 (m, 1H), 1.77 (br. s, 2H), 1.49-1.68 (m, 12H), 1.19-1.40 (m, 40H), 0.99 (br. s., 6H), 0.82-0.93 (m, 9H) ppm.
MS (M+1)=827.2, Rt=2.51 min (LC method 13).

Synthesis of Example 139

Intermediate 139a: 4-(diethylamino)butyl (1-hydroxypentadecan-3-yl) carbonate

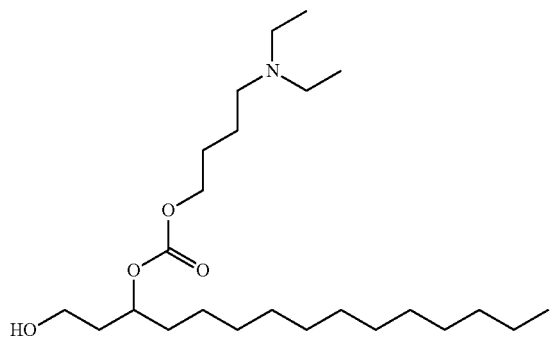 [SMILES: CCCCCCCCCCCCC(CCO)OC(=O)OCCCCN(CC)CC]

Intermediate 139a can be prepared using similar methods to those employed for the synthesis of intermediate 1k.

MS (M+1)=416.7, Rt=1.44 min (LC method 14).

Example 139

2-(11-dodecyl-3-ethyl-9,15-dioxo-8,10,14-trioxa-3-azanonadecan-19-yl)propane-1,3-diyl dioctanoate

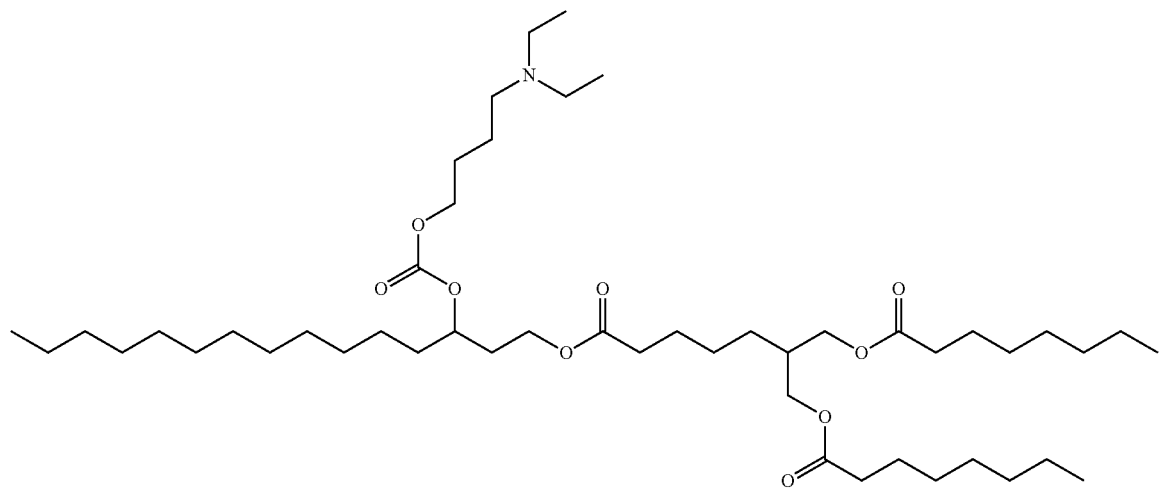 [SMILES: CCCCCCCCCCCCC(CCOC(=O)CCCCC(COC(=O)CCCCCCC)COC(=O)CCCCCCC)OC(=O)OCCCCN(CC)CC]

Example 15 can be prepared using similar methods to those employed for the synthesis of example 1.

$^1$H NMR (400 MHz, $CD_2Cl_2$) δ=4.77 (quin, J=6.24 Hz, 1H), 3.95-4.18 (m, 8H), 2.38-2.60 (m, 6H), 2.23-2.33 (m, 6H), 1.94-2.03 (m, 1H), 1.90 (q, J=6.44 Hz, 2H), 1.46-1.70 (m, 12H), 1.20-1.42 (m, 40H), 1.01 (t, J=6.66 Hz, 6H), 0.82-0.94 (m, 9H) ppm.

MS (M+1)=827.3, Rt=2.57 min (LC method 13).

Synthesis of Example 140

Intermediate 140a: 3-(1H-imidazol-1-yl)propyl (1-hydroxypentadecan-3-yl) carbonate

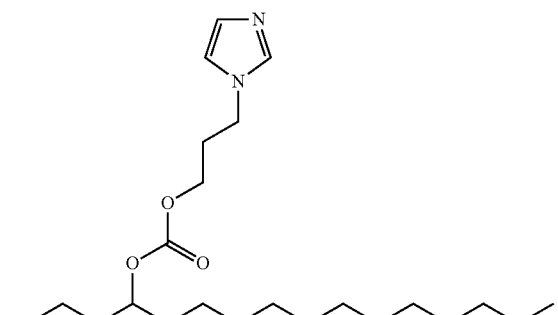

Intermediate 140a can be prepared using similar methods to those employed for the synthesis of intermediate 1k.

MS (M+1)=397.6, Rt=0.53 min (LC method 14).

Example 140

2-(5-((3-(((3-(1H-imidazol-1-yl)propoxy)carbonyl)oxy)pentadecyl)oxy)-5-oxopentyl)propane-13-diyl dioctanoate

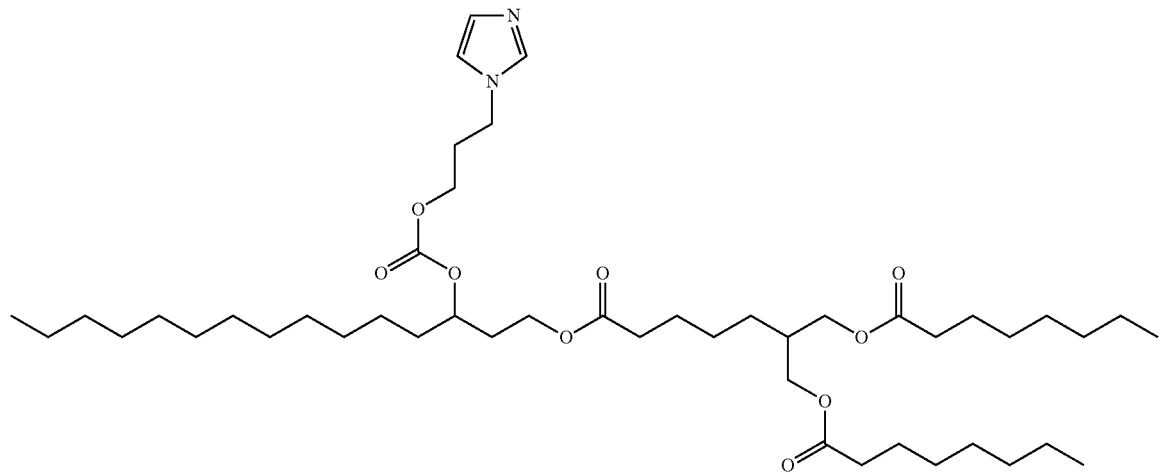 [SMILES: CCCCCCCCCCCCC(CCOC(=O)CCCCC(COC(=O)CCCCCCC)COC(=O)CCCCCCC)OC(=O)OCCCn1ccnc1]

Example 140 can be prepared using similar methods to those employed for the synthesis of example 1.

$^1$H NMR (400 MHz, CD$_2$Cl$_2$) δ=8.13 (br. s., 1H), 7.27 (br. s., 1H), 7.15 (br. s., 1H), 4.72-4.84 (m, 1H), 4.15-4.25 (m, 4H), 4.03 (dd, J=8.19, 5.75 Hz, 6H), 2.25-2.36 (m, 6H), 2.14-2.23 (m, 2H), 1.48-2.00 (m, 11H), 1.17-1.41 (m, 40H), 0.82-0.96 (m, 9H) ppm.

MS (M+1)=808.2, Rt=2.58 min (LC method 13).

Synthesis of Example 141

Intermediate 141a: 1-hydroxypentadecan-3-yl (3-(piperidin-1-yl)propyl) carbonate

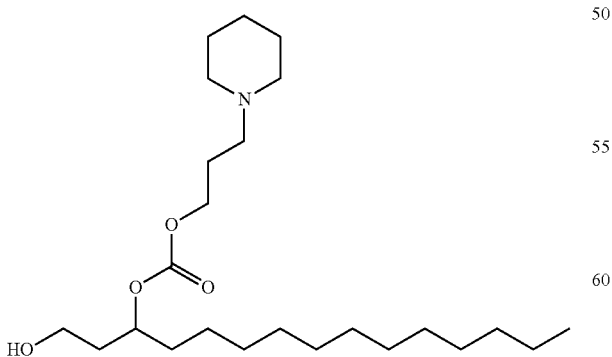

Intermediate 141a can be prepared using similar methods to those employed for the synthesis of intermediate 1k.

MS (M+1)=414.4, Rt=0.53 min (LC method 14).

Example 141

2-(5-oxo-5-((3-(((3-(piperidin-1-yl)propoxy)carbonyl)oxy)pentadecyl)oxy)pentyl)propane-1,3-diyl dioctanoate

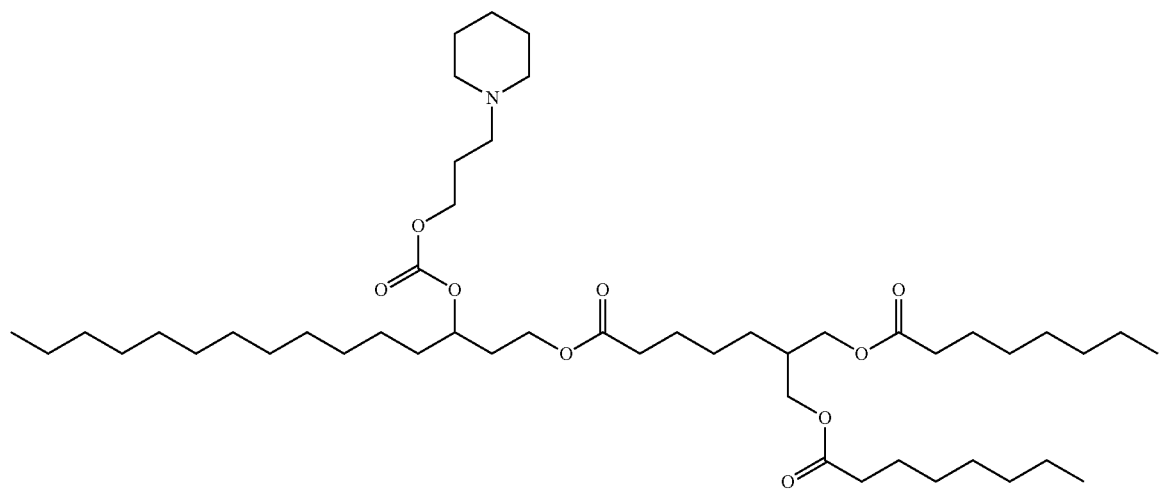 [SMILES: CCCCCCCCCCCCC(CCOC(=O)CCCCC(COC(=O)CCCCCCC)COC(=O)CCCCCCC)OC(=O)OCCCN1CCCCC1]

Example 141 can be prepared using similar methods to those employed for the synthesis of example 1.

$^1$H NMR (400 MHz, CD$_2$Cl$_2$) δ=4.77 (quin, J=6.24 Hz, 1H), 3.95-4.18 (m, 8H), 2.20-2.48 (m, 12H), 1.95-2.03 (m, 1H), 1.90 (m, J=6.40, 6.40, 6.40 Hz, 4H), 1.52-1.69 (m, 12H), 1.19-1.50 (m, 42H), 0.82-0.95 (m, 9H) ppm.

MS (M+1)=825.2, Rt=2.52 min (LC method 13).

Synthesis of Example 142

Intermediate 142a: 3-(benzyloxy)pentadecan-1-ol

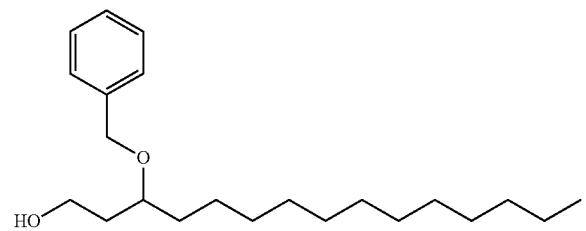 [SMILES: CCCCCCCCCCCCC(CCO)OCc1ccccc1]

To a solution of intermediate 1h (500 mg, 1.39 mmol) in anhydrous DMF (5 mL) at 0° under the presence of nitrogen was added 60% NaH in mineral oil (84 mg, 2.091 mmol). The resulting mixture was stirred at 0° C. for 30 min before benzyl bromide (0.249 mL, 2.091 mmol) was added. The reaction was allowed to warm to ambient temperature and stirred overnight. The reaction was quenched with 5 mL of sat. NH$_4$Cl and 10 mL of water, and diluted with 15 mL of DCM. The separated aq. layer was extracted with an additional 10 mL of DCM. The separated organic layers were combined and washed with 10 mL of water, dried over sodium sulfate, concentrated and purified by flash column chromatography (eluting with 0-50% EtOAc in heptane) to provide 450 mg of impure desired product. This material was used in the next step without further purification.

This compound (450 mg, 1.00 mmol) was then taken into MeOH in a vial charged with a magnetic stir bar. CAN (1.20 g, 2.20 mmol) was added in one portion. The reaction was allowed to stir at ambient temperature under nitrogen for ~1 hour, after which the desired product was the major product observed by LCMS. The reaction was quenched with sat. NaHCO$_3$ and the organics were extracted with DCM (×3). The combined organic layers were washed with brine, dried with Na$_2$SO$_4$, and purified by flash column chromatography (eluting with 0-50% EtOAc in heptane) to provide 30 mg of the desired product.

$^1$H NMR (400 MHz, CD$_2$Cl$_2$) δ=7.17-7.34 (m, 5H), 4.43 (s, 2H), 3.48-3.72 (m, 3H), 1.52-1.71 (m, 2H), 1.30-1.41 (m, 3H), 1.19 (br. s, 20H), 0.81 (t, J=1.00 Hz, 3H) ppm.

Intermediate 142b: 2-(5-((3-(benzyloxy)pentadecyl)oxy)-5-oxopentyl)propane-1,3-diyl dioctanoate

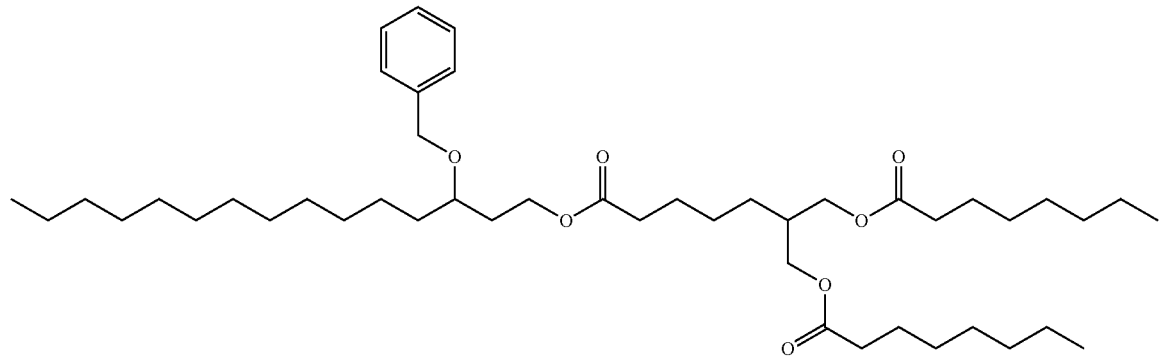 [SMILES: CCCCCCCCCCCCC(CCOC(=O)CCCCC(COC(=O)CCCCCCC)COC(=O)CCCCCCC)OCc1ccccc1]

Intermediate 142a (130 mg, 0.389 mmol), intermediate 1f (250 mg, 0.583 mmol), DMAP (18.99 mg, 0.155 mmol), and DIPEA (0.136 mL, 0.777 mmol) were taken into anhydrous dichloromethane (4 mL) in a vial. EDC.HCl (149 mg, 0.777 mmol) was added in one portion, and the reaction was stirred at ambient temperature over the weekend. The reaction was then diluted with $H_2O$ (10 mL) and DCM (10 mL). The organic layer was separated, and the aqueous layer was washed with DCM (100 mL). The combined organic layers were washed with brine (5 mL), dried with $Na_2SO_4$, filtered, and concentrated in vacuo to provide a crude orange oil. The crude oil was purified by flash column chromatography (eluting with 0-100% EtOAc:heptane) to provide 163 mg of the desired product as a yellow oil.

$^1$H NMR (400 MHz, $CD_2Cl_2$)) δ=7.24-7.39 (m, 5H), 5.00 (quin, J=1.00 Hz, 1H), 4.45 (s, 2H), 3.95-4.10 (m, 4H), 3.47 (td, J=6.42, 4.52 Hz, 2H), 2.20-2.31 (m, 6H), 1.92-2.01 (m, 1H), 1.79-1.87 (m, 2H), 1.51-1.65 (m, 8H), 1.19-1.42 (m, 40H), 0.88 (t, J=1.00 Hz, 9H) ppm.

Intermediate 142c: 2-(5-((1-hydroxypentadecan-3-yl)oxy)-5-oxopentyl)propane-1,3-diyl dioctanoate

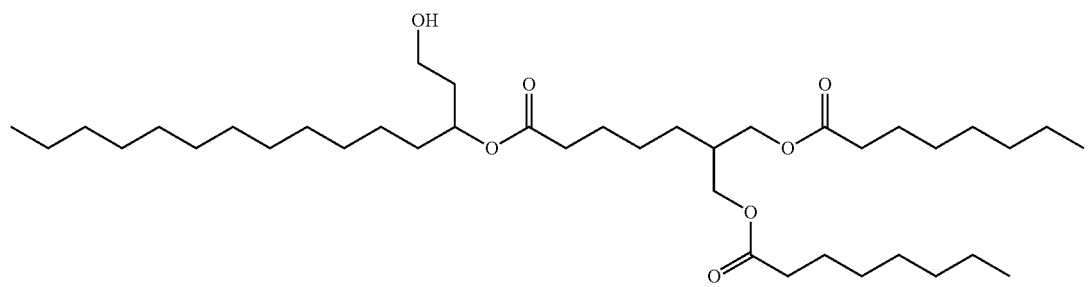 [SMILES: CCCCCCCCCCCCC(CCO)OC(=O)CCCCC(COC(=O)CCCCCCC)COC(=O)CCCCCCC]

A vial containing intermediate 142b (163 mg, 0.218 mmol) and a magnetic stir bar was evacuated and flushed with $N_2$ (×3). Next, 5% Pd/C (ca 50% H2O) was added in one portion, and the $N_2$ flush was repeated. EtOH was then added in one portion via syringe down the sides of the flask. The flask was placed under atmospheric $H_2$ pressure via a balloon and allowed to stir at room temperature for 1 h. The reaction was filtered and the filtrate was concentrated under reduced pressure, which afforded 123 mg of the desired product as a colorless oil.

$^1$H NMR (400 MHz, $CD_2Cl_2$) δ=4.95-5.03 (m, 1H), 3.98-4.08 (m, 4H), 3.44-3.61 (m, 2H), 2.26-2.35 (m, 6H), 1.94-2.02 (m, 1H), 1.73-1.84 (m, 1H), 1.51-1.69 (m, 10H), 1.34-1.41 (m, 4H), 1.20-1.33 (m, 36H), 0.84-0.91 (m, 9H) ppm.

Intermediate 142d: 2-(5-((1-(((4-nitrophenoxy)carbonyl)oxy)pentadecan-3-yl)oxy)-5-oxopentyl)propane-1,3-diyl dioctanoate

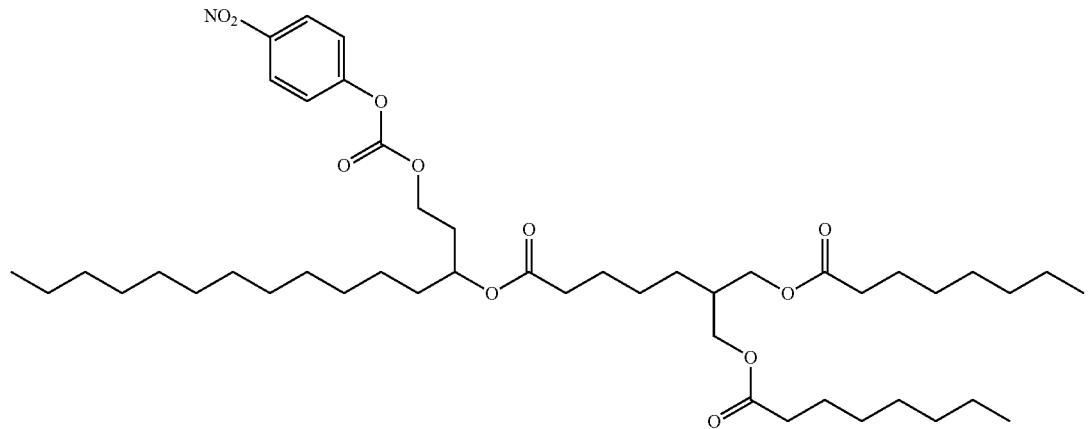 [SMILES: CCCCCCCCCCCCC(CCOC(=O)Oc1ccc([N+](=O)[O-])cc1)OC(=O)CCCCC(COC(=O)CCCCCCC)COC(=O)CCCCCCC]

Intermediate 142c (120 mg, 0.183 mmol) was taken into DCM (3 mL) in a vial charged with a magnetic stir bar. 4-nitrophenyl carbonochloridate was added in one portion. The reaction was capped and placed under nitrogen, after which pyridine was added dropwise via syringe. The reaction was allowed to stir at ambient temperature overnight. The reaction was diluted with H$_2$O (5 mL) and DCM (5 mL). The organic layer was separated, and the aqueous layer was washed with DCM (5 mL). The combined organic layers were washed with brine (10 mL), dried with Na$_2$SO$_4$, concentrated, and purified by flash column chromatography (eluting with 0-50% EtOAc in heptane) to provide 126 mg of the desired product as a white wet solid (contained minor aromatic impurities).

$^1$H NMR (400 MHz, CD$_2$Cl$_2$) δ=8.22-8.32 (m, 2H), 7.33-7.44 (m, 2H), 4.97-5.08 (m, 1H), 4.25-4.36 (m, 2H), 3.94-4.09 (m, 4H), 2.21-2.37 (m, 6H), 1.88-2.07 (m, 3H), 1.49-1.68 (m, 8H), 1.19-1.43 (m, 40H), 0.88 (t, J=1.00 Hz, 9H) ppm.

Example 142

2-(12-dodecyl-3-ethyl-8,14-dioxo-7,9,13-trioxa-3-azaoctadecan-18-yl)propane-1,3-diyl dioctanoate

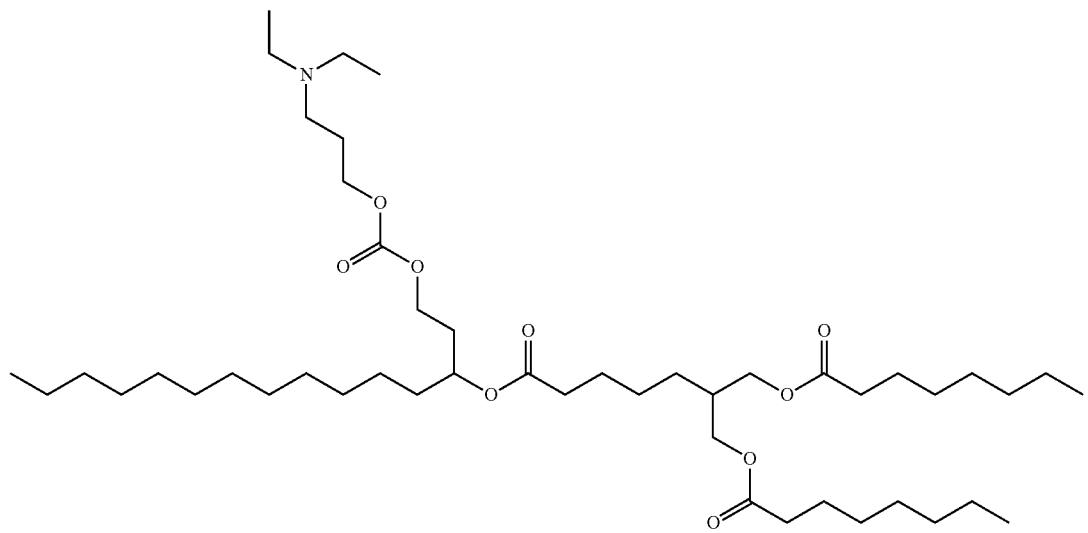 [SMILES: CCCCCCCCCCCCC(CCOC(=O)OCCCN(CC)CC)OC(=O)CCCCC(COC(=O)CCCCCCC)COC(=O)CCCCCCC]

3-(diethylamino)propan-1-ol in 1 mL of anhydrous ACN was added dropwise to a solution of Intermediate 142d (50 mg, 0.061 mmol) in ACN (1 mL) in a vial charged with a magnetic stir bar under $N_2$. Next, pyridine was added via syringe, followed by the addition of DMAP (1.49 mg, 0.012 mmol) (dissolved in 0.1 mL of MeCN) in one portion. The reaction was allowed to stir at ambient temperature overnight. The crude mixture was then diluted with 10 mL of water and extracted with DCM (2×10 mL). The combined organic layers were dried over sodium sulfate, concentrated, and purified by flash column chromatography (eluting with 0-100% EtOAc in heptane) to provide 28 mg of the desired product as a colorless oil.

$^1$H NMR (400 MHz, $CD_2Cl_2$) δ=4.90-5.00 (m, 1H), 4.09-4.17 (m, 4H), 3.94-4.08 (m, 4H), 2.47 (q, J=7.30 Hz, 6H), 2.28 (t, J=7.52 Hz, 6H), 1.71-2.02 (m, 5H), 1.49-1.66 (m, 8H), 1.34-1.41 (m, 4H), 1.19-1.34 (m, 36H), 0.98 (t, J=7.09 Hz, 6H), 0.84-0.93 (m, 9H) ppm.

MS (M+1)=813.2, Rt=2.61 min (LC method 13).

siRNA Lipid Formulations

The lipid nanoparticles (LNPs) were formed by mixing equal volumes of lipids dissolved in alcohol with siRNA dissolved in a citrate buffer by an impinging jet process. The lipid solution contains a cationic lipid compound of the invention, a helper lipid (cholesterol), an optional neutral lipid (DSPC) and a PEG (PEG) lipid at a concentration of 8-16 mg/mL with a target of 12 mg/mL in an alcohol. The siRNA to total lipid ratio is approximately 0.05 (wt/wt). Where a LNP formulation contains four lipid components, the molar ratios of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate: sodium chloride buffer pH 4-6, with a target of 4.5-5.5. The LNPs are formed by mixing equal volumes of lipid solution in ethanol with siRNA dissolved in a citrate buffer by an impinging jet process through a mixing device with ID ranging from 0.25 to 2.0 mm at a flow rate from 10 to 640 mL/min. The mixed LNP solution is held at room temperature for 0-24 hrs prior to a dilution step. The solution is then concentrated and diafiltered with suitable buffer by ultrafiltration or dialysis process using membranes with a MW cutoff from 30 to 500 KD. The final product is sterile filtered and stored at 4° C.

siRNA's

The siRNA used in the lipid nanoparticles described was made up of double stranded siRNA sequences specific to a target mRNA sequence.

1. FVII siRNA duplex sequence

```
                                      (SEQ ID NO: 1)
       5' UUu AAU UGA AAC cAA GAc Auu 3'

(SEQ ID NO: 2)
       5' uGu cuu GGu uuc AAu uAA Auu 3'
```

2. PLK1-424 siRNA duplex sequence

```
                                      (SEQ ID NO: 3)
       5' UAU UUA AgG AGG GUG AuC Uuu 3'

(SEQ ID NO: 4)
       5' AGA Uca cCC Ucc uuA AAU auu 3'
```

The following abbreviations are used in these sequences:
A=adenosine
U=uridine
G=guanosine
C=cytosine
a=2'-O-methyl-adenosine
u=2'-O-methyl-uridine
g=2'-O-methyl-guanosine
c=2'-O-methyl-cytosine
Plasmid's pcDNA3.1(-)Neo from LifeTechnologies Cat# V795-20

```
                                      (SEQ ID NO: 5)
GACGGATCGGGAGATCTCCCGATCCCCTATGGTGCACTCTCAGTACAATC
TGCTCTGATGCCGCATAGTTAAGCCAGTATCTGCTCCCTGCTTGTGTGTT
GGAGGTCGCTGAGTAGTGCGCGAGCAAAATTTAAGCTACAACAAGGCAAG
GCTTGACCGACAATTGCATGAAGAATCTGCTTAGGGTTAGGCGTTTTGCG
CTGCTTCGCGATGTACGGGCCAGATATACGCGTTGACATTGATTATTGAC
TAGTTATTAATAGTAATCAATTACGGGGTCATTAGTTCATAGCCCATATA
TGGAGTTCCGCGTTACATAACTTACGGTAAATGGCCCGCCTGGCTGACCG
CCCAACGACCCCCGCCCATTGACGTCAATAATGACGTATGTTCCCATAGT
AACGCCAATAGGGACTTTCCATTGACGTCAATGGGTGGAGTATTTACGGT
AAACTGCCCACTTGGCAGTACATCAAGTGTATCATATGCCAAGTACGCCC
CCTATTGACGTCAATGACGGTAAATGGCCCGCCTGGCATTATGCCCAGTA
CATGACCTTATGGGACTTTCCTACTTGGCAGTACATCTACGTATTAGTCA
TCGCTATTACCATGGTGATGCGGTTTTGGCAGTACATCAATGGGCGTGGA
TAGCGGTTTGACTCACGGGGATTTCCAAGTCTCCACCCCATTGACGTCAA
TGGGAGTTTGTTTTGGCACCAAAATCAACGGGACTTTCCAAAATGTCGTA
ACAACTCCGCCCCATTGACGCAAATGGGCGGTAGGCGTGTACGGTGGGAG
GTCTATATAAGCAGAGCTCTCTGGCTAACTAGAGAACCCACTGCTTACTG
GCTTATCGAAATTAATACGACTCACTATAGGGAGACCCAAGCTGGCTAGC
GTTTAAACGGGCCCTCTAGATCGAGCGGCCGCCACTGTGCTGGATATCT
GCAGAATTCCACCACACTGGACTAGTGGATCCGAGCTCGGTACCAAGCTT
AAGTTTAAACCGCTGATCAGCCTCGACTGTGCCTTCTAGTTGCCAGCCAT
CTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGG
AGGATTGGGAAGACAATAGCAGGCATGCTGGGGATGCGGTGGGCTCTATG
GCTTCTGAGGCGGAAAGAACCAGCTGGGGCTCTAGGGGGTATCCCCACGC
GCCCTGTAGCGGCGCATTAAGCGCGGCGGGTGTGGTGGTTACGCGCAGCG
TGACCGCTACACTTGCCAGCGCCCTAGCGCCCGCTCCTTTCGCTTTCTTC
```

```
CCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCA
AAAAACTTGATTAGGGTGATGGTTCACGTAGTGGGCCATCGCCCTGATAG
ACGGTTTTTCGCCCTTTGACGTTGGAGTCCACGTTCTTTAATAGTGGACT
CTTGTTCCAAACTGGAACAACACTCAACCCTATCTCGGTCTATTCTTTTG
ATTTATAAGGGATTTTGCCGATTTCGGCCTATTGGTTAAAAAATGAGCTG
ATTTAACAAAAATTTAACGCGAATTAATTCTGTGGAATGTGTGTCAGTTA
GGGTGTGGAAAGTCCCCAGGCTCCCCAGCAGGCAGAAGTATGCAAAGCAT
GCATCTCAATTAGTCAGCAACCAGGTGTGGAAAGTCCCCAGGCTCCCCAG
CAGGCAGAAGTATGCAAAGCATGCATCTCAATTAGTCAGCAACCATAGTC
CCGCCCCTAACTCCGCCCATCCCGCCCCTAACTCCGCCCAGTTCCGCCCA
TTCTCCGCCCCATGGCTGACTAATTTTTTATTTATGCAGAGGCCGAGGCC
GCCTCTGCCTCTGAGCTATTCCAGAAGTAGTGAGGAGGCTTTTTTGGAGG
CCTAGGCTTTTGCAAAAAGCTCCCGGGAGCTTGTATATCCATTTTCGGAT
CTGATCAAGAGACAGGATGAGGATCGTTTCGCATGATTGAACAAGATGGA
TTGCACGCAGGTTCTCCGGCCGCTTGGGTGGAGAGGCTATTCGGCTATGA
CTGGGCACAACAGACAATCGGCTGCTCTGATGCCGCCGTGTTCCGGCTGT
CAGCGCAGGGGCGCCCGGTTCTTTTTGTCAAGACCGACCTGTCCGGTGCC
CTGAATGAACTGCAGGACGAGGCAGCGCGGCTATCGTGGCTGGCCACGAC
GGGCGTTCCTTGCGCAGCTGTGCTCGACGTTGTCACTGAAGCGGGAAGGG
ACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCT
GCATACGCTTGATCCGGCTACCTGCCCATTCGACCACCAAGCGAAACATC
GCATCGAGCGAGCACGTACTCGGATGGAAGCCGGTCTTGTCGATCAGGAT
GATCTGGACGAAGAGCATCAGGGGCTCGCGCCAGCCGAACTGTTCGCCAG
GCTCAAGGCGCGCATGCCCGACGGCGAGGATCTCGTCGTGACCCATGGCG
ATGCCTGCTTGCCGAATATCATGGTGGAAAATGGCCGCTTTTCTGGATTC
ATCGACTGTGGCCGGCTGGGTGTGGCGGACCGCTATCAGGACATAGCGTT
GGCTACCCGTGATATTGCTGAAGAGCTTGGCGGCGAATGGGCTGACCGCT
TCCTCGTGCTTTACGGTATCGCCGCTCCCGATTCGCAGCGCATCGCCTTC
TATCGCCTTCTTGACGAGTTCTTCTGAGCGGGACTCTGGGGTTCGAAATG
ACCGACCAAGCGACGCCCAACCTGCCATCACGAGATTTCGATTCCACCGC
CGCCTTCTATGAAAGGTTGGGCTTCGGAATCGTTTTCCGGGACGCCGGCT
GGATGATCCTCCAGCGCGGGGATCTCATGCTGGAGTTCTTCGCCCACCCC
AACTTGTTTATTGCAGCTTATAATGGTTACAAATAAAGCAATAGCATCAC
AAATTTCACAAATAAAGCATTTTTTTCACTGCATTCTAGTTGTGGTTTGT
CCAAACTCATCAATGTATCTTATCATGTCTGTATACCGTCGACCTCTAGC
TAGAGCTTGGCGTAATCATGGTCATAGCTGTTTCCTGTGTGAAATTGTTA
TCCGCTCACAATTCCACACAACATACGAGCCGGAAGCATAAAGTGTAAAG
CCTGGGGTGCCTAATGAGTGAGCTAACTCACATTAATTGCGTTGCGCTCA
CTGCCCGCTTTCCAGTCGGGAAACCTGTCGTGCCAGCTGCATTAATGAAT

CGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAA
CGCAGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAG
CATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTG
TTCCGACCCTGCCGCTTACCGGATACCTGTCCGCCTTTCTCCCTTCGGGA
AGCGTGGCGCTTTCTCATAGCTCACGCTGTAGGTATCTCAGTTCGGTGTA
GGTCGTTCGCTCCAAGCTGGGCTGTGTGCACGAACCCCCCGTTCAGCCCG
ACCGCTGCGCCTTATCCGGTAACTATCGTCTTGAGTCCAACCCGGTAAGA
CACGACTTATCGCCACTGGCAGCAGCCACTGGTAACAGGATTAGCAGAGC
GAGGTATGTAGGCGGTGCTACAGAGTTCTTGAAGTGGTGGCCTAACTACG
GCTACACTAGAAGAACAGTATTTGGTATCTGCGCTCTGCTGAAGCCAGTT
ACCTTCGGAAAAAGAGTTGGTAGCTCTTGATCCGGCAAACAAACCACCGC
TGGTAGCGGTTTTTTTGTTTGCAAGCAGCAGATTACGCGCAGAAAAAAAG
GATCTCAAGAAGATCCTTTGATCTTTTCTACGGGGTCTGACGCTCAGTGG
AACGAAAACTCACGTTAAGGGATTTTGGTCATGAGATTATCAAAAAGGAT
CTTCACCTAGATCCTTTTAAATTAAAAATGAAGTTTTAAATCAATCTAAA
GTATATATGAGTAAACTTGGTCTGACAGTTACCAATGCTTAATCAGTGAG
GCACCTATCTCAGCGATCTGTCTATTTCGTTCATCCATAGTTGCCTGACT
CCCCGTCGTGTAGATAACTACGATACGGGAGGGCTTACCATCTGGCCCCA
GTGCTGCAATGATACCGCGAGACCCACGCTCACCGGCTCCAGATTTATCA
GCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAGTAA
GTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTC
CCAACGATCAAGGCGAGTTACATGATCCCCCATGTTGTGCAAAAAAGCGG
TTAGCTCCTTCGGTCCTCCGATCGTTGTCAGAAGTAAGTTGGCCGCAGTG
TTATCACTCATGGTTATGGCAGCACTGCATAATTCTCTTACTGTCATGCC
ATCCGTAAGATGCTTTTCTGTGACTGGTGAGTACTCAACCAAGTCATTCT
GAGAATAGTGTATGCGGCGACCGAGTTGCTCTTGCCCGGCGTCAATACGG
GATAATACCGCGCCACATAGCAGAACTTTAAAAGTGCTCATCATTGGAAA
ACGTTCTTCGGGGCGAAAACTCTCAAGGATCTTACCGCTGTTGAGATCCA
GTTCGATGTAACCCACTCGTGCACCCAACTGATCTTCAGCATCTTTTACT
TTCACCAGCGTTTCTGGGTGAGCAAAAACAGGAAGGCAAAATGCCGCAAA
AAAGGGAATAAGGGCGACACGGAAATGTTGAATACTCATACTCTTCCTTT
TTCAATATTATTGAAGCATTTATCAGGGTTATTGTCTCATGAGCGGATAC
ATATTTGAATGTATTTAGAAAAATAAACAAATAGGGGTTCCGCGCACATT
TCCCCGAAAAGTGCCACCTGACGTC
``` pGEM-T7o-TEV-hLeptin-GAopt-2xhBG-120A sequence
(SEQ ID NO: 6)

GATCCGGAGGCCGGAGAATTGTAATACGACTCACTATAGGGAGACGCGTG
TTAAATAACAAATCTCAACACAACATATACAAAACAAACGAATCTCAAGC
AATCAAGCATTCTACTTCTATTGCAGCAATTTAAATCATTTCTTTTAAAG
CAAAAGCAATTTTCTGAAAATTTTCACCATTTACGAACGATAGCCGCCAC
CATGCACTGGGGAACCCTGTGCGGATTCCTGTGGCTGTGGCCCTACCTGT
TCTATGTGCAAGCCGTGCCCATCCAGAAGGTGCAGGACGACACCAAGACC
CTGATCAAGACCATCGTGACCCGGATCAACGACATCAGCCACACCCAGAG
CGTGTCCAGCAAGCAGAAAGTGACCGGCCTGGACTTCATCCCCGGCCTGC
ACCCTATCCTGACCCTGTCCAAGATGGACCAGACCCTGGCCGTGTACCAG
CAGATCCTGACCAGCATGCCCAGCCGGAACGTGATCCAGATCAGCAACGA
CCTGGAAAACCTGCGGGACCTGCTGCACGTGCTGGCCTTCAGCAAGAGCT
GCCATCTGCCTTGGGCCAGCGGCCTGGAAACCCTGGATTCTCTGGGCGGA
GTGCTGGAAGCCAGCGGCTACTCTACAGAGGTGGTGGCCCTGAGCAGACT
GCAGGGCAGCCTGCAGGATATGCTGTGGCAGCTGGATCTGAGCCCCGGCT
GCTAATAGCGGACCGGCGATAGATGAAGCTCGCTTTCTTGCTGTCCAATT
TCTATTAAAGGTTCCTTTGTTCCCTAAGTCCAACTACTAAACTGGGGGAT
ATTATGAAGGGCCTTGAGCATCTGGATTCTGCCTAATAAAAAACATTTAT
TTTCATTGCAGCTCGCTTTCTTGCTGTCCAATTTCTATTAAAGGTTCCTT
TGTTCCCTAAGTCCAACTACTAAACTGGGGGATATTATGAAGGGCCTTGA
GCATCTGGATTCTGCCTAATAAAAAACATTTATTTTCATTGCGGCCGCAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAGAAGAGCAAGCTTTCGATAGCGCTGTTCGTAG
AAAAAAAAGAAGTAAATAATTACTACTTGCCATATAGACTAAATAGCTGC
GCNTAATACATCTACACTTTCTANNATTGACAAGTGATACGTTGCAAAAG
GAGCAACACCCCACAGACTCGATGACTGCGCAGTCATACAGTGAAATTGC
CCTAATGTCTTACCTCTGAAAGGGCTAAACGAAAGTAGAGCACTATTCCG
CGTAGCTATTTAGTGCGATCTTTTAGAAATATCAGCCCAGAGAGCTGGGC
TGATAAATATTTTATCCGACAAGACGAATTTTGCTCAAATGAGTTAAAAC
GATGCTACCACTATCTGCTGCTTTTACGAGATCAGCCCACCATTGCATCA
TCGGACGACGTTGCTCAAGATAATCACTGCGGTTATAAGCGCGACGCACC
TCATTTTGTCTACATGAGCAAGCGCTGCTTCAATGACATCAGGTGGAAA
TCCTTCCTCATTGAGTGCCGTACTGGCGATAGAACGCAAGCCGTGTGAAA
CAAGTACACCTCCTAAGCCAGCACGCTTGAGTGCTGCATTCACTGTTTGG
CTATTCATTGGTTGGTTGGGCTTGATACGGCTAGGAAAGATAAATTCTCG
GCCACCACTGAGAGGCTTCATCATTTCCAGAATAGCAAGAGCCCCATCAG
ATAGTGGAACCGTATGGTCCCGGTTCATCTTCATTCGAGCTGCAGGAATT
TTCCATTCGCTAGCATTGAAATCGATCTCATCCCATCGAGCCTCAGCAGC
TTCGGCAGGGCGGGTGATGGTTAGAAGTTGCCACATGAACAGGCATCTTG
TGGACATGCTGATACTTGCCGTACGCATGGTGTGCATTAGCTGCGGAAGT
TGATCCGGCCGGATGCTTGGCATGTTTTCTTTTGCGGTTTCTCGAAAGC
TTGAGTATTCTATAGTGTCACCTAAATAGCTTGGCGTAATCATGGTCATA
GCTGTTTCCTGTGTGAAATTGTTATCCGCTCACAATTCCACACAACATAC
GAGCCGGAAGCATAAAGTGTAAAGCCTGGGGTGCCTAATGAGTGAGCTAA
CTCACATTAATTGCGTTGCGCTCACTGCCCGCTTTCCAGTCGGGAAACCT
GTCGTGCCAGCTGCATTAATGAATCGGCCAACGCGCGGGGAGAGGCGGTT
TGCGTATTGGGCGCTATTCCGCTTCCTCGCTCACTGACTCGCTGCGCTCG
GTCGTTCGGCTGCGGCGAGCGGTATCAGCTCACTCAAAGGCGGTAATACG
GTTATCCACAGAATCAGGGGATAACGCAGGAAAGAACATGTGAGCAAAAG
GCCAGCAAAAGGCCAGGAACCGTAAAAAGGCCGCGTTGCTGGCGTTTTTC
GATAGGCTCCGCCCCCCTGACGAGCATCACAAAAATCGACGCTCAAGTCA
GAGGTGGCGAAACCCGACAGGACTATAAAGATACCAGGCGTTTCCCCCTG
GAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACG
CTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTAT
CGTCTTGAGTCCAACCCGGTAAGACACGACTTATCGCCACTGGCAGCAGC
CACTGGTAACAGGATTAGCAGAGCGAGGTATGTAGGCGGTGCTACAGAGT
TCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAAATT
AAAAATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTACGA
TACGGGAGGGCTTACCATCTGGCCCCAGTGCTGCAATGATACCGCGAGAC
CCACGCTCACCGGCTCCAGATTTATCAGCAATAAACCAGCCAGCCGGAAG
GGCCGAGCGCAGAAGTGGTCCTGCAACTTTATCCGCCTCCATCCAGTCTA
TTAATTGTTGCCGGGAAGCTAGAGTAAGTAGTTCGCCAGTTAATAGTTTG
CGCAACGTTGTTGGCATTGCTACAGGCATCGTGGTGTCACGCTCGTCGTT
TGGTATGGCTTCATTCAGCTCCGGTTCCCAACGATCAAGGCGAGTTACAT
GATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGC
ACTGCATAATTCTCTTACTGTCATGCCATCCGTAAGATGCTTTTCTGTGA
CTGGTGAGTACTCAACCAAGTCATTCTGAGAATAGTGTATGCGGCGACCG
AGTTGCTCTTGCCCGGCGTCAATACGGGATAATACCGCGCCACATAGCAG
AACTTTAAAAGTGCTCATCATTGGAAAACGTTCTTCGGGGCGAAAACTCT
CAAGGATCTTACCGCTGTTGAGATCCAGTTCGATGTAACCCACTCGTGCA

-continued

```
CCCAACTGATCTTCAGCATCTTTTACTTTCACCAGCGTTTCTGGGTGAGC

AAAAACAGGAAGGCAAAATGCCGCAAAAAAGGGAATAAGGGCGACACGGA

AATGTTGAATACTCATACTCTTCCTTTTTCAATATTATTGAAGCATTTAT

CAGGGTTATTGTCTCATGAGCGGATACATATTTGAATGTATTTAGAAAAA

TAAACAAATAGGGGTTCCGCGCACATTTCCCCGAAAAGTGCCACCTGACG

TCTAAGAAACCATTATTATCATGACATTAACCTATAAAAATAGGCGTATC

ACGAGGCCCTTTCGTCTCGCGCGTTTCGGTGATGACGGTGAAAACCTCTG

ACACATGCAGCTCCCGGAGACGGTCACAGCTTGTCTGTAAGCGGATGCCG

GGAGCAGACAAGCCCGTCAGGGCGCGTCAGCGGGTGTTGGCGGGTGTCGG

GGCTGGCTTAACTATGCGGCATCAGAGCAGATTGTACTGAGAGTGCACCA

TAAATTCGAGCTCGGTACCCGGG
``` mRNA's
Brief Description of mRNA Transcription Protocol

A circular plasmid DNA template is constructed that contains a mRNA transcription cassette consisting of the following features: a consensus T7 bacteriophage DNA-dependent RNA polymerase promoter, a 5' untranslated region (UTR), a Kozak sequence, and open reading frame, a 3' UTR, and a 120 nucleotide long polyadenosine (polyA120) tail (SEQ ID NO: 13). The plasmid DNA template is propagated in E. coli, isolated, and linearized by restriction enzyme digest immediately 3' of the poly120 tail. The plasmid DNA is combined with T7 RNA polymerase, ribonucleotide triphosphates, RNase inhibitor, pyrophosphatase enzyme, dithiothreitol, spermidine, and enzyme reaction buffer and is incubated for 1 hour at 37° C. DNase I enzyme is added to digest the plasmid DNA template and is incubated for 0.5 hours at 37° C. mRNA is isolated by sequential precipitation with lithium chloride, washing of the pellet in 70% ethanol, resuspension of the mRNA pellet in water, re-precipitation with isopropanol and sodium acetate, and washing of the pellet again in 70% ethanol. The final mRNA pellet is resuspended in water.

TEV-hLeptin-GAopt-2xhBG-120A

Sequence features:

Tobacco Etch Virus (TEV) 5' UTR: 14-154

Optimal Kozak sequence: 155-163

Human leptin encoding amino acids 1-167 of Protein Accession # NP_000221, sequence codon optimized by GeneArt: 164-664

2 stop codons: 665-670

2 copies of human beta-globin 3'UTR: 689-954

120 nucleotide polyA tail: 961-1080

(SEQ ID NO: 7)
```
GGGAGACGCGUGUUAAAUAACAAAUCUCAACACAACAUAUACAAAACAAA

CGAAUCUCAAGCAAUCAAGCAUUCUACUUCUAUUGCAGCAAUUUAAAUCA

UUUCUUUUAAAGCAAAAGCAAUUUUCUGAAAAUUUUCACCAUUUACGAAC

GAUAGCCGCCACCAUGCACUGGGGAACCCUGUGCGGAUUCCUGUGGCUGU

GGCCCUACCUGUUCUAUGUGCAAGCCGUGCCCAUCCAGAAGGUGCAGGAC

GACACCAAGACCCUGAUCAAGACCAUCGUGACCCGGAUCAACGACAUCAG

CCACACCCAGAGCGUGUCCAGCAAGCAGAAAGUGACCGGCCUGGACUUCA

UCCCCGGCCUGCACCCUAUCCUGACCCUGUCCAAGAUGGACCAGACCCUG

GCCGUGUACCAGCAGAUCCUGACCAGCAUGCCCAGCCGGAACGUGAUCCA

GAUCAGCAACGACCUGGAAAACCUGCGGGACCUGCUGCACGUGCUGGCCU

UCAGCAAGAGCUGCCAUCUGCCUUGGGCCAGCGGCCUGGAAACCCUGGAU

UCUCUGGGCGGAGUGCUGGAAGCCAGCGGCUACUCUACAGAGGUGGUGGC

CCUGAGCAGACUGCAGGGCAGCCUGCAGGAUAUGCUGUGGCAGCUGGAUC

UGAGCCCCGGCUGCUAAUAGCGGACCGGCGAUAGAUGAAGCUCGCUUUCU

UGCUGUCCAAUUUCUAUUAAAGGUUCCUUUGUUCCCUAAGUCCAACUACU

AAACUGGGGAUAUUAUGAAGGGCCUUGAGCAUCUGGAUUCUGCCUAAUA
```

| Reagent | Concentration | Notes |
|---|---|---|
| Nuclease-free water | Remaining volume | To make 100% PsU mRNA, do not include UTP in reaction. To make 100% unmodified mRNA, do not include PsU in reaction |
| Tris-HCl pH 8.0 (mM) | 40 | |
| MgCl₂ (mM) | 20 | |
| ATP, CTP, GTP, UTP (mM) | 4 | |
| Pseudouridine (mM) | 4 | |
| DTT (mM) | 10 | |
| Spermidine (mM) | 2 | |
| Linearized plasmid DNA (ug/ul) | 0.05 | |
| Pyrophosphatase (U/ul) | 0.004 | |
| RNase inhibitor (U/ul) | 1 | |
| T7 RNA polymerase (U/ul) | 5 | |
| DNase I (U/ul) | 0.04 | |

-continued

AAAAACAUUUAUUUCAUUGCAGCUCGCUUUCUUGCUGUCCAAUUUCUAU

UAAAGGUUCCUUUGUUCCCUAAGUCCAACUACUAAACUGGGGGAUAUUAU

GAAGGGCCUUGAGCAUCUGGAUUCUGCCUAAUAAAAAACAUUUAUUUUCA

UUGCGGCCGCAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAA

TEV-mEpo(NcoI)-2xhBG-120A
Sequence features:

Tobacco Etch Virus (TEV) 5' UTR: 14-154

Optimal Kozak sequence: 155-163

Mouse erythropoietin encoding amino acids 1-191 of

Protein Accession # NP_031968, sequence codon optimized by GeneArt: 164-739

Stop codons: 740-742

2 copies of human beta-globin 3'UTR: 743-1008

120 nucleotide polyA tail: 1009-1128

(SEQ ID NO: 8)
GGGAGACGCGUGUUAAAUAACAAAUCUCAACACAACAUAUACAAAACAAA

CGAAUCUCAAGCAAUCAAGCAUUCUACUUCUAUUGCAGCAAUUUAAAUCA

UUUCUUUUAAAGCAAAAGCAAUUUUCUGAAAAUUUUCACCAUUUACGAAC

GAUAGCCGCCACCAUGGGCGUGCCCGAAAGACCUACACUCCUGCUGCUGC

UGUCACUGCUGCUGAUCCCUCGGGCCUGCCUGUGCUGUGUGCCCCCCCU

AGACUGAUCUGCGACAGCAGAGUGCUGGAACGGUACAUCCUGGAAGCCAA

AGAGGCCGAGAACGUGACGAUGGGAUGUGCCGAGGGCCCCAGACUGAGCG

AGAACAUCACCGUGCCCGACACCAAAGUGAACUUCUACGCCUGGAAGCGG

AUGGAAGUGGAAGAACAGGCCAUCGAAGUGUGGCAGGGCCUGAGCCUGCU

GAGCGAGGCUAUUCUGCAGGCACAGGCUCUGCUGGCCAACAGCAGCCAGC

CUCCUGAGACACUGCAGCUGCACAUCGACAAGGCCAUCAGCGGCCUGAGA

AGCCUGACCUCCCUGCUGAGGGUGCUGGGAGCCCAGAAAGAACUGAUGAG

CCCCCCUGACACCACCCCCCCUGCUCCUCUGAGAACUCUGACCGUGGACA

CCUUCUGCAAGCUGUUCCGGGUGUACGCCAACUUCCUGCGGGGCAAGCUG

AAGCUGUACACCGGCGAAGUGUGCAGACGGGGCGACAGAUGAAGCUCGCU

UUCUUGCUGUCCAAUUUCUAUUAAAGGUUCCUUUGUUCCCUAAGUCCAAC

UACUAAACUGGGGGAUAUUAUGAAGGGCCUUGAGCAUCUGGAUUCUGCCU

AAUAAAAAACAUUUAUUUUCAUUGCAGCUCGCUUUCUUGCUGUCCAAUUU

CUAUUAAAGGUUCCUUUGUUCCCUAAGUCCAACUACUAAACUGGGGGAUA

UUAUGAAGGGCCUUGAGCAUCUGGAUUCUGCCUAAUAAAAAACAUUUAUU

UUCAUUGCAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAA

TEV-hFIX-GAopt-2xhBG-120A

Sequence features:

Tobacco Etch Virus (TEV) 5' UTR: 14-154

Optimal Kozak sequence: 155-163

Human factor IX encoding amino acids 1-461 of

Protein Accession # NP_000124, sequence codon optimized by GeneArt: 164-1962

2 stop codons: 1547-1552

2 copies of human beta-globin 3'UTR: 1571-1836

120 nucleotide polyA tail: 1843-1962

(SEQ ID NO: 9)
GGGAGACGCGUGUUAAAUAACAAAUCUCAACACAACAUAUACAAAACAAA

CGAAUCUCAAGCAAUCAAGCAUUCUACUUCUAUUGCAGCAAUUUAAAUCA

UUUCUUUUAAAGCAAAAGCAAUUUUCUGAAAAUUUUCACCAUUUACGAAC

GAUAGCCGCCACCAUGCAGCGCGUGAACAUGAUUAUGGCCGAGAGCCCUG

GCCUGAUCACCAUCUGCCUGCUGGGCUACCUGCUGAGCGCCGAGUGCACC

GUGUUUCUGGACCACGAGAACGCCAACAAGAUCCUGAACCGGCCCAAGCG

GUACAACAGCGGCAAGCUGGAAGAGUUCGUGCAGGGCAACCUGGAACGCG

AGUGCAUGGAAGAGAAGUGCAGCUUCGAAGAGGCCAGAGAGGUGUUCGAG

AACACCGAGCGGACCACCGAGUUCUGGAAGCAGUACGUGGACGGCGACCA

GUGCGAGAGCAACCCCUGUCUGAAUGGCGGCAGCUGCAAGGACGACAUCA

ACAGCUACGAGUGCUGGUGCCCCUUCGGCUUCGAGGGCAAGAACUGCGAG

CUGGACGUGACCUGCAACAUCAAGAACGGCAGAUGCGAGCAGUUCUGCAA

GAACAGCGCCGACAACAAGGUCGUGUGCUCCUGCACCGAGGGCUACAGAC

UGGCCGAGAACCAGAAGUCCUGCGAGCCCGCCGUGCCUUUCCCAUGUGGA

AGAGUGUCCGUGUCCCAGACCAGCAAGCUGACCAGAGCCGAGACAGUGUU

CCCCGACGUGGACUACGUGAACAGCACCGAGGCCGAGACAAUCCUGGACA

ACAUCACCCAGAGCACCCAGUCCUUCAACGACUUCACCAGAGUCGUGGGC

GGCGAGGAUGCCAAGCCUGGACAGUUCCCGUGGCAGGUGGUGCUGAACGG

AAAGGUGGACGCCUUUUGCGGCGGCAGCAUCGUGAACGAGAAGUGGAUCG

UGACAGCCGCCCACUGCGUGGAAACCGGCGUGAAGAUUACAGUGGUGGCC

GGCGAGCACAACAUCGAGGAAACCGAGCACACAGAGCAGAAACGGAACGU

GAUCAGAAUCAUCCCCCACCACAACUACAACGCCGCCAUCAACAAGUACA

ACCACGAUAUCGCCCUGCUGGAACUGGACGAGCCCUGGUGCUGAAUAGC

UACGUGACCCCCAUCUGUAUCGCCGACAAAGAGUACACCAACAUCUUUCU

GAAGUUCGGCAGCGGCUACGUGUCCGGCUGGGGCAGAGUGUUUCACAAGG

GCAGAUCCGCUCUGGUGCUGCAGUACCUGAGAGUGCCUCUGGUGGACCGG

GCCACCUGUCUGAGAAGCACCAAGUUCACCAUCUACAACAACAUGUUCUG

CGCCGGCUUUCACGAGGGCGGCAGAGAUAGCUGUCAGGGCGAUUCUGGCG

GCCCUCACGUGACAGAGGUGGAAGGCACCAGCUUUCUGACCGGCAUCAUC

AGCUGGGGCGAGGAAUGCGCCAUGAAGGGGAAGUACGGCAUCUACACCAA

```
GGUGUCCAGAUACGUGAACUGGAUCAAAGAAAAGACCAAGCUGACAUAAU
GACGGACCGGCGAUAGAUGAAGCUCGCUUUCUUGCUGUCCAAUUUCUAUU
AAAGGUUCCUUUGUUCCCUAAGUCCAACUACUAAACUGGGGGAUAUUAUG
AAGGGCCUUGAGCAUCUGGAUUCUGCCUAAUAAAAAACAUUUAUUUUCAU
UGCAGCUCGCUUUCUUGCUGUCCAAUUUCUAUUAAAGGUUCCUUUGUUCC
CUAAGUCCAACUACUAAACUGGGGGAUAUUAUGAAGGGCCUUGAGCAUCU
GGAUUCUGCCUAAUAAAAAACAUUUAUUUUCAUUGCGGCCGCAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA
```

TEV-Fluc(sapI)-2xhBG-120A

Sequence features:

Tobacco Etch Virus (TEV) 5' UTR: 14-154

Optimal Kozak sequence: 155-163

Sequence encoding polypeptide 99% identical
(545/550 aa) to Firefly (Photinus pyralis)
luciferase of Protein Accession # P08659: 164-1813

1 stop codon: 1814-1816

2 copies of human beta-globin 3'UTR: 1835-2100

120 nucleotide polyA tail: 2107-2226

(SEQ ID NO: 10)
```
GGGAGACGCGUGUUAAAUAACAAAUCUCAACACAACAUAUACAAAACAAA
CGAAUCUCAAGCAAUCAAGCAUUCUACUUCUAUUGCAGCAAUUUAAAUCA
UUUCUUUUAAAGCAAAAGCAAUUUUCUGAAAAUUUUCACCAUUUACGAAC
GAUAGCCGCCACCAUGGAAGACGCCAAAAACAUAAAGAAAGGCCCGGCGC
CAUUCUAUCCGCUGGAAGAUGGAACCGCUGGAGAGCAACUGCAUAAGGCU
AUGAAGAGAUACGCCCUGGUUCCUGGAACAAUUGCUUUUACAGAUGCACA
UAUCGAGGUGGACAUCACUUACGCUGAGUACUUCGAAAUGUCCGUUCGGU
UGGCAGAAGCUAUGAAACGAUAUGGGCUGAAUACAAAUCACAGAAUCGUC
GUAUGCAGUGAAAACUCUCUUCAAUUCUUUAUGCCGGUGUUGGGCGCGUU
AUUUAUCGGAGUUGCAGUUGCGCCCGCGAACGACAUUUAUAAUGAACGUG
AAUUGCUCAACAGUAUGGGCAUUUCGCAGCCUACCGUGGUGUUCGUUUCC
AAAAAGGGGUUGCAAAAAAUUUUGAACGUGCAAAAAAAGCUCCCAAUCAU
CCAAAAAAUUAUUAUCAUGGAUUCUAAAACGGAUUACCAGGGAUUUCAGU
CGAUGUACACGUUCGUCACAUCUCAUCUACCUCCCGGUUUUAAUGAAUAC
GAUUUUGUGCCAGAGUCCUUCGAUAGGGACAAGACAAUUGCACUGAUCAU
GAACUCCUCUGGAUCUACUGGUCUGCCUAAAGGUGUCGCUCUGCCUCAUA
GAACUGCCUGCGUGAGAUUCUCGCAUGCCAGAGAUCCUAUUUUUGGCAAU
CAAAUCAUUCCGGAUACUGCGAUUUUAAGUGUUGUUCCAUUCCAUCACGG
UUUUGGAAUGUUUACUACACUCGGAUAUUUGAUAUGUGGAUUUCGAGUCG
UCUUAAUGUAUAGAUUUGAAGAGGAGCUGUUUCUGAGGAGCCUUCAGGAU
UACAAGAUUCAAAGUGCGCUGCUGGUGCCAACCCUAUUCUCCUUCUUCGC
CAAAAGCACUCUGAUUGACAAAUACGAUUUAUCUAAUUUACACGAAAUUG
```
```
CUUCUGGUGGCGCUCCCCUCUCUAAGGAAGUCGGGGAAGCGGUUGCCAAG
AGGUUCCAUCUGCCAGGUAUCAGGCAAGGAUAUGGGCUCACUGAGACUAC
AUCAGCUAUUCUGAUUACACCCGAGGGGGAUGAUAAACCGGGCGCGGUCG
GUAAAGUUGUUCCAUUUUUUGAAGCGAAGGUUGUGGAUCUGGAUACCGGG
AAAACGCUGGGCGUUAAUCAAAGAGGCGAACUGUGUGUGAGAGGUCCUAU
GAUUAUGUCCGGUUAUGUAAACAAUCCGGAAGCGACCAACGCCUUGAUUG
ACAAGGAUGGAUGGCUACAUUCUGGAGACAUAGCUUACUGGGACGAAGAC
GAACACUUCUUCAUCGUUGACCGCCUGAAGUCUCUGAUUAAGUACAAAGG
CUAUCAGGUGGCUCCCGCUGAAUUGGAAUCCAUCUUGCUCCAACACCCCA
ACAUCUUCGACGCAGGUGUCGCAGGUCUUCCCGACGAUGACGCCGGUGAA
CUUCCCGCCGCCGUUGUUGUUUUGGAGCACGGAAAGACGAUGACGGAAAA
AGAGAUCGUGGAUUACGUCGCCAGUCAAGUAACAACCGCGAAAAAGUUGC
GCGGAGGAGUUGUGUUUGUGGACGAAGUACCGAAAGGUCUUACCGGAAAA
CUCGACGCAAGAAAAAUCAGAGAGAUCCUCAUAAAGGCCAAGAAGGGCGG
AAAGAUCGCCGUGUGACGGACCGGCGAUAGAUGAAGCUCGCUUUCUUGCU
GUCCAAUUUCUAUUAAAGGUUCCUUUGUUCCCUAAGUCCAACUACUAAAC
UGGGGGAUAUUAUGAAGGGCCUUGAGCAUCUGGAUUCUGCCUAAUAAAAA
ACAUUUAUUUUCAUUGCAGCUCGCUUUCUUGCUGUCCAAUUUCUAUUAAA
GGUUCCUUUGUUCCCUAAGUCCAACUACUAAACUGGGGGAUAUUAUGAAG
GGCCUUGAGCAUCUGGAUUCUGCCUAAUAAAAAACAUUUAUUUUCAUUGC
GGCCGCAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAA
```

Gtx7-Gluc-2xSinV-120A

Sequence features:

5' UTR: 14-127

Kozak sequence: 128-133

Sequence encoding polypeptide identical to
Gaussia princeps luciferase of Protein Accession
AAG54095: 134-688

1 stop codon: 689-691

2 copies of Sindbis Virus 3'UTR: 699-882

120 nucleotide polyA tail: 891-1010

(SEQ ID NO: 11)
```
GGGAGACGCGUGUUUCUGACAUCCGGCGGAAUUCUGACAUCCGGCGGAAU
UCUGACAUCCGGCGGAAUUCUGACAUCCGGCGGAAUUCUGACAUCCGGCG
GAAGACUCACAACCCCAGAAACAGACAGCCACCAUGGGAGUCAAAGUUCU
GUUUGCCCUGAUCUGCAUCGCUGUGGCCGAGGCCAAGCCCACCGAGAACA
ACGAAGACUUCAACAUCGUGGCCGUGGCCAGCAACUUCGCGACCACGGAU
CUCGAUGCUGACCGCGGGAAGUUGCCCGGCAAGAAGCUGCCGCUGGAGGU
GCUCAAAGAGAUGGAAGCCAAUGCCCGGAAAGCUGGCUGCACCAGGGGCU
```

-continued
GUCUGAUCUGCCUGUCCCACAUCAAGUGCACGCCCAAGAUGAAGAAGUUC

AUCCCAGGACGCUGCCACACCUACGAAGGCGACAAAGAGUCCGCACAGGG

CGGCAUAGGCGAGGCGAUCGUCGACAUUCCUGAGAUUCCUGGGUUCAAGG

ACUUGGAGCCAAUGGAGCAGUUCAUCGCACAGGUCGAUCUGUGUGUGGAC

UGCACAACUGGCUGCCUCAAAGGGCUUGCCAACGUGCAGUGUUCUGACCU

GCUCAAGAAGUGGCUGCCGCAACGCUGUGCGACCUUUGCCAGCAAGAUCC

AGGGCCAGGUGGACAAGAUCAAGGGGGCCGGUGGUGACUAACGGACCGAA

AACUCAAUGUAUUUCUGAGGAAGCGUGGUGCAUAAUGCCACGCAGUGUCU

ACAUAAUCAAUUUAUUAUUUCUUUUAUUUUAUUCACAUAAAAACUCAAU

GUAUUUCUGAGGAAGCGUGGUGCAUAAUGCCACGCAGUGUCUACAUAAUC

AAUUUAUUAUUUUCUUUUAUUUUAUUCACAUAGCGGCCGCAAAAAAAAAA

AAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

AAAAA

Biological Evaluation
Packaging of mRNA

All equipment and disposable supplies are certified free of RNase activity by the manufacturer or rendered RNase free by use of the RNaseZap reagent (LifeTechnologies). mRNA is encapsulated at a cationic lipid amine to mRNA phosphate (N:P) molar ratio of 4:1. Lipids (cationic lipid, DSPC, cholesterol and lipidated PEG or stealth lipid) are dissolved in ethanol. The molar ratios are 40:10:38:2, respectively. The mixture is sonicated briefly, then gently agitated for 5 minutes and then maintained at 37° C. until use. mRNA is exchanged into citrate buffer pH 5.8-6.0 by use of Amicon Ultra-15 centrifugal concentrators, and the final concentration is adjusted to 0.5 mg/ml and held at 37° C. until use. An equal volume of lipids in ethanol, mRNA in citrate buffer, and citrate buffer alone are drawn into disposable syringes. Tubing leading from syringes containing lipids and mRNA are attached to the T junction, and tubing leading from the syringe containing citrate buffer alone is paired with the tubing exiting the T-junction over a collection vessel containing a stir bar on an active stir plate. Syringes are placed in a syringe pump set to expel contents at a flow rate of 1 ml per minute.

The pump is activated, and the collected mRNA in lipid nanoparticles is transferred to SnakeSkin dialysis tubing (10,000 MWCO, Thermo Scientific). Material is dialyzed against RNAse- and pyrogen-free 1× phosphate buffered saline overnight at 4° C.

Packaging of siRNA

The lipid nanoparticles (LNPs) were formed by mixing equal volumes of lipids dissolved in alcohol with siRNA dissolved in a citrate buffer by an impinging jet process. The lipid solution contains a cationic lipid compound of the invention, a helper lipid (cholesterol), an optional neutral lipid (DSPC) and a stealth lipid (S010, S024, S027, or S031) at a concentration of 8-16 mg/mL with a target of 12 mg/mL in an alcohol. The siRNA to total lipid ratio is approximately 0.05 (wt/wt). Where a LNP formulation contains four lipid components, the molar ratios of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate: sodium chloride buffer pH 4-6, with a target of 4.5-5.5. The LNPs are formed by mixing equal volumes of lipid solution in ethanol with siRNA dissolved in a citrate buffer by an impinging jet process through a mixing device with ID ranging from 0.25 to 2.0 mm at a flow rate from 10 to 640 mL/min. The mixed LNP solution is held at room temperature for 0-24 hrs prior to a dilution step. The solution is then concentrated and diafiltered with suitable buffer by ultrafiltration process using membranes with a MW cutoff from 30 to 500 KD. The final product is sterile filtered and stored at 4° C.

Measurement of mRNA Encapsulation

Percent encapsulation of mRNA in lipid nanoparticles is determined using the Quant-iT Ribogreen RNA Assay kit (Life Technologies). The LNP-mRNA suspension is assayed in buffer (mRNA outside the particle), and buffer plus Triton X-100 detergent (total mRNA). The difference calculated is the mRNA inside the particle. Prepare a 1000 ng/mL stock from the RNA provided in the kit and use this to generate a standard curve (0 ng/ml, 15.63-1000 ng/ml) in TE and TE+0.75% Triton X-100. Prepare LNP-mRNA samples in TE buffer and TE buffer+0.75% Triton X-100 with appropriate dilution so that reading is in the range of standard curve (400-2,000 fold). In a 384-well plate (Costar non-treated #3573) add 0.04 ml of standard (in duplicate) or sample (in triplicate) per well. Dilute Ribogreen reagent 240-fold in TE buffer and add 0.06 ml per well. Mix contents of wells and measure fluorescence (excitation=480 nm, emission=520 nm). Subtract background values (no RNA) from standard and test sample values and determine the concentrations of RNA in the samples using the standard curves. Determine the percent encapsulation of the sample by dividing the difference in concentrations between sample+triton and sample in buffer alone by the sample+triton concentration.

Measurement of siRNA Encapsulation

SYBR Gold flourescence reagent is used for the determination of siRNA encapsulation in the DLP's. DLP's with and without triton x-100 are used to determine the free siRNA and total siRNA amounts. DLP's samples with and without triton X-100 were excited at 485 nm and flourescence emission is measured at 530 nm. Encapsulation efficiency is calculated based on the following formula:

Encapsulation efficiency: [(free siRNA concentration−total siRNA concentration)/(total siRNA concentration)]×100%

Encapsulation Data

TABLE 2

In-vitro encapsulation data for mRNA and siRNA

| | % encapsulation | |
| --- | --- | --- |
| Example | mRNA Leptin | siRNA FVII |
| 1 | 97.1 | NA |
| 4 | NA | 88.6 |
| 6 | 24.0 | 91.7 |
| 9 | 96.6 | 91.0 |
| 10 | 88.4 | 89.9 |
| 11 | 98.2 | 89.7 |
| 12 | NA | 91.7 |
| 13 | 81.1 | 90.3 |
| 14 | 99.4 | 88.0 |
| 15 | 98.9 | 91.0 |

TABLE 2-continued

In-vitro encapsulation data for mRNA and siRNA

| Example | % encapsulation mRNA Leptin | % encapsulation siRNA FVII |
|---|---|---|
| 16 | 97.7 | 88.9 |
| 17 | 84.6 | 88.3 |
| 18 | 97.1 | 91.2 |
| 19 | NA | 84.5 |
| 20 | NA | 76.7 |
| 21 | 98.2 | 91.2 |
| 22 | 99.2 | 91.7 |
| 23 | 98.0 | 92.0 |
| 24 | NA | 86.8 |
| 25 | NA | 87.1 |
| 26 | NA | 89.8 |
| 27 | NA | 86.6 |
| 29 | NA | 86.1 |
| 43 | NA | 86.8 |
| 44 | NA | 79.8 |
| 45 | 88.2 | 86.4 |
| 46 | NA | 85.2 |
| 48 | NA | 89.3 |
| 49 | NA | 88.4 |
| 50 | NA | 85.3 |
| 51 | NA | 89.2 |
| 52 | NA | 84.6 |
| 53 | NA | 85.6 |
| 54 | NA | 88.6 |
| 58 | 90.2 | NA |
| 59 | NA | 90.2 |
| 60 | NA | 82.4 |
| 61 | NA | 85.5 |
| 62 | NA | 75.2 |
| 63 | NA | 85.6 |
| 64 | 93.0 | NA |
| 65 | NA | 39.5 |
| 66 | NA | 83.4 |
| 70 | 98.3 | 80.0 |
| 71 | NA | 86.7 |
| 72 | NA | 62.5 |
| 80 | NA | 85.2 |
| 81 | NA | 48.8 |
| 82 | 81.9 | NA |
| 83 | 48.9 | NA |
| 84 | 83.1 | 77.5 |
| 85 | NA | 85.7 |
| 86 | 68.5 | NA |
| 87 | NA | 77.5 |
| 88 | 39.2 | 77.4 |
| 89 | 87.0 | NA |
| 90 | NA | 91.4 |
| 91 | 94.4 | NA |
| 93 | 82.0 | NA |
| 94 | 98.1 | 74.8 |
| 95 | NA | 86.9 |
| 98 | 73.4 | NA |
| 100 | 91.5 | NA |
| 103 | 72.5 | 83.2 |
| 106 | 96.3 | NA |
| 107 | 94.5 | NA |
| 108 | 94.6 | NA |
| 109 | 80.6 | NA |
| 110 | 59.3 | NA |
| 111 | 74.7 | NA |
| 112 | 32.9 | NA |
| 113 | 37.5 | NA |
| 114 | 98.4 | NA |
| 115 | 97.8 | NA |
| 116 | 93.3 | NA |
| 117 | 5.0 | NA |
| 118 | 12.8 | NA |
| 119 | 95.7 | NA |
| 120 | 96.1 | NA |
| 121 | 71.2 | NA |
| 122 | 97.5 | NA |
| 123 | 83.8 | NA |
| 124 | 98.0 | NA |
| 125 | 95.1 | NA |
| 126 | 97.4 | NA |
| 127 | 96.7 | NA |
| 128 | 86.2 | NA |
| 129 | 96.8 | NA |
| 130 | 97.8 | NA |
| 131 | 96.4 | NA |
| 132 | 95.5 | NA |
| 133 | 63.3 | NA |
| 134 | 96.6 | NA |
| 135 | 96.2 | NA |
| 136 | 95.2 | NA |
| 137 | 98.1 | NA |
| 138 | 92.9 | NA |
| 139 | 52.4 | NA |
| 141 | 94.9 | NA |
| 142 | 92.5 | NA |

Packaging of Plasmid DNA

All equipment and disposable supplies are certified free of RNase activity by the manufacturer or rendered RNase free by use of the RNaseZap reagent (LifeTechnologies). Plasmid is encapsulated at a cationic lipid amine to DNA phosphate (N:P) molar ratio of 4:1. Lipids (cationic lipid, DSPC, cholesterol and lipidated PEG) are dissolved in ethanol. The molar ratios are 40:10:38:2, respectively. The mixture is sonicated briefly, then gently agitated for 5 minutes and then maintained at 37° C. until use. Plasmid is exchanged into citrate buffer pH 6.0 by use of Amicon Ultra-15 centrifugal concentrators, and the final concentration is adjusted to 0.053 mg/ml and held at 37° C. until use. An equal volume of lipids in ethanol, plasmid in citrate buffer, and citrate buffer alone are drawn into disposable syringes. Tubing leading from syringes containing lipids and DNA are attached to the T junction, and tubing leading from the syringe containing citrate buffer alone is paired with the tubing exiting the T-junction over a collection vessel containing a stir bar on an active stir plate. Syringes are placed in a syringe pump set to expel contents at a flow rate of 1 ml per minute. The pump is activated, and the collected DNA in lipid nanoparticles is transferred to SnakeSkin dialysis tubing (10,000 MWCO, Thermo Scientific). Material is dialyzed against RNAse- and pyrogen-free 1× phosphate buffered saline overnight at 4° C.

Measurement of Plasmid DNA Encapsulation

Percent encapsulation of plasmid DNA in lipid nanoparticles is determined using the Quant-iT Ribogreen RNA Assay kit (Life Technologies). The LNP-DNA suspension is assayed in buffer (DNA outside the particle), and buffer plus Triton X-100 detergent (total DNA). The difference calculated is the DNA inside the particle. Prepare a 1000 ng/mL stock using unpackaged plasmid and use this to generate a standard curve (0 ng/ml, 15.63-1000 ng/ml) in TE and TE+0.75% Triton X-100. Prepare LNP-plasmid samples in TE buffer and TE buffer+0.75% Triton X-100 with appropriate dilution so that reading is in the range of standard curve (25 fold). In a 384-well plate (Costar non-treated #3573) add 0.04 ml of standard (in duplicate) or sample (in triplicate) per well. Dilute Ribogreen reagent 240-fold in TE buffer and add 0.06 ml per well. Mix contents of wells and measure fluorescence (excitation=480 nm, emission=520 nm). Subtract background values (no DNA) from standard and test sample values and determine the concentrations of DNA in the samples using the standard curves. Determine the percent encapsulation of the sample by dividing the difference in concentrations between sample+triton and sample in buffer alone by the sample+triton concentration.

Polydispersity Index (PDI) Measurements

Unless indicated otherwise, all PDIs referred to herein are the PDI of the fully formed nanoparticle, as measured by dynamic light scattering on a Malvern Zetasizer. The nanoparticle sample was diluted in phosphate buffered saline (PBS) so that the count rate was approximately 200-400 kcts. The data is presented in Table 3 as a weighted average of the intensity measure.

The Particle Size of the Lipid Nanoparticle

Unless indicated otherwise, all particle size measurements referred to in Table 3 are the Z-average particle size of the fully formed nanoparticle, as measured by dynamic light scattering on a Malvern Zetasizer. The nanoparticle sample was diluted in phosphate buffered saline (PBS) so that the count rate is approximately 200-400 kcts.

Lipid Nanoparticle Characterization Data

TABLE 3 in vitro data on selected examples

| Nucleic acid | Example 1 | | | Example 94 | | | Example 16 | | | Example 80 | | |
|---|---|---|---|---|---|---|---|---|---|---|---|---|
| | % Encap. | Size (nM) | PDI | % Encap. | Size (nM) | PDI | % Encap. | Size (nM) | PDI | % Encap. | Size (nM) | PDI |
| hLeptin mRNA | 97.1 | 128.1 | 0.071 | 98.1 | 119.1 | 0.101 | 98.1 | 122.6 | 0.103 | | | |
| hFIX mRNA | 94.0 | 95.5 | 0.082 | 96.9 | 148.3 | 0.079 | 96.9 | 102.6 | 0.141 | | | |
| FLuc mRNA | 94.7 | 108.8 | 0.100 | 93.7 | 129.2 | 0.093 | 96.8 | 106.7 | 0.145 | 85.3 | 193.5 | 0.085 |
| Gluc mRNA | 97.3 | 84.7 | 0.093 | 95.9 | 76.9 | 0.113 | 97.9 | 106.7 | 0.145 | | | |
| mEPO mRNA | 95.8 | 104.1 | 0.073 | 96.4 | 108.5 | 0.099 | 97.9 | 83.2 | 0.112 | 96.2 | 166.0 | 0.083 |
| hLep plasmid | 93.5 | 109.8 | 0.138 | 95.0 | 109.8 | 0.153 | 96.7 | 102.6 | 0.155 | | | |
| pDNA | 94.3 | 110 | 0.135 | 89.3 | 123.5 | 0.152 | 96.4 | 101.6 | 0.128 | | | |
| FVII siRNA | | | | 74.8 | 122.6 | 0.073 | 88.9 | 95.7 | 0.075 | 85.2 | 97.3 | 0.051 |

In Vivo Data

Mouse Factor VII Dosing

Female CD-1 mice were received from Harlan Labs and maintained on standard lab chow and water ad libitum. The animals weighed approximately 25 gr at time of dosing. Formulated Factor VII siRNA was administered as a single dose intravenously via the lateral tail vein. Approximately 48 hours after injection, the mice were euthanized by $CO_2$ inhalation followed by exsanguination through the vena cava. The blood was collected in tubes containing 0.105M sodium citrate anticoagulant for plasma Factor VII activity analysis.

Factor VII Activity Assay

Plasma collected from injected mice was assayed for Factor VII enzyme activity using the Biophen FVII kit from Hyphen Biomedical (catalog number 221304). An assay standard curve was prepared using pooled plasma aliquots from the vehicle control animals. All samples were diluted to fall within the linear range of the standard curve and Factor VII activity relative to control plasma was reported.

Lipid nanoparticles comprising lipid compounds of formula (I) and the FVII siRNA duplex sequence listed above were tested in the Factor VII Activity Assay. The results of this assay are given in Table 3 4 below as a percent knock down of plasma Factor VII enzyme activity at a dose of 0.3 mg/kg and 0.03 mg/kg.

Mouse EPO ELISA

A rat anti-mouse Erythropoietin antibody is coated on 384-well white microtiter plates overnight, then blocked for assay. Then, plasma samples are diluted in a casein-based sample diluent and incubated on the plate with buffer controls and mouse EPO standards. The plate is then washed to remove unbound material. A biotinylated rat anti-mouse Erythropoietin antibody is then added to the plate to detect mouse EPO bound by the capture antibody. The plate is washed again and a streptavidin-conjugated horseradish peroxidase reagent is incubated on the plate. A third wash step is performed and a chemiluminescent reagent is added to the plate and immediately read by a capable plate reader using all wavelengths and a 50 millisecond integration time. Unknown samples are interpolated off the mouse EPO standard curve.

Human Factor IX ELISA

An sheep anti-human Factor IX antibody (Cat# FIX-EIA-C) from Enzyme Research Laboratories is coated on 384-well white microtiter plates overnight at a concentration of 5 ug/ml, then blocked for assay using KPL blocker (Cat#50-82-00). Then, plasma samples are diluted in a casein-based sample diluent and incubated on the plate with biological controls and a standard curve created from recombinant protein (Cat#HCIX-0040). The plate is then washed to remove unbound material. A biotinylated sheep anti-human Factor IX antibody (Cat# FIX-EIA-D) from Enzyme Research Laboratories is then added to the plate at 0.6 ug/ml to detect human Factor IX protein bound by the capture antibody. The plate is washed again and a streptavidin-conjugated horseradish peroxidase reagent (Cat#21140) diluted 1:1250, is incubated on the plate. A third wash step is performed and chemiluminescent reagents (Cat#1859678 & Cat#18596789) are combined and added to the plate and immediately read by a capable plate reader using all wavelengths and a 50 millisecond integration time. Unknown samples are interpolated off the human recombinant Factor IX standard curve.

Casein Sample Diluent, pH 7.20

The Sample Diluent contains 0.7% Casein, 1.7 mM Sodium Phosphate Monobasic, 8.1 mM Sodium Phosphate Dibasic Heptahydrate, 0.15M Sodium Chloride, 0.7% Triton X-100, and 0.1% Sodium Azide Biotinylated Antibody Casein Diluent, pH 7.15

The diluent contains 0.4% Casein, 1.7 mM Sodium Phosphate Monobasic, 8.1 mM Sodium Phosphate Dibasic Heptahydrate, 0.15M Sodium Chloride, and 0.1% Sodium Azide HRP Casein Diluent, pH 7.15

The diluent contains 0.4% Casein, 1.7 mM Sodium Phosphate Monobasic, 8.1 mM Sodium Phosphate Dibasic Heptahydrate, 0.15M Sodium Chloride, and 0.1% Chloroacetamide.Leptin hLEPTIN Human leptin in mouse plasma was measured by ELISA. Antibodies purchased from the R&D Systems duoset (Cat#DY398E, part#840279 for capture antibody and part#840280 for detection antibody) were reconstituted using PBS and titered, again using PBS. The capture antibody was coated at 4 ug/ml in 30 ul/well on a white Nunc® Maxisorp 384 well plate (Cat#460372). After an overnight incubation at room temperature the capture antibody was aspirated and the plate blocked for 2 hours at room temperature with 90 ul/well of KPL milk blocker (Cat#50-82-00). Once the incubation was completed the plate was aspirated and recombinant standards and samples were added to the plate at 30 ul/well for 2 hours at 37° C. while shaking at 600 rpm. Sample/standard dilutions were made using casein sample diluent. Washing/aspiration 3 times with 100 ul/well followed, using Teknova plate wash solution (Cat# P1192). Next, detection antibody was diluted using casein detection antibody diluent to 12.5 ng/ml and added at 30 ul/well for 2 hours room temperature. After this incubation, the plate was washed again and a solution of poly-streptavidin-HRP (Cat#21140) at a 1:1250 dilution in HRP dilution buffer was added to each well (30 ul/well) and incubated for 30 minutes room temperature. A final wash/aspiration removed the HRP solution and a chemiluminescent substrate was added at 30 ul/well (Cat#1859678 & 1859679). The plate was quickly read using a SpectramaxM5 plate reader with a 50 ms integration time. The dynamic range of the ELISA is from 100-2,000 µg/ml (6.25-125 pM) of human leptin. The assay is applicable to plasma from mice, rats and cynomolgus monkeys.

Mouse Intravenous Tail Vein Injection of Modified Synthetic Leptin mRNA

Before the tail vein injection, mouse body weights were recorded and diet weighted, with mice grouped according to their body weights. Mice were prepared by warming them under a heating lamp for ~2 minutes, with the mice about 12 inches from heat lamp.

For the tail vein injection procedure, the mice were placed in a restrainer and their tails cleaned with 70% alcohol. A 27 gauge needle (Becton Dickinson, Catalogue #305109) connected with a 1 ml syringe (Becton Dickinson, Catalogue #309659) was inserted into the tail vein, with bevel facing up, and the syringe plunger was pulled backwards to ensure blood is drawn into the syringe. The desired volume of modified synthetic leptin mRNA was injected by hand with moderate pressure and speed. The needle was then withdrawn and bleeding stopped by adding pressure to injection site with gauze.

Single housed, 8-9 week old, male C57BL/6 mice were used for the in vivo study. FPLC purified modified synthetic leptin mRNA (SEQ ID NO:6) in which the uridines were substituted with pseudouridine was packaged in a cationic lipid (N:P molar ratio=8:1) and then were diluted in injectable saline at a dose of 10 µg per average group body weight.

On day 0, animals were weighed and sorted according to average body weight. Mice were dosed, and food intake (FI) was recorded, on each of days 1-7 and days 9, 11, and 16.

Mouse Subcutaneous Injection of Modified Synthetic Leptin mRNA

Prior to subcutaneous injection, mouse body weights were recorded and diet weighted, with mice grouped according to their body weights. The mice were manually restrained and placed on a work surface. Their scruffs were pinched and lifted away from the underlying muscle, the space into which was inserted a 25 gauge needle connected with a 1 ml syringe. The syringe plunger was pulled backwards in such a way as to ensure no fluid was drawn into the syringe, and then the desired volume of leptin mRNA was hand injected with moderate pressure and speed. The needle was then withdrawn and the mice returned to their cages.

8-9 week old, male C57BL/6 mice were used for the in vivo study. FPLC purified modified synthetic leptin mRNA (SEQ ID NO: 6) in which the uridines were substituted with pseudouridine (N:P molar ratio=8:1) packaged in multiple cationic lipid were diluted in injectable saline at a dose of 10 µg per average group body weight.

On day 0, animals were weighed and sorted according to average body weight. ice were dosed at 9 AM and blood was taken at 9 AM on day 0. Blood was also taken at 9 AM on each of days 1 and 2 and assessed for leptin protein levels. Body weight and food intake were also recorded.

TABLE 4

| | In vivo data | | | |
|---|---|---|---|---|
| Nucleic acid | Example 1 | Example 91 | Example 16 | Example 80 |
| | Expression of protein (ng/ml) following IV injection of encapsulated mRNA in C57B6 mice | | | |
| hLeptin | 66.3 ng/mL (0.4 mpk, C57) | 33.6 ng/mL (0.2 mpk, ob/ob) | 21.4 ng/mL (0.2 mpk, ob/ob) | |
| mEPO | 247.6 ng/mL (0.2 mpk, ob/ob) | | | |
| | Expression of protein (ng/ml) following SC injection of encapsulated mRNA in C57B6 mice | | | |
| hLeptin | 16.2 ng/mL (0.2 mpk, ob/ob) 1.2 ng/mL (0.2 mpk, C57) | 3.5 ng/mL (0.2 mpk, ob/ob) | 8.4 ng/mL (0.2 mpk, ob/ob) | |
| | FVII knock-down (%) following IV injection of encapsulated siRNA in XXX mice | | | |
| FVII | 97%/0.03 mpk | | 95%/0.03 mpk | |

Immunogenicity Studies

Plasmid DNA encoding alphavirus replicons encoding the F protein of RSV as a transgene served as a template for synthesis of RNA in vitro. The replicons contain the alphavirus genetic elements required for RNA replication but lack those encoding gene products necessary for particle assembly; the structural proteins are instead replaced by a protein of interest (e.g. an immunogen, such as full-length RSV F protein) and so the replicons are incapable of inducing the generation of infectious particles. A T7bacteriophage promoter upstream of the alphavirus cDNA facilitates the synthesis of the replicon RNA in vitro. Other promoters, such as SP6 could be used as alternatives.

Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of the RNA samples was determined by measuring $OD_{260nm}$. Integrity of the in vitro transcripts was confirmed by denaturing agarose gel electrophoresis.

microplate reader. All liposome formulations were dosed in vivo based on the encapsulated amount of RNA.

RSV Immunogenicity

A self-replicating replicon encoding RSV F protein was administered to BALB/c mice, 8 animals per group, by bilateral intramuscular vaccinations (50 µL per leg) on days 0 and 21 with the replicon (0.1 and 1 ng) formulated as liposomes with the lipids described below. All liposomes tested were composed of 40% cationic lipid, 10% DSPC, 48% cholesterol and 2% PEG-DMG with similar amounts of RNA. The liposomes were all prepared using the same technique as described above.

% entrapment (% E), Concentration of RNA (Conc), particle size measured by DLS, and polydispersity reported by DLS of LNPs prepared with different cationic lipids

|  | % E | | Conc (ug/mL) | | Size (nm) | | PDI | |
| --- | --- | --- | --- | --- | --- | --- | --- | --- |
| example | 1st IM | 2nd IM | 1st IM | 2nd IM | 1st IM | 2nd IM | 1st IM | 2nd IM |
| 1 | 91.11 | 87.13 | 11.824 | 9.475 | 139.1 | 131.3 | 0.105 | 0.045 |
| 18 | 96.15 | 96.25 | 10.225 | 11.484 | 132.2 | 139.8 | 0.13 | 0.065 |
| 105 | 85.22 | 69.54 | 9.804 | 9.929 | 137.2 | 135.7 | 0.107 | 0.123 |
| 98 | 85.91 | 76.36 | 10.388 | 10.128 | 139.4 | 130.9 | 0.07 | 0.065 |
| 58 | 87.48 | 87.03 | 12.16 | 12.309 | 139.4 | 137.1 | 0.111 | 0.075 |
| 70 | 90.75 | 94.24 | 12.099 | 10.324 | 133.7 | 141.7 | 0.121 | 0.118 |
| 115 | 95.76 | 95.78 | 9.013 | 9.336 | 141.3 | 130.9 | 0.075 | 0.065 |
| 131 | 85.31 | 80.31 | 10.153 | 9.325 | 138.3 | 143.5 | 0.119 | 0.07 |

Encapsulation in DlinDMA-Based Liposomes

RNA was encapsulated in liposomes made essentially by the method of Geall et al. (2012) *PNAS* vol. 109 (36): 14604-14609, Jeffs et al. (2005) *Pharmaceutical Research* 22 (3):362-372 and Maurer et al. (2001) *Biophysical Journal*, 80: 2310-2326 The liposomes were made of 10% DSPC (zwitterionic), 40% cationic lipid, 48% cholesterol and 2% PEG-conjugated DMG (2 kDa PEG). These proportions refer to the % moles in the total liposome.

DSPC (1,2-Diastearoyl-sn-glycero-3-phosphocholine) was purchased from Genzyme.

Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N—(N',N'-dimethylaminoethane)-carbamoyl]cholesterol hydrochloride) were from Avanti Polar Lipids.

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was then dialized overnight against 1×PBS. The resulting product contained liposomes, with ~70-95% encapsulation efficiency. For in vitro and in vivo experiments formulations were diluted to the required RNA concentration with 1×PBS.

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1×TE buffer (from kit) before addition of the dye. Separately, liposomes were diluted 10× or 100× in 1×TE buffer containing 0.5% Triton X before addition of the dye (to disrupt the liposomes and thus to assay total RNA). Thereafter an equal amount of dye was added to each solution and then ~180 µL of each solution after dye addition was loaded in duplicate into a 96 well tissue culture plate. The fluorescence (Ex 485 nm, Em 528 nm) was read on a Immunogenicity data two weeks after two immunizations of vA375 RNA expressing RSV-F of LNPs prepared with different cationic lipids. LNPs were prepared fresh for each immunization.

|  | Immunogenicity (2wp2, log 10 IgG titers) | |
| --- | --- | --- |
| Lipid ID | 1 ng | 0.1 ng |
| 1 | 4.22 | 3.98 |
| 18 | 4.26 | 3.5 |
| 105 | 4.53 | 4.21 |
| 98 | 4.64 | 4.28 |
| 58 | 4.26 | 4.19 |
| 70 | 4.37 | 3.90 |
| 115 | 3.31 | 1.91 |
| 131 | 5.22 | 4.43 |

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art-thus, to the extent an element is described in one or more references known to the person having ordinary skill in the art, they may be excluded from the claimed invention by, inter alia, a negative proviso or disclaimer of the feature or combination of features.

What is claimed is:
1. A compound of formula (I) or a pharmaceutically acceptable salt thereof:
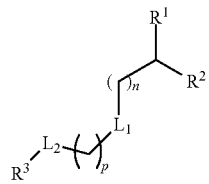 (I)
wherein:
n is 0, 1, 2, 3 or 4;
p is 0, 1, 2, 3, 4, 5, 6, 7 or 8;
$L_1$ is —O— or a bond;
$L_2$ is —OC(O)— or —C(O)O—;
$R^1$ is
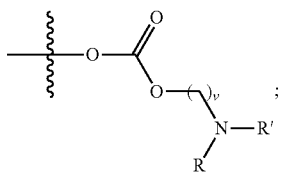
v is 0, 1, 2, 3 or 4;
w is 0, 1, 2 or 3;
R and R' are each, independently, hydrogen or $C_{1-8}$ alkyl;
$R^2$ is selected from: (i) $C_{6-20}$ alkyl optionally substituted with a hydroxyl, and (ii) $C_{15-19}$ alkenyl;
$R^3$ is selected from: $C_{4-22}$ alkyl, $C_{12-22}$ alkenyl,
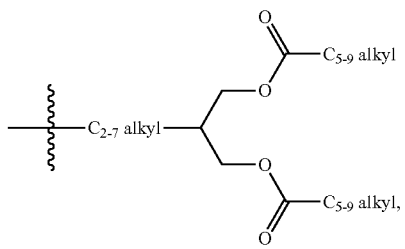
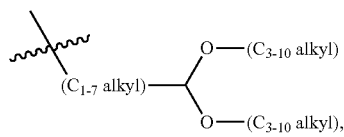
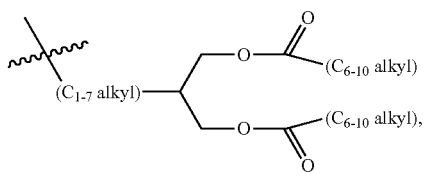
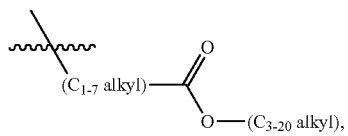
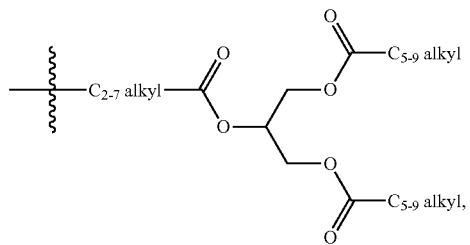
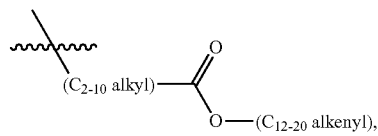
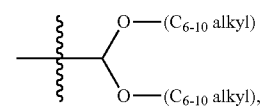
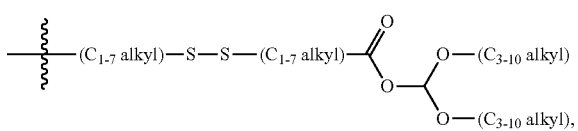
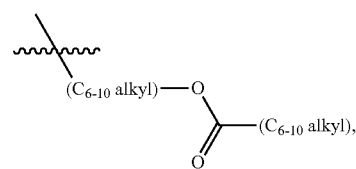
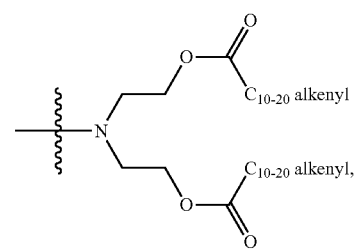
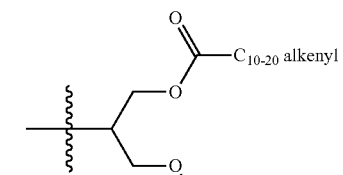
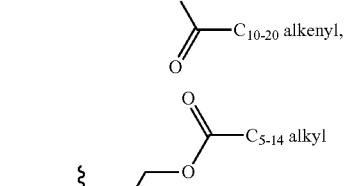
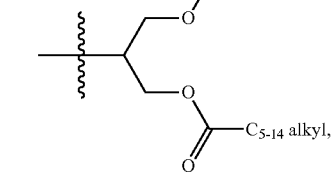

-continued

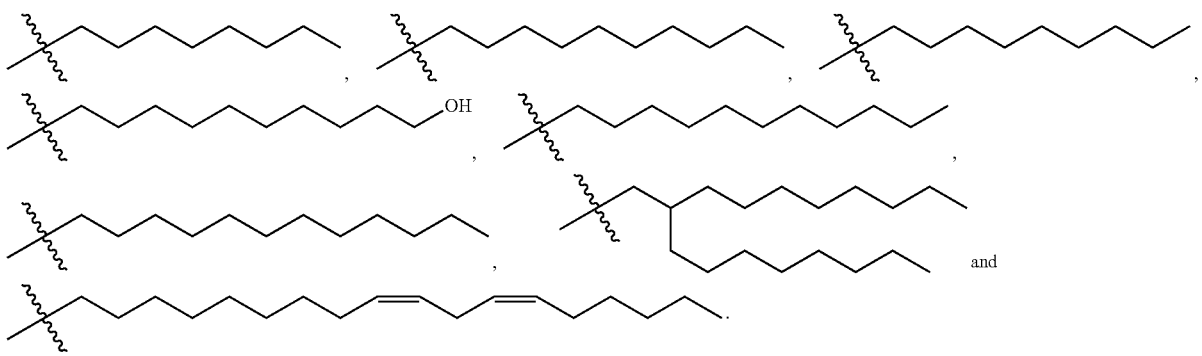

2. The compound of claim 1 or a pharmaceutically acceptable salt thereof, wherein the compound is of formula (II):

(II)

$$\text{structure with } R^1, R^2, R^3, \text{ and } ( )_n$$

3. The compound of claim 1 or a pharmaceutically acceptable salt thereof, wherein the compound is of formula (III):

(III)

4. The compound of claim 1 or a pharmaceutically acceptable salt thereof, wherein $R^2$ is selected from:

5. The compound of claim 1 or a pharmaceutically acceptable salt thereof, wherein the compound is of formula (IV):

(IV)

6. The compound of claim 1 or a pharmaceutically acceptable salt thereof, wherein $R^3$ is selected from:

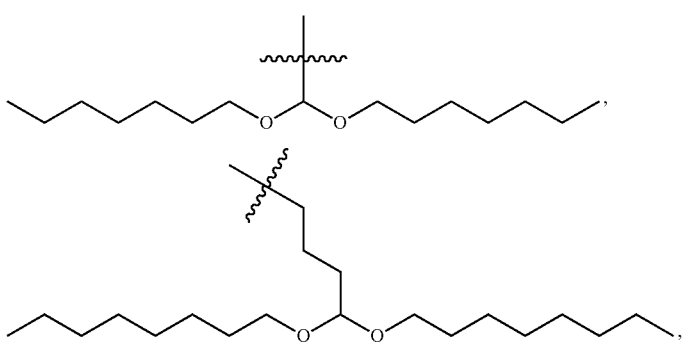

321 322
-continued
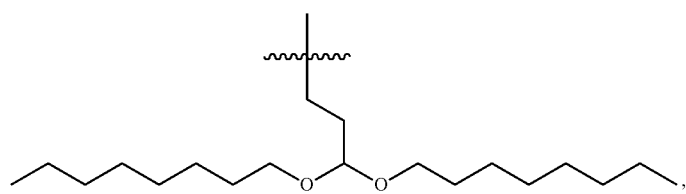
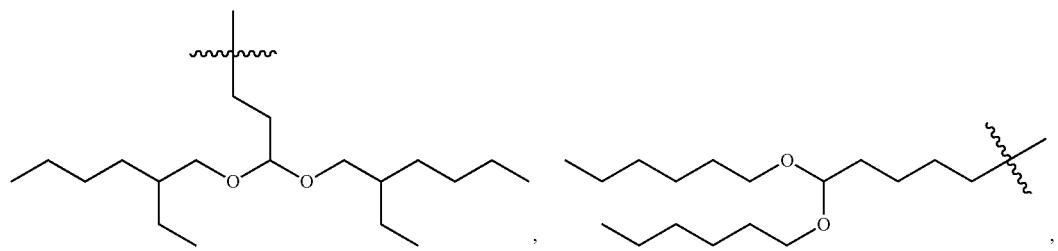
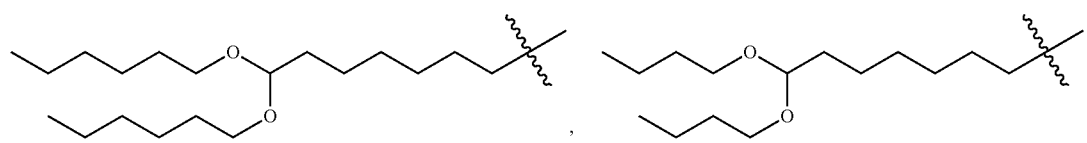
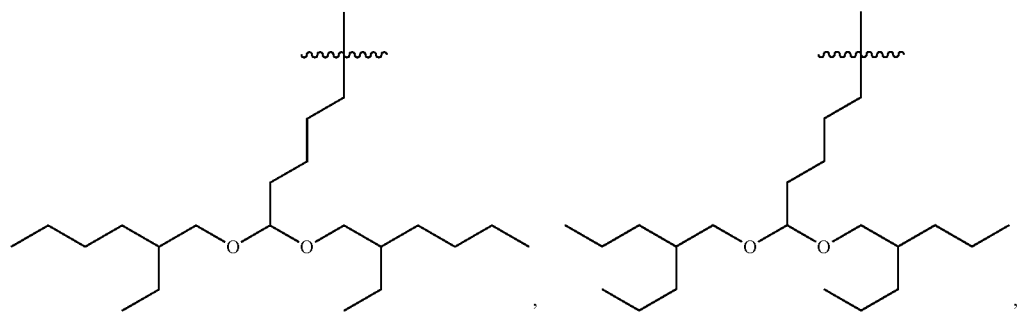
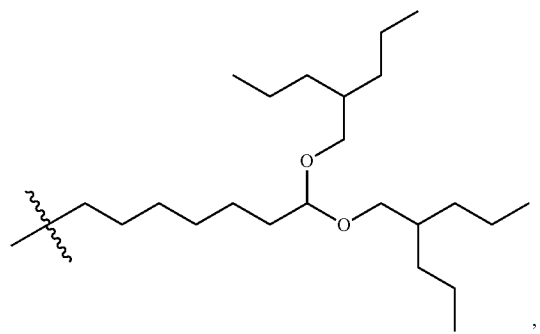
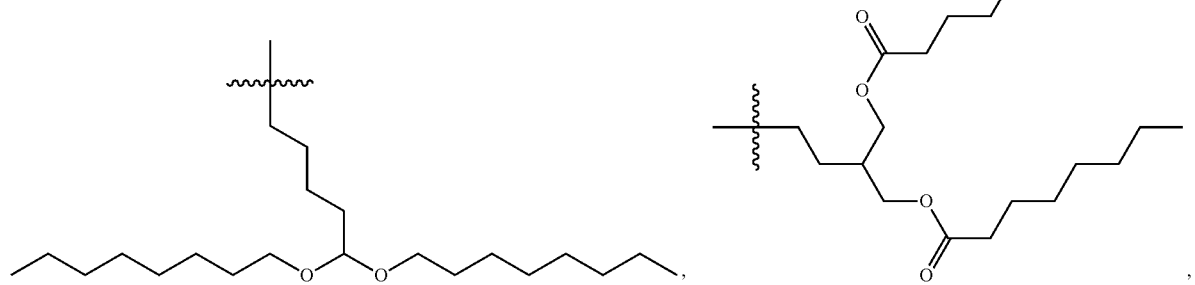

323 324
-continued
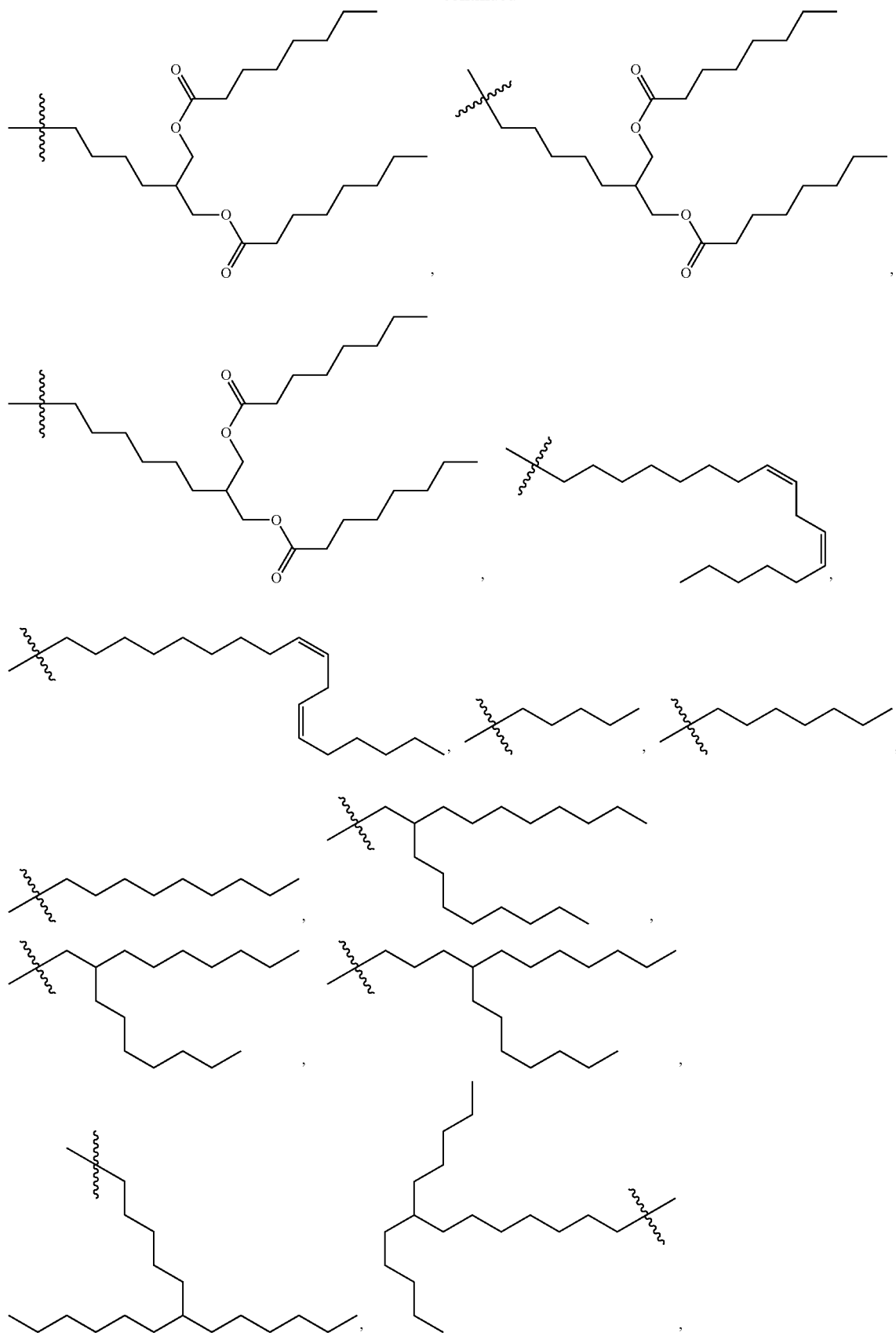

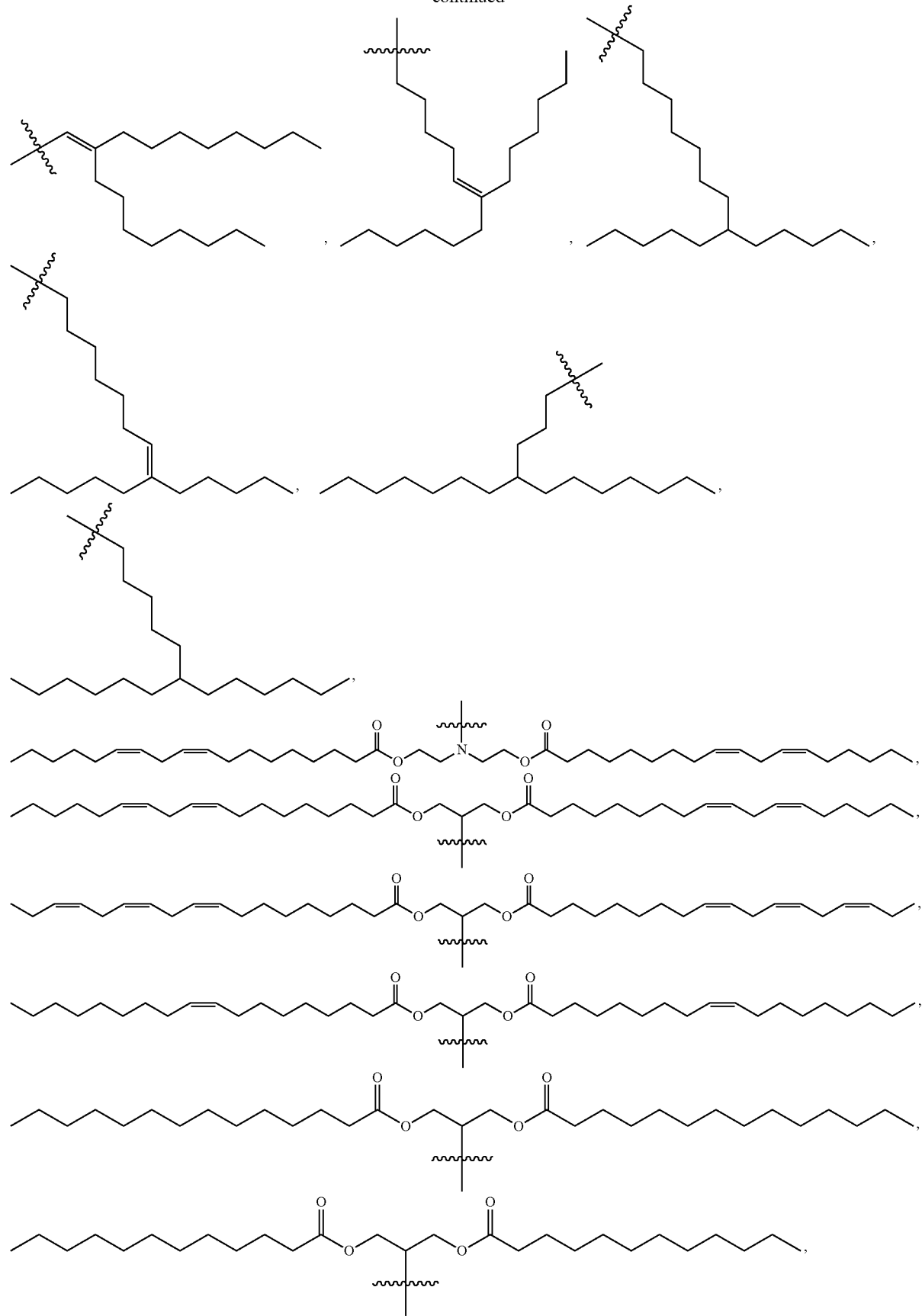

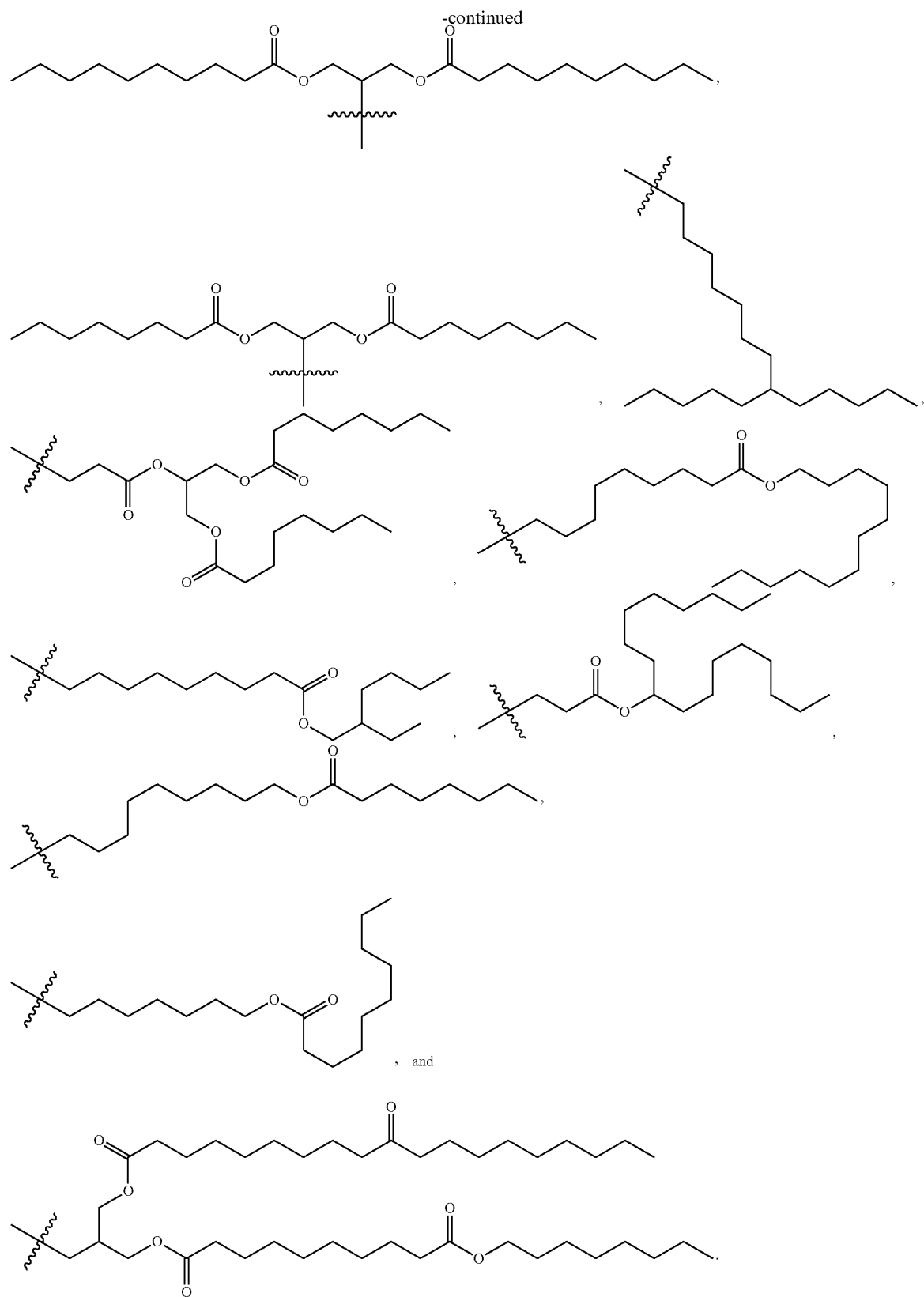
7. The compound of claim 1 or a pharmaceutically acceptable salt thereof, wherein the compound is of formula (V):

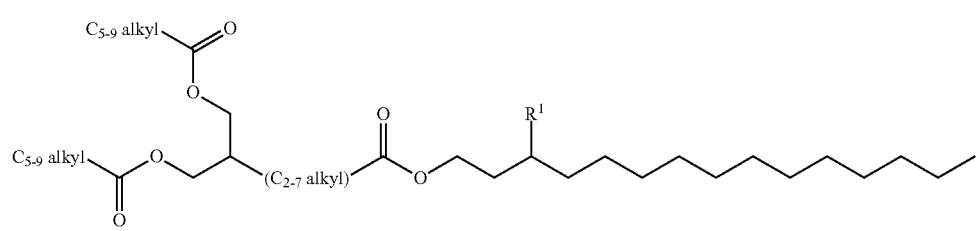
(V)
8. The compound of claim 1 or a pharmaceutically acceptable salt thereof, wherein the compound is of formula (VI):
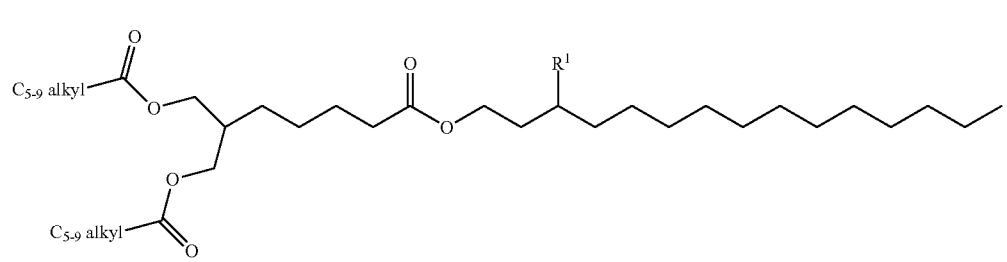
(VI)
9. The compound of claim 1 or a pharmaceutically acceptable salt thereof, wherein the compound is of formula (VII):
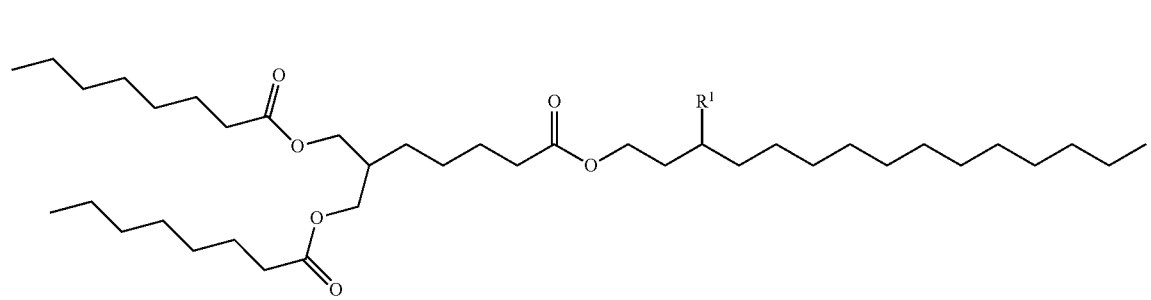
(VII)
10. The compound of claim 1 or a pharmaceutically acceptable salt thereof, wherein $R^1$ is selected from:
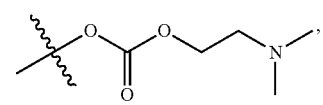
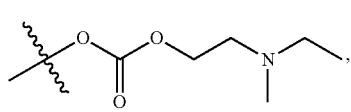
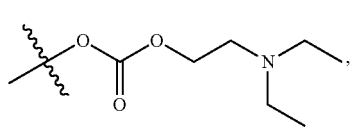
-continued
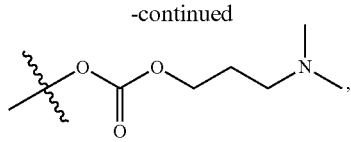
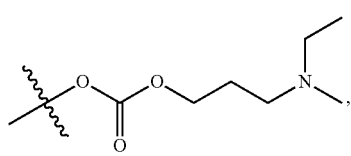
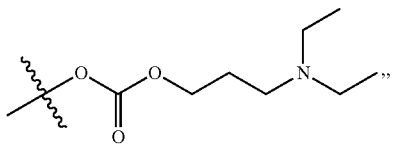

-continued

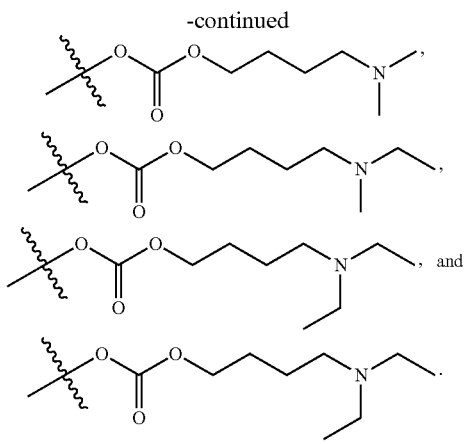

11. The compound of claim 1 or a pharmaceutically acceptable salt, wherein R¹ is

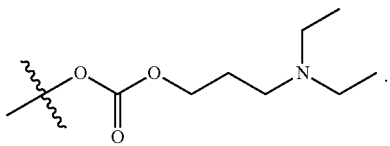 [SMILES: *OC(=O)OCCCN(CC)CC]

12. The compound of claim 1 or a pharmaceutically acceptable salt thereof, wherein the compound is selected from:
 2-(10-dodecyl-3-ethyl-8,14-dioxo-7,9,13-trioxa-3-azaoctadecan-18-yl)propane-1,3-diyl dioctanoate;
 2-(9-dodecyl-2-methyl-7,13-dioxo-6,8,12-trioxa-2-azaheptadecan-17-yl)propane-1,3-diyl dioctanoate;
 2-(9-dodecyl-2-methyl-7,13-dioxo-6,8,12-trioxa-2-azapentadecan-15-yl)propane-1,3-diyl dioctanoate;
 2-(10-dodecyl-3-ethyl-8,14-dioxo-7,9,13-trioxa-3-azahexadecan-16-yl)propane-1,3-diyl dioctanoate;
 2-(8-dodecyl-2-methyl-6,12-dioxo-5,7,11-trioxa-2-azaheptadecan-17-yl)propane-1,3-diyl dioctanoate;
 2-(10-dodecyl-3-ethyl-8,14-dioxo-7,9,13-trioxa-3-azanonadecan-19-yl)propane-1,3-diyl dioctanoate;
 2-(9-dodecyl-2-methyl-7,13-dioxo-6,8,12-trioxa-2-azaoctadecan-18-yl)propane-1,3-diyl dioctanoate;
 2-(8-dodecyl-2-methyl-6,12-dioxo-5,7,11-trioxa-2-azaoctadecan-18-yl)propane-1,3-diyl dioctanoate;
 2-(10-dodecyl-3-ethyl-8,14-dioxo-7,9,13-trioxa-3-azaicosan-20-yl)propane-1,3-diyl dioctanoate;
 2-(9-dodecyl-2-methyl-7,13-dioxo-6,8,12-trioxa-2-azanonadecan-19-yl)propane-1,3-diyl dioctanoate;
 3-(((3-(diethylamino)propoxy)carbonyl)oxy)pentadecyl 4,4-bis(octyloxy)butanoate;
 3-(((3-(diethylamino)propoxy)carbonyl)oxy)pentadecyl 4,4-bis((2-ethyl hexyl)oxy)butanoate;
 3-(((3-(diethylamino)propoxy)carbonyl)oxy)pentadecyl 4,4-bis((2-propylpentyl)oxy)butanoate;
 3-(((3-(ethyl(methyl)amino)propoxy)carbonyl)oxy)pentadecyl 4,4-bis((2-propylpentyl)oxy)butanoate;
 3-(((3-(dimethylamino)propoxy)carbonyl)oxy)pentadecyl 4,4-bis((2-propylpentyl)oxy)butanoate;
 3-(((3-(diethylamino)propoxy)carbonyl)oxy)pentadecyl 6,6-bis(octyloxy)hexanoate;
 3-(((3-(diethylamino)propoxy)carbonyl)oxy)pentadecyl 6,6-bis(hexyloxy)hexanoate;
 3-(((3-(diethylamino)propoxy)carbonyl)oxy)pentadecyl 6,6-bis((2-ethyl hexyl)oxy)hexanoate;
 3-(((3-(diethylamino)propoxy)carbonyl)oxy)pentadecyl 8,8-bis(hexyloxy)octanoate;
 3-(((3-(diethylamino)propoxy)carbonyl)oxy)pentadecyl 8,8-dibutoxyoctanoate;
 3-(((3-(diethylamino)propoxy)carbonyl)oxy)pentadecyl 8,8-bis((2-propylpentyl)oxy)octanoate;
 3-(((3-(ethyl(methyl)amino)propoxy)carbonyl)oxy)pentadecyl 8,8-bis((2-propylpentyl)oxy)octanoate;
 3-(((3-(dimethylamino)propoxy)carbonyl)oxy)pentadecyl 8,8-bis((2-propylpentyl)oxy)octanoate;
 3-(((3-(dimethylamino)propoxy)carbonyl)oxy)pentadecyl 3-octylundecanoate;
 3-(((3-(dimethylamino)propoxy)carbonyl)oxy)pentadecyl 3-octylundec-2-enoate;
 3-(((3-(dimethylamino)propoxy)carbonyl)oxy)pentadecyl 7-hexyltridec-6-enoate;
 3-(((3-(dimethylamino)propoxy)carbonyl)oxy)pentadecyl 9-pentyltetradecanoate;
 3-(((3-(dimethylamino)propoxy)carbonyl)oxy)pentadecyl 9-pentyltetradec-8-enoate;
 3-(((3-(dimethylamino)propoxy)carbonyl)oxy)pentadecyl 5-heptyldodecanoate;
 3-(((3-(dimethylamino)propoxy)carbonyl)oxy)tridecyl 5-heptyldodecanoate;
 3-(((3-(dimethylamino)propoxy)carbonyl)oxy)undecyl 5-heptyldodecanoate;
 1,3-bis(octanoyloxy)propan-2-yl (3-(((2-(dimethylamino)ethoxy)carbonyl)oxy)pentadecyl) succinate;
 1,3-bis(octanoyloxy)propan-2-yl (3-(((3-(dimethylamino)propoxy)carbonyl)oxy)pentadecyl) succinate;
 1-(3-(((3-(dimethylamino)propoxy)carbonyl)oxy)pentadecyl) 10-octyl decanedioate;
 1-(3-(((3-(diethylamino)propoxy)carbonyl)oxy)pentadecyl) 10-octyl decanedioate;
 1-(3-(((3-(ethyl(methyl)amino)propoxy)carbonyl)oxy)pentadecyl) 10-octyl decanedioate;
 1-(3-(((3-(diethylamino)propoxy)carbonyl)oxy)pentadecyl) 10-(2-ethylhexyl) decanedioate;
 1-(3-(((3-(ethyl(methyl)amino)propoxy)carbonyl)oxy)pentadecyl) 10-(2-ethylhexyl) decanedioate;
 3-(((3-(dimethylamino)propoxy)carbonyl)oxy)pentadecyl 10-(octanoyloxy)decanoate;
 8-dodecyl-2-methyl-6,12-dioxo-5,7,11-trioxa-2-azanonadecan-19-yl decanoate;
 3-(((3-(diethylamino)propoxy)carbonyl)oxy)pentadecyl 10-(octanoyloxy)decanoate;
 3-(((3-(ethyl(methyl)amino)propoxy)carbonyl)oxy)pentadecyl 10-(octanoyloxy)decanoate;
 (9Z,12Z)-3-(((3-(dimethylamino)propoxy)carbonyl)oxy)pentadecyl octadeca-9,12-dienoate;
 (9Z,12Z)-3-(((3-(diethylamino)propoxy)carbonyl)oxy)pentadecyl octadeca-9,12-dienoate;
 (9Z,12Z)-3-(((3-(ethyl(methyl)amino)propoxy)carbonyl)oxy)pentadecyl octadeca-9,12-dienoate;
 (9Z,12Z)-3-(((2-(dimethylamino)ethoxy)carbonyl)oxy)pentadecyl octadeca-9,12-dienoate;
 2-(((3-(diethylamino)propoxy)carbonyl)oxy)tetradecyl 4,4-bis((2-ethyl hexyl)oxy)butanoate;
 (13Z,16Z)-4-(((2-(dimethylamino)ethoxy)carbonyl)oxy)docosa-13,16-dien-1-yl 2,2-bis(heptyloxy)acetate;
 (13Z,16Z)-4-(((3-(diethylamino)propoxy)carbonyl)oxy)docosa-13,16-dien-1-yl 2,2-bis(heptyloxy)acetate;
 (13Z,16Z)-4-(((3-(dimethylamino)propoxy)carbonyl)oxy)docosa-13,16-dien-1-yl heptadecan-9-yl succinate;

3-(((3-(dimethylamino)propoxy)carbonyl)oxy)-13-hydroxytridecyl 5-heptyldodecanoate;

3-(((3-(dimethylamino)propoxy)carbonyl)oxy)-13-hydroxytridecyl 9-pentyltetradecanoate;

(9Z,12Z)-3-(((3-(dimethylamino)propoxy)carbonyl)oxy)-5-octyltridecyl octadeca-9,12-dienoate;

3-(((3-(dimethylamino)propoxy)carbonyl)oxy)-5-octyltridecyl decanoate;

5-(((3-(dimethylamino)propoxy)carbonyl)oxy)-7-octylpentadecyl octanoate;

(9Z,12Z)-5-(((3-(dimethylamino)propoxy)carbonyl)oxy)-7-octylpentadecyl octadeca-9,12-dienoate;

9-(((3-(dimethylamino)propoxy)carbonyl)oxy)-11-octylnonadecyl octanoate;

9-(((3-(dimethylamino)propoxy)carbonyl)oxy)-11-octylnonadecyl decanoate;

(9Z,12Z)-9-(((3-(dimethylamino)propoxy)carbonyl)oxy)nonadecyl octadeca-9,12-dienoate;

9-(((3-(dimethylamino)propoxy)carbonyl)oxy)nonadecyl hexanoate;

9-(((3-(dimethylamino)propoxy)carbonyl)oxy)nonadecyl 3-octylundecanoate;

(9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate);

(9Z,9'Z,12Z,12'Z)-2-((4-(((3-(diethylamino)propoxy)carbonyl)oxy)hexadecanoyl)oxy)propane-1,3-diyl bis(octadeca-9,12-dienoate);

(9Z,9'Z,12Z,12'Z,15Z,15'Z)-2-((4-(((3-(dimethylamino)propoxy)carbonyl)oxy) hexadecanoyl)oxy)propane-1,3-diyl bis(octadeca-9,12,15-trienoate);

(Z)-2-((4-(((3-(dimethylamino)propoxy)carbonyl)oxy)hexadecanoyl)oxy)propane-1,3-diyl dioleate;

2-((4-(((3-(diethylamino)propoxy)carbonyl)oxy)hexadecanoyl)oxy)propane-1,3-diyl ditetradecanoate;

2-((4-(((3-(dimethylamino)propoxy)carbonyl)oxy)hexadecanoyl)oxy)propane-1,3-diyl ditetradecanoate;

2-((4-(((3-(ethyl(methyl)amino)propoxy)carbonyl)oxy)hexadecanoyl)oxy)propane-1,3-diyl ditetradecanoate;

2-((4-(((3-(dimethylamino)propoxy)carbonyl)oxy)hexadecanoyl)oxy)propane-1,3-diyl didodecanoate;

2-((4-(((3-(diethylamino)propoxy)carbonyl)oxy)hexadecanoyl)oxy)propane-1,3-diyl didodecanoate;

2-((4-(((3-(ethyl(methyl)amino)propoxy)carbonyl)oxy)hexadecanoyl)oxy)propane-1,3-diyl didodecanoate;

2-((4-(((3-(diethylamino)propoxy)carbonyl)oxy)hexadecanoyl)oxy)propane-1,3-diyl bis(decanoate);

2-((4-(((3-(ethyl(methyl)amino)propoxy)carbonyl)oxy)hexadecanoyl)oxy)propane-1,3-diyl bis(decanoate);

2-((4-(((3-(diethylamino)propoxy)carbonyl)oxy)hexadecanoyl)oxy)propane-1,3-diyl dioctanoate;

2-((4-(((3-(ethyl(methyl)amino)propoxy)carbonyl)oxy)hexadecanoyl)oxy)propane-1,3-diyl dioctanoate;

2-(((13Z,16Z)-4-(((3-(dimethylamino)propoxy)carbonyl)oxy)docosa-13,16-dienoyl)oxy)propane-1,3-diyl dioctanoate;

2-(((13Z,16Z)-4-(((3-(diethylamino)propoxy)carbonyl)oxy)docosa-13,16-dienoyl)oxy)propane-1,3-diyl dioctanoate;

(9Z,9'Z,12Z,12'Z)-2-((2-(((3-(diethylamino)propoxy)carbonyl)oxy)tetradecanoyl)oxy)propane-1,3-diyl bis(octadeca-9,12-dienoate);

(9Z,9'Z,12Z,12'Z)-2-((2-(((3-(dimethylamino)propoxy)carbonyl)oxy)dodecanoyl)oxy)propane-1,3-diyl bis(octadeca-9,12-dienoate);

(9Z,9'Z,12Z,12'Z)-2-((2-(((3-(dimethylamino)propoxy)carbonyl)oxy)tetradecanoyl)oxy)propane-1,3-diyl bis(octadeca-9,12-dienoate);

(9Z,9'Z,12Z,12'Z)-2-((2-(((3-(diethylamino)propoxy)carbonyl)oxy)dodecanoyl)oxy)propane-1,3-diyl bis(octadeca-9,12-dienoate);

2-((2-(((3-(diethylamino)propoxy)carbonyl)oxy)tetradecanoyl)oxy)propane-1,3-diyl dioctanoate;

4,4-bis(octyloxy)butyl 4-(((3-(dimethylamino)propoxy)carbonyl)oxy)hexadecanoate;

4,4-bis(octyloxy)butyl 2-(((3-(diethylamino)propoxy)carbonyl)oxy)dodecanoate;

3-(((3-(dimethylamino)propoxy)carbonyl)oxy)pentadecyl 4,4-bis(octyloxy)butanoate;

3-(((4-(diethylamino)butoxy)carbonyl)oxy)pentadecyl 6,6-bis(octyloxy)hexanoate;

3-(((2-(diethylamino)ethoxy)carbonyl)oxy)pentadecyl 6,6-bis(octyloxy)hexanoate;

3-(((3-(dimethylamino)propoxy)carbonyl)oxy)pentadecyl 6,6-bis(octyloxy)hexanoate;

3-(((3-(diethylamino)propoxy)carbonyl)oxy)pentadecyl 6,6-bis((2-propylpentyl)oxy)hexanoate;

3-(((3-(dimethylamino)propoxy)carbonyl)oxy)pentadecyl 6,6-bis((2-propylpentyl)oxy)hexanoate;

3-(((3-(dimethylamino)propoxy)carbonyl)oxy)pentadecyl 6,6-bis((3-ethylpentyl)oxy)hexanoate;

3-(((3-(diethylamino)propoxy)carbonyl)oxy)pentadecyl 5-(4,6-diheptyl-1,3-dioxan-2-yl)pentanoate;

3-(((3-(diethylamino)propoxy)carbonyl)oxy)undecyl 6,6-bis(octyloxy)hexanoate;

3-(((3-(diethylamino)propoxy)carbonyl)oxy)tridecyl 6,6-bis(octyloxy)hexanoate;

(12Z,15Z)-3-(((3-(diethylamino)propoxy)carbonyl)oxy)henicosa-12,15-dien-1-yl 6,6-bis(octyloxy)hexanoate;

4,4-bis(octyloxy)butyl 5-(((3-(diethylamino)propoxy)carbonyl)oxy)heptadecanoate;

4,4-bis(octyloxy)butyl (3-(diethylamino)propyl) pentadecane-1,3-diyl dicarbonate;

2-(10-dodecyl-3-ethyl-8,15-dioxo-7,9,14-trioxa-3-azanonadecan-19-yl)propane-1,3-diyl dioctanoate; and 2-(11-dodecyl-3-ethyl-9,15-dioxo-8,10,14-trioxa-3-azanonadecan-19-yl)propane-1,3-diyl dioctanoate.

13. A lipid composition comprising the compound of claim 1 or a pharmaceutically acceptable salt thereof.

14. The lipid composition of claim 13, further comprising a biologically active agent.

15. The lipid composition of claim 13, wherein the lipid composition is in the form of a lipid nanoparticle.

16. A pharmaceutical composition comprising the lipid composition of claim 13, and a pharmaceutically acceptable carrier or excipient.

17. The composition of claim 14, wherein the composition comprises a RNA molecule that encodes an immunogen, optionally wherein the RNA is a self replicating RNA.

18. The composition of claim 17, wherein the immunogen can elicit an immune response in vivo against a bacterium, a virus, a fungus or a parasite.

19. A compound:

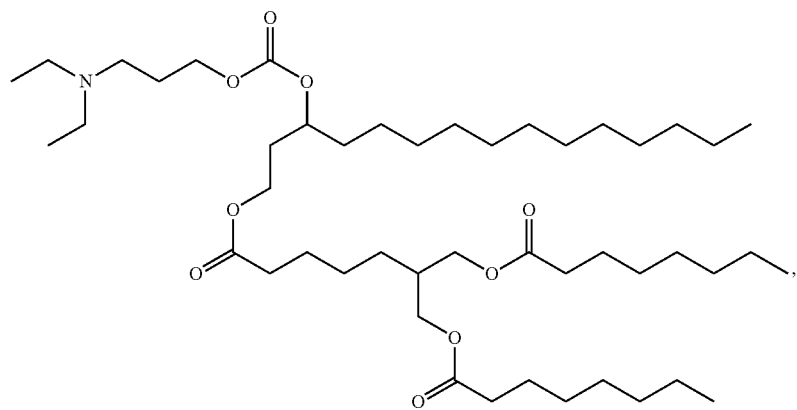 [SMILES: CCCCCCCCCCCCC(CCOC(=O)CCCCC(COC(=O)CCCCCCC)COC(=O)CCCCCCC)OC(=O)OCCCN(CC)CC]

2-(10-dodecyl-3-ethyl-8,14-dioxo-7,9,13-trioxa-3-azaoctadecan-18-yl)propane-1,3-diyl dioctanoate or a pharmaceutically acceptable salt thereof.

20. A compound:

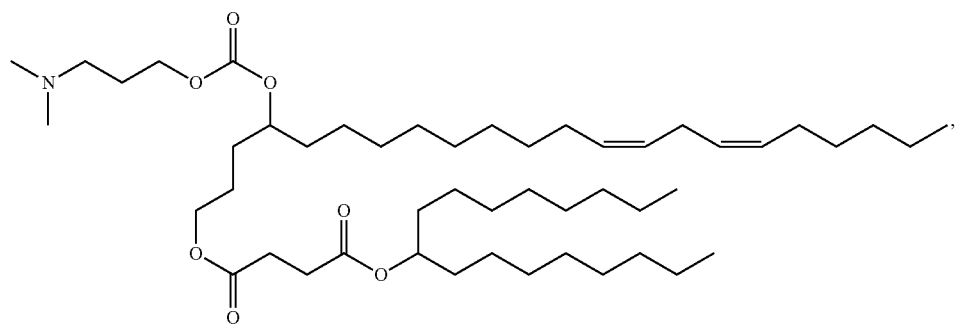 [SMILES: CCCCC/C=C\C/C=C\CCCCCCCCC(CCCOC(=O)CCC(=O)OC(CCCCCCCC)CCCCCCCC)OC(=O)OCCCN(C)C]

(13Z,16Z)-4-(((3-(dimethylamino)propoxy)carbonyl)oxy)docosa-13,16-dien-1-yl heptadecan-9-yl succinate or a pharmaceutically acceptable salt thereof.

21. A compound:

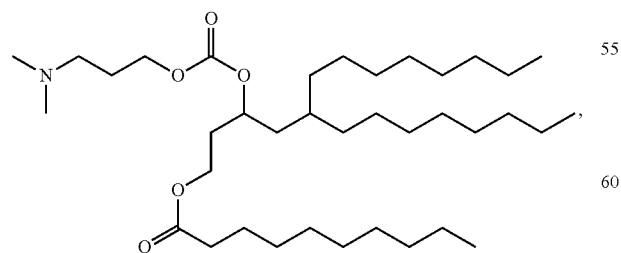

3-(((3-(dimethylamino)propoxy)carbonyl)oxy)-5-octyltridecyl decanoate or pharmaceutically acceptable salt thereof.

22. A compound:

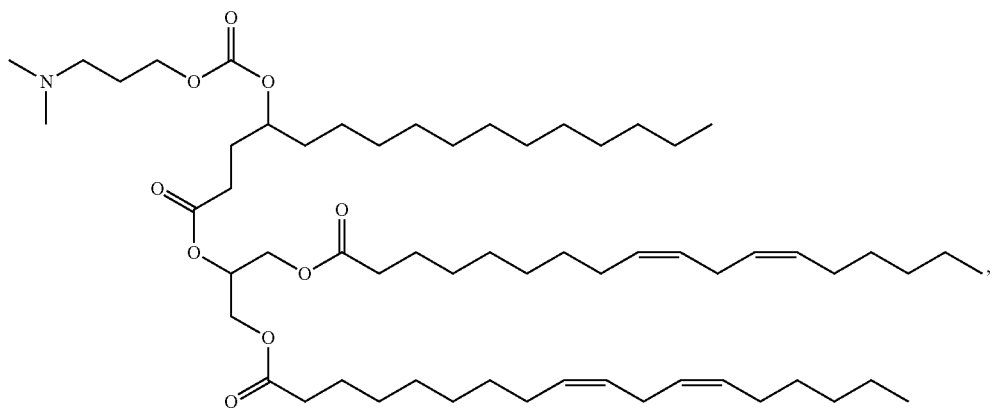 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

(9Z,9'Z,12Z,12'Z)-2-((4-(((3-(dimethylamino)propoxy)
carbonyl)oxy)hexadecanoyl)oxy)propane-1,3-diyl bis
(octadeca-9,12-dienoate) or a pharmaceutically acceptable salt thereof.

23. A compound:

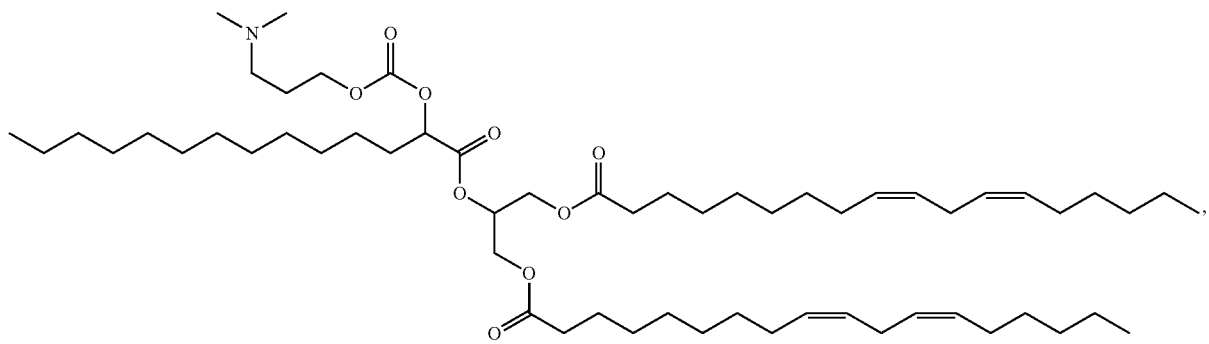 [SMILES: CCCCC/C=C\C/C=C\CCCCCCCC(=O)OCC(COC(=O)CCCCCCC/C=C\C/C=C\CCCCC)OC(=O)C(CCCCCCCCCCCC)OC(=O)OCCCN(C)C]

(9Z,9'Z,12Z,12'Z)-2-((2-(((3-(dimethylamino)propoxy)
carbonyl)oxy)tetradecanoyl)oxy)propane-1,3-diyl bis
(octadeca-9,12-dienoate) or a pharmaceutically acceptable salt thereof.

24. The lipid composition of claim 14, wherein the biologically active agent is an mRNA.

25. The lipid composition of claim 13, wherein the lipid composition comprises 2-(10-dodecyl-3-ethyl-8,14-dioxo-7,9,13-trioxa-3-azaoctadecan-18-yl)propane-1,3-diyl dioctanoate or a pharmaceutically acceptable salt thereof; and a mRNA.

26. The lipid composition of claim 13, wherein the lipid composition comprises (13Z,16Z)-4-(((3-(dimethylamino)propoxy)carbonyl)oxy)docosa-13,16-dien-1-yl heptadecan-9-yl succinate or a pharmaceutically acceptable salt thereof; and a mRNA.

27. The lipid composition of claim 13, wherein the lipid composition comprises 3-(((3-(dimethylamino)propoxy)carbonyl)oxy)-5-octyltridecyl decanoate or a pharmaceutically acceptable salt thereof; and a mRNA.

28. The lipid composition of claim 13, wherein the lipid composition comprises (9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate) or a pharmaceutically acceptable salt thereof; and a mRNA.

29. The lipid composition of claim 13, wherein the lipid composition comprises a compound (9Z,9'Z,12Z,12'Z)-2-((2-(((3-(dimethylamino)propoxy)carbonyl)oxy)tetradecanoyl)oxy)propane-1,3-diyl bis(octadeca-9,12-dienoate) or a pharmaceutically acceptable salt thereof; and a mRNA.

* * * * *

UNITED STATES PATENT AND TRADEMARK OFFICE
CERTIFICATE OF CORRECTION

PATENT NO. : 10,426,737 B2
APPLICATION NO. : 15/104723
DATED : October 1, 2019
INVENTOR(S) : Brito et al.

Page 1 of 2

It is certified that error appears in the above-identified patent and that said Letters Patent is hereby corrected as shown below:

In the Claims

Column 317, Claim 1, between Lines 55 and 60, delete the third compound

" 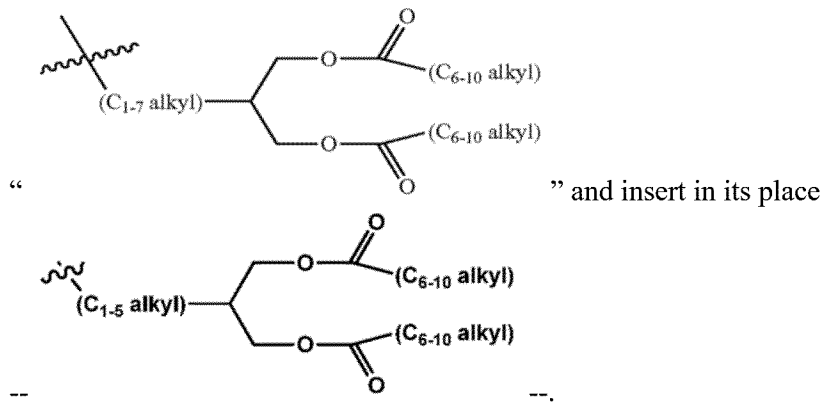 " and insert in its place

-- 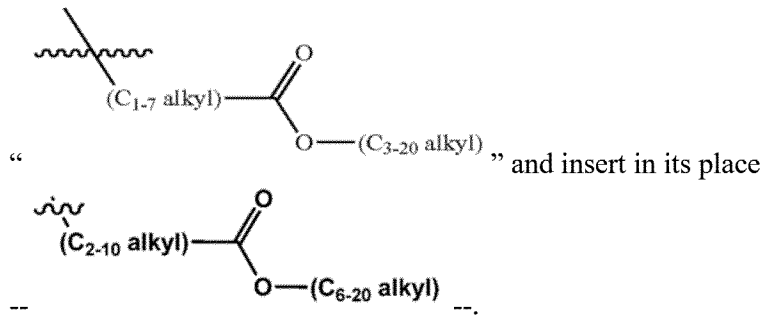 --.

Column 317, Claim 1, between Lines 62 and 65, delete the fourth compound

" 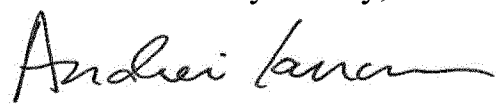 " and insert in its place

-- 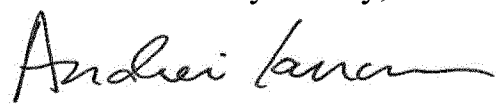 --.

Signed and Sealed this
Fourteenth Day of July, 2020

Andrei Iancu
*Director of the United States Patent and Trademark Office*

CERTIFICATE OF CORRECTION (continued)
U.S. Pat. No. 10,426,737 B2

Column 328, Claim 6, delete the sixth from the last compound

" 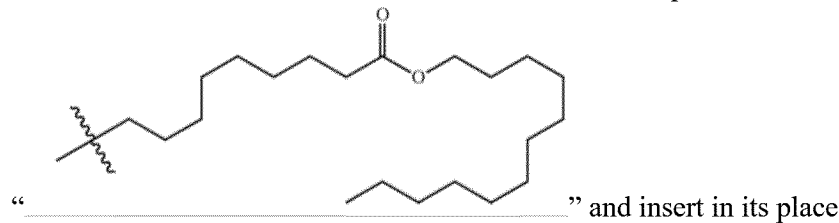 " and insert in its place

" 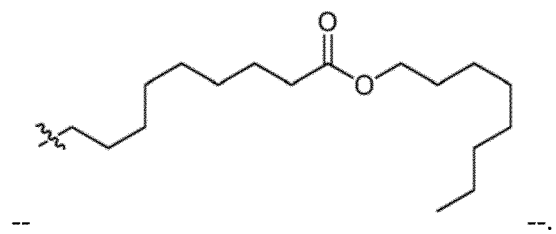 --.